US010584351B2

(12) United States Patent
Roeth et al.

(10) Patent No.: US 10,584,351 B2
(45) Date of Patent: Mar. 10, 2020

(54) VECTORS CONDITIONALLY EXPRESSING THERAPEUTIC PROTEINS, HOST CELLS COMPRISING THE VECTORS, AND USES THEREOF

(71) Applicant: Intrexon Corporation, Blacksburg, VA (US)

(72) Inventors: Jeremiah F. Roeth, Blacksburg, VA (US); Charles C. Reed, Souderton, PA (US); Brandon Cuthbertson, Newland, CT (US); Sunil Chada, Missouri City, TX (US); William E. Fogler, Rockville, MD (US)

(73) Assignee: Intrexon Corporation, Blacksburg, VA (US)

(*) Notice: Subject to any disclaimer, the term of this patent is extended or adjusted under 35 U.S.C. 154(b) by 0 days.

(21) Appl. No.: 15/648,623

(22) Filed: Jul. 13, 2017

(65) Prior Publication Data

US 2018/0002719 A1 Jan. 4, 2018

Related U.S. Application Data

(60) Division of application No. 14/982,815, filed on Dec. 29, 2015, now abandoned, which is a continuation of application No. 13/636,473, filed as application No. PCT/US2011/029682 on Mar. 23, 2011, now abandoned.

(60) Provisional application No. 61/431,364, filed on Jan. 10, 2011, provisional application No. 61/366,731, filed on Jul. 22, 2010, provisional application No. 61/316,792, filed on Mar. 23, 2010.

(51) Int. Cl.

| | |
|---|---|
| ***C12N 15/861*** | (2006.01) |
| ***C07K 14/55*** | (2006.01) |
| ***A61K 38/20*** | (2006.01) |
| ***C07K 14/47*** | (2006.01) |
| ***C12N 15/85*** | (2006.01) |
| ***C12N 15/86*** | (2006.01) |
| ***C07K 14/54*** | (2006.01) |
| ***A61K 38/19*** | (2006.01) |
| ***A61K 38/21*** | (2006.01) |
| ***A61K 38/44*** | (2006.01) |
| ***A61K 48/00*** | (2006.01) |
| ***C12N 5/0784*** | (2010.01) |

(52) U.S. Cl.

CPC ............ *C12N 15/85* (2013.01); *A61K 38/191* (2013.01); *A61K 38/208* (2013.01); *A61K 38/212* (2013.01); *A61K 38/44* (2013.01); *A61K 48/0066* (2013.01); *C07K 14/5434* (2013.01); *C12N 5/0639* (2013.01); *C12N 15/86* (2013.01); *C12N 15/861* (2013.01); *C12N 2710/10343* (2013.01); *C12N 2830/002* (2013.01); *C12N 2840/203* (2013.01)

(58) Field of Classification Search
None
See application file for complete search history.

(56) References Cited

U.S. PATENT DOCUMENTS

| | | | | |
|---|---|---|---|---|
| 7,138,511 | B1 | 11/2006 | Nguyen et al. | |
| 2003/0082722 | A1* | 5/2003 | Fang ...................... | C12N 15/85 435/69.1 |
| 2003/0109683 | A1 | 6/2003 | O'Malley et al. | |
| 2003/0180719 | A1 | 9/2003 | Herget et al. | |
| 2004/0082535 | A1 | 4/2004 | Mahuran et al. | |
| 2004/0235169 | A1 | 11/2004 | Evans et al. | |
| 2005/0267027 | A1 | 12/2005 | Lounsbury et al. | |
| 2006/0281703 | A1 | 12/2006 | Bauzon et al. | |
| 2007/0224170 | A1 | 9/2007 | Qian et al. | |
| 2008/0076729 | A1 | 3/2008 | Bauzon et al. | |
| 2008/0241100 | A1 | 10/2008 | Strobl et al. | |
| 2008/0260690 | A1 | 10/2008 | De Luca | |
| 2009/0017108 | A1 | 1/2009 | Yuzhakov | |
| 2009/0123441 | A1 | 5/2009 | Braughler et al. | |
| 2009/0136465 | A1 | 5/2009 | Merenick et al. | |
| 2010/0184838 | A1 | 7/2010 | Kumar-Singh et al. | |
| 2010/0292307 | A1 | 11/2010 | Hyde et al. | |
| 2011/0268766 | A1* | 11/2011 | Beech .................... | C12N 15/86 424/277.1 |

FOREIGN PATENT DOCUMENTS

| | | | |
|---|---|---|---|
| CN | 101235387 | A | 8/2008 |
| CN | 101565718 | A | 10/2009 |
| WO | WO 2000/075292 | A1 | 12/2000 |
| WO | WO 2000/078951 | A1 | 12/2000 |
| WO | WO 2003/029412 | A2 | 4/2003 |
| WO | WO 2004/066947 | A2 | 4/2005 |
| WO | WO 2006/052302 | A2 | 5/2006 |
| WO | WO 2007/110628 | A2 | 10/2007 |
| WO | WO 2009/048560 | A1 | 4/2009 |
| WO | WO 2011/119773 | A1 | 9/2011 |

OTHER PUBLICATIONS

Fumoto et al, Targeted Gene Delivery: Importance of Administration Routes, Chapter 1, Intech, 2013, pp. 3-31.*
Shanks et al, Are animal models predictive for humans? Philosophy, Ethics, and Humanities in Medicine, 2009, pp. 1-20.*
Socher et al, An Autogenously Regulated Expression System for Gene Therapeutic Ocular Applications, Scientific Reports, 2015, pp. 1-8.*

(Continued)

*Primary Examiner* — Maria Marvich
(74) *Attorney, Agent, or Firm* — Sterne, Kessler, Goldstein and Fox P.L.L.C.

(57) ABSTRACT

This invention relates to the field of therapeutics. Most specifically, the invention provides methods of generating conditionally expressing vectors for one or more immuunomodulators under the control of a gene expression modulation system in the presence of activating ligand and uses for therapeutic purposes in animals. These vector may be provided to treat a variety of disorders, e.g., neoplastic disorders, through direct injection or through in vitro engineered cells, such as dendritic cells.

30 Claims, 40 Drawing Sheets

Specification includes a Sequence Listing.

(56) References Cited

OTHER PUBLICATIONS

Chiocca et al, A Phase 1 Study of Ad-RTS-hIL-12 + Veledimex in Adult Recurrent Glioblastoma: Dose determination with updated overall survival, Ziopharm Oncology, downloaded Feb. 18, 2018.*
Campochiaro, P.A., et al., "Adenoviral vector-delivered pigment epithelium-derived factor for neovascular age-related macular degeneration: results of a phase I clinical trial," *Human Gene Therapy 17(2)*:167-176, Mary Ann Liebert, Inc., United States (2006).
Conley, S.M., et al., "Non-Viral Ocular Gene Therapy: Assessment and Future Directions," *Current Opinion in Molecular Therapeutics 10(5)*:456-463, Thomson Reuters, England (2008).
Green, N.K. And Seymour, L.W., "Adenoviral vectors: systemic delivery and tumor targeting," *Cancer Gene Therapy 9(12)*:1036-1042, Nature Publishing Group, England (2002).
Orkin, S.H. And Motulsky, A.G., "Report and Recommendations of the Panel to Assess the NIH Investment in Research on Gene Therapy," http://osp.od.nih.gov, accessed at http://osp.od.nih.gov/office-biotechnology-activities/orkin-motulsky-report, accessed on Mar. 22, 2016, 37 pages (1995).
Raty, J.K., et al., "Gene therapy: the first approved gene-based medicines, molecular mechanisms and clinical indications," *Current Molecular Pharmacology 1(1)*:13-23, Bentham Science Publishers Ltd., United Arab Emirates (2008).
Komita, H., et al., "Conditional interleukin-12 gene therapy promotes safe and effective antitumor immunity," *Cancer Gene Therapy 16*(12):883-891, Nature Publishing Group, England (2009).
Karzenowski, D., et al., "Inducible control of transgene expression with ecdysone receptor: gene switches with high sensitivity, robust expression, and reduced size," *BioTechniques 39*:191-200, Informa BioSciences, United States (2005).
Fumoto, S., et al., "Targeted Gene Delivery: Importance of Administration Routes", *Novel Gene Therapy Approaches*, pp. 3-31, Intech (2013).
Shanks, N., et al., "Are animal models predictive for humans", *Philosophy, Ethics, and Humanities in Medicine 4*:2, (2009) 20 pages.
Sochor, M., et al., "An Autogenously Regulated Expression System for Gene Therapeutic Ocular Applications", *Scientific Reports 5*:17105, Nature Publishing Group, England (Nov. 24, 2015).
Addison, CL., et al., "Intratumoral coinjection of adenoviral vectors expressing IL-2 and IL-12 results in enhanced frequency of regression of injected and untreated distal tumors'," *Gene therapy 5(10)*1400-1409, Nature Publishing Group, United Kingdom (1998).
Bruni, S., et al., "Update on treatment of lysosomal storage diseases," *Acta Myologica 26(1)*:87-92, Pacini Editore, Italy (2007).
Carter, QL., et al., "Interleukin-12 (IL-12) ameliorates the effects of porcine respiratory and reproductive syndrome virus (PRRSV) infection," *Veterinary Immunology and Immunopathology 107*:105-118, Elsevier, Netherlands (2005).
Hallahan, D.E., et al., "Spatial and temporal control of gene therapy using ionizing radiation," *Nature Medicine 1(8)*:786-791, Nature Publishing Group, United Kingdom (1995).
Horsley, M., et al., "Anti-VEGF therapy for glaucoma," *Opinion in Ophthalmology 21*:112-117, Wolters Kluwer, Netherlands (2010).
Huang, J., et al., "Construction of eukaryotic expression vector and establishment of cell line solely producing human TNF-α in secretory form," *Xibao Yu Fenzi Mianyixue Zazhi 16(1)*:6-9, Institute of Chinese Materia Medica, China (2000).
IP, M., et al., "Anti-Vascular Endothelial Growth Factor Pharmacotherapy for Age-Related Macular Degeneration," *Ophthalmology 115(10)*: 1837-1846, Elsevier, Netherlands (2008).
Kraunus, J., et al., "Self-inactivating retroviral vectors with improved RNA processing," *Gene Therapy 11(21)*:1568-1578, Nature Publishing Group, United Kingdom (2004).
Okada, Y., et al., "An investigation of adverse effects caused by the injection of high-dose TNFα-expressing advenovirus vector into established murine melanoma," *Gene Therapy 10*:700-705, Nature Publishing Group, United Kingdom (2003).
Parkin, J., et al., "An overview of the immune system," *Lancet 357(9270)*:1777-1789, Elsevier, Netherlands (2001).
Sabel, M.S., et al., "Intratumoral IL-12 and TNF-alpha loaded microspheres lead to regression of breast cancer and systemic antitumor immunity," *Ann Surg Oncol. 11(2)*:147-156, Springer Science+Business Media, Germany (2004).
Sangro B., et al., "Phase I trial of intratumoral injection of an adenovirus encoding interleukin-12 for advanced digestive tumors," *Journal of Clinical Oncology 22(8)*:1389-1397, American Society of Clinical Oncology, United States (2004).
Scheinberg, I.H., et al., "Deficiency of Ceruloplasmin in Patients with Hepatolenticular Degeneration (Wilson's Disease)," *Science 116(3018)*:484-485, American Association for the Advancement of Science, United States (1952).
Van Horssen, R., et al., "TNF-alpha in cancer treatment: molecular insights, antitumor effects, and clinical utility," *Oncologist 11(4)*:397-408, AlphaMed Press, United States (2006).
Weichselbaum, R.R., et al., "Gene Therapy Targeted by Radiation Preferentially Radiosensitizes Tumor Cells," *Cancer Research 54*:4266-4269, American Association of Cancer Research, United States (1994).
Whitcup, S.M., et al., "IL-12 inhibits endotoxin-induced inflammation in the eye," *European Journal of Immunology 26*:995-999, Wiley Online Library, Germany (1996).
Zagozdzon, R., et al., "Augmented Antitumor Effects of Combination Therapy with Interleukin-12, Cisplatin, and Tumor Necrosis Factor-α in a Murine Melanoma Model," *Anticancer Research 17(6d)*:4493-4498, International Institute of Anticancer Research, Greece (1997).
Zeng, J., et al., "The differences between mechanisms of TNF-α synthesis and secretion and typical secretory protein," *Zhonghua Weishengwu xue He Mianyixue Zazhi 19(1)*:66-69, East View China Academic Journals Medicine, China (1999).
Zhang, P., "Preparation of endostatin protein and the measurement of its biologic activity," *Int. J. Opthamol. 115(3)*:195-199, Chinese Medical Association, China (2008).

* cited by examiner

Technology

| Effect (positive or negative) on gene product (mRNA or peptide): | Transcription: RheoSwitch technology | Transcription: Artificial promoters | Post-transcription: 5' UTRs | Post-transcription: 3'Reg | Translation: Codon optimization | Post-translation: Signal peptides | Post-translation: N-end rule residues | Post-translation: Localization sequences |
|---|---|---|---|---|---|---|---|---|
| Expression level | ✓ | ✓ | ✓ | ✓ | ✓ | ✓ | ✓ | ✓ |
| Localization | | | ✓ | ✓ | | ✓ | | ✓ |
| Stability | | | ✓ | ✓ | | | ✓ | ✓ |
| Maturation | | | ✓ | | | ✓ | | ✓ |

FIG. 10

INTREXON

Figure 3: Diagram Adenovirus compatible UltraVector backbone with switch and inducible modular synthetic gene.

5U2 versus the wtUV TNF 5UTR p = 0.001

| | Average induced TNF alpha secretion, ng/mL |
|---|---|
| wtTNF | 1207 |
| 5U2 | 2827.5 |

Days Post Tumor Cell Inoculation

SEQUENCE LISTING

```
<160> NUMBER OF SEQ ID NOS: 66

<210> SEQ ID NO 1
<211> LENGTH: 13294
<212> TYPE: DNA
<213> ORGANISM: Artificial Sequence
<220> FEATURE:
<223> OTHER INFORMATION: Synthetic mIL-12 and mIL-21

<400> SEQUENCE: 1

taaacaaata ggggttccgc gcacatttcc ccgaaaagtg ccacctgacg tctaagaaac      60

cattattatc atgacattaa cctataaaaa taggcgtatc acgaggccct ttcgtcttca     120

attaatcgca ccggtatcta tgtcgggtgc ggagaaagag gtaatgaaat ggcagctagc     180

atcatcaata atatacctta ttttggattg aagccaatat gataatgagg gggtggagtt     240

tgtgacgtgg cgcggggcgt gggaacgggg cgggtgacgt agtagtgtgg cggaagtgtg     300

atgttgcaag tgtggcggaa cacatgtaag cgacggatgt ggcaaaagtg acgtttttgg     360

tgtgcgccgg tgtacacagg aagtgacaat tttcgcgcgg ttttaggcgg atgttgtagt     420

aaatttgggc gtaaccgagt aagatttggc cattttcgcg ggaaaactga ataagaggaa     480

gtgaaatctg aataattttg tgttactcat agcgcgtaat atttgtctag ggagatccgg     540

taccgatatc ctagacaacg atgctgagct aactataacg gtcctaaggt agcgaccgcg     600
```

-continued gagactaggt gtatttatct aagcgatcgc ttaattaagg ccggccgccg caataaaata 660
tctttatttt cattacatct gtgtgttggt tttttgtgtg aatccatagt actaacatac 720
gctctccatc aaaacaaaac gaaacaaaac aaactagcaa aataggctgt ccccagtgca 780
agtccaggtg ccagaacatt tctctatcca taatgcaggg gtaccgggtg atgacggtga 840
aaacctccaa ttgcggagta ctgtcctccg agcggagtac tgtcctccga gcggagtact 900
gtcctccgag cggagtactg tcctccgagc ggagtactgt cctccgagcg gagtactgtc 960
ctccgagcgg agagtccccg gggacctaga gggtatataa tgggtgcctt agctggtgtg 1020
tgacctcatc ttcctgtacg cccctgcagg ggcgcgccac gcgtcgaaga aggtgagtaa 1080
tcttaacatg ctcttttttt ttttttttgc taatcccttt tgtgtgctga tgttaggatg 1140
acatttacaa caaatgtttg ttcctgacag gaaaaacctt gctgggtacc ttcgttgccg 1200
gacacttctt gtcctctact ttggaaaaaa ggaattgaga gccgctagcc caccatgtgc 1260
ccccagaagc tgaccatcag ctggttcgcc atcgtgctgc tggtgagccc cctgatggcc 1320
atgtgggagc tggagaagga cgtgtacgtg gtggaggtgg actggacccc cgacgccccc 1380
ggcgagaccg tgaacctgac ttgcgacacc cccgaggagg acgacatcac ctggaccagc 1440
gaccagagac acggcgtcat cggcagcggc aagaccctga ccatcaccgt gaaggagttc 1500
ctggacgccg gacagtacac ctgtcacaag ggcggcgaga ccctgagcca cagccacctg 1560
ttgctgcaca agaaggagaa cggcatctgg agcaccgaga tcctgaagaa cttcaagaac 1620
aagaccttcc tgaagtgcga ggcccccaac tacagcggca gattcacctg tagctggctg 1680
gtgcagagaa acatggacct gaagttcaac atcaagagca gcagcagcag ccccgacagc 1740
agagccgtga catgcggcat ggccagcctg agcgccgaga aggtgaccct ggaccagaga 1800
gactacgaga agtacagcgt gagctgccag gaggacgtga cctgtcccac cgccgaggag 1860
accctgccca tcgagcttgc cctggaagcc agacagcaga acaagtacga gaactacagc 1920
accagcttct tcatcagaga catcatcaag cccgaccccc ccaagaacct ccagatgaag 1980
cccctgaaga acagccaggt ggaggtgtcc tgggagtacc ccgacagctg gagcaccccc 2040
cacagctact tcagcctgaa gttcttcgtg agaatccaga gaaagaagga gaagatgaag 2100
gagaccgagg agggctgcaa ccagaagggc gctttcctgg tggagaaaac cagcaccgag 2160
gtgcagtgca agggcggcaa cgtgtgtgtg caggcccagg acagatacta caacagcagc 2220
tgctccaagt gggcctgcgt gccctgccgc gtgagaagct gaatcgattg cgcaaagctc 2280
cccctctccc tccccccccc ctaacgttac tggccgaagc cgcttggaat aaggccggtg 2340
tgcgtttgtc tatatgttat tttccaccat attgccgtct tttggcaatg tgagggcccg 2400
gaaacctggc cctgtcttct tgacgagcat tcctaggggt ctttcccctc tcgccaaagg 2460
aatgcaaggt ctgttgaatg tcgtgaagga agcagttcct ctggaagctt cttgaagaca 2520
aacaacgtct gtagcgaccc tttgcaggca gcggaacccc ccacctggcg acaggtgcct 2580
ctgcggccaa aagccacgtg tataagatac acctgcaaag gcggcacaac cccagtgcca 2640
cgttgtgagt tggatagttg tggaaagagt caaatggctc tcctcaagcg tattcaacaa 2700
ggggctgaag gatgcccaga aggtacccca ttgtatggga tctgatctgg ggcctcggtg 2760
cacatgcttt acatgtgttt agtcgaggtt aaaaaacgtc taggcccccc gaaccacggg 2820
gacgtggttt tcctttgaaa aacacgatct cttaagtcta gcgccaccat gtgccagagc 2880
agatacctgt tgttcctggc taccctggcc ctgctgaacc acctgagcct ggcccgcgtg 2940
atccccgtga gcggccccgc cagatgcctg agccagagca gaaacctgtt gaaaacaacc 3000

-continued

```
gacgacatgg tgaaaaccgc cagagagaag ctgaagcact acagctgcac cgccgaggac   3060
atcgaccacg aggacatcac cagagaccag accagcaccc tgaaaacctg tctgcccctg   3120
gagctgcaca agaacgagag ctgcctggct accagagaga ccagcagcac caccagaggc   3180
agctgcctgc ccccccagaa aaccagcctg atgatgaccc tgtgcctggg cagcatctac   3240
gaggacctga agatgtacca gaccgagttc caggccatca acgccgccct gcaaaaccac   3300
aaccaccagc agatcatcct ggacaagggc atgttggtgg ccatcgacga gctgatgcag   3360
agcctgaacc acaacggcga gaccctgaga cagaagcccc ccgtgggcga ggccgacccc   3420
tacagagtga agatgaagct gtgcatcctg ctgcacgcct tcagcaccag agtggtgacc   3480
atcaacagag tgatgggcta cctgagcagc gcctgaatcg aatgcgcact cgagtggtat   3540
tacgctcaac ttcagaatct cactaaaaga atagatagtc ttcctttaac tgaaaatttt   3600
tccttacaaa cagatatgga cgtcactagc accaccatgg agaggaccct ggtgtgcctg   3660
gtggtgatct tcctgggcac cgtggcccac aagagcagcc cccagggacc cgacaggctg   3720
ctgatccggc tgagacacct gatcgacatc gtggagcagc tgaagattta cgagaacgac   3780
ctggaccccg agctgctgtc cgcccccccag gacgtgaagg gccactgcga gcacgccgcc   3840
ttcgcctgct tccagaaggc caagctgaag cccagcaacc ccggcaacaa caagaccttc   3900
atcatcgacc tggtggccca gctgagaagg aggctgcccg ccaggagggg cggcaagaag   3960
cagaagcaca tcgccaagtg ccccagctgc gacagctacg agaagcggac ccccaaggag   4020
ttcctggaga ggctgaagtg gctgctgcaa aagatgatcc accagcacct gagctgaatc   4080
gcctgcgcag catgctcgcg acctaagtcg gccgctaaag tttacgtagc ggccgcgtcg   4140
acgatagctt gatgggtggc atccctgtga cccctcccca gtgcctctcc tggccctgga   4200
agttgccact ccagtgccca ccagccttgt cctaataaaa ttaagttgca tcattttgtc   4260
tgactaggtg tccttctata atattatggg gtggaggggg gtggtatgga gcaaggggca   4320
agttgggaag acaacctgta gggcctgcgg ggtctattgg gaaccaagct ggagtgcagt   4380
ggcacaatct tggctcactg caatctccgc ctcctgggtt caagcgattc tcctgcctca   4440
gcctcccgag ttgttgggat tccaggcatg catgaccagg ctcagctaat tttgtttttt   4500
ttggtagaga cggggtttca ccatattggc caggctggtc tccaactcct aatctcaggt   4560
gatctaccca ccttggcctc ccaaattgct gggattacag gcgtgaacca ctgctccctt   4620
ccctgtcctt ctgattttaa aataactata ccagcaggag gacgtccaga cacagcatag   4680
gctacctggc catgcccaac cggtgggaca tttgagttgc ttgcttggca ctgtcctctc   4740
atgcgttggg tccactcagt agatgcctgt tgaattctga tttaaatcgg tccgcgtacg   4800
gcgtggtagg tccgaacgaa tccatggatt accctgttat ccctatccgg agttaacctc   4860
gaggacttcg gaacttctag aaccagaccg ttcagtttaa acgctcttct ccccctcgag   4920
ggcctccgcg ccgggttttg gcgcctcccg cgggcgcccc cctcctcacg gcgagcgctg   4980
ccacgtcaga cgaagggcgc agcgagcgtc ctgatccttc cgcccggacg ctcaggacag   5040
cggcccgctg ctcataagac tcggccttag aaccccagta tcagcagaag gacattttag   5100
gacgggactt gggtgactct agggcactgg ttttctttcc agagagcgga acaggcgagg   5160
aaaagtagtc ccttctcggc gattctgcgg agggatctcc gtggggcggt gaacgccgat   5220
gattatataa ggacgcgccg ggtgtggcac agctagttcc gtcgcagccg ggatttgggt   5280
cgcggttctt gtttgtggat cgctgtgatc gtcacttggt gagtagcggg ctgctgggct   5340
```

-continued

```
gggtacgtgc gctcggggtt ggcgagtgtg ttttgtgaag ttttttaggc accttttgaa   5400
atgtaatcat ttgggtcaat atgtaatttt cagtgttaga ctagtaaatt gtccgctaaa   5460
ttctggccgt ttttggcttt tttgttagac ggcatgcggg gggggggggg ggcaattggc   5520
caccatgggc cccaagaaga aaaggaaggt ggcccccccc accgacgtga gcctgggcga   5580
cgagctgcac ctggacggcg aggacgtggc catggcccac gccgacgccc tggacgactt   5640
cgacctggac atgctgggcg acggcgacag ccccggcccc ggcttcaccc cccacgacag   5700
cgccccctac ggcgccctgg acatggccga cttcgagttc gagcagatgt tcaccgacgc   5760
cctgggcatc gacgagtacg gcggccatat ggagatgccc gtggacagga ttctggaggc   5820
cgaactcgcc gtggagcaga aaagcgacca gggcgtggag ggccccggcg gaaccggcgg   5880
cagcggcagc agccccaacg accccgtgac caacatctgc caggccgccg acaagcagct   5940
gttcaccctg gtggagtggg ccaagaggat tccccacttc agcagcctgc ccctggacga   6000
ccaggtgatc ctgctgaggg ccggatggaa cgagctgctg atcgccagct tcagccacag   6060
gagcatcgac gtgagggacg gcatcctgct ggccaccggc ctgcacgtcc ataggaacag   6120
cgcccacagc gccggagtgg gcgccatctt cgacagggtg ctgaccgagc tggtgagcaa   6180
gatgagggac atgaggatgg acaagaccga gctgggctgc ctgagggcca tcatcctgtt   6240
caaccccgag gtgaggggcc tgaaaagcgc ccaggaggtg gagctgctga gggagaaggt   6300
gtacgccgcc ctggaggagt acaccaggac cacccacccc gacgagcccg gcagattcgc   6360
caagctgctg ctgaggctgc ccagcctgag gagcatcggc ctgaagtgcc tggagcacct   6420
gttcttcttc aggctgatcg gcgacgtgcc catcgacacc ttcctgatgg agatgctgga   6480
gagccccagc gacagctgag ccggcaactc gctgtagtaa ttccagcgag aggcagaggg   6540
agcgagcggg cggcgggcta gggtggagga gcccggcgag cagagctgcg ctgcgggcgt   6600
cctgggaagg gagatccgga gcgaataggg ggcttcgcct ctggcccagc cctcccgctg   6660
atcccccagc cagcggtgcg caaccctagc cgcatccacg aaactttgcc catagcagcg   6720
ggcgggcact ttgcactgga acttacaaca cccgagcaag gacgcgactc tcccgacgcg   6780
gggaggctat tctgcccatt tggggacact tccccgccgc tgccaggacc cgcttctctg   6840
aaaggctctc cttgcagctg cttagacgct ggattttttt cgggtagtgg aaaaccagca   6900
gcctcccgcg accagatctg ccaccatgaa gctgctgagc agcatcgagc aggcttgcga   6960
catctgcagg ctgaagaagc tgaagtgcag caaggagaag cccaagtgcg ccaagtgcct   7020
gaagaacaac tgggagtgca gatacagccc caagaccaag aggagccccc tgaccagggc   7080
ccacctgacc gaggtggaga gcaggctgga gaggctggag cagctgttcc tgctgatctt   7140
ccccagggag gacctggaca tgatcctgaa gatggacagc ctgcaagaca tcaaggccct   7200
gctgaccggc ctgttcgtgc aggacaacgt gaacaaggac gccgtgaccg acaggctggc   7260
cagcgtggag accgacatgc ccctgaccct gaggcagcac aggatcagcg ccaccagcag   7320
cagcgaggag agcagcaaca agggccagag gcagctgacc gtgagccccg agtttcccgg   7380
gatcaggccc gagtgcgtgg tgcccgagac ccagtgcgcc atgaaaagga aggagaagaa   7440
ggcccagaag gagaaggaca agctgcccgt gagcaccacc accgtcgatg accacatgcc   7500
ccccatcatg cagtgcgagc cccccccccc cgaggccgcc aggattcacg aggtcgtgcc   7560
caggttcctg agcgacaagc tgctggtgac caacaggcag aagaacatcc cccagctgac   7620
cgccaaccag cagttcctga tcgccaggct gatctggtat caggacggct acgagcagcc   7680
cagcgacgag gacctgaaaa ggatcaccca gacctggcag caggccgacg acgagaacga   7740
```

```
ggagagcgac accccccttca ggcagatcac cgagatgacc atcctgaccg tgcagctgat   7800
cgtggagttc gccaagggcc tgcccggatt cgccaagatc agccagcccg accagatcac   7860
cctgctgaag gcttgcagca gcgaggtgat gatgctgagg gtggccagga ggtacgacgc   7920
cgccagcgac agcatcctgt tcgccaacaa ccaggcttac accagggaca actacaggaa   7980
ggctggcatg gccgaggtga tcgaggacct cctgcacttc tgcagatgta tgtacagcat   8040
ggccctggac aacatccact acgccctgct gaccgccgtg gtgatcttca gcgacaggcc   8100
cggcctggag cagccccagc tggtggagga gatccagagg tactacctga acaccctgag   8160
gatctacatc ctgaaccagc tgagcggcag cgccaggagc agcgtgatct acggcaagat   8220
cctgagcatc ctgagcgagc tgaggaccct gggaatgcag aacagcaata tgtgtatcag   8280
cctgaagctg aagaacagga agctgccccc cttcctggag gagatttggg acgtggccga   8340
catgagccac acccagcccc cccccatcct ggagagcccc accaacctgt gaatcgatta   8400
gacatgataa gatacattga tgagtttgga caaaccacaa ctagaatgca gtgaaaaaaa   8460
tgcttaattt gtgaaatttg tgatgctatt gcttaatttg taaccattat aagctgcaat   8520
aaacaagtta ataaaacatt tgcattcatt ttatgtttca ggttcagggg gagatgtggg   8580
aggtttttta aagcaagtaa aacctctaca aatgtggtat ctagagctct tccaaataga   8640
tctggaaggt gctgaggtac gatgagaccc gcaccaggtg cagaccctgc gagtgtggcg   8700
gtaaacatat taggaaccag cctgtgatgc tggatgtgac cgaggagctg aggcccgatc   8760
acttggtgct ggcctgcacc cgcgctgagt ttggctctag cgatgaagat acagattgag   8820
gtactgaaat gtgtgggcgt ggcttaaggg tgggaaagaa tatataaggt gggggtctta   8880
tgtagttttg tatctgtttt gcagcagccg ccgccgccat gagcaccaac tcgtttgatg   8940
gaagcattgt gagctcatat ttgacaacgc gcatgccccc atgggccggg gtgcgtcaga   9000
atgtgatggg ctccagcatt gatggtcgcc ccgtcctgcc cgcaaactct actaccttga   9060
cctacgagac cgtgtctgga acgccgttgg agactgcagc ctccgccgcc gcttcagccg   9120
ctgcagccac cgcccgcggg attgtgactg actttgcttt cctgagcccg cttgcaagca   9180
gtgcagcttc ccgttcatcc gcccgcgatg acaagttgac ggctcttttg gcacaattgg   9240
attctttgac ccgggaactt aatgtcgttt ctcagcagct gttggatctg cgccagcagg   9300
tttctgccct gaaggcttcc tcccctccca atgcggttta aaacataaat aaaaaaccag   9360
actctgtttg gatttggatc aagcaagtgt cttgctgtct ttatttaggg gttttgcgcg   9420
cgcggtaggc ccgggaccag cggtctcggt cgttgagggt cctgtgtatt ttttccagga   9480
cgtggtaaag gtgactctgg atgttcagat acatgggcat aagcccgtct ctggggtgga   9540
ggtagcacca ctgcagagct tcatgctgcg gggtggtgtt gtagatgatc cagtcgtagc   9600
aggagcgctg ggcgtggtgc ctaaaaatgt ctttcagtag caagctgatt gccaggggca   9660
ggcccttggt gtaagtgttt acaaagcggt taagctggga tgggtgcata cgtggggata   9720
tgagatgcat cttggactgt atttttaggt tggctatgtt cccagccata tccctccggg   9780
gattcatgtt gtgcagaacc accagcacag tgtatccggt gcacttggga aatttgtcat   9840
gtagcttaga aggaaatgcg tggaagaact tggagacgcc cttgtgacct ccaagatttt   9900
ccatgcattc gtccataatg atggcaatgg gcccacgggc ggcggcctgg gcgaagatat   9960
ttctgggatc actaacgtca tagttgtgtt ccaggatgag atcgtcatag gccattttta  10020
caaagcgcgg gcggagggtg ccagactgcg gtataatggt tccatccggc ccaggggcgt  10080
```

-continued

```
agttaccctc acagatttgc atttcccacg ctttgagttc agatgggggg atcatgtcta  10140
cctgcggggc gatgaagaaa acggtttccg ggtaggggga gatcagctgg gaagaaagca  10200
ggttcctgag cagctgcgac ttaccgcagc cggtgggccc gtaaatcaca cctattaccg  10260
ggtgcaactg gtagttaaga gagctgcagc tgccgtcatc cctgagcagg ggggccactt  10320
cgttaagcat gtccctgact cgcatgtttt ccctgaccaa atccgccaga aggcgctcgc  10380
cgcccagcga tagcagttct tgcaaggaag caaagttttt caacggtttg agaccgtccg  10440
ccgtaggcat gcttttgagc gtttgaccaa gcagttccag gcggtcccac agctcggtca  10500
cctgctctac ggcatctcga tccagcatat ctcctcgttt cgcgggttgg ggcggctttc  10560
gctgtacggc agtagtcggt gctcgtccag acgggccagg gtcatgtctt tccacgggcg  10620
cagggtcctc gtcagcgtag tctgggtcac ggtgaagggg tgcgctccgg gctgcgcgct  10680
ggccagggtg cgcttgaggc tggtcctgct ggtgctgaag cgctgccggt cttcgccctg  10740
cgcgtcggcc aggtagcatt tgaccatggt gtcatagtcc agcccctccg cggcgtggcc  10800
cttggcgcgc agcttgccct tggaggaggc gccgcacgag gggcagtgca gacttttgag  10860
ggcgtagagc ttgggcgcga gaaataccga ttccggggag taggcatccg cgccgcaggc  10920
cccgcagacg gtctcgcatt ccacgagcca ggtgagctct ggccgttcgg ggtcaaaaac  10980
caggtttccc ccatgctttt tgatgcgttt cttacctctg gtttccatga gccggtgtcc  11040
acgctcggtg acgaaaaggc tgtccgtgtc cccgtataca gacttgagag gcctgtcctc  11100
gaccgatgcc cttgagagcc ttcaacccag tcagctcctt ccggtgggcg cggggcatga  11160
ctatcgtcgc cgcacttatg actgtcttct ttatcatgca actcgtagga caggtgccgg  11220
cagcgctctg ggtcattttc ggcgaggacc gctttcgctg gagcgcgacg atgatcggcc  11280
tgtcgcttgc ggtattcgga atcttgcacg ccctcgctca agccttcgtc actggtcccg  11340
ccaccaaacg tttcggcgag aagcaggcca ttatcgccgg catggcggcc gacgcgctgg  11400
gctacgtctt gctggcgttc gcgacgcgag gctggatggc cttccccatt atgattcttc  11460
tcgcttccgg cggcatcggg atgcccgcgt tgcaggccat gctgtccagg caggtagatg  11520
acgaccatca gggacagctt caaggccagc aaaaggccag gaaccgtaaa aaggccgcgt  11580
tgctggcgtt tttccatagg ctccgccccc ctgacgagca tcacaaaaat cgacgctcaa  11640
gtcagaggtg gcgaaacccg acaggactat aaagatacca ggcgtttccc cctggaagct  11700
ccctcgtgcg ctctcctgtt ccgaccctgc cgcttaccgg atacctgtcc gcctttctcc  11760
cttcgggaag cgtggcgctt tctcatagct cacgctgtag gtatctcagt tcggtgtagg  11820
tcgttcgctc caagctgggc tgtgtgcacg aaccccccgt tcagcccgac cgctgcgcct  11880
tatccggtaa ctatcgtctt gagtccaacc cggtaagaca cgacttatcg ccactggcag  11940
cagccactgg taacaggatt agcagagcga ggtatgtagg cggtgctaca gagttcttga  12000
agtggtggcc taactacggc tacactagaa ggacagtatt tggtatctgc gctctgctga  12060
agccagttac cttcggaaaa agagttggta gctcttgatc cggcaaacaa accaccgctg  12120
gtagcggtgg tttttttgtt tgcaagcagc agattacgcg cagaaaaaaa ggatctcaag  12180
aagatccttt gatcttttct acggggtctg acgctcagtg gaacgaaaac tcacgttaag  12240
ggattttggt catgagatta tcaaaaagga tcttcaccta gatcctttta aattaaaaat  12300
gaagttttaa atcaatctaa agtatatatg agtaaacttg gtctgacagt taccaatgct  12360
taatcagtga ggcacctatc tcagcgatct gtctatttcg ttcatccata gttgcctgac  12420
tccccgtcgt gtagataact acgatacggg agggcttacc atctggcccc agtgctgcaa  12480
```

```
tgataccgcg agacccacgc tcaccggctc cagatttatc agcaataaac cagccagccg  12540
gaagggccga gcgcagaagt ggtcctgcaa ctttatccgc ctccatccag tctattaatt  12600
gttgccggga agctagagta agtagttcgc cagttaatag tttgcgcaac gttgttgcca  12660
ttgctgcagg catcgtggtg tcacgctcgt cgtttggtat ggcttcattc agctccggtt  12720
cccaacgatc aaggcgagtt acatgatccc ccatgttgtg caaaaaagcg gttagctcct  12780
tcggtcctcc gatcgttgtc agaagtaagt tggccgcagt gttatcactc atggttatgg  12840
cagcactgca taattctctt actgtcatgc catccgtaag atgcttttct gtgactggtg  12900
agtactcaac caagtcattc tgagaatagt gtatgcggcg accgagttgc tcttgcccgg  12960
cgtcaacacg ggataatacc gcgccacata gcagaacttt aaaagtgctc atcattggaa  13020
aacgttcttc ggggcgaaaa ctctcaagga tcttaccgct gttgagatcc agttcgatgt  13080
aacccactcg tgcacccaac tgatcttcag catcttttac tttcaccagc gtttctgggt  13140
gagcaaaaac aggaaggcaa aatgccgcaa aaaagggaat aagggcgaca cggaaatgtt  13200
gaatactcat actcttcctt tttcaatatt attgaagcat ttatcagggt tattgtctca  13260
tgagcggata catatttgaa tgtatttaga aaaa                              13294
```

<210> SEQ ID NO 2
<211> LENGTH: 13333
<212> TYPE: DNA
<213> ORGANISM: Artificial Sequence
<220> FEATURE:
<223> OTHER INFORMATION: Synthetic hIL-12 and hIL-21

<400> SEQUENCE: 2

```
taaacaaata ggggttccgc gcacatttcc ccgaaaagtg ccacctgacg tctaagaaac     60
cattattatc atgacattaa cctataaaaa taggcgtatc acgaggccct ttcgtcttca    120
attaatcgca ccggtatcta tgtcgggtgc ggagaaagag gtaatgaaat ggcagctagc    180
atcatcaata atatacctta ttttggattg aagccaatat gataatgagg gggtggagtt    240
tgtgacgtgg cgcggggcgt gggaacgggg cgggtgacgt agtagtgtgg cggaagtgtg    300
atgttgcaag tgtggcggaa cacatgtaag cgacggatgt ggcaaaagtg acgtttttgg    360
tgtgcgccgg tgtacacagg aagtgacaat tttcgcgcgg ttttaggcgg atgttgtagt    420
aaatttgggc gtaaccgagt aagatttggc cattttcgcg ggaaaactga ataagaggaa    480
gtgaaatctg aataattttg tgttactcat agcgcgtaat atttgtctag ggagatccgg    540
taccgatatc ctagacaacg atgctgagct aactataacg gtcctaaggt agcgaccgcg    600
gagactaggt gtatttatct aagcgatcgc ttaattaagg ccggccgccg caataaaata    660
tctttatttt cattacatct gtgtgttggt tttttgtgtg aatccatagt actaacatac    720
gctctccatc aaaacaaaac gaaacaaaac aaactagcaa aataggctgt ccccagtgca    780
agtccaggtg ccagaacatt tctctatcca taatgcaggg gtaccgggtg atgacggtga    840
aaacctccaa ttgcggagta ctgtcctccg agcggagtac tgtcctccga gcggagtact    900
gtcctccgag cggagtactg tcctccgagc ggagtactgt cctccgagcg gagtactgtc    960
ctccgagcgg agagtccccg gggacctaga gggtatataa tgggtgcctt agctggtgtg   1020
tgacctcatc ttcctgtacg cccctgcagg ggcgcgccac gcgtcgaaga aggtgagtaa   1080
tcttaacatg ctcttttttt ttttttttgc taatcccttt tgtgtgctga tgttaggatg   1140
acatttacaa caaatgtttg ttcctgacag gaaaaacctt gctgggtacc ttcgttgccg   1200
```

-continued

```
gacacttctt gtcctctact ttggaaaaaa ggaattgaga gccgctagcc caccatgggt   1260
caccagcagt tggtcatctc ttggttttcc ctggtttttc tggcatctcc cctcgtggcc   1320
atatgggaac tgaagaaaga tgtttatgtc gtagaattgg attggtatcc ggatgcccct   1380
ggagaaatgg tggtcctcac ctgtgacacc cctgaagaag atggtatcac ctggaccttg   1440
gaccagagca gtgaggtctt aggctctggc aaaaccctga ccatccaagt caaagagttt   1500
ggagatgctg gccagtacac ctgtcacaaa ggaggcgagg ttctaagcca ttcgctcctg   1560
ctgcttcaca aaaaggaaga tggaatttgg tccactgata ttttaaagga ccagaaagaa   1620
cccaaaaata agacctttct aagatgcgag gccaagaatt attctggacg tttcacctgc   1680
tggtggctga cgacaatcag tactgatttg acattcagtg tcaaaagcag cagaggctct   1740
tctgaccccc aaggggtgac gtgcggagct gctacactct ctgcagagag agtcagaggg   1800
gacaacaagg agtatgagta ctcagtggag tgccaggagg acagtgcctg cccagctgct   1860
gaggagagtc tgcccattga ggtcatggtg gatgccgttc acaagctcaa gtatgaaaac   1920
tacaccagca gcttcttcat cagggacatc atcaaacctg acccacccaa gaacttgcag   1980
ctgaagccat taaagaattc tcggcaggtg gaggtcagct gggagtaccc tgacacctgg   2040
agtactccac attcctactt ctccctgaca ttctgcgttc aggtccaggg caagagcaag   2100
agagaaaaga aagatagagt cttcacggac aagacctcag ccacggtcat ctgccgcaaa   2160
aatgccagca ttagcgtgcg ggcccaggac cgctactata gctcatcttg gagcgaatgg   2220
gcatctgtgc cctgcagtta gatcgattgc gcaaagctcc ccctctccct cccccccccc   2280
taacgttact ggccgaagcc gcttggaata aggccggtgt gcgtttgtct atatgttatt   2340
ttccaccata ttgccgtctt ttggcaatgt gagggcccgg aaacctggcc ctgtcttctt   2400
gacgagcatt cctaggggtc tttcccctct cgccaaagga atgcaaggtc tgttgaatgt   2460
cgtgaaggaa gcagttcctc tggaagcttc ttgaagacaa acaacgtctg tagcgaccct   2520
ttgcaggcag cggaaccccc cacctggcga caggtgcctc tgcggccaaa agccacgtgt   2580
ataagataca cctgcaaagg cggcacaacc ccagtgccac gttgtgagtt ggatagttgt   2640
ggaaagagtc aaatggctct cctcaagcgt attcaacaag gggctgaagg atgcccagaa   2700
ggtaccccat tgtatgggat ctgatctggg gcctcggtgc acatgcttta catgtgttta   2760
gtcgaggtta aaaaacgtct aggccccccg aaccacgggg acgtggtttt cctttgaaaa   2820
acacgatctc ttaagtctag cgccaccatg ggtccagcgc gcagcctcct ccttgtggct   2880
accctggtcc tcctggacca cctcagtttg gccagaaacc tccccgtggc cactccagac   2940
ccaggaatgt tcccatgcct tcaccactcc caaaacctgc tgagggccgt cagcaacatg   3000
ctccagaagg ccagacaaac tctagaattt tacccttgca cttctgaaga gattgatcat   3060
gaagatatca caaaagataa aaccagcaca gtggaggcct gtttaccatt ggaattaacc   3120
aagaatgaga gttgcctaaa ttccagagag acctctttca taactaatgg gagttgcctg   3180
gcctccagaa agacctcttt tatgatggcc ctgtgcctta gtagtattta tgaagacttg   3240
aagatgtacc aggtggagtt caagaccatg aatgcaaagc ttctgatgga tcctaagagg   3300
cagatctttc tagatcaaaa catgctggca gttattgatg agctgatgca ggccctgaat   3360
ttcaacagtg agactgtgcc acaaaaatcc tcccttgaag aaccggattt ttataaaact   3420
aaaatcaagc tctgcatact tcttcatgct ttcagaattc gggcagtgac tattgataga   3480
gtgatgagct atctgaatgc ttcctaaatc gaatgcgcac tcgagtggta ttacgctcaa   3540
cttcagaatc tcactaaaag aatagatagt cttcctttaa ctgaaaattt ttccttacaa   3600
```

-continued acagatatgg acgtcactag caccaccatg agaagcagcc ccggcaacat ggagagaatc 3660
gtgatctgcc tgatggtgat cttcctgggc accctggtgc ataagagcag cagccagggc 3720
caggacagac acatgatccg catgagacag ctgatcgaca tcgtggacca gctgaagaac 3780
tacgtgaacg acctggtgcc cgagttcctg cccgcccccg aggacgtgga gaccaactgc 3840
gagtggagcg ccttcagctg cttccagaag gcccagctga agtccgccaa caccggcaac 3900
aacgagagaa tcatcaacgt gagcatcaag aagctgaagc ggaagccccc cagcaccaac 3960
gccggaagaa gacagaagca cagactgacc tgtcccagct gcgacagcta cgagaagaag 4020
ccccccaagg agttcctgga gagattcaag agcctgctgc aaaagatgat ccaccagcac 4080
ctgagcagca gaacccacgg cagcgaggac agctgaatcg cctgcgcagc atgctcgcga 4140
cctaagtcgg ccgctaaagt ttacgtagcg gccgcgtcga cgatagcttg atgggtggca 4200
tccctgtgac ccctccccag tgcctctcct ggccctggaa gttgccactc cagtgcccac 4260
cagccttgtc ctaataaaat taagttgcat cattttgtct gactaggtgt ccttctataa 4320
tattatgggg tggagggggg tggtatggag caaggggcaa gttgggaaga caacctgtag 4380
ggcctgcggg gtctattggg aaccaagctg gagtgcagtg gcacaatctt ggctcactgc 4440
aatctccgcc tcctgggttc aagcgattct cctgcctcag cctcccgagt tgttgggatt 4500
ccaggcatgc atgaccaggc tcagctaatt tttgtttttt tggtagagac ggggtttcac 4560
catattggcc aggctggtct ccaactccta atctcaggtg atctacccac cttggcctcc 4620
caaattgctg ggattacagg cgtgaaccac tgctcccttc cctgtccttc tgattttaaa 4680
ataactatac cagcaggagg acgtccagac acagcatagg ctacctggcc atgcccaacc 4740
ggtgggacat ttgagttgct tgcttggcac tgtcctctca tgcgttgggt ccactcagta 4800
gatgcctgtt gaattctgat ttaaatcggt ccgcgtacgg cgtggtaggt ccgaacgaat 4860
ccatggatta ccctgttatc cctatccgga gttaacctcg aggacttcgg aacttctaga 4920
accagaccgt tcagtttaaa cgctcttctc cccctcgagg gcctccgcgc cgggttttgg 4980
cgcctcccgc gggcgccccc ctcctcacgg cgagcgctgc cacgtcagac gaagggcgca 5040
gcgagcgtcc tgatccttcc gcccggacgc tcaggacagc ggcccgctgc tcataagact 5100
cggccttaga accccagtat cagcagaagg acattttagg acgggacttg ggtgactcta 5160
gggcactggt tttctttcca gagagcggaa caggcgagga aaagtagtcc cttctcggcg 5220
attctgcgga gggatctccg tggggcggtg aacgccgatg attatataag gacgcgccgg 5280
gtgtggcaca gctagttccg tcgcagccgg gatttgggtc gcggttcttg tttgtggatc 5340
gctgtgatcg tcacttggtg agtagcgggc tgctgggctg ggtacgtgcg ctcggggttg 5400
gcgagtgtgt tttgtgaagt tttttaggca ccttttgaaa tgtaatcatt tgggtcaata 5460
tgtaattttc agtgttagac tagtaaattg tccgctaaat tctggccgtt tttggctttt 5520
ttgttagacg gcatgcgggg gggggggggg gcaattggcc accatgggcc ccaagaagaa 5580
aaggaaggtg gccccccccca ccgacgtgag cctgggcgac gagctgcacc tggacggcga 5640
ggacgtggcc atggcccacg ccgacgccct ggacgacttc gacctggaca tgctgggcga 5700
cggcgacagc cccggccccg gcttcacccc ccacgacagc gccccctacg gcgccctgga 5760
catggccgac ttcgagttcg agcagatgtt caccgacgcc ctgggcatcg acgagtacgg 5820
cggccatatg gagatgcccg tggacaggat tctggaggcc gaactcgccg tggagcagaa 5880
aagcgaccag ggcgtggagg gccccggcgg aaccggcggc agcggcagca gccccaacga 5940

-continued ccccgtgacc aacatctgcc aggccgccga caagcagctg ttcaccctgg tggagtgggc 6000
caagaggatt ccccacttca gcagcctgcc cctggacgac caggtgatcc tgctgagggc 6060
cggatggaac gagctgctga tcgccagctt cagccacagg agcatcgacg tgagggacgg 6120
catcctgctg gccaccggcc tgcacgtcca taggaacagc gcccacagcg ccggagtggg 6180
cgccatcttc gacagggtgc tgaccgagct ggtgagcaag atgagggaca tgaggatgga 6240
caagaccgag ctgggctgcc tgagggccat catcctgttc aaccccgagg tgaggggcct 6300
gaaaagcgcc caggaggtgg agctgctgag ggagaaggtg tacgccgccc tggaggagta 6360
caccaggacc acccaccccg acgagcccgg cagattcgcc aagctgctgc tgaggctgcc 6420
cagcctgagg agcatcggcc tgaagtgcct ggagcacctg ttcttcttca ggctgatcgg 6480
cgacgtgccc atcgacacct tcctgatgga gatgctggag agccccagcg acagctgagc 6540
cggcaactcg ctgtagtaat tccagcgaga ggcagaggga gcgagcgggc ggcgggctag 6600
ggtggaggag cccggcgagc agagctgcgc tgcgggcgtc ctgggaaggg agatccggag 6660
cgaatagggg gcttcgcctc tggcccagcc ctcccgctga tcccccagcc agcggtgcgc 6720
aaccctagcc gcatccacga aactttgccc atagcagcgg gcgggcactt tgcactggaa 6780
cttacaacac ccgagcaagg acgcgactct cccgacgcgg ggaggctatt ctgcccattt 6840
ggggacactt ccccgccgct gccaggaccc gcttctctga aaggctctcc ttgcagctgc 6900
ttagacgctg gattttttc gggtagtgga aaaccagcag cctcccgcga ccagatctgc 6960
caccatgaag ctgctgagca gcatcgagca ggcttgcgac atctgcaggc tgaagaagct 7020
gaagtgcagc aaggagaagc ccaagtgcgc caagtgcctg aagaacaact gggagtgcag 7080
atacagcccc aagaccaaga ggagcccct gaccagggcc cacctgaccg aggtggagag 7140
caggctggag aggctggagc agctgttcct gctgatcttc cccagggagg acctggacat 7200
gatcctgaag atggacagcc tgcaagacat caaggccctg ctgaccggcc tgttcgtgca 7260
ggacaacgtg aacaaggacg ccgtgaccga caggctggcc agcgtggaga ccgacatgcc 7320
cctgaccctg aggcagcaca ggatcagcgc caccagcagc agcgaggaga gcagcaacaa 7380
gggccagagg cagctgaccg tgagccccga gtttcccggg atcaggcccg agtgcgtggt 7440
gcccgagacc cagtgcgcca tgaaaaggaa ggagaagaag gcccagaagg agaaggacaa 7500
gctgcccgtg agcaccacca ccgtcgatga ccacatgccc cccatcatgc agtgcgagcc 7560 ccccccccc gaggccgcca ggattcacga ggtcgtgccc aggttcctga gcgacaagct 7620
gctggtgacc aacaggcaga agaacatccc ccagctgacc gccaaccagc agttcctgat 7680
cgccaggctg atctggtatc aggacggcta cgagcagccc agcgacgagg acctgaaaag 7740
gatcacccag acctggcagc aggccgacga cgagaacgag gagagcgaca ccccccttcag 7800 gcagatcacc gagatgacca tcctgaccgt gcagctgatc gtggagttcg ccaagggcct 7860
gcccggattc gccaagatca gccagcccga ccagatcacc ctgctgaagg cttgcagcag 7920
cgaggtgatg atgctgaggg tggccaggag gtacgacgcc gccagcgaca gcatcctgtt 7980
cgccaacaac caggcttaca ccagggacaa ctacaggaag gctggcatgg ccgaggtgat 8040
cgaggacctc ctgcacttct gcagatgtat gtacagcatg gccctggaca acatccacta 8100
cgccctgctg accgccgtgg tgatcttcag cgacaggccc ggcctggagc agccccagct 8160
ggtggaggag atccagaggt actacctgaa caccctgagg atctacatcc tgaaccagct 8220
gagcggcagc gccaggagca gcgtgatcta cggcaagatc ctgagcatcc tgagcgagct 8280
gaggaccctg ggaatgcaga acagcaatat gtgtatcagc ctgaagctga agaacaggaa 8340

-continued

```
gctgcccccc ttcctggagg agatttggga cgtggccgac atgagccaca cccagccccc   8400
ccccatcctg gagagcccca ccaacctgtg aatcgattag acatgataag atacattgat   8460
gagtttggac aaaccacaac tagaatgcag tgaaaaaaat gcttaatttg tgaaatttgt   8520
gatgctattg cttaatttgt aaccattata agctgcaata aacaagttaa taaaacattt   8580
gcattcattt tatgtttcag gttcaggggg agatgtggga ggttttttaa agcaagtaaa   8640
acctctacaa atgtggtatc tagagctctt ccaaatagat ctggaaggtg ctgaggtacg   8700
atgagacccg caccaggtgc agaccctgcg agtgtggcgg taaacatatt aggaaccagc   8760
ctgtgatgct ggatgtgacc gaggagctga ggcccgatca cttggtgctg gcctgcaccc   8820
gcgctgagtt tggctctagc gatgaagata cagattgagg tactgaaatg tgtgggcgtg   8880
gcttaagggt gggaaagaat atataaggtg ggggtcttat gtagttttgt atctgttttg   8940
cagcagccgc cgccgccatg agcaccaact cgtttgatgg aagcattgtg agctcatatt   9000
tgacaacgcg catgccccca tgggccgggg tgcgtcagaa tgtgatgggc tccagcattg   9060
atggtcgccc cgtcctgccc gcaaactcta ctaccttgac ctacgagacc gtgtctggaa   9120
cgccgttgga gactgcagcc tccgccgccg cttcagccgc tgcagccacc gcccgcggga   9180
ttgtgactga ctttgctttc ctgagcccgc ttgcaagcag tgcagcttcc cgttcatccg   9240
cccgcgatga caagttgacg gctcttttgg cacaattgga ttctttgacc cgggaactta   9300
atgtcgtttc tcagcagctg ttggatctgc gccagcaggt ttctgccctg aaggcttcct   9360
cccctcccaa tgcggtttaa aacataaata aaaaaccaga ctctgtttgg atttggatca   9420
agcaagtgtc ttgctgtctt tatttagggg ttttgcgcgc gcggtaggcc cgggaccagc   9480
ggtctcggtc gttgagggtc ctgtgtattt tttccaggac gtggtaaagg tgactctgga   9540
tgttcagata catgggcata agcccgtctc tggggtggag gtagcaccac tgcagagctt   9600
catgctgcgg ggtggtgttg tagatgatcc agtcgtagca ggagcgctgg gcgtggtgcc   9660
taaaaatgtc tttcagtagc aagctgattg ccaggggcag gcccttggtg taagtgttta   9720
caaagcggtt aagctgggat gggtgcatac gtggggatat gagatgcatc ttggactgta   9780
tttttaggtt ggctatgttc ccagccatat ccctccgggg attcatgttg tgcagaacca   9840
ccagcacagt gtatccggtg cacttgggaa atttgtcatg tagcttagaa ggaaatgcgt   9900
ggaagaactt ggagacgccc ttgtgacctc caagattttc catgcattcg tccataatga   9960
tggcaatggg cccacgggcg gcggcctggg cgaagatatt tctgggatca ctaacgtcat  10020
agttgtgttc caggatgaga tcgtcatagg ccatttttac aaagcgcggg cggagggtgc  10080
cagactgcgg tataatggtt ccatccggcc caggggcgta gttaccctca cagatttgca  10140
tttcccacgc tttgagttca gatgggggga tcatgtctac ctgcggggcg atgaagaaaa  10200
cggtttccgg ggtaggggag atcagctggg aagaaagcag gttcctgagc agctgcgact  10260
taccgcagcc ggtgggcccg taaatcacac ctattaccgg gtgcaactgg tagttaagag  10320
agctgcagct gccgtcatcc ctgagcaggg gggccacttc gttaagcatg tccctgactc  10380
gcatgttttc cctgaccaaa tccgccagaa ggcgctcgcc gcccagcgat agcagttctt  10440
gcaaggaagc aaagtttttc aacggtttga gaccgtccgc cgtaggcatg cttttgagcg  10500
tttgaccaag cagttccagg cggtcccaca gctcggtcac ctgctctacg gcatctcgat  10560
ccagcatatc tcctcgtttc gcgggttggg gcggctttcg ctgtacggca gtagtcggtg  10620
ctcgtccaga cgggccaggg tcatgtcttt ccacgggcgc agggtcctcg tcagcgtagt  10680
```

-continued

```
ctgggtcacg gtgaaggggt gcgctccggg ctgcgcgctg gccagggtgc gcttgaggct 10740
ggtcctgctg gtgctgaagc gctgccggtc ttcgccctgc gcgtcggcca ggtagcattt 10800
gaccatggtg tcatagtcca gcccctccgc ggcgtggccc ttggcgcgca gcttgccctt 10860
ggaggaggcg ccgcacgagg ggcagtgcag acttttgagg gcgtagagct tgggcgcgag 10920
aaataccgat tccggggagt aggcatccgc gccgcaggcc ccgcagacgg tctcgcattc 10980
cacgagccag gtgagctctg gccgttcggg gtcaaaaacc aggtttcccc catgcttttt 11040
gatgcgtttc ttacctctgg tttccatgag ccggtgtcca cgctcggtga cgaaaaggct 11100
gtccgtgtcc ccgtatacag acttgagagg cctgtcctcg accgatgccc ttgagagcct 11160
tcaacccagt cagctccttc cggtgggcgc ggggcatgac tatcgtcgcc gcacttatga 11220
ctgtcttctt tatcatgcaa ctcgtaggac aggtgccggc agcgctctgg gtcattttcg 11280
gcgaggaccg ctttcgctgg agcgcgacga tgatcggcct gtcgcttgcg gtattcggaa 11340
tcttgcacgc cctcgctcaa gccttcgtca ctggtcccgc caccaaacgt ttcggcgaga 11400
agcaggccat tatcgccggc atggcggccg acgcgctggg ctacgtcttg ctggcgttcg 11460
cgacgcgagg ctggatggcc ttccccatta tgattcttct cgcttccggc ggcatcggga 11520
tgcccgcgtt gcaggccatg ctgtccaggc aggtagatga cgaccatcag ggacagcttc 11580
aaggccagca aaaggccagg aaccgtaaaa aggccgcgtt gctggcgttt ttccataggc 11640
tccgcccccc tgacgagcat cacaaaaatc gacgctcaag tcagaggtgg cgaaacccga 11700
caggactata aagataccag gcgtttcccc ctggaagctc cctcgtgcgc tctcctgttc 11760
cgaccctgcc gcttaccgga tacctgtccg cctttctccc ttcgggaagc gtggcgcttt 11820
ctcatagctc acgctgtagg tatctcagtt cggtgtaggt cgttcgctcc aagctgggct 11880
gtgtgcacga accccccgtt cagcccgacc gctgcgcctt atccggtaac tatcgtcttg 11940
agtccaaccc ggtaagacac gacttatcgc cactggcagc agccactggt aacaggatta 12000
gcagagcgag gtatgtaggc ggtgctacag agttcttgaa gtggtggcct aactacggct 12060
acactagaag gacagtattt ggtatctgcg ctctgctgaa gccagttacc ttcggaaaaa 12120
gagttggtag ctcttgatcc ggcaaacaaa ccaccgctgg tagcggtggt ttttttgttt 12180
gcaagcagca gattacgcgc agaaaaaaag gatctcaaga agatcctttg atcttttcta 12240
cggggtctga cgctcagtgg aacgaaaact cacgttaagg gattttggtc atgagattat 12300
caaaaaggat cttcacctag atccttttaa attaaaaatg aagttttaaa tcaatctaaa 12360
gtatatatga gtaaacttgg tctgacagtt accaatgctt aatcagtgag gcacctatct 12420
cagcgatctg tctatttcgt tcatccatag ttgcctgact ccccgtcgtg tagataacta 12480
cgatacggga gggcttacca tctggcccca gtgctgcaat gataccgcga gacccacgct 12540
caccggctcc agatttatca gcaataaacc agccagccgg aagggccgag cgcagaagtg 12600
gtcctgcaac tttatccgcc tccatccagt ctattaattg ttgccgggaa gctagagtaa 12660
gtagttcgcc agttaatagt ttgcgcaacg ttgttgccat tgctgcaggc atcgtggtgt 12720
cacgctcgtc gtttggtatg gcttcattca gctccggttc ccaacgatca aggcgagtta 12780
catgatcccc catgttgtgc aaaaaagcgg ttagctcctt cggtcctccg atcgttgtca 12840
gaagtaagtt ggccgcagtg ttatcactca tggttatggc agcactgcat aattctctta 12900
ctgtcatgcc atccgtaaga tgcttttctg tgactggtga gtactcaacc aagtcattct 12960
gagaatagtg tatgcggcga ccgagttgct cttgcccggc gtcaacacgg gataataccg 13020
cgccacatag cagaacttta aaagtgctca tcattggaaa acgttcttcg gggcgaaaac 13080
```

tctcaaggat cttaccgctg ttgagatcca gttcgatgta acccactcgt gcacccaact 13140
gatcttcagc atcttttact ttcaccagcg tttctgggtg agcaaaaaca ggaaggcaaa 13200
atgccgcaaa aaagggaata agggcgacac ggaaatgttg aatactcata ctcttccttt 13260
ttcaatatta ttgaagcatt tatcagggtt attgtctcat gagcggatac atatttgaat 13320
gtatttagaa aaa 13333

<210> SEQ ID NO 3
<211> LENGTH: 11553
<212> TYPE: DNA
<213> ORGANISM: Artificial Sequence
<220> FEATURE:
<223> OTHER INFORMATION: Synthetic mIL-21 and mIL-15

<400> SEQUENCE: 3
taaacaaata ggggttccgc gcacatttcc ccgaaaagtg ccacctgacg tctaagaaac 60
cattattatc atgacattaa cctataaaaa taggcgtatc acgaggccct ttcgtcttca 120
attaatcgca ccggtatcta tgtcgggtgc ggagaaagag gtaatgaaat ggcagctagc 180
atcatcaata atatacctta ttttggattg aagccaatat gataatgagg gggtggagtt 240
tgtgacgtgg cgcggggcgt gggaacgggg cgggtgacgt agtagtgtgg cggaagtgtg 300
atgttgcaag tgtggcggaa cacatgtaag cgacggatgt ggcaaaagtg acgtttttgg 360
tgtgcgccgg tgtacacagg aagtgacaat tttcgcgcgg ttttaggcgg atgttgtagt 420
aaatttgggc gtaaccgagt aagatttggc cattttcgcg ggaaaactga ataagaggaa 480
gtgaaatctg aataattttg tgttactcat agcgcgtaat atttgtctag ggagatccgg 540
taccgatatc ctagacaacg atgctgagct aactataacg gtcctaaggt agcgaccgcg 600
gagactaggt gtatttatct aagcgatcgc ttaattaagg ccggccgccg caataaaata 660
tctttatttt cattacatct gtgtgttggt tttttgtgtg aatcgatagt actaacatac 720
gctctccatc aaaacaaaac gaaacaaaac aaactagcaa aataggctgt ccccagtgca 780
agtgcaggtg ccagaacatt tctctatcga taatgcaggt cggagtactg tcctccgagc 840
ggagtactgt cctccgagcg gagtactgtc ctccgagcgg agtactgtcc tccgagcgga 900
gtactgtcct ccgagcggag tactgtcctc cgagcggaga ctcttcgaag gaagaggggc 960
ggggtcgatc gaccccgccc ctcttccttc gaaggaagag ggcggggtc gaagacctag 1020 agggtatata atgggtgcct tagctggtgt gtgagctcat cttcctgtag atcacgcgtc 1080
gaagaaggtg agtaatctta acatgctctt tttttttttt tttgctaatc ccttttgtgt 1140
gctgatgtta ggatgacatt tacaacaaat gtttgttcct gacaggaaaa accttgctgg 1200
gtaccttcgt tgccggacac ttcttgtcct ctactttgga aaaaaggaat tgagagccgc 1260
tagcgccacc atggagagga ccctggtgtg cctggtggtg atcttcctgg gcaccgtggc 1320
ccacaagagc agcccccagg gacccgacag gctgctgatc cggctgagac acctgatcga 1380
catcgtggag cagctgaaga tttacgagaa cgacctggac cccgagctgc tgtccgcccc 1440
ccaggacgtg aagggccact gcgagcacgc cgccttcgcc tgcttccaga aggccaagct 1500
gaagcccagc aaccccggca acaacaagac cttcatcatc gacctggtgg cccagctgag 1560
aaggaggctg cccgccagga ggggcggcaa gaagcagaag cacatcgcca agtgccccag 1620
ctgcgacagc tacgagaagc ggacccccaa ggagttcctg gagaggctga agtggctgct 1680
gcaaaagatg atccaccagc acctgagctg agttgggcga gctcgaattc attgatcccc 1740

-continued

```
cgggctgcag gaattcgata tcaagctcgg gatccgaatt ccgccccccc cccccccccc   1800
cccctaacgt tactggccga agccgcttgg aataaggccg gtgtgcgttt gtctatatgt   1860
tattttccac catattgccg tcttttggca atgtgagggc ccggaaacct ggccctgtct   1920
tcttgacgag cattcctagg ggtctttccc ctctcgccaa aggaatgcaa ggtctgttga   1980
atgtcgtgaa ggaagcagtt cctctggaag cttcttgaag acaaacaacg tctgtagcga   2040
ccctttgcag gcagcggaac cccccacctg gcgacaggtg cctctgcggc caaaagccac   2100
gtgtataaga tacacctgca aaggcggcac aaccccagtg ccacgttgtg agttggatag   2160
ttgtggaaag agtcaaatgg ctctcctcaa gcgtattcaa caaggggctg aaggatgccc   2220
agaaggtacc ccattgtatg ggatctgatc tggggcctcg gtgcacatgc tttacatgtg   2280
tttagtcgag gttaaaaaaa cgtctaggcc ccccgaacca cggggacgtg gttttccttt   2340
gaaaaacacg atgataatat ggccacaacc atgaagatcc tgaagcccta catgaggaac   2400
accagcatca gctgttacct gtgcttcctg ctgaacagcc acttcctgac cgaggccgga   2460
atccacgtct tcatcctggg ctgcgtgagc gtgggcctgc ccaagaccga ggccaactgg   2520
atcgacgtga ggtacgacct ggagaagatc gagagcctga tccagagcat ccacatcgac   2580
accaccctgt acaccgacag cgacttccac cccagctgca aggtgaccgc catgaactgc   2640
ttcctgctgg agctgcaagt gatcctgcac gagtacagca acatgaccct gaacgagacc   2700
gtgaggaacg tgctgtacct ggctaacagc accctgagca gcaacaagaa cgtggccgag   2760
agcggctgca aggagtgtga ggagctggag gagaagacct tcaccgagtt cctccagagc   2820
ttcatcagga tcgtgcagat gttcatcaac accagctgaa tcgattgcgc aaagctttcg   2880
cgataggcga gaccaatggg tgtgtacgta gcggccgctc gagaacttgt ttattgcagc   2940
ttataatggt tacaaataaa gcaatagcat cacaaatttc acaaataaag cattttttc    3000
actgcattct agttgtggtt tgtccaaact catcaatgta tcttatcatg tctcgtacgg   3060
cgtggtaggt ccgaacgaat ccatggatta ccctgttatc cctatccgga gttaacctcg   3120
aggacttcgg aacttctaga accagaccgt tcagtttaaa cgctcttctc cccctcgagg   3180
gcctccgcgc cgggttttgg cgcctcccgc gggcgccccc ctcctcacgg cgagcgctgc   3240
cacgtcagac gaagggcgca gcgagcgtcc tgatccttcc gcccggacgc tcaggacagc   3300
ggcccgctgc tcataagact cggccttaga accccagtat cagcagaagg acattttagg   3360
acgggacttg ggtgactcta gggcactggt tttctttcca gagagcggaa caggcgagga   3420
aaagtagtcc cttctcggcg attctgcgga gggatctccg tggggcggtg aacgccgatg   3480
attatataag gacgcgccgg gtgtggcaca gctagttccg tcgcagccgg gatttgggtc   3540
gcggttcttg tttgtggatc gctgtgatcg tcacttggtg agtagcgggc tgctgggctg   3600
ggtacgtgcg ctcggggttg gcgagtgtgt tttgtgaagt tttttaggca ccttttgaaa   3660
tgtaatcatt tgggtcaata tgtaattttc agtgttagac tagtaaattg tccgctaaat   3720
tctggccgtt tttggctttt ttgttagacg gcatgcgggg gggggggggg gcaattggcc   3780
accatgggcc ccaagaagaa aaggaaggtg gccccccca ccgacgtgag cctgggcgac    3840
gagctgcacc tggacggcga ggacgtggcc atggcccacg ccgacgccct ggacgacttc   3900
gacctggaca tgctgggcga cggcgacagc cccggccccg gcttcacccc ccacgacagc   3960
gccccctacg gcgccctgga catggccgac ttcgagttcg agcagatgtt caccgacgcc   4020
ctgggcatcg acgagtacgg cggccatatg gagatgcccg tggacaggat tctggaggcc   4080
gaactcgccg tggagcagaa aagcgaccag ggcgtggagg gccccggcgg aaccggcggc   4140
```

-continued agcggcagca gccccaacga ccccgtgacc aacatctgcc aggccgccga caagcagctg 4200
ttcaccctgg tggagtgggc caagaggatt ccccacttca gcagcctgcc cctggacgac 4260
caggtgatcc tgctgagggc cggatggaac gagctgctga tcgccagctt cagccacagg 4320
agcatcgacg tgagggacgg catcctgctg gccaccggcc tgcacgtcca taggaacagc 4380
gcccacagcg ccggagtggg cgccatcttc gacagggtgc tgaccgagct ggtgagcaag 4440
atgagggaca tgaggatgga caagaccgag ctgggctgcc tgagggccat catcctgttc 4500
aaccccgagg tgaggggcct gaaaagcgcc caggaggtgg agctgctgag ggagaaggtg 4560
tacgccgccc tggaggagta caccaggacc acccaccccg acgagcccgg cagattcgcc 4620
aagctgctgc tgaggctgcc cagcctgagg agcatcggcc tgaagtgcct ggagcacctg 4680
ttcttcttca ggctgatcgg cgacgtgccc atcgacacct tcctgatgga gatgctggag 4740
agccccagcg acagctgagc cggcaactcg ctgtagtaat tccagcgaga ggcagaggga 4800
gcgagcgggc ggcgggctag ggtggaggag cccggcgagc agagctgcgc tgcgggcgtc 4860
ctgggaaggg agatccggag cgaatagggg gcttcgcctc tggcccagcc ctcccgctga 4920
tcccccagcc agcggtgcgc aaccctagcc gcatccacga aactttgccc atagcagcgg 4980
gcgggcactt tgcactggaa cttacaacac ccgagcaagg acgcgactct cccgacgcgg 5040
ggaggctatt ctgcccattt ggggacactt ccccgccgct gccaggaccc gcttctctga 5100
aaggctctcc ttgcagctgc ttagacgctg gatttttttc gggtagtgga aaaccagcag 5160
cctcccgcga ccagatctgc caccatgaag ctgctgagca gcatcgagca ggcttgcgac 5220
atctgcaggc tgaagaagct gaagtgcagc aaggagaagc ccaagtgcgc caagtgcctg 5280
aagaacaact gggagtgcag atacagcccc aagaccaaga ggagcccccct gaccagggcc 5340 cacctgaccg aggtggagag caggctggag aggctggagc agctgttcct gctgatcttc 5400
cccagggagg acctggacat gatcctgaag atggacagcc tgcaagacat caaggccctg 5460
ctgaccggcc tgttcgtgca ggacaacgtg aacaaggacg ccgtgaccga caggctggcc 5520
agcgtggaga ccgacatgcc cctgaccctg aggcagcaca ggatcagcgc caccagcagc 5580
agcgaggaga gcagcaacaa gggccagagg cagctgaccg tgagccccga gtttcccggg 5640
atcaggcccg agtgcgtggt gcccgagacc cagtgcgcca tgaaaaggaa ggagaagaag 5700
gcccagaagg agaaggacaa gctgcccgtg agcaccacca ccgtcgatga ccacatgccc 5760
cccatcatgc agtgcgagcc cccccccccc gaggccgcca ggattcacga ggtcgtgccc 5820
aggttcctga gcgacaagct gctggtgacc aacaggcaga agaacatccc ccagctgacc 5880
gccaaccagc agttcctgat cgccaggctg atctggtatc aggacggcta cgagcagccc 5940
agcgacgagg acctgaaaag gatcacccag acctggcagc aggccgacga cgagaacgag 6000
gagagcgaca ccccccttcag gcagatcacc gagatgacca tcctgaccgt gcagctgatc 6060
gtggagttcg ccaagggcct gcccggattc gccaagatca gccagcccga ccagatcacc 6120
ctgctgaagg cttgcagcag cgaggtgatg atgctgaggg tggccaggag gtacgacgcc 6180
gccagcgaca gcatcctgtt cgccaacaac caggcttaca ccagggacaa ctacaggaag 6240
gctggcatgg ccgaggtgat cgaggacctc ctgcacttct gcagatgtat gtacagcatg 6300
gccctggaca acatccacta cgccctgctg accgccgtgg tgatcttcag cgacaggccc 6360
ggcctggagc agccccagct ggtggaggag atccagaggt actacctgaa caccctgagg 6420
atctacatcc tgaaccagct gagcggcagc gccaggagca gcgtgatcta cggcaagatc 6480

-continued

```
ctgagcatcc tgagcgagct gaggaccctg ggaatgcaga acagcaatat gtgtatcagc   6540
ctgaagctga agaacaggaa gctgcccccc ttcctggagg agatttggga cgtggccgac   6600
atgagccaca cccagccccc ccccatcctg gagagcccca ccaacctgtg aatcgattag   6660
acatgataag atacattgat gagtttggac aaaccacaac tagaatgcag tgaaaaaaat   6720
gcttaatttg tgaaatttgt gatgctattg cttaatttgt aaccattata agctgcaata   6780
aacaagttaa taaaacattt gcattcattt tatgtttcag gttcaggggg agatgtggga   6840
ggttttttaa agcaagtaaa acctctacaa atgtggtatc tagagctctt ccaaatagat   6900
ctggaaggtg ctgaggtacg atgagacccg caccaggtgc agaccctgcg agtgtggcgg   6960
taaacatatt aggaaccagc ctgtgatgct ggatgtgacc gaggagctga ggcccgatca   7020
cttggtgctg gcctgcaccc gcgctgagtt tggctctagc gatgaagata cagattgagg   7080
tactgaaatg tgtgggcgtg gcttaagggt gggaaagaat atataaggtg ggggtcttat   7140
gtagttttgt atctgttttg cagcagccgc cgccgccatg agcaccaact cgtttgatgg   7200
aagcattgtg agctcatatt tgacaacgcg catgccccca tgggccgggg tgcgtcagaa   7260
tgtgatgggc tccagcattg atggtcgccc cgtcctgccc gcaaactcta ctaccttgac   7320
ctacgagacc gtgtctggaa cgccgttgga gactgcagcc tccgccgccg cttcagccgc   7380
tgcagccacc gcccgcggga ttgtgactga ctttgctttc ctgagcccgc ttgcaagcag   7440
tgcagcttcc cgttcatccg cccgcgatga caagttgacg gctcttttgg cacaattgga   7500
ttctttgacc cgggaactta atgtcgtttc tcagcagctg ttggatctgc gccagcaggt   7560
ttctgccctg aaggcttcct cccctcccaa tgcggtttaa aacataaata aaaaaccaga   7620
ctctgtttgg atttggatca agcaagtgtc ttgctgtctt tatttagggg ttttgcgcgc   7680
gcggtaggcc cgggaccagc ggtctcggtc gttgagggtc ctgtgtattt tttccaggac   7740
gtggtaaagg tgactctgga tgttcagata catgggcata agcccgtctc tggggtggag   7800
gtagcaccac tgcagagctt catgctgcgg ggtggtgttg tagatgatcc agtcgtagca   7860
ggagcgctgg gcgtggtgcc taaaaatgtc tttcagtagc aagctgattg ccaggggcag   7920
gcccttggtg taagtgttta caaagcggtt aagctgggat gggtgcatac gtggggatat   7980
gagatgcatc ttggactgta tttttaggtt ggctatgttc ccagccatat ccctccgggg   8040
attcatgttg tgcagaacca ccagcacagt gtatccggtg cacttgggaa atttgtcatg   8100
tagcttagaa ggaaatgcgt ggaagaactt ggagacgccc ttgtgacctc caagattttc   8160
catgcattcg tccataatga tggcaatggg cccacgggcg gcggcctggg cgaagatatt   8220
tctgggatca ctaacgtcat agttgtgttc caggatgaga tcgtcatagg ccatttttac   8280
aaagcgcggg cggagggtgc cagactgcgg tataatggtt ccatccggcc caggggcgta   8340
gttaccctca cagatttgca tttcccacgc tttgagttca gatgggggga tcatgtctac   8400
ctgcggggcg atgaagaaaa cggtttccgg ggtaggggag atcagctggg aagaaagcag   8460
gttcctgagc agctgcgact taccgcagcc ggtgggcccg taaatcacac ctattaccgg   8520
gtgcaactgg tagttaagag agctgcagct gccgtcatcc ctgagcaggg gggccacttc   8580
gttaagcatg tccctgactc gcatgttttc cctgaccaaa tccgccagaa ggcgctcgcc   8640
gcccagcgat agcagttctt gcaaggaagc aaagtttttc aacggtttga gaccgtccgc   8700
cgtaggcatg cttttgagcg tttgaccaag cagttccagg cggtcccaca gctcggtcac   8760
ctgctctacg gcatctcgat ccagcatatc tcctcgtttc gcgggttggg gcggctttcg   8820
ctgtacggca gtagtcggtg ctcgtccaga cgggccaggg tcatgtcttt ccacgggcgc   8880
```

agggtcctcg tcagcgtagt ctgggtcacg gtgaaggggt gcgctccggg ctgcgcgctg 8940
gccagggtgc gcttgaggct ggtcctgctg gtgctgaagc gctgccggtc ttcgccctgc 9000
gcgtcggcca ggtagcattt gaccatggtg tcatagtcca gcccctccgc ggcgtggccc 9060
ttggcgcgca gcttgccctt ggaggaggcg ccgcacgagg ggcagtgcag acttttgagg 9120
gcgtagagct tgggcgcgag aaataccgat tccggggagt aggcatccgc gccgcaggcc 9180
ccgcagacgg tctcgcattc cacgagccag gtgagctctg gccgttcggg gtcaaaaacc 9240
aggtttcccc catgcttttt gatgcgtttc ttacctctgg tttccatgag ccggtgtcca 9300
cgctcggtga cgaaaaggct gtccgtgtcc ccgtatacag acttgagagg cctgtcctcg 9360
accgatgccc ttgagagcct tcaacccagt cagctccttc cggtgggcgc ggggcatgac 9420
tatcgtcgcc gcacttatga ctgtcttctt tatcatgcaa ctcgtaggac aggtgccggc 9480
agcgctctgg gtcattttcg gcgaggaccg ctttcgctgg agcgcgacga tgatcggcct 9540
gtcgcttgcg gtattcggaa tcttgcacgc cctcgctcaa gccttcgtca ctggtcccgc 9600
caccaaacgt ttcggcgaga agcaggccat tatcgccggc atggcggccg acgcgctggg 9660
ctacgtcttg ctggcgttcg cgacgcgagg ctggatggcc ttccccatta tgattcttct 9720
cgcttccggc ggcatcggga tgcccgcgtt gcaggccatg ctgtccaggc aggtagatga 9780
cgaccatcag ggacagcttc aaggccagca aaaggccagg aaccgtaaaa aggccgcgtt 9840
gctggcgttt ttccataggc tccgcccccc tgacgagcat cacaaaaatc gacgctcaag 9900
tcagaggtgg cgaaacccga caggactata aagataccag gcgtttcccc ctggaagctc 9960
cctcgtgcgc tctcctgttc cgaccctgcc gcttaccgga tacctgtccg cctttctccc 10020
ttcgggaagc gtggcgcttt ctcatagctc acgctgtagg tatctcagtt cggtgtaggt 10080
cgttcgctcc aagctgggct gtgtgcacga accccccgtt cagcccgacc gctgcgcctt 10140
atccggtaac tatcgtcttg agtccaaccc ggtaagacac gacttatcgc cactggcagc 10200
agccactggt aacaggatta gcagagcgag gtatgtaggc ggtgctacag agttcttgaa 10260
gtggtggcct aactacggct acactagaag gacagtattt ggtatctgcg ctctgctgaa 10320
gccagttacc ttcggaaaaa gagttggtag ctcttgatcc ggcaaacaaa ccaccgctgg 10380
tagcggtggt ttttttgttt gcaagcagca gattacgcgc agaaaaaaag gatctcaaga 10440
agatcctttg atcttttcta cggggtctga cgctcagtgg aacgaaaact cacgttaagg 10500
gattttggtc atgagattat caaaaaggat cttcacctag atccttttaa attaaaaatg 10560
aagttttaaa tcaatctaaa gtatatatga gtaaacttgg tctgacagtt accaatgctt 10620
aatcagtgag gcacctatct cagcgatctg tctatttcgt tcatccatag ttgcctgact 10680
ccccgtcgtg tagataacta cgatacggga gggcttacca tctggcccca gtgctgcaat 10740
gataccgcga gacccacgct caccggctcc agatttatca gcaataaacc agccagccgg 10800
aagggccgag cgcagaagtg gtcctgcaac tttatccgcc tccatccagt ctattaattg 10860
ttgccgggaa gctagagtaa gtagttcgcc agttaatagt ttgcgcaacg ttgttgccat 10920
tgctgcaggc atcgtggtgt cacgctcgtc gtttggtatg gcttcattca gctccggttc 10980
ccaacgatca aggcgagtta catgatcccc catgttgtgc aaaaaagcgg ttagctcctt 11040
cggtcctccg atcgttgtca gaagtaagtt ggccgcagtg ttatcactca tggttatggc 11100
agcactgcat aattctctta ctgtcatgcc atccgtaaga tgcttttctg tgactggtga 11160
gtactcaacc aagtcattct gagaatagtg tatgcggcga ccgagttgct cttgcccggc 11220

-continued

```
gtcaacacgg gataataccg cgccacatag cagaacttta aaagtgctca tcattggaaa  11280

acgttcttcg gggcgaaaac tctcaaggat cttaccgctg ttgagatcca gttcgatgta  11340

acccactcgt gcacccaact gatcttcagc atcttttact ttcaccagcg tttctgggtg  11400

agcaaaaaca ggaaggcaaa atgccgcaaa aaagggaata agggcgacac ggaaatgttg  11460

aatactcata ctcttccttt ttcaatatta ttgaagcatt tatcagggtt attgtctcat  11520

gagcggatac atatttgaat gtatttagaa aaa                               11553
```

<210> SEQ ID NO 4
<211> LENGTH: 12279
<212> TYPE: DNA
<213> ORGANISM: Artificial Sequence
<220> FEATURE:
<223> OTHER INFORMATION: Synthetic mIL-12

<400> SEQUENCE: 4

```
taaacaaata ggggttccgc gcacatttcc ccgaaaagtg ccacctgacg tctaagaaac     60

cattattatc atgacattaa cctataaaaa taggcgtatc acgaggccct ttcgtcttca    120

attaatcgca ccggtatcta tgtcgggtgc ggagaaagag gtaatgaaat ggcagctagc    180

atcatcaata atatacctta ttttggattg aagccaatat gataatgagg gggtggagtt    240

tgtgacgtgg cgcggggcgt gggaacgggg cgggtgacgt agtagtgtgg cggaagtgtg    300

atgttgcaag tgtggcggaa cacatgtaag cgacggatgt ggcaaaagtg acgtttttgg    360

tgtgcgccgg tgtacacagg aagtgacaat tttcgcgcgg ttttaggcgg atgttgtagt    420

aaatttgggc gtaaccgagt aagatttggc cattttcgcg ggaaaactga ataagaggaa    480

gtgaaatctg aataattttg tgttactcat agcgcgtaat atttgtctag ggagatccgg    540

taccgatatc ctagacaacg atgctgagct aactataacg gtcctaaggt agcgaccgcg    600

gagactaggt gtatttatct aagcgatcgc ttaattaagg ccggccgccg caataaaata    660

tctttatttt cattacatct gtgtgttggt tttttgtgtg aatcgatagt actaacatac    720

gctctccatc aaaacaaaac gaaacaaaac aaactagcaa aataggctgt ccccagtgca    780

agtgcaggtg ccagaacatt tctctatcga taatgcaggt cggagtactg tcctccgagc    840

ggagtactgt cctccgagcg gagtactgtc ctccgagcgg agtactgtcc tccgagcgga    900

gtactgtcct ccgagcggag tactgtcctc cgagcggaga ctcttcgaag gaagaggggc    960

ggggtcgatc gaccccgccc ctcttccttc gaaggaagag ggcggggtc gaagacctag    1020

agggtatata atgggtgcct tagctggtgt gtgagctcat cttcctgtag atcacgcgtc   1080

gaagaaggtg agtaatctta acatgctctt tttttttttt tttgctaatc ccttttgtgt   1140

gctgatgtta ggatgacatt tacaacaaat gtttgttcct gacaggaaaa accttgctgg   1200

gtaccttcgt tgccggacac ttcttgtcct ctactttgga aaaaaggaat tgagagccgc   1260

tagcgccacc atgtgccccc agaagctgac catcagctgg ttcgccatcg tgctgctggt   1320

gagcccccctg atggccatgt gggagctgga gaaggacgtg tacgtggtgg aggtggactg  1380

gacccccgac gcccccggcg agaccgtgaa cctgacttgc gacacccccg aggaggacga   1440

catcacctgg accagcgacc agagacacgg cgtcatcggc agcggcaaga ccctgaccat   1500

caccgtgaag gagttcctgg acgccggaca gtacacctgt cacaagggcg gcgagaccct   1560

gagccacagc cacctgttgc tgcacaagaa ggagaacggc atctggagca ccgagatcct   1620

gaagaacttc aagaacaaga ccttcctgaa gtgcgaggcc cccaactaca gcggcagatt   1680

cacctgtagc tggctggtgc agagaaacat ggacctgaag ttcaacatca agagcagcag   1740
```

-continued cagcagcccc gacagcagag ccgtgacatg cggcatggcc agcctgagcg ccgagaaggt 1800
gaccctggac cagagagact acgagaagta cagcgtgagc tgccaggagg acgtgacctg 1860
tcccaccgcc gaggagaccc tgcccatcga gcttgccctg gaagccagac agcagaacaa 1920
gtacgagaac tacagcacca gcttcttcat cagagacatc atcaagcccg acccccccaa 1980
gaacctccag atgaagcccc tgaagaacag ccaggtggag gtgtcctggg agtaccccga 2040
cagctggagc accccccaca gctacttcag cctgaagttc ttcgtgagaa tccagagaaa 2100
gaaggagaag atgaaggaga ccgaggaggg ctgcaaccag aagggcgctt tcctggtgga 2160
gaaaaccagc accgaggtgc agtgcaaggg cggcaacgtg tgtgtgcagg cccaggacag 2220
atactacaac agcagctgct ccaagtgggc ctgcgtgccc tgccgcgtga gaagctgagt 2280
tgggcgagct cgaattcatt gatcccccgg gctgcaggaa ttcgatatca agctcgggat 2340
ccgaattccg cccccccccc cccccccccc ctaacgttac tggccgaagc cgcttggaat 2400
aaggccggtg tgcgtttgtc tatatgttat tttccaccat attgccgtct tttggcaatg 2460
tgagggcccg gaaacctggc cctgtcttct tgacgagcat tcctaggggt ctttcccctc 2520
tcgccaaagg aatgcaaggt ctgttgaatg tcgtgaagga agcagttcct ctggaagctt 2580
cttgaagaca aacaacgtct gtagcgaccc tttgcaggca gcggaacccc ccacctggcg 2640
acaggtgcct ctgcggccaa aagccacgtg tataagatac acctgcaaag gcggcacaac 2700
cccagtgcca cgttgtgagt tggatagttg tggaaagagt caaatggctc tcctcaagcg 2760
tattcaacaa ggggctgaag gatgcccaga aggtacccca ttgtatggga tctgatctgg 2820
ggcctcggtg cacatgcttt acatgtgttt agtcgaggtt aaaaaaacgt ctaggccccc 2880
cgaaccacgg ggacgtggtt ttcctttgaa aaacacgatg ataatatggc cacaaccatg 2940
tgccagagca gatacctgtt gttcctggct accctggccc tgctgaacca cctgagcctg 3000
gcccgcgtga tccccgtgag cggccccgcc agatgcctga gccagagcag aaacctgttg 3060
aaaacaaccg acgacatggt gaaaaccgcc agagagaagc tgaagcacta cagctgcacc 3120
gccgaggaca tcgaccacga ggacatcacc agagaccaga ccagcaccct gaaaacctgt 3180
ctgcccctgg agctgcacaa gaacgagagc tgcctggcta ccagagagac cagcagcacc 3240
accagaggca gctgcctgcc cccccagaaa accagcctga tgatgaccct gtgcctgggc 3300
agcatctacg aggacctgaa gatgtaccag accgagttcc aggccatcaa cgccgccctg 3360
caaaaccaca accaccagca gatcatcctg gacaagggca tgttggtggc catcgacgag 3420
ctgatgcaga gcctgaacca caacggcgag accctgagac agaagccccc cgtgggcgag 3480
gccgacccct acagagtgaa gatgaagctg tgcatcctgc tgcacgcctt cagcaccaga 3540
gtggtgacca tcaacagagt gatgggctac ctgagcagcg cctgaatcga ttgcgcaaag 3600
ctttcgcgat aggcgagacc aatgggtgtg tacgtagcgg ccgctcgaga acttgtttat 3660
tgcagcttat aatggttaca aataaagcaa tagcatcaca aatttcacaa ataaagcatt 3720
tttttcactg cattctagtt gtggtttgtc caaactcatc aatgtatctt atcatgtctc 3780
gtacggcgtg gtaggtccga acgaatccat ggattaccct gttatcccta tccggagtta 3840
acctcgagga cttcggaact tctagaacca gaccgttcag tttaaacgct cttctccccc 3900
tcgagggcct ccgcgccggg ttttggcgcc tcccgcgggc gcccccctcc tcacggcgag 3960
cgctgccacg tcagacgaag ggcgcagcga gcgtcctgat ccttccgccc ggacgctcag 4020
gacagcggcc cgctgctcat aagactcggc cttagaaccc cagtatcagc agaaggacat 4080

-continued

```
tttaggacgg gacttgggtg actctagggc actggttttc tttccagaga gcggaacagg   4140
cgaggaaaag tagtcccttc tcggcgattc tgcggaggga tctccgtggg gcggtgaacg   4200
ccgatgatta tataaggacg cgccgggtgt ggcacagcta gttccgtcgc agccgggatt   4260
tgggtcgcgg ttcttgtttg tggatcgctg tgatcgtcac ttggtgagta gcgggctgct   4320
gggctgggta cgtgcgctcg ggttggcga gtgtgttttg tgaagttttt taggcacctt   4380
ttgaaatgta atcatttggg tcaatatgta attttcagtg ttagactagt aaattgtccg   4440
ctaaattctg gccgtttttg gcttttttgt tagacggcat gcgggggggg gggggggcaa   4500
ttggccacca tgggccccaa gaagaaaagg aaggtggccc cccccaccga cgtgagcctg   4560
ggcgacgagc tgcacctgga cggcgaggac gtggccatgg cccacgccga cgccctggac   4620
gacttcgacc tggacatgct gggcgacggc gacagccccg gccccggctt cacccccac    4680
gacagcgccc cctacggcgc cctggacatg gccgacttcg agttcgagca gatgttcacc   4740
gacgccctgg gcatcgacga gtacggcggc catatggaga tgcccgtgga caggattctg   4800
gaggccgaac tcgccgtgga gcagaaaagc gaccagggcg tggagggccc cggcggaacc   4860
ggcggcagcg gcagcagccc caacgacccc gtgaccaaca tctgccaggc cgccgacaag   4920
cagctgttca ccctggtgga gtgggccaag aggattcccc acttcagcag cctgcccctg   4980
gacgaccagg tgatcctgct gagggccgga tggaacgagc tgctgatcgc cagcttcagc   5040
cacaggagca tcgacgtgag ggacggcatc ctgctggcca ccggcctgca cgtccatagg   5100
aacagcgccc acagcgccgg agtgggcgcc atcttcgaca gggtgctgac cgagctggtg   5160
agcaagatga gggacatgag gatggacaag accgagctgg gctgcctgag ggccatcatc   5220
ctgttcaacc ccgaggtgag gggcctgaaa agcgcccagg aggtggagct gctgagggag   5280
aaggtgtacg ccgccctgga ggagtacacc aggaccaccc accccgacga gcccggcaga   5340
ttcgccaagc tgctgctgag gctgcccagc ctgaggagca tcggcctgaa gtgcctggag   5400
cacctgttct tcttcaggct gatcggcgac gtgcccatcg acaccttcct gatggagatg   5460
ctggagagcc ccagcgacag ctgagccggc aactcgctgt agtaattcca gcgagaggca   5520
gagggagcga gcgggcggcg ggctagggtg gaggagcccg gcgagcagag ctgcgctgcg   5580
ggcgtcctgg gaagggagat ccggagcgaa tagggggctt cgcctctggc ccagccctcc   5640
cgctgatccc ccagccagcg gtgcgcaacc ctagccgcat ccacgaaact ttgcccatag   5700
cagcgggcgg gcactttgca ctggaactta caacacccga gcaaggacgc gactctcccg   5760
acgcggggag gctattctgc ccatttgggg acacttcccc gccgctgcca ggacccgctt   5820
ctctgaaagg ctctccttgc agctgcttag acgctggatt tttttcgggt agtggaaaac   5880
cagcagcctc ccgcgaccag atctgccacc atgaagctgc tgagcagcat cgagcaggct   5940
tgcgacatct gcaggctgaa gaagctgaag tgcagcaagg agaagcccaa gtgcgccaag   6000
tgcctgaaga acaactggga gtgcagatac agccccaaga ccaagaggag ccccctgacc   6060
agggcccacc tgaccgaggt ggagagcagg ctggagaggc tggagcagct gttcctgctg   6120
atcttcccca gggaggacct ggacatgatc ctgaagatgg acagcctgca agacatcaag   6180
gccctgctga ccggcctgtt cgtgcaggac aacgtgaaca aggacgccgt gaccgacagg   6240
ctggccagcg tggagaccga catgcccctg accctgaggc agcacaggat cagcgccacc   6300
agcagcagcg aggagagcag caacaagggc cagaggcagc tgaccgtgag ccccgagttt   6360
cccgggatca ggcccgagtg cgtggtgccc gagacccagt gcgccatgaa aaggaaggag   6420
aagaaggccc agaaggagaa ggacaagctg cccgtgagca ccaccaccgt cgatgaccac   6480
```

-continued

```
atgcccccca tcatgcagtg cgagccccc ccccccgagg ccgccaggat tcacgaggtc   6540
gtgcccaggt tcctgagcga caagctgctg gtgaccaaca ggcagaagaa catcccccag   6600
ctgaccgcca accagcagtt cctgatcgcc aggctgatct ggtatcagga cggctacgag   6660
cagcccagcg acgaggacct gaaaaggatc acccagacct ggcagcaggc cgacgacgag   6720
aacgaggaga gcgacacccc cttcaggcag atcaccgaga tgaccatcct gaccgtgcag   6780
ctgatcgtgg agttcgccaa gggcctgccc ggattcgcca agatcagcca gcccgaccag   6840
atcaccctgc tgaaggcttg cagcagcgag gtgatgatgc tgagggtggc caggaggtac   6900
gacgccgcca gcgacagcat cctgttcgcc aacaaccagg cttacaccag ggacaactac   6960
aggaaggctg gcatggccga ggtgatcgag gacctcctgc acttctgcag atgtatgtac   7020
agcatggccc tggacaacat ccactacgcc ctgctgaccg ccgtggtgat cttcagcgac   7080
aggcccggcc tggagcagcc ccagctggtg gaggagatcc agaggtacta cctgaacacc   7140
ctgaggatct acatcctgaa ccagctgagc ggcagcgcca ggagcagcgt gatctacggc   7200
aagatcctga gcatcctgag cgagctgagg accctgggaa tgcagaacag caatatgtgt   7260
atcagcctga agctgaagaa caggaagctg ccccccttcc tggaggagat ttgggacgtg   7320
gccgacatga gccacaccca gcccccccc atcctggaga gccccaccaa cctgtgaatc   7380
gattagacat gataagatac attgatgagt ttggacaaac cacaactaga atgcagtgaa   7440
aaaaatgctt aatttgtgaa atttgtgatg ctattgctta atttgtaacc attataagct   7500
gcaataaaca agttaataaa acatttgcat tcattttatg tttcaggttc agggggagat   7560
gtgggaggtt ttttaaagca agtaaaacct ctacaaatgt ggtatctaga gctcttccaa   7620
atagatctgg aaggtgctga ggtacgatga gacccgcacc aggtgcagac cctgcgagtg   7680
tggcggtaaa catattagga accagcctgt gatgctggat gtgaccgagg agctgaggcc   7740
cgatcacttg gtgctggcct gcacccgcgc tgagtttggc tctagcgatg aagatacaga   7800
ttgaggtact gaaatgtgtg ggcgtggctt aagggtggga aagaatatat aaggtggggg   7860
tcttatgtag ttttgtatct gttttgcagc agccgccgcc gccatgagca ccaactcgtt   7920
tgatggaagc attgtgagct catatttgac aacgcgcatg cccccatggg ccggggtgcg   7980
tcagaatgtg atgggctcca gcattgatgg tcgccccgtc ctgcccgcaa actctactac   8040
cttgacctac gagaccgtgt ctggaacgcc gttggagact gcagcctccg ccgccgcttc   8100
agccgctgca gccaccgccc gcgggattgt gactgacttt gctttcctga gcccgcttgc   8160
aagcagtgca gcttcccgtt catccgcccg cgatgacaag ttgacggctc ttttggcaca   8220
attggattct ttgacccggg aacttaatgt cgtttctcag cagctgttgg atctgcgcca   8280
gcaggtttct gccctgaagg cttcctcccc tcccaatgcg gtttaaaaca taaataaaaa   8340
accagactct gtttggattt ggatcaagca agtgtcttgc tgtctttatt taggggtttt   8400
gcgcgcgcgg taggcccggg accagcggtc tcggtcgttg agggtcctgt gtattttttc   8460
caggacgtgg taaaggtgac tctggatgtt cagatacatg ggcataagcc cgtctctggg   8520
gtggaggtag caccactgca gagcttcatg ctgcggggtg gtgttgtaga tgatccagtc   8580
gtagcaggag cgctgggcgt ggtgcctaaa aatgtctttc agtagcaagc tgattgccag   8640
gggcaggccc ttggtgtaag tgtttacaaa gcggttaagc tgggatgggt gcatacgtgg   8700
ggatatgaga tgcatcttgg actgtatttt taggttggct atgttcccag ccatatccct   8760
ccggggattc atgttgtgca gaaccaccag cacagtgtat ccggtgcact tgggaaattt   8820
```

-continued

```
gtcatgtagc ttagaaggaa atgcgtggaa gaacttggag acgcccttgt gacctccaag   8880
attttccatg cattcgtcca taatgatggc aatgggccca cgggcggcgg cctgggcgaa   8940
gatatttctg ggatcactaa cgtcatagtt gtgttccagg atgagatcgt cataggccat   9000
ttttacaaag cgcgggcgga gggtgccaga ctgcggtata atggttccat ccggcccagg   9060
ggcgtagtta ccctcacaga tttgcatttc ccacgctttg agttcagatg gggggatcat   9120
gtctacctgc ggggcgatga agaaaacggt ttccggggta ggggagatca gctgggaaga   9180
aagcaggttc ctgagcagct gcgacttacc gcagccggtg ggcccgtaaa tcacacctat   9240
taccgggtgc aactggtagt taagagagct gcagctgccg tcatccctga gcaggggggc   9300
cacttcgtta agcatgtccc tgactcgcat gttttccctg accaaatccg ccagaaggcg   9360
ctcgccgccc agcgatagca gttcttgcaa ggaagcaaag tttttcaacg gtttgagacc   9420
gtccgccgta ggcatgcttt tgagcgtttg accaagcagt tccaggcggt cccacagctc   9480
ggtcacctgc tctacggcat ctcgatccag catatctcct cgtttcgcgg gttggggcgg   9540
ctttcgctgt acggcagtag tcggtgctcg tccagacggg ccagggtcat gtctttccac   9600
gggcgcaggg tcctcgtcag cgtagtctgg gtcacggtga aggggtgcgc tccgggctgc   9660
gcgctggcca gggtgcgctt gaggctggtc ctgctggtgc tgaagcgctg ccggtcttcg   9720
ccctgcgcgt cggccaggta gcatttgacc atggtgtcat agtccagccc ctccgcggcg   9780
tggcccttgg cgcgcagctt gcccttggag gaggcgccgc acgaggggca gtgcagactt   9840
ttgagggcgt agagcttggg cgcgagaaat accgattccg gggagtaggc atccgcgccg   9900
caggccccgc agacggtctc gcattccacg agccaggtga gctctggccg ttcggggtca   9960
aaaaccaggt ttcccccatg ctttttgatg cgtttcttac ctctggtttc catgagccgg  10020
tgtccacgct cggtgacgaa aaggctgtcc gtgtccccgt atacagactt gagaggcctg  10080
tcctcgaccg atgcccttga gagccttcaa cccagtcagc tccttccggt gggcgcgggg  10140
catgactatc gtcgccgcac ttatgactgt cttctttatc atgcaactcg taggacaggt  10200
gccggcagcg ctctgggtca ttttcggcga ggaccgcttt cgctggagcg cgacgatgat  10260
cggcctgtcg cttgcggtat tcggaatctt gcacgccctc gctcaagcct tcgtcactgg  10320
tcccgccacc aaacgtttcg gcgagaagca ggccattatc gccggcatgg cggccgacgc  10380
gctgggctac gtcttgctgg cgttcgcgac gcgaggctgg atggccttcc ccattatgat  10440
tcttctcgct tccggcggca tcgggatgcc cgcgttgcag gccatgctgt ccaggcaggt  10500
agatgacgac catcagggac agcttcaagg ccagcaaaag gccaggaacc gtaaaaaggc  10560
cgcgttgctg gcgtttttcc ataggctccg cccccctgac gagcatcaca aaaatcgacg  10620
ctcaagtcag aggtggcgaa acccgacagg actataaaga taccaggcgt ttccccctgg  10680
aagctccctc gtgcgctctc ctgttccgac cctgccgctt accggatacc tgtccgcctt  10740
tctcccttcg ggaagcgtgg cgctttctca tagctcacgc tgtaggtatc tcagttcggt  10800
gtaggtcgtt cgctccaagc tgggctgtgt gcacgaaccc cccgttcagc ccgaccgctg  10860
cgccttatcc ggtaactatc gtcttgagtc caacccggta agacacgact tatcgccact  10920
ggcagcagcc actggtaaca ggattagcag agcgaggtat gtaggcggtg ctacagagtt  10980
cttgaagtgg tggcctaact acggctacac tagaaggaca gtatttggta tctgcgctct  11040
gctgaagcca gttaccttcg gaaaaagagt tggtagctct tgatccggca aacaaaccac  11100
cgctggtagc ggtggttttt ttgtttgcaa gcagcagatt acgcgcagaa aaaaaggatc  11160
tcaagaagat cctttgatct tttctacggg gtctgacgct cagtggaacg aaaactcacg  11220
```

```
ttaagggatt ttggtcatga gattatcaaa aaggatcttc acctagatcc ttttaaatta  11280

aaaatgaagt tttaaatcaa tctaaagtat atatgagtaa acttggtctg acagttacca  11340

atgcttaatc agtgaggcac ctatctcagc gatctgtcta tttcgttcat ccatagttgc  11400

ctgactcccc gtcgtgtaga taactacgat acgggagggc ttaccatctg gccccagtgc  11460

tgcaatgata ccgcgagacc cacgctcacc ggctccagat ttatcagcaa taaaccagcc  11520

agccggaagg gccgagcgca gaagtggtcc tgcaacttta tccgcctcca tccagtctat  11580

taattgttgc cgggaagcta gagtaagtag ttcgccagtt aatagtttgc gcaacgttgt  11640

tgccattgct gcaggcatcg tggtgtcacg ctcgtcgttt ggtatggctt cattcagctc  11700

cggttcccaa cgatcaaggc gagttacatg atcccccatg ttgtgcaaaa aagcggttag  11760

ctccttcggt cctccgatcg ttgtcagaag taagttggcc gcagtgttat cactcatggt  11820

tatggcagca ctgcataatt ctcttactgt catgccatcc gtaagatgct tttctgtgac  11880

tggtgagtac tcaaccaagt cattctgaga atagtgtatg cggcgaccga gttgctcttg  11940

cccggcgtca acacgggata ataccgcgcc acatagcaga actttaaaag tgctcatcat  12000

tggaaaacgt tcttcggggc gaaaactctc aaggatctta ccgctgttga gatccagttc  12060

gatgtaaccc actcgtgcac ccaactgatc ttcagcatct tttactttca ccagcgtttc  12120

tgggtgagca aaaacaggaa ggcaaaatgc cgcaaaaaag ggaataaggg cgacacggaa  12180

atgttgaata ctcatactct tcctttttca atattattga agcatttatc agggttattg  12240

tctcatgagc ggatacatat ttgaatgtat ttagaaaaa                         12279
```

<210> SEQ ID NO 5
<211> LENGTH: 11601
<212> TYPE: DNA
<213> ORGANISM: Artificial Sequence
<220> FEATURE:
<223> OTHER INFORMATION: Synthetic hIL-21 and hIL-15

<400> SEQUENCE: 5

```
taaacaaata ggggttccgc gcacatttcc ccgaaaagtg ccacctgacg tctaagaaac     60

cattattatc atgacattaa cctataaaaa taggcgtatc acgaggccct ttcgtcttca    120

attaatcgca ccggtatcta tgtcgggtgc ggagaaagag gtaatgaaat ggcagctagc    180

atcatcaata atatacctta ttttggattg aagccaatat gataatgagg gggtggagtt    240

tgtgacgtgg cgcggggcgt gggaacgggg cgggtgacgt agtagtgtgg cggaagtgtg    300

atgttgcaag tgtggcggaa cacatgtaag cgacggatgt ggcaaaagtg acgtttttgg    360

tgtgcgccgg tgtacacagg aagtgacaat tttcgcgcgg ttttaggcgg atgttgtagt    420

aaatttgggc gtaaccgagt aagatttggc cattttcgcg ggaaaactga ataagaggaa    480

gtgaaatctg aataattttg tgttactcat agcgcgtaat atttgtctag ggagatccgg    540

taccgatatc ctagacaacg atgctgagct aactataacg gtcctaaggt agcgaccgcg    600

gagactaggt gtatttatct aagcgatcgc ttaattaagg ccggccgccg caataaaata    660

tctttatttt cattacatct gtgtgttggt tttttgtgtg aatcgatagt actaacatac    720

gctctccatc aaaacaaaac gaaacaaaac aaactagcaa aataggctgt ccccagtgca    780

agtgcaggtg ccagaacatt tctctatcga taatgcaggt cggagtactg tcctccgagc    840

ggagtactgt cctccgagcg gagtactgtc ctccgagcgg agtactgtcc tccgagcgga    900

gtactgtcct ccgagcggag tactgtcctc cgagcggaga ctcttcgaag gaagaggggc    960
```

-continued

```
ggggtcgatc gaccccgccc ctcttccttc gaaggaagag gggcggggtc gaagacctag   1020
agggtatata atgggtgcct tagctggtgt gtgagctcat cttcctgtag atcacgcgtc   1080
gaagaaggtg agtaatctta acatgctctt tttttttttt tttgctaatc ccttttgtgt   1140
gctgatgtta ggatgacatt tacaacaaat gtttgttcct gacaggaaaa accttgctgg   1200
gtaccttcgt tgccggacac ttcttgtcct ctactttgga aaaaaggaat tgagagccgc   1260
tagcgccacc atgagaagca gccccggcaa catggagaga atcgtgatct gcctgatggt   1320
gatcttcctg ggcaccctgg tgcataagag cagcagccag ggccaggaca gacacatgat   1380
ccgcatgaga cagctgatcg acatcgtgga ccagctgaag aactacgtga acgacctggt   1440
gcccgagttc ctgcccgccc ccgaggacgt ggagaccaac tgcgagtgga gcgccttcag   1500
ctgcttccag aaggcccagc tgaagtccgc caacaccggc aacaacgaga gaatcatcaa   1560
cgtgagcatc aagaagctga agcggaagcc ccccagcacc aacgccggaa gaagacagaa   1620
gcacagactg acctgtccca gctgcgacag ctacgagaag aagcccccca aggagttcct   1680
ggagagattc aagagcctgc tgcaaaagat gatccaccag cacctgagca gcagaaccca   1740
cggcagcgag gacagctgag ttgggcgagc tcgaattcat tgatcccccg ggctgcagga   1800
attcgatatc aagctcggga tccgaattcc gccccccccc cccccccccc cctaacgtta   1860
ctggccgaag ccgcttggaa taaggccggt gtgcgtttgt ctatatgtta ttttccacca   1920
tattgccgtc ttttggcaat gtgagggccc ggaaacctgg ccctgtcttc ttgacgagca   1980
ttcctagggg tctttcccct ctcgccaaag gaatgcaagg tctgttgaat gtcgtgaagg   2040
aagcagttcc tctggaagct tcttgaagac aaacaacgtc tgtagcgacc ctttgcaggc   2100
agcggaaccc cccacctggc gacaggtgcc tctgcggcca aaagccacgt gtataagata   2160
cacctgcaaa ggcggcacaa ccccagtgcc acgttgtgag ttggatagtt gtggaaagag   2220
tcaaatggct ctcctcaagc gtattcaaca aggggctgaa ggatgcccag aaggtacccc   2280
attgtatggg atctgatctg gggcctcggt gcacatgctt tacatgtgtt tagtcgaggt   2340
taaaaaaacg tctaggcccc ccgaaccacg gggacgtggt tttcctttga aaaacacgat   2400
gataatatgg ccacaaccat gagaatcagc aagccccacc tgagaagcat cagcatccag   2460
tgttacctgt gcctgctgct gaacagccac ttcctgaccg aggccggtat ccacgtcttc   2520
atcctgggct gcttcagcgc cggactgccc aagaccgagg ccaactgggt gaacgtgatc   2580
tctgacctga agaagatcga ggacctgatc cagtccatgc acatcgacgc caccctgtac   2640
accgagagcg acgttcatcc cagctgcaag gtgaccgcca tgaagtgctt cctgctggag   2700
ctgcaagtga tctccctgga gagcggcgac gccagcatcc acgacaccgt ggagaacctg   2760
attatcctgg ctaacaacag cctgagcagc aacggcaacg tgaccgagag cggctgcaag   2820
gagtgtgagg agctggagga gaagaacatc aaggagttcc tccagagctt cgtgcatatc   2880
gtccagatgt tcatcaacac cagctgaatc gattgcgcaa agctttcgcg ataggcgaga   2940
ccaatgggtg tgtacgtagc ggccgctcga gaacttgttt attgcagctt ataatggtta   3000
caaataaagc aatagcatca caaatttcac aaataaagca tttttttcac tgcattctag   3060
ttgtggtttg tccaaactca tcaatgtatc ttatcatgtc tcgtacggcg tggtaggtcc   3120
gaacgaatcc atggattacc ctgttatccc tatccggagt taacctcgag gacttcggaa   3180
cttctagaac cagaccgttc agtttaaacg ctcttctccc cctcgagggc ctccgcgccg   3240
ggttttggcg cctcccgcgg gcgccccccct cctcacggcg agcgctgcca cgtcagacga   3300
agggcgcagc gagcgtcctg atccttccgc ccggacgctc aggacagcgg cccgctgctc   3360
```

```
ataagactcg gccttagaac cccagtatca gcagaaggac attttaggac gggacttggg   3420
tgactctagg gcactggttt tctttccaga gagcggaaca ggcgaggaaa agtagtccct   3480
tctcggcgat tctgcggagg gatctccgtg gggcggtgaa cgccgatgat tatataagga   3540
cgcgccgggt gtggcacagc tagttccgtc gcagccggga tttgggtcgc ggttcttgtt   3600
tgtggatcgc tgtgatcgtc acttggtgag tagcgggctg ctgggctggg tacgtgcgct   3660
cggggttggc gagtgtgttt tgtgaagttt tttaggcacc ttttgaaatg taatcatttg   3720
ggtcaatatg taattttcag tgttagacta gtaaattgtc cgctaaattc tggccgtttt   3780
tggctttttt gttagacggc atgcgggggg gggggggggc aattggccac catgggcccc   3840
aagaagaaaa ggaaggtggc ccccccccacc gacgtgagcc tgggcgacga gctgcacctg   3900
gacggcgagg acgtggccat ggcccacgcc gacgccctgg acgacttcga cctggacatg   3960
ctgggcgacg gcgacagccc cggccccggc ttcacccccc acgacagcgc cccctacggc   4020
gccctggaca tggccgactt cgagttcgag cagatgttca ccgacgccct gggcatcgac   4080
gagtacggcg gccatatgga gatgcccgtg gacaggattc tggaggccga actcgccgtg   4140
gagcagaaaa gcgaccaggg cgtggagggc cccggcggaa ccggcggcag cggcagcagc   4200
cccaacgacc ccgtgaccaa catctgccag gccgccgaca agcagctgtt caccctggtg   4260
gagtgggcca agaggattcc ccacttcagc agcctgcccc tggacgacca ggtgatcctg   4320
ctgagggccg gatggaacga gctgctgatc gccagcttca gccacaggag catcgacgtg   4380
agggacggca tcctgctggc caccggcctg cacgtccata ggaacagcgc ccacagcgcc   4440
ggagtgggcg ccatcttcga cagggtgctg accgagctgg tgagcaagat gagggacatg   4500
aggatggaca agaccgagct gggctgcctg agggccatca tcctgttcaa ccccgaggtg   4560
aggggcctga aaagcgccca ggaggtggag ctgctgaggg agaaggtgta cgccgccctg   4620
gaggagtaca ccaggaccac ccaccccgac gagcccggca gattcgccaa gctgctgctg   4680
aggctgccca gcctgaggag catcggcctg aagtgcctgg agcacctgtt cttcttcagg   4740
ctgatcggcg acgtgcccat cgacaccttc ctgatggaga tgctggagag ccccagcgac   4800
agctgagccg gcaactcgct gtagtaattc cagcgagagg cagagggagc gagcgggcgg   4860
cgggctaggg tggaggagcc cggcgagcag agctgcgctg cgggcgtcct gggaagggag   4920
atccggagcg aatagggggc ttcgcctctg gcccagccct cccgctgatc cccccagccag   4980
cggtgcgcaa ccctagccgc atccacgaaa ctttgcccat agcagcgggc gggcactttg   5040
cactggaact tacaacaccc gagcaaggac gcgactctcc cgacgcgggg aggctattct   5100
gcccatttgg ggacacttcc ccgccgctgc caggacccgc ttctctgaaa ggctctcctt   5160
gcagctgctt agacgctgga tttttttcgg gtagtggaaa accagcagcc tcccgcgacc   5220
agatctgcca ccatgaagct gctgagcagc atcgagcagg cttgcgacat ctgcaggctg   5280
aagaagctga agtgcagcaa ggagaagccc aagtgcgcca agtgcctgaa gaacaactgg   5340
gagtgcagat acagccccaa gaccaagagg agcccccctga ccagggccca cctgaccgag   5400
gtggagagca ggctggagag gctggagcag ctgttcctgc tgatcttccc cagggaggac   5460
ctggacatga tcctgaagat ggacagcctg caagacatca aggccctgct gaccggcctg   5520
ttcgtgcagg acaacgtgaa caaggacgcc gtgaccgaca ggctggccag cgtggagacc   5580
gacatgcccc tgaccctgag gcagcacagg atcagcgcca ccagcagcag cgaggagagc   5640
agcaacaagg gccagaggca gctgaccgtg agccccgagt ttcccgggat caggcccgag   5700
```

-continued

```
tgcgtggtgc ccgagaccca gtgcgccatg aaaaggaagg agaagaaggc ccagaaggag   5760
aaggacaagc tgcccgtgag caccaccacc gtcgatgacc acatgccccc catcatgcag   5820
tgcgagcccc cccccccga ggccgccagg attcacgagg tcgtgcccag gttcctgagc   5880
gacaagctgc tggtgaccaa caggcagaag aacatccccc agctgaccgc caaccagcag   5940
ttcctgatcg ccaggctgat ctggtatcag gacggctacg agcagcccag cgacgaggac   6000
ctgaaaagga tcacccagac ctggcagcag gccgacgacg agaacgagga gagcgacacc   6060
cccttcaggc agatcaccga gatgaccatc ctgaccgtgc agctgatcgt ggagttcgcc   6120
aagggcctgc ccggattcgc caagatcagc cagcccgacc agatcaccct gctgaaggct   6180
tgcagcagcg aggtgatgat gctgagggtg gccaggaggt acgacgccgc cagcgacagc   6240
atcctgttcg ccaacaacca ggcttacacc agggacaact acaggaaggc tggcatggcc   6300
gaggtgatcg aggacctcct gcacttctgc agatgtatgt acagcatggc cctggacaac   6360
atccactacg ccctgctgac cgccgtggtg atcttcagcg acaggcccgg cctggagcag   6420
ccccagctgg tggaggagat ccagaggtac tacctgaaca ccctgaggat ctacatcctg   6480
aaccagctga gcggcagcgc caggagcagc gtgatctacg gcaagatcct gagcatcctg   6540
agcgagctga ggaccctggg aatgcagaac agcaatatgt gtatcagcct gaagctgaag   6600
aacaggaagc tgcccccctt cctggaggag atttgggacg tggccgacat gagccacacc   6660
cagccccccc ccatcctgga gagccccacc aacctgtgaa tcgattagac atgataagat   6720
acattgatga gtttggacaa accacaacta gaatgcagtg aaaaaaatgc ttaatttgtg   6780
aaatttgtga tgctattgct taatttgtaa ccattataag ctgcaataaa caagttaata   6840
aaacatttgc attcatttta tgtttcaggt tcagggggag atgtgggagg tttttaaag    6900
caagtaaaac ctctacaaat gtggtatcta gagctcttcc aaatagatct ggaaggtgct   6960
gaggtacgat gagacccgca ccaggtgcag accctgcgag tgtggcggta aacatattag   7020
gaaccagcct gtgatgctgg atgtgaccga ggagctgagg cccgatcact tggtgctggc   7080
ctgcacccgc gctgagtttg gctctagcga tgaagataca gattgaggta ctgaaatgtg   7140
tgggcgtggc ttaagggtgg gaaagaatat ataaggtggg ggtcttatgt agttttgtat   7200
ctgttttgca gcagccgccg ccgccatgag caccaactcg tttgatggaa gcattgtgag   7260
ctcatatttg acaacgcgca tgcccccatg ggccggggtg cgtcagaatg tgatgggctc   7320
cagcattgat ggtcgccccg tcctgcccgc aaactctact accttgacct acgagaccgt   7380
gtctggaacg ccgttggaga ctgcagcctc cgccgccgct tcagccgctg cagccaccgc   7440
ccgcgggatt gtgactgact ttgctttcct gagcccgctt gcaagcagtg cagcttcccg   7500
ttcatccgcc cgcgatgaca agttgacggc tcttttggca caattggatt ctttgacccg   7560
ggaacttaat gtcgtttctc agcagctgtt ggatctgcgc cagcaggttt ctgccctgaa   7620
ggcttcctcc cctcccaatg cggtttaaaa cataaataaa aaccagact ctgtttggat    7680
ttggatcaag caagtgtctt gctgtcttta tttaggggtt ttgcgcgcgc ggtaggcccg   7740
ggaccagcgg tctcggtcgt tgagggtcct gtgtattttt tccaggacgt ggtaaaggtg   7800
actctggatg ttcagataca tgggcataag cccgtctctg gggtggaggt agcaccactg   7860
cagagcttca tgctgcgggg tggtgttgta gatgatccag tcgtagcagg agcgctgggc   7920
gtggtgccta aaaatgtctt tcagtagcaa gctgattgcc aggggcaggc ccttggtgta   7980
agtgtttaca aagcggttaa gctgggatgg gtgcatacgt ggggatatga gatgcatctt   8040
ggactgtatt tttaggttgg ctatgttccc agccatatcc ctccggggat tcatgttgtg   8100
```

-continued

```
cagaaccacc agcacagtgt atccggtgca cttgggaaat ttgtcatgta gcttagaagg   8160
aaatgcgtgg aagaacttgg agacgccctt gtgacctcca agattttcca tgcattcgtc   8220
cataatgatg gcaatgggcc cacgggcggc ggcctgggcg aagatatttc tgggatcact   8280
aacgtcatag ttgtgttcca ggatgagatc gtcataggcc atttttacaa agcgcgggcg   8340
gagggtgcca gactgcggta taatggttcc atccggccca ggggcgtagt taccctcaca   8400
gatttgcatt tcccacgctt tgagttcaga tgggggggatc atgtctacct gcggggcgat   8460
gaagaaaacg gtttccgggg taggggagat cagctgggaa gaaagcaggt tcctgagcag   8520
ctgcgactta ccgcagccgg tgggcccgta aatcacacct attaccgggt gcaactggta   8580
gttaagagag ctgcagctgc cgtcatccct gagcaggggg gccacttcgt taagcatgtc   8640
cctgactcgc atgttttccc tgaccaaatc cgccagaagg cgctcgccgc ccagcgatag   8700
cagttcttgc aaggaagcaa agtttttcaa cggtttgaga ccgtccgccg taggcatgct   8760
tttgagcgtt tgaccaagca gttccaggcg gtcccacagc tcggtcacct gctctacggc   8820
atctcgatcc agcatatctc ctcgtttcgc gggttggggc ggctttcgct gtacggcagt   8880
agtcggtgct cgtccagacg ggccagggtc atgtctttcc acgggcgcag ggtcctcgtc   8940
agcgtagtct gggtcacggt gaaggggtgc gctccgggct gcgcgctggc cagggtgcgc   9000
ttgaggctgg tcctgctggt gctgaagcgc tgccggtctt cgccctgcgc gtcggccagg   9060
tagcatttga ccatggtgtc atagtccagc ccctccgcgg cgtggccctt ggcgcgcagc   9120
ttgcccttgg aggaggcgcc gcacgagggg cagtgcagac ttttgagggc gtagagcttg   9180
ggcgcgagaa ataccgattc cggggagtag gcatccgcgc cgcaggcccc gcagacggtc   9240
tcgcattcca cgagccaggt gagctctggc cgttcggggt caaaaaccag gtttccccca   9300
tgctttttga tgcgtttctt acctctggtt tccatgagcc ggtgtccacg ctcggtgacg   9360
aaaaggctgt ccgtgtcccc gtatacagac ttgagaggcc tgtcctcgac cgatgccctt   9420
gagagccttc aacccagtca gctccttccg gtgggcgcgg ggcatgacta tcgtcgccgc   9480
acttatgact gtcttcttta tcatgcaact cgtaggacag gtgccggcag cgctctgggt   9540
cattttcggc gaggaccgct ttcgctggag cgcgacgatg atcggcctgt cgcttgcggt   9600
attcggaatc ttgcacgccc tcgctcaagc cttcgtcact ggtcccgcca ccaaacgttt   9660
cggcgagaag caggccatta tcgccggcat ggcggccgac gcgctgggct acgtcttgct   9720
ggcgttcgcg acgcgaggct ggatggcctt ccccattatg attcttctcg cttccggcgg   9780
catcgggatg cccgcgttgc aggccatgct gtccaggcag gtagatgacg accatcaggg   9840
acagcttcaa ggccagcaaa aggccaggaa ccgtaaaaag gccgcgttgc tggcgttttt   9900
ccataggctc cgcccccctg acgagcatca caaaaatcga cgctcaagtc agaggtggcg   9960
aaacccgaca ggactataaa gataccaggc gtttccccct ggaagctccc tcgtgcgctc  10020
tcctgttccg accctgccgc ttaccggata cctgtccgcc tttctccctt cgggaagcgt  10080
ggcgctttct catagctcac gctgtaggta tctcagttcg gtgtaggtcg ttcgctccaa  10140
gctgggctgt gtgcacgaac cccccgttca gcccgaccgc tgcgccttat ccggtaacta  10200
tcgtcttgag tccaacccgg taagacacga cttatcgcca ctggcagcag ccactggtaa  10260
caggattagc agagcgaggt atgtaggcgg tgctacagag ttcttgaagt ggtggcctaa  10320
ctacggctac actagaagga cagtatttgg tatctgcgct ctgctgaagc cagttacctt  10380
cggaaaaaga gttggtagct cttgatccgg caaacaaacc accgctggta gcggtggttt  10440
```

-continued ttttgtttgc aagcagcaga ttacgcgcag aaaaaaagga tctcaagaag atcctttgat 10500
cttttctacg gggtctgacg ctcagtggaa cgaaaactca cgttaaggga ttttggtcat 10560
gagattatca aaaaggatct tcacctagat ccttttaaat taaaaatgaa gttttaaatc 10620
aatctaaagt atatatgagt aaacttggtc tgacagttac caatgcttaa tcagtgaggc 10680
acctatctca gcgatctgtc tatttcgttc atccatagtt gcctgactcc ccgtcgtgta 10740
gataactacg atacgggagg gcttaccatc tggccccagt gctgcaatga taccgcgaga 10800
cccacgctca ccggctccag atttatcagc aataaaccag ccagccggaa gggccgagcg 10860
cagaagtggt cctgcaactt tatccgcctc catccagtct attaattgtt gccgggaagc 10920
tagagtaagt agttcgccag ttaatagttt gcgcaacgtt gttgccattg ctgcaggcat 10980
cgtggtgtca cgctcgtcgt ttggtatggc ttcattcagc tccggttccc aacgatcaag 11040
gcgagttaca tgatccccca tgttgtgcaa aaaagcggtt agctccttcg gtcctccgat 11100
cgttgtcaga agtaagttgg ccgcagtgtt atcactcatg gttatggcag cactgcataa 11160
ttctcttact gtcatgccat ccgtaagatg cttttctgtg actggtgagt actcaaccaa 11220
gtcattctga gaatagtgta tgcggcgacc gagttgctct tgcccggcgt caacacggga 11280
taataccgcg ccacatagca gaactttaaa agtgctcatc attggaaaac gttcttcggg 11340
gcgaaaactc tcaaggatct taccgctgtt gagatccagt tcgatgtaac ccactcgtgc 11400
acccaactga tcttcagcat cttttacttt caccagcgtt tctgggtgag caaaaacagg 11460
aaggcaaaat gccgcaaaaa agggaataag ggcgacacgg aaatgttgaa tactcatact 11520
cttccttttt caatattatt gaagcattta tcagggttat tgtctcatga gcggatacat 11580
atttgaatgt atttagaaaa a 11601

<210> SEQ ID NO 6
<211> LENGTH: 12270
<212> TYPE: DNA
<213> ORGANISM: Artificial Sequence
<220> FEATURE:
<223> OTHER INFORMATION: Synthetic hIL-12

<400> SEQUENCE: 6
taaacaaata ggggttccgc gcacatttcc ccgaaaagtg ccacctgacg tctaagaaac 60
cattattatc atgacattaa cctataaaaa taggcgtatc acgaggccct ttcgtcttca 120
attaatcgca ccggtatcta tgtcgggtgc ggagaaagag gtaatgaaat ggcagctagc 180
atcatcaata atatacctta ttttggattg aagccaatat gataatgagg gggtggagtt 240
tgtgacgtgg cgcggggcgt gggaacgggg cgggtgacgt agtagtgtgg cggaagtgtg 300
atgttgcaag tgtggcggaa cacatgtaag cgacggatgt ggcaaaagtg acgtttttgg 360
tgtgcgccgg tgtacacagg aagtgacaat tttcgcgcgg ttttaggcgg atgttgtagt 420
aaatttgggc gtaaccgagt aagatttggc cattttcgcg ggaaaactga ataagaggaa 480
gtgaaatctg aataattttg tgttactcat agcgcgtaat atttgtctag ggagatccgg 540
taccgatatc ctagacaacg atgctgagct aactataacg gtcctaaggt agcgaccgcg 600
gagactaggt gtatttatct aagcgatcgc ttaattaagg ccggccgccg caataaaata 660
tctttatttt cattacatct gtgtgttggt tttttgtgtg aatcgatagt actaacatac 720
gctctccatc aaaacaaaac gaaacaaaac aaactagcaa aataggctgt ccccagtgca 780
agtgcaggtg ccagaacatt tctctatcga taatgcaggt cggagtactg tcctccgagc 840
ggagtactgt cctccgagcg gagtactgtc ctccgagcgg agtactgtcc tccgagcgga 900

-continued

```
gtactgtcct ccgagcggag tactgtcctc cgagcggaga ctcttcgaag gaagaggggc     960
ggggtcgatc gaccccgccc ctcttccttc gaaggaagag gggcggggtc gaagacctag    1020
agggtatata atgggtgcct tagctggtgt gtgagctcat cttcctgtag atcacgcgtc    1080
gaagaaggtg agtaatctta acatgctctt tttttttttt tttgctaatc ccttttgtgt    1140
gctgatgtta ggatgacatt tacaacaaat gtttgttcct gacaggaaaa accttgctgg    1200
gtaccttcgt tgccggacac ttcttgtcct ctactttgga aaaaaggaat tgagagccgc    1260
tagcgccacc atgggtcacc agcagttggt catctcttgg ttttccctgg tttttctggc    1320
atctcccctc gtggccatat gggaactgaa gaaagatgtt tatgtcgtag aattggattg    1380
gtatccggat gcccctggag aaatggtggt cctcacctgt gacacccctg aagaagatgg    1440
tatcacctgg accttggacc agagcagtga ggtcttaggc tctggcaaaa ccctgaccat    1500
ccaagtcaaa gagtttggag atgctggcca gtacacctgt cacaaaggag gcgaggttct    1560
aagccattcg ctcctgctgc ttcacaaaaa ggaagatgga atttggtcca ctgatatttt    1620
aaaggaccag aaagaaccca aaaataagac ctttctaaga tgcgaggcca agaattattc    1680
tggacgtttc acctgctggt ggctgacgac aatcagtact gatttgacat tcagtgtcaa    1740
aagcagcaga ggctcttctg acccccaagg ggtgacgtgc ggagctgcta cactctctgc    1800
agagagagtc agaggggaca acaaggagta tgagtactca gtggagtgcc aggaggacag    1860
tgcctgccca gctgctgagg agagtctgcc cattgaggtc atggtggatg ccgttcacaa    1920
gctcaagtat gaaaactaca ccagcagctt cttcatcagg gacatcatca aacctgaccc    1980
acccaagaac ttgcagctga agccattaaa gaattctcgg caggtggagg tcagctggga    2040
gtaccctgac acctggagta ctccacattc ctacttctcc ctgacattct gcgttcaggt    2100
ccagggcaag agcaagagag aaaagaaaga tagagtcttc acggacaaga cctcagccac    2160
ggtcatctgc cgcaaaaatg ccagcattag cgtgcgggcc caggaccgct actatagctc    2220
atcttggagc gaatgggcat ctgtgccctg cagttaggtt gggcgagctc gaattcattg    2280
atcccccggg ctgcaggaat tcgatatcaa gctcgggatc cgaattccgc cccccccccc    2340
cccccccccc taacgttact ggccgaagcc gcttggaata aggccggtgt gcgtttgtct    2400
atatgttatt ttccaccata ttgccgtctt ttggcaatgt gagggcccgg aaacctggcc    2460
ctgtcttctt gacgagcatt cctaggggtc tttcccctct cgccaaagga atgcaaggtc    2520
tgttgaatgt cgtgaaggaa gcagttcctc tggaagcttc ttgaagacaa acaacgtctg    2580
tagcgaccct ttgcaggcag cggaaccccc cacctggcga caggtgcctc tgcggccaaa    2640
agccacgtgt ataagataca cctgcaaagg cggcacaacc ccagtgccac gttgtgagtt    2700
ggatagttgt ggaaagagtc aaatggctct cctcaagcgt attcaacaag gggctgaagg    2760
atgcccagaa ggtaccccat tgtatgggat ctgatctggg gcctcggtgc acatgcttta    2820
catgtgttta gtcgaggtta aaaaaacgtc taggcccccc gaaccacggg gacgtggttt    2880
tcctttgaaa aacacgatga taatatggcc acaaccatgg gtccagcgcg cagcctcctc    2940
cttgtggcta ccctggtcct cctggaccac ctcagtttgg ccagaaacct ccccgtggcc    3000
actccagacc caggaatgtt cccatgcctt caccactccc aaaacctgct gagggccgtc    3060
agcaacatgc tccagaaggc cagacaaact ctagaatttt acccttgcac ttctgaagag    3120
attgatcatg aagatatcac aaaagataaa accagcacag tggaggcctg tttaccattg    3180
gaattaacca agaatgagag ttgcctaaat tccagagaga cctctttcat aactaatggg    3240
```

-continued

```
agttgcctgg cctccagaaa gacctctttt atgatggccc tgtgccttag tagtatttat   3300
gaagacttga agatgtacca ggtggagttc aagaccatga atgcaaagct tctgatggat   3360
cctaagaggc agatctttct agatcaaaac atgctggcag ttattgatga gctgatgcag   3420
gccctgaatt tcaacagtga gactgtgcca caaaaatcct cccttgaaga accggatttt   3480
tataaaacta aaatcaagct ctgcatactt cttcatgctt tcagaattcg ggcagtgact   3540
attgatagag tgatgagcta tctgaatgct tcctaaatcg attgcgcaaa gctttcgcga   3600
taggcgagac caatgggtgt gtacgtagcg gccgctcgag aacttgttta ttgcagctta   3660
taatggttac aaataaagca atagcatcac aaatttcaca aataaagcat ttttttcact   3720
gcattctagt tgtggtttgt ccaaactcat caatgtatct tatcatgtct cgtacggcgt   3780
ggtaggtccg aacgaatcca tggattaccc tgttatccct atccggagtt aacctcgagg   3840
acttcggaac ttctagaacc agaccgttca gtttaaacgc tcttctcccc ctcgagggcc   3900
tccgcgccgg gttttggcgc ctcccgcggg cgcccccctc ctcacggcga gcgctgccac   3960
gtcagacgaa gggcgcagcg agcgtcctga tccttccgcc cggacgctca ggacagcggc   4020
ccgctgctca taagactcgg ccttagaacc ccagtatcag cagaaggaca ttttaggacg   4080
ggacttgggt gactctaggg cactggtttt ctttccagag agcggaacag gcgaggaaaa   4140
gtagtccctt ctcggcgatt ctgcggaggg atctccgtgg ggcggtgaac gccgatgatt   4200
atataaggac gcgccgggtg tggcacagct agttccgtcg cagccgggat ttgggtcgcg   4260
gttcttgttt gtggatcgct gtgatcgtca cttggtgagt agcgggctgc tgggctgggt   4320
acgtgcgctc ggggttggcg agtgtgtttt gtgaagtttt ttaggcacct tttgaaatgt   4380
aatcatttgg gtcaatatgt aattttcagt gttagactag taaattgtcc gctaaattct   4440
ggccgttttt ggcttttttg ttagacggca tgcggggggg ggggggggca attggccacc   4500
atgggcccca agaagaaaag gaaggtggcc ccccccaccg acgtgagcct gggcgacgag   4560
ctgcacctgg acggcgagga cgtggccatg gcccacgccg acgccctgga cgacttcgac   4620
ctggacatgc tgggcgacgg cgacagcccc ggccccggct tcacccccca cgacagcgcc   4680
ccctacggcg ccctggacat ggccgacttc gagttcgagc agatgttcac cgacgccctg   4740
ggcatcgacg agtacggcgg ccatatggag atgcccgtgg acaggattct ggaggccgaa   4800
ctcgccgtgg agcagaaaag cgaccagggc gtggagggcc ccggcggaac cggcggcagc   4860
ggcagcagcc ccaacgaccc cgtgaccaac atctgccagg ccgccgacaa gcagctgttc   4920
accctggtgg agtgggccaa gaggattccc cacttcagca gcctgcccct ggacgaccag   4980
gtgatcctgc tgagggccgg atggaacgag ctgctgatcg ccagcttcag ccacaggagc   5040
atcgacgtga gggacggcat cctgctggcc accggcctgc acgtccatag gaacagcgcc   5100
cacagcgccg gagtgggcgc catcttcgac agggtgctga ccgagctggt gagcaagatg   5160
agggacatga ggatggacaa gaccgagctg ggctgcctga gggccatcat cctgttcaac   5220
cccgaggtga ggggcctgaa aagcgcccag gaggtggagc tgctgaggga gaaggtgtac   5280
gccgccctgg aggagtacac caggaccacc caccccgacg agcccggcag attcgccaag   5340
ctgctgctga ggctgcccag cctgaggagc atcggcctga agtgcctgga gcacctgttc   5400
ttcttcaggc tgatcggcga cgtgcccatc gacaccttcc tgatggagat gctggagagc   5460
cccagcgaca gctgagccgg caactcgctg tagtaattcc agcgagaggc agagggagcg   5520
agcgggcggc gggctagggt ggaggagccc ggcgagcaga gctgcgctgc gggcgtcctg   5580
ggaagggaga tccggagcga atagggggct tcgcctctgg cccagccctc ccgctgatcc   5640
```

```
cccagccagc ggtgcgcaac cctagccgca tccacgaaac tttgcccata gcagcgggcg   5700
ggcactttgc actggaactt acaacacccg agcaaggacg cgactctccc gacgcgggga   5760
ggctattctg cccatttggg gacacttccc cgccgctgcc aggacccgct tctctgaaag   5820
gctctccttg cagctgctta gacgctggat ttttttcggg tagtggaaaa ccagcagcct   5880
cccgcgacca gatctgccac catgaagctg ctgagcagca tcgagcaggc ttgcgacatc   5940
tgcaggctga agaagctgaa gtgcagcaag gagaagccca agtgcgccaa gtgcctgaag   6000
aacaactggg agtgcagata cagccccaag accaagagga gcccccctgac caggcccac   6060
ctgaccgagg tggagagcag gctggagagg ctggagcagc tgttcctgct gatcttcccc   6120
agggaggacc tggacatgat cctgaagatg gacagcctgc aagacatcaa ggccctgctg   6180
accggcctgt tcgtgcagga caacgtgaac aaggacgccg tgaccgacag gctggccagc   6240
gtggagaccg acatgcccct gaccctgagg cagcacagga tcagcgccac cagcagcagc   6300
gaggagagca gcaacaaggg ccagaggcag ctgaccgtga gccccgagtt tcccgggatc   6360
aggcccgagt gcgtggtgcc cgagacccag tgcgccatga aaaggaagga gaagaaggcc   6420
cagaaggaga aggacaagct gcccgtgagc accaccaccg tcgatgacca catgcccccc   6480
atcatgcagt gcgagccccc cccccccgag gccgccagga ttcacgaggt cgtgcccagg   6540
ttcctgagcg acaagctgct ggtgaccaac aggcagaaga acatccccca gctgaccgcc   6600
aaccagcagt tcctgatcgc caggctgatc tggtatcagg acggctacga gcagcccagc   6660
gacgaggacc tgaaaaggat cacccagacc tggcagcagg ccgacgacga gaacgaggag   6720
agcgacaccc ccttcaggca gatcaccgag atgaccatcc tgaccgtgca gctgatcgtg   6780
gagttcgcca agggcctgcc cggattcgcc aagatcagcc agcccgacca gatcaccctg   6840
ctgaaggctt gcagcagcga ggtgatgatg ctgagggtgg ccaggaggta cgacgccgcc   6900
agcgacagca tcctgttcgc caacaaccag gcttacacca gggacaacta caggaaggct   6960
ggcatggccg aggtgatcga ggacctcctg cacttctgca gatgtatgta cagcatggcc   7020
ctggacaaca tccactacgc cctgctgacc gccgtggtga tcttcagcga caggcccggc   7080
ctggagcagc cccagctggt ggaggagatc cagaggtact acctgaacac cctgaggatc   7140
tacatcctga accagctgag cggcagcgcc aggagcagcg tgatctacgg caagatcctg   7200
agcatcctga gcgagctgag gaccctggga atgcagaaca gcaatatgtg tatcagcctg   7260
aagctgaaga acaggaagct gccccccttc ctggaggaga tttgggacgt ggccgacatg   7320
agccacaccc agcccccccc catcctggag agccccacca acctgtgaat cgattagaca   7380
tgataagata cattgatgag tttggacaaa ccacaactag aatgcagtga aaaaaatgct   7440
taatttgtga aatttgtgat gctattgctt aatttgtaac cattataagc tgcaataaac   7500
aagttaataa aacatttgca ttcattttat gtttcaggtt cagggggaga tgtgggaggt   7560
tttttaaagc aagtaaaacc tctacaaatg tggtatctag agctcttcca aatagatctg   7620
gaaggtgctg aggtacgatg agacccgcac caggtgcaga ccctgcgagt gtggcggtaa   7680
acatattagg aaccagcctg tgatgctgga tgtgaccgag gagctgaggc ccgatcactt   7740
ggtgctggcc tgcacccgcg ctgagtttgg ctctagcgat gaagatacag attgaggtac   7800
tgaaatgtgt gggcgtggct taagggtggg aaagaatata taaggtgggg gtcttatgta   7860
gttttgtatc tgttttgcag cagccgccgc cgccatgagc accaactcgt ttgatggaag   7920
cattgtgagc tcatatttga caacgcgcat gcccccatgg gccggggtgc gtcagaatgt   7980
```

-continued

```
gatgggctcc agcattgatg gtcgccccgt cctgcccgca aactctacta ccttgaccta   8040
cgagaccgtg tctggaacgc cgttggagac tgcagcctcc gccgccgctt cagccgctgc   8100
agccaccgcc cgcgggattg tgactgactt tgctttcctg agcccgcttg caagcagtgc   8160
agcttcccgt tcatccgccc gcgatgacaa gttgacggct cttttggcac aattggattc   8220
tttgacccgg gaacttaatg tcgtttctca gcagctgttg gatctgcgcc agcaggtttc   8280
tgccctgaag gcttcctccc ctcccaatgc ggtttaaaac ataaataaaa aaccagactc   8340
tgtttggatt tggatcaagc aagtgtcttg ctgtctttat ttaggggttt tgcgcgcgcg   8400
gtaggcccgg gaccagcggt ctcggtcgtt gagggtcctg tgtatttttt ccaggacgtg   8460
gtaaaggtga ctctggatgt tcagatacat gggcataagc ccgtctctgg ggtggaggta   8520
gcaccactgc agagcttcat gctgcggggt ggtgttgtag atgatccagt cgtagcagga   8580
gcgctgggcg tggtgcctaa aaatgtcttt cagtagcaag ctgattgcca ggggcaggcc   8640
cttggtgtaa gtgtttacaa agcggttaag ctgggatggg tgcatacgtg gggatatgag   8700
atgcatcttg gactgtattt ttaggttggc tatgttccca gccatatccc tccggggatt   8760
catgttgtgc agaaccacca gcacagtgta tccggtgcac ttgggaaatt tgtcatgtag   8820
cttagaagga aatgcgtgga agaacttgga gacgcccttg tgacctccaa gattttccat   8880
gcattcgtcc ataatgatgg caatgggccc acgggcggcg gcctgggcga agatatttct   8940
gggatcacta acgtcatagt tgtgttccag gatgagatcg tcataggcca tttttacaaa   9000
gcgcgggcgg agggtgccag actgcggtat aatggttcca tccggcccag gggcgtagtt   9060
accctcacag atttgcattt cccacgcttt gagttcagat ggggggatca tgtctacctg   9120
cggggcgatg aagaaaacgg tttccggggt aggggagatc agctgggaag aaagcaggtt   9180
cctgagcagc tgcgacttac cgcagccggt gggcccgtaa atcacaccta ttaccgggtg   9240
caactggtag ttaagagagc tgcagctgcc gtcatccctg agcagggggg ccacttcgtt   9300
aagcatgtcc ctgactcgca tgttttccct gaccaaatcc gccagaaggc gctcgccgcc   9360
cagcgatagc agttcttgca aggaagcaaa gtttttcaac ggtttgagac cgtccgccgt   9420
aggcatgctt ttgagcgttt gaccaagcag ttccaggcgg tcccacagct cggtcacctg   9480
ctctacggca tctcgatcca gcatatctcc tcgtttcgcg ggttggggcg gctttcgctg   9540
tacggcagta gtcggtgctc gtccagacgg gccagggtca tgtctttcca cgggcgcagg   9600
gtcctcgtca gcgtagtctg ggtcacggtg aaggggtgcg ctccgggctg cgcgctggcc   9660
agggtgcgct tgaggctggt cctgctggtg ctgaagcgct gccggtcttc gccctgcgcg   9720
tcggccaggt agcatttgac catggtgtca tagtccagcc cctccgcggc gtggcccttg   9780
gcgcgcagct tgcccttgga ggaggcgccg cacgaggggc agtgcagact tttgagggcg   9840
tagagcttgg gcgcgagaaa taccgattcc ggggagtagg catccgcgcc gcaggccccg   9900
cagacggtct cgcattccac gagccaggtg agctctggcc gttcggggtc aaaaaccagg   9960
tttcccccat gctttttgat gcgtttctta cctctggttt ccatgagccg gtgtccacgc  10020
tcggtgacga aaaggctgtc cgtgtccccg tatacagact tgagaggcct gtcctcgacc  10080
gatgcccttg agagccttca acccagtcag ctccttccgg tgggcgcggg gcatgactat  10140
cgtcgccgca cttatgactg tcttctttat catgcaactc gtaggacagg tgccggcagc  10200
gctctgggtc attttcggcg aggaccgctt tcgctggagc gcgacgatga tcggcctgtc  10260
gcttgcggta ttcggaatct tgcacgccct cgctcaagcc ttcgtcactg gtcccgccac  10320
caaacgtttc ggcgagaagc aggccattat cgccggcatg gcggccgacg cgctgggcta  10380
```

cgtcttgctg gcgttcgcga cgcgaggctg gatggccttc cccattatga ttcttctcgc 10440
ttccggcggc atcgggatgc ccgcgttgca ggccatgctg tccaggcagg tagatgacga 10500
ccatcaggga cagcttcaag gccagcaaaa ggccaggaac cgtaaaaagg ccgcgttgct 10560
ggcgtttttc cataggctcc gcccccctga cgagcatcac aaaaatcgac gctcaagtca 10620
gaggtggcga aacccgacag gactataaag ataccaggcg tttccccctg gaagctccct 10680
cgtgcgctct cctgttccga ccctgccgct taccggatac ctgtccgcct ttctcccttc 10740
gggaagcgtg gcgctttctc atagctcacg ctgtaggtat ctcagttcgg tgtaggtcgt 10800
tcgctccaag ctgggctgtg tgcacgaacc ccccgttcag cccgaccgct gcgccttatc 10860
cggtaactat cgtcttgagt ccaacccggt aagacacgac ttatcgccac tggcagcagc 10920
cactggtaac aggattagca gagcgaggta tgtaggcggt gctacagagt tcttgaagtg 10980
gtggcctaac tacggctaca ctagaaggac agtatttggt atctgcgctc tgctgaagcc 11040
agttaccttc ggaaaaagag ttggtagctc ttgatccggc aaacaaacca ccgctggtag 11100
cggtggtttt tttgtttgca agcagcagat tacgcgcaga aaaaaaggat ctcaagaaga 11160
tcctttgatc ttttctacgg ggtctgacgc tcagtggaac gaaaactcac gttaagggat 11220
tttggtcatg agattatcaa aaaggatctt cacctagatc cttttaaatt aaaaatgaag 11280
ttttaaatca atctaaagta tatatgagta aacttggtct gacagttacc aatgcttaat 11340
cagtgaggca cctatctcag cgatctgtct atttcgttca tccatagttg cctgactccc 11400
cgtcgtgtag ataactacga tacgggaggg cttaccatct ggccccagtg ctgcaatgat 11460
accgcgagac ccacgctcac cggctccaga tttatcagca ataaaccagc cagccggaag 11520
ggccgagcgc agaagtggtc ctgcaacttt atccgcctcc atccagtcta ttaattgttg 11580
ccgggaagct agagtaagta gttcgccagt taatagtttg cgcaacgttg ttgccattgc 11640
tgcaggcatc gtggtgtcac gctcgtcgtt tggtatggct tcattcagct ccggttccca 11700
acgatcaagg cgagttacat gatcccccat gttgtgcaaa aaagcggtta gctccttcgg 11760
tcctccgatc gttgtcagaa gtaagttggc cgcagtgtta tcactcatgg ttatggcagc 11820
actgcataat tctcttactg tcatgccatc cgtaagatgc ttttctgtga ctggtgagta 11880
ctcaaccaag tcattctgag aatagtgtat gcggcgaccg agttgctctt gcccggcgtc 11940
aacacgggat aataccgcgc cacatagcag aactttaaaa gtgctcatca ttggaaaacg 12000
ttcttcgggg cgaaaactct caaggatctt accgctgttg agatccagtt cgatgtaacc 12060
cactcgtgca cccaactgat cttcagcatc ttttactttc accagcgttt ctgggtgagc 12120
aaaaacagga aggcaaaatg ccgcaaaaaa gggaataagg gcgacacgga aatgttgaat 12180
actcatactc ttcctttttc aatattattg aagcatttat cagggttatt gtctcatgag 12240
cggatacata tttgaatgta tttagaaaaa 12270

<210> SEQ ID NO 7
<211> LENGTH: 10404
<212> TYPE: DNA
<213> ORGANISM: Artificial Sequence
<220> FEATURE:
<223> OTHER INFORMATION: Synthetic mIL-21

<400> SEQUENCE: 7
taaacaaata ggggttccgc gcacatttcc ccgaaaagtg ccacctgacg tctaagaaac 60
cattattatc atgacattaa cctataaaaa taggcgtatc acgaggccct ttcgtcttca 120

```
attaatcgca ccggtatcta tgtcgggtgc ggagaaagag gtaatgaaat ggcagctagc    180
atcatcaata atataccta ttttggattg aagccaatat gataatgagg gggtggagtt    240
tgtgacgtgg cgcggggcgt gggaacgggg cgggtgacgt agtagtgtgg cggaagtgtg    300
atgttgcaag tgtggcggaa cacatgtaag cgacggatgt ggcaaaagtg acgtttttgg    360
tgtgcgccgg tgtacacagg aagtgacaat tttcgcgcgg ttttaggcgg atgttgtagt    420
aaatttgggc gtaaccgagt aagatttggc cattttcgcg ggaaaactga ataagaggaa    480
gtgaaatctg aataattttg tgttactcat agcgcgtaat atttgtctag ggagatccgg    540
taccgatatc ctagacaacg atgctgagct aactataacg gtcctaaggt agcgaccgcg    600
gagactaggt gtatttatct aagcgatcgc ttaattaagg ccggccgccg caataaaata    660
tctttatttt cattacatct gtgtgttggt tttttgtgtg aatcgatagt actaacatac    720
gctctccatc aaaacaaaac gaaacaaaac aaactagcaa aataggctgt ccccagtgca    780
agtgcaggtg ccagaacatt tctctatcga taatgcaggt cggagtactg tcctccgagc    840
ggagtactgt cctccgagcg gagtactgtc ctccgagcgg agtactgtcc tccgagcgga    900
gtactgtcct ccgagcggag tactgtcctc cgagcggaga ctcttcgaag gaagaggggc    960
ggggtcgatc gaccccgccc ctcttccttc gaaggaagag gggcggggtc gaagacctag   1020
agggtatata atgggtgcct tagctggtgt gtgagctcat cttcctgtag atcacgcgtc   1080
gaagaaggtg agtaatctta acatgctctt tttttttttt tttgctaatc ccttttgtgt   1140
gctgatgtta ggatgacatt tacaacaaat gtttgttcct gacaggaaaa accttgctgg   1200
gtaccttcgt tgccggacac ttcttgtcct ctactttgga aaaaaggaat tgagagccgc   1260
tagcccacca tggagaggac cctggtgtgc ctggtggtga tcttcctggg caccgtggcc   1320
cacaagagca gcccccaggg acccgacagg ctgctgatcc ggctgagaca cctgatcgac   1380
atcgtggagc agctgaagat ttacgagaac gacctggacc ccgagctgct gtccgccccc   1440
caggacgtga agggccactg cgagcacgcc gccttcgcct gcttccagaa ggccaagctg   1500
aagcccagca accccggcaa caacaagacc ttcatcatcg acctggtggc ccagctgaga   1560
aggaggctgc ccgccaggag gggcggcaag aagcagaagc acatcgccaa gtgccccagc   1620
tgcgacagct acgagaagcg gacccccaag gagttcctgg agaggctgaa gtggctgctg   1680
caaaagatga tccaccagca cctgagctga atcgattgcg caaagctttc gcgataggcg   1740
agaccaatgg gtgtgtacgt agcggccgct cgagaacttg tttattgcag cttataatgg   1800
ttacaaataa agcaatagca tcacaaattt cacaaataaa gcattttttt cactgcattc   1860
tagttgtggt ttgtccaaac tcatcaatgt atcttatcat gtctcgtacg gcgtggtagg   1920
tccgaacgaa tccatggatt accctgttat ccctatccgg agttaacctc gaggacttcg   1980
gaacttctag aaccagaccg ttcagtttaa acgctcttct ccccctcgag ggcctccgcg   2040
ccgggttttg gcgcctcccg cgggcgcccc cctcctcacg gcgagcgctg ccacgtcaga   2100
cgaagggcgc agcgagcgtc ctgatccttc cgcccggacg ctcaggacag cggcccgctg   2160
ctcataagac tcggccttag aaccccagta tcagcagaag gacattttag gacgggactt   2220
gggtgactct agggcactgg ttttctttcc agagagcgga acaggcgagg aaaagtagtc   2280
ccttctcggc gattctgcgg agggatctcc gtggggcggt gaacgccgat gattatataa   2340
ggacgcgccg ggtgtggcac agctagttcc gtcgcagccg ggatttgggt cgcggttctt   2400
gtttgtggat cgctgtgatc gtcacttggt gagtagcggg ctgctgggct gggtacgtgc   2460
gctcggggtt ggcgagtgtg ttttgtgaag ttttttaggc accttttgaa atgtaatcat   2520
```

ttgggtcaat atgtaatttt cagtgttaga ctagtaaatt gtccgctaaa ttctggccgt 2580
ttttggcttt tttgttagac ggcatgcggg gggggggggg ggcaattggc caccatgggc 2640
cccaagaaga aaaggaaggt ggcccccccc accgacgtga gcctgggcga cgagctgcac 2700
ctggacggcg aggacgtggc catggcccac gccgacgccc tggacgactt cgacctggac 2760
atgctgggcg acggcgacag ccccggcccc ggcttcaccc cccacgacag cgccccctac 2820
ggcgccctgg acatggccga cttcgagttc gagcagatgt tcaccgacgc cctgggcatc 2880
gacgagtacg gcggccatat ggagatgccc gtggacagga ttctggaggc cgaactcgcc 2940
gtggagcaga aaagcgacca gggcgtggag ggcccccggcg gaaccggcgg cagcggcagc 3000
agccccaacg accccgtgac caacatctgc caggccgccg acaagcagct gttcaccctg 3060
gtggagtggg ccaagaggat tccccacttc agcagcctgc ccctggacga ccaggtgatc 3120
ctgctgaggg ccggatggaa cgagctgctg atcgccagct tcagccacag gagcatcgac 3180
gtgagggacg gcatcctgct ggccaccggc ctgcacgtcc ataggaacag cgcccacagc 3240
gccggagtgg gcgccatctt cgacagggtg ctgaccgagc tggtgagcaa gatgagggac 3300
atgaggatgg acaagaccga gctgggctgc ctgagggcca tcatcctgtt caaccccgag 3360
gtgaggggcc tgaaaagcgc ccaggaggtg gagctgctga gggagaaggt gtacgccgcc 3420
ctggaggagt acaccaggac cacccacccc gacgagcccg gcagattcgc caagctgctg 3480
ctgaggctgc ccagcctgag gagcatcggc ctgaagtgcc tggagcacct gttcttcttc 3540
aggctgatcg gcgacgtgcc catcgacacc ttcctgatgg agatgctgga gagcccccagc 3600
gacagctgag ccggcaactc gctgtagtaa ttccagcgag aggcagaggg agcgagcggg 3660
cggcgggcta gggtggagga gcccggcgag cagagctgcg ctgcgggcgt cctgggaagg 3720
gagatccgga gcgaataggg ggcttcgcct ctggcccagc cctcccgctg atcccccagc 3780
cagcggtgcg caaccctagc cgcatccacg aaactttgcc catagcagcg ggcgggcact 3840
ttgcactgga acttacaaca cccgagcaag gacgcgactc tcccgacgcg gggaggctat 3900
tctgcccatt tggggacact tccccgccgc tgccaggacc cgcttctctg aaaggctctc 3960
cttgcagctg cttagacgct ggattttttt cgggtagtgg aaaaccagca gcctcccgcg 4020
accagatctg ccaccatgaa gctgctgagc agcatcgagc aggcttgcga catctgcagg 4080
ctgaagaagc tgaagtgcag caaggagaag cccaagtgcg ccaagtgcct gaagaacaac 4140
tgggagtgca gatacagccc caagaccaag aggagccccc tgaccagggc ccacctgacc 4200
gaggtggaga gcaggctgga gaggctggag cagctgttcc tgctgatctt ccccagggag 4260
gacctggaca tgatcctgaa gatggacagc ctgcaagaca tcaaggccct gctgaccggc 4320
ctgttcgtgc aggacaacgt gaacaaggac gccgtgaccg acaggctggc cagcgtggag 4380
accgacatgc ccctgaccct gaggcagcac aggatcagcg ccaccagcag cagcgaggag 4440
agcagcaaca agggccagag gcagctgacc gtgagccccg agtttcccgg gatcaggccc 4500
gagtgcgtgg tgcccgagac ccagtgcgcc atgaaaagga aggagaagaa ggcccagaag 4560
gagaaggaca agctgcccgt gagcaccacc accgtcgatg accacatgcc ccccatcatg 4620
cagtgcgagc cccccccccc cgaggccgcc aggattcacg aggtcgtgcc caggttcctg 4680
agcgacaagc tgctggtgac caacaggcag aagaacatcc cccagctgac cgccaaccag 4740
cagttcctga tcgccaggct gatctggtat caggacggct acgagcagcc cagcgacgag 4800
gacctgaaaa ggatcaccca gacctggcag caggccgacg acgagaacga ggagagcgac 4860
acccccttca ggcagatcac cgagatgacc atcctgaccg tgcagctgat cgtggagttc 4920
gccaagggcc tgcccggatt cgccaagatc agccagcccg accagatcac cctgctgaag 4980
gcttgcagca gcgaggtgat gatgctgagg gtggccagga ggtacgacgc cgccagcgac 5040
agcatcctgt tcgccaacaa ccaggcttac accagggaca actacaggaa ggctggcatg 5100
gccgaggtga tcgaggacct cctgcacttc tgcagatgta tgtacagcat ggccctggac 5160
aacatccact acgccctgct gaccgccgtg gtgatcttca gcgacaggcc cggcctggag 5220
cagccccagc tggtggagga gatccagagg tactacctga acaccctgag gatctacatc 5280
ctgaaccagc tgagcggcag cgccaggagc agcgtgatct acggcaagat cctgagcatc 5340
ctgagcgagc tgaggaccct gggaatgcag aacagcaata tgtgtatcag cctgaagctg 5400
aagaacagga agctgccccc cttcctggag gagatttggg acgtggccga catgagccac 5460
acccagcccc cccccatcct ggagagcccc accaacctgt gaatcgatta gacatgataa 5520
gatacattga tgagtttgga caaaccacaa ctagaatgca gtgaaaaaaa tgcttaattt 5580
gtgaaatttg tgatgctatt gcttaatttg taaccattat aagctgcaat aaacaagtta 5640
ataaaacatt tgcattcatt ttatgtttca ggttcagggg gagatgtggg aggtttttta 5700
aagcaagtaa aacctctaca aatgtggtat ctagagctct tccaaataga tctggaaggt 5760
gctgaggtac gatgagaccc gcaccaggtg cagaccctgc gagtgtggcg gtaaacatat 5820
taggaaccag cctgtgatgc tggatgtgac cgaggagctg aggcccgatc acttggtgct 5880
ggcctgcacc cgcgctgagt ttggctctag cgatgaagat acagattgag gtactgaaat 5940
gtgtgggcgt ggcttaaggg tgggaaagaa tatataaggt gggggtctta tgtagttttg 6000
tatctgtttt gcagcagccg ccgccgccat gagcaccaac tcgtttgatg gaagcattgt 6060
gagctcatat ttgacaacgc gcatgccccc atgggccggg gtgcgtcaga atgtgatggg 6120
ctccagcatt gatggtcgcc ccgtcctgcc cgcaaactct actaccttga cctacgagac 6180
cgtgtctgga acgccgttgg agactgcagc ctccgccgcc gcttcagccg ctgcagccac 6240
cgcccgcggg attgtgactg actttgcttt cctgagcccg cttgcaagca gtgcagcttc 6300
ccgttcatcc gcccgcgatg acaagttgac ggctcttttg gcacaattgg attctttgac 6360
ccgggaactt aatgtcgttt ctcagcagct gttggatctg cgccagcagg tttctgccct 6420
gaaggcttcc tcccctccca atgcggttta aaacataaat aaaaaaccag actctgtttg 6480
gatttggatc aagcaagtgt cttgctgtct ttatttaggg gttttgcgcg cgcggtaggc 6540
ccgggaccag cggtctcggt cgttgagggt cctgtgtatt ttttccagga cgtggtaaag 6600
gtgactctgg atgttcagat acatgggcat aagcccgtct ctggggtgga ggtagcacca 6660
ctgcagagct tcatgctgcg gggtggtgtt gtagatgatc cagtcgtagc aggagcgctg 6720
ggcgtggtgc ctaaaaatgt ctttcagtag caagctgatt gccaggggca ggcccttggt 6780
gtaagtgttt acaaagcggt taagctggga tgggtgcata cgtggggata tgagatgcat 6840
cttggactgt atttttaggt tggctatgtt cccagccata tccctccggg gattcatgtt 6900
gtgcagaacc accagcacag tgtatccggt gcacttggga aatttgtcat gtagcttaga 6960
aggaaatgcg tggaagaact tggagacgcc cttgtgacct ccaagatttt ccatgcattc 7020
gtccataatg atggcaatgg gcccacgggc ggcggcctgg gcgaagatat ttctgggatc 7080
actaacgtca tagttgtgtt ccaggatgag atcgtcatag gccattttta caaagcgcgg 7140
gcggagggtg ccagactgcg gtataatggt tccatccggc ccaggggcgt agttaccctc 7200
acagatttgc atttcccacg ctttgagttc agatgggggg atcatgtcta cctgcggggc 7260

-continued

```
gatgaagaaa acggtttccg gggtagggga gatcagctgg gaagaaagca ggttcctgag   7320
cagctgcgac ttaccgcagc cggtgggccc gtaaatcaca cctattaccg ggtgcaactg   7380
gtagttaaga gagctgcagc tgccgtcatc cctgagcagg ggggccactt cgttaagcat   7440
gtccctgact cgcatgtttt ccctgaccaa atccgccaga aggcgctcgc cgcccagcga   7500
tagcagttct tgcaaggaag caaagttttt caacggtttg agaccgtccg ccgtaggcat   7560
gcttttgagc gtttgaccaa gcagttccag gcggtcccac agctcggtca cctgctctac   7620
ggcatctcga tccagcatat ctcctcgttt cgcgggttgg ggcggctttc gctgtacggc   7680
agtagtcggt gctcgtccag acgggccagg gtcatgtctt tccacgggcg cagggtcctc   7740
gtcagcgtag tctgggtcac ggtgaagggg tgcgctccgg gctgcgcgct ggccagggtg   7800
cgcttgaggc tggtcctgct ggtgctgaag cgctgccggt cttcgccctg cgcgtcggcc   7860
aggtagcatt tgaccatggt gtcatagtcc agcccctccg cggcgtggcc cttggcgcgc   7920
agcttgccct tggaggaggc gccgcacgag gggcagtgca gacttttgag ggcgtagagc   7980
ttgggcgcga gaaataccga ttccggggag taggcatccg cgccgcaggc cccgcagacg   8040
gtctcgcatt ccacgagcca ggtgagctct ggccgttcgg ggtcaaaaac caggtttccc   8100
ccatgctttt tgatgcgttt cttacctctg gtttccatga gccggtgtcc acgctcggtg   8160
acgaaaaggc tgtccgtgtc cccgtataca gacttgagag gcctgtcctc gaccgatgcc   8220
cttgagagcc ttcaacccag tcagctcctt ccggtgggcg cggggcatga ctatcgtcgc   8280
cgcacttatg actgtcttct ttatcatgca actcgtagga caggtgccgg cagcgctctg   8340
ggtcattttc ggcgaggacc gctttcgctg gagcgcgacg atgatcggcc tgtcgcttgc   8400
ggtattcgga atcttgcacg ccctcgctca agccttcgtc actggtcccg ccaccaaacg   8460
tttcggcgag aagcaggcca ttatcgccgg catggcggcc gacgcgctgg gctacgtctt   8520
gctggcgttc gcgacgcgag gctggatggc cttccccatt atgattcttc tcgcttccgg   8580
cggcatcggg atgcccgcgt tgcaggccat gctgtccagg caggtagatg acgaccatca   8640
gggacagctt caaggccagc aaaaggccag gaaccgtaaa aaggccgcgt tgctggcgtt   8700
tttccatagg ctccgccccc ctgacgagca tcacaaaaat cgacgctcaa gtcagaggtg   8760
gcgaaacccg acaggactat aaagatacca ggcgtttccc cctggaagct ccctcgtgcg   8820
ctctcctgtt ccgaccctgc cgcttaccgg atacctgtcc gcctttctcc cttcgggaag   8880
cgtggcgctt tctcatagct cacgctgtag gtatctcagt tcggtgtagg tcgttcgctc   8940
caagctgggc tgtgtgcacg aaccccccgt tcagcccgac cgctgcgcct tatccggtaa   9000
ctatcgtctt gagtccaacc cggtaagaca cgacttatcg ccactggcag cagccactgg   9060
taacaggatt agcagagcga ggtatgtagg cggtgctaca gagttcttga agtggtggcc   9120
taactacggc tacactagaa ggacagtatt tggtatctgc gctctgctga agccagttac   9180
cttcggaaaa agagttggta gctcttgatc cggcaaacaa accaccgctg gtagcggtgg   9240
tttttttgtt tgcaagcagc agattacgcg cagaaaaaaa ggatctcaag aagatccttt   9300
gatcttttct acggggtctg acgctcagtg gaacgaaaac tcacgttaag ggattttggt   9360
catgagatta tcaaaaagga tcttcaccta gatcctttta aattaaaaat gaagttttaa   9420
atcaatctaa agtatatatg agtaaacttg gtctgacagt taccaatgct taatcagtga   9480
ggcacctatc tcagcgatct gtctatttcg ttcatccata gttgcctgac tccccgtcgt   9540
gtagataact acgatacggg agggcttacc atctggcccc agtgctgcaa tgataccgcg   9600
```

-continued

```
agacccacgc tcaccggctc cagatttatc agcaataaac cagccagccg gaagggccga   9660

gcgcagaagt ggtcctgcaa ctttatccgc ctccatccag tctattaatt gttgccggga   9720

agctagagta agtagttcgc cagttaatag tttgcgcaac gttgttgcca ttgctgcagg   9780

catcgtggtg tcacgctcgt cgtttggtat ggcttcattc agctccggtt cccaacgatc   9840

aaggcgagtt acatgatccc ccatgttgtg caaaaaagcg gttagctcct tcggtcctcc   9900

gatcgttgtc agaagtaagt tggccgcagt gttatcactc atggttatgg cagcactgca   9960

taattctctt actgtcatgc catccgtaag atgcttttct gtgactggtg agtactcaac  10020

caagtcattc tgagaatagt gtatgcggcg accgagttgc tcttgcccgg cgtcaacacg  10080

ggataatacc gcgccacata gcagaacttt aaaagtgctc atcattggaa aacgttcttc  10140

ggggcgaaaa ctctcaagga tcttaccgct gttgagatcc agttcgatgt aacccactcg  10200

tgcacccaac tgatcttcag catcttttac tttcaccagc gtttctgggt gagcaaaaac  10260

aggaaggcaa aatgccgcaa aaaagggaat aagggcgaca cggaaatgtt gaatactcat  10320

actcttcctt tttcaatatt attgaagcat ttatcagggt tattgtctca tgagcggata  10380

catatttgaa tgtatttaga aaaa                                         10404
```

<210> SEQ ID NO 8
<211> LENGTH: 10452
<212> TYPE: DNA
<213> ORGANISM: Artificial Sequence
<220> FEATURE:
<223> OTHER INFORMATION: Synthetic hIL-21

<400> SEQUENCE: 8

```
taaacaaata ggggttccgc gcacatttcc ccgaaaagtg ccacctgacg tctaagaaac     60

cattattatc atgacattaa cctataaaaa taggcgtatc acgaggccct ttcgtcttca    120

attaatcgca ccggtatcta tgtcgggtgc ggagaaagag gtaatgaaat ggcagctagc    180

atcatcaata atataccta ttttggattg aagccaatat gataatgagg gggtggagtt    240

tgtgacgtgg cgcggggcgt gggaacgggg cgggtgacgt agtagtgtgg cggaagtgtg    300

atgttgcaag tgtggcggaa cacatgtaag cgacggatgt ggcaaaagtg acgtttttgg    360

tgtgcgccgg tgtacacagg aagtgacaat tttcgcgcgg ttttaggcgg atgttgtagt    420

aaatttgggc gtaaccgagt aagatttggc cattttcgcg ggaaaactga ataagaggaa    480

gtgaaatctg aataattttg tgttactcat agcgcgtaat atttgtctag ggagatccgg    540

taccgatatc ctagacaacg atgctgagct aactataacg gtcctaaggt agcgaccgcg    600

gagactaggt gtatttatct aagcgatcgc ttaattaagg ccggccgccg caataaaata    660

tctttatttt cattacatct gtgtgttggt tttttgtgtg aatcgatagt actaacatac    720

gctctccatc aaaacaaaac gaaacaaaac aaactagcaa aataggctgt ccccagtgca    780

agtgcaggtg ccagaacatt tctctatcga taatgcaggt cggagtactg tcctccgagc    840

ggagtactgt cctccgagcg gagtactgtc ctccgagcgg agtactgtcc tccgagcgga    900

gtactgtcct ccgagcggag tactgtcctc cgagcggaga ctcttcgaag gaagaggggc    960

ggggtcgatc gaccccgccc ctcttccttc gaaggaagag gggcggggtc gaagacctag   1020

agggtatata atgggtgcct tagctggtgt gtgagctcat cttcctgtag atcacgcgtc   1080

gaagaaggtg agtaatctta acatgctctt tttttttttt tttgctaatc ccttttgtgt   1140

gctgatgtta ggatgacatt tacaacaaat gtttgttcct gacaggaaaa accttgctgg   1200

gtaccttcgt tgccggacac ttcttgtcct ctactttgga aaaaaggaat tgagagccgc   1260
```

-continued

```
tagcccacca tgagaagcag ccccggcaac atggagagaa tcgtgatctg cctgatggtg   1320
atcttcctgg gcaccctggt gcataagagc agcagccagg gccaggacag acacatgatc   1380
cgcatgagac agctgatcga catcgtggac cagctgaaga actacgtgaa cgacctggtg   1440
cccgagttcc tgcccgcccc cgaggacgtg gagaccaact gcgagtggag cgccttcagc   1500
tgcttccaga aggcccagct gaagtccgcc aacaccggca acaacgagag aatcatcaac   1560
gtgagcatca agaagctgaa gcggaagccc cccagcacca acgccggaag aagacagaag   1620
cacagactga cctgtcccag ctgcgacagc tacgagaaga agcccccccaa ggagttcctg   1680
gagagattca agagcctgct gcaaaagatg atccaccagc acctgagcag cagaacccac   1740
ggcagcgagg acagctgaat cgattgcgca aagctttcgc gataggcgag accaatgggt   1800
gtgtacgtag cggccgctcg agaacttgtt tattgcagct tataatggtt acaaataaag   1860
caatagcatc acaaatttca caaataaagc atttttttca ctgcattcta gttgtggttt   1920
gtccaaactc atcaatgtat cttatcatgt ctcgtacggc gtggtaggtc cgaacgaatc   1980
catggattac cctgttatcc ctatccggag ttaacctcga ggacttcgga acttctagaa   2040
ccagaccgtt cagtttaaac gctcttctcc ccctcgaggg cctccgcgcc gggttttggc   2100
gcctcccgcg ggcgcccccc tcctcacggc gagcgctgcc acgtcagacg aagggcgcag   2160
cgagcgtcct gatccttccg cccggacgct caggacagcg gcccgctgct cataagactc   2220
ggccttagaa ccccagtatc agcagaagga cattttagga cgggacttgg gtgactctag   2280
ggcactggtt ttctttccag agagcggaac aggcgaggaa aagtagtccc ttctcggcga   2340
ttctgcggag ggatctccgt ggggcggtga acgccgatga ttatataagg acgcgccggg   2400
tgtggcacag ctagttccgt cgcagccggg atttgggtcg cggttcttgt ttgtggatcg   2460
ctgtgatcgt cacttggtga gtagcgggct gctgggctgg gtacgtgcgc tcggggttgg   2520
cgagtgtgtt ttgtgaagtt ttttaggcac cttttgaaat gtaatcattt gggtcaatat   2580
gtaattttca gtgttagact agtaaattgt ccgctaaatt ctggccgttt ttggcttttt   2640
tgttagacgg catgcggggg gggggggggg caattggcca ccatgggccc caagaagaaa   2700
aggaaggtgg ccccccccac cgacgtgagc ctgggcgacg agctgcacct ggacggcgag   2760
gacgtggcca tggcccacgc cgacgccctg gacgacttcg acctggacat gctgggcgac   2820
ggcgacagcc ccggccccgg cttcaccccc cacgacagcg ccccctacgg cgccctggac   2880
atggccgact tcgagttcga gcagatgttc accgacgccc tgggcatcga cgagtacggc   2940
ggccatatgg agatgcccgt ggacaggatt ctggaggccg aactcgccgt ggagcagaaa   3000
agcgaccagg gcgtggaggg ccccggcgga accggcggca gcggcagcag ccccaacgac   3060
cccgtgacca acatctgcca ggccgccgac aagcagctgt tcaccctggt ggagtgggcc   3120
aagaggattc cccacttcag cagcctgccc ctggacgacc aggtgatcct gctgagggcc   3180
ggatggaacg agctgctgat cgccagcttc agccacagga gcatcgacgt gagggacggc   3240
atcctgctgg ccaccggcct gcacgtccat aggaacagcg cccacagcgc cggagtgggc   3300
gccatcttcg acagggtgct gaccgagctg gtgagcaaga tgagggacat gaggatggac   3360
aagaccgagc tgggctgcct gagggccatc atcctgttca accccgaggt gaggggcctg   3420
aaaagcgccc aggaggtgga gctgctgagg gagaaggtgt acgccgccct ggaggagtac   3480
accaggacca cccaccccga cgagcccggc agattcgcca agctgctgct gaggctgccc   3540
agcctgagga gcatcggcct gaagtgcctg gagcacctgt tcttcttcag gctgatcggc   3600
```

-continued

```
gacgtgccca tcgacacctt cctgatggag atgctggaga gccccagcga cagctgagcc   3660
ggcaactcgc tgtagtaatt ccagcgagag gcagagggag cgagcgggcg gcgggctagg   3720
gtggaggagc ccggcgagca gagctgcgct gcgggcgtcc tgggaaggga gatccggagc   3780
gaataggggg cttcgcctct ggcccagccc tcccgctgat cccccagcca gcggtgcgca   3840
accctagccg catccacgaa actttgccca tagcagcggg cgggcacttt gcactggaac   3900
ttacaacacc cgagcaagga cgcgactctc ccgacgcggg gaggctattc tgcccatttg   3960
gggacacttc cccgccgctg ccaggacccg cttctctgaa aggctctcct tgcagctgct   4020
tagacgctgg atttttttcg ggtagtggaa aaccagcagc ctcccgcgac cagatctgcc   4080
accatgaagc tgctgagcag catcgagcag gcttgcgaca tctgcaggct gaagaagctg   4140
aagtgcagca aggagaagcc caagtgcgcc aagtgcctga agaacaactg ggagtgcaga   4200
tacagcccca agaccaagag gagcccccctg accagggccc acctgaccga ggtggagagc   4260
aggctggaga ggctggagca gctgttcctg ctgatcttcc ccagggagga cctggacatg   4320
atcctgaaga tggacagcct gcaagacatc aaggccctgc tgaccggcct gttcgtgcag   4380
gacaacgtga acaaggacgc cgtgaccgac aggctggcca gcgtggagac cgacatgccc   4440
ctgaccctga ggcagcacag gatcagcgcc accagcagca gcgaggagag cagcaacaag   4500
ggccagaggc agctgaccgt gagccccgag tttcccggga tcaggcccga gtgcgtggtg   4560
cccgagaccc agtgcgccat gaaaaggaag gagaagaagg cccagaagga gaaggacaag   4620
ctgcccgtga gcaccaccac cgtcgatgac cacatgcccc ccatcatgca gtgcgagccc   4680
cccccccccg aggccgccag gattcacgag gtcgtgccca ggttcctgag cgacaagctg   4740
ctggtgacca acaggcagaa gaacatcccc cagctgaccg ccaaccagca gttcctgatc   4800
gccaggctga tctggtatca ggacggctac gagcagccca gcgacgagga cctgaaaagg   4860
atcacccaga cctggcagca ggccgacgac gagaacgagg agagcgacac cccccttcagg   4920
cagatcaccg agatgaccat cctgaccgtg cagctgatcg tggagttcgc caagggcctg   4980
cccggattcg ccaagatcag ccagcccgac cagatcaccc tgctgaaggc ttgcagcagc   5040
gaggtgatga tgctgagggt ggccaggagg tacgacgccg ccagcgacag catcctgttc   5100
gccaacaacc aggcttacac cagggacaac tacaggaagg ctggcatggc cgaggtgatc   5160
gaggacctcc tgcacttctg cagatgtatg tacagcatgg ccctggacaa catccactac   5220
gccctgctga ccgccgtggt gatcttcagc gacaggcccg gcctggagca gccccagctg   5280
gtggaggaga tccagaggta ctacctgaac accctgagga tctacatcct gaaccagctg   5340
agcggcagcg ccaggagcag cgtgatctac ggcaagatcc tgagcatcct gagcgagctg   5400
aggaccctgg gaatgcagaa cagcaatatg tgtatcagcc tgaagctgaa gaacaggaag   5460
ctgcccccct tcctggagga gatttgggac gtggccgaca tgagccacac ccagcccccc   5520
cccatcctgg agagccccac caacctgtga atcgattaga catgataaga tacattgatg   5580
agtttggaca aaccacaact agaatgcagt gaaaaaaatg cttaatttgt gaaatttgtg   5640
atgctattgc ttaatttgta accattataa gctgcaataa acaagttaat aaaacatttg   5700
cattcatttt atgtttcagg ttcaggggga gatgtgggag gtttttttaaa gcaagtaaaa   5760
cctctacaaa tgtggtatct agagctcttc caaatagatc tggaaggtgc tgaggtacga   5820
tgagacccgc accaggtgca gaccctgcga gtgtggcggt aaacatatta ggaaccagcc   5880
tgtgatgctg gatgtgaccg aggagctgag gcccgatcac ttggtgctgg cctgcacccg   5940
cgctgagttt ggctctagcg atgaagatac agattgaggt actgaaatgt gtgggcgtgg   6000
```

cttaagggtg ggaaagaata tataaggtgg gggtcttatg tagttttgta tctgttttgc 6060
agcagccgcc gccgccatga gcaccaactc gtttgatgga agcattgtga gctcatattt 6120
gacaacgcgc atgcccccat gggccggggt gcgtcagaat gtgatgggct ccagcattga 6180
tggtcgcccc gtcctgcccg caaactctac taccttgacc tacgagaccg tgtctggaac 6240
gccgttggag actgcagcct ccgccgccgc ttcagccgct gcagccaccg cccgcgggat 6300
tgtgactgac tttgctttcc tgagcccgct tgcaagcagt gcagcttccc gttcatccgc 6360
ccgcgatgac aagttgacgg ctcttttggc acaattggat tctttgaccc gggaacttaa 6420
tgtcgtttct cagcagctgt tggatctgcg ccagcaggtt tctgccctga aggcttcctc 6480
ccctcccaat gcggtttaaa acataaataa aaaaccagac tctgtttgga tttggatcaa 6540
gcaagtgtct tgctgtcttt atttaggggt tttgcgcgcg cggtaggccc gggaccagcg 6600
gtctcggtcg ttgagggtcc tgtgtatttt ttccaggacg tggtaaaggt gactctggat 6660
gttcagatac atgggcataa gcccgtctct ggggtggagg tagcaccact gcagagcttc 6720
atgctgcggg gtggtgttgt agatgatcca gtcgtagcag gagcgctggg cgtggtgcct 6780
aaaaatgtct ttcagtagca agctgattgc caggggcagg cccttggtgt aagtgtttac 6840
aaagcggtta agctgggatg ggtgcatacg tggggatatg agatgcatct tggactgtat 6900
ttttaggttg gctatgttcc cagccatatc cctccgggga ttcatgttgt gcagaaccac 6960
cagcacagtg tatccggtgc acttgggaaa tttgtcatgt agcttagaag gaaatgcgtg 7020
gaagaacttg gagacgccct tgtgacctcc aagattttcc atgcattcgt ccataatgat 7080
ggcaatgggc ccacgggcgg cggcctgggc gaagatattt ctgggatcac taacgtcata 7140
gttgtgttcc aggatgagat cgtcataggc catttttaca aagcgcgggc ggagggtgcc 7200
agactgcggt ataatggttc catccggccc aggggcgtag ttaccctcac agatttgcat 7260
ttcccacgct ttgagttcag atggggggat catgtctacc tgcggggcga tgaagaaaac 7320
ggtttccggg gtaggggaga tcagctggga agaaagcagg ttcctgagca gctgcgactt 7380
accgcagccg gtgggcccgt aaatcacacc tattaccggg tgcaactggt agttaagaga 7440
gctgcagctg ccgtcatccc tgagcagggg ggccacttcg ttaagcatgt ccctgactcg 7500
catgttttcc ctgaccaaat ccgccagaag gcgctcgccg cccagcgata gcagttcttg 7560
caaggaagca aagtttttca acggtttgag accgtccgcc gtaggcatgc ttttgagcgt 7620
ttgaccaagc agttccaggc ggtcccacag ctcggtcacc tgctctacgg catctcgatc 7680
cagcatatct cctcgtttcg cgggttgggg cggctttcgc tgtacggcag tagtcggtgc 7740
tcgtccagac gggccagggt catgtctttc cacgggcgca gggtcctcgt cagcgtagtc 7800
tgggtcacgg tgaaggggtg cgctccgggc tgcgcgctgg ccagggtgcg cttgaggctg 7860
gtcctgctgg tgctgaagcg ctgccggtct tcgccctgcg cgtcggccag gtagcatttg 7920
accatggtgt catagtccag cccctccgcg gcgtggccct tggcgcgcag cttgcccttg 7980
gaggaggcgc cgcacgaggg gcagtgcaga cttttgaggg cgtagagctt gggcgcgaga 8040
aataccgatt ccggggagta ggcatccgcg ccgcaggccc cgcagacggt ctcgcattcc 8100
acgagccagg tgagctctgg ccgttcgggg tcaaaaacca ggtttccccc atgctttttg 8160
atgcgtttct tacctctggt ttccatgagc cggtgtccac gctcggtgac gaaaaggctg 8220
tccgtgtccc cgtatacaga cttgagaggc ctgtcctcga ccgatgccct tgagagcctt 8280
caacccagtc agctccttcc ggtgggcgcg gggcatgact atcgtcgccg cacttatgac 8340

-continued

```
tgtcttcttt atcatgcaac tcgtaggaca ggtgccggca gcgctctggg tcattttcgg   8400
cgaggaccgc tttcgctgga gcgcgacgat gatcggcctg tcgcttgcgg tattcggaat   8460
cttgcacgcc ctcgctcaag ccttcgtcac tggtcccgcc accaaacgtt tcggcgagaa   8520
gcaggccatt atcgccggca tggcggccga cgcgctgggc tacgtcttgc tggcgttcgc   8580
gacgcgaggc tggatggcct tccccattat gattcttctc gcttccggcg gcatcgggat   8640
gcccgcgttg caggccatgc tgtccaggca ggtagatgac gaccatcagg gacagcttca   8700
aggccagcaa aaggccagga accgtaaaaa ggccgcgttg ctggcgtttt tccataggct   8760
ccgcccccct gacgagcatc acaaaaatcg acgctcaagt cagaggtggc gaaacccgac   8820
aggactataa agataccagg cgtttccccc tggaagctcc ctcgtgcgct ctcctgttcc   8880
gaccctgccg cttaccggat acctgtccgc ctttctccct tcgggaagcg tggcgctttc   8940
tcatagctca cgctgtaggt atctcagttc ggtgtaggtc gttcgctcca agctgggctg   9000
tgtgcacgaa ccccccgttc agcccgaccg ctgcgcctta tccggtaact atcgtcttga   9060
gtccaacccg gtaagacacg acttatcgcc actggcagca gccactggta acaggattag   9120
cagagcgagg tatgtaggcg gtgctacaga gttcttgaag tggtggccta actacggcta   9180
cactagaagg acagtatttg gtatctgcgc tctgctgaag ccagttacct tcggaaaaag   9240
agttggtagc tcttgatccg gcaaacaaac caccgctggt agcggtggtt tttttgtttg   9300
caagcagcag attacgcgca gaaaaaaagg atctcaagaa gatcctttga tcttttctac   9360
ggggtctgac gctcagtgga acgaaaactc acgttaaggg attttggtca tgagattatc   9420
aaaaaggatc ttcacctaga tccttttaaa ttaaaaatga agttttaaat caatctaaag   9480
tatatatgag taaacttggt ctgacagtta ccaatgctta atcagtgagg cacctatctc   9540
agcgatctgt ctatttcgtt catccatagt tgcctgactc cccgtcgtgt agataactac   9600
gatacgggag ggcttaccat ctggccccag tgctgcaatg ataccgcgag acccacgctc   9660
accggctcca gatttatcag caataaacca gccagccgga agggccgagc gcagaagtgg   9720
tcctgcaact ttatccgcct ccatccagtc tattaattgt tgccgggaag ctagagtaag   9780
tagttcgcca gttaatagtt tgcgcaacgt tgttgccatt gctgcaggca tcgtggtgtc   9840
acgctcgtcg tttggtatgg cttcattcag ctccggttcc caacgatcaa ggcgagttac   9900
atgatccccc atgttgtgca aaaaagcggt tagctccttc ggtcctccga tcgttgtcag   9960
aagtaagttg gccgcagtgt tatcactcat ggttatggca gcactgcata attctcttac  10020
tgtcatgcca tccgtaagat gcttttctgt gactggtgag tactcaacca agtcattctg  10080
agaatagtgt atgcggcgac cgagttgctc ttgcccggcg tcaacacggg ataataccgc  10140
gccacatagc agaactttaa aagtgctcat cattggaaaa cgttcttcgg ggcgaaaact  10200
ctcaaggatc ttaccgctgt tgagatccag ttcgatgtaa cccactcgtg cacccaactg  10260
atcttcagca tcttttactt tcaccagcgt ttctgggtga gcaaaaacag gaaggcaaaa  10320
tgccgcaaaa aagggaataa gggcgacacg gaaatgttga atactcatac tcttcctttt  10380
tcaatattat tgaagcattt atcagggtta ttgtctcatg agcggataca tatttgaatg  10440
tatttagaaa aa                                                      10452
```

<210> SEQ ID NO 9
<211> LENGTH: 489
<212> TYPE: DNA
<213> ORGANISM: Artificial Sequence
<220> FEATURE:
<223> OTHER INFORMATION: Synthetic mIL-21

```
<220> FEATURE:
<221> NAME/KEY: CDS
<222> LOCATION: (1)..(489)

<400> SEQUENCE: 9

atg aag atc ctg aag ccc tac atg agg aac acc agc atc agc tgt tac       48
Met Lys Ile Leu Lys Pro Tyr Met Arg Asn Thr Ser Ile Ser Cys Tyr
1               5                   10                  15

ctg tgc ttc ctg ctg aac agc cac ttc ctg acc gag gcc gga atc cac       96
Leu Cys Phe Leu Leu Asn Ser His Phe Leu Thr Glu Ala Gly Ile His
            20                  25                  30

gtc ttc atc ctg ggc tgc gtg agc gtg ggc ctg ccc aag acc gag gcc      144
Val Phe Ile Leu Gly Cys Val Ser Val Gly Leu Pro Lys Thr Glu Ala
        35                  40                  45

aac tgg atc gac gtg agg tac gac ctg gag aag atc gag agc ctg atc      192
Asn Trp Ile Asp Val Arg Tyr Asp Leu Glu Lys Ile Glu Ser Leu Ile
    50                  55                  60

cag agc atc cac atc gac acc acc ctg tac acc gac agc gac ttc cac      240
Gln Ser Ile His Ile Asp Thr Thr Leu Tyr Thr Asp Ser Asp Phe His
65                  70                  75                  80

ccc agc tgc aag gtg acc gcc atg aac tgc ttc ctg ctg gag ctg caa      288
Pro Ser Cys Lys Val Thr Ala Met Asn Cys Phe Leu Leu Glu Leu Gln
                85                  90                  95

gtg atc ctg cac gag tac agc aac atg acc ctg aac gag acc gtg agg      336
Val Ile Leu His Glu Tyr Ser Asn Met Thr Leu Asn Glu Thr Val Arg
            100                 105                 110

aac gtg ctg tac ctg gct aac agc acc ctg agc agc aac aag aac gtg      384
Asn Val Leu Tyr Leu Ala Asn Ser Thr Leu Ser Ser Asn Lys Asn Val
        115                 120                 125

gcc gag agc ggc tgc aag gag tgt gag gag ctg gag gag aag acc ttc      432
Ala Glu Ser Gly Cys Lys Glu Cys Glu Glu Leu Glu Glu Lys Thr Phe
    130                 135                 140

acc gag ttc ctc cag agc ttc atc agg atc gtg cag atg ttc atc aac      480
Thr Glu Phe Leu Gln Ser Phe Ile Arg Ile Val Gln Met Phe Ile Asn
145                 150                 155                 160

acc agc tga                                                          489
Thr Ser


<210> SEQ ID NO 10
<211> LENGTH: 162
<212> TYPE: PRT
<213> ORGANISM: Artificial Sequence
<220> FEATURE:
<223> OTHER INFORMATION: Synthetic Construct

<400> SEQUENCE: 10

Met Lys Ile Leu Lys Pro Tyr Met Arg Asn Thr Ser Ile Ser Cys Tyr
1               5                   10                  15

Leu Cys Phe Leu Leu Asn Ser His Phe Leu Thr Glu Ala Gly Ile His
            20                  25                  30

Val Phe Ile Leu Gly Cys Val Ser Val Gly Leu Pro Lys Thr Glu Ala
        35                  40                  45

Asn Trp Ile Asp Val Arg Tyr Asp Leu Glu Lys Ile Glu Ser Leu Ile
    50                  55                  60

Gln Ser Ile His Ile Asp Thr Thr Leu Tyr Thr Asp Ser Asp Phe His
65                  70                  75                  80

Pro Ser Cys Lys Val Thr Ala Met Asn Cys Phe Leu Leu Glu Leu Gln
                85                  90                  95

Val Ile Leu His Glu Tyr Ser Asn Met Thr Leu Asn Glu Thr Val Arg
            100                 105                 110
```

```
Asn Val Leu Tyr Leu Ala Asn Ser Thr Leu Ser Ser Asn Lys Asn Val
        115                 120                 125

Ala Glu Ser Gly Cys Lys Glu Cys Glu Glu Leu Glu Glu Lys Thr Phe
    130                 135                 140

Thr Glu Phe Leu Gln Ser Phe Ile Arg Ile Val Gln Met Phe Ile Asn
145                 150                 155                 160

Thr Ser


<210> SEQ ID NO 11
<211> LENGTH: 489
<212> TYPE: DNA
<213> ORGANISM: Artificial Sequence
<220> FEATURE:
<223> OTHER INFORMATION: Synthetic mIL-15
<220> FEATURE:
<221> NAME/KEY: CDS
<222> LOCATION: (1)..(489)

<400> SEQUENCE: 11

atg aag atc ctg aag ccc tac atg agg aac acc agc atc agc tgt tac       48
Met Lys Ile Leu Lys Pro Tyr Met Arg Asn Thr Ser Ile Ser Cys Tyr
1               5                   10                  15

ctg tgc ttc ctg ctg aac agc cac ttc ctg acc gag gcc gga atc cac       96
Leu Cys Phe Leu Leu Asn Ser His Phe Leu Thr Glu Ala Gly Ile His
            20                  25                  30

gtc ttc atc ctg ggc tgc gtg agc gtg ggc ctg ccc aag acc gag gcc      144
Val Phe Ile Leu Gly Cys Val Ser Val Gly Leu Pro Lys Thr Glu Ala
        35                  40                  45

aac tgg atc gac gtg agg tac gac ctg gag aag atc gag agc ctg atc      192
Asn Trp Ile Asp Val Arg Tyr Asp Leu Glu Lys Ile Glu Ser Leu Ile
    50                  55                  60

cag agc atc cac atc gac acc acc ctg tac acc gac agc gac ttc cac      240
Gln Ser Ile His Ile Asp Thr Thr Leu Tyr Thr Asp Ser Asp Phe His
65                  70                  75                  80

ccc agc tgc aag gtg acc gcc atg aac tgc ttc ctg ctg gag ctg caa      288
Pro Ser Cys Lys Val Thr Ala Met Asn Cys Phe Leu Leu Glu Leu Gln
                85                  90                  95

gtg atc ctg cac gag tac agc aac atg acc ctg aac gag acc gtg agg      336
Val Ile Leu His Glu Tyr Ser Asn Met Thr Leu Asn Glu Thr Val Arg
            100                 105                 110

aac gtg ctg tac ctg gct aac agc acc ctg agc agc aac aag aac gtg      384
Asn Val Leu Tyr Leu Ala Asn Ser Thr Leu Ser Ser Asn Lys Asn Val
        115                 120                 125

gcc gag agc ggc tgc aag gag tgt gag gag ctg gag gag aag acc ttc      432
Ala Glu Ser Gly Cys Lys Glu Cys Glu Glu Leu Glu Glu Lys Thr Phe
    130                 135                 140

acc gag ttc ctc cag agc ttc atc agg atc gtg cag atg ttc atc aac      480
Thr Glu Phe Leu Gln Ser Phe Ile Arg Ile Val Gln Met Phe Ile Asn
145                 150                 155                 160

acc agc tga                                                           489
Thr Ser


<210> SEQ ID NO 12
<211> LENGTH: 162
<212> TYPE: PRT
<213> ORGANISM: Artificial Sequence
<220> FEATURE:
<223> OTHER INFORMATION: Synthetic Construct

<400> SEQUENCE: 12

Met Lys Ile Leu Lys Pro Tyr Met Arg Asn Thr Ser Ile Ser Cys Tyr
```

```
1               5                   10                  15

Leu Cys Phe Leu Leu Asn Ser His Phe Leu Thr Glu Ala Gly Ile His
            20                  25                  30

Val Phe Ile Leu Gly Cys Val Ser Val Gly Leu Pro Lys Thr Glu Ala
        35                  40                  45

Asn Trp Ile Asp Val Arg Tyr Asp Leu Glu Lys Ile Glu Ser Leu Ile
    50                  55                  60

Gln Ser Ile His Ile Asp Thr Thr Leu Tyr Thr Asp Ser Asp Phe His
65                  70                  75                  80

Pro Ser Cys Lys Val Thr Ala Met Asn Cys Phe Leu Leu Glu Leu Gln
                85                  90                  95

Val Ile Leu His Glu Tyr Ser Asn Met Thr Leu Asn Glu Thr Val Arg
            100                 105                 110

Asn Val Leu Tyr Leu Ala Asn Ser Thr Leu Ser Ser Asn Lys Asn Val
        115                 120                 125

Ala Glu Ser Gly Cys Lys Glu Cys Glu Glu Leu Glu Glu Lys Thr Phe
    130                 135                 140

Thr Glu Phe Leu Gln Ser Phe Ile Arg Ile Val Gln Met Phe Ile Asn
145                 150                 155                 160

Thr Ser


<210> SEQ ID NO 13
<211> LENGTH: 1008
<212> TYPE: DNA
<213> ORGANISM: Artificial Sequence
<220> FEATURE:
<223> OTHER INFORMATION: Synthetic mIL-12, mp40
<220> FEATURE:
<221> NAME/KEY: CDS
<222> LOCATION: (1)..(1008)

<400> SEQUENCE: 13

atg tgc ccc cag aag ctg acc atc agc tgg ttc gcc atc gtg ctg ctg       48
Met Cys Pro Gln Lys Leu Thr Ile Ser Trp Phe Ala Ile Val Leu Leu
1               5                   10                  15

gtg agc ccc ctg atg gcc atg tgg gag ctg gag aag gac gtg tac gtg       96
Val Ser Pro Leu Met Ala Met Trp Glu Leu Glu Lys Asp Val Tyr Val
            20                  25                  30

gtg gag gtg gac tgg acc ccc gac gcc ccc ggc gag acc gtg aac ctg      144
Val Glu Val Asp Trp Thr Pro Asp Ala Pro Gly Glu Thr Val Asn Leu
        35                  40                  45

act tgc gac acc ccc gag gag gac gac atc acc tgg acc agc gac cag      192
Thr Cys Asp Thr Pro Glu Glu Asp Asp Ile Thr Trp Thr Ser Asp Gln
    50                  55                  60

aga cac ggc gtc atc ggc agc ggc aag acc ctg acc atc acc gtg aag      240
Arg His Gly Val Ile Gly Ser Gly Lys Thr Leu Thr Ile Thr Val Lys
65                  70                  75                  80

gag ttc ctg gac gcc gga cag tac acc tgt cac aag ggc ggc gag acc      288
Glu Phe Leu Asp Ala Gly Gln Tyr Thr Cys His Lys Gly Gly Glu Thr
                85                  90                  95

ctg agc cac agc cac ctg ttg ctg cac aag aag gag aac ggc atc tgg      336
Leu Ser His Ser His Leu Leu Leu His Lys Lys Glu Asn Gly Ile Trp
            100                 105                 110

agc acc gag atc ctg aag aac ttc aag aac aag acc ttc ctg aag tgc      384
Ser Thr Glu Ile Leu Lys Asn Phe Lys Asn Lys Thr Phe Leu Lys Cys
        115                 120                 125

gag gcc ccc aac tac agc ggc aga ttc acc tgt agc tgg ctg gtg cag      432
Glu Ala Pro Asn Tyr Ser Gly Arg Phe Thr Cys Ser Trp Leu Val Gln
    130                 135                 140
```

```
aga aac atg gac ctg aag ttc aac atc aag agc agc agc agc agc ccc      480
Arg Asn Met Asp Leu Lys Phe Asn Ile Lys Ser Ser Ser Ser Ser Pro
145                 150                 155                 160

gac agc aga gcc gtg aca tgc ggc atg gcc agc ctg agc gcc gag aag      528
Asp Ser Arg Ala Val Thr Cys Gly Met Ala Ser Leu Ser Ala Glu Lys
                165                 170                 175

gtg acc ctg gac cag aga gac tac gag aag tac agc gtg agc tgc cag      576
Val Thr Leu Asp Gln Arg Asp Tyr Glu Lys Tyr Ser Val Ser Cys Gln
            180                 185                 190

gag gac gtg acc tgt ccc acc gcc gag gag acc ctg ccc atc gag ctt      624
Glu Asp Val Thr Cys Pro Thr Ala Glu Glu Thr Leu Pro Ile Glu Leu
        195                 200                 205

gcc ctg gaa gcc aga cag cag aac aag tac gag aac tac agc acc agc      672
Ala Leu Glu Ala Arg Gln Gln Asn Lys Tyr Glu Asn Tyr Ser Thr Ser
    210                 215                 220

ttc ttc atc aga gac atc atc aag ccc gac ccc ccc aag aac ctc cag      720
Phe Phe Ile Arg Asp Ile Ile Lys Pro Asp Pro Pro Lys Asn Leu Gln
225                 230                 235                 240

atg aag ccc ctg aag aac agc cag gtg gag gtg tcc tgg gag tac ccc      768
Met Lys Pro Leu Lys Asn Ser Gln Val Glu Val Ser Trp Glu Tyr Pro
                245                 250                 255

gac agc tgg agc acc ccc cac agc tac ttc agc ctg aag ttc ttc gtg      816
Asp Ser Trp Ser Thr Pro His Ser Tyr Phe Ser Leu Lys Phe Phe Val
            260                 265                 270

aga atc cag aga aag aag gag aag atg aag gag acc gag gag ggc tgc      864
Arg Ile Gln Arg Lys Lys Glu Lys Met Lys Glu Thr Glu Glu Gly Cys
        275                 280                 285

aac cag aag ggc gct ttc ctg gtg gag aaa acc agc acc gag gtg cag      912
Asn Gln Lys Gly Ala Phe Leu Val Glu Lys Thr Ser Thr Glu Val Gln
    290                 295                 300

tgc aag ggc ggc aac gtg tgt gtg cag gcc cag gac aga tac tac aac      960
Cys Lys Gly Gly Asn Val Cys Val Gln Ala Gln Asp Arg Tyr Tyr Asn
305                 310                 315                 320

agc agc tgc tcc aag tgg gcc tgc gtg ccc tgc cgc gtg aga agc tga     1008
Ser Ser Cys Ser Lys Trp Ala Cys Val Pro Cys Arg Val Arg Ser
                325                 330                 335
```

```
<210> SEQ ID NO 14
<211> LENGTH: 335
<212> TYPE: PRT
<213> ORGANISM: Artificial Sequence
<220> FEATURE:
<223> OTHER INFORMATION: Synthetic Construct

<400> SEQUENCE: 14

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110
```

```
Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                325                 330                 335


<210> SEQ ID NO 15
<211> LENGTH: 648
<212> TYPE: DNA
<213> ORGANISM: Artificial Sequence
<220> FEATURE:
<223> OTHER INFORMATION: Synthetic mIL-12, mp35
<220> FEATURE:
<221> NAME/KEY: CDS
<222> LOCATION: (1)..(648)

<400> SEQUENCE: 15

atg tgc cag agc aga tac ctg ttg ttc ctg gct acc ctg gcc ctg ctg       48
Met Cys Gln Ser Arg Tyr Leu Leu Phe Leu Ala Thr Leu Ala Leu Leu
1               5                   10                  15

aac cac ctg agc ctg gcc cgc gtg atc ccc gtg agc ggc ccc gcc aga       96
Asn His Leu Ser Leu Ala Arg Val Ile Pro Val Ser Gly Pro Ala Arg
            20                  25                  30

tgc ctg agc cag agc aga aac ctg ttg aaa aca acc gac gac atg gtg      144
Cys Leu Ser Gln Ser Arg Asn Leu Leu Lys Thr Thr Asp Asp Met Val
        35                  40                  45

aaa acc gcc aga gag aag ctg aag cac tac agc tgc acc gcc gag gac      192
Lys Thr Ala Arg Glu Lys Leu Lys His Tyr Ser Cys Thr Ala Glu Asp
    50                  55                  60

atc gac cac gag gac atc acc aga gac cag acc agc acc ctg aaa acc      240
Ile Asp His Glu Asp Ile Thr Arg Asp Gln Thr Ser Thr Leu Lys Thr
65                  70                  75                  80

tgt ctg ccc ctg gag ctg cac aag aac gag agc tgc ctg gct acc aga      288
Cys Leu Pro Leu Glu Leu His Lys Asn Glu Ser Cys Leu Ala Thr Arg
                85                  90                  95
```

```
gag acc agc agc acc acc aga ggc agc tgc ctg ccc ccc cag aaa acc      336
Glu Thr Ser Ser Thr Thr Arg Gly Ser Cys Leu Pro Pro Gln Lys Thr
            100                 105                 110

agc ctg atg atg acc ctg tgc ctg ggc agc atc tac gag gac ctg aag      384
Ser Leu Met Met Thr Leu Cys Leu Gly Ser Ile Tyr Glu Asp Leu Lys
        115                 120                 125

atg tac cag acc gag ttc cag gcc atc aac gcc gcc ctg caa aac cac      432
Met Tyr Gln Thr Glu Phe Gln Ala Ile Asn Ala Ala Leu Gln Asn His
    130                 135                 140

aac cac cag cag atc atc ctg gac aag ggc atg ttg gtg gcc atc gac      480
Asn His Gln Gln Ile Ile Leu Asp Lys Gly Met Leu Val Ala Ile Asp
145                 150                 155                 160

gag ctg atg cag agc ctg aac cac aac ggc gag acc ctg aga cag aag      528
Glu Leu Met Gln Ser Leu Asn His Asn Gly Glu Thr Leu Arg Gln Lys
                165                 170                 175

ccc ccc gtg ggc gag gcc gac ccc tac aga gtg aag atg aag ctg tgc      576
Pro Pro Val Gly Glu Ala Asp Pro Tyr Arg Val Lys Met Lys Leu Cys
            180                 185                 190

atc ctg ctg cac gcc ttc agc acc aga gtg gtg acc atc aac aga gtg      624
Ile Leu Leu His Ala Phe Ser Thr Arg Val Val Thr Ile Asn Arg Val
        195                 200                 205

atg ggc tac ctg agc agc gcc tga                                      648
Met Gly Tyr Leu Ser Ser Ala
    210                 215


<210> SEQ ID NO 16
<211> LENGTH: 215
<212> TYPE: PRT
<213> ORGANISM: Artificial Sequence
<220> FEATURE:
<223> OTHER INFORMATION: Synthetic Construct

<400> SEQUENCE: 16

Met Cys Gln Ser Arg Tyr Leu Leu Phe Leu Ala Thr Leu Ala Leu Leu
1               5                   10                  15

Asn His Leu Ser Leu Ala Arg Val Ile Pro Val Ser Gly Pro Ala Arg
            20                  25                  30

Cys Leu Ser Gln Ser Arg Asn Leu Leu Lys Thr Thr Asp Asp Met Val
        35                  40                  45

Lys Thr Ala Arg Glu Lys Leu Lys His Tyr Ser Cys Thr Ala Glu Asp
    50                  55                  60

Ile Asp His Glu Asp Ile Thr Arg Asp Gln Thr Ser Thr Leu Lys Thr
65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190
```

```
Ile Leu Leu His Ala Phe Ser Thr Arg Val Val Thr Ile Asn Arg Val
        195                 200                 205

Met Gly Tyr Leu Ser Ser Ala
    210                 215


<210> SEQ ID NO 17
<211> LENGTH: 489
<212> TYPE: DNA
<213> ORGANISM: Artificial Sequence
<220> FEATURE:
<223> OTHER INFORMATION: Synthetic hIL-21
<220> FEATURE:
<221> NAME/KEY: CDS
<222> LOCATION: (1)..(489)

<400> SEQUENCE: 17

atg aga agc agc ccc ggc aac atg gag aga atc gtg atc tgc ctg atg       48
Met Arg Ser Ser Pro Gly Asn Met Glu Arg Ile Val Ile Cys Leu Met
1               5                   10                  15

gtg atc ttc ctg ggc acc ctg gtg cat aag agc agc agc cag ggc cag       96
Val Ile Phe Leu Gly Thr Leu Val His Lys Ser Ser Ser Gln Gly Gln
            20                  25                  30

gac aga cac atg atc cgc atg aga cag ctg atc gac atc gtg gac cag      144
Asp Arg His Met Ile Arg Met Arg Gln Leu Ile Asp Ile Val Asp Gln
        35                  40                  45

ctg aag aac tac gtg aac gac ctg gtg ccc gag ttc ctg ccc gcc ccc      192
Leu Lys Asn Tyr Val Asn Asp Leu Val Pro Glu Phe Leu Pro Ala Pro
    50                  55                  60

gag gac gtg gag acc aac tgc gag tgg agc gcc ttc agc tgc ttc cag      240
Glu Asp Val Glu Thr Asn Cys Glu Trp Ser Ala Phe Ser Cys Phe Gln
65                  70                  75                  80

aag gcc cag ctg aag tcc gcc aac acc ggc aac aac gag aga atc atc      288
Lys Ala Gln Leu Lys Ser Ala Asn Thr Gly Asn Asn Glu Arg Ile Ile
                85                  90                  95

aac gtg agc atc aag aag ctg aag cgg aag ccc ccc agc acc aac gcc      336
Asn Val Ser Ile Lys Lys Leu Lys Arg Lys Pro Pro Ser Thr Asn Ala
            100                 105                 110

gga aga aga cag aag cac aga ctg acc tgt ccc agc tgc gac agc tac      384
Gly Arg Arg Gln Lys His Arg Leu Thr Cys Pro Ser Cys Asp Ser Tyr
        115                 120                 125

gag aag aag ccc ccc aag gag ttc ctg gag aga ttc aag agc ctg ctg      432
Glu Lys Lys Pro Pro Lys Glu Phe Leu Glu Arg Phe Lys Ser Leu Leu
    130                 135                 140

caa aag atg atc cac cag cac ctg agc agc aga acc cac ggc agc gag      480
Gln Lys Met Ile His Gln His Leu Ser Ser Arg Thr His Gly Ser Glu
145                 150                 155                 160

gac agc tga                                                          489
Asp Ser


<210> SEQ ID NO 18
<211> LENGTH: 162
<212> TYPE: PRT
<213> ORGANISM: Artificial Sequence
<220> FEATURE:
<223> OTHER INFORMATION: Synthetic Construct

<400> SEQUENCE: 18

Met Arg Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
            20                  25                  30

Asp Arg His Met Ile Arg Met Arg Gln Leu Ile Asp Ile Val Asp Gln
```

-continued

```
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser


<210> SEQ ID NO 19
<211> LENGTH: 489
<212> TYPE: DNA
<213> ORGANISM: Artificial Sequence
<220> FEATURE:
<223> OTHER INFORMATION: Synthetic hIL-15
<220> FEATURE:
<221> NAME/KEY: CDS
<222> LOCATION: (1)..(489)

<400> SEQUENCE: 19

atg aga atc agc aag ccc cac ctg aga agc atc agc atc cag tgt tac       48
Met Arg Ile Ser Lys Pro His Leu Arg Ser Ile Ser Ile Gln Cys Tyr
1               5                   10                  15

ctg tgc ctg ctg ctg aac agc cac ttc ctg acc gag gcc ggt atc cac       96
Leu Cys Leu Leu Leu Asn Ser His Phe Leu Thr Glu Ala Gly Ile His
            20                  25                  30

gtc ttc atc ctg ggc tgc ttc agc gcc gga ctg ccc aag acc gag gcc      144
Val Phe Ile Leu Gly Cys Phe Ser Ala Gly Leu Pro Lys Thr Glu Ala
        35                  40                  45

aac tgg gtg aac gtg atc tct gac ctg aag aag atc gag gac ctg atc      192
Asn Trp Val Asn Val Ile Ser Asp Leu Lys Lys Ile Glu Asp Leu Ile
    50                  55                  60

cag tcc atg cac atc gac gcc acc ctg tac acc gag agc gac gtt cat      240
Gln Ser Met His Ile Asp Ala Thr Leu Tyr Thr Glu Ser Asp Val His
65                  70                  75                  80

ccc agc tgc aag gtg acc gcc atg aag tgc ttc ctg ctg gag ctg caa      288
Pro Ser Cys Lys Val Thr Ala Met Lys Cys Phe Leu Leu Glu Leu Gln
                85                  90                  95

gtg atc tcc ctg gag agc ggc gac gcc agc atc cac gac acc gtg gag      336
Val Ile Ser Leu Glu Ser Gly Asp Ala Ser Ile His Asp Thr Val Glu
            100                 105                 110

aac ctg att atc ctg gct aac aac agc ctg agc agc aac ggc aac gtg      384
Asn Leu Ile Ile Leu Ala Asn Asn Ser Leu Ser Ser Asn Gly Asn Val
        115                 120                 125

acc gag agc ggc tgc aag gag tgt gag gag ctg gag gag aag aac atc      432
Thr Glu Ser Gly Cys Lys Glu Cys Glu Glu Leu Glu Glu Lys Asn Ile
    130                 135                 140

aag gag ttc ctc cag agc ttc gtg cat atc gtc cag atg ttc atc aac      480
Lys Glu Phe Leu Gln Ser Phe Val His Ile Val Gln Met Phe Ile Asn
145                 150                 155                 160

acc agc tga                                                          489
```

Thr Ser

<210> SEQ ID NO 20
<211> LENGTH: 162
<212> TYPE: PRT
<213> ORGANISM: Artificial Sequence
<220> FEATURE:
<223> OTHER INFORMATION: Synthetic Construct

<400> SEQUENCE: 20

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser
```

<210> SEQ ID NO 21
<211> LENGTH: 987
<212> TYPE: DNA
<213> ORGANISM: Artificial Sequence
<220> FEATURE:
<223> OTHER INFORMATION: Synthetic hIL-12, p40
<220> FEATURE:
<221> NAME/KEY: CDS
<222> LOCATION: (1)..(987)

<400> SEQUENCE: 21

```
atg ggt cac cag cag ttg gtc atc tct tgg ttt tcc ctg gtt ttt ctg       48
Met Gly His Gln Gln Leu Val Ile Ser Trp Phe Ser Leu Val Phe Leu
1               5                   10                  15

gca tct ccc ctc gtg gcc ata tgg gaa ctg aag aaa gat gtt tat gtc       96
Ala Ser Pro Leu Val Ala Ile Trp Glu Leu Lys Lys Asp Val Tyr Val
            20                  25                  30

gta gaa ttg gat tgg tat ccg gat gcc cct gga gaa atg gtg gtc ctc      144
Val Glu Leu Asp Trp Tyr Pro Asp Ala Pro Gly Glu Met Val Val Leu
        35                  40                  45

acc tgt gac acc cct gaa gaa gat ggt atc acc tgg acc ttg gac cag      192
Thr Cys Asp Thr Pro Glu Glu Asp Gly Ile Thr Trp Thr Leu Asp Gln
    50                  55                  60

agc agt gag gtc tta ggc tct ggc aaa acc ctg acc atc caa gtc aaa      240
Ser Ser Glu Val Leu Gly Ser Gly Lys Thr Leu Thr Ile Gln Val Lys
65                  70                  75                  80

gag ttt gga gat gct ggc cag tac acc tgt cac aaa gga ggc gag gtt      288
Glu Phe Gly Asp Ala Gly Gln Tyr Thr Cys His Lys Gly Gly Glu Val
```

```
                85                  90                  95

cta agc cat tcg ctc ctg ctg ctt cac aaa aag gaa gat gga att tgg      336
Leu Ser His Ser Leu Leu Leu Leu His Lys Lys Glu Asp Gly Ile Trp
            100                 105                 110

tcc act gat att tta aag gac cag aaa gaa ccc aaa aat aag acc ttt      384
Ser Thr Asp Ile Leu Lys Asp Gln Lys Glu Pro Lys Asn Lys Thr Phe
        115                 120                 125

cta aga tgc gag gcc aag aat tat tct gga cgt ttc acc tgc tgg tgg      432
Leu Arg Cys Glu Ala Lys Asn Tyr Ser Gly Arg Phe Thr Cys Trp Trp
    130                 135                 140

ctg acg aca atc agt act gat ttg aca ttc agt gtc aaa agc agc aga      480
Leu Thr Thr Ile Ser Thr Asp Leu Thr Phe Ser Val Lys Ser Ser Arg
145                 150                 155                 160

ggc tct tct gac ccc caa ggg gtg acg tgc gga gct gct aca ctc tct      528
Gly Ser Ser Asp Pro Gln Gly Val Thr Cys Gly Ala Ala Thr Leu Ser
                165                 170                 175

gca gag aga gtc aga ggg gac aac aag gag tat gag tac tca gtg gag      576
Ala Glu Arg Val Arg Gly Asp Asn Lys Glu Tyr Glu Tyr Ser Val Glu
            180                 185                 190

tgc cag gag gac agt gcc tgc cca gct gct gag gag agt ctg ccc att      624
Cys Gln Glu Asp Ser Ala Cys Pro Ala Ala Glu Glu Ser Leu Pro Ile
        195                 200                 205

gag gtc atg gtg gat gcc gtt cac aag ctc aag tat gaa aac tac acc      672
Glu Val Met Val Asp Ala Val His Lys Leu Lys Tyr Glu Asn Tyr Thr
    210                 215                 220

agc agc ttc ttc atc agg gac atc atc aaa cct gac cca ccc aag aac      720
Ser Ser Phe Phe Ile Arg Asp Ile Ile Lys Pro Asp Pro Pro Lys Asn
225                 230                 235                 240

ttg cag ctg aag cca tta aag aat tct cgg cag gtg gag gtc agc tgg      768
Leu Gln Leu Lys Pro Leu Lys Asn Ser Arg Gln Val Glu Val Ser Trp
                245                 250                 255

gag tac cct gac acc tgg agt act cca cat tcc tac ttc tcc ctg aca      816
Glu Tyr Pro Asp Thr Trp Ser Thr Pro His Ser Tyr Phe Ser Leu Thr
            260                 265                 270

ttc tgc gtt cag gtc cag ggc aag agc aag aga gaa aag aaa gat aga      864
Phe Cys Val Gln Val Gln Gly Lys Ser Lys Arg Glu Lys Lys Asp Arg
        275                 280                 285

gtc ttc acg gac aag acc tca gcc acg gtc atc tgc cgc aaa aat gcc      912
Val Phe Thr Asp Lys Thr Ser Ala Thr Val Ile Cys Arg Lys Asn Ala
    290                 295                 300

agc att agc gtg cgg gcc cag gac cgc tac tat agc tca tct tgg agc      960
Ser Ile Ser Val Arg Ala Gln Asp Arg Tyr Tyr Ser Ser Ser Trp Ser
305                 310                 315                 320

gaa tgg gca tct gtg ccc tgc agt tag                                  987
Glu Trp Ala Ser Val Pro Cys Ser
                325
```

<210> SEQ ID NO 22
<211> LENGTH: 328
<212> TYPE: PRT
<213> ORGANISM: Artificial Sequence
<220> FEATURE:
<223> OTHER INFORMATION: Synthetic Construct

<400> SEQUENCE: 22

```
Met Gly His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
```

```
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325


<210> SEQ ID NO 23
<211> LENGTH: 660
<212> TYPE: DNA
<213> ORGANISM: Artificial Sequence
<220> FEATURE:
<223> OTHER INFORMATION: Synthetic hIL-12, p35
<220> FEATURE:
<221> NAME/KEY: CDS
<222> LOCATION: (1)..(660)

<400> SEQUENCE: 23

atg ggt cca gcg cgc agc ctc ctc ctt gtg gct acc ctg gtc ctc ctg       48
Met Gly Pro Ala Arg Ser Leu Leu Leu Val Ala Thr Leu Val Leu Leu
1               5                   10                  15

gac cac ctc agt ttg gcc aga aac ctc ccc gtg gcc act cca gac cca       96
Asp His Leu Ser Leu Ala Arg Asn Leu Pro Val Ala Thr Pro Asp Pro
            20                  25                  30

gga atg ttc cca tgc ctt cac cac tcc caa aac ctg ctg agg gcc gtc      144
Gly Met Phe Pro Cys Leu His His Ser Gln Asn Leu Leu Arg Ala Val
```

```
        35                  40                  45

agc aac atg ctc cag aag gcc aga caa act cta gaa ttt tac cct tgc      192
Ser Asn Met Leu Gln Lys Ala Arg Gln Thr Leu Glu Phe Tyr Pro Cys
    50                  55                  60

act tct gaa gag att gat cat gaa gat atc aca aaa gat aaa acc agc      240
Thr Ser Glu Glu Ile Asp His Glu Asp Ile Thr Lys Asp Lys Thr Ser
65                  70                  75                  80

aca gtg gag gcc tgt tta cca ttg gaa tta acc aag aat gag agt tgc      288
Thr Val Glu Ala Cys Leu Pro Leu Glu Leu Thr Lys Asn Glu Ser Cys
                85                  90                  95

cta aat tcc aga gag acc tct ttc ata act aat ggg agt tgc ctg gcc      336
Leu Asn Ser Arg Glu Thr Ser Phe Ile Thr Asn Gly Ser Cys Leu Ala
            100                 105                 110

tcc aga aag acc tct ttt atg atg gcc ctg tgc ctt agt agt att tat      384
Ser Arg Lys Thr Ser Phe Met Met Ala Leu Cys Leu Ser Ser Ile Tyr
        115                 120                 125

gaa gac ttg aag atg tac cag gtg gag ttc aag acc atg aat gca aag      432
Glu Asp Leu Lys Met Tyr Gln Val Glu Phe Lys Thr Met Asn Ala Lys
    130                 135                 140

ctt ctg atg gat cct aag agg cag atc ttt cta gat caa aac atg ctg      480
Leu Leu Met Asp Pro Lys Arg Gln Ile Phe Leu Asp Gln Asn Met Leu
145                 150                 155                 160

gca gtt att gat gag ctg atg cag gcc ctg aat ttc aac agt gag act      528
Ala Val Ile Asp Glu Leu Met Gln Ala Leu Asn Phe Asn Ser Glu Thr
                165                 170                 175

gtg cca caa aaa tcc tcc ctt gaa gaa ccg gat ttt tat aaa act aaa      576
Val Pro Gln Lys Ser Ser Leu Glu Glu Pro Asp Phe Tyr Lys Thr Lys
            180                 185                 190

atc aag ctc tgc ata ctt ctt cat gct ttc aga att cgg gca gtg act      624
Ile Lys Leu Cys Ile Leu Leu His Ala Phe Arg Ile Arg Ala Val Thr
        195                 200                 205

att gat aga gtg atg agc tat ctg aat gct tcc taa                      660
Ile Asp Arg Val Met Ser Tyr Leu Asn Ala Ser
    210                 215


<210> SEQ ID NO 24
<211> LENGTH: 219
<212> TYPE: PRT
<213> ORGANISM: Artificial Sequence
<220> FEATURE:
<223> OTHER INFORMATION: Synthetic Construct

<400> SEQUENCE: 24

Met Gly Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125
```

```
Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215


<210> SEQ ID NO 25
<211> LENGTH: 17
<212> TYPE: PRT
<213> ORGANISM: Drosophila melanogaster

<400> SEQUENCE: 25

Arg Arg Gly Gly Thr Thr Cys Ala Asn Thr Gly Ala Cys Ala Cys Tyr
1               5                   10                  15

Tyr


<210> SEQ ID NO 26
<211> LENGTH: 13
<212> TYPE: DNA
<213> ORGANISM: Drosophila melanogaster
<220> FEATURE:
<221> NAME/KEY: misc_feature
<222> LOCATION: (7)..(7)
<223> OTHER INFORMATION: n is a, c, g, or t

<400> SEQUENCE: 26

aggtcanagg tca                                                          13


<210> SEQ ID NO 27
<211> LENGTH: 15
<212> TYPE: DNA
<213> ORGANISM: Drosophila melanogaster

<400> SEQUENCE: 27

gggttgaatg aattt                                                        15


<210> SEQ ID NO 28
<211> LENGTH: 18
<212> TYPE: DNA
<213> ORGANISM: Artificial Sequence
<220> FEATURE:
<223> OTHER INFORMATION: Synthetic homing endonuclease (HE) enzyme
      (I-SceI)

<400> SEQUENCE: 28

tagggataac agggtaat                                                     18


<210> SEQ ID NO 29
<211> LENGTH: 37323
<212> TYPE: DNA
<213> ORGANISM: Artificial Sequence
<220> FEATURE:
<223> OTHER INFORMATION: Synthetic Ad-RTS-hIL-12 (SP1-RheoIL-12)

<400> SEQUENCE: 29
```

-continued

```
catcatcaat aatatacctt attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggagatccg    360
gtaccggcgc gcgcgccgtt tggccgcctc gagtctagag atccggtgag tattaggcgc    420
gcaccaggtg ccgcaataaa atatctttat tttcattaca tctgtgtgtt ggttttttgt    480
gtgaatcgat agtactaaca tacgctctcc atcaaaacaa aacgaaacaa aacaaactag    540
caaaataggc tgtccccagt gcaagtgcag gtgccagaac atttctctat cgataatgca    600
ggtcggagta ctgtcctccg agcggagtac tgtcctccga gcggagtact gtcctccgag    660
cggagtactg tcctccgagc ggagtactgt cctccgagcg gagtactgtc ctccgagcgg    720
agactcttcg aaggaagagg ggcggggtcg atcgaccccg cccctcttcc ttcgaaggaa    780
gaggggcggg gtcgaagacc tagagggtat ataatgggtg ccttagctgg tgtgtgagct    840
catcttcctg tagatcacgc gtgccaccat gggtcaccag cagttggtca tctcttggtt    900
ttccctggtt tttctggcat ctcccctcgt ggccatatgg gaactgaaga aagatgttta    960
tgtcgtagaa ttggattggt atccggatgc ccctggagaa atggtggtcc tcacctgtga   1020
cacccctgaa gaagatggta tcacctggac cttggaccag agcagtgagg tcttaggctc   1080
tggcaaaacc ctgaccatcc aagtcaaaga gtttggagat gctggccagt acacctgtca   1140
caaaggaggc gaggttctaa gccattcgct cctgctgctt cacaaaaagg aagatggaat   1200
ttggtccact gatattttaa aggaccagaa agaacccaaa aataagacct ttctaagatg   1260
cgaggccaag aattattctg gacgtttcac ctgctggtgg ctgacgacaa tcagtactga   1320
tttgacattc agtgtcaaaa gcagcagagg ctcttctgac ccccaagggg tgacgtgcgg   1380
agctgctaca ctctctgcag agagagtcag aggggacaac aaggagtatg agtactcagt   1440
ggagtgccag gaggacagtg cctgcccagc tgctgaggag agtctgccca ttgaggtcat   1500
ggtggatgcc gttcacaagc tcaagtatga aaactacacc agcagcttct tcatcaggga   1560
catcatcaaa cctgacccac ccaagaactt gcagctgaag ccattaaaga attctcggca   1620
ggtggaggtc agctgggagt accctgacac ctggagtact ccacattcct acttctccct   1680
gacattctgc gttcaggtcc agggcaagag caagagagaa aagaaagata gagtcttcac   1740
ggacaagacc tcagccacgg tcatctgccg caaaaatgcc agcattagcg tgcgggccca   1800
ggaccgctac tatagctcat cttggagcga atgggcatct gtgccctgca gttaggttgg   1860
gcgagctcga attcattgat cccccgggct gcaggaattc gatatcaagc tcgggatccg   1920
aattccgccc cccccccccc cccccccta acgttactgg ccgaagccgc ttggaataag   1980
gccggtgtgc gtttgtctat atgttatttt ccaccatatt gccgtctttt ggcaatgtga   2040
gggcccggaa acctggccct gtcttcttga cgagcattcc taggggtctt tcccctctcg   2100
ccaaaggaat gcaaggtctg ttgaatgtcg tgaaggaagc agttcctctg gaagcttctt   2160
gaagacaaac aacgtctgta gcgacccttt gcaggcagcg gaacccccca cctggcgaca   2220
ggtgcctctg cggccaaaag ccacgtgtat aagatacacc tgcaaaggcg gcacaacccc   2280
agtgccacgt tgtgagttgg atagttgtgg aaagagtcaa atggctctcc tcaagcgtat   2340
tcaacaaggg gctgaaggat gcccagaagg taccccattg tatgggatct gatctggggc   2400
```

ctcggtgcac atgctttaca tgtgtttagt cgaggttaaa aaaacgtcta ggccccccga 2460
accacgggga cgtggttttc ctttgaaaaa cacgatgata atatggccac aaccatgggt 2520
ccagcgcgca gcctcctcct tgtggctacc ctggtcctcc tggaccacct cagtttggcc 2580
agaaacctcc ccgtggccac tccagaccca ggaatgttcc catgccttca ccactcccaa 2640
aacctgctga gggccgtcag caacatgctc cagaaggcca gacaaactct agaattttac 2700
ccttgcactt ctgaagagat tgatcatgaa gatatcacaa aagataaaac cagcacagtg 2760
gaggcctgtt taccattgga attaaccaag aatgagagtt gcctaaattc cagagagacc 2820
tctttcataa ctaatgggag ttgcctggcc tccagaaaga cctcttttat gatggccctg 2880
tgccttagta gtatttatga agacttgaag atgtaccagg tggagttcaa gaccatgaat 2940
gcaaagcttc tgatggatcc taagaggcag atctttctag atcaaaacat gctggcagtt 3000
attgatgagc tgatgcaggc cctgaatttc aacagtgaga ctgtgccaca aaaatcctcc 3060
cttgaagaac cggattttta taaaactaaa atcaagctct gcatacttct tcatgctttc 3120
agaattcggg cagtgactat tgatagagtg atgagctatc tgaatgcttc ctaacgtacg 3180
tcgacatcga gaacttgttt attgcagctt ataatggtta caaataaagc aatagcatca 3240
caaatttcac aaataaagca tttttttcac tgcattctag ttgtggtttg tccaaactca 3300
tcaatgtatc ttatcatgtc tgggcgcgcc ggcctccgcg ccgggttttg gcgcctcccg 3360
cgggcgcccc cctcctcacg gcgagcgctg ccacgtcaga cgaagggcgc agcgagcgtc 3420
ctgatccttc cgcccggacg ctcaggacag cggcccgctg ctcataagac tcggccttag 3480
aaccccagta tcagcagaag gacattttag gacgggactt gggtgactct agggcactgg 3540
ttttctttcc agagagcgga acaggcgagg aaaagtagtc ccttctcggc gattctgcgg 3600
agggatctcc gtggggcggt gaacgccgat gattatataa ggacgcgccg ggtgtggcac 3660
agctagttcc gtcgcagccg ggatttgggt cgcggttctt gtttgtggat cgctgtgatc 3720
gtcacttggt gagtagcggg ctgctgggct gggtacgtgc gctcggggtt ggcgagtgtg 3780
ttttgtgaag ttttttaggc accttttgaa atgtaatcat ttgggtcaat atgtaatttt 3840
cagtgttaga ctagtaaatt gtccgctaaa ttctggccgt ttttggcttt tttgttagac 3900
gagctagcgc cgccaccatg ggccctaaaa agaagcgtaa agtcgccccc ccgaccgatg 3960
tcagcctggg ggacgagctc cacttagacg gcgaggacgt ggcgatggcg catgccgacg 4020
cgctagacga tttcgatctg gacatgttgg gggacgggga ttccccgggt ccgggattta 4080
ccccccacga ctccgccccc tacggcgctc tggatatggc cgacttcgag tttgagcaga 4140
tgtttaccga tgcccttgga attgacgagt acggtgggga attcgagatg cctgtggaca 4200
ggatcctgga ggcagagctt gctgtggaac agaagagtga ccagggcgtt gagggtcctg 4260
ggggaaccgg gggtagcggc agcagcccaa atgaccctgt gactaacatc tgtcaggcag 4320
ctgacaaaca gctattcacg cttgttgagt gggcgaagag gatcccacac ttttcctcct 4380
tgcctctgga tgatcaggtc atattgctgc gggcaggctg gaatgaactc ctcattgcct 4440
ccttttcaca ccgatccatt gatgttcgag atggcatcct ccttgccaca ggtcttcacg 4500
tgcaccgcaa ctcagcccat tcagcaggag taggagccat ctttgatcgg gtgctgacag 4560
agctagtgtc caaaatgcgt gacatgagga tggacaagac agagcttggc tgcctgaggg 4620
caatcattct gtttaatcca gaggtgaggg gtttgaaatc cgcccaggaa gttgaacttc 4680
tacgtgaaaa agtatatgcc gctttggaag aatatactag aacaacacat cccgatgaac 4740

-continued

```
caggaagatt tgcaaaactt ttgcttcgtc tgccttcttt acgttccata ggccttaagt   4800

gtttggagca tttgtttttc tttcgcctta ttggagatgt tccaattgat acgttcctga   4860

tggagatgct tgaatcacct tctgattcat aatctagcct agccccccctc tccctccccc   4920

cccccctaacg ttactggccg aagccgcttg gaataaggcc ggtgtgcgtt tgtctatatg   4980

ttattttcca ccatattgcc gtcttttggc aatgtgaggg cccggaaacc tggccctgtc   5040

ttcttgacga gcattcctag gggtctttcc cctctcgcca aaggaatgca aggtctgttg   5100

aatgtcgtga aggaagcagt tcctctggaa gcttcttgaa gacaaacaac gtctgtagcg   5160

accctttgca ggcagcggaa ccccccacct ggcgacaggt gcctctgcgg ccaaaagcca   5220

cgtgtataag atacacctgc aaaggcggca caaccccagt gccacgttgt gagttggata   5280

gttgtggaaa gagtcaaatg gctctcctca agcgtattca acaaggggct gaaggatgcc   5340

cagaaggtac cccattgtat gggatctgat ctggggcctc ggtgcacatg ctttacatgt   5400

gtttagtcga ggttaaaaaa cgtctaggcc ccccgaacca cggggacgtg gttttccttt   5460

gaaaaacacg atctctaggc gccaccatga agctactgtc ttctatcgaa caagcatgcg   5520

atatttgccg acttaaaaag ctcaagtgct ccaaagaaaa accgaagtgc gccaagtgtc   5580

tgaagaacaa ctgggagtgt cgctactctc ccaaaaccaa aaggtctccg ctgactaggg   5640

cacatctgac agaagtggaa tcaaggctag aaagactgga acagctattt ctactgattt   5700

ttcctcgaga agaccttgac atgattttga aaatggattc tttacaggat ataaaagcat   5760

tgttaacagg attatttgta caagataatg tgaataaaga tgccgtcaca gatagattgg   5820

cttcagtgga gactgatatg cctctaacat tgagacagca tagaataagt gcgacatcat   5880

catcggaaga gagtagtaac aaaggtcaaa gacagttgac tgtatcgccg gaattcccgg   5940

ggatccggcc tgagtgcgta gtacccgaga ctcagtgcgc catgaagcgg aaagagaaga   6000

aagcacagaa ggagaaggac aaactgcctg tcagcacgac gacggtggac gaccacatgc   6060

cgcccattat gcagtgtgaa cctccacctc ctgaagcagc aaggattcac gaagtggtcc   6120

caaggtttct ctccgacaag ctgttggtga caaaccggca gaaaaacatc ccccagttga   6180

cagccaacca gcagttcctt atcgccaggc tcatctggta ccaggacggg tacgagcagc   6240

cttctgatga agatttgaag aggattacgc agacgtggca gcaagcggac gatgaaaacg   6300

aagagtcgga cactcccttc cgccagatca cagagatgac tatcctcacg gtccaactta   6360

tcgtggagtt cgcgaaggga ttgccagggt tcgccaagat ctcgcagcct gatcaaatta   6420

cgctgcttaa ggcttgctca agtgaggtaa tgatgctccg agtcgcgcga cgatacgatg   6480

cggcctcaga cagtattctg ttcgcgaaca accaagcgta cactcgcgac aactaccgca   6540

aggctggcat ggccgaggtc atcgaggatc tactgcactt ctgccggtgc atgtactcta   6600

tggcgttgga caacatccat tacgcgctgc tcacggctgt cgtcatcttt tctgaccggc   6660

cagggttgga gcagccgcaa ctggtggaag agatccagcg gtactacctg aatacgctcc   6720

gcatctatat cctgaaccag ctgagcgggt cggcgcgttc gtccgtcata tacggcaaga   6780

tcctctcaat cctctctgag ctacgcacgc tcggcatgca aaactccaac atgtgcatct   6840

ccctcaagct caagaacaga aagctgccgc ctttcctcga ggagatctgg gatgtggcgg   6900

acatgtcgca cacccaaccg ccgcctatcc tcgagtcccc cacgaatctc taggcggcct   6960

ctagagcggc cgccaccgcg gggagatcca gacatgataa gatacattga tgagtttgga   7020

caaaccacaa ctagaatgca gtgaaaaaaa tgctttattt gtgaaatttg tgatgctatt   7080

gctttatttg taaccattat aagctgcaat aaacaagtta acaacaacaa ttgcattcat   7140
```

-continued

```
tttatgtttc aggttcaggg ggaggtgtgg gaggtttttt aaagcaagta aaacctctac   7200
aaatgtggta tggctgatta tgatccggct gcctcgcgcg tttcggtgat gacggtgaaa   7260
acctctgaca catgcagctc ccggagacgg tcacagcttg tctgtaagcg gatgccggga   7320
gcagacaagc ccgtcagggc gcgtcagcgg gtgttggcgg gtgtcggggc gcagccatga   7380
ggtcgactct agtccccgcg gtggcagatc tggaaggtgc tgaggtacga tgagacccgc   7440
accaggtgca gaccctgcga gtgtggcggt aaacatatta ggaaccagcc tgtgatgctg   7500
gatgtgaccg aggagctgag gcccgatcac ttggtgctgg cctgcacccg cgctgagttt   7560
ggctctagcg atgaagatac agattgaggt actgaaatgt gtgggcgtgg cttaagggtg   7620
ggaaagaata tataaggtgg gggtcttatg tagttttgta tctgttttgc agcagccgcc   7680
gccgccatga gcaccaactc gtttgatgga agcattgtga gctcatattt gacaacgcgc   7740
atgcccccat gggccggggt gcgtcagaat gtgatgggct ccagcattga tggtcgcccc   7800
gtcctgcccg caaactctac taccttgacc tacgagaccg tgtctggaac gccgttggag   7860
actgcagcct ccgccgccgc ttcagccgct gcagccaccg cccgcgggat tgtgactgac   7920
tttgctttcc tgagcccgct tgcaagcagt gcagcttccc gttcatccgc ccgcgatgac   7980
aagttgacgg ctcttttggc acaattggat tctttgaccc gggaacttaa tgtcgtttct   8040
cagcagctgt tggatctgcg ccagcaggtt tctgccctga aggcttcctc ccctcccaat   8100
gcggtttaaa acataaataa aaaaccagac tctgtttgga tttggatcaa gcaagtgtct   8160
tgctgtcttt atttaggggt tttgcgcgcg cggtaggccc gggaccagcg gtctcggtcg   8220
ttgagggtcc tgtgtatttt ttccaggacg tggtaaaggt gactctggat gttcagatac   8280
atgggcataa gcccgtctct ggggtggagg tagcaccact gcagagcttc atgctgcggg   8340
gtggtgttgt agatgatcca gtcgtagcag gagcgctggg cgtggtgcct aaaaatgtct   8400
ttcagtagca agctgattgc caggggcagg cccttggtgt aagtgtttac aaagcggtta   8460
agctgggatg ggtgcatacg tggggatatg agatgcatct tggactgtat ttttaggttg   8520
gctatgttcc cagccatatc cctccgggga ttcatgttgt gcagaaccac cagcacagtg   8580
tatccggtgc acttgggaaa tttgtcatgt agcttagaag gaaatgcgtg gaagaacttg   8640
gagacgccct tgtgacctcc aagattttcc atgcattcgt ccataatgat ggcaatgggc   8700
ccacgggcgg cggcctgggc gaagatattt ctgggatcac taacgtcata gttgtgttcc   8760
aggatgagat cgtcataggc cattttaca aagcgcgggc ggagggtgcc agactgcggt   8820
ataatggttc catccggccc aggggcgtag ttaccctcac agatttgcat ttcccacgct   8880
ttgagttcag atggggggat catgtctacc tgcggggcga tgaagaaaac ggtttccggg   8940
gtaggggaga tcagctggga agaaagcagg ttcctgagca gctgcgactt accgcagccg   9000
gtgggcccgt aaatcacacc tattaccggc tgcaactggt agttaagaga gctgcagctg   9060
ccgtcatccc tgagcagggg ggccacttcg ttaagcatgt ccctgactcg catgttttcc   9120
ctgaccaaat ccgccagaag gcgctcgccg cccagcgata gcagttcttg caaggaagca   9180
aagtttttca acggtttgag accgtccgcc gtaggcatgc ttttgagcgt ttgaccaagc   9240
agttccaggc ggtcccacag ctcggtcacc tgctctacgg catctcgatc cagcatatct   9300
cctcgtttcg cgggttgggg cggctttcgc tgtacggcag tagtcggtgc tcgtccagac   9360
gggccagggt catgtctttc cacgggcgca gggtcctcgt cagcgtagtc tgggtcacgg   9420
tgaaggggtg cgctccgggc tgcgcgctgg ccagggtgcg cttgaggctg gtcctgctgg   9480
```

-continued

```
tgctgaagcg ctgccggtct tcgccctgcg cgtcggccag gtagcatttg accatggtgt   9540
catagtccag cccctccgcg gcgtggccct tggcgcgcag cttgcccttg gaggaggcgc   9600
cgcacgaggg gcagtgcaga cttttgaggg cgtagagctt gggcgcgaga aataccgatt   9660
ccggggagta ggcatccgcg ccgcaggccc cgcagacggt ctcgcattcc acgagccagg   9720
tgagctctgg ccgttcgggg tcaaaaacca ggtttccccc atgctttttg atgcgtttct   9780
tacctctggt ttccatgagc cggtgtccac gctcggtgac gaaaaggctg tccgtgtccc   9840
cgtatacaga cttgagaggc ctgtcctcga gcggtgttcc gcggtcctcc tcgtatagaa   9900
actcggacca ctctgagaca aaggctcgcg tccaggccag cacgaaggag gctaagtggg   9960
aggggtagcg gtcgttgtcc actagggggt ccactcgctc cagggtgtga agacacatgt  10020
cgccctcttc ggcatcaagg aaggtgattg gtttgtaggt gtaggccacg tgaccgggtg  10080
ttcctgaagg ggggctataa aagggggtgg gggcgcgttc gtcctcactc tcttccgcat  10140
cgctgtctgc gagggccagc tgttggggtg agtactccct ctgaaaagcg ggcatgactt  10200
ctgcgctaag attgtcagtt tccaaaaacg aggaggattt gatattcacc tggcccgcgg  10260
tgatgccttt gagggtggcc gcatccatct ggtcagaaaa gacaatcttt ttgttgtcaa  10320
gcttggtggc aaacgacccg tagagggcgt tggacagcaa cttggcgatg gagcgcaggg  10380
tttggttttt gtcgcgatcg gcgcgctcct tggccgcgat gtttagctgc acgtattcgc  10440
gcgcaacgca ccgccattcg ggaaagacgg tggtgcgctc gtcgggcacc aggtgcacgc  10500
gccaaccgcg gttgtgcagg gtgacaaggt caacgctggt ggctacctct ccgcgtaggc  10560
gctcgttggt ccagcagagg cggccgccct tgcgcgagca gaatggcggt agggggtcta  10620
gctgcgtctc gtccgggggg tctgcgtcca cggtaaagac cccgggcagc aggcgcgcgt  10680
cgaagtagtc tatcttgcat ccttgcaagt ctagcgcctg ctgccatgcg cgggcggcaa  10740
gcgcgcgctc gtatgggttg agtgggggac cccatggcat ggggtgggtg agcgcggagg  10800
cgtacatgcc gcaaatgtcg taaacgtaga ggggctctct gagtattcca agatatgtag  10860
ggtagcatct tccaccgcgg atgctggcgc gcacgtaatc gtatagttcg tgcgagggag  10920
cgaggaggtc gggaccgagg ttgctacggg cgggctgctc tgctcggaag actatctgcc  10980
tgaagatggc atgtgagttg gatgatatgg ttggacgctg gaagacgttg aagctggcgt  11040
ctgtgagacc taccgcgtca cgcacgaagg aggcgtagga gtcgcgcagc ttgttgacca  11100
gctcggcggt gacctgcacg tctagggcgc agtagtccag ggtttccttg atgatgtcat  11160
acttatcctg tccctttttt ttccacagct cgcggttgag gacaaactct tcgcggtctt  11220
tccagtactc ttggatcgga aacccgtcgg cctccgaacg gtaagagcct agcatgtaga  11280
actggttgac ggcctggtag gcgcagcatc cctttttctac gggtagcgcg tatgcctgcg  11340
cggccttccg gagcgaggtg tgggtgagcg caaaggtgtc cctgaccatg actttgaggt  11400
actggtattt gaagtcagtg tcgtcgcatc cgccctgctc ccagagcaaa aagtccgtgc  11460
gctttttgga acgcggattt ggcagggcga aggtgacatc gttgaagagt atctttcccg  11520
cgcgaggcat aaagttgcgt gtgatgcgga agggtcccgg cacctcggaa cggttgttaa  11580
ttacctgggc ggcgagcacg atctcgtcaa agccgttgat gttgtggccc acaatgtaaa  11640
gttccaagaa gcgcgggatg cccttgatgg aaggcaattt tttaagttcc tcgtaggtga  11700
gctcttcagg ggagctgagc ccgtgctctg aaagggccca gtctgcaaga tgagggttgg  11760
aagcgacgaa tgagctccac aggtcacggg ccattagcat ttgcaggtgg tcgcgaaagg  11820
tcctaaactg gcgacctatg gccatttttt ctggggtgat gcagtagaag gtaagcgggt  11880
```

-continued

```
cttgttccca gcggtcccat ccaaggttcg cggctaggtc tcgcgcggca gtcactagag  11940
gctcatctcc gccgaacttc atgaccagca tgaagggcac gagctgcttc ccaaaggccc  12000
ccatccaagt ataggtctct acatcgtagg tgacaaagag acgctcggtg cgaggatgcg  12060
agccgatcgg gaagaactgg atctcccgcc accaattgga ggagtggcta ttgatgtggt  12120
gaaagtagaa gtccctgcga cgggccgaac actcgtgctg gcttttgtaa aaacgtgcgc  12180
agtactggca gcggtgcacg ggctgtacat cctgcacgag gttgacctga cgaccgcgca  12240
caaggaagca gagtgggaat ttgagcccct cgcctggcgg gtttggctgg tggtcttcta  12300
cttcggctgc ttgtccttga ccgtctggct gctcgagggg agttacggtg gatcggacca  12360
ccacgccgcg cgagcccaaa gtccagatgt ccgcgcgcgg cggtcggagc ttgatgacaa  12420
catcgcgcag atgggagctg tccatggtct ggagctcccg cggcgtcagg tcaggcggga  12480
gctcctgcag gtttacctcg catagacggg tcagggcgcg ggctagatcc aggtgatacc  12540
taatttccag gggctggttg gtggcggcgt cgatggcttg caagaggccg catccccgcg  12600
gcgcgactac ggtaccgcgc ggcgggcggt gggccgcggg ggtgtccttg gatgatgcat  12660
ctaaaagcgg tgacgcgggc gagcccccgg aggtaggggg ggctccggac ccgccgggag  12720
agggggcagg ggcacgtcgg cgccgcgcgc gggcaggagc tggtgctgcg cgcgtaggtt  12780
gctggcgaac gcgacgacgc ggcggttgat ctcctgaatc tggcgcctct gcgtgaagac  12840
gacgggcccg gtgagcttga acctgaaaga gagttcgaca gaatcaattt cggtgtcgtt  12900
gacggcggcc tggcgcaaaa tctcctgcac gtctcctgag ttgtcttgat aggcgatctc  12960
ggccatgaac tgctcgatct cttcctcctg gagatctccg cgtccggctc gctccacggt  13020
ggcggcgagg tcgttggaaa tgcgggccat gagctgcgag aaggcgttga ggcctccctc  13080
gttccagacg cggctgtaga ccacgccccc ttcggcatcg cgggcgcgca tgaccacctg  13140
cgcgagattg agctccacgt gccgggcgaa gacggcgtag tttcgcaggc gctgaaagag  13200
gtagttgagg gtggtggcgg tgtgttctgc cacgaagaag tacataaccc agcgtcgcaa  13260
cgtggattcg ttgatatccc ccaaggcctc aaggcgctcc atggcctcgt agaagtccac  13320
ggcgaagttg aaaaactggg agttgcgcgc cgacacggtt aactcctcct ccagaagacg  13380
gatgagctcg gcgacagtgt cgcgcacctc gcgctcaaag gctacagggg cctcttcttc  13440
ttcttcaatc tcctcttcca taagggcctc cccttcttct tcttctggcg gcggtggggg  13500
agggggggaca cggcggcgac gacggcgcac cgggaggcgg tcgacaaagc gctcgatcat  13560
ctccccgcgg cgacggcgca tggtctcggt gacggcgcgg ccgttctcgc gggggcgcag  13620
ttggaagacg ccgcccgtca tgtcccggtt atgggttggc ggggggctgc catgcggcag  13680
ggatacggcg ctaacgatgc atctcaacaa ttgttgtgta ggtactccgc cgccgaggga  13740
cctgagcgag tccgcatcga ccggatcgga aaacctctcg agaaaggcgt ctaaccagtc  13800
acagtcgcaa ggtaggctga gcaccgtggc gggcggcagc gggcggcggt cggggttgtt  13860
tctggcggag gtgctgctga tgatgtaatt aaagtaggcg gtcttgagac ggcggatggt  13920
cgacagaagc accatgtcct tgggtccggc ctgctgaatg cgcaggcggt cggccatgcc  13980
ccaggcttcg ttttgacatc ggcgcaggtc tttgtagtag tcttgcatga gcctttctac  14040
cggcacttct tcttctcctt cctcttgtcc tgcatctctt gcatctatcg ctgcggcggc  14100
ggcggagttt ggccgtaggt ggcgccctct tcctcccatg cgtgtgaccc cgaagcccct  14160
catcggctga agcagggcta ggtcggcgac aacgcgctcg gctaatatgg cctgctgcac  14220
```

ctgcgtgagg gtagactgga agtcatccat gtccacaaag cggtggtatg cgcccgtgtt 14280
gatggtgtaa gtgcagttgg ccataacgga ccagttaacg gtctggtgac ccggctgcga 14340
gagctcggtg tacctgagac gcgagtaagc cctcgagtca aatacgtagt cgttgcaagt 14400
ccgcaccagg tactggtatc ccaccaaaaa gtgcggcggc ggctggcggt agaggggcca 14460
gcgtagggtg gccggggctc cgggggcgag atcttccaac ataaggcgat gatatccgta 14520
gatgtacctg gacatccagg tgatgccggc ggcggtggtg gaggcgcgcg gaaagtcgcg 14580
gacgcggttc cagatgttgc gcagcggcaa aaagtgctcc atggtcggga cgctctggcc 14640
ggtcaggcgc gcgcaatcgt tgacgctcta gcgtgcaaaa ggagagcctg taagcgggca 14700
ctcttccgtg gtctggtgga taaattcgca agggtatcat ggcggacgac cggggttcga 14760
gccccgtatc cggccgtccg ccgtgatcca tgcggttacc gcccgcgtgt cgaacccagg 14820
tgtgcgacgt cagacaacgg gggagtgctc cttttggctt ccttccaggc gcggcggctg 14880
ctgcgctagc ttttttggcc actggccgcg cgcagcgtaa gcggttaggc tggaaagcga 14940
aagcattaag tggctcgctc cctgtagccg gagggttatt ttccaagggt tgagtcgcgg 15000
gacccccggt tcgagtctcg gaccggccgg actgcggcga acgggggttt gcctccccgt 15060
catgcaagac cccgcttgca aattcctccg gaaacaggga cgagcccctt ttttgctttt 15120
cccagatgca tccggtgctg cggcagatgc gcccccctcc tcagcagcgg caagagcaag 15180
agcagcggca gacatgcagg gcaccctccc ctcctcctac cgcgtcagga ggggcgacat 15240
ccgcggttga cgcggcagca gatggtgatt acgaaccccc gcggcgccgg gcccggcact 15300
acctggactt ggaggagggc gagggcctgg cgcggctagg agcgccctct cctgagcggc 15360
acccaagggt gcagctgaag cgtgatacgc gtgaggcgta cgtgccgcgg cagaacctgt 15420
ttcgcgaccg cgagggagag gagcccgagg agatgcggga tcgaaagttc cacgcagggc 15480
gcgagctgcg gcatggcctg aatcgcgagc ggttgctgcg cgaggaggac tttgagcccg 15540
acgcgcgaac cgggattagt cccgcgcgcg cacacgtggc ggccgccgac ctggtaaccg 15600
catacgagca gacggtgaac caggagatta actttcaaaa aagctttaac aaccacgtgc 15660
gtacgcttgt ggcgcgcgag gaggtggcta taggactgat gcatctgtgg gactttgtaa 15720
gcgcgctgga gcaaaaccca aatagcaagc cgctcatggc gcagctgttc cttatagtgc 15780
agcacagcag ggacaacgag gcattcaggg atgcgctgct aaacatagta gagcccgagg 15840
gccgctggct gctcgatttg ataaacatcc tgcagagcat agtggtgcag gagcgcagct 15900
tgagcctggc tgacaaggtg gccgccatca actattccat gcttagcctg ggcaagtttt 15960
acgcccgcaa gatataccat accccttacg ttcccataga caaggaggta aagatcgagg 16020
ggttctacat gcgcatggcg ctgaaggtgc ttaccttgag cgacgacctg ggcgtttatc 16080
gcaacgagcg catccacaag gccgtgagcg tgagccggcg gcgcgagctc agcgaccgcg 16140
agctgatgca cagcctgcaa agggccctgg ctggcacggg cagcggcgat agagaggccg 16200
agtcctactt tgacgcgggc gctgacctgc gctgggcccc aagccgacgc gccctggagg 16260
cagctggggc cggacctggg ctggcggtgg cacccgcgcg cgctggcaac gtcggcggcg 16320
tggaggaata tgacgaggac gatgagtacg agccagagga cggcgagtac taagcggtga 16380
tgtttctgat cagatgatgc aagacgcaac ggacccggcg gtgcgggcgg cgctgcagag 16440
ccagccgtcc ggccttaact ccacggacga ctggcgccag gtcatggacc gcatcatgtc 16500
gctgactgcg cgcaatcctg acgcgttccg gcagcagccg caggccaacc ggctctccgc 16560
aattctggaa gcggtggtcc cggcgcgcgc aaaccccacg cacgagaagg tgctggcgat 16620

```
cgtaaacgcg ctggccgaaa acagggccat ccggcccgac gaggccggcc tggtctacga  16680
cgcgctgctt cagcgcgtgg ctcgttacaa cagcggcaac gtgcagacca acctggaccg  16740
gctggtgggg gatgtgcgcg aggccgtggc gcagcgtgag cgcgcgcagc agcagggcaa  16800
cctgggctcc atggttgcac taaacgcctt cctgagtaca cagcccgcca acgtgccgcg  16860
gggacaggag gactacacca actttgtgag cgcactgcgg ctaatggtga ctgagacacc  16920
gcaaagtgag gtgtaccagt ctgggccaga ctattttttc cagaccagta gacaaggcct  16980
gcagaccgta aacctgagcc aggctttcaa aaacttgcag gggctgtggg gggtgcgggc  17040
tcccacaggc gaccgcgcga ccgtgtctag cttgctgacg cccaactcgc gcctgttgct  17100
gctgctaata gcgcccttca cggacagtgg cagcgtgtcc cgggacacat acctaggtca  17160
cttgctgaca ctgtaccgcg aggccatagg tcaggcgcat gtggacgagc atactttcca  17220
ggagattaca agtgtcagcc gcgcgctggg gcaggaggac acgggcagcc tggaggcaac  17280
cctaaactac ctgctgacca accggcggca gaagatcccc tcgttgcaca gtttaaacag  17340
cgaggaggag cgcattttgc gctacgtgca gcagagcgtg agccttaacc tgatgcgcga  17400
cggggtaacg cccagcgtgg cgctggacat gaccgcgcgc aacatggaac cgggcatgta  17460
tgcctcaaac cggccgttta tcaaccgcct aatggactac ttgcatcgcg cggccgccgt  17520
gaaccccgag tatttcacca atgccatctt gaacccgcac tggctaccgc cccctggttt  17580
ctacaccggg ggattcgagg tgcccgaggg taacgatgga ttcctctggg acgacataga  17640
cgacagcgtg ttttccccgc aaccgcagac cctgctagag ttgcaacagc gcgagcaggc  17700
agaggcggcg ctgcgaaagg aaagcttccg caggccaagc agcttgtccg atctaggcgc  17760
tgcggccccg cggtcagatg ctagtagccc atttccaagc ttgatagggt ctcttaccag  17820
cactcgcacc acccgcccgc gcctgctggg cgaggaggag tacctaaaca actcgctgct  17880
gcagccgcag cgcgaaaaaa acctgcctcc ggcatttccc aacaacggga tagagagcct  17940
agtggacaag atgagtagat ggaagacgta cgcgcaggag cacagggacg tgccaggccc  18000
gcgcccgccc acccgtcgtc aaaggcacga ccgtcagcgg ggtctggtgt gggaggacga  18060
tgactcggca gacgacagca gcgtcctgga tttgggaggg agtggcaacc cgtttgcgca  18120
ccttcgcccc aggctgggga gaatgtttta aaaaaaaaaa aagcatgatg caaaataaaa  18180
aactcaccaa ggccatggca ccgagcgttg gttttcttgt attcccctta gtatgcggcg  18240
cgcggcgatg tatgaggaag gtcctcctcc ctcctacgag agtgtggtga gcgcggcgcc  18300
agtggcggcg gcgctgggtt ctcccttcga tgctcccctg gacccgccgt ttgtgcctcc  18360
gcggtacctg cggcctaccg gggggagaaa cagcatccgt tactctgagt tggcacccct  18420
attcgacacc acccgtgtgt acctggtgga caacaagtca acggatgtgg catccctgaa  18480
ctaccagaac gaccacagca actttctgac cacggtcatt caaaacaatg actacagccc  18540
gggggaggca agcacacaga ccatcaatct tgacgaccgg tcgcactggg gcggcgacct  18600
gaaaaccatc ctgcatacca acatgccaaa tgtgaacgag ttcatgttta ccaataagtt  18660
taaggcgcgg gtgatggtgt cgcgcttgcc tactaaggac aatcaggtgg agctgaaata  18720
cgagtgggtg gagttcacgc tgcccgaggg caactactcc gagaccatga ccatagacct  18780
tatgaacaac gcgatcgtgg agcactactt gaaagtgggc agacagaacg gggttctgga  18840
aagcgacatc ggggtaaagt ttgacacccg caacttcaga ctggggtttg accccgtcac  18900
tggtcttgtc atgcctgggg tatatacaaa cgaagccttc catccagaca tcattttgct  18960
```

-continued gccaggatgc ggggtggact tcacccacag ccgcctgagc aacttgttgg gcatccgcaa 19020
gcggcaaccc ttccaggagg gctttaggat cacctacgat gatctggagg gtggtaacat 19080
tcccgcactg ttggatgtgg acgcctacca ggcgagcttg aaagatgaca ccgaacaggg 19140
cgggggtggc gcaggcggca gcaacagcag tggcagcggc gcggaagaga actccaacgc 19200
ggcagccgcg gcaatgcagc cggtggagga catgaacgat catgccattc gcggcgacac 19260
ctttgccaca cgggctgagg agaagcgcgc tgaggccgaa gcagcggccg aagctgccgc 19320
ccccgctgcg caacccgagg tcgagaagcc tcagaagaaa ccggtgatca aacccctgac 19380
agaggacagc aagaaacgca gttacaacct aataagcaat gacagcacct tcacccagta 19440
ccgcagctgg taccttgcat acaactacgg cgaccctcag accggaatcc gctcatggac 19500
cctgctttgc actcctgacg taacctgcgg ctcggagcag gtctactggt cgttgccaga 19560
catgatgcaa gaccccgtga ccttccgctc cacgcgccag atcagcaact ttccggtggt 19620
gggcgccgag ctgttgcccg tgcactccaa gagcttctac aacgaccagg ccgtctactc 19680
ccaactcatc cgccagttta cctctctgac ccacgtgttc aatcgctttc ccgagaacca 19740
gattttggcg cgcccgccag cccccaccat caccaccgtc agtgaaaacg ttcctgctct 19800
cacagatcac gggacgctac cgctgcgcaa cagcatcgga ggagtccagc gagtgaccat 19860
tactgacgcc agacgccgca cctgccccta cgtttacaag gccctgggca tagtctcgcc 19920
gcgcgtccta tcgagccgca ctttttgagc aagcatgtcc atccttatat cgcccagcaa 19980
taacacaggc tggggcctgc gcttcccaag caagatgttt ggcggggcca agaagcgctc 20040
cgaccaacac ccagtgcgcg tgcgcgggca ctaccgcgcg ccctggggcg cgcacaaacg 20100
cggccgcact gggcgcacca ccgtcgatga cgccatcgac gcggtggtgg aggaggcgcg 20160
caactacacg cccacgccgc caccagtgtc cacagtggac gcggccattc agaccgtggt 20220
gcgcggagcc cggcgctatg ctaaaatgaa gagacggcgg aggcgcgtag cacgtcgcca 20280
ccgccgccga cccggcactg ccgcccaacg cgcggcggcg gccctgctta accgcgcacg 20340
tcgcaccggc cgacgggcgg ccatgcgggc cgctcgaagg ctggccgcgg gtattgtcac 20400
tgtgcccccc aggtccaggc gacgagcggc cgccgcagca gccgcggcca ttagtgctat 20460
gactcagggt cgcaggggca acgtgtattg ggtgcgcgac tcggttagcg gcctgcgcgt 20520
gcccgtgcgc acccgccccc cgcgcaacta gattgcaaga aaaaactact tagactcgta 20580
ctgttgtatg tatccagcgg cggcggcgcg caacgaagct atgtccaagc gcaaaatcaa 20640
agaagagatg ctccaggtca tcgcgccgga gatctatggc cccccgaaga aggaagagca 20700
ggattacaag ccccgaaagc taaagcgggt caaaaagaaa aagaaagatg atgatgatga 20760
acttgacgac gaggtggaac tgctgcacgc taccgcgccc aggcgacggg tacagtggaa 20820
aggtcgacgc gtaaaacgtg ttttgcgacc cggcaccacc gtagtcttta cgcccggtga 20880
gcgctccacc cgcacctaca agcgcgtgta tgatgaggtg tacggcgacg aggacctgct 20940
tgagcaggcc aacgagcgcc tcggggagtt tgcctacgga aagcggcata aggacatgct 21000
ggcgttgccg ctggacgagg gcaacccaac acctagccta aagcccgtaa cactgcagca 21060
ggtgctgccc gcgcttgcac cgtccgaaga aaagcgcggc ctaaagcgcg agtctggtga 21120
cttggcaccc accgtgcagc tgatggtacc caagcgccag cgactggaag atgtcttgga 21180
aaaaatgacc gtggaacctg ggctggagcc cgaggtccgc gtgcggccaa tcaagcaggt 21240
ggcgccggga ctgggcgtgc agaccgtgga cgttcagata cccactacca gtagcaccag 21300
tattgccacc gccacagagg gcatggagac acaaacgtcc ccggttgcct cagcggtggc 21360
ggatgccgcg gtgcaggcgg tcgctgcggc cgcgtccaag acctctacgg aggtgcaaac 21420
ggacccgtgg atgtttcgcg tttcagcccc ccggcgcccg cgccgttcga ggaagtacgg 21480
cgccgccagc gcgctactgc ccgaatatgc cctacatcct tccattgcgc ctaccccccgg 21540
ctatcgtggc tacacctacc gccccagaag acgagcaact acccgacgcc gaaccaccac 21600
tggaacccgc cgccgccgtc gccgtcgcca gcccgtgctg gccccgattt ccgtgcgcag 21660
ggtggctcgc gaaggaggca ggaccctggt gctgccaaca gcgcgctacc accccagcat 21720
cgtttaaaag ccggtctttg tggttcttgc agatatggcc ctcacctgcc gcctccgttt 21780
cccggtgccg ggattccgag gaagaatgca ccgtaggagg ggcatggccg gccacggcct 21840
gacgggcggc atgcgtcgtg cgcaccaccg gcggcggcgc gcgtcgcacc gtcgcatgcg 21900
cggcggtatc ctgcccctcc ttattccact gatcgccgcg gcgattggcg ccgtgcccgg 21960
aattgcatcc gtggccttgc aggcgcagag acactgatta aaaacaagtt gcatgtggaa 22020
aaatcaaaat aaaaagtctg gactctcacg ctcgcttggt cctgtaacta ttttgtagaa 22080
tggaagacat caactttgcg tctctggccc cgcgacacgg ctcgcgcccg ttcatgggaa 22140
actggcaaga tatcggcacc agcaatatga gcggtggcgc cttcagctgg ggctcgctgt 22200
ggagcggcat taaaaatttc ggttccaccg ttaagaacta tggcagcaag gcctggaaca 22260
gcagcacagg ccagatgctg agggataagt tgaaagagca aaatttccaa caaaaggtgg 22320
tagatggcct ggcctctggc attagcgggg tggtggacct ggccaaccag gcagtgcaaa 22380
ataagattaa cagtaagctt gatccccgcc ctcccgtaga ggagcctcca ccggccgtgg 22440
agacagtgtc tccagagggg cgtggcgaaa agcgtccgcg ccccgacagg gaagaaactc 22500
tggtgacgca aatagacgag cctccctcgt acgaggaggc actaaagcaa ggcctgccca 22560
ccacccgtcc catcgcgccc atggctaccg gagtgctggg ccagcacaca cccgtaacgc 22620
tggacctgcc tccccccgcc gacacccagc agaaacctgt gctgccaggc ccgaccgccg 22680
ttgttgtaac ccgtcctagc cgcgcgtccc tgcgccgcgc cgccagcggt ccgcgatcgt 22740
tgcggcccgt agccagtggc aactggcaaa gcacactgaa cagcatcgtg ggtctggggg 22800
tgcaatccct gaagcgccga cgatgcttct gatagctaac gtgtcgtatg tgtgtcatgt 22860
atgcgtccat gtcgccgcca gaggagctgc tgagccgccg cgcgcccgct ttccaagatg 22920
gctacccctt cgatgatgcc gcagtggtct tacatgcaca tctcgggcca ggacgcctcg 22980
gagtacctga gccccgggct ggtgcagttt gcccgcgcca ccgagacgta cttcagcctg 23040
aataacaagt ttagaaaccc cacggtggcg cctacgcacg acgtgaccac agaccggtcc 23100
cagcgtttga cgctgcggtt catccctgtg gaccgtgagg atactgcgta ctcgtacaag 23160
gcgcggttca ccctagctgt gggtgataac cgtgtgctgg acatggcttc cacgtacttt 23220
gacatccgcg gcgtgctgga caggggccct acttttaagc cctactctgg cactgcctac 23280
aacgccctgg ctcccaaggg tgccccaaat ccttgcgaat gggatgaagc tgctactgct 23340
cttgaaataa acctagaaga agaggacgat gacaacgaag acgaagtaga cgagcaagct 23400
gagcagcaaa aaactcacgt atttgggcag gcgccttatt ctggtataaa tattacaaag 23460
gagggtattc aaataggtgt cgaaggtcaa acacctaaat atgccgataa aacatttcaa 23520
cctgaacctc aaataggaga atctcagtgg tacgaaacag aaattaatca tgcagctggg 23580
agagtcctaa aaaagactac cccaatgaaa ccatgttacg gttcatatgc aaaacccaca 23640
aatgaaaatg gagggcaagg cattcttgta aagcaacaaa atggaaagct agaaagtcaa 23700

```
gtggaaatgc aatttttctc aactactgag gcagccgcag gcaatggtga taacttgact  23760
cctaaagtgg tattgtacag tgaagatgta gatatagaaa ccccagacac tcatatttct  23820
tacatgccca ctattaagga aggtaactca cgagaactaa tgggccaaca atctatgccc  23880
aacaggccta attacattgc ttttagggac aattttattg gtctaatgta ttacaacagc  23940
acgggtaata tgggtgttct ggcgggccaa gcatcgcagt tgaatgctgt tgtagatttg  24000
caagacagaa acacagagct ttcataccag cttttgcttg attccattgg tgatagaacc  24060
aggtactttt ctatgtggaa tcaggctgtt gacagctatg atccagatgt tagaattatt  24120
gaaaatcatg gaactgaaga tgaacttcca aattactgct ttccactggg aggtgtgatt  24180
aatacagaga ctcttaccaa ggtaaaacct aaaacaggtc aggaaaatgg atgggaaaaa  24240
gatgctacag aattttcaga taaaaatgaa ataagagttg gaaataattt tgccatggaa  24300
atcaatctaa atgccaacct gtggagaaat ttcctgtact ccaacatagc gctgtatttg  24360
cccgacaagc taaagtacag tccttccaac gtaaaaattt ctgataaccc aaacacctac  24420
gactacatga acaagcgagt ggtggctccc gggctagtgg actgctacat taaccttgga  24480
gcacgctggt cccttgacta tatggacaac gtcaacccat ttaaccacca ccgcaatgct  24540
ggcctgcgct accgctcaat gttgctgggc aatggtcgct atgtgccctt ccacatccag  24600
gtgcctcaga agttctttgc cattaaaaac ctccttctcc tgccgggctc atacacctac  24660
gagtggaact tcaggaagga tgttaacatg gttctgcaga gctccctagg aaatgaccta  24720
agggttgacg gagccagcat taagtttgat agcatttgcc tttacgccac cttcttcccc  24780
atggcccaca acaccgcctc cacgcttgag gccatgctta gaaacgacac caacgaccag  24840
tcctttaacg actatctctc cgccgccaac atgctctacc ctatacccgc caacgctacc  24900
aacgtgccca tatccatccc ctcccgcaac tgggcggctt tccgcggctg ggccttcacg  24960
cgccttaaga ctaaggaaac cccatcactg ggctcgggct acgaccctta ttacacctac  25020
tctggctcta taccctacct agatggaacc ttttacctca accacacctt taagaaggtg  25080
gccattacct ttgactcttc tgtcagctgg cctggcaatg accgcctgct tacccccaac  25140
gagtttgaaa ttaagcgctc agttgacggg gagggttaca acgttgccca gtgtaacatg  25200
accaaagact ggttcctggt acaaatgcta gctaactata acattggcta ccagggcttc  25260
tatatcccag agagctacaa ggaccgcatg tactccttct ttagaaactt ccagcccatg  25320
agccgtcagg tggtggatga tactaaatac aaggactacc aacaggtggg catcctacac  25380
caacacaaca actctggatt tgttggctac cttgccccca ccatgcgcga aggacaggcc  25440
taccctgcta acttccccta tccgcttata ggcaagaccg cagttgacag cattacccag  25500
aaaaagtttc tttgcgatcg caccctttgg cgcatcccat tctccagtaa ctttatgtcc  25560
atgggcgcac tcacagacct gggccaaaac cttctctacg ccaactccgc ccacgcgcta  25620
gacatgactt ttgaggtgga tcccatggac gagcccaccc ttctttatgt tttgtttgaa  25680
gtctttgacg tggtccgtgt gcaccagccg caccgcggcg tcatcgaaac cgtgtacctg  25740
cgcacgccct tctcggccgg caacgccaca acataaagaa gcaagcaaca tcaacaacag  25800
ctgccgccat gggctccagt gagcaggaac tgaaagccat tgtcaaagat cttggttgtg  25860
ggccatattt tttgggcacc tatgacaagc gctttccagg ctttgtttct ccacacaagc  25920
tcgcctgcgc catagtcaat acggccggtc gcgagactgg gggcgtacac tggatggcct  25980
ttgcctggaa cccgcactca aaaacatgct acctctttga gccctttggc ttttctgacc  26040
agcgactcaa gcaggtttac cagtttgagt acgagtcact cctgcgccgt agcgccattg  26100
```

-continued

```
cttcttcccc cgaccgctgt ataacgctgg aaaagtccac ccaaagcgta caggggccca  26160
actcggccgc ctgtggacta ttctgctgca tgtttctcca cgcctttgcc aactggcccc  26220
aaactcccat ggatcacaac cccaccatga accttattac cggggtaccc aactccatgc  26280
tcaacagtcc ccaggtacag cccaccctgc gtcgcaacca ggaacagctc tacagcttcc  26340
tggagcgcca ctcgccctac ttccgcagcc acagtgcgca gattaggagc gccacttctt  26400
tttgtcactt gaaaaacatg taaaaataat gtactagaga cactttcaat aaaggcaaat  26460
gcttttattt gtacactctc gggtgattat ttacccccac ccttgccgtc tgcgccgttt  26520
aaaaatcaaa ggggttctgc cgcgcatcgc tatgcgccac tggcagggac acgttgcgat  26580
actggtgttt agtgctccac ttaaactcag gcacaaccat ccgcggcagc tcggtgaagt  26640
tttcactcca caggctgcgc accatcacca acgcgtttag caggtcgggc gccgatatct  26700
tgaagtcgca gttggggcct ccgccctgcg cgcgcgagtt gcgatacaca gggttgcagc  26760
actggaacac tatcagcgcc gggtggtgca cgctggccag cacgctcttg tcggagatca  26820
gatccgcgtc caggtcctcc gcgttgctca gggcgaacgg agtcaacttt ggtagctgcc  26880
ttcccaaaaa gggcgcgtgc ccaggctttg agttgcactc gcaccgtagt ggcatcaaaa  26940
ggtgaccgtg cccggtctgg gcgttaggat acagcgcctg cataaaagcc ttgatctgct  27000
taaaagccac ctgagccttt gcgccttcag agaagaacat gccgcaagac ttgccggaaa  27060
actgattggc cggacaggcc gcgtcgtgca cgcagcacct tgcgtcggtg ttggagatct  27120
gcaccacatt tcggccccac cggttcttca cgatcttggc cttgctagac tgctccttca  27180
gcgcgcgctg cccgttttcg ctcgtcacat ccatttcaat cacgtgctcc ttatttatca  27240
taatgcttcc gtgtagacac ttaagctcgc cttcgatctc agcgcagcgg tgcagccaca  27300
acgcgcagcc cgtgggctcg tgatgcttgt aggtcacctc tgcaaacgac tgcaggtacg  27360
cctgcaggaa tcgccccatc atcgtcacaa aggtcttgtt gctggtgaag gtcagctgca  27420
acccgcggtg ctcctcgttc agccaggtct tgcatacggc cgccagagct tccacttggt  27480
caggcagtag tttgaagttc gcctttagat cgttatccac gtggtacttg tccatcagcg  27540
cgcgcgcagc ctccatgccc ttctcccacg cagacacgat cggcacactc agcgggttca  27600
tcaccgtaat ttcactttcc gcttcgctgg gctcttcctc ttcctcttgc gtccgcatac  27660
cacgcgccac tgggtcgtct tcattcagcc gccgcactgt gcgcttacct cctttgccat  27720
gcttgattag caccggtggg ttgctgaaac ccaccatttg tagcgccaca tcttctcttt  27780
cttcctcgct gtccacgatt acctctggtg atggcgggcg ctcgggcttg ggagaagggc  27840
gcttcttttt cttcttgggc gcaatggcca aatccgccgc cgaggtcgat ggccgcgggc  27900
tgggtgtgcg cggcaccagc gcgtcttgtg atgagtcttc ctcgtcctcg gactcgatac  27960
gccgcctcat ccgctttttt gggggcgccc ggggaggcgg cggcgacggg gacggggacg  28020
acacgtcctc catggttggg ggacgtcgcg ccgcaccgcg tccgcgctcg ggggtggttt  28080
cgcgctgctc ctcttcccga ctggccattt ccttctccta taggcagaaa aagatcatgg  28140
agtcagtcga gaagaaggac agcctaaccg ccccctctga gttcgccacc accgcctcca  28200
ccgatgccgc caacgcgcct accaccttcc ccgtcgaggc acccccgctt gaggaggagg  28260
aagtgattat cgagcaggac ccaggttttg taagcgaaga cgacgaggac cgctcagtac  28320
caacagagga taaaaagcaa gaccaggaca acgcagaggc aaacgaggaa caagtcgggc  28380
ggggggacga aaggcatggc gactacctag atgtgggaga cgacgtgctg ttgaagcatc  28440
```

-continued

```
tgcagcgcca gtgcgccatt atctgcgacg cgttgcaaga gcgcagcgat gtgcccctcg  28500
ccatagcgga tgtcagcctt gcctacgaac gccacctatt ctcaccgcgc gtacccccca  28560
aacgccaaga aaacggcaca tgcgagccca acccgcgcct caacttctac cccgtatttg  28620
ccgtgccaga ggtgcttgcc acctatcaca tctttttcca aaactgcaag ataccccctat  28680
cctgccgtgc caaccgcagc cgagcggaca agcagctggc cttgcggcag ggcgctgtca  28740
tacctgatat cgcctcgctc aacgaagtgc caaaaatctt tgagggtctt ggacgcgacg  28800
agaagcgcgc ggcaaacgct ctgcaacagg aaaacagcga aaatgaaagt cactctggag  28860
tgttggtgga actcgagggt gacaacgcgc gcctagccgt actaaaacgc agcatcgagg  28920
tcacccactt tgcctacccg gcacttaacc taccccccaa ggtcatgagc acagtcatga  28980
gtgagctgat cgtgcgccgt gcgcagcccc tggagaggga tgcaaatttg caagaacaaa  29040
cagaggaggg cctacccgca gttggcgacg agcagctagc gcgctggctt caaacgcgcg  29100
agcctgccga cttggaggag cgacgcaaac taatgatggc cgcagtgctc gttaccgtgg  29160
agcttgagtg catgcagcgg ttctttgctg acccggagat gcagcgcaag ctagaggaaa  29220
cattgcacta cacctttcga cagggctacg tacgccaggc ctgcaagatc tccaacgtgg  29280
agctctgcaa cctggtctcc taccttggaa ttttgcacga aaaccgcctt gggcaaaacg  29340
tgcttcattc cacgctcaag ggcgaggcgc gccgcgacta cgtccgcgac tgcgtttact  29400
tatttctatg ctacacctgg cagacggcca tgggcgtttg gcagcagtgc ttggaggagt  29460
gcaacctcaa ggagctgcag aaactgctaa agcaaaactt gaaggaccta tggacggcct  29520
tcaacgagcg ctccgtggcc gcgcacctgg cggacatcat tttccccgaa cgcctgctta  29580
aaaccctgca acagggtctg ccagacttca ccagtcaaag catgttgcag aactttagga  29640
actttatcct agagcgctca ggaatcttgc ccgccacctg ctgtgcactt cctagcgact  29700
ttgtgcccat taagtaccgc gaatgccctc cgccgctttg gggccactgc taccttctgc  29760
agctagccaa ctaccttgcc taccactctg acataatgga agacgtgagc ggtgacggtc  29820
tactggagtg tcactgtcgc tgcaacctat gcaccccgca ccgctccctg gtttgcaatt  29880
cgcagctgct taacgaaagt caaattatcg gtacctttga gctgcagggt ccctcgcctg  29940
acgaaaagtc cgcggctccg gggttgaaac tcactccggg gctgtggacg tcggcttacc  30000
ttcgcaaatt tgtacctgag gactaccacg cccacgagat taggttctac gaagaccaat  30060
cccgcccgcc taatgcggag cttaccgcct gcgtcattac ccagggccac attcttggcc  30120
aattgcaagc catcaacaaa gcccgccaag agtttctgct acgaaaggga cgggggggttt  30180
acttggaccc ccagtccggc gaggagctca acccaatccc cccgccgccg cagccctatc  30240
agcagcagcc gcgggccctt gcttcccagg atggcaccca aaaagaagct gcagctgccg  30300
ccgccaccca cggacgagga ggaatactgg gacagtcagg cagaggaggt tttggacgag  30360
gaggaggagg acatgatgga agactgggag agcctagacg aggaagcttc cgaggtcgaa  30420
gaggtgtcag acgaaacacc gtcaccctcg gtcgcattcc cctcgccggc gccccagaaa  30480
tcggcaaccg gttccagcat ggctacaacc tccgctcctc aggcgccgcc ggcactgccc  30540
gttcgccgac ccaaccgtag atgggacacc actggaacca gggccggtaa gtccaagcag  30600
ccgccgccgt tagcccaaga gcaacaacag cgccaaggct accgctcatg gcgcgggcac  30660
aagaacgcca tagttgcttg cttgcaagac tgtgggggca acatctcctt cgcccgccgc  30720
tttcttctct accatcacgg cgtggccttc ccccgtaaca tcctgcatta ctaccgtcat  30780
ctctacagcc catactgcac cggcggcagc ggcagcaaca gcagcggcca cacagaagca  30840
```

aaggcgaccg gatagcaaga ctctgacaaa gcccaagaaa tccacagcgg cggcagcagc 30900
aggaggagga gcgctgcgtc tggcgcccaa cgaacccgta tcgacccgcg agcttagaaa 30960
caggattttt cccactctgt atgctatatt tcaacagagc aggggccaag aacaagagct 31020
gaaaataaaa aacaggtctc tgcgatccct cacccgcagc tgcctgtatc acaaaagcga 31080
agatcagctt cggcgcacgc tggaagacgc ggaggctctc ttcagtaaat actgcgcgct 31140
gactcttaag gactagtttc gcgccctttc tcaaatttaa gcgcgaaaac tacgtcatct 31200
ccagcggcca cacccggcgc cagcacctgt tgtcagcgcc attatgagca aggaaattcc 31260
cacgccctac atgtggagtt accagccaca aatgggactt gcggctggag ctgcccaaga 31320
ctactcaacc cgaataaact acatgagcgc gggaccccac atgatatccc gggtcaacgg 31380
aatacgcgcc caccgaaacc gaattctcct ggaacaggcg gctattacca ccacacctcg 31440
taataacctt aatccccgta gttggcccgc tgccctggtg taccaggaaa gtcccgctcc 31500
caccactgtg gtacttccca gagacgccca ggccgaagtt cagatgacta actcaggggc 31560
gcagcttgcg ggcggctttc gtcacagggt gcggtcgccc gggcagggta taactcacct 31620
gacaatcaga gggcgaggta ttcagctcaa cgacgagtcg gtgagctcct cgcttggtct 31680
ccgtccggac gggacatttc agatcggcgg cgccggccgc tcttcattca cgcctcgtca 31740
ggcaatccta actctgcaga cctcgtcctc tgagccgcgc tctggaggca ttggaactct 31800
gcaatttatt gaggagtttg tgccatcggt ctactttaac cccttctcgg gacctcccgg 31860
ccactatccg gatcaattta ttcctaactt tgacgcggta aaggactcgg cggacggcta 31920
cgactgaatg ttaagtggag aggcagagca actgcgcctg aaacacctgg tccactgtcg 31980
ccgccacaag tgctttgccc gcgactccgg tgagttttgc tactttgaat tgcccgagga 32040
tcatatcgag ggcccggcgc acggcgtccg gcttaccgcc cagggagagc ttgcccgtag 32100
cctgattcgg gagtttaccc agcgccccct gctagttgag cgggacaggg gaccctgtgt 32160
tctcactgtg atttgcaact gtcctaaccc tggattacat caagatctta ttccctttaa 32220
ctaataaaaa aaaataataa agcatcactt acttaaaatc agttagcaaa tttctgtcca 32280
gtttattcag cagcacctcc ttgccctcct cccagctctg gtattgcagc ttcctcctgg 32340
ctgcaaactt tctccacaat ctaaatggaa tgtcagtttc ctcctgttcc tgtccatccg 32400
cacccactat cttcatgttg ttgcagatga agcgcgcaag accgtctgaa gataccttca 32460
accccgtgta tccatatgac acggaaaccg gtcctccaac tgtgcctttt cttactcctc 32520
cctttgtatc ccccaatggg tttcaagaga gtccccctgg ggtactctct ttgcgcctat 32580
ccgaacctct agttacctcc aatggcatgc ttgcgctcaa aatgggcaac ggcctctctc 32640
tggacgaggc cggcaacctt acctcccaaa atgtaaccac tgtgagccca cctctcaaaa 32700
aaaccaagtc aaacataaac ctggaaatat ctgcacccct cacagttacc tcagaagccc 32760
taactgtggc tgccgccgca cctctaatgg tcgcgggcaa cacactcacc atgcaatcac 32820
aggccccgct aaccgtgcac gactccaaac ttagcattgc cacccaagga cccctcacag 32880
tgtcagaagg aaagctagcc ctgcaaacat caggccccct caccaccacc gatagcagta 32940
cccttactat cactgcctca ccccctctaa ctactgccac tggtagcttg ggcattgact 33000
tgaaagagcc catttataca caaaatggaa aactaggact aaagtacggg gctcctttgc 33060
atgtaacaga cgacctaaac actttgaccg tagcaactgg tccaggtgtg actattaata 33120
atacttcctt gcaaactaaa gttactggag ccttgggttt tgattcacaa ggcaatatgc 33180

```
aacttaatgt agcaggagga ctaaggattg attctcaaaa cagacgcctt atacttgatg  33240
ttagttatcc gtttgatgct caaaaccaac taaatctaag actaggacag ggccctcttt  33300
ttataaactc agcccacaac ttggatatta actacaacaa aggcctttac ttgtttacag  33360
cttcaaacaa ttccaaaaag cttgaggtta acctaagcac tgccaagggg ttgatgtttg  33420
acgctacagc catagccatt aatgcaggag atgggcttga atttggttca cctaatgcac  33480
caaacacaaa tcccctcaaa acaaaaattg gccatggcct agaatttgat tcaaacaagg  33540
ctatggttcc taaactagga actggcctta gttttgacag cacaggtgcc attacagtag  33600
gaaacaaaaa taatgataag ctaactttgt ggaccacacc agctccatct cctaactgta  33660
gactaaatgc agagaaagat gctaaactca ctttggtctt aacaaaatgt ggcagtcaaa  33720
tacttgctac agtttcagtt ttggctgtta aaggcagttt ggctccaata tctggaacag  33780
ttcaaagtgc tcatcttatt ataagatttg acgaaaatgg agtgctacta aacaattcct  33840
tcctggaccc agaatattgg aactttagaa atggagatct tactgaaggc acagcctata  33900
caaacgctgt tggatttatg cctaacctat cagcttatcc aaaatctcac ggtaaaactg  33960
ccaaaagtaa cattgtcagt caagtttact taaacggaga caaaactaaa cctgtaacac  34020
taaccattac actaaacggt acacaggaaa caggagacac aactccaagt gcatactcta  34080
tgtcattttc atgggactgg tctggccaca actacattaa tgaaatattt gccacatcct  34140
cttacacttt ttcatacatt gcccaagaat aaagaatcgt ttgtgttatg tttcaacgtg  34200
tttatttttc aattgcagaa aatttcaagt catttttcat tcagtagtat agccccacca  34260
ccacatagct tatacagatc accgtacctt aatcaaactc acagaaccct agtattcaac  34320
ctgccacctc cctcccaaca cacagagtac acagtccttt ctccccggct ggccttaaaa  34380
agcatcatat catgggtaac agacatattc ttaggtgtta tattccacac ggtttcctgt  34440
cgagccaaac gctcatcagt gatattaata aactccccgg gcagctcact taagttcatg  34500
tcgctgtcca gctgctgagc cacaggctgc tgtccaactt gcggttgctt aacgggcggc  34560
gaaggagaag tccacgccta catgggggta gagtcataat cgtgcatcag gatagggcgg  34620
tggtgctgca gcagcgcgcg aataaactgc tgccgccgcc gctccgtcct gcaggaatac  34680
aacatggcag tggtctcctc agcgatgatt cgcaccgccc gcagcataag gcgccttgtc  34740
ctccgggcac agcagcgcac cctgatctca cttaaatcag cacagtaact gcagcacagc  34800
accacaatat tgttcaaaat cccacagtgc aaggcgctgt atccaaagct catggcgggg  34860
accacagaac ccacgtggcc atcataccac aagcgcaggt agattaagtg gcgacccctc  34920
ataaacacgc tggacataaa cattacctct tttggcatgt tgtaattcac cacctcccgg  34980
taccatataa acctctgatt aaacatggcg ccatccacca ccatcctaaa ccagctggcc  35040
aaaacctgcc cgccggctat acactgcagg gaaccgggac tggaacaatg acagtggaga  35100
gcccaggact cgtaaccatg gatcatcatg ctcgtcatga tatcaatgtt ggcacaacac  35160
aggcacacgt gcatacactt cctcaggatt acaagctcct cccgcgttag aaccatatcc  35220
cagggaacaa cccattcctg aatcagcgta aatcccacac tgcagggaag acctcgcacg  35280
taactcacgt tgtgcattgt caaagtgtta cattcgggca gcagcggatg atcctccagt  35340
atggtagcgc gggtttctgt ctcaaaagga ggtagacgat ccctactgta cggagtgcgc  35400
cgagacaacc gagatcgtgt tggtcgtagt gtcatgccaa atggaacgcc ggacgtagtc  35460
atatttcctg aagcaaaacc aggtgcgggc gtgacaaaca gatctgcgtc tccggtctcg  35520
ccgcttagat cgctctgtgt agtagttgta gtatatccac tctctcaaag catccaggcg  35580
```

-continued cccccctggct tcgggttcta tgtaaactcc ttcatgcgcc gctgccctga taacatccac 35640
caccgcagaa taagccacac ccagccaacc tacacattcg ttctgcgagt cacacacggg 35700
aggagcggga agagctggaa gaaccatgtt ttttttttta ttccaaaaga ttatccaaaa 35760
cctcaaaatg aagatctatt aagtgaacgc gctcccctcc ggtggcgtgg tcaaactcta 35820
cagccaaaga acagataatg gcatttgtaa gatgttgcac aatggcttcc aaaaggcaaa 35880
cggccctcac gtccaagtgg acgtaaaggc taaacccttc agggtgaatc tcctctataa 35940
acattccagc accttcaacc atgcccaaat aattctcatc tcgccacctt ctcaatatat 36000
ctctaagcaa atcccgaata ttaagtccgg ccattgtaaa aatctgctcc agagcgccct 36060
ccaccttcag cctcaagcag cgaatcatga ttgcaaaaat tcaggttcct cacagacctg 36120
tataagattc aaaagcggaa cattaacaaa aataccgcga tcccgtaggt cccttcgcag 36180
ggccagctga acataatcgt gcaggtctgc acggaccagc gcggccactt ccccgccagg 36240
aaccatgaca aaagaaccca cactgattat gacacgcata ctcggagcta tgctaaccag 36300
cgtagccccg atgtaagctt gttgcatggg cggcgatata aaatgcaagg tgctgctcaa 36360
aaaatcaggc aaagcctcgc gcaaaaaaga aagcacatcg tagtcatgct catgcagata 36420
aaggcaggta agctccggaa ccaccacaga aaaagacacc atttttctct caaacatgtc 36480
tgcgggtttc tgcataaaca caaaataaaa taacaaaaaa acatttaaac attagaagcc 36540
tgtcttacaa caggaaaaac aacccttata agcataagac ggactacggc catgccggcg 36600
tgaccgtaaa aaaactggtc accgtgatta aaaagcacca ccgacagctc ctcggtcatg 36660
tccggagtca taatgtaaga ctcggtaaac acatcaggtt gattcacatc ggtcagtgct 36720
aaaaagcgac cgaaatagcc cgggggaata catacccgca ggcgtagaga caacattaca 36780
gcccccatag gaggtataac aaaattaata ggagagaaaa acacataaac acctgaaaaa 36840
ccctcctgcc taggcaaaat agcaccctcc cgctccagaa caacatacag cgcttccaca 36900
gcggcagcca taacagtcag ccttaccagt aaaaaagaaa acctattaaa aaaacaccac 36960
tcgacacggc accagctcaa tcagtcacag tgtaaaaaag ggccaagtgc agagcgagta 37020
tatataggac taaaaaatga cgtaacggtt aaagtccaca aaaaacaccc agaaaaccgc 37080
acgcgaacct acgcccagaa acgaaagcca aaaaacccac aacttcctca aatcgtcact 37140
tccgttttcc cacgttacgt cacttcccat tttaagaaaa ctacaattcc caacacatac 37200
aagttactcc gccctaaaac ctacgtcacc cgccccgttc ccacgccccg cgccacgtca 37260
caaactccac cccctcatta tcatattggc ttcaatccaa aataaggtat attattgatg 37320
atg 37323

<210> SEQ ID NO 30
<211> LENGTH: 169
<212> TYPE: DNA
<213> ORGANISM: Artificial Sequence
<220> FEATURE:
<223> OTHER INFORMATION: Human Tumor necrosis factor WT 5' UTR

<400> SEQUENCE: 30
ctccctcagc aaggacagca gaggaccagc taagagggag agaagcaact acagaccccc 60
cctgaaaaca accctcagac gccacatccc ctgacaagct gccaggcagg ttctcttcct 120
ctcacatact gacccacggc tccaccctct ctcccctgga aaggacacc 169

<210> SEQ ID NO 31

<211> LENGTH: 179
<212> TYPE: DNA
<213> ORGANISM: Artificial Sequence
<220> FEATURE:
<223> OTHER INFORMATION: 5u2

<400> SEQUENCE: 31
cgaagaaggt gagtaatctt aacatgctct ttttttttt ttttgctaat cccttttgtg 60
tgctgatgtt aggatgacat ttacaacaaa tgtttgttcc tgacaggaaa aaccttgctg 120
ggtaccttcg ttgccggaca cttcttgtcc tctactttgg aaaaaaggaa ttgagagcc 179

<210> SEQ ID NO 32
<211> LENGTH: 72
<212> TYPE: DNA
<213> ORGANISM: Artificial Sequence
<220> FEATURE:
<223> OTHER INFORMATION: optUV 1:2 signal peptide - IL-2

<400> SEQUENCE: 32
atgtatagaa tgcagctcct gtcctgcatt gccctgagcc tcgccctcgt gacaaactcc 60
gcccctacct cc 72

<210> SEQ ID NO 33
<211> LENGTH: 228
<212> TYPE: DNA
<213> ORGANISM: Artificial Sequence
<220> FEATURE:
<223> OTHER INFORMATION: wtUV signal peptide - human TNF (TNF
      superfamily, member 2)

<400> SEQUENCE: 33
atgagcactg aaagcatgat ccgggacgtg gagctggccg aggaagccct ccccaagaaa 60
accggcggcc cccaggggag cagaagatgt ttgttcctga gcctgttctc cttcctgatc 120
gtggcaggcg ctaccaccct gttctgcctg ctgcactttg gagtgatcgg cccccagagg 180
gaggagttcc ccagggacct ctctctaatc agccctctgg cccaggca 228

<210> SEQ ID NO 34
<211> LENGTH: 228
<212> TYPE: DNA
<213> ORGANISM: Artificial Sequence
<220> FEATURE:
<223> OTHER INFORMATION: optUV 1:2 signal peptide - human tumor necrosis
      factor (TNF superfamily, member 2)

<400> SEQUENCE: 34
atgtccaccg aaagcatgat ccgggacgtg gagctggccg aggaagccct gcctaagaaa 60
accggaggcc ctcagggaag caggagatgt ctgtttctgt ccctgtttag ctttctgatt 120
gtggctggcg ctaccacact gttttgcctc ctgcatttcg gagtgattgg ccctcagagg 180
gaggagttcc ctagagacct gtccctgatt agccctctgg ctcaggct 228

<210> SEQ ID NO 35
<211> LENGTH: 474
<212> TYPE: DNA
<213> ORGANISM: Artificial Sequence
<220> FEATURE:
<223> OTHER INFORMATION: wtUV coding sequence human TNF (TNF
      superfamily, member 2)

<400> SEQUENCE: 35
gtcagatcat cttctcgaac cccgagtgac aagcctgtag cccatgttgt agcaaaccct 60

```
caagccgagg gccagctcca gtggctgaac cgccgggcca atgccctgct cgccaacggc    120

gtcgagctga gagataacca gctggtggtg ccatcagagg gcctgtacct catctactcc    180

caggtcctgt tcaagggcca aggctgcccc tccacccatg tgctcctcac ccacaccatc    240

agccgcatcg ccgtgagcta ccagaccaag gtcaacctcc tctctgccat caagagcccc    300

tgccagaggg agaccccaga gggggccgag gccaagccct ggtatgagcc catctacctc    360

ggcggggtgt tccagctgga gaagggtgac cgactcagcg ctgagatcaa tagacccgac    420

tatctcgact ttgccgagag cggccaggtg tactttggga tcattgccct gtga          474
```

<210> SEQ ID NO 36
<211> LENGTH: 474
<212> TYPE: DNA
<213> ORGANISM: Artificial Sequence
<220> FEATURE:
<223> OTHER INFORMATION: optUV 1:2 coding sequence Homo sapiens tumor necrosis factor (TNF superfamily, member 2)

<400> SEQUENCE: 36

```
gtgagaagca gcagcaggac ccctagcgat aagcctgtgg ctcacgtcgt cgctaaccct     60

caggccgagg gccagctcca gtggctgaat agaagggcca atgccctgct cgccaacggc    120

gtcgagctga gagacaatca gctcgtggtc ccctccgagg gactgtatct gatttactcc    180

caggtcctgt ttaagggaca gggatgccct agcacacacg tcctgctgac ccacaccatt    240

agcaggatcg ctgtgtccta ccaaaccaaa gtgaatctgc tgtccgctat caaaagccct    300

tgccaaagag aaacccctga gggagccgaa gccaaaccct ggtacgaacc catttacctc    360

ggcggagtgt ttcagctgga gaaaggcgat agactcagcg ctgagattaa caggcccgat    420

tacctcgact ttgccgaaag cggacaggtc tactttggca ttatcgctct gtaa          474
```

<210> SEQ ID NO 37
<211> LENGTH: 157
<212> TYPE: PRT
<213> ORGANISM: Artificial Sequence
<220> FEATURE:
<223> OTHER INFORMATION: amino acid sequence of TNF-alpha

<400> SEQUENCE: 37

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
```

145 150 155

<210> SEQ ID NO 38
<211> LENGTH: 132
<212> TYPE: DNA
<213> ORGANISM: Artificial Sequence
<220> FEATURE:
<223> OTHER INFORMATION: SV40e 3Reg containing polyA

<400> SEQUENCE: 38
aacttgttta ttgcagctta taatggttac aaataaagca atagcatcac aaatttcaca 60
aataaagcat ttttttcact gcattctagt tgtggtttgt ccaaactcat caatgtatct 120
tatcatgtct gg 132

<210> SEQ ID NO 39
<211> LENGTH: 627
<212> TYPE: DNA
<213> ORGANISM: Artificial Sequence
<220> FEATURE:
<223> OTHER INFORMATION: hGH 3Reg containing PolyA

<400> SEQUENCE: 39
tgatgggtgg catccctgtg acccctcccc agtgcctctc ctggccctgg aagttgccac 60
tccagtgccc accagccttg tcctaataaa attaagttgc atcattttgt ctgactaggt 120
gtccttctat aatattatgg ggtggagggg ggtggtatgg agcaaggggc aagttgggaa 180
gacaacctgt agggcctgcg gggtctattg ggaaccaagc tggagtgcag tggcacaatc 240
ttggctcact gcaatctccg cctcctgggt tcaagcgatt ctcctgcctc agcctcccga 300
gttgttggga ttccaggcat gcatgaccag gctcagctaa tttttgtttt tttggtagag 360
acggggtttc accatattgg ccaggctggt ctccaactcc taatctcagg tgatctaccc 420
accttggcct cccaaattgc tgggattaca ggcgtgaacc actgctccct tccctgtcct 480
tctgatttta aaataactat accagcagga ggacgtccag acacagcata ggctacctgg 540
ccatgcccaa ccggtgggac atttgagttg cttgcttggc actgtcctct catgcgttgg 600
gtccactcag tagatgcctg ttgaatt 627

<210> SEQ ID NO 40
<211> LENGTH: 1155
<212> TYPE: DNA
<213> ORGANISM: Artificial Sequence
<220> FEATURE:
<223> OTHER INFORMATION: Human TNF alpha 3'UTR

<400> SEQUENCE: 40
ggaggacgaa catccaacct tcccaaacgc ctcccctgcc ccaatccctt tattaccccc 60
tccttcagac accctcaacc tcttctggct caaaaagaga attgggggct tagggtcgga 120
acccaagctt agaactttaa gcaacaagac caccacttcg aaacctggga ttcaggaatg 180
tgtggcctgc acagtgaagt gctggcaacc actaagaatt caaactgggg cctccagaac 240
tcactggggc ctacagcttt gatccctgac atctggaatc tggagaccag ggagcctttg 300
gttctggcca gaatgctgca ggacttgaga agacctcacc tagaaattga cacaagtgga 360
ccttaggcct tcctctctcc agatgtttcc agacttcctt gagacacgga gcccagccct 420
ccccatggag ccagctccct ctatttatgt ttgcacttgt gattatttat tatttattta 480
ttatttattt atttacagat gaatgtattt atttgggaga ccggggtatc ctgggggacc 540
caatgtagga gctgccttgg ctcagacatg ttttccgtga aaacggagct gaacaatagg 600

-continued ctgttcccat gtagcccccct ggcctctgtg ccttcttttg attatgtttt ttaaaatatt 660
tatctgatta agttgtctaa acaatgctga tttggtgacc aactgtcact cattgctgag 720
cctctgctcc ccaggggagt tgtgtctgta atcgccctac tattcagtgg cgagaaataa 780
agtttgctta gaaaagaaac atggtctcct tcttggaatt aattctgcat ctgcctcttc 840
ttgtgggtgg gaagaagctc cctaagtcct ctctccacag gctttaagat ccctcggacc 900
cagtcccatc cttagactcc tagggccctg gagaccctac ataaacaaag cccaacagaa 960
tattccccat cccccaggaa acaagagcct gaacctaatt acctctccct cagggcatgg 1020
gaatttccaa ctctgggaat tccaatcctt gctgggaaaa tcctgcagct caggtgagat 1080
ttccggctgt tgcagctggc cagcagtccg gagagagctg gagaggagcc gcattctcag 1140
gtacctgaat cacac 1155

<210> SEQ ID NO 41
<211> LENGTH: 1155
<212> TYPE: DNA
<213> ORGANISM: Artificial Sequence
<220> FEATURE:
<223> OTHER INFORMATION: Human TNF alpha 3'UTR AtoC mutant

<400> SEQUENCE: 41
ggaggacgaa catccaacct tcccaaacgc ctcccctgcc ccaatccctt tattaccccc 60
tccttcagac accctcaacc tcttctggct caaaaagaga attgggggct tagggtcgga 120
acccaagctt agaactttaa gcaacaagac caccacttcg aaacctggga ttcaggaatg 180
tgtggcctgc acagtgaagt gctggcaacc actaagaatt caaactgggg cctccagaac 240
tcactggggc ctacagcttt gatccctgac atctggaatc tggagaccag ggagcctttg 300
gttctggcca gaatgctgca ggacttgaga agacctcacc tagaaattga cacaagtgga 360
ccttaggcct tcctctctcc agatgtttcc agacttcctt gagacacgga gcccagccct 420
ccccatggag ccagctccct ctatttatgt ttgcacttgt gattctttct tctttctttc 480
ttctttcttt ctttacagat gaatgtattt atttgggaga ccggggtatc ctgggggacc 540
caatgtagga gctgccttgg ctcagacatg ttttccgtga aaacggagct gaacaatagg 600
ctgttcccat gtagcccccct ggcctctgtg ccttcttttg attatgtttt ttaaaatatt 660
tatctgatta agttgtctaa acaatgctga tttggtgacc aactgtcact cattgctgag 720
cctctgctcc ccaggggagt tgtgtctgta atcgccctac tattcagtgg cgagaaataa 780
agtttgctta gaaaagaaac atggtctcct tcttggaatt aattctgcat ctgcctcttc 840
ttgtgggtgg gaagaagctc cctaagtcct ctctccacag gctttaagat ccctcggacc 900
cagtcccatc cttagactcc tagggccctg gagaccctac ataaacaaag cccaacagaa 960
tattccccat cccccaggaa acaagagcct gaacctaatt acctctccct cagggcatgg 1020
gaatttccaa ctctgggaat tccaatcctt gctgggaaaa tcctgcagct caggtgagat 1080
ttccggctgt tgcagctggc cagcagtccg gagagagctg gagaggagcc gcattctcag 1140
gtacctgaat cacac 1155

<210> SEQ ID NO 42
<211> LENGTH: 618
<212> TYPE: DNA
<213> ORGANISM: Artificial Sequence
<220> FEATURE:
<223> OTHER INFORMATION: Human GAST, 3' -UTR

<400> SEQUENCE: 42
caatcctaga accaagcttc agagcctagc cacctcccac cccactccag ccctgtcccc 60
tgaaaaactg atcaaaaata aactagtttc cagtggatca atggactgtg tcagtgttgt 120
agggcagagg agggggactc atctgggctc atctgggggt gaagttgtgg cagggactaa 180
gagctgagtg cctcttaggg gcagggaccg tcccccagag ccccacattg aacgagaatc 240
cacaggtatg ggcaggataa tatatggtag ggttcatagc cagagtaacc ttttttttta 300
atttttattt tattttattt ttgagatgga gtttcgctct tgtctcccag gctggagtgc 360
aataatgaga cctcagctca ctgcaacctc tgcctcctag gttcaagcga ttttcctgcc 420
tcagcctccc aagtagctgg gattacaggt gcccgccacc acacctggct aatttttttg 480
tatttttagt ggggacgggg tttcaccatg ttggccaggc tggtcttgaa ctcctgacct 540
cagtgatcca cccgcctcgg cctcccaaag tgctgggatt acagcatgag ccaccgtgcc 600
cagcctcaga gtaagctt 618

<210> SEQ ID NO 43
<211> LENGTH: 589
<212> TYPE: DNA
<213> ORGANISM: Artificial Sequence
<220> FEATURE:
<223> OTHER INFORMATION: Synthetic 3' REG

<400> SEQUENCE: 43
ttctcaagaa agccctcatt tttataacct ggcaaaatct tgttaatgtc attgctaaaa 60
aataaataaa agctagatac tggaaaccta actgcaatgt ggatgtttta cccacatgac 120
ttattatgca taaagccaaa tttccagttt aagtaattgc ctacaataaa aagaaatttt 180
gcctgccatt ttcagaatca tcttttgaag ctttctgttg atgttaactg agctactaga 240
gatattctta tttcactaaa tgtaaaattt ggagtaaata tatatgtcaa tatttagtaa 300
agcttttctt ttttaatttc caggaaaaaa taaaaagagt atgagtcttc tgtaattcat 360
tgagcagtta gctcatttga gataaagtca aatgccaaac actagctctg tattaatccc 420
catcattact ggaataaaag atctttattt tcattagatc tgtgtgttgg ttttttgtgt 480
gggccttggg ggagggggag gccagaatgg ccttgggga gggggaggcc agaatggcct 540
tgggggaggg ggaggccaga atggccttgg gggaggggga ggccagaat 589

<210> SEQ ID NO 44
<211> LENGTH: 102
<212> TYPE: DNA
<213> ORGANISM: Artificial Sequence
<220> FEATURE:
<223> OTHER INFORMATION: Hum GAPDH 5UTR

<400> SEQUENCE: 44
aaattgagcc cgcagcctcc cgcttcgctc tctgctcctc ctgttcgaca gtcagccgca 60
tcttcttttg cgtcgccagc cgagccacat cgctcagaca cc 102

<210> SEQ ID NO 45
<211> LENGTH: 72
<212> TYPE: DNA
<213> ORGANISM: Artificial Sequence
<220> FEATURE:
<223> OTHER INFORMATION: wtUV Insulin SP coding sequence

<400> SEQUENCE: 45
atggccctgt ggatgcgcct cctgcccctg ctggcgctgc tggccctctg gggacctgac 60
ccagccgcag cc 72

<210> SEQ ID NO 46
<211> LENGTH: 96
<212> TYPE: DNA
<213> ORGANISM: Artificial Sequence
<220> FEATURE:
<223> OTHER INFORMATION: wtUV Human FGF-19 signal peptide

<400> SEQUENCE: 46
atgcggagcg ggtgtgtggt ggtccacgta tggatcttgg ccggactgtg gctggccgtg 60
gccgggagac ccctcgcctt ctcggacgcc ggaccc 96

<210> SEQ ID NO 47
<211> LENGTH: 10780
<212> TYPE: DNA
<213> ORGANISM: Artificial Sequence
<220> FEATURE:
<223> OTHER INFORMATION: PolyDNA_from_VVN_43318

<400> SEQUENCE: 47
taaacaaata ggggttccgc gcacatttcc ccgaaaagtg ccacctgacg tctaagaaac 60
cattattatc atgacattaa cctataaaaa taggcgtatc acgaggccct ttcgtcttca 120
attaattaag ctagcatcat caataatata ccttattttg gattgaagcc aatatgataa 180
tgagggggtg gagtttgtga cgtggcgcgg ggcgtgggaa cggggcgggt gacgtagtag 240
tgtggcggaa gtgtgatgtt gcaagtgtgg cggaacacat gtaagcgacg gatgtggcaa 300
aagtgacgtt tttggtgtgc gccggtgtac acaggaagtg acaattttcg cgcggtttta 360
ggcggatgtt gtagtaaatt tgggcgtaac cgagtaagat ttggccattt tcgcgggaaa 420
actgaataag aggaagtgaa atctgaataa ttttgtgtta ctcatagcgc gtaatatttg 480
tctagggaga tccggtaccg gcgcgcgcgc cgtttggccg cctcgagtct agagatccgg 540
tgagtattag gcgcgcacca ggtgccgcaa taaaatatct ttattttcat tacatctgtg 600
tgttggtttt ttgtgtgaat cgatagtact aacatacgct ctccatcaaa acaaaacgaa 660
acaaaacaaa ctagcaaaat aggctgtccc cagtgcaagt gcaggtgcca gaacatttct 720
ctatcgataa tgcaggtcgg agtactgtcc tccgagcgga gtactgtcct ccgagcggag 780
tactgtcctc cgagcggagt actgtcctcc gagcggagta ctgtcctccg agcggagtac 840
tgtcctccga gcggagactc ttcgaaggaa gaggggcggg gtcgatcgac cccgcccctc 900
ttccttcgaa ggaagagggg cggggtcgaa gacctagagg gtatataatg ggtgccttag 960
ctggtgtgtg agctcatctt cctgtagatc acgcgtctcc ctcagcaagg acagcagagg 1020
accagctaag agggagagaa gcaactacag acccccccctg aaaacaaccc tcagacgcca 1080
catcccctga caagctgcca ggcaggttct cttcctctca catactgacc cacggctcca 1140
ccctctctcc cctggaaagg acaccgctag cgccaccatg agcactgaaa gcatgatccg 1200
ggacgtggag ctggccgagg aagccctccc caagaaaacc ggcggccccc aggggagcag 1260
aagatgtttg ttcctgagcc tgttttcctt cctgatcgtg gcaggcgcta ccaccctgtt 1320
ctgcctgctg cactttggag tgatcggccc ccagagggag gagttcccca gggacctctc 1380
tctaatcagc cctctggccc aggcaggatc cgtcagatca tcttctcgaa ccccgagtga 1440
caagcctgta gcccatgttg tagcaaaccc tcaagccgag ggccagctcc agtggctgaa 1500
ccgccgggcc aatgccctgc tcgccaacgg cgtcgagctg agagataacc agctggtggt 1560

-continued

```
gccatcagag ggcctgtacc tcatctactc ccaggtcctg ttcaagggcc aaggctgccc   1620
ctccacccat gtgctcctca cccacaccat cagccgcatc gccgtgagct accagaccaa   1680
ggtcaacctc ctctctgcca tcaagagccc ctgccagagg gagaccccag agggggccga   1740
ggccaagccc tggtatgagc ccatctacct cggcggggtg ttccagctgg agaagggtga   1800
ccgactcagc gctgagatca atagacccga ctatctcgac tttgccgaga gcggccaggt   1860
gtactttggg atcattgccc tgtgaatcga ttcgtacgtc gacatcgaga acttgtttat   1920
tgcagcttat aatggttaca aataaagcaa tagcatcaca aatttcacaa ataaagcatt   1980
tttttcactg cattctagtt gtggtttgtc caaactcatc aatgtatctt atcatgtctg   2040
ggcgcgccgg cctccgcgcc gggttttggc gcctcccgcg ggcgcccccc tcctcacggc   2100
gagcgctgcc acgtcagacg aagggcgcag cgagcgtcct gatccttccg cccggacgct   2160
caggacagcg gcccgctgct cataagactc ggccttagaa ccccagtatc agcagaagga   2220
cattttagga cgggacttgg gtgactctag ggcactggtt ttctttccag agagcggaac   2280
aggcgaggaa aagtagtccc ttctcggcga ttctgcggag ggatctccgt ggggcggtga   2340
acgccgatga ttatataagg acgcgccggg tgtggcacag ctagttccgt cgcagccggg   2400
atttgggtcg cggttcttgt ttgtggatcg ctgtgatcgt cacttggtga gtagcgggct   2460
gctgggctgg gtacgtgcgc tcggggttgg cgagtgtgtt ttgtgaagtt ttttaggcac   2520
cttttgaaat gtaatcattt gggtcaatat gtaattttca gtgttagact agtaaattgt   2580
ccgctaaatt ctggccgttt ttggcttttt tgttagacga gctagcgccg ccaccatggg   2640
ccctaaaaag aagcgtaaag tcgccccccc gaccgatgtc agcctggggg acgagctcca   2700
cttagacggc gaggacgtgg cgatggcgca tgccgacgcg ctagacgatt tcgatctgga   2760
catgttgggg gacggggatt ccccgggtcc gggatttacc ccccacgact ccgcccccta   2820
cggcgctctg gatatggccg acttcgagtt tgagcagatg tttaccgatg cccttggaat   2880
tgacgagtac ggtggggaat tcgagatgcc tgtggacagg atcctggagg cagagcttgc   2940
tgtggaacag aagagtgacc agggcgttga gggtcctggg ggaaccgggg gtagcggcag   3000
cagcccaaat gaccctgtga ctaacatctg tcaggcagct gacaaacagc tattcacgct   3060
tgttgagtgg gcgaagagga tcccacactt ttcctccttg cctctggatg atcaggtcat   3120
attgctgcgg gcaggctgga atgaactcct cattgcctcc ttttcacacc gatccattga   3180
tgttcgagat ggcatcctcc ttgccacagg tcttcacgtg caccgcaact cagcccattc   3240
agcaggagta ggagccatct ttgatcgggt gctgacagag ctagtgtcca aaatgcgtga   3300
catgaggatg gacaagacag agcttggctg cctgagggca atcattctgt ttaatccaga   3360
ggtgaggggt ttgaaatccg cccaggaagt tgaacttcta cgtgaaaaag tatatgccgc   3420
tttggaagaa tatactagaa caacacatcc cgatgaacca ggaagatttg caaaactttt   3480
gcttcgtctg ccttctttac gttccatagg ccttaagtgt ttggagcatt tgtttttctt   3540
tcgccttatt ggagatgttc caattgatac gttcctgatg gagatgcttg aatcaccttc   3600
tgattcataa tctagcctag ccccccctctc cctccccccc ccctaacgtt actggccgaa   3660
gccgcttgga ataaggccgg tgtgcgtttg tctatatgtt attttccacc atattgccgt   3720
cttttggcaa tgtgagggcc cggaaacctg gccctgtctt cttgacgagc attcctaggg   3780
gtctttcccc tctcgccaaa ggaatgcaag gtctgttgaa tgtcgtgaag gaagcagttc   3840
ctctggaagc ttcttgaaga caaacaacgt ctgtagcgac cctttgcagg cagcggaacc   3900
ccccacctgg cgacaggtgc ctctgcggcc aaaagccacg tgtataagat acacctgcaa   3960
```

-continued

```
aggcggcaca accccagtgc cacgttgtga gttggatagt tgtggaaaga gtcaaatggc   4020
tctcctcaag cgtattcaac aaggggctga aggatgccca gaaggtaccc cattgtatgg   4080
gatctgatct ggggcctcgg tgcacatgct ttacatgtgt ttagtcgagg ttaaaaaacg   4140
tctaggcccc ccgaaccacg gggacgtggt tttcctttga aaaacacgat ctctaggcgc   4200
caccatgaag ctactgtctt ctatcgaaca agcatgcgat atttgccgac ttaaaaagct   4260
caagtgctcc aaagaaaaac cgaagtgcgc caagtgtctg aagaacaact gggagtgtcg   4320
ctactctccc aaaaccaaaa ggtctccgct gactagggca catctgacag aagtggaatc   4380
aaggctagaa agactggaac agctatttct actgattttt cctcgagaag accttgacat   4440
gattttgaaa atggattctt tacaggatat aaaagcattg ttaacaggat tatttgtaca   4500
agataatgtg aataaagatg ccgtcacaga tagattggct tcagtggaga ctgatatgcc   4560
tctaacattg agacagcata gaataagtgc gacatcatca tcggaagaga gtagtaacaa   4620
aggtcaaaga cagttgactg tatcgccgga attcccgggg atccggcctg agtgcgtagt   4680
acccgagact cagtgcgcca tgaagcggaa agagaagaaa gcacagaagg agaaggacaa   4740
actgcctgtc agcacgacga cggtggacga ccacatgccg cccattatgc agtgtgaacc   4800
tccacctcct gaagcagcaa ggattcacga agtggtccca aggtttctct ccgacaagct   4860
gttggtgaca aaccggcaga aaaacatccc ccagttgaca gccaaccagc agttccttat   4920
cgccaggctc atctggtacc aggacgggta cgagcagcct tctgatgaag atttgaagag   4980
gattacgcag acgtggcagc aagcggacga tgaaaacgaa gagtcggaca ctcccttccg   5040
ccagatcaca gagatgacta tcctcacggt ccaacttatc gtggagttcg cgaagggatt   5100
gccagggttc gccaagatct cgcagcctga tcaaattacg ctgcttaagg cttgctcaag   5160
tgaggtaatg atgctccgag tcgcgcgacg atacgatgcg gcctcagaca gtattctgtt   5220
cgcgaacaac caagcgtaca ctcgcgacaa ctaccgcaag gctggcatgg ccgaggtcat   5280
cgaggatcta ctgcacttct gccggtgcat gtactctatg gcgttggaca acatccatta   5340
cgcgctgctc acggctgtcg tcatcttttc tgaccggcca gggttggagc agccgcaact   5400
ggtggaagag atccagcggt actacctgaa tacgctccgc atctatatcc tgaaccagct   5460
gagcgggtcg gcgcgttcgt ccgtcatata cggcaagatc ctctcaatcc tctctgagct   5520
acgcacgctc ggcatgcaaa actccaacat gtgcatctcc ctcaagctca agaacagaaa   5580
gctgccgcct ttcctcgagg agatctggga tgtggcggac atgtcgcaca cccaaccgcc   5640
gcctatcctc gagtccccca cgaatctcta ggcggcctct agagcggccg ccaccgcggg   5700
gagatccaga catgataaga tacattgatg agtttggaca aaccacaact agaatgcagt   5760
gaaaaaaatg ctttatttgt gaaatttgtg atgctattgc tttatttgta accattataa   5820
gctgcaataa acaagttaac aacaacaatt gcattcattt tatgtttcag gttcaggggg   5880
aggtgtggga ggttttttaa agcaagtaaa acctctacaa atgtggtatg gctgattatg   5940
atccggctgc ctcgcgcgtt tcggtgatga cggtgaaaac ctctgacaca tgcagctccc   6000
ggagacggtc acagcttgtc tgtaagcgga tgccgggagc agacaagccc gtcagggcgc   6060
gtcagcgggt gttggcgggt gtcggggcgc agccatgagg tcgactctag tccccgcggt   6120
ggcagatctg gaaggtgctg aggtacgatg agacccgcac caggtgcaga ccctgcgagt   6180
gtggcggtaa acatattagg aaccagcctg tgatgctgga tgtgaccgag gagctgaggc   6240
ccgatcactt ggtgctggcc tgcacccgcg ctgagtttgg ctctagcgat gaagatacag   6300
```

-continued

```
attgaggtac tgaaatgtgt gggcgtggct taagggtggg aaagaatata taaggtgggg   6360
gtcttatgta gttttgtatc tgttttgcag cagccgccgc cgccatgagc accaactcgt   6420
ttgatggaag cattgtgagc tcatatttga caacgcgcat gcccccatgg gccggggtgc   6480
gtcagaatgt gatgggctcc agcattgatg gtcgccccgt cctgcccgca aactctacta   6540
ccttgaccta cgagaccgtg tctggaacgc cgttggagac tgcagcctcc gccgccgctt   6600
cagccgctgc agccaccgcc cgcgggattg tgactgactt tgctttcctg agcccgcttg   6660
caagcagtgc agcttcccgt tcatccgccc gcgatgacaa gttgacggct cttttggcac   6720
aattggattc tttgacccgg gaacttaatg tcgtttctca gcagctgttg gatctgcgcc   6780
agcaggtttc tgccctgaag gcttcctccc ctcccaatgc ggtttaaaac ataaataaaa   6840
aaccagactc tgtttggatt tggatcaagc aagtgtcttg ctgtctttat ttaggggttt   6900
tgcgcgcgcg gtaggcccgg gaccagcggt ctcggtcgtt gagggtcctg tgtatttttt   6960
ccaggacgtg gtaaaggtga ctctggatgt tcagatacat gggcataagc ccgtctctgg   7020
ggtggaggta gcaccactgc agagcttcat gctgcggggt ggtgttgtag atgatccagt   7080
cgtagcagga gcgctgggcg tggtgcctaa aaatgtcttt cagtagcaag ctgattgcca   7140
ggggcaggcc cttggtgtaa gtgtttacaa agcggttaag ctgggatggg tgcatacgtg   7200
gggatatgag atgcatcttg gactgtattt ttaggttggc tatgttccca gccatatccc   7260
tccggggatt catgttgtgc agaaccacca gcacagtgta tccggtgcac ttgggaaatt   7320
tgtcatgtag cttagaagga aatgcgtgga agaacttgga gacgcccttg tgacctccaa   7380
gattttccat gcattcgtcc ataatgatgg caatgggccc acgggcggcg gcctgggcga   7440
agatatttct gggatcacta acgtcatagt tgtgttccag gatgagatcg tcataggcca   7500
tttttacaaa gcgcgggcgg agggtgccag actgcggtat aatggttcca tccggcccag   7560
gggcgtagtt accctcacag atttgcattt cccacgcttt gagttcagat ggggggatca   7620
tgtctacctg cggggcgatg aagaaaacgg tttccggggt aggggagatc agctgggaag   7680
aaagcaggtt cctgagcagc tgcgacttac cgcagccggt gggcccgtaa atcacaccta   7740
ttaccggctg caactggtag ttaagagagc tgcagctgcc gtcatccctg agcagggggg   7800
ccacttcgtt aagcatgtcc ctgactcgca tgttttccct gaccaaatcc gccagaaggc   7860
gctcgccgcc cagcgatagc agttcttgca aggaagcaaa gtttttcaac ggtttgagac   7920
cgtccgccgt aggcatgctt ttgagcgttt gaccaagcag ttccaggcgg tcccacagct   7980
cggtcacctg ctctacggca tctcgatcca gcatatctcc tcgtttcgcg ggttggggcg   8040
gctttcgctg tacggcagta gtcggtgctc gtccagacgg gccagggtca tgtctttcca   8100
cgggcgcagg gtcctcgtca gcgtagtctg ggtcacggtg aaggggtgcg ctccgggctg   8160
cgcgctggcc agggtgcgct tgaggctggt cctgctggtg ctgaagcgct gccggtcttc   8220
gccctgcgcg tcggccaggt agcatttgac catggtgtca tagtccagcc cctccgcggc   8280
gtggcccttg gcgcgcagct tgcccttgga ggaggcgccg cacgaggggc agtgcagact   8340
tttgagggcg tagagcttgg gcgcgagaaa taccgattcc ggggagtagg catccgcgcc   8400
gcaggccccg cagacggtct cgcattccac gagccaggtg agctctggcc gttcggggtc   8460
aaaaaccagg tttcccccat gctttttgat gcgtttctta cctctggttt ccatgagccg   8520
gtgtccacgc tcggtgacga aaaggctgtc cgtgtccccg tatacagact tgagaggcct   8580
gtcctcgacc gatgcccttg agagccttca acccagtcag ctccttccgg tgggcgcggg   8640
gcatgactat cgtcgccgca cttatgactg tcttctttat catgcaactc gtaggacagg   8700
```

-continued tgccggcagc gctctgggtc attttcggcg aggaccgctt tcgctggagc gcgacgatga 8760
tcggcctgtc gcttgcggta ttcggaatct tgcacgccct cgctcaagcc ttcgtcactg 8820
gtcccgccac caaacgtttc ggcgagaagc aggccattat cgccggcatg gcggccgacg 8880
cgctgggcta cgtcttgctg gcgttcgcga cgcgaggctg gatggccttc cccattatga 8940
ttcttctcgc ttccggcggc atcgggatgc ccgcgttgca ggccatgctg tccaggcagg 9000
tagatgacga ccatcaggga cagcttcaag gccagcaaaa ggccaggaac cgtaaaaagg 9060
ccgcgttgct ggcgtttttc cataggctcc gcccccctga cgagcatcac aaaaatcgac 9120
gctcaagtca gaggtggcga aacccgacag gactataaag ataccaggcg tttccccctg 9180
gaagctccct cgtgcgctct cctgttccga ccctgccgct taccggatac ctgtccgcct 9240
ttctcccttc gggaagcgtg gcgctttctc atagctcacg ctgtaggtat ctcagttcgg 9300
tgtaggtcgt tcgctccaag ctgggctgtg tgcacgaacc ccccgttcag cccgaccgct 9360
gcgccttatc cggtaactat cgtcttgagt ccaacccggt aagacacgac ttatcgccac 9420
tggcagcagc cactggtaac aggattagca gagcgaggta tgtaggcggt gctacagagt 9480
tcttgaagtg gtggcctaac tacggctaca ctagaaggac agtatttggt atctgcgctc 9540
tgctgaagcc agttaccttc ggaaaaagag ttggtagctc ttgatccggc aaacaaacca 9600
ccgctggtag cggtggtttt tttgtttgca agcagcagat tacgcgcaga aaaaaaggat 9660
ctcaagaaga tcctttgatc ttttctacgg ggtctgacgc tcagtggaac gaaaactcac 9720
gttaagggat tttggtcatg agattatcaa aaaggatctt cacctagatc cttttaaatt 9780
aaaaatgaag ttttaaatca atctaaagta tatatgagta aacttggtct gacagttacc 9840
aatgcttaat cagtgaggca cctatctcag cgatctgtct atttcgttca tccatagttg 9900
cctgactccc cgtcgtgtag ataactacga tacgggaggg cttaccatct ggccccagtg 9960
ctgcaatgat accgcgagac ccacgctcac cggctccaga tttatcagca ataaaccagc 10020
cagccggaag ggccgagcgc agaagtggtc ctgcaacttt atccgcctcc atccagtcta 10080
ttaattgttg ccgggaagct agagtaagta gttcgccagt taatagtttg cgcaacgttg 10140
ttgccattgc tgcaggcatc gtggtgtcac gctcgtcgtt tggtatggct tcattcagct 10200
ccggttccca acgatcaagg cgagttacat gatcccccat gttgtgcaaa aaagcggtta 10260
gctccttcgg tcctccgatc gttgtcagaa gtaagttggc cgcagtgtta tcactcatgg 10320
ttatggcagc actgcataat tctcttactg tcatgccatc cgtaagatgc ttttctgtga 10380
ctggtgagta ctcaaccaag tcattctgag aatagtgtat gcggcgaccg agttgctctt 10440
gcccggcgtc aacacgggat aataccgcgc cacatagcag aactttaaaa gtgctcatca 10500
ttggaaaacg ttcttcgggg cgaaaactct caaggatctt accgctgttg agatccagtt 10560
cgatgtaacc cactcgtgca cccaactgat cttcagcatc ttttactttc accagcgttt 10620
ctgggtgagc aaaaacagga aggcaaaatg ccgcaaaaaa gggaataagg gcgacacgga 10680
aatgttgaat actcatactc ttcctttttc aatattattg aagcatttat cagggttatt 10740
gtctcatgag cggatacata tttgaatgta tttagaaaaa 10780

<210> SEQ ID NO 48
<211> LENGTH: 10780
<212> TYPE: DNA
<213> ORGANISM: Artificial Sequence
<220> FEATURE:
<223> OTHER INFORMATION: PolyDNA_from_VVN-43319

<400> SEQUENCE: 48
taaacaaata ggggttccgc gcacatttcc ccgaaaagtg ccacctgacg tctaagaaac 60
cattattatc atgacattaa cctataaaaa taggcgtatc acgaggccct ttcgtcttca 120
attaattaag ctagcatcat caataatata ccttattttg gattgaagcc aatatgataa 180
tgagggggtg gagtttgtga cgtggcgcgg ggcgtgggaa cggggcgggt gacgtagtag 240
tgtggcggaa gtgtgatgtt gcaagtgtgg cggaacacat gtaagcgacg gatgtggcaa 300
aagtgacgtt tttggtgtgc gccggtgtac acaggaagtg acaattttcg cgcggtttta 360
ggcggatgtt gtagtaaatt tgggcgtaac cgagtaagat ttggccattt tcgcgggaaa 420
actgaataag aggaagtgaa atctgaataa ttttgtgtta ctcatagcgc gtaatatttg 480
tctagggaga tccggtaccg gcgcgcgcgc cgtttggccg cctcgagtct agagatccgg 540
tgagtattag gcgcgcacca ggtgccgcaa taaaatatct ttattttcat tacatctgtg 600
tgttggtttt ttgtgtgaat cgatagtact aacatacgct ctccatcaaa acaaaacgaa 660
acaaaacaaa ctagcaaaat aggctgtccc cagtgcaagt gcaggtgcca gaacatttct 720
ctatcgataa tgcaggtcgg agtactgtcc tccgagcgga gtactgtcct ccgagcggag 780
tactgtcctc cgagcggagt actgtcctcc gagcggagta ctgtcctccg agcggagtac 840
tgtcctccga gcggagactc ttcgaaggaa gaggggcggg gtcgatcgac cccgcccctc 900
ttccttcgaa ggaagagggg cggggtcgaa gacctagagg gtatataatg ggtgccttag 960
ctggtgtgtg agctcatctt cctgtagatc acgcgtctcc ctcagcaagg acagcagagg 1020
accagctaag agggagagaa gcaactacag acccccccctg aaaacaaccc tcagacgcca 1080
catcccctga caagctgcca ggcaggttct cttcctctca catactgacc cacggctcca 1140
ccctctctcc cctggaaagg acaccgctag cgccaccatg tccaccgaaa gcatgatccg 1200
ggacgtggag ctggccgagg aagccctgcc taagaaaacc ggaggccctc agggaagcag 1260
gagatgtctg tttctgtccc tgtttagctt tctgattgtg gctggcgcta ccacactgtt 1320
ttgcctcctg catttcggag tgattggccc tcagagggag gagttcccta gagacctgtc 1380
cctgattagc cctctggctc aggctggatc cgtgagaagc agcagcagga cccctagcga 1440
taagcctgtg gctcacgtcg tcgctaaccc tcaggccgag ggccagctcc agtggctgaa 1500
tagaagggcc aatgccctgc tcgccaacgg cgtcgagctg agagacaatc agctcgtggt 1560
cccctccgag ggactgtatc tgatttactc ccaggtcctg tttaagggac agggatgccc 1620
tagcacacac gtcctgctga cccacaccat tagcaggatc gctgtgtcct accaaaccaa 1680
agtgaatctg ctgtccgcta tcaaaagccc ttgccaaaga gaaacccctg agggagccga 1740
agccaaaccc tggtacgaac ccatttacct cggcggagtg tttcagctgg agaaaggcga 1800
tagactcagc gctgagatta acaggcccga ttacctcgac tttgccgaaa gcggacaggt 1860
ctactttggc attatcgctc tgtaaatcga ttcgtacgtc gacatcgaga acttgtttat 1920
tgcagcttat aatggttaca aataaagcaa tagcatcaca aatttcacaa ataaagcatt 1980
tttttcactg cattctagtt gtggtttgtc caaactcatc aatgtatctt atcatgtctg 2040
ggcgcgccgg cctccgcgcc gggttttggc gcctcccgcg ggcgcccccc tcctcacggc 2100
gagcgctgcc acgtcagacg aagggcgcag cgagcgtcct gatccttccg cccggacgct 2160
caggacagcg gcccgctgct cataagactc ggccttagaa ccccagtatc agcagaagga 2220
cattttagga cgggacttgg gtgactctag ggcactggtt ttctttccag agagcggaac 2280
aggcgaggaa aagtagtccc ttctcggcga ttctgcggag ggatctccgt ggggcggtga 2340

-continued

```
acgccgatga ttatataagg acgcgccggg tgtggcacag ctagttccgt cgcagccggg   2400
atttgggtcg cggttcttgt ttgtggatcg ctgtgatcgt cacttggtga gtagcgggct   2460
gctgggctgg gtacgtgcgc tcggggttgg cgagtgtgtt ttgtgaagtt ttttaggcac   2520
cttttgaaat gtaatcattt gggtcaatat gtaattttca gtgttagact agtaaattgt   2580
ccgctaaatt ctggccgttt ttggcttttt tgttagacga gctagcgccg ccaccatggg   2640
ccctaaaaag aagcgtaaag tcgccccccc gaccgatgtc agcctggggg acgagctcca   2700
cttagacggc gaggacgtgg cgatggcgca tgccgacgcg ctagacgatt tcgatctgga   2760
catgttgggg gacggggatt ccccgggtcc gggatttacc ccccacgact ccgcccccta   2820
cggcgctctg gatatggccg acttcgagtt tgagcagatg tttaccgatg cccttggaat   2880
tgacgagtac ggtggggaat tcgagatgcc tgtggacagg atcctggagg cagagcttgc   2940
tgtggaacag aagagtgacc agggcgttga gggtcctggg ggaaccgggg gtagcggcag   3000
cagcccaaat gaccctgtga ctaacatctg tcaggcagct gacaaacagc tattcacgct   3060
tgttgagtgg gcgaagagga tcccacactt ttcctccttg cctctggatg atcaggtcat   3120
attgctgcgg gcaggctgga atgaactcct cattgcctcc ttttcacacc gatccattga   3180
tgttcgagat ggcatcctcc ttgccacagg tcttcacgtg caccgcaact cagcccattc   3240
agcaggagta ggagccatct ttgatcgggt gctgacagag ctagtgtcca aaatgcgtga   3300
catgaggatg gacaagacag agcttggctg cctgagggca atcattctgt ttaatccaga   3360
ggtgaggggt ttgaaatccg cccaggaagt tgaacttcta cgtgaaaaag tatatgccgc   3420
tttggaagaa tatactagaa caacacatcc cgatgaacca ggaagatttg caaaactttt   3480
gcttcgtctg ccttctttac gttccatagg ccttaagtgt ttggagcatt tgtttttctt   3540
tcgccttatt ggagatgttc caattgatac gttcctgatg gagatgcttg aatcaccttc   3600
tgattcataa tctagcctag ccccccctctc cctccccccc ccctaacgtt actggccgaa   3660
gccgcttgga ataaggccgg tgtgcgtttg tctatatgtt attttccacc atattgccgt   3720
cttttggcaa tgtgagggcc cggaaacctg gccctgtctt cttgacgagc attcctaggg   3780
gtctttcccc tctcgccaaa ggaatgcaag gtctgttgaa tgtcgtgaag gaagcagttc   3840
ctctggaagc ttcttgaaga caaacaacgt ctgtagcgac cctttgcagg cagcggaacc   3900
ccccacctgg cgacaggtgc ctctgcggcc aaaagccacg tgtataagat acacctgcaa   3960
aggcggcaca accccagtgc cacgttgtga gttggatagt tgtggaaaga gtcaaatggc   4020
tctcctcaag cgtattcaac aaggggctga aggatgccca gaaggtaccc cattgtatgg   4080
gatctgatct ggggcctcgg tgcacatgct ttacatgtgt ttagtcgagg ttaaaaaacg   4140
tctaggcccc ccgaaccacg gggacgtggt tttcctttga aaaacacgat ctctaggcgc   4200
caccatgaag ctactgtctt ctatcgaaca agcatgcgat atttgccgac ttaaaaagct   4260
caagtgctcc aaagaaaaac cgaagtgcgc caagtgtctg aagaacaact gggagtgtcg   4320
ctactctccc aaaaccaaaa ggtctccgct gactagggca catctgacag aagtggaatc   4380
aaggctagaa agactggaac agctatttct actgattttt cctcgagaag accttgacat   4440
gattttgaaa atggattctt tacaggatat aaaagcattg ttaacaggat tatttgtaca   4500
agataatgtg aataaagatg ccgtcacaga tagattggct tcagtggaga ctgatatgcc   4560
tctaacattg agacagcata gaataagtgc gacatcatca tcggaagaga gtagtaacaa   4620
aggtcaaaga cagttgactg tatcgccgga attcccgggg atccggcctg agtgcgtagt   4680
```

-continued

```
acccgagact cagtgcgcca tgaagcggaa agagaagaaa gcacagaagg agaaggacaa   4740
actgcctgtc agcacgacga cggtggacga ccacatgccg cccattatgc agtgtgaacc   4800
tccacctcct gaagcagcaa ggattcacga agtggtccca aggtttctct ccgacaagct   4860
gttggtgaca aaccggcaga aaaacatccc ccagttgaca gccaaccagc agttccttat   4920
cgccaggctc atctggtacc aggacgggta cgagcagcct tctgatgaag atttgaagag   4980
gattacgcag acgtggcagc aagcggacga tgaaaacgaa gagtcggaca ctcccttccg   5040
ccagatcaca gagatgacta tcctcacggt ccaacttatc gtggagttcg cgaagggatt   5100
gccagggttc gccaagatct cgcagcctga tcaaattacg ctgcttaagg cttgctcaag   5160
tgaggtaatg atgctccgag tcgcgcgacg atacgatgcg gcctcagaca gtattctgtt   5220
cgcgaacaac caagcgtaca ctcgcgacaa ctaccgcaag gctggcatgg ccgaggtcat   5280
cgaggatcta ctgcacttct gccggtgcat gtactctatg gcgttggaca acatccatta   5340
cgcgctgctc acggctgtcg tcatcttttc tgaccggcca gggttggagc agccgcaact   5400
ggtggaagag atccagcggt actacctgaa tacgctccgc atctatatcc tgaaccagct   5460
gagcgggtcg gcgcgttcgt ccgtcatata cggcaagatc ctctcaatcc tctctgagct   5520
acgcacgctc ggcatgcaaa actccaacat gtgcatctcc ctcaagctca agaacagaaa   5580
gctgccgcct ttcctcgagg agatctggga tgtggcggac atgtcgcaca cccaaccgcc   5640
gcctatcctc gagtccccca cgaatctcta ggcggcctct agagcggccg ccaccgcggg   5700
gagatccaga catgataaga tacattgatg agtttggaca aaccacaact agaatgcagt   5760
gaaaaaaatg ctttatttgt gaaatttgtg atgctattgc tttatttgta accattataa   5820
gctgcaataa acaagttaac aacaacaatt gcattcattt tatgtttcag gttcaggggg   5880
aggtgtggga ggttttttaa agcaagtaaa acctctacaa atgtggtatg gctgattatg   5940
atccggctgc ctcgcgcgtt tcggtgatga cggtgaaaac ctctgacaca tgcagctccc   6000
ggagacggtc acagcttgtc tgtaagcgga tgccgggagc agacaagccc gtcagggcgc   6060
gtcagcgggt gttggcgggt gtcggggcgc agccatgagg tcgactctag tccccgcggt   6120
ggcagatctg gaaggtgctg aggtacgatg agacccgcac caggtgcaga ccctgcgagt   6180
gtggcggtaa acatattagg aaccagcctg tgatgctgga tgtgaccgag gagctgaggc   6240
ccgatcactt ggtgctggcc tgcacccgcg ctgagtttgg ctctagcgat gaagatacag   6300
attgaggtac tgaaatgtgt gggcgtggct taagggtggg aaagaatata taaggtgggg   6360
gtcttatgta gttttgtatc tgttttgcag cagccgccgc cgccatgagc accaactcgt   6420
ttgatggaag cattgtgagc tcatatttga caacgcgcat gcccccatgg gccggggtgc   6480
gtcagaatgt gatgggctcc agcattgatg gtcgccccgt cctgcccgca aactctacta   6540
ccttgaccta cgagaccgtg tctggaacgc cgttggagac tgcagcctcc gccgccgctt   6600
cagccgctgc agccaccgcc cgcgggattg tgactgactt tgctttcctg agcccgcttg   6660
caagcagtgc agcttcccgt tcatccgccc gcgatgacaa gttgacggct cttttggcac   6720
aattggattc tttgacccgg gaacttaatg tcgtttctca gcagctgttg gatctgcgcc   6780
agcaggtttc tgccctgaag gcttcctccc ctcccaatgc ggtttaaaac ataaataaaa   6840
aaccagactc tgtttggatt tggatcaagc aagtgtcttg ctgtctttat ttaggggttt   6900
tgcgcgcgcg gtaggcccgg gaccagcggt ctcggtcgtt gagggtcctg tgtatttttt   6960
ccaggacgtg gtaaaggtga ctctggatgt tcagatacat gggcataagc ccgtctctgg   7020
ggtggaggta gcaccactgc agagcttcat gctgcggggt ggtgttgtag atgatccagt   7080
```

-continued cgtagcagga gcgctgggcg tggtgcctaa aaatgtcttt cagtagcaag ctgattgcca 7140
ggggcaggcc cttggtgtaa gtgtttacaa agcggttaag ctgggatggg tgcatacgtg 7200
gggatatgag atgcatcttg gactgtattt ttaggttggc tatgttccca gccatatccc 7260
tccggggatt catgttgtgc agaaccacca gcacagtgta tccggtgcac ttgggaaatt 7320
tgtcatgtag cttagaagga aatgcgtgga agaacttgga gacgcccttg tgacctccaa 7380
gattttccat gcattcgtcc ataatgatgg caatgggccc acgggcggcg gcctgggcga 7440
agatatttct gggatcacta acgtcatagt tgtgttccag gatgagatcg tcataggcca 7500
tttttacaaa gcgcgggcgg agggtgccag actgcggtat aatggttcca tccggcccag 7560
gggcgtagtt accctcacag atttgcattt cccacgcttt gagttcagat ggggggatca 7620
tgtctacctg cggggcgatg aagaaaacgg tttccggggt aggggagatc agctgggaag 7680
aaagcaggtt cctgagcagc tgcgacttac cgcagccggt gggcccgtaa atcacaccta 7740
ttaccggctg caactggtag ttaagagagc tgcagctgcc gtcatccctg agcagggggg 7800
ccacttcgtt aagcatgtcc ctgactcgca tgttttccct gaccaaatcc gccagaaggc 7860
gctcgccgcc cagcgatagc agttcttgca aggaagcaaa gtttttcaac ggtttgagac 7920
cgtccgccgt aggcatgctt ttgagcgttt gaccaagcag ttccaggcgg tcccacagct 7980
cggtcacctg ctctacggca tctcgatcca gcatatctcc tcgtttcgcg ggttggggcg 8040
gctttcgctg tacggcagta gtcggtgctc gtccagacgg gccagggtca tgtctttcca 8100
cgggcgcagg gtcctcgtca gcgtagtctg ggtcacggtg aaggggtgcg ctccgggctg 8160
cgcgctggcc agggtgcgct tgaggctggt cctgctggtg ctgaagcgct gccggtcttc 8220
gccctgcgcg tcggccaggt agcatttgac catggtgtca tagtccagcc cctccgcggc 8280
gtggcccttg gcgcgcagct tgcccttgga ggaggcgccg cacgaggggc agtgcagact 8340
tttgagggcg tagagcttgg gcgcgagaaa taccgattcc ggggagtagg catccgcgcc 8400
gcaggccccg cagacggtct cgcattccac gagccaggtg agctctggcc gttcggggtc 8460
aaaaaccagg tttcccccat gctttttgat gcgtttctta cctctggttt ccatgagccg 8520
gtgtccacgc tcggtgacga aaaggctgtc cgtgtccccg tatacagact tgagaggcct 8580
gtcctcgacc gatgcccttg agagccttca acccagtcag ctccttccgg tgggcgcggg 8640
gcatgactat cgtcgccgca cttatgactg tcttctttat catgcaactc gtaggacagg 8700
tgccggcagc gctctgggtc attttcggcg aggaccgctt tcgctggagc gcgacgatga 8760
tcggcctgtc gcttgcggta ttcggaatct tgcacgccct cgctcaagcc ttcgtcactg 8820
gtcccgccac caaacgtttc ggcgagaagc aggccattat cgccggcatg gcggccgacg 8880
cgctgggcta cgtcttgctg gcgttcgcga cgcgaggctg gatggccttc cccattatga 8940
ttcttctcgc ttccggcggc atcgggatgc ccgcgttgca ggccatgctg tccaggcagg 9000
tagatgacga ccatcaggga cagcttcaag gccagcaaaa ggccaggaac cgtaaaaagg 9060
ccgcgttgct ggcgtttttc cataggctcc gcccccctga cgagcatcac aaaaatcgac 9120
gctcaagtca gaggtggcga aacccgacag gactataaag ataccaggcg tttccccctg 9180
gaagctccct cgtgcgctct cctgttccga ccctgccgct taccggatac ctgtccgcct 9240
ttctcccttc gggaagcgtg gcgctttctc atagctcacg ctgtaggtat ctcagttcgg 9300
tgtaggtcgt tcgctccaag ctgggctgtg tgcacgaacc ccccgttcag cccgaccgct 9360
gcgccttatc cggtaactat cgtcttgagt ccaacccggt aagacacgac ttatcgccac 9420
tggcagcagc cactggtaac aggattagca gagcgaggta tgtaggcggt gctacagagt 9480
tcttgaagtg gtggcctaac tacggctaca ctagaaggac agtatttggt atctgcgctc 9540
tgctgaagcc agttaccttc ggaaaaagag ttggtagctc ttgatccggc aaacaaacca 9600
ccgctggtag cggtggtttt tttgtttgca agcagcagat tacgcgcaga aaaaaaggat 9660
ctcaagaaga tcctttgatc ttttctacgg ggtctgacgc tcagtggaac gaaaactcac 9720
gttaagggat tttggtcatg agattatcaa aaaggatctt cacctagatc cttttaaatt 9780
aaaaatgaag ttttaaatca atctaaagta tatatgagta aacttggtct gacagttacc 9840
aatgcttaat cagtgaggca cctatctcag cgatctgtct atttcgttca tccatagttg 9900
cctgactccc cgtcgtgtag ataactacga tacgggaggg cttaccatct ggccccagtg 9960
ctgcaatgat accgcgagac ccacgctcac cggctccaga tttatcagca ataaaccagc 10020
cagccggaag ggccgagcgc agaagtggtc ctgcaacttt atccgcctcc atccagtcta 10080
ttaattgttg ccgggaagct agagtaagta gttcgccagt taatagtttg cgcaacgttg 10140
ttgccattgc tgcaggcatc gtggtgtcac gctcgtcgtt tggtatggct tcattcagct 10200
ccggttccca acgatcaagg cgagttacat gatcccccat gttgtgcaaa aaagcggtta 10260
gctccttcgg tcctccgatc gttgtcagaa gtaagttggc cgcagtgtta tcactcatgg 10320
ttatggcagc actgcataat tctcttactg tcatgccatc cgtaagatgc ttttctgtga 10380
ctggtgagta ctcaaccaag tcattctgag aatagtgtat gcggcgaccg agttgctctt 10440
gcccggcgtc aacacgggat aataccgcgc cacatagcag aactttaaaa gtgctcatca 10500
ttggaaaacg ttcttcgggg cgaaaactct caaggatctt accgctgttg agatccagtt 10560
cgatgtaacc cactcgtgca cccaactgat cttcagcatc ttttactttc accagcgttt 10620
ctgggtgagc aaaaacagga aggcaaaatg ccgcaaaaaa gggaataagg gcgacacgga 10680
aatgttgaat actcatactc ttcctttttc aatattattg aagcatttat cagggttatt 10740
gtctcatgag cggatacata tttgaatgta tttagaaaaa 10780

<210> SEQ ID NO 49
<211> LENGTH: 10624
<212> TYPE: DNA
<213> ORGANISM: Artificial Sequence
<220> FEATURE:
<223> OTHER INFORMATION: PolyDNA_from_VVN-43320

<400> SEQUENCE: 49
taaacaaata ggggttccgc gcacatttcc ccgaaaagtg ccacctgacg tctaagaaac 60
cattattatc atgacattaa cctataaaaa taggcgtatc acgaggccct ttcgtcttca 120
attaattaag ctagcatcat caataatata ccttattttg gattgaagcc aatatgataa 180
tgagggggtg gagtttgtga cgtggcgcgg ggcgtgggaa cggggcgggt gacgtagtag 240
tgtggcggaa gtgtgatgtt gcaagtgtgg cggaacacat gtaagcgacg gatgtggcaa 300
aagtgacgtt tttggtgtgc gccggtgtac acaggaagtg acaattttcg cgcggtttta 360
ggcggatgtt gtagtaaatt tgggcgtaac cgagtaagat ttggccattt tcgcgggaaa 420
actgaataag aggaagtgaa atctgaataa ttttgtgtta ctcatagcgc gtaatatttg 480
tctagggaga tccggtaccg gcgcgcgcgc cgtttggccg cctcgagtct agagatccgg 540
tgagtattag gcgcgcacca ggtgccgcaa taaaatatct ttattttcat tacatctgtg 600
tgttggtttt ttgtgtgaat cgatagtact aacatacgct ctccatcaaa acaaaacgaa 660
acaaaacaaa ctagcaaaat aggctgtccc cagtgcaagt gcaggtgcca gaacatttct 720

-continued

```
ctatcgataa tgcaggtcgg agtactgtcc tccgagcgga gtactgtcct ccgagcggag    780
tactgtcctc cgagcggagt actgtcctcc gagcggagta ctgtcctccg agcggagtac    840
tgtcctccga gcggagactc ttcgaaggaa gaggggcggg gtcgatcgac cccgcccctc    900
ttccttcgaa ggaagagggg cggggtcgaa gacctagagg gtatataatg ggtgccttag    960
ctggtgtgtg agctcatctt cctgtagatc acgcgtctcc ctcagcaagg acagcagagg   1020
accagctaag agggagagaa gcaactacag acccccccctg aaaacaaccc tcagacgcca   1080
catcccctga caagctgcca ggcaggttct cttcctctca catactgacc cacggctcca   1140
ccctctctcc cctggaaagg acaccgctag cgccaccatg tatagaatgc agctcctgtc   1200
ctgcattgcc ctgagcctcg ccctcgtgac aaactccgcc cctaccagcg gatccgtgag   1260
aagcagcagc aggacccta gcgataagcc tgtggctcac gtcgtcgcta accctcaggc   1320
cgagggccag ctccagtggc tgaatagaag ggccaatgcc ctgctcgcca acggcgtcga   1380
gctgagagac aatcagctcg tggtcccctc cgagggactg tatctgattt actcccaggt   1440
cctgtttaag ggacagggat gccctagcac acacgtcctg ctgacccaca ccattagcag   1500
gatcgctgtg tcctaccaaa ccaaagtgaa tctgctgtcc gctatcaaaa gcccttgcca   1560
aagagaaacc cctgagggag ccgaagccaa accctggtac gaacccattt acctcggcgg   1620
agtgtttcag ctggagaaag gcgatagact cagcgctgag attaacaggc ccgattacct   1680
cgactttgcc gaaagcggac aggtctactt tggcattatc gctctgtaaa tcgattcgta   1740
cgtcgacatc gagaacttgt ttattgcagc ttataatggt tacaaataaa gcaatagcat   1800
cacaaatttc acaaataaag catttttttc actgcattct agttgtggtt tgtccaaact   1860
catcaatgta tcttatcatg tctgggcgcg ccggcctccg cgccgggttt tggcgcctcc   1920
cgcgggcgcc cccctcctca cggcgagcgc tgccacgtca gacgaagggc gcagcgagcg   1980
tcctgatcct tccgcccgga cgctcaggac agcggcccgc tgctcataag actcggcctt   2040
agaaccccag tatcagcaga aggacatttt aggacgggac ttgggtgact ctagggcact   2100
ggttttcttt ccagagagcg gaacaggcga ggaaaagtag tcccttctcg gcgattctgc   2160
ggagggatct ccgtggggcg gtgaacgccg atgattatat aaggacgcgc cgggtgtggc   2220
acagctagtt ccgtcgcagc cgggatttgg gtcgcggttc ttgtttgtgg atcgctgtga   2280
tcgtcacttg gtgagtagcg ggctgctggg ctgggtacgt gcgctcgggg ttggcgagtg   2340
tgttttgtga agttttttag gcaccttttg aaatgtaatc atttgggtca atatgtaatt   2400
ttcagtgtta gactagtaaa ttgtccgcta aattctggcc gtttttggct tttttgttag   2460
acgagctagc gccgccacca tgggccctaa aaagaagcgt aaagtcgccc ccccgaccga   2520
tgtcagcctg gggacgagc tccacttaga cggcgaggac gtggcgatgg cgcatgccga   2580
cgcgctagac gatttcgatc tggacatgtt gggggacggg gattccccgg gtccgggatt   2640
tacccccac gactccgccc cctacggcgc tctggatatg gccgacttcg agtttgagca   2700
gatgtttacc gatgcccttg gaattgacga gtacggtggg gaattcgaga tgcctgtgga   2760
caggatcctg gaggcagagc ttgctgtgga acagaagagt gaccagggcg ttgagggtcc   2820
tgggggaacc gggggtagcg gcagcagccc aaatgaccct gtgactaaca tctgtcaggc   2880
agctgacaaa cagctattca cgcttgttga gtgggcgaag aggatcccac acttttcctc   2940
cttgcctctg gatgatcagg tcatattgct gcgggcaggc tggaatgaac tcctcattgc   3000
ctcctttca caccgatcca ttgatgttcg agatggcatc ctccttgcca caggtcttca   3060
```

```
cgtgcaccgc aactcagccc attcagcagg agtaggagcc atctttgatc gggtgctgac   3120
agagctagtg tccaaaatgc gtgacatgag gatggacaag acagagcttg gctgcctgag   3180
ggcaatcatt ctgtttaatc cagaggtgag gggtttgaaa tccgcccagg aagttgaact   3240
tctacgtgaa aaagtatatg ccgctttgga agaatatact agaacaacac atcccgatga   3300
accaggaaga tttgcaaaac ttttgcttcg tctgccttct ttacgttcca taggccttaa   3360
gtgtttggag catttgtttt tctttcgcct tattggagat gttccaattg atacgttcct   3420
gatggagatg cttgaatcac cttctgattc ataatctagc ctagcccccc tctccctccc   3480
cccccctaa cgttactggc cgaagccgct tggaataagg ccggtgtgcg tttgtctata   3540
tgttattttc caccatattg ccgtcttttg gcaatgtgag ggcccggaaa cctggccctg   3600
tcttcttgac gagcattcct aggggtcttt cccctctcgc caaaggaatg caaggtctgt   3660
tgaatgtcgt gaaggaagca gttcctctgg aagcttcttg aagacaaaca acgtctgtag   3720
cgaccctttg caggcagcgg aaccccccac ctggcgacag gtgcctctgc ggccaaaagc   3780
cacgtgtata agatacacct gcaaaggcgg cacaacccca gtgccacgtt gtgagttgga   3840
tagttgtgga aagagtcaaa tggctctcct caagcgtatt caacaagggg ctgaaggatg   3900
cccagaaggt accccattgt atgggatctg atctggggcc tcggtgcaca tgctttacat   3960
gtgtttagtc gaggttaaaa aacgtctagg ccccccgaac cacggggacg tggttttcct   4020
ttgaaaaaca cgatctctag gcgccaccat gaagctactg tcttctatcg aacaagcatg   4080
cgatatttgc cgacttaaaa agctcaagtg ctccaaagaa aaaccgaagt gcgccaagtg   4140
tctgaagaac aactgggagt gtcgctactc tcccaaaacc aaaaggtctc cgctgactag   4200
ggcacatctg acagaagtgg aatcaaggct agaaagactg gaacagctat ttctactgat   4260
ttttcctcga gaagaccttg acatgatttt gaaaatggat tctttacagg atataaaagc   4320
attgttaaca ggattatttg tacaagataa tgtgaataaa gatgccgtca cagatagatt   4380
ggcttcagtg gagactgata tgcctctaac attgagacag catagaataa gtgcgacatc   4440
atcatcggaa gagagtagta acaaaggtca aagacagttg actgtatcgc cggaattccc   4500
ggggatccgg cctgagtgcg tagtacccga gactcagtgc gccatgaagc ggaaagagaa   4560
gaaagcacag aaggagaagg acaaactgcc tgtcagcacg acgacggtgg acgaccacat   4620
gccgcccatt atgcagtgtg aacctccacc tcctgaagca gcaaggattc acgaagtggt   4680
cccaaggttt ctctccgaca agctgttggt gacaaaccgg cagaaaaaca tcccccagtt   4740
gacagccaac cagcagttcc ttatcgccag gctcatctgg taccaggacg ggtacgagca   4800
gccttctgat gaagatttga agaggattac gcagacgtgg cagcaagcgg acgatgaaaa   4860
cgaagagtcg gacactccct tccgccagat cacagagatg actatcctca cggtccaact   4920
tatcgtggag ttcgcgaagg gattgccagg gttcgccaag atctcgcagc ctgatcaaat   4980
tacgctgctt aaggcttgct caagtgaggt aatgatgctc cgagtcgcgc gacgatacga   5040
tgcggcctca gacagtattc tgttcgcgaa caaccaagcg tacactcgcg acaactaccg   5100
caaggctggc atggccgagg tcatcgagga tctactgcac ttctgccggt gcatgtactc   5160
tatggcgttg gacaacatcc attacgcgct gctcacggct gtcgtcatct tttctgaccg   5220
gccagggttg gagcagccgc aactggtgga agagatccag cggtactacc tgaatacgct   5280
ccgcatctat atcctgaacc agctgagcgg gtcggcgcgt tcgtccgtca tatacggcaa   5340
gatcctctca atcctctctg agctacgcac gctcggcatg caaaactcca acatgtgcat   5400
ctccctcaag ctcaagaaca gaaagctgcc gcctttcctc gaggagatct gggatgtggc   5460
```

-continued

```
ggacatgtcg cacacccaac cgccgcctat cctcgagtcc cccacgaatc tctaggcggc   5520
ctctagagcg gccgccaccg cggggagatc cagacatgat aagatacatt gatgagtttg   5580
gacaaaccac aactagaatg cagtgaaaaa aatgctttat ttgtgaaatt tgtgatgcta   5640
ttgctttatt tgtaaccatt ataagctgca ataaacaagt taacaacaac aattgcattc   5700
attttatgtt tcaggttcag ggggaggtgt gggaggtttt ttaaagcaag taaaacctct   5760
acaaatgtgg tatggctgat tatgatccgg ctgcctcgcg cgtttcggtg atgacggtga   5820
aaacctctga cacatgcagc tcccggagac ggtcacagct tgtctgtaag cggatgccgg   5880
gagcagacaa gcccgtcagg gcgcgtcagc gggtgttggc gggtgtcggg gcgcagccat   5940
gaggtcgact ctagtccccg cggtggcaga tctggaaggt gctgaggtac gatgagaccc   6000
gcaccaggtg cagaccctgc gagtgtggcg gtaaacatat taggaaccag cctgtgatgc   6060
tggatgtgac cgaggagctg aggcccgatc acttggtgct ggcctgcacc cgcgctgagt   6120
ttggctctag cgatgaagat acagattgag gtactgaaat gtgtgggcgt ggcttaaggg   6180
tgggaaagaa tatataaggt gggggtctta tgtagttttg tatctgtttt gcagcagccg   6240
ccgccgccat gagcaccaac tcgtttgatg gaagcattgt gagctcatat ttgacaacgc   6300
gcatgccccc atgggccggg gtgcgtcaga atgtgatggg ctccagcatt gatggtcgcc   6360
ccgtcctgcc cgcaaactct actaccttga cctacgagac cgtgtctgga acgccgttgg   6420
agactgcagc ctccgccgcc gcttcagccg ctgcagccac cgcccgcggg attgtgactg   6480
actttgcttt cctgagcccg cttgcaagca gtgcagcttc ccgttcatcc gcccgcgatg   6540
acaagttgac ggctcttttg gcacaattgg attctttgac ccgggaactt aatgtcgttt   6600
ctcagcagct gttggatctg cgccagcagg tttctgccct gaaggcttcc tcccctccca   6660
atgcggttta aaacataaat aaaaaaccag actctgtttg gatttggatc aagcaagtgt   6720
cttgctgtct ttatttaggg gttttgcgcg cgcggtaggc ccgggaccag cggtctcggt   6780
cgttgagggt cctgtgtatt ttttccagga cgtggtaaag gtgactctgg atgttcagat   6840
acatgggcat aagcccgtct ctggggtgga ggtagcacca ctgcagagct tcatgctgcg   6900
gggtggtgtt gtagatgatc cagtcgtagc aggagcgctg ggcgtggtgc ctaaaaatgt   6960
ctttcagtag caagctgatt gccaggggca ggcccttggt gtaagtgttt acaaagcggt   7020
taagctggga tgggtgcata cgtgggggata tgagatgcat cttggactgt atttttaggt   7080
tggctatgtt cccagccata tccctccggg gattcatgtt gtgcagaacc accagcacag   7140
tgtatccggt gcacttggga aatttgtcat gtagcttaga aggaaatgcg tggaagaact   7200
tggagacgcc cttgtgacct ccaagatttt ccatgcattc gtccataatg atggcaatgg   7260
gcccacgggc ggcggcctgg gcgaagatat ttctgggatc actaacgtca tagttgtgtt   7320
ccaggatgag atcgtcatag gccattttta caaagcgcgg gcggagggtg ccagactgcg   7380
gtataatggt tccatccggc ccaggggcgt agttaccctc acagatttgc atttcccacg   7440
ctttgagttc agatgggggg atcatgtcta cctgcggggc gatgaagaaa acggtttccg   7500
gggtagggga gatcagctgg gaagaaagca ggttcctgag cagctgcgac ttaccgcagc   7560
cggtgggccc gtaaatcaca cctattaccg gctgcaactg gtagttaaga gagctgcagc   7620
tgccgtcatc cctgagcagg ggggccactt cgttaagcat gtccctgact cgcatgtttt   7680
ccctgaccaa atccgccaga aggcgctcgc cgcccagcga tagcagttct tgcaaggaag   7740
caaagttttt caacggtttg agaccgtccg ccgtaggcat gcttttgagc gtttgaccaa   7800
```

gcagttccag gcggtcccac agctcggtca cctgctctac ggcatctcga tccagcatat 7860
ctcctcgttt cgcgggttgg ggcggctttc gctgtacggc agtagtcggt gctcgtccag 7920
acgggccagg gtcatgtctt tccacgggcg cagggtcctc gtcagcgtag tctgggtcac 7980
ggtgaagggg tgcgctccgg gctgcgcgct ggccagggtg cgcttgaggc tggtcctgct 8040
ggtgctgaag cgctgccggt cttcgccctg cgcgtcggcc aggtagcatt tgaccatggt 8100
gtcatagtcc agcccctccg cggcgtggcc cttggcgcgc agcttgccct tggaggaggc 8160
gccgcacgag gggcagtgca gacttttgag ggcgtagagc ttgggcgcga gaaataccga 8220
ttccggggag taggcatccg cgccgcaggc cccgcagacg gtctcgcatt ccacgagcca 8280
ggtgagctct ggccgttcgg ggtcaaaaac caggtttccc ccatgctttt tgatgcgttt 8340
cttacctctg gtttccatga gccggtgtcc acgctcggtg acgaaaaggc tgtccgtgtc 8400
cccgtataca gacttgagag gcctgtcctc gaccgatgcc cttgagagcc ttcaacccag 8460
tcagctcctt ccggtgggcg cggggcatga ctatcgtcgc cgcacttatg actgtcttct 8520
ttatcatgca actcgtagga caggtgccgg cagcgctctg ggtcattttc ggcgaggacc 8580
gctttcgctg gagcgcgacg atgatcggcc tgtcgcttgc ggtattcgga atcttgcacg 8640
ccctcgctca agccttcgtc actggtcccg ccaccaaacg tttcggcgag aagcaggcca 8700
ttatcgccgg catggcggcc gacgcgctgg gctacgtctt gctggcgttc gcgacgcgag 8760
gctggatggc cttccccatt atgattcttc tcgcttccgg cggcatcggg atgcccgcgt 8820
tgcaggccat gctgtccagg caggtagatg acgaccatca gggacagctt caaggccagc 8880
aaaaggccag gaaccgtaaa aaggccgcgt tgctggcgtt tttccatagg ctccgccccc 8940
ctgacgagca tcacaaaaat cgacgctcaa gtcagaggtg gcgaaacccg acaggactat 9000
aaagatacca ggcgtttccc cctggaagct ccctcgtgcg ctctcctgtt ccgaccctgc 9060
cgcttaccgg atacctgtcc gcctttctcc cttcgggaag cgtggcgctt tctcatagct 9120
cacgctgtag gtatctcagt tcggtgtagg tcgttcgctc caagctgggc tgtgtgcacg 9180
aaccccccgt tcagcccgac cgctgcgcct tatccggtaa ctatcgtctt gagtccaacc 9240
cggtaagaca cgacttatcg ccactggcag cagccactgg taacaggatt agcagagcga 9300
ggtatgtagg cggtgctaca gagttcttga agtggtggcc taactacggc tacactagaa 9360
ggacagtatt tggtatctgc gctctgctga agccagttac cttcggaaaa agagttggta 9420
gctcttgatc cggcaaacaa accaccgctg gtagcggtgg tttttttgtt tgcaagcagc 9480
agattacgcg cagaaaaaaa ggatctcaag aagatccttt gatcttttct acggggtctg 9540
acgctcagtg gaacgaaaac tcacgttaag ggattttggt catgagatta tcaaaaagga 9600
tcttcaccta gatcctttta aattaaaaat gaagttttaa atcaatctaa agtatatatg 9660
agtaaacttg gtctgacagt taccaatgct taatcagtga ggcacctatc tcagcgatct 9720
gtctatttcg ttcatccata gttgcctgac tccccgtcgt gtagataact acgatacggg 9780
agggcttacc atctggcccc agtgctgcaa tgataccgcg agacccacgc tcaccggctc 9840
cagatttatc agcaataaac cagccagccg gaagggccga gcgcagaagt ggtcctgcaa 9900
ctttatccgc ctccatccag tctattaatt gttgccggga agctagagta agtagttcgc 9960
cagttaatag tttgcgcaac gttgttgcca ttgctgcagg catcgtggtg tcacgctcgt 10020
cgtttggtat ggcttcattc agctccggtt cccaacgatc aaggcgagtt acatgatccc 10080
ccatgttgtg caaaaaagcg gttagctcct tcggtcctcc gatcgttgtc agaagtaagt 10140
tggccgcagt gttatcactc atggttatgg cagcactgca taattctctt actgtcatgc 10200

```
catccgtaag atgcttttct gtgactggtg agtactcaac caagtcattc tgagaatagt  10260

gtatgcggcg accgagttgc tcttgcccgg cgtcaacacg ggataatacc gcgccacata  10320

gcagaacttt aaaagtgctc atcattggaa aacgttcttc ggggcgaaaa ctctcaagga  10380

tcttaccgct gttgagatcc agttcgatgt aacccactcg tgcacccaac tgatcttcag  10440

catcttttac tttcaccagc gtttctgggt gagcaaaaac aggaaggcaa aatgccgcaa  10500

aaaagggaat aagggcgaca cggaaatgtt gaatactcat actcttcctt tttcaatatt  10560

attgaagcat ttatcagggt tattgtctca tgagcggata catatttgaa tgtatttaga  10620

aaaa                                                               10624
```

<210> SEQ ID NO 50
<211> LENGTH: 10790
<212> TYPE: DNA
<213> ORGANISM: Artificial Sequence
<220> FEATURE:
<223> OTHER INFORMATION: PolyDNA_from_VVN-43321 5u2

<400> SEQUENCE: 50

```
taaacaaata ggggttccgc gcacatttcc ccgaaaagtg ccacctgacg tctaagaaac     60

cattattatc atgacattaa cctataaaaa taggcgtatc acgaggccct ttcgtcttca    120

attaattaag ctagcatcat caataatata ccttattttg gattgaagcc aatatgataa    180

tgagggggtg gagtttgtga cgtggcgcgg ggcgtgggaa cggggcgggt gacgtagtag    240

tgtggcggaa gtgtgatgtt gcaagtgtgg cggaacacat gtaagcgacg gatgtggcaa    300

aagtgacgtt tttggtgtgc gccggtgtac acaggaagtg acaattttcg cgcggtttta    360

ggcggatgtt gtagtaaatt tgggcgtaac cgagtaagat ttggccattt tcgcgggaaa    420

actgaataag aggaagtgaa atctgaataa ttttgtgtta ctcatagcgc gtaatatttg    480

tctagggaga tccggtaccg gcgcgcgcgc cgtttggccg cctcgagtct agagatccgg    540

tgagtattag gcgcgcacca ggtgccgcaa taaaatatct ttattttcat tacatctgtg    600

tgttggtttt ttgtgtgaat cgatagtact aacatacgct ctccatcaaa acaaaacgaa    660

acaaaacaaa ctagcaaaat aggctgtccc cagtgcaagt gcaggtgcca gaacatttct    720

ctatcgataa tgcaggtcgg agtactgtcc tccgagcgga gtactgtcct ccgagcggag    780

tactgtcctc cgagcggagt actgtcctcc gagcggagta ctgtcctccg agcggagtac    840

tgtcctccga gcggagactc ttcgaaggaa gaggggcggg gtcgatcgac cccgcccctc    900

ttccttcgaa ggaagagggg cggggtcgaa gacctagagg gtatataatg ggtgccttag    960

ctggtgtgtg agctcatctt cctgtagatc acgcgtcgaa gaaggtgagt aatcttaaca   1020

tgctcttttt tttttttttt gctaatccct tttgtgtgct gatgttagga tgacatttac   1080

aacaaatgtt tgttcctgac aggaaaaacc ttgctgggta ccttcgttgc cggacacttc   1140

ttgtcctcta ctttggaaaa aaggaattga gagccgctag cgccaccatg agcactgaaa   1200

gcatgatccg ggacgtggag ctggccgagg aagccctccc caagaaaacc ggcggccccc   1260

aggggagcag aagatgtttg ttcctgagcc tgttttcctt cctgatcgtg gcaggcgcta   1320

ccaccctgtt ctgcctgctg cactttggag tgatcggccc ccagagggag gagttcccca   1380

gggacctctc tctaatcagc cctctggccc aggcaggatc cgtcagatca tcttctcgaa   1440

ccccgagtga caagcctgta gcccatgttg tagcaaaccc tcaagccgag ggccagctcc   1500

agtggctgaa ccgccgggcc aatgccctgc tcgccaacgg cgtcgagctg agagataacc   1560
```

-continued agctggtggt gccatcagag ggcctgtacc tcatctactc ccaggtcctg ttcaagggcc 1620
aaggctgccc ctccacccat gtgctcctca cccacaccat cagccgcatc gccgtgagct 1680
accagaccaa ggtcaacctc ctctctgcca tcaagagccc ctgccagagg gagaccccag 1740
agggggccga ggccaagccc tggtatgagc ccatctacct cggcggggtg ttccagctgg 1800
agaagggtga ccgactcagc gctgagatca atagacccga ctatctcgac tttgccgaga 1860
gcggccaggt gtactttggg atcattgccc tgtgaatcga ttcgtacgtc gacatcgaga 1920
acttgtttat tgcagcttat aatggttaca aataaagcaa tagcatcaca aatttcacaa 1980
ataaagcatt tttttcactg cattctagtt gtggtttgtc caaactcatc aatgtatctt 2040
atcatgtctg ggcgcgccgg cctccgcgcc gggttttggc gcctcccgcg ggcgcccccc 2100
tcctcacggc gagcgctgcc acgtcagacg aagggcgcag cgagcgtcct gatccttccg 2160
cccggacgct caggacagcg gcccgctgct cataagactc ggccttagaa ccccagtatc 2220
agcagaagga cattttagga cgggacttgg gtgactctag ggcactggtt ttctttccag 2280
agagcggaac aggcgaggaa aagtagtccc ttctcggcga ttctgcggag ggatctccgt 2340
ggggcggtga acgccgatga ttatataagg acgcgccggg tgtggcacag ctagttccgt 2400
cgcagccggg atttgggtcg cggttcttgt ttgtggatcg ctgtgatcgt cacttggtga 2460
gtagcgggct gctgggctgg gtacgtgcgc tcggggttgg cgagtgtgtt ttgtgaagtt 2520
ttttaggcac cttttgaaat gtaatcattt gggtcaatat gtaattttca gtgttagact 2580
agtaaattgt ccgctaaatt ctggccgttt ttggcttttt tgttagacga gctagcgccg 2640
ccaccatggg ccctaaaaag aagcgtaaag tcgccccccc gaccgatgtc agcctggggg 2700
acgagctcca cttagacggc gaggacgtgg cgatggcgca tgccgacgcg ctagacgatt 2760
tcgatctgga catgttgggg gacggggatt ccccgggtcc gggatttacc ccccacgact 2820
ccgcccccta cggcgctctg gatatggccg acttcgagtt tgagcagatg tttaccgatg 2880
cccttggaat tgacgagtac ggtggggaat tcgagatgcc tgtggacagg atcctggagg 2940
cagagcttgc tgtggaacag aagagtgacc agggcgttga gggtcctggg ggaaccgggg 3000
gtagcggcag cagcccaaat gaccctgtga ctaacatctg tcaggcagct gacaaacagc 3060
tattcacgct tgttgagtgg gcgaagagga tcccacactt ttcctccttg cctctggatg 3120
atcaggtcat attgctgcgg gcaggctgga atgaactcct cattgcctcc ttttcacacc 3180
gatccattga tgttcgagat ggcatcctcc ttgccacagg tcttcacgtg caccgcaact 3240
cagcccattc agcaggagta ggagccatct ttgatcgggt gctgacagag ctagtgtcca 3300
aaatgcgtga catgaggatg gacaagacag agcttggctg cctgagggca atcattctgt 3360
ttaatccaga ggtgaggggt ttgaaatccg cccaggaagt tgaacttcta cgtgaaaaag 3420
tatatgccgc tttggaagaa tatactagaa caacacatcc cgatgaacca ggaagatttg 3480
caaaactttt gcttcgtctg ccttctttac gttccatagg ccttaagtgt ttggagcatt 3540
tgtttttctt tcgccttatt ggagatgttc caattgatac gttcctgatg gagatgcttg 3600
aatcaccttc tgattcataa tctagcctag ccccctctc cctcccccc ccctaacgtt 3660 actggccgaa gccgcttgga ataaggccgg tgtgcgtttg tctatatgtt attttccacc 3720
atattgccgt cttttggcaa tgtgagggcc cggaaacctg gccctgtctt cttgacgagc 3780
attcctaggg gtctttcccc tctcgccaaa ggaatgcaag gtctgttgaa tgtcgtgaag 3840
gaagcagttc ctctggaagc ttcttgaaga caaacaacgt ctgtagcgac cctttgcagg 3900
cagcggaacc ccccacctgg cgacaggtgc ctctgcggcc aaaagccacg tgtataagat 3960
acacctgcaa aggcggcaca accccagtgc cacgttgtga gttggatagt tgtggaaaga 4020
gtcaaatggc tctcctcaag cgtattcaac aaggggctga aggatgccca gaaggtaccc 4080
cattgtatgg gatctgatct ggggcctcgg tgcacatgct ttacatgtgt ttagtcgagg 4140
ttaaaaaacg tctaggcccc ccgaaccacg gggacgtggt tttcctttga aaaacacgat 4200
ctctaggcgc caccatgaag ctactgtctt ctatcgaaca agcatgcgat atttgccgac 4260
ttaaaaagct caagtgctcc aaagaaaaac cgaagtgcgc caagtgtctg aagaacaact 4320
gggagtgtcg ctactctccc aaaaccaaaa ggtctccgct gactagggca catctgacag 4380
aagtggaatc aaggctagaa agactggaac agctatttct actgattttt cctcgagaag 4440
accttgacat gattttgaaa atggattctt tacaggatat aaaagcattg ttaacaggat 4500
tatttgtaca agataatgtg aataaagatg ccgtcacaga tagattggct tcagtggaga 4560
ctgatatgcc tctaacattg agacagcata gaataagtgc gacatcatca tcggaagaga 4620
gtagtaacaa aggtcaaaga cagttgactg tatcgccgga attcccgggg atccggcctg 4680
agtgcgtagt acccgagact cagtgcgcca tgaagcggaa agagaagaaa gcacagaagg 4740
agaaggacaa actgcctgtc agcacgacga cggtggacga ccacatgccg cccattatgc 4800
agtgtgaacc tccacctcct gaagcagcaa ggattcacga agtggtccca aggtttctct 4860
ccgacaagct gttggtgaca aaccggcaga aaaacatccc ccagttgaca gccaaccagc 4920
agttccttat cgccaggctc atctggtacc aggacgggta cgagcagcct tctgatgaag 4980
atttgaagag gattacgcag acgtggcagc aagcggacga tgaaaacgaa gagtcggaca 5040
ctcccttccg ccagatcaca gagatgacta tcctcacggt ccaacttatc gtggagttcg 5100
cgaagggatt gccagggttc gccaagatct cgcagcctga tcaaattacg ctgcttaagg 5160
cttgctcaag tgaggtaatg atgctccgag tcgcgcgacg atacgatgcg gcctcagaca 5220
gtattctgtt cgcgaacaac caagcgtaca ctcgcgacaa ctaccgcaag gctggcatgg 5280
ccgaggtcat cgaggatcta ctgcacttct gccggtgcat gtactctatg gcgttggaca 5340
acatccatta cgcgctgctc acggctgtcg tcatcttttc tgaccggcca gggttggagc 5400
agccgcaact ggtggaagag atccagcggt actacctgaa tacgctccgc atctatatcc 5460
tgaaccagct gagcgggtcg gcgcgttcgt ccgtcatata cggcaagatc ctctcaatcc 5520
tctctgagct acgcacgctc ggcatgcaaa actccaacat gtgcatctcc ctcaagctca 5580
agaacagaaa gctgccgcct ttcctcgagg agatctggga tgtggcggac atgtcgcaca 5640
cccaaccgcc gcctatcctc gagtccccca cgaatctcta ggcggcctct agagcggccg 5700
ccaccgcggg gagatccaga catgataaga tacattgatg agtttggaca aaccacaact 5760
agaatgcagt gaaaaaaatg ctttatttgt gaaatttgtg atgctattgc tttatttgta 5820
accattataa gctgcaataa acaagttaac aacaacaatt gcattcattt tatgtttcag 5880
gttcaggggg aggtgtggga ggttttttaa agcaagtaaa acctctacaa atgtggtatg 5940
gctgattatg atccggctgc ctcgcgcgtt tcggtgatga cggtgaaaac ctctgacaca 6000
tgcagctccc ggagacggtc acagcttgtc tgtaagcgga tgccgggagc agacaagccc 6060
gtcagggcgc gtcagcgggt gttggcgggt gtcggggcgc agccatgagg tcgactctag 6120
tccccgcggt ggcagatctg gaaggtgctg aggtacgatg agacccgcac caggtgcaga 6180
ccctgcgagt gtggcggtaa acatattagg aaccagcctg tgatgctgga tgtgaccgag 6240
gagctgaggc ccgatcactt ggtgctggcc tgcacccgcg ctgagtttgg ctctagcgat 6300

-continued

```
gaagatacag attgaggtac tgaaatgtgt gggcgtggct taagggtggg aaagaatata   6360
taaggtgggg gtcttatgta gttttgtatc tgttttgcag cagccgccgc cgccatgagc   6420
accaactcgt ttgatggaag cattgtgagc tcatatttga caacgcgcat gcccccatgg   6480
gccggggtgc gtcagaatgt gatgggctcc agcattgatg gtcgccccgt cctgcccgca   6540
aactctacta ccttgaccta cgagaccgtg tctggaacgc cgttggagac tgcagcctcc   6600
gccgccgctt cagccgctgc agccaccgcc cgcgggattg tgactgactt tgctttcctg   6660
agcccgcttg caagcagtgc agcttcccgt tcatccgccc gcgatgacaa gttgacggct   6720
cttttggcac aattggattc tttgacccgg gaacttaatg tcgtttctca gcagctgttg   6780
gatctgcgcc agcaggtttc tgccctgaag gcttcctccc ctcccaatgc ggtttaaaac   6840
ataaataaaa aaccagactc tgtttggatt tggatcaagc aagtgtcttg ctgtctttat   6900
ttaggggttt tgcgcgcgcg gtaggcccgg gaccagcggt ctcggtcgtt gagggtcctg   6960
tgtatttttt ccaggacgtg gtaaaggtga ctctggatgt tcagatacat gggcataagc   7020
ccgtctctgg ggtggaggta gcaccactgc agagcttcat gctgcggggt ggtgttgtag   7080
atgatccagt cgtagcagga gcgctgggcg tggtgcctaa aaatgtcttt cagtagcaag   7140
ctgattgcca ggggcaggcc cttggtgtaa gtgtttacaa agcggttaag ctgggatggg   7200
tgcatacgtg gggatatgag atgcatcttg gactgtattt ttaggttggc tatgttccca   7260
gccatatccc tccggggatt catgttgtgc agaaccacca gcacagtgta tccggtgcac   7320
ttgggaaatt tgtcatgtag cttagaagga aatgcgtgga agaacttgga gacgcccttg   7380
tgacctccaa gattttccat gcattcgtcc ataatgatgg caatgggccc acgggcggcg   7440
gcctgggcga agatatttct gggatcacta acgtcatagt tgtgttccag gatgagatcg   7500
tcataggcca tttttacaaa gcgcgggcgg agggtgccag actgcggtat aatggttcca   7560
tccggcccag gggcgtagtt accctcacag atttgcattt cccacgcttt gagttcagat   7620
ggggggatca tgtctacctg cggggcgatg aagaaaacgg tttccggggt aggggagatc   7680
agctgggaag aaagcaggtt cctgagcagc tgcgacttac cgcagccggt gggcccgtaa   7740
atcacaccta ttaccggctg caactggtag ttaagagagc tgcagctgcc gtcatccctg   7800
agcagggggg ccacttcgtt aagcatgtcc ctgactcgca tgttttccct gaccaaatcc   7860
gccagaaggc gctcgccgcc cagcgatagc agttcttgca aggaagcaaa gtttttcaac   7920
ggtttgagac cgtccgccgt aggcatgctt ttgagcgttt gaccaagcag ttccaggcgg   7980
tcccacagct cggtcacctg ctctacggca tctcgatcca gcatatctcc tcgtttcgcg   8040
ggttggggcg gctttcgctg tacggcagta gtcggtgctc gtccagacgg gccagggtca   8100
tgtctttcca cgggcgcagg gtcctcgtca gcgtagtctg ggtcacggtg aaggggtgcg   8160
ctccgggctg cgcgctggcc agggtgcgct tgaggctggt cctgctggtg ctgaagcgct   8220
gccggtcttc gccctgcgcg tcggccaggt agcatttgac catggtgtca tagtccagcc   8280
cctccgcggc gtggcccttg gcgcgcagct tgcccttgga ggaggcgccg cacgaggggc   8340
agtgcagact tttgagggcg tagagcttgg gcgcgagaaa taccgattcc ggggagtagg   8400
catccgcgcc gcaggccccg cagacggtct cgcattccac gagccaggtg agctctggcc   8460
gttcggggtc aaaaaccagg tttcccccat gctttttgat gcgtttctta cctctggttt   8520
ccatgagccg gtgtccacgc tcggtgacga aaaggctgtc cgtgtccccg tatacagact   8580
tgagaggcct gtcctcgacc gatgcccttg agagccttca acccagtcag ctccttccgg   8640
tgggcgcggg gcatgactat cgtcgccgca cttatgactg tcttctttat catgcaactc   8700
```

-continued gtaggacagg tgccggcagc gctctgggtc attttcggcg aggaccgctt tcgctggagc 8760
gcgacgatga tcggcctgtc gcttgcggta ttcggaatct tgcacgccct cgctcaagcc 8820
ttcgtcactg gtcccgccac caaacgtttc ggcgagaagc aggccattat cgccggcatg 8880
gcggccgacg cgctgggcta cgtcttgctg gcgttcgcga cgcgaggctg gatggccttc 8940
cccattatga ttcttctcgc ttccggcggc atcgggatgc ccgcgttgca ggccatgctg 9000
tccaggcagg tagatgacga ccatcaggga cagcttcaag gccagcaaaa ggccaggaac 9060
cgtaaaaagg ccgcgttgct ggcgtttttc cataggctcc gcccccctga cgagcatcac 9120
aaaaatcgac gctcaagtca gaggtggcga aacccgacag gactataaag ataccaggcg 9180
tttccccctg gaagctccct cgtgcgctct cctgttccga ccctgccgct taccggatac 9240
ctgtccgcct ttctcccttc gggaagcgtg gcgctttctc atagctcacg ctgtaggtat 9300
ctcagttcgg tgtaggtcgt tcgctccaag ctgggctgtg tgcacgaacc ccccgttcag 9360
cccgaccgct gcgccttatc cggtaactat cgtcttgagt ccaacccggt aagacacgac 9420
ttatcgccac tggcagcagc cactggtaac aggattagca gagcgaggta tgtaggcggt 9480
gctacagagt tcttgaagtg gtggcctaac tacggctaca ctagaaggac agtatttggt 9540
atctgcgctc tgctgaagcc agttaccttc ggaaaaagag ttggtagctc ttgatccggc 9600
aaacaaacca ccgctggtag cggtggtttt tttgtttgca agcagcagat tacgcgcaga 9660
aaaaaaggat ctcaagaaga tcctttgatc ttttctacgg ggtctgacgc tcagtggaac 9720
gaaaactcac gttaagggat tttggtcatg agattatcaa aaaggatctt cacctagatc 9780
cttttaaatt aaaaatgaag ttttaaatca atctaaagta tatatgagta aacttggtct 9840
gacagttacc aatgcttaat cagtgaggca cctatctcag cgatctgtct atttcgttca 9900
tccatagttg cctgactccc cgtcgtgtag ataactacga tacgggaggg cttaccatct 9960
ggccccagtg ctgcaatgat accgcgagac ccacgctcac cggctccaga tttatcagca 10020
ataaaccagc cagccggaag ggccgagcgc agaagtggtc ctgcaacttt atccgcctcc 10080
atccagtcta ttaattgttg ccgggaagct agagtaagta gttcgccagt taatagtttg 10140
cgcaacgttg ttgccattgc tgcaggcatc gtggtgtcac gctcgtcgtt tggtatggct 10200
tcattcagct ccggttccca acgatcaagg cgagttacat gatcccccat gttgtgcaaa 10260
aaagcggtta gctccttcgg tcctccgatc gttgtcagaa gtaagttggc cgcagtgtta 10320
tcactcatgg ttatggcagc actgcataat tctcttactg tcatgccatc cgtaagatgc 10380
ttttctgtga ctggtgagta ctcaaccaag tcattctgag aatagtgtat gcggcgaccg 10440
agttgctctt gcccggcgtc aacacgggat aataccgcgc cacatagcag aactttaaaa 10500
gtgctcatca ttggaaaacg ttcttcgggg cgaaaactct caaggatctt accgctgttg 10560
agatccagtt cgatgtaacc cactcgtgca cccaactgat cttcagcatc ttttactttc 10620
accagcgttt ctgggtgagc aaaaacagga aggcaaaatg ccgcaaaaaa gggaataagg 10680
gcgacacgga aatgttgaat actcatactc ttcctttttc aatattattg aagcatttat 10740
cagggttatt gtctcatgag cggatacata tttgaatgta tttagaaaaa 10790

<210> SEQ ID NO 51
<211> LENGTH: 10790
<212> TYPE: DNA
<213> ORGANISM: Artificial Sequence
<220> FEATURE:
<223> OTHER INFORMATION: PolyDNA_from_VVN-43322 5U2

<400> SEQUENCE: 51
taaacaaata ggggttccgc gcacatttcc ccgaaaagtg ccacctgacg tctaagaaac 60
cattattatc atgacattaa cctataaaaa taggcgtatc acgaggccct ttcgtcttca 120
attaattaag ctagcatcat caataatata ccttattttg gattgaagcc aatatgataa 180
tgagggggtg gagtttgtga cgtggcgcgg ggcgtgggaa cggggcgggt gacgtagtag 240
tgtggcggaa gtgtgatgtt gcaagtgtgg cggaacacat gtaagcgacg gatgtggcaa 300
aagtgacgtt tttggtgtgc gccggtgtac acaggaagtg acaattttcg cgcggtttta 360
ggcggatgtt gtagtaaatt tgggcgtaac cgagtaagat ttggccattt tcgcgggaaa 420
actgaataag aggaagtgaa atctgaataa ttttgtgtta ctcatagcgc gtaatatttg 480
tctagggaga tccggtaccg gcgcgcgcgc cgtttggccg cctcgagtct agagatccgg 540
tgagtattag gcgcgcacca ggtgccgcaa taaaatatct ttattttcat tacatctgtg 600
tgttggtttt ttgtgtgaat cgatagtact aacatacgct ctccatcaaa acaaaacgaa 660
acaaaacaaa ctagcaaaat aggctgtccc cagtgcaagt gcaggtgcca gaacatttct 720
ctatcgataa tgcaggtcgg agtactgtcc tccgagcgga gtactgtcct ccgagcggag 780
tactgtcctc cgagcggagt actgtcctcc gagcggagta ctgtcctccg agcggagtac 840
tgtcctccga gcggagactc ttcgaaggaa gaggggcggg gtcgatcgac cccgcccctc 900
ttccttcgaa ggaagagggg cggggtcgaa gacctagagg gtatataatg ggtgccttag 960
ctggtgtgtg agctcatctt cctgtagatc acgcgtcgaa gaaggtgagt aatcttaaca 1020
tgctcttttt tttttttttt gctaatccct tttgtgtgct gatgttagga tgacatttac 1080
aacaaatgtt tgttcctgac aggaaaaacc ttgctgggta ccttcgttgc cggacacttc 1140
ttgtcctcta ctttggaaaa aaggaattga gagccgctag cgccaccatg tccaccgaaa 1200
gcatgatccg ggacgtggag ctggccgagg aagccctgcc taagaaaacc ggaggccctc 1260
agggaagcag gagatgtctg tttctgtccc tgtttagctt tctgattgtg gctggcgcta 1320
ccacactgtt ttgcctcctg catttcggag tgattggccc tcagagggag gagttcccta 1380
gagacctgtc cctgattagc cctctggctc aggctggatc cgtgagaagc agcagcagga 1440
cccctagcga taagcctgtg gctcacgtcg tcgctaaccc tcaggccgag ggccagctcc 1500
agtggctgaa tagaagggcc aatgccctgc tcgccaacgg cgtcgagctg agagacaatc 1560
agctcgtggt cccctccgag ggactgtatc tgatttactc ccaggtcctg tttaagggac 1620
agggatgccc tagcacacac gtcctgctga cccacaccat tagcaggatc gctgtgtcct 1680
accaaaccaa agtgaatctg ctgtccgcta tcaaaagccc ttgccaaaga gaaacccctg 1740
agggagccga agccaaaccc tggtacgaac ccatttacct cggcggagtg tttcagctgg 1800
agaaaggcga tagactcagc gctgagatta acaggcccga ttacctcgac tttgccgaaa 1860
gcggacaggt ctactttggc attatcgctc tgtaaatcga ttcgtacgtc gacatcgaga 1920
acttgtttat tgcagcttat aatggttaca aataaagcaa tagcatcaca aatttcacaa 1980
ataaagcatt tttttcactg cattctagtt gtggtttgtc caaactcatc aatgtatctt 2040
atcatgtctg ggcgcgccgg cctccgcgcc gggttttggc gcctcccgcg ggcgcccccc 2100
tcctcacggc gagcgctgcc acgtcagacg aagggcgcag cgagcgtcct gatccttccg 2160
cccggacgct caggacagcg gcccgctgct cataagactc ggccttagaa ccccagtatc 2220
agcagaagga cattttagga cgggacttgg gtgactctag ggcactggtt ttctttccag 2280
agagcggaac aggcgaggaa aagtagtccc ttctcggcga ttctgcggag ggatctccgt 2340

-continued

```
ggggcggtga acgccgatga ttatataagg acgcgccggg tgtggcacag ctagttccgt   2400
cgcagccggg atttgggtcg cggttcttgt ttgtggatcg ctgtgatcgt cacttggtga   2460
gtagcgggct gctgggctgg gtacgtgcgc tcggggttgg cgagtgtgtt ttgtgaagtt   2520
ttttaggcac cttttgaaat gtaatcattt gggtcaatat gtaattttca gtgttagact   2580
agtaaattgt ccgctaaatt ctggccgttt ttggcttttt tgttagacga gctagcgccg   2640
ccaccatggg ccctaaaaag aagcgtaaag tcgccccccc gaccgatgtc agcctggggg   2700
acgagctcca cttagacggc gaggacgtgg cgatggcgca tgccgacgcg ctagacgatt   2760
tcgatctgga catgttgggg gacggggatt ccccgggtcc gggatttacc ccccacgact   2820
ccgcccccta cggcgctctg gatatggccg acttcgagtt tgagcagatg tttaccgatg   2880
cccttggaat tgacgagtac ggtggggaat tcgagatgcc tgtggacagg atcctggagg   2940
cagagcttgc tgtggaacag aagagtgacc agggcgttga gggtcctggg ggaaccgggg   3000
gtagcggcag cagcccaaat gaccctgtga ctaacatctg tcaggcagct gacaaacagc   3060
tattcacgct tgttgagtgg gcgaagagga tcccacactt ttcctccttg cctctggatg   3120
atcaggtcat attgctgcgg gcaggctgga atgaactcct cattgcctcc ttttcacacc   3180
gatccattga tgttcgagat ggcatcctcc ttgccacagg tcttcacgtg caccgcaact   3240
cagcccattc agcaggagta ggagccatct ttgatcgggt gctgacagag ctagtgtcca   3300
aaatgcgtga catgaggatg gacaagacag agcttggctg cctgagggca atcattctgt   3360
ttaatccaga ggtgaggggt ttgaaatccg cccaggaagt tgaacttcta cgtgaaaaag   3420
tatatgccgc tttggaagaa tatactagaa caacacatcc cgatgaacca ggaagatttg   3480
caaaactttt gcttcgtctg ccttctttac gttccatagg ccttaagtgt ttggagcatt   3540
tgtttttctt tcgccttatt ggagatgttc caattgatac gttcctgatg gagatgcttg   3600
aatcaccttc tgattcataa tctagcctag ccccccctctc cctccccccc ccctaacgtt   3660
actggccgaa gccgcttgga ataaggccgg tgtgcgtttg tctatatgtt attttccacc   3720
atattgccgt cttttggcaa tgtgagggcc cggaaacctg gccctgtctt cttgacgagc   3780
attcctaggg gtctttcccc tctcgccaaa ggaatgcaag gtctgttgaa tgtcgtgaag   3840
gaagcagttc ctctggaagc ttcttgaaga caaacaacgt ctgtagcgac cctttgcagg   3900
cagcggaacc ccccacctgg cgacaggtgc ctctgcggcc aaaagccacg tgtataagat   3960
acacctgcaa aggcggcaca accccagtgc cacgttgtga gttggatagt tgtggaaaga   4020
gtcaaatggc tctcctcaag cgtattcaac aaggggctga aggatgccca gaaggtaccc   4080
cattgtatgg gatctgatct ggggcctcgg tgcacatgct ttacatgtgt ttagtcgagg   4140
ttaaaaaacg tctaggcccc ccgaaccacg gggacgtggt tttcctttga aaaacacgat   4200
ctctaggcgc caccatgaag ctactgtctt ctatcgaaca agcatgcgat atttgccgac   4260
ttaaaaagct caagtgctcc aaagaaaaac cgaagtgcgc caagtgtctg aagaacaact   4320
gggagtgtcg ctactctccc aaaaccaaaa ggtctccgct gactagggca catctgacag   4380
aagtggaatc aaggctagaa agactggaac agctatttct actgattttt cctcgagaag   4440
accttgacat gattttgaaa atggattctt tacaggatat aaaagcattg ttaacaggat   4500
tatttgtaca agataatgtg aataaagatg ccgtcacaga tagattggct tcagtggaga   4560
ctgatatgcc tctaacattg agacagcata gaataagtgc gacatcatca tcggaagaga   4620
gtagtaacaa aggtcaaaga cagttgactg tatcgccgga attcccgggg atccggcctg   4680
```

-continued

```
agtgcgtagt acccgagact cagtgcgcca tgaagcggaa agagaagaaa gcacagaagg   4740
agaaggacaa actgcctgtc agcacgacga cggtggacga ccacatgccg cccattatgc   4800
agtgtgaacc tccacctcct gaagcagcaa ggattcacga agtggtccca aggtttctct   4860
ccgacaagct gttggtgaca aaccggcaga aaaacatccc ccagttgaca gccaaccagc   4920
agttccttat cgccaggctc atctggtacc aggacgggta cgagcagcct tctgatgaag   4980
atttgaagag gattacgcag acgtggcagc aagcggacga tgaaaacgaa gagtcggaca   5040
ctcccttccg ccagatcaca gagatgacta tcctcacggt ccaacttatc gtggagttcg   5100
cgaagggatt gccagggttc gccaagatct cgcagcctga tcaaattacg ctgcttaagg   5160
cttgctcaag tgaggtaatg atgctccgag tcgcgcgacg atacgatgcg gcctcagaca   5220
gtattctgtt cgcgaacaac caagcgtaca ctcgcgacaa ctaccgcaag gctggcatgg   5280
ccgaggtcat cgaggatcta ctgcacttct gccggtgcat gtactctatg gcgttggaca   5340
acatccatta cgcgctgctc acggctgtcg tcatcttttc tgaccggcca gggttggagc   5400
agccgcaact ggtggaagag atccagcggt actacctgaa tacgctccgc atctatatcc   5460
tgaaccagct gagcgggtcg gcgcgttcgt ccgtcatata cggcaagatc ctctcaatcc   5520
tctctgagct acgcacgctc ggcatgcaaa actccaacat gtgcatctcc ctcaagctca   5580
agaacagaaa gctgccgcct ttcctcgagg agatctggga tgtggcggac atgtcgcaca   5640
cccaaccgcc gcctatcctc gagtccccca cgaatctcta ggcggcctct agagcggccg   5700
ccaccgcggg gagatccaga catgataaga tacattgatg agtttggaca aaccacaact   5760
agaatgcagt gaaaaaaatg ctttatttgt gaaatttgtg atgctattgc tttatttgta   5820
accattataa gctgcaataa acaagttaac aacaacaatt gcattcattt tatgtttcag   5880
gttcaggggg aggtgtggga ggttttttaa agcaagtaaa acctctacaa atgtggtatg   5940
gctgattatg atccggctgc ctcgcgcgtt tcggtgatga cggtgaaaac ctctgacaca   6000
tgcagctccc ggagacggtc acagcttgtc tgtaagcgga tgccgggagc agacaagccc   6060
gtcagggcgc gtcagcgggt gttggcgggt gtcggggcgc agccatgagg tcgactctag   6120
tccccgcggt ggcagatctg gaaggtgctg aggtacgatg agacccgcac caggtgcaga   6180
ccctgcgagt gtggcggtaa acatattagg aaccagcctg tgatgctgga tgtgaccgag   6240
gagctgaggc ccgatcactt ggtgctggcc tgcacccgcg ctgagtttgg ctctagcgat   6300
gaagatacag attgaggtac tgaaatgtgt gggcgtggct taagggtggg aaagaatata   6360
taaggtgggg gtcttatgta gttttgtatc tgttttgcag cagccgccgc cgccatgagc   6420
accaactcgt ttgatggaag cattgtgagc tcatatttga caacgcgcat gcccccatgg   6480
gccggggtgc gtcagaatgt gatgggctcc agcattgatg gtcgccccgt cctgcccgca   6540
aactctacta ccttgaccta cgagaccgtg tctggaacgc cgttggagac tgcagcctcc   6600
gccgccgctt cagccgctgc agccaccgcc cgcgggattg tgactgactt tgctttcctg   6660
agcccgcttg caagcagtgc agcttcccgt tcatccgccc gcgatgacaa gttgacggct   6720
cttttggcac aattggattc tttgacccgg gaacttaatg tcgtttctca gcagctgttg   6780
gatctgcgcc agcaggtttc tgccctgaag gcttcctccc ctcccaatgc ggtttaaaac   6840
ataaataaaa aaccagactc tgtttggatt tggatcaagc aagtgtcttg ctgtctttat   6900
ttaggggttt tgcgcgcgcg gtaggcccgg gaccagcggt ctcggtcgtt gagggtcctg   6960
tgtatttttt ccaggacgtg gtaaaggtga ctctggatgt tcagatacat gggcataagc   7020
ccgtctctgg ggtggaggta gcaccactgc agagcttcat gctgcggggt ggtgttgtag   7080
```

-continued

```
atgatccagt cgtagcagga gcgctgggcg tggtgcctaa aaatgtcttt cagtagcaag   7140
ctgattgcca ggggcaggcc cttggtgtaa gtgtttacaa agcggttaag ctgggatggg   7200
tgcatacgtg gggatatgag atgcatcttg gactgtattt ttaggttggc tatgttccca   7260
gccatatccc tccggggatt catgttgtgc agaaccacca gcacagtgta tccggtgcac   7320
ttgggaaatt tgtcatgtag cttagaagga aatgcgtgga agaacttgga gacgcccttg   7380
tgacctccaa gattttccat gcattcgtcc ataatgatgg caatgggccc acgggcggcg   7440
gcctgggcga agatatttct gggatcacta acgtcatagt tgtgttccag gatgagatcg   7500
tcataggcca tttttacaaa gcgcgggcgg agggtgccag actgcggtat aatggttcca   7560
tccggcccag gggcgtagtt accctcacag atttgcattt cccacgcttt gagttcagat   7620
ggggggatca tgtctacctg cggggcgatg aagaaaacgg tttccggggt aggggagatc   7680
agctgggaag aaagcaggtt cctgagcagc tgcgacttac cgcagccggt gggcccgtaa   7740
atcacaccta ttaccggctg caactggtag ttaagagagc tgcagctgcc gtcatccctg   7800
agcagggggg ccacttcgtt aagcatgtcc ctgactcgca tgttttccct gaccaaatcc   7860
gccagaaggc gctcgccgcc cagcgatagc agttcttgca aggaagcaaa gtttttcaac   7920
ggtttgagac cgtccgccgt aggcatgctt ttgagcgttt gaccaagcag ttccaggcgg   7980
tcccacagct cggtcacctg ctctacggca tctcgatcca gcatatctcc tcgtttcgcg   8040
ggttggggcg gctttcgctg tacggcagta gtcggtgctc gtccagacgg gccagggtca   8100
tgtctttcca cgggcgcagg gtcctcgtca gcgtagtctg ggtcacggtg aaggggtgcg   8160
ctccgggctg cgcgctggcc agggtgcgct tgaggctggt cctgctggtg ctgaagcgct   8220
gccggtcttc gccctgcgcg tcggccaggt agcatttgac catggtgtca tagtccagcc   8280
cctccgcggc gtggcccttg gcgcgcagct tgcccttgga ggaggcgccg cacgaggggc   8340
agtgcagact tttgagggcg tagagcttgg gcgcgagaaa taccgattcc ggggagtagg   8400
catccgcgcc gcaggccccg cagacggtct cgcattccac gagccaggtg agctctggcc   8460
gttcggggtc aaaaaccagg tttcccccat gctttttgat gcgtttctta cctctggttt   8520
ccatgagccg gtgtccacgc tcggtgacga aaaggctgtc cgtgtccccg tatacagact   8580
tgagaggcct gtcctcgacc gatgcccttg agagccttca acccagtcag ctccttccgg   8640
tgggcgcggg gcatgactat cgtcgccgca cttatgactg tcttctttat catgcaactc   8700
gtaggacagg tgccggcagc gctctgggtc attttcggcg aggaccgctt tcgctggagc   8760
gcgacgatga tcggcctgtc gcttgcggta ttcggaatct tgcacgccct cgctcaagcc   8820
ttcgtcactg gtcccgccac caaacgtttc ggcgagaagc aggccattat cgccggcatg   8880
gcggccgacg cgctgggcta cgtcttgctg gcgttcgcga cgcgaggctg gatggccttc   8940
cccattatga ttcttctcgc ttccggcggc atcgggatgc ccgcgttgca ggccatgctg   9000
tccaggcagg tagatgacga ccatcaggga cagcttcaag gccagcaaaa ggccaggaac   9060
cgtaaaaagg ccgcgttgct ggcgtttttc cataggctcc gcccccctga cgagcatcac   9120
aaaaatcgac gctcaagtca gaggtggcga aacccgacag gactataaag ataccaggcg   9180
tttccccctg gaagctccct cgtgcgctct cctgttccga ccctgccgct taccggatac   9240
ctgtccgcct ttctcccttc gggaagcgtg gcgctttctc atagctcacg ctgtaggtat   9300
ctcagttcgg tgtaggtcgt tcgctccaag ctgggctgtg tgcacgaacc ccccgttcag   9360
cccgaccgct gcgccttatc cggtaactat cgtcttgagt ccaacccggt aagacacgac   9420
```

```
ttatcgccac tggcagcagc cactggtaac aggattagca gagcgaggta tgtaggcggt   9480

gctacagagt tcttgaagtg gtggcctaac tacggctaca ctagaaggac agtatttggt   9540

atctgcgctc tgctgaagcc agttaccttc ggaaaaagag ttggtagctc ttgatccggc   9600

aaacaaacca ccgctggtag cggtggtttt tttgtttgca agcagcagat tacgcgcaga   9660

aaaaaaggat ctcaagaaga tcctttgatc ttttctacgg ggtctgacgc tcagtggaac   9720

gaaaactcac gttaagggat tttggtcatg agattatcaa aaaggatctt cacctagatc   9780

cttttaaatt aaaaatgaag ttttaaatca atctaaagta tatatgagta aacttggtct   9840

gacagttacc aatgcttaat cagtgaggca cctatctcag cgatctgtct atttcgttca   9900

tccatagttg cctgactccc cgtcgtgtag ataactacga tacgggaggg cttaccatct   9960

ggccccagtg ctgcaatgat accgcgagac ccacgctcac cggctccaga tttatcagca  10020

ataaaccagc cagccggaag ggccgagcgc agaagtggtc ctgcaacttt atccgcctcc  10080

atccagtcta ttaattgttg ccgggaagct agagtaagta gttcgccagt taatagtttg  10140

cgcaacgttg ttgccattgc tgcaggcatc gtggtgtcac gctcgtcgtt tggtatggct  10200

tcattcagct ccggttccca acgatcaagg cgagttacat gatcccccat gttgtgcaaa  10260

aaagcggtta gctccttcgg tcctccgatc gttgtcagaa gtaagttggc cgcagtgtta  10320

tcactcatgg ttatggcagc actgcataat tctcttactg tcatgccatc cgtaagatgc  10380

ttttctgtga ctggtgagta ctcaaccaag tcattctgag aatagtgtat gcggcgaccg  10440

agttgctctt gcccggcgtc aacacgggat aataccgcgc cacatagcag aactttaaaa  10500

gtgctcatca ttggaaaacg ttcttcgggg cgaaaactct caaggatctt accgctgttg  10560

agatccagtt cgatgtaacc cactcgtgca cccaactgat cttcagcatc ttttactttc  10620

accagcgttt ctgggtgagc aaaaacagga aggcaaaatg ccgcaaaaaa gggaataagg  10680

gcgacacgga aatgttgaat actcatactc ttcctttttc aatattattg aagcatttat  10740

cagggttatt gtctcatgag cggatacata tttgaatgta tttagaaaaa             10790
```

<210> SEQ ID NO 52
<211> LENGTH: 10575
<212> TYPE: DNA
<213> ORGANISM: Artificial Sequence
<220> FEATURE:
<223> OTHER INFORMATION: PolyDNA_from_VVN-43323 5U2

<400> SEQUENCE: 52

```
taaacaaata ggggttccgc gcacatttcc ccgaaaagtg ccacctgacg tctaagaaac     60

cattattatc atgacattaa cctataaaaa taggcgtatc acgaggccct ttcgtcttca    120

attaattaag ctagcatcat caataatata ccttattttg gattgaagcc aatatgataa    180

tgagggggtg gagtttgtga cgtggcgcgg ggcgtgggaa cggggcgggt gacgtagtag    240

tgtggcggaa gtgtgatgtt gcaagtgtgg cggaacacat gtaagcgacg gatgtggcaa    300

aagtgacgtt tttggtgtgc gccggtgtac acaggaagtg acaattttcg cgcggtttta    360

ggcggatgtt gtagtaaatt tgggcgtaac cgagtaagat ttggccattt tcgcgggaaa    420

actgaataag aggaagtgaa atctgaataa ttttgtgtta ctcatagcgc gtaatatttg    480

tctagggaga tccggtaccg gcgcgcgcgc cgtttggccg cctcgagtct agagatccgg    540

tgagtattag gcgcgcacca ggtgccgcaa taaaatatct ttattttcat tacatctgtg    600

tgttggtttt ttgtgtgaat cgatagtact aacatacgct ctccatcaaa acaaaacgaa    660

acaaaacaaa ctagcaaaat aggctgtccc cagtgcaagt gcaggtgcca gaacatttct    720
```

```
ctatcgataa tgcaggtcgg agtactgtcc tccgagcgga gtactgtcct ccgagcggag    780
tactgtcctc cgagcggagt actgtcctcc gagcggagta ctgtcctccg agcggagtac    840
tgtcctccga gcggagactc ttcgaaggaa gaggggcggg gtcgatcgac cccgcccctc    900
ttccttcgaa ggaagagggg cggggtcgaa gacctagagg gtatataatg ggtgccttag    960
ctggtgtgtg agctcatctt cctgtagatc acgcgtcgaa gaaggtgagt aatcttaaca   1020
tgctcttttt tttttttttt gctaatccct tttgtgtgct gatgttagga tgacatttac   1080
aacaaatgtt tgttcctgac aggaaaaacc ttgctgggta ccttcgttgc cggacacttc   1140
ttgtcctcta ctttggaaaa aaggaattga gagccgctag cgccaccatg tatagaatgc   1200
agctcctgtc ctgcattgcc ctgagcctcg ccctcgtgac aaactccgcc cctaccagcg   1260
gatccgtgag aagcagcagc aggaccccta gcgataagcc tgtggctcac gtcgtcgcta   1320
accctcaggc cgagggccag ctccagtggc tgaatagaag ggccaatgcc ctgctcgcca   1380
acggcgtcga gctgagagac aatcagctcg tggtcccctc cgagggactg tatctgattt   1440
actcccaggt cctgtttaag ggacagggat gccctagcac acacgtcctg ctgacccaca   1500
ccattagcag gatcgctgtg tcctaccaaa ccaaagtgaa tctgctgtcc gctatcaaaa   1560
gcccttgcca aagagaaacc cctgagggag ccgaagccaa accctggtac gaacccattt   1620
acctcggcgg agtgtttcag ctggagaaag gcgatagact cagcgctgag attaacaggc   1680
ccgattacct cgactttgcc gaaagcggac aggtctactt tggcattatc gctctgtaaa   1740
tcgattcgta cgtcgacatc gagaacttgt ttattgcagc ttataatggt tacaaataaa   1800
gcaatagcat cacaaatttc acaaataaag catttttttc actgcattct agttgtggtt   1860
tgtccaaact catcaatgta tcttatcatg tctgggcgcg ccggcctccg cgccgggttt   1920
tggcgcctcc cgcgggcgcc cccctcctca cggcgagcgc tgccacgtca gacgaagggc   1980
gcagcgagcg tcctgatcct tccgcccgga cgctcaggac agcggcccgc tgctcataag   2040
actcggcctt agaaccccag tatcagcaga aggacatttt aggacgggac ttgggtgact   2100
ctagggcact ggttttcttt ccagagagcg gaacaggcga ggaaaagtag tcccttctcg   2160
gcgattctgc ggagggatct ccgtggggcg gtgaacgccg atgattatat aaggacgcgc   2220
cgggtgtggc acagctagtt ccgtcgcagc cgggatttgg gtcgcggttc ttgtttgtgg   2280
atcgctgtga tcgtcacttg gtgagtagcg ggctgctggg ctgggtacgt gcgctcgggg   2340
ttggcgagtg tgttttgtga agttttttag gcaccttttg aaatgtaatc atttgggtca   2400
atatgtaatt ttcagtgtta gactagtaaa ttgtccgcta aattctggcc gtttttggct   2460
tttttgttag acgagctagc gccgccacca tgggccctaa aaagaagcgt aaagtcgccc   2520
ccccgaccga tgtcagcctg ggggacgagc tccacttaga cggcgaggac gtggcgatgg   2580
cgcatgccga cgcgctagac gatttcgatc tggacatgtt gggggacggg gattccccgg   2640
gtccgggatt tacccccccac gactccgccc cctacggcgc tctggatatg gccgacttcg   2700
agtttgagca gatgtttacc gatgcccttg gaattgacga gtacggtggg gaattcgaga   2760
tgcctgtgga caggatcctg gaggcagagc ttgctgtgga acagaagagt gaccagggcg   2820
ttgagggtcc tgggggaacc gggggtagcg gcagcagccc aaatgaccct gtgactaaca   2880
tctgtcaggc agctgacaaa cagctattca cgcttgttga gtgggcgaag aggatcccac   2940
acttttcctc cttgcctctg gatgatcagg tcatattgct gcgggcaggc tggaatgaac   3000
tcctcattgc ctccttttca caccgatcca ttgatgttcg agatggcatc ctccttgcca   3060
```

-continued

```
caggtcttca cgtgcaccgc aactcagccc attcagcagg agtaggagcc atctttgatc   3120
gggtgctgac agagctagtg tccaaaatgc gtgacatgag gatggacaag acagagcttg   3180
gctgcctgag ggcaatcatt ctgtttaatc cagaggtgag gggtttgaaa tccgcccagg   3240
aagttgaact tctacgtgaa aaagtatatg ccgctttgga agaatatact agaacaacac   3300
atcccgatga accaggaaga tttgcaaaac ttttgcttcg tctgccttct ttacgttcca   3360
taggccttaa gtgtttggag catttgtttt tctttcgcct tattggagat gttccaattg   3420
atacgttcct gatggagatg cttgaatcac cttctgattc ataatctagc ctagcccccc   3480
tctccctccc ccccccctaa cgttactggc cgaagccgct tggaataagg ccggtgtgcg   3540
tttgtctata tgttattttc caccatattg ccgtcttttg gcaatgtgag ggcccggaaa   3600
cctggccctg tcttcttgac gagcattcct aggggtcttt cccctctcgc caaaggaatg   3660
caaggtctgt tgaatgtcgt gaaggaagca gttcctctgg aagcttcttg aagacaaaca   3720
acgtctgtag cgaccctttg caggcagcgg aaccccccac ctggcgacag gtgcctctgc   3780
ggccaaaagc cacgtgtata agatacacct gcaaaggcgg cacaacccca gtgccacgtt   3840
gtgagttgga tagttgtgga aagagtcaaa tggctctcct caagcgtatt caacaagggg   3900
ctgaaggatg cccagaaggt accccattgt atgggatctg atctggggcc tcggtgcaca   3960
tgctttacat gtgtttagtc gaggttaaaa aacgtctagg ccccccgaac cacggggacg   4020
tggttttcct ttgaaaaaca cgatctctag gcgccaccat gaagctactg tcttctatcg   4080
aacaagcatg cgatatttgc cgacttaaaa agctcaagtg ctccaaagaa aaaccgaagt   4140
gcgccaagtg tctgaagaac aactgggagt gtcgctactc tcccaaaacc aaaaggtctc   4200
cgctgactag ggcacatctg acagaagtgg aatcaaggct agaaagactg gaacagctat   4260
ttctactgat tttcctcga gaagaccttg acatgatttt gaaaatggat tctttacagg   4320
atataaaagc attgttaaca ggattatttg tacaagataa tgtgaataaa gatgccgtca   4380
cagatagatt ggcttcagtg gagactgata tgcctctaac attgagacag catagaataa   4440
gtgcgacatc atcatcggaa gagagtagta acaaaggtca aagacagttg actgtatcgc   4500
cggaattccc ggggatccgg cctgagtgcg tagtacccga gactcagtgc gccatgaagc   4560
ggaaagagaa gaaagcacag aaggagaagg acaaactgcc tgtcagcacg acgacggtgg   4620
acgaccacat gccgcccatt atgcagtgtg aacctccacc tcctgaagca gcaaggattc   4680
acgaagtggt cccaaggttt ctctccgaca agctgttggt gacaaaccgg cagaaaaaca   4740
tcccccagtt gacagccaac cagcagttcc ttatcgccag gctcatctgg taccaggacg   4800
ggtacgagca gccttctgat gaagatttga agaggattac gcagacgtgg cagcaagcgg   4860
acgatgaaaa cgaagagtcg gacactccct tccgccagat cacagagatg actatcctca   4920
cggtccaact tatcgtggag ttcgcgaagg gattgccagg gttcgccaag atctcgcagc   4980
ctgatcaaat tacgctgctt aaggcttgct caagtgaggt aatgatgctc cgagtcgcgc   5040
gacgatacga tgcggcctca gacagtattc tgttcgcgaa caaccaagcg tacactcgcg   5100
acaactaccg caaggctggc atggccgagg tcatcgagga tctactgcac ttctgccggt   5160
gcatgtactc tatggcgttg gacaacatcc attacgcgct gctcacggct gtcgtcatct   5220
ttctgaccg gccagggttg gagcagccgc aactggtgga agagatccag cggtactacc   5280
tgaatacgct ccgcatctat atcctgaacc agctgagcgg gtcggcgcgt tcgtccgtca   5340
tatacggcaa gatcctctca atcctctctg agctacgcac gctcggcatg caaaactcca   5400
acatgtgcat ctccctcaag ctcaagaaca gaaagctgcc gcctttcctc gaggagatct   5460
```

gggatgtggc ggacatgtcg cacacccaac cgccgcctat cctcgagtcc cccacgaatc 5520
tctaggcggc ctctagagcg gccgccaccg cggggagatc cagacatgat aagatacatt 5580
gatgagtttg gacaaaccac aactagaatg cagtgaaaaa aatgctttat ttgtgaaatt 5640
tgtgatgcta ttgctttatt tgtaaccatt ataagctgca ataaacaagt taacaacaac 5700
aattgcattc attttatgtt tcaggttcag ggggaggtgt gggaggtttt ttaaagcaag 5760
taaaacctct acaaatgtgg tatggctgat tatgatccgg ctgcctcgcg cgtttcggtg 5820
atgacggtga aaacctctga cacatgcagc tcccggagac ggtcacagct tgtctgtaag 5880
cggatgccgg gagcagacaa gcccgtcagg gcgcgtcagc gggtgttggc gggtgtcggg 5940
gcgcagccat gaggtcgact ctagtccccg cggtggcaga tctggaaggt gctgaggtac 6000
gatgagaccc gcaccaggtg cagaccctgc gagtgtggcg gtaaacatat taggaaccag 6060
cctgtgatgc tggatgtgac cgaggagctg aggcccgatc acttggtgct ggcctgcacc 6120
cgcgctgagt ttggctctag cgatgaagat acagattgag gtactgaaat gtgtgggcgt 6180
ggcttaaggg tgggaaagaa tatataaggt gggggtctta tgtagttttg tatctgtttt 6240
gcagcagccg ccgccgccat gagcaccaac tcgtttgatg gaagcattgt gagctcatat 6300
ttgacaacgc gcatgccccc atgggccggg gtgcgtcaga atgtgatggg ctccagcatt 6360
gatggtcgcc ccgtcctgcc cgcaaactct actaccttga cctacgagac cgtgtctgga 6420
acgccgttgg agactgcagc ctccgccgcc gcttcagccg ctgcagccac cgcccgcggg 6480
attgtgactg actttgcttt cctgagcccg cttgcaagca gtgcagcttc ccgttcatcc 6540
gcccgcgatg acaagttgac ggctcttttg gcacaattgg attctttgac ccgggaactt 6600
aatgtcgttt ctcagcagct gttggatctg cgccagcagg tttctgccct gaaggcttcc 6660
tcccctccca atgcggttta aaacataaat aaaaaaccag actctgtttg gatttggatc 6720
aagcaagtgt cttgctgtct ttatttaggg gttttgcgcg cgcggtaggc ccgggaccag 6780
cggtctcggt cgttgagggt cctgtgtatt ttttccagga cgtggtaaag gtgactctgg 6840
atgttcagat acatgggcat aagcccgtct ctggggtgga ggtagcacca ctgcagagct 6900
tcatgctgcg gggtggtgtt gtagatgatc cagtcgtagc aggagcgctg ggcgtggtgc 6960
ctaaaaatgt ctttcagtag caagctgatt gccaggggca ggcccttggt gtaagtgttt 7020
acaaagcggt taagctggga tgggtgcata cgtggggata tgagatgcat cttggactgt 7080
atttttaggt tggctatgtt cccagccata tccctccggg gattcatgtt gtgcagaacc 7140
accagcacag tgtatccggt gcacttggga aatttgtcat gtagcttaga aggaaatgcg 7200
tggaagaact tggagacgcc cttgtgacct ccaagatttt ccatgcattc gtccataatg 7260
atggcaatgg gcccacgggc ggcggcctgg gcgaagatat ttctgggatc actaacgtca 7320
tagttgtgtt ccaggatgag atcgtcatag gccattttta caaagcgcgg gcggagggtg 7380
ccagactgcg gtataatggt tccatccggc ccaggggcgt agttaccctc acagatttgc 7440
atttcccacg ctttgagttc agatgggggg atcatgtcta cctgcggggc gatgaagaaa 7500
acggtttccg ggtaggggga gatcagctgg gaagaaagca ggttcctgag cagctgcgac 7560
ttaccgcagc cggtgggccc gtaaatcaca cctattaccg gctgcaactg gtagttaaga 7620
gagctgcagc tgccgtcatc cctgagcagg ggggccactt cgttaagcat gtccctgact 7680
cgcatgtttt ccctgaccaa atccgccaga aggcgctcgc cgcccagcga tagcagttct 7740
tgcaaggaag caaagttttt caacggtttg agaccgtccg ccgtaggcat gcttttgagc 7800
gtttgaccaa gcagttccag gcggtcccac agctcggtca cctgctctac ggcatctcga 7860
tccagcatat ctcctcgttt cgcgggttgg ggcggctttc gctgtacggc agtagtcggt 7920
gctcgtccag acgggccagg gtcatgtctt tccacgggcg cagggtcctc gtcagcgtag 7980
tctgggtcac ggtgaagggg tgcgctccgg gctgcgcgct ggccagggtg cgcttgaggc 8040
tggtcctgct ggtgctgaag cgctgccggt cttcgccctg cgcgtcggcc aggtagcatt 8100
tgaccatggt gtcatagtcc agcccctccg cggcgtggcc cttggcgcgc agcttgccct 8160
tggaggaggc gccgcacgag gggcagtgca gacttttgag ggcgtagagc ttgggcgcga 8220
gaaataccga ttccggggag taggcatccg cgccgcaggc cccgcagacg gtctcgcatt 8280
ccacgagcca ggtgagctct ggccgttcgg ggtcaaaaac caggtttccc ccatgctttt 8340
tgatgcgttt cttacctctg gtttccatga gccggtgtcc acgctcggtg acgaaaaggc 8400
tgtccgtgtc cccgtataca gacttgagag gcctgtcctc gaccgatgcc cttgagagcc 8460
ttcaacccag tcagctcctt ccggtgggcg cggggcatga ctatcgtcgc cgcacttatg 8520
actgtcttct ttatcatgca actcgtagga caggtgccgg cagcgctctg ggtcattttc 8580
ggcgaggacc gctttcgctg gagcgcgacg atgatcggcc tgtcgcttgc ggtattcgga 8640
atcttgcacg ccctcgctca agccttcgtc actggtcccg ccaccaaacg tttcggcgag 8700
aagcaggcca ttatcgccgg catggcggcc gacgcgctgg gctacgtctt gctggcgttc 8760
gcgacgcgag gctggatggc cttccccatt atgattcttc tcgcttccgg cggcatcggg 8820
atgcccgcgt tgcaggccat gctgtccagg caggtagatg acgaccatca gggacagctt 8880
caaggccagc aaaaggccag gaaccgtaaa aaggccgcgt tgctggcgtt tttccatagg 8940
ctccgccccc ctgacgagca tcacaaaaat cgacgctcaa gtcagaggtg gcgaaacccg 9000
acaggactat aaagatacca ggcgtttccc cctggaagct ccctcgtgcg ctctcctgtt 9060
ccgaccctgc cgcttaccgg atacctgtcc gcctttctcc cttcgggaag cgtggcgctt 9120
tctcatagct cacgctgtag gtatctcagt tcggtgtagg tcgttcgctc caagctgggc 9180
tgtgtgcacg aaccccccgt tcagcccgac cgctgcgcct tatccggtaa ctatcgtctt 9240
gagtccaacc cggtaagaca cgacttatcg ccactggcag cagccactgg taacaggatt 9300
agcagagcga ggtatgtagg cggtgctaca gagttcttga agtggtggcc taactacggc 9360
tacactagaa ggacagtatt tggtatctgc gctctgctga agccagttac cttcggaaaa 9420
agagttggta gctcttgatc cggcaaacaa accaccgctg gtagcggtgg tttttttgtt 9480
tgcaagcagc agattacgcg cagaaaaaaa ggatctcaag aagatccttt gatcttttct 9540
acggggtctg acgctcagtg gaacgaaaac tcacgttaag ggattttggt catgagatta 9600
tcaaaaagga tcttcaccta gatcctttta aattaaaaat gaagttttaa atcaatctaa 9660
agtatatatg agtaaacttg gtctgacagt taccaatgct taatcagtga ggcacctatc 9720
tcagcgatct gtctatttcg ttcatccata gttgcctgac tccccgtcgt gtagataact 9780
acgatacggg agggcttacc atctggcccc agtgctgcaa tgataccgcg agacccacgc 9840
tcaccggctc cagatttatc agcaataaac cagccagccg gaagggccga gcgcagaagt 9900
ggtcctgcaa ctttatccgc ctccatccag tctattaatt gttgccggga agctagagta 9960
agtagttcgc cagttaatag tttgcgcaac gttgttgcca ttgctgcagg catcgtggtg 10020
tcacgctcgt cgtttggtat ggcttcattc agctccggtt cccaacgatc aaggcgagtt 10080
acatgatccc ccatgttgtg caaaaaagcg gttagctcct tcggtcctcc gatcgttgtc 10140
agaagtaagt tggccgcagt gttatcactc atggttatgg cagcactgca taattctctt 10200
actgtcatgc catccgtaag atgcttttct gtgactggtg agtactcaac caagtcattc 10260
tgagaatagt gtatgcggcg accgagttgc tcttgcccgg cgtcaacacg ggataatacc 10320
gcgccacata gcagaacttt aaaagtgctc atcattggaa aacgttcttc ggggcgaaaa 10380
ctctcaagga tcttaccgct gttgagatcc agttcgatgt aacccactcg tgcacccaac 10440
tgatcttcag catcttttac tttcaccagc gtttctgggt gagcaaaaac aggaaggcaa 10500
aatgccgcaa aaaagggaat aagggcgaca cggaaatgtt gaatactcat actcttcctt 10560
tttcaatatt attga 10575

<210> SEQ ID NO 53
<211> LENGTH: 11276
<212> TYPE: DNA
<213> ORGANISM: Artificial Sequence
<220> FEATURE:
<223> OTHER INFORMATION: PolyDNA_from_VVN-43324

<400> SEQUENCE: 53
taaacaaata ggggttccgc gcacatttcc ccgaaaagtg ccacctgacg tctaagaaac 60
cattattatc atgacattaa cctataaaaa taggcgtatc acgaggccct ttcgtcttca 120
attaattaag ctagcatcat caataatata ccttattttg gattgaagcc aatatgataa 180
tgagggggtg gagtttgtga cgtggcgcgg ggcgtgggaa cggggcgggt gacgtagtag 240
tgtggcggaa gtgtgatgtt gcaagtgtgg cggaacacat gtaagcgacg gatgtggcaa 300
aagtgacgtt tttggtgtgc gccggtgtac acaggaagtg acaattttcg cgcggtttta 360
ggcggatgtt gtagtaaatt tgggcgtaac cgagtaagat ttggccattt tcgcgggaaa 420
actgaataag aggaagtgaa atctgaataa ttttgtgtta ctcatagcgc gtaatatttg 480
tctagggaga tccggtaccg gcgcgcgcgc cgtttggccg cctcgagtct agagatccgg 540
tgagtattag gcgcgcacca ggtgccgcaa taaaatatct ttattttcat tacatctgtg 600
tgttggtttt ttgtgtgaat cgatagtact aacatacgct ctccatcaaa acaaaacgaa 660
acaaaacaaa ctagcaaaat aggctgtccc cagtgcaagt gcaggtgcca gaacatttct 720
ctatcgataa tgcaggtcgg agtactgtcc tccgagcgga gtactgtcct ccgagcggag 780
tactgtcctc cgagcggagt actgtcctcc gagcggagta ctgtcctccg agcggagtac 840
tgtcctccga gcggagactc ttcgaaggaa gaggggcggg gtcgatcgac cccgcccctc 900
ttccttcgaa ggaagagggg cggggtcgaa gacctagagg gtatataatg ggtgccttag 960
ctggtgtgtg agctcatctt cctgtagatc acgcgtctcc ctcagcaagg acagcagagg 1020
accagctaag agggagagaa gcaactacag acccccccctg aaaacaaccc tcagacgcca 1080
catcccctga caagctgcca ggcaggttct cttcctctca catactgacc cacggctcca 1140
ccctctctcc cctggaaagg acaccgctag cgccaccatg agcactgaaa gcatgatccg 1200
ggacgtggag ctggccgagg aagccctccc caagaaaacc ggcggccccc aggggagcag 1260
aagatgtttg ttcctgagcc tgttttcctt cctgatcgtg gcaggcgcta ccaccctgtt 1320
ctgcctgctg cactttggag tgatcggccc ccagagggag gagttcccca gggacctctc 1380
tctaatcagc cctctggccc aggcaggatc cgtcagatca tcttctcgaa ccccgagtga 1440
caagcctgta gcccatgttg tagcaaaccc tcaagccgag ggccagctcc agtggctgaa 1500
ccgccgggcc aatgccctgc tcgccaacgg cgtcgagctg agagataacc agctggtggt 1560
gccatcagag ggcctgtacc tcatctactc ccaggtcctg ttcaagggcc aaggctgccc 1620

```
ctccacccat gtgctcctca cccacaccat cagccgcatc gccgtgagct accagaccaa   1680
ggtcaacctc ctctctgcca tcaagagccc ctgccagagg gagaccccag agggggccga   1740
ggccaagccc tggtatgagc ccatctacct cggcggggtg ttccagctgg agaagggtga   1800
ccgactcagc gctgagatca atagacccga ctatctcgac tttgccgaga gcggccaggt   1860
gtactttggg atcattgccc tgtgaatcga ttcgtacgtc gacatcgagt gatgggtggc   1920
atccctgtga cccctcccca gtgcctctcc tggccctgga agttgccact ccagtgccca   1980
ccagccttgt cctaataaaa ttaagttgca tcattttgtc tgactaggtg tccttctata   2040
atattatggg gtggaggggg gtggtatgga gcaaggggca agttgggaag acaacctgta   2100
gggcctgcgg ggtctattgg gaaccaagct ggagtgcagt ggcacaatct tggctcactg   2160
caatctccgc ctcctgggtt caagcgattc tcctgcctca gcctcccgag ttgttgggat   2220
tccaggcatg catgaccagg ctcagctaat ttttgttttt ttggtagaga cggggtttca   2280
ccatattggc caggctggtc tccaactcct aatctcaggt gatctaccca ccttggcctc   2340
ccaaattgct gggattacag gcgtgaacca ctgctccctt ccctgtcctt ctgattttaa   2400
aataactata ccagcaggag gacgtccaga cacagcatag gctacctggc catgcccaac   2460
cggtgggaca tttgagttgc ttgcttggca ctgtcctctc atgcgttggg tccactcagt   2520
agatgcctgt tgaattggcg cgccggcctc cgcgccgggt tttggcgcct cccgcgggcg   2580
ccccccctcct cacggcgagc gctgccacgt cagacgaagg gcgcagcgag cgtcctgatc   2640
cttccgcccg gacgctcagg acagcggccc gctgctcata agactcggcc ttagaacccc   2700
agtatcagca gaaggacatt ttaggacggg acttgggtga ctctagggca ctggttttct   2760
ttccagagag cggaacaggc gaggaaaagt agtcccttct cggcgattct gcggagggat   2820
ctccgtgggg cggtgaacgc cgatgattat ataaggacgc gccgggtgtg gcacagctag   2880
ttccgtcgca gccgggattt gggtcgcggt tcttgtttgt ggatcgctgt gatcgtcact   2940
tggtgagtag cgggctgctg ggctgggtac gtgcgctcgg ggttggcgag tgtgttttgt   3000
gaagtttttt aggcaccttt tgaaatgtaa tcatttgggt caatatgtaa ttttcagtgt   3060
tagactagta aattgtccgc taaattctgg ccgtttttgg cttttttgtt agacgagcta   3120
gcgccgccac catgggccct aaaaagaagc gtaaagtcgc ccccccgacc gatgtcagcc   3180
tgggggacga gctccactta gacggcgagg acgtggcgat ggcgcatgcc gacgcgctag   3240
acgatttcga tctggacatg ttgggggacg gggattcccc gggtccggga tttacccccc   3300
acgactccgc cccctacggc gctctggata tggccgactt cgagtttgag cagatgttta   3360
ccgatgccct tggaattgac gagtacggtg gggaattcga gatgcctgtg gacaggatcc   3420
tggaggcaga gcttgctgtg gaacagaaga gtgaccaggg cgttgagggt cctgggggaa   3480
ccgggggtag cggcagcagc ccaaatgacc ctgtgactaa catctgtcag gcagctgaca   3540
aacagctatt cacgcttgtt gagtgggcga agaggatccc acacttttcc tccttgcctc   3600
tggatgatca ggtcatattg ctgcgggcag gctggaatga actcctcatt gcctcctttt   3660
cacaccgatc cattgatgtt cgagatggca tcctccttgc cacaggtctt cacgtgcacc   3720
gcaactcagc ccattcagca ggagtaggag ccatctttga tcgggtgctg acagagctag   3780
tgtccaaaat gcgtgacatg aggatggaca agacagagct tggctgcctg agggcaatca   3840
ttctgtttaa tccagaggtg aggggtttga aatccgccca ggaagttgaa cttctacgtg   3900
aaaaagtata tgccgctttg gaagaatata ctagaacaac acatcccgat gaaccaggaa   3960
gatttgcaaa acttttgctt cgtctgcctt ctttacgttc cataggcctt aagtgtttgg   4020
```

agcatttgtt tttctttcgc cttattggag atgttccaat tgatacgttc ctgatggaga 4080
tgcttgaatc accttctgat tcataatcta gcctagcccc cctctccctc cccccccccct 4140 aacgttactg gccgaagccg cttggaataa ggccggtgtg cgtttgtcta tatgttattt 4200
tccaccatat tgccgtcttt tggcaatgtg agggcccgga aacctggccc tgtcttcttg 4260
acgagcattc ctaggggtct ttcccctctc gccaaaggaa tgcaaggtct gttgaatgtc 4320
gtgaaggaag cagttcctct ggaagcttct tgaagacaaa caacgtctgt agcgaccctt 4380
tgcaggcagc ggaacccccc acctggcgac aggtgcctct gcggccaaaa gccacgtgta 4440
taagatacac ctgcaaaggc ggcacaaccc cagtgccacg ttgtgagttg gatagttgtg 4500
gaaagagtca aatggctctc ctcaagcgta ttcaacaagg ggctgaagga tgcccagaag 4560
gtaccccatt gtatgggatc tgatctgggg cctcggtgca catgctttac atgtgtttag 4620
tcgaggttaa aaaacgtcta ggccccccga accacgggga cgtggttttc ctttgaaaaa 4680
cacgatctct aggcgccacc atgaagctac tgtcttctat cgaacaagca tgcgatattt 4740
gccgacttaa aaagctcaag tgctccaaag aaaaaccgaa gtgcgccaag tgtctgaaga 4800
acaactggga gtgtcgctac tctcccaaaa ccaaaaggtc tccgctgact agggcacatc 4860
tgacagaagt ggaatcaagg ctagaaagac tggaacagct atttctactg atttttcctc 4920
gagaagacct tgacatgatt ttgaaaatgg attctttaca ggatataaaa gcattgttaa 4980
caggattatt tgtacaagat aatgtgaata aagatgccgt cacagataga ttggcttcag 5040
tggagactga tatgcctcta acattgagac agcatagaat aagtgcgaca tcatcatcgg 5100
aagagagtag taacaaaggt caaagacagt tgactgtatc gccggaattc ccggggatcc 5160
ggcctgagtg cgtagtaccc gagactcagt gcgccatgaa gcggaaagag aagaaagcac 5220
agaaggagaa ggacaaactg cctgtcagca cgacgacggt ggacgaccac atgccgccca 5280
ttatgcagtg tgaacctcca cctcctgaag cagcaaggat tcacgaagtg gtcccaaggt 5340
ttctctccga caagctgttg gtgacaaacc ggcagaaaaa catcccccag ttgacagcca 5400
accagcagtt ccttatcgcc aggctcatct ggtaccagga cgggtacgag cagccttctg 5460
atgaagattt gaagaggatt acgcagacgt ggcagcaagc ggacgatgaa aacgaagagt 5520
cggacactcc cttccgccag atcacagaga tgactatcct cacggtccaa cttatcgtgg 5580
agttcgcgaa gggattgcca gggttcgcca agatctcgca gcctgatcaa attacgctgc 5640
ttaaggcttg ctcaagtgag gtaatgatgc tccgagtcgc gcgacgatac gatgcggcct 5700
cagacagtat tctgttcgcg aacaaccaag cgtacactcg cgacaactac cgcaaggctg 5760
gcatggccga ggtcatcgag gatctactgc acttctgccg gtgcatgtac tctatggcgt 5820
tggacaacat ccattacgcg ctgctcacgg ctgtcgtcat cttttctgac cggccagggt 5880
tggagcagcc gcaactggtg gaagagatcc agcggtacta cctgaatacg ctccgcatct 5940
atatcctgaa ccagctgagc gggtcggcgc gttcgtccgt catatacggc aagatcctct 6000
caatcctctc tgagctacgc acgctcggca tgcaaaactc caacatgtgc atctccctca 6060
agctcaagaa cagaaagctg ccgcctttcc tcgaggagat ctgggatgtg gcggacatgt 6120
cgcacaccca accgccgcct atcctcgagt cccccacgaa tctctaggcg gcctctagag 6180
cggccgccac cgcggggaga tccagacatg ataagataca ttgatgagtt tggacaaacc 6240
acaactagaa tgcagtgaaa aaaatgcttt atttgtgaaa tttgtgatgc tattgcttta 6300
tttgtaacca ttataagctg caataaacaa gttaacaaca acaattgcat tcattttatg 6360

-continued

```
tttcaggttc aggggaggt gtgggaggtt ttttaaagca agtaaaacct ctacaaatgt   6420
ggtatggctg attatgatcc ggctgcctcg cgcgtttcgg tgatgacggt gaaaacctct   6480
gacacatgca gctcccggag acggtcacag cttgtctgta agcggatgcc gggagcagac   6540
aagcccgtca gggcgcgtca gcgggtgttg gcgggtgtcg gggcgcagcc atgaggtcga   6600
ctctagtccc cgcggtggca gatctggaag gtgctgaggt acgatgagac ccgcaccagg   6660
tgcagaccct gcgagtgtgg cggtaaacat attaggaacc agcctgtgat gctggatgtg   6720
accgaggagc tgaggcccga tcacttggtg ctggcctgca cccgcgctga gtttggctct   6780
agcgatgaag atacagattg aggtactgaa atgtgtgggc gtggcttaag ggtgggaaag   6840
aatatataag gtgggggtct tatgtagttt tgtatctgtt ttgcagcagc cgccgccgcc   6900
atgagcacca actcgtttga tggaagcatt gtgagctcat atttgacaac gcgcatgccc   6960
ccatgggccg gggtgcgtca gaatgtgatg ggctccagca ttgatggtcg ccccgtcctg   7020
cccgcaaact ctactacctt gacctacgag accgtgtctg gaacgccgtt ggagactgca   7080
gcctccgccg ccgcttcagc cgctgcagcc accgcccgcg ggattgtgac tgactttgct   7140
ttcctgagcc cgcttgcaag cagtgcagct tcccgttcat ccgcccgcga tgacaagttg   7200
acggctcttt tggcacaatt ggattctttg acccgggaac ttaatgtcgt ttctcagcag   7260
ctgttggatc tgcgccagca ggtttctgcc ctgaaggctt cctcccctcc caatgcggtt   7320
taaaacataa ataaaaaacc agactctgtt tggatttgga tcaagcaagt gtcttgctgt   7380
ctttatttag gggttttgcg cgcgcggtag gcccgggacc agcggtctcg gtcgttgagg   7440
gtcctgtgta tttttttccag gacgtggtaa aggtgactct ggatgttcag atacatgggc   7500
ataagcccgt ctctggggtg gaggtagcac cactgcagag cttcatgctg cggggtggtg   7560
ttgtagatga tccagtcgta gcaggagcgc tgggcgtggt gcctaaaaat gtctttcagt   7620
agcaagctga ttgccagggg caggcccttg gtgtaagtgt ttacaaagcg gttaagctgg   7680
gatgggtgca tacgtgggga tatgagatgc atcttggact gtatttttag gttggctatg   7740
ttcccagcca tatccctccg gggattcatg ttgtgcagaa ccaccagcac agtgtatccg   7800
gtgcacttgg gaaatttgtc atgtagctta gaaggaaatg cgtggaagaa cttggagacg   7860
cccttgtgac ctccaagatt ttccatgcat tcgtccataa tgatggcaat gggcccacgg   7920
gcggcggcct gggcgaagat atttctggga tcactaacgt catagttgtg ttccaggatg   7980
agatcgtcat aggccatttt tacaaagcgc gggcggaggg tgccagactg cggtataatg   8040
gttccatccg gcccaggggc gtagttaccc tcacagattt gcatttccca cgctttgagt   8100
tcagatgggg ggatcatgtc tacctgcggg gcgatgaaga aaacggtttc cggggtaggg   8160
gagatcagct gggaagaaag caggttcctg agcagctgcg acttaccgca gccggtgggc   8220
ccgtaaatca cacctattac cggctgcaac tggtagttaa gagagctgca gctgccgtca   8280
tccctgagca ggggggccac ttcgttaagc atgtccctga ctcgcatgtt ttccctgacc   8340
aaatccgcca gaaggcgctc gccgcccagc gatagcagtt cttgcaagga agcaaagttt   8400
ttcaacggtt tgagaccgtc cgccgtaggc atgcttttga gcgtttgacc aagcagttcc   8460
aggcggtccc acagctcggt cacctgctct acggcatctc gatccagcat atctcctcgt   8520
ttcgcgggtt ggggcggctt tcgctgtacg gcagtagtcg gtgctcgtcc agacgggcca   8580
gggtcatgtc tttccacggg cgcagggtcc tcgtcagcgt agtctgggtc acggtgaagg   8640
ggtgcgctcc gggctgcgcg ctggccaggg tgcgcttgag gctggtcctg ctggtgctga   8700
agcgctgccg gtcttcgccc tgcgcgtcgg ccaggtagca tttgaccatg gtgtcatagt   8760
```

ccagcccctc cgcggcgtgg cccttggcgc gcagcttgcc cttggaggag gcgccgcacg 8820
aggggcagtg cagacttttg agggcgtaga gcttgggcgc gagaaatacc gattccgggg 8880
agtaggcatc cgcgccgcag gccccgcaga cggtctcgca ttccacgagc caggtgagct 8940
ctggccgttc ggggtcaaaa accaggtttc ccccatgctt tttgatgcgt ttcttacctc 9000
tggtttccat gagccggtgt ccacgctcgg tgacgaaaag gctgtccgtg tccccgtata 9060
cagacttgag aggcctgtcc tcgaccgatg cccttgagag ccttcaaccc agtcagctcc 9120
ttccggtggg cgcggggcat gactatcgtc gccgcactta tgactgtctt ctttatcatg 9180
caactcgtag gacaggtgcc ggcagcgctc tgggtcattt tcggcgagga ccgctttcgc 9240
tggagcgcga cgatgatcgg cctgtcgctt gcggtattcg gaatcttgca cgccctcgct 9300
caagccttcg tcactggtcc cgccaccaaa cgtttcggcg agaagcaggc cattatcgcc 9360
ggcatggcgg ccgacgcgct gggctacgtc ttgctggcgt tcgcgacgcg aggctggatg 9420
gccttcccca ttatgattct tctcgcttcc ggcggcatcg ggatgcccgc gttgcaggcc 9480
atgctgtcca ggcaggtaga tgacgaccat cagggacagc ttcaaggcca gcaaaaggcc 9540
aggaaccgta aaaaggccgc gttgctggcg tttttccata ggctccgccc ccctgacgag 9600
catcacaaaa atcgacgctc aagtcagagg tggcgaaacc cgacaggact ataaagatac 9660
caggcgtttc cccctggaag ctccctcgtg cgctctcctg ttccgaccct gccgcttacc 9720
ggatacctgt ccgcctttct cccttcggga agcgtggcgc tttctcatag ctcacgctgt 9780
aggtatctca gttcggtgta ggtcgttcgc tccaagctgg gctgtgtgca cgaacccccc 9840
gttcagcccg accgctgcgc cttatccggt aactatcgtc ttgagtccaa cccggtaaga 9900
cacgacttat cgccactggc agcagccact ggtaacagga ttagcagagc gaggtatgta 9960
ggcggtgcta cagagttctt gaagtggtgg cctaactacg gctacactag aaggacagta 10020
tttggtatct gcgctctgct gaagccagtt accttcggaa aaagagttgg tagctcttga 10080
tccggcaaac aaaccaccgc tggtagcggt ggtttttttg tttgcaagca gcagattacg 10140
cgcagaaaaa aaggatctca agaagatcct ttgatctttt ctacggggtc tgacgctcag 10200
tggaacgaaa actcacgtta agggattttg gtcatgagat tatcaaaaag gatcttcacc 10260
tagatccttt taaattaaaa atgaagtttt aaatcaatct aaagtatata tgagtaaact 10320
tggtctgaca gttaccaatg cttaatcagt gaggcaccta tctcagcgat ctgtctattt 10380
cgttcatcca tagttgcctg actccccgtc gtgtagataa ctacgatacg ggagggctta 10440
ccatctggcc ccagtgctgc aatgataccg cgagacccac gctcaccggc tccagattta 10500
tcagcaataa accagccagc cggaagggcc gagcgcagaa gtggtcctgc aactttatcc 10560
gcctccatcc agtctattaa ttgttgccgg gaagctagag taagtagttc gccagttaat 10620
agtttgcgca acgttgttgc cattgctgca ggcatcgtgg tgtcacgctc gtcgtttggt 10680
atggcttcat tcagctccgg ttcccaacga tcaaggcgag ttacatgatc ccccatgttg 10740
tgcaaaaaag cggttagctc cttcggtcct ccgatcgttg tcagaagtaa gttggccgca 10800
gtgttatcac tcatggttat ggcagcactg cataattctc ttactgtcat gccatccgta 10860
agatgctttt ctgtgactgg tgagtactca accaagtcat tctgagaata gtgtatgcgg 10920
cgaccgagtt gctcttgccc ggcgtcaaca cgggataata ccgcgccaca tagcagaact 10980
ttaaaagtgc tcatcattgg aaaacgttct tcggggcgaa aactctcaag gatcttaccg 11040
ctgttgagat ccagttcgat gtaacccact cgtgcaccca actgatcttc agcatctttt 11100
actttcacca gcgtttctgg gtgagcaaaa acaggaaggc aaaatgccgc aaaaaaggga 11160
ataagggcga cacggaaatg ttgaatactc atactcttcc tttttcaata ttattgaagc 11220
atttatcagg gttattgtct catgagcgga tacatatttg aatgtattta gaaaaa 11276

<210> SEQ ID NO 54
<211> LENGTH: 11276
<212> TYPE: DNA
<213> ORGANISM: Artificial Sequence
<220> FEATURE:
<223> OTHER INFORMATION: PolyDNA_from_VVN-43325

<400> SEQUENCE: 54
taaacaaata ggggttccgc gcacatttcc ccgaaaagtg ccacctgacg tctaagaaac 60
cattattatc atgacattaa cctataaaaa taggcgtatc acgaggccct ttcgtcttca 120
attaattaag ctagcatcat caataatata ccttattttg gattgaagcc aatatgataa 180 tgaggggtg gagtttgtga cgtggcgcgg ggcgtgggaa cggggcgggt gacgtagtag 240
tgtggcggaa gtgtgatgtt gcaagtgtgg cggaacacat gtaagcgacg gatgtggcaa 300
aagtgacgtt tttggtgtgc gccggtgtac acaggaagtg acaattttcg cgcggtttta 360
ggcggatgtt gtagtaaatt tgggcgtaac cgagtaagat ttggccattt tcgcgggaaa 420
actgaataag aggaagtgaa atctgaataa ttttgtgtta ctcatagcgc gtaatatttg 480
tctagggaga tccggtaccg gcgcgcgcgc cgtttggccg cctcgagtct agagatccgg 540
tgagtattag gcgcgcacca ggtgccgcaa taaaatatct ttattttcat tacatctgtg 600
tgttggtttt ttgtgtgaat cgatagtact aacatacgct ctccatcaaa acaaaacgaa 660
acaaaacaaa ctagcaaaat aggctgtccc cagtgcaagt gcaggtgcca gaacatttct 720
ctatcgataa tgcaggtcgg agtactgtcc tccgagcgga gtactgtcct ccgagcggag 780
tactgtcctc cgagcggagt actgtcctcc gagcggagta ctgtcctccg agcggagtac 840
tgtcctccga gcggagactc ttcgaaggaa gaggggcggg gtcgatcgac cccgcccctc 900
ttccttcgaa ggaagagggg cggggtcgaa gacctagagg gtatataatg ggtgccttag 960
ctggtgtgtg agctcatctt cctgtagatc acgcgtctcc ctcagcaagg acagcagagg 1020
accagctaag agggagagaa gcaactacag acccccccctg aaaacaaccc tcagacgcca 1080
catcccctga caagctgcca ggcaggttct cttcctctca catactgacc cacggctcca 1140
ccctctctcc cctggaaagg acaccgctag cgccaccatg tccaccgaaa gcatgatccg 1200
ggacgtggag ctggccgagg aagccctgcc taagaaaacc ggaggccctc agggaagcag 1260
gagatgtctg tttctgtccc tgtttagctt tctgattgtg gctggcgcta ccacactgtt 1320
ttgcctcctg catttcggag tgattggccc tcagagggag gagttcccta gagacctgtc 1380
cctgattagc cctctggctc aggctggatc cgtgagaagc agcagcagga cccctagcga 1440
taagcctgtg gctcacgtcg tcgctaaccc tcaggccgag ggccagctcc agtggctgaa 1500
tagaagggcc aatgccctgc tcgccaacgg cgtcgagctg agagacaatc agctcgtggt 1560
cccctccgag ggactgtatc tgatttactc ccaggtcctg tttaagggac agggatgccc 1620
tagcacacac gtcctgctga cccacaccat tagcaggatc gctgtgtcct accaaaccaa 1680
agtgaatctg ctgtccgcta tcaaaagccc ttgccaaaga gaaacccctg agggagccga 1740
agccaaaccc tggtacgaac ccatttacct cggcggagtg tttcagctgg agaaaggcga 1800
tagactcagc gctgagatta acaggcccga ttacctcgac tttgccgaaa gcggacaggt 1860
ctactttggc attatcgctc tgtaaatcga ttcgtacgtc gacatcgagt gatgggtggc 1920

-continued

```
atccctgtga cccctcccca gtgcctctcc tggccctgga agttgccact ccagtgccca   1980
ccagccttgt cctaataaaa ttaagttgca tcattttgtc tgactaggtg tccttctata   2040
atattatggg gtggaggggg gtggtatgga gcaaggggca agttgggaag acaacctgta   2100
gggcctgcgg ggtctattgg gaaccaagct ggagtgcagt ggcacaatct tggctcactg   2160
caatctccgc ctcctgggtt caagcgattc tcctgcctca gcctcccgag ttgttgggat   2220
tccaggcatg catgaccagg ctcagctaat ttttgttttt ttggtagaga cggggtttca   2280
ccatattggc caggctggtc tccaactcct aatctcaggt gatctaccca ccttggcctc   2340
ccaaattgct gggattacag gcgtgaacca ctgctccctt ccctgtcctt ctgattttaa   2400
aataactata ccagcaggag gacgtccaga cacagcatag gctacctggc catgcccaac   2460
cggtgggaca tttgagttgc ttgcttggca ctgtcctctc atgcgttggg tccactcagt   2520
agatgcctgt tgaattggcg cgccggcctc cgcgccgggt tttggcgcct cccgcgggcg   2580
ccccctcct cacggcgagc gctgccacgt cagacgaagg gcgcagcgag cgtcctgatc   2640
cttccgcccg gacgctcagg acagcggccc gctgctcata agactcggcc ttagaacccc   2700
agtatcagca gaaggacatt ttaggacggg acttgggtga ctctagggca ctggttttct   2760
ttccagagag cggaacaggc gaggaaaagt agtcccttct cggcgattct gcggagggat   2820
ctccgtgggg cggtgaacgc cgatgattat ataaggacgc gccgggtgtg gcacagctag   2880
ttccgtcgca gccgggattt gggtcgcggt tcttgtttgt ggatcgctgt gatcgtcact   2940
tggtgagtag cgggctgctg ggctgggtac gtgcgctcgg ggttggcgag tgtgttttgt   3000
gaagtttttt aggcaccttt tgaaatgtaa tcatttgggt caatatgtaa ttttcagtgt   3060
tagactagta aattgtccgc taaattctgg ccgtttttgg ctttttttgtt agacgagcta   3120
gcgccgccac catgggccct aaaaagaagc gtaaagtcgc ccccccgacc gatgtcagcc   3180
tgggggacga gctccactta gacggcgagg acgtggcgat ggcgcatgcc gacgcgctag   3240
acgatttcga tctggacatg ttgggggacg gggattcccc gggtccggga tttacccccc   3300
acgactccgc cccctacggc gctctggata tggccgactt cgagtttgag cagatgttta   3360
ccgatgccct tggaattgac gagtacggtg gggaattcga gatgcctgtg gacaggatcc   3420
tggaggcaga gcttgctgtg gaacagaaga gtgaccaggg cgttgagggt cctgggggaa   3480
ccgggggtag cggcagcagc ccaaatgacc ctgtgactaa catctgtcag gcagctgaca   3540
aacagctatt cacgcttgtt gagtgggcga agaggatccc acacttttcc tccttgcctc   3600
tggatgatca ggtcatattg ctgcgggcag gctggaatga actcctcatt gcctcctttt   3660
cacaccgatc cattgatgtt cgagatggca tcctccttgc cacaggtctt cacgtgcacc   3720
gcaactcagc ccattcagca ggagtaggag ccatctttga tcgggtgctg acagagctag   3780
tgtccaaaat gcgtgacatg aggatggaca agacagagct tggctgcctg agggcaatca   3840
ttctgtttaa tccagaggtg aggggtttga aatccgccca ggaagttgaa cttctacgtg   3900
aaaaagtata tgccgctttg gaagaatata ctagaacaac acatcccgat gaaccaggaa   3960
gatttgcaaa acttttgctt cgtctgcctt ctttacgttc cataggcctt aagtgtttgg   4020
agcatttgtt tttctttcgc cttattggag atgttccaat tgatacgttc ctgatggaga   4080
tgcttgaatc accttctgat tcataatcta gcctagcccc cctctccctc cccccccct   4140
aacgttactg gccgaagccg cttggaataa ggccggtgtg cgtttgtcta tatgttattt   4200
tccaccatat tgccgtcttt tggcaatgtg agggcccgga aacctggccc tgtcttcttg   4260
```

-continued acgagcattc ctaggggtct ttcccctctc gccaaaggaa tgcaaggtct gttgaatgtc 4320
gtgaaggaag cagttcctct ggaagcttct tgaagacaaa caacgtctgt agcgaccctt 4380
tgcaggcagc ggaacccccc acctggcgac aggtgcctct gcggccaaaa gccacgtgta 4440
taagatacac ctgcaaaggc ggcacaaccc cagtgccacg ttgtgagttg gatagttgtg 4500
gaaagagtca aatggctctc ctcaagcgta ttcaacaagg ggctgaagga tgcccagaag 4560
gtaccccatt gtatgggatc tgatctgggg cctcggtgca catgctttac atgtgtttag 4620
tcgaggttaa aaaacgtcta ggccccccga accacgggga cgtggttttc ctttgaaaaa 4680
cacgatctct aggcgccacc atgaagctac tgtcttctat cgaacaagca tgcgatattt 4740
gccgacttaa aaagctcaag tgctccaaag aaaaaccgaa gtgcgccaag tgtctgaaga 4800
acaactggga gtgtcgctac tctcccaaaa ccaaaaggtc tccgctgact agggcacatc 4860
tgacagaagt ggaatcaagg ctagaaagac tggaacagct atttctactg atttttcctc 4920
gagaagacct tgacatgatt ttgaaaatgg attctttaca ggatataaaa gcattgttaa 4980
caggattatt tgtacaagat aatgtgaata aagatgccgt cacagataga ttggcttcag 5040
tggagactga tatgcctcta acattgagac agcatagaat aagtgcgaca tcatcatcgg 5100
aagagagtag taacaaaggt caaagacagt tgactgtatc gccggaattc ccggggatcc 5160
ggcctgagtg cgtagtaccc gagactcagt gcgccatgaa gcggaaagag aagaaagcac 5220
agaaggagaa ggacaaactg cctgtcagca cgacgacggt ggacgaccac atgccgccca 5280
ttatgcagtg tgaacctcca cctcctgaag cagcaaggat tcacgaagtg gtcccaaggt 5340
ttctctccga caagctgttg gtgacaaacc ggcagaaaaa catcccccag ttgacagcca 5400
accagcagtt ccttatcgcc aggctcatct ggtaccagga cgggtacgag cagccttctg 5460
atgaagattt gaagaggatt acgcagacgt ggcagcaagc ggacgatgaa aacgaagagt 5520
cggacactcc cttccgccag atcacagaga tgactatcct cacggtccaa cttatcgtgg 5580
agttcgcgaa gggattgcca gggttcgcca agatctcgca gcctgatcaa attacgctgc 5640
ttaaggcttg ctcaagtgag gtaatgatgc tccgagtcgc gcgacgatac gatgcggcct 5700
cagacagtat tctgttcgcg aacaaccaag cgtacactcg cgacaactac cgcaaggctg 5760
gcatggccga ggtcatcgag gatctactgc acttctgccg gtgcatgtac tctatggcgt 5820
tggacaacat ccattacgcg ctgctcacgg ctgtcgtcat cttttctgac cggccagggt 5880
tggagcagcc gcaactggtg gaagagatcc agcggtacta cctgaatacg ctccgcatct 5940
atatcctgaa ccagctgagc gggtcggcgc gttcgtccgt catatacggc aagatcctct 6000
caatcctctc tgagctacgc acgctcggca tgcaaaactc caacatgtgc atctccctca 6060
agctcaagaa cagaaagctg ccgcctttcc tcgaggagat ctgggatgtg gcggacatgt 6120
cgcacaccca accgccgcct atcctcgagt cccccacgaa tctctaggcg gcctctagag 6180
cggccgccac cgcggggaga tccagacatg ataagataca ttgatgagtt tggacaaacc 6240
acaactagaa tgcagtgaaa aaaatgcttt atttgtgaaa tttgtgatgc tattgcttta 6300
tttgtaacca ttataagctg caataaacaa gttaacaaca acaattgcat tcattttatg 6360
tttcaggttc agggggaggt gtgggaggtt ttttaaagca agtaaaacct ctacaaatgt 6420
ggtatggctg attatgatcc ggctgcctcg cgcgtttcgg tgatgacggt gaaaacctct 6480
gacacatgca gctcccggag acggtcacag cttgtctgta agcggatgcc gggagcagac 6540
aagcccgtca gggcgcgtca gcgggtgttg gcgggtgtcg gggcgcagcc atgaggtcga 6600
ctctagtccc cgcggtggca gatctggaag gtgctgaggt acgatgagac ccgcaccagg 6660

```
tgcagaccct gcgagtgtgg cggtaaacat attaggaacc agcctgtgat gctggatgtg   6720
accgaggagc tgaggcccga tcacttggtg ctggcctgca cccgcgctga gtttggctct   6780
agcgatgaag atacagattg aggtactgaa atgtgtgggc gtggcttaag ggtgggaaag   6840
aatatataag gtgggggtct tatgtagttt tgtatctgtt ttgcagcagc cgccgccgcc   6900
atgagcacca actcgtttga tggaagcatt gtgagctcat atttgacaac gcgcatgccc   6960
ccatgggccg gggtgcgtca gaatgtgatg ggctccagca ttgatggtcg ccccgtcctg   7020
cccgcaaact ctactacctt gacctacgag accgtgtctg gaacgccgtt ggagactgca   7080
gcctccgccg ccgcttcagc cgctgcagcc accgcccgcg ggattgtgac tgactttgct   7140
ttcctgagcc cgcttgcaag cagtgcagct tcccgttcat ccgcccgcga tgacaagttg   7200
acggctcttt tggcacaatt ggattctttg acccgggaac ttaatgtcgt ttctcagcag   7260
ctgttggatc tgcgccagca ggtttctgcc ctgaaggctt cctcccctcc caatgcggtt   7320
taaaacataa ataaaaaacc agactctgtt tggatttgga tcaagcaagt gtcttgctgt   7380
ctttatttag gggttttgcg cgcgcggtag gcccgggacc agcggtctcg gtcgttgagg   7440
gtcctgtgta tttttttccag gacgtggtaa aggtgactct ggatgttcag atacatgggc   7500
ataagcccgt ctctggggtg gaggtagcac cactgcagag cttcatgctg cggggtggtg   7560
ttgtagatga tccagtcgta gcaggagcgc tgggcgtggt gcctaaaaat gtctttcagt   7620
agcaagctga ttgccagggg caggcccttg gtgtaagtgt ttacaaagcg gttaagctgg   7680
gatgggtgca tacgtgggga tatgagatgc atcttggact gtatttttag gttggctatg   7740
ttcccagcca tatccctccg ggattcatg ttgtgcagaa ccaccagcac agtgtatccg   7800
gtgcacttgg gaaatttgtc atgtagctta gaaggaaatg cgtggaagaa cttggagacg   7860
cccttgtgac ctccaagatt ttccatgcat tcgtccataa tgatggcaat gggcccacgg   7920
gcggcggcct gggcgaagat atttctggga tcactaacgt catagttgtg ttccaggatg   7980
agatcgtcat aggccatttt tacaaagcgc gggcggaggg tgccagactg cggtataatg   8040
gttccatccg gcccaggggc gtagttaccc tcacagattt gcatttccca cgctttgagt   8100
tcagatgggg ggatcatgtc tacctgcggg gcgatgaaga aaacggtttc cggggtaggg   8160
gagatcagct gggaagaaag caggttcctg agcagctgcg acttaccgca gccggtgggc   8220
ccgtaaatca cacctattac cggctgcaac tggtagttaa gagagctgca gctgccgtca   8280
tccctgagca ggggggccac ttcgttaagc atgtccctga ctcgcatgtt ttccctgacc   8340
aaatccgcca gaaggcgctc gccgcccagc gatagcagtt cttgcaagga agcaaagttt   8400
ttcaacggtt tgagaccgtc cgccgtaggc atgcttttga gcgtttgacc aagcagttcc   8460
aggcggtccc acagctcggt cacctgctct acggcatctc gatccagcat atctcctcgt   8520
ttcgcgggtt ggggcggctt tcgctgtacg gcagtagtcg gtgctcgtcc agacgggcca   8580
gggtcatgtc tttccacggg cgcagggtcc tcgtcagcgt agtctgggtc acggtgaagg   8640
ggtgcgctcc gggctgcgcg ctggccaggg tgcgcttgag gctggtcctg ctggtgctga   8700
agcgctgccg gtcttcgccc tgcgcgtcgg ccaggtagca tttgaccatg gtgtcatagt   8760
ccagcccctc cgcggcgtgg ccccttggcgc gcagcttgcc cttggaggag gcgccgcacg   8820
aggggcagtg cagacttttg agggcgtaga gcttgggcgc gagaaatacc gattccgggg   8880
agtaggcatc cgcgccgcag gccccgcaga cggtctcgca ttccacgagc caggtgagct   8940
ctggccgttc ggggtcaaaa accaggtttc cccatgctt tttgatgcgt ttcttacctc   9000
```

-continued

```
tggtttccat gagccggtgt ccacgctcgg tgacgaaaag gctgtccgtg tccccgtata   9060
cagacttgag aggcctgtcc tcgaccgatg cccttgagag ccttcaaccc agtcagctcc   9120
ttccggtggg cgcggggcat gactatcgtc gccgcactta tgactgtctt ctttatcatg   9180
caactcgtag gacaggtgcc ggcagcgctc tgggtcattt tcggcgagga ccgctttcgc   9240
tggagcgcga cgatgatcgg cctgtcgctt gcggtattcg gaatcttgca cgccctcgct   9300
caagccttcg tcactggtcc cgccaccaaa cgtttcggcg agaagcaggc cattatcgcc   9360
ggcatggcgg ccgacgcgct gggctacgtc ttgctggcgt tcgcgacgcg aggctggatg   9420
gccttcccca ttatgattct tctcgcttcc ggcggcatcg ggatgcccgc gttgcaggcc   9480
atgctgtcca ggcaggtaga tgacgaccat cagggacagc ttcaaggcca gcaaaaggcc   9540
aggaaccgta aaaaggccgc gttgctggcg tttttccata ggctccgccc ccctgacgag   9600
catcacaaaa atcgacgctc aagtcagagg tggcgaaacc cgacaggact ataaagatac   9660
caggcgtttc cccctggaag ctccctcgtg cgctctcctg ttccgaccct gccgcttacc   9720
ggatacctgt ccgcctttct cccttcggga agcgtggcgc tttctcatag ctcacgctgt   9780
aggtatctca gttcggtgta ggtcgttcgc tccaagctgg gctgtgtgca cgaacccccc   9840
gttcagcccg accgctgcgc cttatccggt aactatcgtc ttgagtccaa cccggtaaga   9900
cacgacttat cgccactggc agcagccact ggtaacagga ttagcagagc gaggtatgta   9960
ggcggtgcta cagagttctt gaagtggtgg cctaactacg gctacactag aaggacagta  10020
tttggtatct gcgctctgct gaagccagtt accttcggaa aaagagttgg tagctcttga  10080
tccggcaaac aaaccaccgc tggtagcggt ggtttttttg tttgcaagca gcagattacg  10140
cgcagaaaaa aaggatctca agaagatcct ttgatctttt ctacggggtc tgacgctcag  10200
tggaacgaaa actcacgtta agggattttg gtcatgagat tatcaaaaag gatcttcacc  10260
tagatccttt taaattaaaa atgaagtttt aaatcaatct aaagtatata tgagtaaact  10320
tggtctgaca gttaccaatg cttaatcagt gaggcaccta tctcagcgat ctgtctattt  10380
cgttcatcca tagttgcctg actccccgtc gtgtagataa ctacgatacg ggagggctta  10440
ccatctggcc ccagtgctgc aatgataccg cgagacccac gctcaccggc tccagattta  10500
tcagcaataa accagccagc cggaagggcc gagcgcagaa gtggtcctgc aactttatcc  10560
gcctccatcc agtctattaa ttgttgccgg gaagctagag taagtagttc gccagttaat  10620
agtttgcgca acgttgttgc cattgctgca ggcatcgtgg tgtcacgctc gtcgtttggt  10680
atggcttcat tcagctccgg ttcccaacga tcaaggcgag ttacatgatc ccccatgttg  10740
tgcaaaaaag cggttagctc cttcggtcct ccgatcgttg tcagaagtaa gttggccgca  10800
gtgttatcac tcatggttat ggcagcactg cataattctc ttactgtcat gccatccgta  10860
agatgctttt ctgtgactgg tgagtactca accaagtcat tctgagaata gtgtatgcgg  10920
cgaccgagtt gctcttgccc ggcgtcaaca cgggataata ccgcgccaca tagcagaact  10980
ttaaaagtgc tcatcattgg aaaacgttct tcggggcgaa aactctcaag gatcttaccg  11040
ctgttgagat ccagttcgat gtaacccact cgtgcaccca actgatcttc agcatctttt  11100
actttcacca gcgtttctgg gtgagcaaaa acaggaaggc aaaatgccgc aaaaaaggga  11160
ataagggcga cacggaaatg ttgaatactc atactcttcc tttttcaata ttattgaagc  11220
atttatcagg gttattgtct catgagcgga tacatatttg aatgtattta gaaaaa      11276
```

<210> SEQ ID NO 55
<211> LENGTH: 11120

-continued

<212> TYPE: DNA
<213> ORGANISM: Artificial Sequence
<220> FEATURE:
<223> OTHER INFORMATION: 5PolyDNA_from_VVN-43326

<400> SEQUENCE: 55
taaacaaata ggggttccgc gcacatttcc ccgaaaagtg ccacctgacg tctaagaaac 60
cattattatc atgacattaa cctataaaaa taggcgtatc acgaggccct ttcgtcttca 120
attaattaag ctagcatcat caataatata ccttattttg gattgaagcc aatatgataa 180
tgagggggtg gagtttgtga cgtggcgcgg ggcgtgggaa cggggcgggt gacgtagtag 240
tgtggcggaa gtgtgatgtt gcaagtgtgg cggaacacat gtaagcgacg gatgtggcaa 300
aagtgacgtt tttggtgtgc gccggtgtac acaggaagtg acaattttcg cgcggtttta 360
ggcggatgtt gtagtaaatt tgggcgtaac cgagtaagat ttggccattt tcgcgggaaa 420
actgaataag aggaagtgaa atctgaataa ttttgtgtta ctcatagcgc gtaatatttg 480
tctagggaga tccggtaccg gcgcgcgcgc cgtttggccg cctcgagtct agagatccgg 540
tgagtattag gcgcgcacca ggtgccgcaa taaaatatct ttattttcat tacatctgtg 600
tgttggtttt ttgtgtgaat cgatagtact aacatacgct ctccatcaaa acaaaacgaa 660
acaaaacaaa ctagcaaaat aggctgtccc cagtgcaagt gcaggtgcca gaacatttct 720
ctatcgataa tgcaggtcgg agtactgtcc tccgagcgga gtactgtcct ccgagcggag 780
tactgtcctc cgagcggagt actgtcctcc gagcggagta ctgtcctccg agcggagtac 840
tgtcctccga gcggagactc ttcgaaggaa gaggggcggg gtcgatcgac cccgcccctc 900
ttccttcgaa ggaagagggg cggggtcgaa gacctagagg gtatataatg ggtgccttag 960
ctggtgtgtg agctcatctt cctgtagatc acgcgtctcc ctcagcaagg acagcagagg 1020
accagctaag agggagagaa gcaactacag acccccccctg aaaacaaccc tcagacgcca 1080
catcccctga caagctgcca ggcaggttct cttcctctca catactgacc cacggctcca 1140
ccctctctcc cctggaaagg acaccgctag cgccaccatg tatagaatgc agctcctgtc 1200
ctgcattgcc ctgagcctcg ccctcgtgac aaactccgcc cctaccagcg gatccgtgag 1260
aagcagcagc aggaccccta gcgataagcc tgtggctcac gtcgtcgcta accctcaggc 1320
cgagggccag ctccagtggc tgaatagaag ggccaatgcc ctgctcgcca acggcgtcga 1380
gctgagagac aatcagctcg tggtcccctc cgagggactg tatctgattt actcccaggt 1440
cctgtttaag ggacagggat gccctagcac acacgtcctg ctgacccaca ccattagcag 1500
gatcgctgtg tcctaccaaa ccaaagtgaa tctgctgtcc gctatcaaaa gcccttgcca 1560
aagagaaacc cctgagggag ccgaagccaa accctggtac gaacccattt acctcggcgg 1620
agtgtttcag ctggagaaag gcgatagact cagcgctgag attaacaggc ccgattacct 1680
cgactttgcc gaaagcggac aggtctactt tggcattatc gctctgtaaa tcgattcgta 1740
cgtcgacatc gagtgatggg tggcatccct gtgacccctc cccagtgcct ctcctggccc 1800
tggaagttgc cactccagtg cccaccagcc ttgtcctaat aaaattaagt tgcatcattt 1860
tgtctgacta ggtgtccttc tataatatta tggggtggag gggggtggta tggagcaagg 1920
ggcaagttgg gaagacaacc tgtagggcct gcggggtcta ttgggaacca agctggagtg 1980
cagtggcaca atcttggctc actgcaatct ccgcctcctg ggttcaagcg attctcctgc 2040
ctcagcctcc cgagttgttg ggattccagg catgcatgac caggctcagc taatttttgt 2100 tttttggta gagacggggt ttcaccatat tggccaggct ggtctccaac tcctaatctc 2160

-continued

```
aggtgatcta cccaccttgg cctcccaaat tgctgggatt acaggcgtga accactgctc   2220
ccttccctgt ccttctgatt ttaaaataac tataccagca ggaggacgtc cagacacagc   2280
ataggctacc tggccatgcc caaccggtgg gacatttgag ttgcttgctt ggcactgtcc   2340
tctcatgcgt tgggtccact cagtagatgc ctgttgaatt ggcgcgccgg cctccgcgcc   2400
gggttttggc gcctcccgcg ggcgcccccc tcctcacggc gagcgctgcc acgtcagacg   2460
aagggcgcag cgagcgtcct gatccttccg cccggacgct caggacagcg gcccgctgct   2520
cataagactc ggccttagaa ccccagtatc agcagaagga cattttagga cgggacttgg   2580
gtgactctag ggcactggtt ttctttccag agagcggaac aggcgaggaa aagtagtccc   2640
ttctcggcga ttctgcggag ggatctccgt ggggcggtga acgccgatga ttatataagg   2700
acgcgccggg tgtggcacag ctagttccgt cgcagccggg atttgggtcg cggttcttgt   2760
ttgtggatcg ctgtgatcgt cacttggtga gtagcgggct gctgggctgg gtacgtgcgc   2820
tcggggttgg cgagtgtgtt ttgtgaagtt ttttaggcac cttttgaaat gtaatcattt   2880
gggtcaatat gtaattttca gtgttagact agtaaattgt ccgctaaatt ctggccgttt   2940
ttggcttttt tgttagacga gctagcgccg ccaccatggg ccctaaaaag aagcgtaaag   3000
tcgccccccc gaccgatgtc agcctggggg acgagctcca cttagacggc gaggacgtgg   3060
cgatggcgca tgccgacgcg ctagacgatt tcgatctgga catgttgggg gacggggatt   3120
ccccgggtcc gggatttacc ccccacgact ccgcccccta cggcgctctg gatatggccg   3180
acttcgagtt tgagcagatg tttaccgatg cccttggaat tgacgagtac ggtggggaat   3240
tcgagatgcc tgtggacagg atcctggagg cagagcttgc tgtggaacag aagagtgacc   3300
agggcgttga gggtcctggg ggaaccgggg gtagcggcag cagcccaaat gaccctgtga   3360
ctaacatctg tcaggcagct gacaaacagc tattcacgct tgttgagtgg gcgaagagga   3420
tcccacactt ttcctccttg cctctggatg atcaggtcat attgctgcgg gcaggctgga   3480
atgaactcct cattgcctcc ttttcacacc gatccattga tgttcgagat ggcatcctcc   3540
ttgccacagg tcttcacgtg caccgcaact cagcccattc agcaggagta ggagccatct   3600
ttgatcgggt gctgacagag ctagtgtcca aaatgcgtga catgaggatg gacaagacag   3660
agcttggctg cctgagggca atcattctgt ttaatccaga ggtgaggggt ttgaaatccg   3720
cccaggaagt tgaacttcta cgtgaaaaag tatatgccgc tttggaagaa tatactagaa   3780
caacacatcc cgatgaacca ggaagatttg caaaactttt gcttcgtctg ccttctttac   3840
gttccatagg ccttaagtgt ttggagcatt tgtttttctt tcgccttatt ggagatgttc   3900
caattgatac gttcctgatg gagatgcttg aatcaccttc tgattcataa tctagcctag   3960
ccccctctc cctcccccc ccctaacgtt actggccgaa gccgcttgga ataaggccgg   4020
tgtgcgtttg tctatatgtt attttccacc atattgccgt cttttggcaa tgtgagggcc   4080
cggaaacctg gccctgtctt cttgacgagc attcctaggg gtctttcccc tctcgccaaa   4140
ggaatgcaag gtctgttgaa tgtcgtgaag gaagcagttc ctctggaagc ttcttgaaga   4200
caaacaacgt ctgtagcgac cctttgcagg cagcggaacc ccccacctgg cgacaggtgc   4260
ctctgcggcc aaaagccacg tgtataagat acacctgcaa aggcggcaca accccagtgc   4320
cacgttgtga gttggatagt tgtggaaaga gtcaaatggc tctcctcaag cgtattcaac   4380
aaggggctga aggatgccca gaaggtaccc cattgtatgg gatctgatct ggggcctcgg   4440
tgcacatgct ttacatgtgt ttagtcgagg ttaaaaaacg tctaggcccc ccgaaccacg   4500
gggacgtggt tttcctttga aaaacacgat ctctaggcgc caccatgaag ctactgtctt   4560
```

ctatcgaaca agcatgcgat atttgccgac ttaaaaagct caagtgctcc aaagaaaaac 4620
cgaagtgcgc caagtgtctg aagaacaact gggagtgtcg ctactctccc aaaaccaaaa 4680
ggtctccgct gactagggca catctgacag aagtggaatc aaggctagaa agactggaac 4740
agctatttct actgattttt cctcgagaag accttgacat gattttgaaa atggattctt 4800
tacaggatat aaaagcattg ttaacaggat tatttgtaca agataatgtg aataaagatg 4860
ccgtcacaga tagattggct tcagtggaga ctgatatgcc tctaacattg agacagcata 4920
gaataagtgc gacatcatca tcggaagaga gtagtaacaa aggtcaaaga cagttgactg 4980
tatcgccgga attcccgggg atccggcctg agtgcgtagt acccgagact cagtgcgcca 5040
tgaagcggaa agagaagaaa gcacagaagg agaaggacaa actgcctgtc agcacgacga 5100
cggtggacga ccacatgccg cccattatgc agtgtgaacc tccacctcct gaagcagcaa 5160
ggattcacga agtggtccca aggtttctct ccgacaagct gttggtgaca aaccggcaga 5220
aaaacatccc ccagttgaca gccaaccagc agttccttat cgccaggctc atctggtacc 5280
aggacgggta cgagcagcct tctgatgaag atttgaagag gattacgcag acgtggcagc 5340
aagcggacga tgaaaacgaa gagtcggaca ctcccttccg ccagatcaca gagatgacta 5400
tcctcacggt ccaacttatc gtggagttcg cgaagggatt gccagggttc gccaagatct 5460
cgcagcctga tcaaattacg ctgcttaagg cttgctcaag tgaggtaatg atgctccgag 5520
tcgcgcgacg atacgatgcg gcctcagaca gtattctgtt cgcgaacaac caagcgtaca 5580
ctcgcgacaa ctaccgcaag gctggcatgg ccgaggtcat cgaggatcta ctgcacttct 5640
gccggtgcat gtactctatg gcgttggaca acatccatta cgcgctgctc acggctgtcg 5700
tcatcttttc tgaccggcca gggttggagc agccgcaact ggtggaagag atccagcggt 5760
actacctgaa tacgctccgc atctatatcc tgaaccagct gagcgggtcg gcgcgttcgt 5820
ccgtcatata cggcaagatc ctctcaatcc tctctgagct acgcacgctc ggcatgcaaa 5880
actccaacat gtgcatctcc ctcaagctca agaacagaaa gctgccgcct ttcctcgagg 5940
agatctggga tgtggcggac atgtcgcaca cccaaccgcc gcctatcctc gagtccccca 6000
cgaatctcta ggcggcctct agagcggccg ccaccgcggg gagatccaga catgataaga 6060
tacattgatg agtttggaca aaccacaact agaatgcagt gaaaaaaatg ctttatttgt 6120
gaaatttgtg atgctattgc tttatttgta accattataa gctgcaataa acaagttaac 6180
aacaacaatt gcattcattt tatgtttcag gttcaggggg aggtgtggga ggttttttaa 6240
agcaagtaaa acctctacaa atgtggtatg gctgattatg atccggctgc ctcgcgcgtt 6300
tcggtgatga cggtgaaaac ctctgacaca tgcagctccc ggagacggtc acagcttgtc 6360
tgtaagcgga tgccgggagc agacaagccc gtcagggcgc gtcagcgggt gttggcgggt 6420
gtcggggcgc agccatgagg tcgactctag tccccgcggt ggcagatctg gaaggtgctg 6480
aggtacgatg agacccgcac caggtgcaga ccctgcgagt gtggcggtaa acatattagg 6540
aaccagcctg tgatgctgga tgtgaccgag gagctgaggc ccgatcactt ggtgctggcc 6600
tgcacccgcg ctgagtttgg ctctagcgat gaagatacag attgaggtac tgaaatgtgt 6660
gggcgtggct taagggtggg aaagaatata taaggtgggg gtcttatgta gttttgtatc 6720
tgttttgcag cagccgccgc cgccatgagc accaactcgt ttgatggaag cattgtgagc 6780
tcatatttga caacgcgcat gcccccatgg gccggggtgc gtcagaatgt gatgggctcc 6840
agcattgatg gtcgccccgt cctgcccgca aactctacta ccttgaccta cgagaccgtg 6900

-continued

```
tctggaacgc cgttggagac tgcagcctcc gccgccgctt cagccgctgc agccaccgcc   6960
cgcgggattg tgactgactt tgctttcctg agcccgcttg caagcagtgc agcttcccgt   7020
tcatccgccc gcgatgacaa gttgacggct cttttggcac aattggattc tttgacccgg   7080
gaacttaatg tcgtttctca gcagctgttg gatctgcgcc agcaggtttc tgccctgaag   7140
gcttcctccc ctcccaatgc ggtttaaaac ataaataaaa aaccagactc tgtttggatt   7200
tggatcaagc aagtgtcttg ctgtctttat ttaggggttt tgcgcgcgcg gtaggcccgg   7260
gaccagcggt ctcggtcgtt gagggtcctg tgtatttttt ccaggacgtg gtaaaggtga   7320
ctctggatgt tcagatacat gggcataagc ccgtctctgg ggtggaggta gcaccactgc   7380
agagcttcat gctgcggggt ggtgttgtag atgatccagt cgtagcagga gcgctgggcg   7440
tggtgcctaa aaatgtcttt cagtagcaag ctgattgcca ggggcaggcc cttggtgtaa   7500
gtgtttacaa agcggttaag ctgggatggg tgcatacgtg gggatatgag atgcatcttg   7560
gactgtattt ttaggttggc tatgttccca gccatatccc tccggggatt catgttgtgc   7620
agaaccacca gcacagtgta tccggtgcac ttgggaaatt tgtcatgtag cttagaagga   7680
aatgcgtgga agaacttgga gacgcccttg tgacctccaa gattttccat gcattcgtcc   7740
ataatgatgg caatgggccc acgggcggcg gcctgggcga agatatttct gggatcacta   7800
acgtcatagt tgtgttccag gatgagatcg tcataggcca tttttacaaa gcgcgggcgg   7860
agggtgccag actgcggtat aatggttcca tccggcccag gggcgtagtt accctcacag   7920
atttgcattt cccacgcttt gagttcagat gggggggatca tgtctacctg cggggcgatg   7980
aagaaaacgg tttccggggt aggggagatc agctgggaag aaagcaggtt cctgagcagc   8040
tgcgacttac cgcagccggt gggcccgtaa atcacaccta ttaccggctg caactggtag   8100
ttaagagagc tgcagctgcc gtcatccctg agcagggggg ccacttcgtt aagcatgtcc   8160
ctgactcgca tgttttccct gaccaaatcc gccagaaggc gctcgccgcc cagcgatagc   8220
agttcttgca aggaagcaaa gtttttcaac ggtttgagac cgtccgccgt aggcatgctt   8280
ttgagcgttt gaccaagcag ttccaggcgg tcccacagct cggtcacctg ctctacggca   8340
tctcgatcca gcatatctcc tcgtttcgcg ggttggggcg gctttcgctg tacggcagta   8400
gtcggtgctc gtccagacgg gccagggtca tgtctttcca cgggcgcagg gtcctcgtca   8460
gcgtagtctg ggtcacggtg aaggggtgcg ctccgggctg cgcgctggcc agggtgcgct   8520
tgaggctggt cctgctggtg ctgaagcgct gccggtcttc gccctgcgcg tcggccaggt   8580
agcatttgac catggtgtca tagtccagcc cctccgcggc gtggcccttg gcgcgcagct   8640
tgcccttgga ggaggcgccg cacgaggggc agtgcagact tttgagggcg tagagcttgg   8700
gcgcgagaaa taccgattcc ggggagtagg catccgcgcc gcaggccccg cagacggtct   8760
cgcattccac gagccaggtg agctctggcc gttcggggtc aaaaaccagg tttcccccat   8820
gctttttgat gcgtttctta cctctggttt ccatgagccg gtgtccacgc tcggtgacga   8880
aaaggctgtc cgtgtccccg tatacagact tgagaggcct gtcctcgacc gatgcccttg   8940
agagccttca acccagtcag ctccttccgg tgggcgcggg gcatgactat cgtcgccgca   9000
cttatgactg tcttctttat catgcaactc gtaggacagg tgccggcagc gctctgggtc   9060
attttcggcg aggaccgctt tcgctggagc gcgacgatga tcggcctgtc gcttgcggta   9120
ttcggaatct tgcacgccct cgctcaagcc ttcgtcactg gtcccgccac caaacgtttc   9180
ggcgagaagc aggccattat cgccggcatg gcggccgacg cgctgggcta cgtcttgctg   9240
gcgttcgcga cgcgaggctg gatggccttc cccattatga ttcttctcgc ttccggcggc   9300
```

atcgggatgc ccgcgttgca ggccatgctg tccaggcagg tagatgacga ccatcaggga 9360
cagcttcaag gccagcaaaa ggccaggaac cgtaaaaagg ccgcgttgct ggcgtttttc 9420
cataggctcc gcccccctga cgagcatcac aaaaatcgac gctcaagtca gaggtggcga 9480
aacccgacag gactataaag ataccaggcg tttccccctg gaagctccct cgtgcgctct 9540
cctgttccga ccctgccgct taccggatac ctgtccgcct ttctcccttc gggaagcgtg 9600
gcgctttctc atagctcacg ctgtaggtat ctcagttcgg tgtaggtcgt tcgctccaag 9660
ctgggctgtg tgcacgaacc ccccgttcag cccgaccgct gcgccttatc cggtaactat 9720
cgtcttgagt ccaacccggt aagacacgac ttatcgccac tggcagcagc cactggtaac 9780
aggattagca gagcgaggta tgtaggcggt gctacagagt tcttgaagtg gtggcctaac 9840
tacggctaca ctagaaggac agtatttggt atctgcgctc tgctgaagcc agttaccttc 9900
ggaaaaagag ttggtagctc ttgatccggc aaacaaacca ccgctggtag cggtggtttt 9960
tttgtttgca agcagcagat tacgcgcaga aaaaaaggat ctcaagaaga tcctttgatc 10020
ttttctacgg ggtctgacgc tcagtggaac gaaaactcac gttaagggat tttggtcatg 10080
agattatcaa aaaggatctt cacctagatc cttttaaatt aaaaatgaag ttttaaatca 10140
atctaaagta tatatgagta aacttggtct gacagttacc aatgcttaat cagtgaggca 10200
cctatctcag cgatctgtct atttcgttca tccatagttg cctgactccc cgtcgtgtag 10260
ataactacga tacgggaggg cttaccatct ggccccagtg ctgcaatgat accgcgagac 10320
ccacgctcac cggctccaga tttatcagca ataaaccagc cagccggaag ggccgagcgc 10380
agaagtggtc ctgcaacttt atccgcctcc atccagtcta ttaattgttg ccgggaagct 10440
agagtaagta gttcgccagt taatagtttg cgcaacgttg ttgccattgc tgcaggcatc 10500
gtggtgtcac gctcgtcgtt tggtatggct tcattcagct ccggttccca acgatcaagg 10560
cgagttacat gatcccccat gttgtgcaaa aaagcggtta gctccttcgg tcctccgatc 10620
gttgtcagaa gtaagttggc cgcagtgtta tcactcatgg ttatggcagc actgcataat 10680
tctcttactg tcatgccatc cgtaagatgc ttttctgtga ctggtgagta ctcaaccaag 10740
tcattctgag aatagtgtat gcggcgaccg agttgctctt gcccggcgtc aacacgggat 10800
aataccgcgc cacatagcag aactttaaaa gtgctcatca ttggaaaacg ttcttcgggg 10860
cgaaaactct caaggatctt accgctgttg agatccagtt cgatgtaacc cactcgtgca 10920
cccaactgat cttcagcatc ttttactttc accagcgttt ctgggtgagc aaaaacagga 10980
aggcaaaatg ccgcaaaaaa gggaataagg gcgacacgga aatgttgaat actcatactc 11040
ttcctttttc aatattattg aagcatttat cagggttatt gtctcatgag cggatacata 11100
tttgaatgta tttagaaaaa 11120

<210> SEQ ID NO 56
<211> LENGTH: 11286
<212> TYPE: DNA
<213> ORGANISM: Artificial Sequence
<220> FEATURE:
<223> OTHER INFORMATION: PolyDNA_from_VVN-43327 5U2

<400> SEQUENCE: 56
taaacaaata ggggttccgc gcacatttcc ccgaaaagtg ccacctgacg tctaagaaac 60
cattattatc atgacattaa cctataaaaa taggcgtatc acgaggccct ttcgtcttca 120
attaattaag ctagcatcat caataatata ccttattttg gattgaagcc aatatgataa 180

-continued

```
tgagggggtg gagtttgtga cgtggcgcgg ggcgtgggaa cggggcgggt gacgtagtag    240
tgtggcggaa gtgtgatgtt gcaagtgtgg cggaacacat gtaagcgacg gatgtggcaa    300
aagtgacgtt tttggtgtgc gccggtgtac acaggaagtg acaattttcg cgcggtttta    360
ggcggatgtt gtagtaaatt tgggcgtaac cgagtaagat ttggccattt tcgcgggaaa    420
actgaataag aggaagtgaa atctgaataa ttttgtgtta ctcatagcgc gtaatatttg    480
tctagggaga tccggtaccg gcgcgcgcgc cgtttggccg cctcgagtct agagatccgg    540
tgagtattag gcgcgcacca ggtgccgcaa taaaatatct ttattttcat tacatctgtg    600
tgttggtttt ttgtgtgaat cgatagtact aacatacgct ctccatcaaa acaaaacgaa    660
acaaaacaaa ctagcaaaat aggctgtccc cagtgcaagt gcaggtgcca gaacatttct    720
ctatcgataa tgcaggtcgg agtactgtcc tccgagcgga gtactgtcct ccgagcggag    780
tactgtcctc cgagcggagt actgtcctcc gagcggagta ctgtcctccg agcggagtac    840
tgtcctccga gcggagactc ttcgaaggaa gaggggcggg gtcgatcgac cccgcccctc    900
ttccttcgaa ggaagagggg cggggtcgaa gacctagagg gtatataatg ggtgccttag    960
ctggtgtgtg agctcatctt cctgtagatc acgcgtcgaa gaaggtgagt aatcttaaca   1020
tgctcttttt tttttttttt gctaatccct tttgtgtgct gatgttagga tgacatttac   1080
aacaaatgtt tgttcctgac aggaaaaacc ttgctgggta ccttcgttgc cggacacttc   1140
ttgtcctcta ctttggaaaa aaggaattga gagccgctag cgccaccatg agcactgaaa   1200
gcatgatccg ggacgtggag ctggccgagg aagccctccc caagaaaacc ggcggccccc   1260
aggggagcag aagatgtttg ttcctgagcc tgttttcctt cctgatcgtg gcaggcgcta   1320
ccaccctgtt ctgcctgctg cactttggag tgatcggccc ccagagggag gagttcccca   1380
gggacctctc tctaatcagc cctctggccc aggcaggatc cgtcagatca tcttctcgaa   1440
ccccgagtga caagcctgta gcccatgttg tagcaaaccc tcaagccgag ggccagctcc   1500
agtggctgaa ccgccgggcc aatgccctgc tcgccaacgg cgtcgagctg agagataacc   1560
agctggtggt gccatcagag ggcctgtacc tcatctactc ccaggtcctg ttcaagggcc   1620
aaggctgccc ctccacccat gtgctcctca cccacaccat cagccgcatc gccgtgagct   1680
accagaccaa ggtcaacctc ctctctgcca tcaagagccc ctgccagagg gagaccccag   1740
agggggccga ggccaagccc tggtatgagc ccatctacct cggcggggtg ttccagctgg   1800
agaagggtga ccgactcagc gctgagatca atagacccga ctatctcgac tttgccgaga   1860
gcggccaggt gtactttggg atcattgccc tgtgaatcga ttcgtacgtc gacatcgagt   1920
gatgggtggc atccctgtga cccctcccca gtgcctctcc tggccctgga agttgccact   1980
ccagtgccca ccagccttgt cctaataaaa ttaagttgca tcattttgtc tgactaggtg   2040
tccttctata atattatggg gtggaggggg gtggtatgga gcaaggggca agttgggaag   2100
acaacctgta gggcctgcgg ggtctattgg gaaccaagct ggagtgcagt ggcacaatct   2160
tggctcactg caatctccgc ctcctgggtt caagcgattc tcctgcctca gcctcccgag   2220
ttgttgggat tccaggcatg catgaccagg ctcagctaat ttttgttttt ttggtagaga   2280
cggggtttca ccatattggc caggctggtc tccaactcct aatctcaggt gatctaccca   2340
ccttggcctc ccaaattgct gggattacag gcgtgaacca ctgctccctt ccctgtcctt   2400
ctgattttaa aataactata ccagcaggag gacgtccaga cacagcatag gctacctggc   2460
catgcccaac cggtgggaca tttgagttgc ttgcttggca ctgtcctctc atgcgttggg   2520
tccactcagt agatgcctgt tgaattggcg cgccggcctc cgcgccgggt tttggcgcct   2580
```

cccgcgggcg cccccctcct cacggcgagc gctgccacgt cagacgaagg gcgcagcgag 2640
cgtcctgatc cttccgcccg gacgctcagg acagcggccc gctgctcata agactcggcc 2700
ttagaacccc agtatcagca gaaggacatt ttaggacggg acttgggtga ctctagggca 2760
ctggttttct ttccagagag cggaacaggc gaggaaaagt agtcccttct cggcgattct 2820
gcggagggat ctccgtgggg cggtgaacgc cgatgattat ataaggacgc gccgggtgtg 2880
gcacagctag ttccgtcgca gccgggattt gggtcgcggt tcttgtttgt ggatcgctgt 2940
gatcgtcact tggtgagtag cgggctgctg ggctgggtac gtgcgctcgg ggttggcgag 3000
tgtgttttgt gaagtttttt aggcaccttt tgaaatgtaa tcatttgggt caatatgtaa 3060
ttttcagtgt tagactagta aattgtccgc taaattctgg ccgtttttgg ctttttttgtt 3120
agacgagcta gcgccgccac catgggccct aaaaagaagc gtaaagtcgc ccccccgacc 3180
gatgtcagcc tgggggacga gctccactta gacggcgagg acgtggcgat ggcgcatgcc 3240
gacgcgctag acgatttcga tctggacatg ttgggggacg gggattcccc gggtccggga 3300
tttacccccc acgactccgc cccctacggc gctctggata tggccgactt cgagtttgag 3360
cagatgttta ccgatgccct tggaattgac gagtacggtg gggaattcga gatgcctgtg 3420
gacaggatcc tggaggcaga gcttgctgtg gaacagaaga gtgaccaggg cgttgagggt 3480
cctgggggaa ccgggggtag cggcagcagc ccaaatgacc ctgtgactaa catctgtcag 3540
gcagctgaca aacagctatt cacgcttgtt gagtgggcga agaggatccc acacttttcc 3600
tccttgcctc tggatgatca ggtcatattg ctgcgggcag gctggaatga actcctcatt 3660
gcctcctttt cacaccgatc cattgatgtt cgagatggca tcctccttgc cacaggtctt 3720
cacgtgcacc gcaactcagc ccattcagca ggagtaggag ccatctttga tcgggtgctg 3780
acagagctag tgtccaaaat gcgtgacatg aggatggaca agacagagct tggctgcctg 3840
agggcaatca ttctgtttaa tccagaggtg aggggtttga aatccgccca ggaagttgaa 3900
cttctacgtg aaaaagtata tgccgctttg gaagaatata ctagaacaac acatcccgat 3960
gaaccaggaa gatttgcaaa acttttgctt cgtctgcctt ctttacgttc cataggcctt 4020
aagtgtttgg agcatttgtt tttctttcgc cttattggag atgttccaat tgatacgttc 4080
ctgatggaga tgcttgaatc accttctgat tcataatcta gcctagcccc cctctccctc 4140
cccccccct aacgttactg gccgaagccg cttggaataa ggccggtgtg cgtttgtcta 4200
tatgttattt tccaccatat tgccgtcttt tggcaatgtg agggcccgga aacctggccc 4260
tgtcttcttg acgagcattc ctaggggtct ttcccctctc gccaaaggaa tgcaaggtct 4320
gttgaatgtc gtgaaggaag cagttcctct ggaagcttct tgaagacaaa caacgtctgt 4380
agcgaccctt tgcaggcagc ggaacccccc acctggcgac aggtgcctct gcggccaaaa 4440
gccacgtgta taagatacac ctgcaaaggc ggcacaaccc cagtgccacg ttgtgagttg 4500
gatagttgtg gaaagagtca aatggctctc ctcaagcgta ttcaacaagg ggctgaagga 4560
tgcccagaag gtaccccatt gtatgggatc tgatctgggg cctcggtgca catgctttac 4620
atgtgtttag tcgaggttaa aaaacgtcta ggccccccga accacgggga cgtggttttc 4680
ctttgaaaaa cacgatctct aggcgccacc atgaagctac tgtcttctat cgaacaagca 4740
tgcgatattt gccgacttaa aaagctcaag tgctccaaag aaaaaccgaa gtgcgccaag 4800
tgtctgaaga acaactggga gtgtcgctac tctcccaaaa ccaaaaggtc tccgctgact 4860
agggcacatc tgacagaagt ggaatcaagg ctagaaagac tggaacagct atttctactg 4920

-continued atttttcctc gagaagacct tgacatgatt ttgaaaatgg attctttaca ggatataaaa 4980
gcattgttaa caggattatt tgtacaagat aatgtgaata aagatgccgt cacagataga 5040
ttggcttcag tggagactga tatgcctcta acattgagac agcatagaat aagtgcgaca 5100
tcatcatcgg aagagagtag taacaaaggt caaagacagt tgactgtatc gccggaattc 5160
ccggggatcc ggcctgagtg cgtagtaccc gagactcagt gcgccatgaa gcggaaagag 5220
aagaaagcac agaaggagaa ggacaaactg cctgtcagca cgacgacggt ggacgaccac 5280
atgccgccca ttatgcagtg tgaacctcca cctcctgaag cagcaaggat tcacgaagtg 5340
gtcccaaggt ttctctccga caagctgttg gtgacaaacc ggcagaaaaa catcccccag 5400
ttgacagcca accagcagtt ccttatcgcc aggctcatct ggtaccagga cgggtacgag 5460
cagccttctg atgaagattt gaagaggatt acgcagacgt ggcagcaagc ggacgatgaa 5520
aacgaagagt cggacactcc cttccgccag atcacagaga tgactatcct cacggtccaa 5580
cttatcgtgg agttcgcgaa gggattgcca gggttcgcca agatctcgca gcctgatcaa 5640
attacgctgc ttaaggcttg ctcaagtgag gtaatgatgc tccgagtcgc gcgacgatac 5700
gatgcggcct cagacagtat tctgttcgcg aacaaccaag cgtacactcg cgacaactac 5760
cgcaaggctg gcatggccga ggtcatcgag gatctactgc acttctgccg gtgcatgtac 5820
tctatggcgt tggacaacat ccattacgcg ctgctcacgg ctgtcgtcat cttttctgac 5880
cggccagggt tggagcagcc gcaactggtg gaagagatcc agcggtacta cctgaatacg 5940
ctccgcatct atatcctgaa ccagctgagc gggtcggcgc gttcgtccgt catatacggc 6000
aagatcctct caatcctctc tgagctacgc acgctcggca tgcaaaactc caacatgtgc 6060
atctccctca agctcaagaa cagaaagctg ccgcctttcc tcgaggagat ctgggatgtg 6120
gcggacatgt cgcacaccca accgccgcct atcctcgagt cccccacgaa tctctaggcg 6180
gcctctagag cggccgccac cgcggggaga tccagacatg ataagataca ttgatgagtt 6240
tggacaaacc acaactagaa tgcagtgaaa aaaatgcttt atttgtgaaa tttgtgatgc 6300
tattgcttta tttgtaacca ttataagctg caataaacaa gttaacaaca acaattgcat 6360
tcattttatg tttcaggttc agggggaggt gtgggaggtt ttttaaagca agtaaaacct 6420
ctacaaatgt ggtatggctg attatgatcc ggctgcctcg cgcgtttcgg tgatgacggt 6480
gaaaacctct gacacatgca gctcccggag acggtcacag cttgtctgta agcggatgcc 6540
gggagcagac aagcccgtca gggcgcgtca gcgggtgttg gcgggtgtcg gggcgcagcc 6600
atgaggtcga ctctagtccc cgcggtggca gatctggaag gtgctgaggt acgatgagac 6660
ccgcaccagg tgcagaccct gcgagtgtgg cggtaaacat attaggaacc agcctgtgat 6720
gctggatgtg accgaggagc tgaggcccga tcacttggtg ctggcctgca cccgcgctga 6780
gtttggctct agcgatgaag atacagattg aggtactgaa atgtgtgggc gtggcttaag 6840
ggtgggaaag aatatataag gtgggggtct tatgtagttt tgtatctgtt ttgcagcagc 6900
cgccgccgcc atgagcacca actcgtttga tggaagcatt gtgagctcat atttgacaac 6960
gcgcatgccc ccatgggccg gggtgcgtca gaatgtgatg ggctccagca ttgatggtcg 7020
ccccgtcctg cccgcaaact ctactacctt gacctacgag accgtgtctg gaacgccgtt 7080
ggagactgca gcctccgccg ccgcttcagc cgctgcagcc accgcccgcg ggattgtgac 7140
tgactttgct ttcctgagcc cgcttgcaag cagtgcagct tcccgttcat ccgcccgcga 7200
tgacaagttg acggctcttt tggcacaatt ggattctttg acccgggaac ttaatgtcgt 7260
ttctcagcag ctgttggatc tgcgccagca ggtttctgcc ctgaaggctt cctcccctcc 7320

```
caatgcggtt taaaacataa ataaaaaacc agactctgtt tggatttgga tcaagcaagt   7380
gtcttgctgt ctttatttag ggttttgcg cgcgcggtag gcccgggacc agcggtctcg   7440
gtcgttgagg gtcctgtgta ttttttccag gacgtggtaa aggtgactct ggatgttcag   7500
atacatgggc ataagcccgt ctctggggtg gaggtagcac cactgcagag cttcatgctg   7560
cggggtggtg ttgtagatga tccagtcgta gcaggagcgc tgggcgtggt gcctaaaaat   7620
gtctttcagt agcaagctga ttgccagggg caggcccttg gtgtaagtgt ttacaaagcg   7680
gttaagctgg gatgggtgca tacgtgggga tatgagatgc atcttggact gtatttttag   7740
gttggctatg ttcccagcca tatccctccg gggattcatg ttgtgcagaa ccaccagcac   7800
agtgtatccg gtgcacttgg gaaatttgtc atgtagctta gaaggaaatg cgtggaagaa   7860
cttggagacg cccttgtgac ctccaagatt ttccatgcat tcgtccataa tgatggcaat   7920
gggcccacgg gcggcggcct gggcgaagat atttctggga tcactaacgt catagttgtg   7980
ttccaggatg agatcgtcat aggccatttt tacaaagcgc gggcggaggg tgccagactg   8040
cggtataatg gttccatccg gcccaggggc gtagttaccc tcacagattt gcatttccca   8100
cgctttgagt tcagatgggg ggatcatgtc tacctgcggg gcgatgaaga aaacggtttc   8160
cggggtaggg gagatcagct gggaagaaag caggttcctg agcagctgcg acttaccgca   8220
gccggtgggc ccgtaaatca cacctattac cggctgcaac tggtagttaa gagagctgca   8280
gctgccgtca tccctgagca ggggggccac ttcgttaagc atgtccctga ctcgcatgtt   8340
ttccctgacc aaatccgcca gaaggcgctc gccgcccagc gatagcagtt cttgcaagga   8400
agcaaagttt ttcaacggtt tgagaccgtc cgccgtaggc atgcttttga gcgtttgacc   8460
aagcagttcc aggcggtccc acagctcggt cacctgctct acggcatctc gatccagcat   8520
atctcctcgt ttcgcgggtt ggggcggctt tcgctgtacg gcagtagtcg gtgctcgtcc   8580
agacgggcca gggtcatgtc tttccacggg cgcagggtcc tcgtcagcgt agtctgggtc   8640
acggtgaagg ggtgcgctcc gggctgcgcg ctggccaggg tgcgcttgag gctggtcctg   8700
ctggtgctga agcgctgccg gtcttcgccc tgcgcgtcgg ccaggtagca tttgaccatg   8760
gtgtcatagt ccagcccctc cgcggcgtgg cccttggcgc gcagcttgcc cttggaggag   8820
gcgccgcacg aggggcagtg cagacttttg agggcgtaga gcttgggcgc gagaaatacc   8880
gattccgggg agtaggcatc cgcgccgcag gccccgcaga cggtctcgca ttccacgagc   8940
caggtgagct ctggccgttc ggggtcaaaa accaggtttc ccccatgctt tttgatgcgt   9000
ttcttacctc tggtttccat gagccggtgt ccacgctcgg tgacgaaaag gctgtccgtg   9060
tccccgtata cagacttgag aggcctgtcc tcgaccgatg cccttgagag ccttcaaccc   9120
agtcagctcc ttccggtggg cgcggggcat gactatcgtc gccgcactta tgactgtctt   9180
ctttatcatg caactcgtag gacaggtgcc ggcagcgctc tgggtcattt tcggcgagga   9240
ccgctttcgc tggagcgcga cgatgatcgg cctgtcgctt gcggtattcg gaatcttgca   9300
cgccctcgct caagccttcg tcactggtcc cgccaccaaa cgtttcggcg agaagcaggc   9360
cattatcgcc ggcatggcgg ccgacgcgct gggctacgtc ttgctggcgt tcgcgacgcg   9420
aggctggatg gccttcccca ttatgattct tctcgcttcc ggcggcatcg ggatgcccgc   9480
gttgcaggcc atgctgtcca ggcaggtaga tgacgaccat cagggacagc ttcaaggcca   9540
gcaaaaggcc aggaaccgta aaaaggccgc gttgctggcg tttttccata ggctccgccc   9600
ccctgacgag catcacaaaa atcgacgctc aagtcagagg tggcgaaacc cgacaggact   9660
```

ataaagatac caggcgtttc cccctggaag ctccctcgtg cgctctcctg ttccgaccct 9720
gccgcttacc ggatacctgt ccgcctttct cccttcggga agcgtggcgc tttctcatag 9780
ctcacgctgt aggtatctca gttcggtgta ggtcgttcgc tccaagctgg gctgtgtgca 9840
cgaacccccc gttcagcccg accgctgcgc cttatccggt aactatcgtc ttgagtccaa 9900
cccggtaaga cacgacttat cgccactggc agcagccact ggtaacagga ttagcagagc 9960
gaggtatgta ggcggtgcta cagagttctt gaagtggtgg cctaactacg gctacactag 10020
aaggacagta tttggtatct gcgctctgct gaagccagtt accttcggaa aaagagttgg 10080
tagctcttga tccggcaaac aaaccaccgc tggtagcggt ggtttttttg tttgcaagca 10140
gcagattacg cgcagaaaaa aaggatctca agaagatcct ttgatctttt ctacggggtc 10200
tgacgctcag tggaacgaaa actcacgtta agggattttg gtcatgagat tatcaaaaag 10260
gatcttcacc tagatccttt taaattaaaa atgaagtttt aaatcaatct aaagtatata 10320
tgagtaaact tggtctgaca gttaccaatg cttaatcagt gaggcaccta tctcagcgat 10380
ctgtctattt cgttcatcca tagttgcctg actccccgtc gtgtagataa ctacgatacg 10440
ggagggctta ccatctggcc ccagtgctgc aatgataccg cgagacccac gctcaccggc 10500
tccagattta tcagcaataa accagccagc cggaagggcc gagcgcagaa gtggtcctgc 10560
aactttatcc gcctccatcc agtctattaa ttgttgccgg gaagctagag taagtagttc 10620
gccagttaat agtttgcgca acgttgttgc cattgctgca ggcatcgtgg tgtcacgctc 10680
gtcgtttggt atggcttcat tcagctccgg ttcccaacga tcaaggcgag ttacatgatc 10740
ccccatgttg tgcaaaaaag cggttagctc cttcggtcct ccgatcgttg tcagaagtaa 10800
gttggccgca gtgttatcac tcatggttat ggcagcactg cataattctc ttactgtcat 10860
gccatccgta agatgctttt ctgtgactgg tgagtactca accaagtcat tctgagaata 10920
gtgtatgcgg cgaccgagtt gctcttgccc ggcgtcaaca cgggataata ccgcgccaca 10980
tagcagaact ttaaaagtgc tcatcattgg aaaacgttct tcggggcgaa aactctcaag 11040
gatcttaccg ctgttgagat ccagttcgat gtaacccact cgtgcaccca actgatcttc 11100
agcatctttt actttcacca gcgtttctgg gtgagcaaaa acaggaaggc aaaatgccgc 11160
aaaaaaggga ataagggcga cacggaaatg ttgaatactc atactcttcc tttttcaata 11220
ttattgaagc atttatcagg gttattgtct catgagcgga tacatatttg aatgtattta 11280
gaaaaa 11286

<210> SEQ ID NO 57
<211> LENGTH: 11286
<212> TYPE: DNA
<213> ORGANISM: Artificial Sequence
<220> FEATURE:
<223> OTHER INFORMATION: PolyDNA_from_VVN-43328

<400> SEQUENCE: 57
taaacaaata ggggttccgc gcacatttcc ccgaaaagtg ccacctgacg tctaagaaac 60
cattattatc atgacattaa cctataaaaa taggcgtatc acgaggccct ttcgtcttca 120
attaattaag ctagcatcat caataatata ccttattttg gattgaagcc aatatgataa 180
tgagggggtg gagtttgtga cgtggcgcgg ggcgtgggaa cggggcgggt gacgtagtag 240
tgtggcggaa gtgtgatgtt gcaagtgtgg cggaacacat gtaagcgacg gatgtggcaa 300
aagtgacgtt tttggtgtgc gccggtgtac acaggaagtg acaattttcg cgcggtttta 360
ggcggatgtt gtagtaaatt tgggcgtaac cgagtaagat ttggccattt tcgcgggaaa 420

-continued

```
actgaataag aggaagtgaa atctgaataa ttttgtgtta ctcatagcgc gtaatatttg    480
tctagggaga tccggtaccg gcgcgcgcgc cgtttggccg cctcgagtct agagatccgg    540
tgagtattag gcgcgcacca ggtgccgcaa taaaatatct ttattttcat tacatctgtg    600
tgttggtttt ttgtgtgaat cgatagtact aacatacgct ctccatcaaa acaaaacgaa    660
acaaaacaaa ctagcaaaat aggctgtccc cagtgcaagt gcaggtgcca gaacatttct    720
ctatcgataa tgcaggtcgg agtactgtcc tccgagcgga gtactgtcct ccgagcggag    780
tactgtcctc cgagcggagt actgtcctcc gagcggagta ctgtcctccg agcggagtac    840
tgtcctccga gcggagactc ttcgaaggaa gaggggcggg gtcgatcgac cccgcccctc    900
ttccttcgaa ggaagagggg cggggtcgaa gacctagagg gtatataatg ggtgccttag    960
ctggtgtgtg agctcatctt cctgtagatc acgcgtcgaa gaaggtgagt aatcttaaca   1020
tgctcttttt tttttttttt gctaatccct tttgtgtgct gatgttagga tgacatttac   1080
aacaaatgtt tgttcctgac aggaaaaacc ttgctgggta ccttcgttgc cggacacttc   1140
ttgtcctcta ctttggaaaa aaggaattga gagccgctag cgccaccatg tccaccgaaa   1200
gcatgatccg ggacgtggag ctggccgagg aagccctgcc taagaaaacc ggaggccctc   1260
agggaagcag gagatgtctg tttctgtccc tgtttagctt tctgattgtg gctggcgcta   1320
ccacactgtt ttgcctcctg catttcggag tgattggccc tcagagggag gagttcccta   1380
gagacctgtc cctgattagc cctctggctc aggctggatc cgtgagaagc agcagcagga   1440
cccctagcga taagcctgtg gctcacgtcg tcgctaaccc tcaggccgag ggccagctcc   1500
agtggctgaa tagaagggcc aatgccctgc tcgccaacgg cgtcgagctg agagacaatc   1560
agctcgtggt cccctccgag ggactgtatc tgatttactc ccaggtcctg tttaagggac   1620
agggatgccc tagcacacac gtcctgctga cccacaccat tagcaggatc gctgtgtcct   1680
accaaaccaa agtgaatctg ctgtccgcta tcaaaagccc ttgccaaaga gaaacccctg   1740
agggagccga agccaaaccc tggtacgaac ccatttacct cggcggagtg tttcagctgg   1800
agaaaggcga tagactcagc gctgagatta acaggcccga ttacctcgac tttgccgaaa   1860
gcggacaggt ctactttggc attatcgctc tgtaaatcga ttcgtacgtc gacatcgagt   1920
gatgggtggc atccctgtga cccctcccca gtgcctctcc tggccctgga agttgccact   1980
ccagtgccca ccagccttgt cctaataaaa ttaagttgca tcattttgtc tgactaggtg   2040
tccttctata atattatggg gtggaggggg gtggtatgga gcaaggggca agttgggaag   2100
acaacctgta gggcctgcgg ggtctattgg gaaccaagct ggagtgcagt ggcacaatct   2160
tggctcactg caatctccgc ctcctgggtt caagcgattc tcctgcctca gcctcccgag   2220
ttgttgggat tccaggcatg catgaccagg ctcagctaat ttttgttttt ttggtagaga   2280
cggggtttca ccatattggc caggctggtc tccaactcct aatctcaggt gatctaccca   2340
ccttggcctc ccaaattgct gggattacag gcgtgaacca ctgctccctt ccctgtcctt   2400
ctgattttaa aataactata ccagcaggag gacgtccaga cacagcatag gctacctggc   2460
catgcccaac cggtgggaca tttgagttgc ttgcttggca ctgtcctctc atgcgttggg   2520
tccactcagt agatgcctgt tgaattggcg cgccggcctc cgcgccgggt tttggcgcct   2580
cccgcgggcg ccccccctcct cacggcgagc gctgccacgt cagacgaagg gcgcagcgag   2640
cgtcctgatc cttccgcccg gacgctcagg acagcggccc gctgctcata agactcggcc   2700
ttagaacccc agtatcagca gaaggacatt ttaggacggg acttgggtga ctctagggca   2760
```

-continued

```
ctggttttct ttccagagag cggaacaggc gaggaaaagt agtcccttct cggcgattct   2820
gcggagggat ctccgtgggg cggtgaacgc cgatgattat ataaggacgc gccgggtgtg   2880
gcacagctag ttccgtcgca gccgggattt gggtcgcggt tcttgtttgt ggatcgctgt   2940
gatcgtcact tggtgagtag cgggctgctg ggctgggtac gtgcgctcgg ggttggcgag   3000
tgtgttttgt gaagtttttt aggcaccttt tgaaatgtaa tcatttgggt caatatgtaa   3060
ttttcagtgt tagactagta aattgtccgc taaattctgg ccgtttttgg cttttttgtt   3120
agacgagcta gcgccgccac catgggccct aaaaagaagc gtaaagtcgc ccccccgacc   3180
gatgtcagcc tgggggacga gctccactta gacggcgagg acgtggcgat ggcgcatgcc   3240
gacgcgctag acgatttcga tctggacatg ttgggggacg gggattcccc gggtccggga   3300
tttacccccc acgactccgc cccctacggc gctctggata tggccgactt cgagtttgag   3360
cagatgttta ccgatgccct tggaattgac gagtacggtg gggaattcga gatgcctgtg   3420
gacaggatcc tggaggcaga gcttgctgtg gaacagaaga gtgaccaggg cgttgagggt   3480
cctgggggaa ccgggggtag cggcagcagc ccaaatgacc ctgtgactaa catctgtcag   3540
gcagctgaca aacagctatt cacgcttgtt gagtgggcga agaggatccc acacttttcc   3600
tccttgcctc tggatgatca ggtcatattg ctgcgggcag gctggaatga actcctcatt   3660
gcctcctttt cacaccgatc cattgatgtt cgagatggca tcctccttgc cacaggtctt   3720
cacgtgcacc gcaactcagc ccattcagca ggagtaggag ccatctttga tcgggtgctg   3780
acagagctag tgtccaaaat gcgtgacatg aggatggaca agacagagct tggctgcctg   3840
agggcaatca ttctgtttaa tccagaggtg aggggtttga aatccgccca ggaagttgaa   3900
cttctacgtg aaaaagtata tgccgctttg gaagaatata ctagaacaac acatcccgat   3960
gaaccaggaa gatttgcaaa acttttgctt cgtctgcctt ctttacgttc cataggcctt   4020
aagtgtttgg agcatttgtt tttctttcgc cttattggag atgttccaat tgatacgttc   4080
ctgatggaga tgcttgaatc accttctgat tcataatcta gcctagcccc cctctccctc   4140
cccccccct aacgttactg gccgaagccg cttggaataa ggccggtgtg cgtttgtcta   4200
tatgttattt tccaccatat tgccgtcttt tggcaatgtg agggcccgga aacctggccc   4260
tgtcttcttg acgagcattc ctaggggtct ttcccctctc gccaaaggaa tgcaaggtct   4320
gttgaatgtc gtgaaggaag cagttcctct ggaagcttct tgaagacaaa caacgtctgt   4380
agcgaccctt tgcaggcagc ggaacccccc acctggcgac aggtgcctct gcggccaaaa   4440
gccacgtgta taagatacac ctgcaaaggc ggcacaaccc cagtgccacg ttgtgagttg   4500
gatagttgtg gaaagagtca aatggctctc ctcaagcgta ttcaacaagg ggctgaagga   4560
tgcccagaag gtaccccatt gtatgggatc tgatctgggg cctcggtgca catgctttac   4620
atgtgtttag tcgaggttaa aaaacgtcta ggccccccga accacgggga cgtggttttc   4680
ctttgaaaaa cacgatctct aggcgccacc atgaagctac tgtcttctat cgaacaagca   4740
tgcgatattt gccgacttaa aaagctcaag tgctccaaag aaaaaccgaa gtgcgccaag   4800
tgtctgaaga acaactggga gtgtcgctac tctcccaaaa ccaaaaggtc tccgctgact   4860
agggcacatc tgacagaagt ggaatcaagg ctagaaagac tggaacagct atttctactg   4920
atttttcctc gagaagacct tgacatgatt ttgaaaatgg attctttaca ggatataaaa   4980
gcattgttaa caggattatt tgtacaagat aatgtgaata aagatgccgt cacagataga   5040
ttggcttcag tggagactga tatgcctcta acattgagac agcatagaat aagtgcgaca   5100
tcatcatcgg aagagagtag taacaaaggt caaagacagt tgactgtatc gccggaattc   5160
```

-continued

```
ccggggatcc ggcctgagtg cgtagtaccc gagactcagt gcgccatgaa gcggaaagag   5220
aagaaagcac agaaggagaa ggacaaactg cctgtcagca cgacgacggt ggacgaccac   5280
atgccgccca ttatgcagtg tgaacctcca cctcctgaag cagcaaggat tcacgaagtg   5340
gtcccaaggt ttctctccga caagctgttg gtgacaaacc ggcagaaaaa catcccccag   5400
ttgacagcca accagcagtt ccttatcgcc aggctcatct ggtaccagga cgggtacgag   5460
cagccttctg atgaagattt gaagaggatt acgcagacgt ggcagcaagc ggacgatgaa   5520
aacgaagagt cggacactcc cttccgccag atcacagaga tgactatcct cacggtccaa   5580
cttatcgtgg agttcgcgaa gggattgcca gggttcgcca agatctcgca gcctgatcaa   5640
attacgctgc ttaaggcttg ctcaagtgag gtaatgatgc tccgagtcgc gcgacgatac   5700
gatgcggcct cagacagtat tctgttcgcg aacaaccaag cgtacactcg cgacaactac   5760
cgcaaggctg gcatggccga ggtcatcgag gatctactgc acttctgccg gtgcatgtac   5820
tctatggcgt tggacaacat ccattacgcg ctgctcacgg ctgtcgtcat cttttctgac   5880
cggccagggt tggagcagcc gcaactggtg gaagagatcc agcggtacta cctgaatacg   5940
ctccgcatct atatcctgaa ccagctgagc gggtcggcgc gttcgtccgt catatacggc   6000
aagatcctct caatcctctc tgagctacgc acgctcggca tgcaaaactc caacatgtgc   6060
atctccctca agctcaagaa cagaaagctg ccgcctttcc tcgaggagat ctgggatgtg   6120
gcggacatgt cgcacaccca accgccgcct atcctcgagt cccccacgaa tctctaggcg   6180
gcctctagag cggccgccac cgcggggaga tccagacatg ataagataca ttgatgagtt   6240
tggacaaacc acaactagaa tgcagtgaaa aaaatgcttt atttgtgaaa tttgtgatgc   6300
tattgcttta tttgtaacca ttataagctg caataaacaa gttaacaaca acaattgcat   6360
tcattttatg tttcaggttc agggggaggt gtgggaggtt ttttaaagca agtaaaacct   6420
ctacaaatgt ggtatggctg attatgatcc ggctgcctcg cgcgtttcgg tgatgacggt   6480
gaaaacctct gacacatgca gctcccggag acggtcacag cttgtctgta agcggatgcc   6540
gggagcagac aagcccgtca gggcgcgtca gcgggtgttg gcgggtgtcg gggcgcagcc   6600
atgaggtcga ctctagtccc cgcggtggca gatctggaag gtgctgaggt acgatgagac   6660
ccgcaccagg tgcagaccct gcgagtgtgg cggtaaacat attaggaacc agcctgtgat   6720
gctggatgtg accgaggagc tgaggcccga tcacttggtg ctggcctgca cccgcgctga   6780
gtttggctct agcgatgaag atacagattg aggtactgaa atgtgtgggc gtggcttaag   6840
ggtgggaaag aatatataag gtgggggtct tatgtagttt tgtatctgtt ttgcagcagc   6900
cgccgccgcc atgagcacca actcgtttga tggaagcatt gtgagctcat atttgacaac   6960
gcgcatgccc ccatgggccg gggtgcgtca gaatgtgatg ggctccagca ttgatggtcg   7020
ccccgtcctg cccgcaaact ctactacctt gacctacgag accgtgtctg gaacgccgtt   7080
ggagactgca gcctccgccg ccgcttcagc cgctgcagcc accgcccgcg ggattgtgac   7140
tgactttgct ttcctgagcc cgcttgcaag cagtgcagct tcccgttcat ccgcccgcga   7200
tgacaagttg acggctcttt tggcacaatt ggattctttg acccgggaac ttaatgtcgt   7260
ttctcagcag ctgttggatc tgcgccagca ggtttctgcc ctgaaggctt cctcccctcc   7320
caatgcggtt taaaacataa ataaaaaacc agactctgtt tggatttgga tcaagcaagt   7380
gtcttgctgt ctttatttag gggttttgcg cgcgcggtag gcccgggacc agcggtctcg   7440
gtcgttgagg gtcctgtgta ttttttccag gacgtggtaa aggtgactct ggatgttcag   7500
```

-continued atacatgggc ataagcccgt ctctggggtg gaggtagcac cactgcagag cttcatgctg 7560
cggggtggtg ttgtagatga tccagtcgta gcaggagcgc tgggcgtggt gcctaaaaat 7620
gtctttcagt agcaagctga ttgccagggg caggcccttg gtgtaagtgt ttacaaagcg 7680
gttaagctgg gatgggtgca tacgtgggga tatgagatgc atcttggact gtatttttag 7740
gttggctatg ttcccagcca tatccctccg gggattcatg ttgtgcagaa ccaccagcac 7800
agtgtatccg gtgcacttgg gaaatttgtc atgtagctta gaaggaaatg cgtggaagaa 7860
cttggagacg cccttgtgac ctccaagatt ttccatgcat tcgtccataa tgatggcaat 7920
gggcccacgg gcggcggcct gggcgaagat atttctggga tcactaacgt catagttgtg 7980
ttccaggatg agatcgtcat aggccatttt tacaaagcgc gggcggaggg tgccagactg 8040
cggtataatg gttccatccg gcccaggggc gtagttaccc tcacagattt gcatttccca 8100
cgctttgagt tcagatgggg ggatcatgtc tacctgcggg gcgatgaaga aaacggtttc 8160
cggggtaggg gagatcagct gggaagaaag caggttcctg agcagctgcg acttaccgca 8220
gccggtgggc ccgtaaatca cacctattac cggctgcaac tggtagttaa gagagctgca 8280
gctgccgtca tccctgagca ggggggccac ttcgttaagc atgtccctga ctcgcatgtt 8340
ttccctgacc aaatccgcca gaaggcgctc gccgcccagc gatagcagtt cttgcaagga 8400
agcaaagttt ttcaacggtt tgagaccgtc cgccgtaggc atgcttttga gcgtttgacc 8460
aagcagttcc aggcggtccc acagctcggt cacctgctct acggcatctc gatccagcat 8520
atctcctcgt ttcgcgggtt ggggcggctt tcgctgtacg gcagtagtcg gtgctcgtcc 8580
agacgggcca gggtcatgtc tttccacggg cgcagggtcc tcgtcagcgt agtctgggtc 8640
acggtgaagg ggtgcgctcc gggctgcgcg ctggccaggg tgcgcttgag gctggtcctg 8700
ctggtgctga agcgctgccg gtcttcgccc tgcgcgtcgg ccaggtagca tttgaccatg 8760
gtgtcatagt ccagcccctc cgcggcgtgg cccttggcgc gcagcttgcc cttggaggag 8820
gcgccgcacg aggggcagtg cagacttttg agggcgtaga gcttgggcgc gagaaatacc 8880
gattccgggg agtaggcatc cgcgccgcag gccccgcaga cggtctcgca ttccacgagc 8940
caggtgagct ctggccgttc ggggtcaaaa accaggtttc ccccatgctt tttgatgcgt 9000
ttcttacctc tggtttccat gagccggtgt ccacgctcgg tgacgaaaag gctgtccgtg 9060
tccccgtata cagacttgag aggcctgtcc tcgaccgatg cccttgagag ccttcaaccc 9120
agtcagctcc ttccggtggg cgcggggcat gactatcgtc gccgcactta tgactgtctt 9180
ctttatcatg caactcgtag gacaggtgcc ggcagcgctc tgggtcattt tcggcgagga 9240
ccgctttcgc tggagcgcga cgatgatcgg cctgtcgctt gcggtattcg gaatcttgca 9300
cgccctcgct caagccttcg tcactggtcc cgccaccaaa cgtttcggcg agaagcaggc 9360
cattatcgcc ggcatggcgg ccgacgcgct gggctacgtc ttgctggcgt tcgcgacgcg 9420
aggctggatg gccttcccca ttatgattct tctcgcttcc ggcggcatcg ggatgcccgc 9480
gttgcaggcc atgctgtcca ggcaggtaga tgacgaccat cagggacagc ttcaaggcca 9540
gcaaaaggcc aggaaccgta aaaaggccgc gttgctggcg tttttccata ggctccgccc 9600
ccctgacgag catcacaaaa atcgacgctc aagtcagagg tggcgaaacc cgacaggact 9660
ataaagatac caggcgtttc cccctggaag ctccctcgtg cgctctcctg ttccgaccct 9720
gccgcttacc ggatacctgt ccgcctttct cccttcggga agcgtggcgc tttctcatag 9780
ctcacgctgt aggtatctca gttcggtgta ggtcgttcgc tccaagctgg gctgtgtgca 9840
cgaacccccc gttcagcccg accgctgcgc cttatccggt aactatcgtc ttgagtccaa 9900
cccggtaaga cacgacttat cgccactggc agcagccact ggtaacagga ttagcagagc 9960
gaggtatgta ggcggtgcta cagagttctt gaagtggtgg cctaactacg gctacactag 10020
aaggacagta tttggtatct gcgctctgct gaagccagtt accttcggaa aaagagttgg 10080
tagctcttga tccggcaaac aaaccaccgc tggtagcggt ggtttttttg tttgcaagca 10140
gcagattacg cgcagaaaaa aaggatctca agaagatcct ttgatctttt ctacggggtc 10200
tgacgctcag tggaacgaaa actcacgtta agggattttg gtcatgagat tatcaaaaag 10260
gatcttcacc tagatccttt taaattaaaa atgaagtttt aaatcaatct aaagtatata 10320
tgagtaaact tggtctgaca gttaccaatg cttaatcagt gaggcaccta tctcagcgat 10380
ctgtctattt cgttcatcca tagttgcctg actccccgtc gtgtagataa ctacgatacg 10440
ggagggctta ccatctggcc ccagtgctgc aatgataccg cgagacccac gctcaccggc 10500
tccagattta tcagcaataa accagccagc cggaagggcc gagcgcagaa gtggtcctgc 10560
aactttatcc gcctccatcc agtctattaa ttgttgccgg gaagctagag taagtagttc 10620
gccagttaat agtttgcgca acgttgttgc cattgctgca ggcatcgtgg tgtcacgctc 10680
gtcgtttggt atggcttcat tcagctccgg ttcccaacga tcaaggcgag ttacatgatc 10740
ccccatgttg tgcaaaaaag cggttagctc cttcggtcct ccgatcgttg tcagaagtaa 10800
gttggccgca gtgttatcac tcatggttat ggcagcactg cataattctc ttactgtcat 10860
gccatccgta agatgctttt ctgtgactgg tgagtactca accaagtcat tctgagaata 10920
gtgtatgcgg cgaccgagtt gctcttgccc ggcgtcaaca cgggataata ccgcgccaca 10980
tagcagaact ttaaaagtgc tcatcattgg aaaacgttct tcggggcgaa aactctcaag 11040
gatcttaccg ctgttgagat ccagttcgat gtaacccact cgtgcaccca actgatcttc 11100
agcatctttt actttcacca gcgtttctgg gtgagcaaaa acaggaaggc aaaatgccgc 11160
aaaaaaggga ataagggcga cacggaaatg ttgaatactc atactcttcc tttttcaata 11220
ttattgaagc atttatcagg gttattgtct catgagcgga tacatatttg aatgtattta 11280
gaaaaa 11286

<210> SEQ ID NO 58
<211> LENGTH: 11130
<212> TYPE: DNA
<213> ORGANISM: Artificial Sequence
<220> FEATURE:
<223> OTHER INFORMATION: PolyDNA_from_VVN-43329

<400> SEQUENCE: 58
taaacaaata ggggttccgc gcacatttcc ccgaaaagtg ccacctgacg tctaagaaac 60
cattattatc atgacattaa cctataaaaa taggcgtatc acgaggccct ttcgtcttca 120
attaattaag ctagcatcat caataatata ccttattttg gattgaagcc aatatgataa 180
tgagggggtg gagtttgtga cgtggcgcgg ggcgtgggaa cggggcgggt gacgtagtag 240
tgtggcggaa gtgtgatgtt gcaagtgtgg cggaacacat gtaagcgacg gatgtggcaa 300
aagtgacgtt tttggtgtgc gccggtgtac acaggaagtg acaattttcg cgcggtttta 360
ggcggatgtt gtagtaaatt tgggcgtaac cgagtaagat ttggccattt tcgcgggaaa 420
actgaataag aggaagtgaa atctgaataa ttttgtgtta ctcatagcgc gtaatatttg 480
tctagggaga tccggtaccg gcgcgcgcgc cgtttggccg cctcgagtct agagatccgg 540
tgagtattag gcgcgcacca ggtgccgcaa taaaatatct ttattttcat tacatctgtg 600

-continued

```
tgttggtttt ttgtgtgaat cgatagtact aacatacgct ctccatcaaa acaaaacgaa    660
acaaaacaaa ctagcaaaat aggctgtccc cagtgcaagt gcaggtgcca gaacatttct    720
ctatcgataa tgcaggtcgg agtactgtcc tccgagcgga gtactgtcct ccgagcggag    780
tactgtcctc cgagcggagt actgtcctcc gagcggagta ctgtcctccg agcggagtac    840
tgtcctccga gcggagactc ttcgaaggaa gaggggcggg gtcgatcgac cccgcccctc    900
ttccttcgaa ggaagagggg cggggtcgaa gacctagagg gtatataatg ggtgccttag    960
ctggtgtgtg agctcatctt cctgtagatc acgcgtcgaa gaaggtgagt aatcttaaca   1020
tgctcttttt tttttttttt gctaatccct tttgtgtgct gatgttagga tgacatttac   1080
aacaaatgtt tgttcctgac aggaaaaacc ttgctgggta ccttcgttgc cggacacttc   1140
ttgtcctcta ctttggaaaa aaggaattga gagccgctag cgccaccatg tatagaatgc   1200
agctcctgtc ctgcattgcc ctgagcctcg ccctcgtgac aaactccgcc cctaccagcg   1260
gatccgtgag aagcagcagc aggaccccta gcgataagcc tgtggctcac gtcgtcgcta   1320
accctcaggc cgagggccag ctccagtggc tgaatagaag ggccaatgcc ctgctcgcca   1380
acggcgtcga gctgagagac aatcagctcg tggtcccctc cgagggactg tatctgattt   1440
actcccaggt cctgtttaag ggacagggat gccctagcac acacgtcctg ctgacccaca   1500
ccattagcag gatcgctgtg tcctaccaaa ccaaagtgaa tctgctgtcc gctatcaaaa   1560
gcccttgcca aagagaaacc cctgagggag ccgaagccaa accctggtac gaacccattt   1620
acctcggcgg agtgtttcag ctggagaaag gcgatagact cagcgctgag attaacaggc   1680
ccgattacct cgactttgcc gaaagcggac aggtctactt tggcattatc gctctgtaaa   1740
tcgattcgta cgtcgacatc gagtgatggg tggcatccct gtgacccctc cccagtgcct   1800
ctcctggccc tggaagttgc cactccagtg cccaccagcc ttgtcctaat aaaattaagt   1860
tgcatcattt tgtctgacta ggtgtccttc tataatatta tggggtggag gggggtggta   1920
tggagcaagg ggcaagttgg gaagacaacc tgtagggcct gcggggtcta ttgggaacca   1980
agctggagtg cagtggcaca atcttggctc actgcaatct ccgcctcctg ggttcaagcg   2040
attctcctgc ctcagcctcc cgagttgttg ggattccagg catgcatgac caggctcagc   2100
taatttttgt ttttttggta gagacggggt ttcaccatat tggccaggct ggtctccaac   2160
tcctaatctc aggtgatcta cccaccttgg cctcccaaat tgctgggatt acaggcgtga   2220
accactgctc ccttccctgt ccttctgatt ttaaaataac tataccagca ggaggacgtc   2280
cagacacagc ataggctacc tggccatgcc caaccggtgg gacatttgag ttgcttgctt   2340
ggcactgtcc tctcatgcgt tgggtccact cagtagatgc ctgttgaatt ggcgcgccgg   2400
cctccgcgcc gggttttggc gcctcccgcg ggcgcccccc tcctcacggc gagcgctgcc   2460
acgtcagacg aagggcgcag cgagcgtcct gatccttccg cccggacgct caggacagcg   2520
gcccgctgct cataagactc ggccttagaa ccccagtatc agcagaagga cattttagga   2580
cgggacttgg gtgactctag ggcactggtt ttctttccag agagcggaac aggcgaggaa   2640
aagtagtccc ttctcggcga ttctgcggag ggatctccgt ggggcggtga acgccgatga   2700
ttatataagg acgcgccggg tgtggcacag ctagttccgt cgcagccggg atttgggtcg   2760
cggttcttgt ttgtggatcg ctgtgatcgt cacttggtga gtagcgggct gctgggctgg   2820
gtacgtgcgc tcggggttgg cgagtgtgtt ttgtgaagtt ttttaggcac cttttgaaat   2880
gtaatcattt gggtcaatat gtaattttca gtgttagact agtaaattgt ccgctaaatt   2940
ctggccgttt ttggcttttt tgttagacga gctagcgccg ccaccatggg ccctaaaaag   3000
```

aagcgtaaag tcgccccccc gaccgatgtc agcctggggg acgagctcca cttagacggc 3060
gaggacgtgg cgatggcgca tgccgacgcg ctagacgatt tcgatctgga catgttgggg 3120
gacggggatt ccccgggtcc gggatttacc ccccacgact ccgcccccta cggcgctctg 3180
gatatggccg acttcgagtt tgagcagatg tttaccgatg cccttggaat tgacgagtac 3240
ggtggggaat tcgagatgcc tgtggacagg atcctggagg cagagcttgc tgtggaacag 3300
aagagtgacc agggcgttga gggtcctggg ggaaccgggg gtagcggcag cagcccaaat 3360
gaccctgtga ctaacatctg tcaggcagct gacaaacagc tattcacgct tgttgagtgg 3420
gcgaagagga tcccacactt ttcctccttg cctctggatg atcaggtcat attgctgcgg 3480
gcaggctgga atgaactcct cattgcctcc ttttcacacc gatccattga tgttcgagat 3540
ggcatcctcc ttgccacagg tcttcacgtg caccgcaact cagcccattc agcaggagta 3600
ggagccatct ttgatcgggt gctgacagag ctagtgtcca aaatgcgtga catgaggatg 3660
gacaagacag agcttggctg cctgagggca atcattctgt ttaatccaga ggtgaggggt 3720
ttgaaatccg cccaggaagt tgaacttcta cgtgaaaaag tatatgccgc tttggaagaa 3780
tatactagaa caacacatcc cgatgaacca ggaagatttg caaaactttt gcttcgtctg 3840
ccttctttac gttccatagg ccttaagtgt ttggagcatt tgtttttctt tcgccttatt 3900
ggagatgttc caattgatac gttcctgatg gagatgcttg aatcaccttc tgattcataa 3960
tctagcctag cccccctctc cctccccccc ccctaacgtt actggccgaa gccgcttgga 4020
ataaggccgg tgtgcgtttg tctatatgtt attttccacc atattgccgt cttttggcaa 4080
tgtgagggcc cggaaacctg gccctgtctt cttgacgagc attcctaggg gtctttcccc 4140
tctcgccaaa ggaatgcaag gtctgttgaa tgtcgtgaag gaagcagttc ctctggaagc 4200
ttcttgaaga caaacaacgt ctgtagcgac cctttgcagg cagcggaacc ccccacctgg 4260
cgacaggtgc ctctgcggcc aaaagccacg tgtataagat acacctgcaa aggcggcaca 4320
accccagtgc cacgttgtga gttggatagt tgtggaaaga gtcaaatggc tctcctcaag 4380
cgtattcaac aaggggctga aggatgccca gaaggtaccc cattgtatgg gatctgatct 4440
ggggcctcgg tgcacatgct ttacatgtgt ttagtcgagg ttaaaaaacg tctaggcccc 4500
ccgaaccacg gggacgtggt tttcctttga aaaacacgat ctctaggcgc caccatgaag 4560
ctactgtctt ctatcgaaca agcatgcgat atttgccgac ttaaaaagct caagtgctcc 4620
aaagaaaaac cgaagtgcgc caagtgtctg aagaacaact gggagtgtcg ctactctccc 4680
aaaaccaaaa ggtctccgct gactagggca catctgacag aagtggaatc aaggctagaa 4740
agactggaac agctatttct actgattttt cctcgagaag accttgacat gattttgaaa 4800
atggattctt tacaggatat aaaagcattg ttaacaggat tatttgtaca agataatgtg 4860
aataaagatg ccgtcacaga tagattggct tcagtggaga ctgatatgcc tctaacattg 4920
agacagcata gaataagtgc gacatcatca tcggaagaga gtagtaacaa aggtcaaaga 4980
cagttgactg tatcgccgga attcccgggg atccggcctg agtgcgtagt acccgagact 5040
cagtgcgcca tgaagcggaa agagaagaaa gcacagaagg agaaggacaa actgcctgtc 5100
agcacgacga cggtggacga ccacatgccg cccattatgc agtgtgaacc tccacctcct 5160
gaagcagcaa ggattcacga agtggtccca aggtttctct ccgacaagct gttggtgaca 5220
aaccggcaga aaaacatccc ccagttgaca gccaaccagc agttccttat cgccaggctc 5280
atctggtacc aggacgggta cgagcagcct tctgatgaag atttgaagag gattacgcag 5340

-continued

```
acgtggcagc aagcggacga tgaaaacgaa gagtcggaca ctcccttccg ccagatcaca   5400
gagatgacta tcctcacggt ccaacttatc gtggagttcg cgaagggatt gccagggttc   5460
gccaagatct cgcagcctga tcaaattacg ctgcttaagg cttgctcaag tgaggtaatg   5520
atgctccgag tcgcgcgacg atacgatgcg gcctcagaca gtattctgtt cgcgaacaac   5580
caagcgtaca ctcgcgacaa ctaccgcaag gctggcatgg ccgaggtcat cgaggatcta   5640
ctgcacttct gccggtgcat gtactctatg gcgttggaca acatccatta cgcgctgctc   5700
acggctgtcg tcatcttttc tgaccggcca gggttggagc agccgcaact ggtggaagag   5760
atccagcggt actacctgaa tacgctccgc atctatatcc tgaaccagct gagcgggtcg   5820
gcgcgttcgt ccgtcatata cggcaagatc ctctcaatcc tctctgagct acgcacgctc   5880
ggcatgcaaa actccaacat gtgcatctcc ctcaagctca agaacagaaa gctgccgcct   5940
ttcctcgagg agatctggga tgtggcggac atgtcgcaca cccaaccgcc gcctatcctc   6000
gagtccccca cgaatctcta ggcggcctct agagcggccg ccaccgcggg gagatccaga   6060
catgataaga tacattgatg agtttggaca aaccacaact agaatgcagt gaaaaaaatg   6120
ctttatttgt gaaatttgtg atgctattgc tttatttgta accattataa gctgcaataa   6180
acaagttaac aacaacaatt gcattcattt tatgtttcag gttcaggggg aggtgtggga   6240
ggttttttaa agcaagtaaa acctctacaa atgtggtatg gctgattatg atccggctgc   6300
ctcgcgcgtt tcggtgatga cggtgaaaac ctctgacaca tgcagctccc ggagacggtc   6360
acagcttgtc tgtaagcgga tgccgggagc agacaagccc gtcagggcgc gtcagcgggt   6420
gttggcgggt gtcggggcgc agccatgagg tcgactctag tccccgcggt ggcagatctg   6480
gaaggtgctg aggtacgatg agacccgcac caggtgcaga ccctgcgagt gtggcggtaa   6540
acatattagg aaccagcctg tgatgctgga tgtgaccgag gagctgaggc ccgatcactt   6600
ggtgctggcc tgcacccgcg ctgagtttgg ctctagcgat gaagatacag attgaggtac   6660
tgaaatgtgt gggcgtggct taagggtggg aaagaatata taaggtgggg gtcttatgta   6720
gttttgtatc tgttttgcag cagccgccgc cgccatgagc accaactcgt ttgatggaag   6780
cattgtgagc tcatatttga caacgcgcat gcccccatgg gccggggtgc gtcagaatgt   6840
gatgggctcc agcattgatg gtcgccccgt cctgcccgca aactctacta ccttgaccta   6900
cgagaccgtg tctggaacgc cgttggagac tgcagcctcc gccgccgctt cagccgctgc   6960
agccaccgcc cgcgggattg tgactgactt tgctttcctg agcccgcttg caagcagtgc   7020
agcttcccgt tcatccgccc gcgatgacaa gttgacggct cttttggcac aattggattc   7080
tttgacccgg gaacttaatg tcgtttctca gcagctgttg gatctgcgcc agcaggtttc   7140
tgccctgaag gcttcctccc ctcccaatgc ggtttaaaac ataaataaaa aaccagactc   7200
tgtttggatt tggatcaagc aagtgtcttg ctgtctttat ttaggggttt tgcgcgcgcg   7260
gtaggcccgg gaccagcggt ctcggtcgtt gagggtcctg tgtatttttt ccaggacgtg   7320
gtaaaggtga ctctggatgt tcagatacat gggcataagc ccgtctctgg ggtggaggta   7380
gcaccactgc agagcttcat gctgcggggt ggtgttgtag atgatccagt cgtagcagga   7440
gcgctgggcg tggtgcctaa aaatgtcttt cagtagcaag ctgattgcca ggggcaggcc   7500
cttggtgtaa gtgtttacaa agcggttaag ctgggatggg tgcatacgtg ggatatgag    7560
atgcatcttg gactgtattt ttaggttggc tatgttccca gccatatccc tccggggatt   7620
catgttgtgc agaaccacca gcacagtgta tccggtgcac ttgggaaatt tgtcatgtag   7680
cttagaagga aatgcgtgga agaacttgga gacgcccttg tgacctccaa gattttccat   7740
```

-continued

```
gcattcgtcc ataatgatgg caatgggccc acgggcggcg gcctgggcga agatatttct   7800
gggatcacta acgtcatagt tgtgttccag gatgagatcg tcataggcca tttttacaaa   7860
gcgcgggcgg agggtgccag actgcggtat aatggttcca tccggcccag gggcgtagtt   7920
accctcacag atttgcattt cccacgcttt gagttcagat ggggggatca tgtctacctg   7980
cggggcgatg aagaaaacgg tttccggggt aggggagatc agctgggaag aaagcaggtt   8040
cctgagcagc tgcgacttac cgcagccggt gggcccgtaa atcacaccta ttaccggctg   8100
caactggtag ttaagagagc tgcagctgcc gtcatccctg agcagggggg ccacttcgtt   8160
aagcatgtcc ctgactcgca tgttttccct gaccaaatcc gccagaaggc gctcgccgcc   8220
cagcgatagc agttcttgca aggaagcaaa gtttttcaac ggtttgagac cgtccgccgt   8280
aggcatgctt ttgagcgttt gaccaagcag ttccaggcgg tcccacagct cggtcacctg   8340
ctctacggca tctcgatcca gcatatctcc tcgtttcgcg ggttggggcg gctttcgctg   8400
tacggcagta gtcggtgctc gtccagacgg gccagggtca tgtctttcca cgggcgcagg   8460
gtcctcgtca gcgtagtctg ggtcacggtg aaggggtgcg ctccgggctg cgcgctggcc   8520
agggtgcgct tgaggctggt cctgctggtg ctgaagcgct gccggtcttc gccctgcgcg   8580
tcggccaggt agcatttgac catggtgtca tagtccagcc cctccgcggc gtggcccttg   8640
gcgcgcagct tgcccttgga ggaggcgccg cacgaggggc agtgcagact tttgagggcg   8700
tagagcttgg gcgcgagaaa taccgattcc ggggagtagg catccgcgcc gcaggccccg   8760
cagacggtct cgcattccac gagccaggtg agctctggcc gttcggggtc aaaaaccagg   8820
tttcccccat gctttttgat gcgtttctta cctctggttt ccatgagccg gtgtccacgc   8880
tcggtgacga aaaggctgtc cgtgtccccg tatacagact tgagaggcct gtcctcgacc   8940
gatgcccttg agagccttca acccagtcag ctccttccgg tgggcgcggg gcatgactat   9000
cgtcgccgca cttatgactg tcttctttat catgcaactc gtaggacagg tgccggcagc   9060
gctctgggtc attttcggcg aggaccgctt tcgctggagc gcgacgatga tcggcctgtc   9120
gcttgcggta ttcggaatct tgcacgccct cgctcaagcc ttcgtcactg gtcccgccac   9180
caaacgtttc ggcgagaagc aggccattat cgccggcatg gcggccgacg cgctgggcta   9240
cgtcttgctg gcgttcgcga cgcgaggctg gatggccttc cccattatga ttcttctcgc   9300
ttccggcggc atcgggatgc ccgcgttgca ggccatgctg tccaggcagg tagatgacga   9360
ccatcaggga cagcttcaag gccagcaaaa ggccaggaac cgtaaaaagg ccgcgttgct   9420
ggcgtttttc cataggctcc gcccccctga cgagcatcac aaaaatcgac gctcaagtca   9480
gaggtggcga aacccgacag gactataaag ataccaggcg tttccccctg gaagctccct   9540
cgtgcgctct cctgttccga ccctgccgct taccggatac ctgtccgcct ttctcccttc   9600
gggaagcgtg gcgctttctc atagctcacg ctgtaggtat ctcagttcgg tgtaggtcgt   9660
tcgctccaag ctgggctgtg tgcacgaacc ccccgttcag cccgaccgct gcgccttatc   9720
cggtaactat cgtcttgagt ccaacccggt aagacacgac ttatcgccac tggcagcagc   9780
cactggtaac aggattagca gagcgaggta tgtaggcggt gctacagagt tcttgaagtg   9840
gtggcctaac tacggctaca ctagaaggac agtatttggt atctgcgctc tgctgaagcc   9900
agttaccttc ggaaaaagag ttggtagctc ttgatccggc aaacaaacca ccgctggtag   9960
cggtggtttt tttgtttgca agcagcagat tacgcgcaga aaaaaaggat ctcaagaaga  10020
tcctttgatc ttttctacgg ggtctgacgc tcagtggaac gaaaactcac gttaagggat  10080
```

-continued tttggtcatg agattatcaa aaaggatctt cacctagatc cttttaaatt aaaaatgaag 10140
ttttaaatca atctaaagta tatatgagta aacttggtct gacagttacc aatgcttaat 10200
cagtgaggca cctatctcag cgatctgtct atttcgttca tccatagttg cctgactccc 10260
cgtcgtgtag ataactacga tacgggaggg cttaccatct ggccccagtg ctgcaatgat 10320
accgcgagac ccacgctcac cggctccaga tttatcagca ataaaccagc cagccggaag 10380
ggccgagcgc agaagtggtc ctgcaacttt atccgcctcc atccagtcta ttaattgttg 10440
ccgggaagct agagtaagta gttcgccagt taatagtttg cgcaacgttg ttgccattgc 10500
tgcaggcatc gtggtgtcac gctcgtcgtt tggtatggct tcattcagct ccggttccca 10560
acgatcaagg cgagttacat gatcccccat gttgtgcaaa aaagcggtta gctccttcgg 10620
tcctccgatc gttgtcagaa gtaagttggc cgcagtgtta tcactcatgg ttatggcagc 10680
actgcataat tctcttactg tcatgccatc cgtaagatgc ttttctgtga ctggtgagta 10740
ctcaaccaag tcattctgag aatagtgtat gcggcgaccg agttgctctt gcccggcgtc 10800
aacacgggat aataccgcgc cacatagcag aactttaaaa gtgctcatca ttggaaaacg 10860
ttcttcgggg cgaaaactct caaggatctt accgctgttg agatccagtt cgatgtaacc 10920
cactcgtgca cccaactgat cttcagcatc ttttactttc accagcgttt ctgggtgagc 10980
aaaaacagga aggcaaaatg ccgcaaaaaa gggaataagg gcgacacgga aatgttgaat 11040
actcatactc ttcctttttc aatattattg aagcatttat cagggttatt gtctcatgag 11100
cggatacata tttgaatgta tttagaaaaa 11130

<210> SEQ ID NO 59
<211> LENGTH: 11824
<212> TYPE: DNA
<213> ORGANISM: Artificial Sequence
<220> FEATURE:
<223> OTHER INFORMATION: PolyDNA_from_VVN-43533

<400> SEQUENCE: 59
taaacaaata ggggttccgc gcacatttcc ccgaaaagtg ccacctgacg tctaagaaac 60
cattattatc atgacattaa cctataaaaa taggcgtatc acgaggccct ttcgtcttca 120
attaattaag ctagcatcat caataatata ccttattttg gattgaagcc aatatgataa 180
tgagggggtg gagtttgtga cgtggcgcgg ggcgtgggaa cggggcgggt gacgtagtag 240
tgtggcggaa gtgtgatgtt gcaagtgtgg cggaacacat gtaagcgacg gatgtggcaa 300
aagtgacgtt tttggtgtgc gccggtgtac acaggaagtg acaattttcg cgcggtttta 360
ggcggatgtt gtagtaaatt tgggcgtaac cgagtaagat ttggccattt tcgcgggaaa 420
actgaataag aggaagtgaa atctgaataa ttttgtgtta ctcatagcgc gtaatatttg 480
tctagggaga tccggtaccg gcgcgcgcgc cgtttggccg cctcgagtct agagatccgg 540
tgagtattag gcgcgcacca ggtgccgcaa taaaatatct ttattttcat tacatctgtg 600
tgttggtttt ttgtgtgaat cgatagtact aacatacgct ctccatcaaa acaaaacgaa 660
acaaaacaaa ctagcaaaat aggctgtccc cagtgcaagt gcaggtgcca gaacatttct 720
ctatcgataa tgcaggtcgg agtactgtcc tccgagcgga gtactgtcct ccgagcggag 780
tactgtcctc cgagcggagt actgtcctcc gagcggagta ctgtcctccg agcggagtac 840
tgtcctccga gcggagactc ttcgaaggaa gaggggcggg gtcgatcgac cccgcccctc 900
ttccttcgaa ggaagagggg cggggtcgaa gacctagagg gtatataatg ggtgccttag 960
ctggtgtgtg agctcatctt cctgtagatc acgcgtctcc ctcagcaagg acagcagagg 1020

-continued

```
accagctaag agggagagaa gcaactacag acccccccctg aaaacaaccc tcagacgcca   1080
catcccctga caagctgcca ggcaggttct cttcctctca catactgacc cacggctcca   1140
ccctctctcc cctggaaagg acaccgctag cgccaccatg agcactgaaa gcatgatccg   1200
ggacgtggag ctggccgagg aagccctccc caagaaaacc ggcggccccc aggggagcag   1260
aagatgtttg ttcctgagcc tgttttcctt cctgatcgtg gcaggcgcta ccaccctgtt   1320
ctgcctgctg cactttggag tgatcggccc ccagagggag gagttcccca gggacctctc   1380
tctaatcagc cctctggccc aggcaggatc cgtcagatca tcttctcgaa ccccgagtga   1440
caagcctgta gcccatgttg tagcaaaccc tcaagccgag ggccagctcc agtggctgaa   1500
ccgccgggcc aatgccctgc tcgccaacgg cgtcgagctg agagataacc agctggtggt   1560
gccatcagag ggcctgtacc tcatctactc ccaggtcctg ttcaagggcc aaggctgccc   1620
ctccacccat gtgctcctca cccacaccat cagccgcatc gccgtgagct accagaccaa   1680
ggtcaacctc ctctctgcca tcaagagccc ctgccagagg gagaccccag agggggccga   1740
ggccaagccc tggtatgagc ccatctacct cggcggggtg ttccagctgg agaagggtga   1800
ccgactcagc gctgagatca atagacccga ctatctcgac tttgccgaga gcggccaggt   1860
gtactttggg atcattgccc tgtgaatcga ttacgtagcg gccgcgtcga cggaggacga   1920
acatccaacc ttcccaaacg cctcccctgc cccaatccct ttattacccc ctccttcaga   1980
caccctcaac ctcttctggc tcaaaaagag aattgggggc ttagggtcgg aacccaagct   2040
tagaacttta agcaacaaga ccaccacttc gaaacctggg attcaggaat gtgtggcctg   2100
cacagtgaag tgctggcaac cactaagaat tcaaactggg gcctccagaa ctcactgggg   2160
cctacagctt tgatccctga catctggaat ctggagacca gggagccttt ggttctggcc   2220
agaatgctgc aggacttgag aagacctcac ctagaaattg acacaagtgg accttaggcc   2280
ttcctctctc cagatgtttc cagacttcct tgagacacgg agcccagccc tccccatgga   2340
gccagctccc tctatttatg tttgcacttg tgattattta ttatttattt attatttatt   2400
tatttacaga tgaatgtatt tatttgggag accggggtat cctgggggac ccaatgtagg   2460
agctgccttg gctcagacat gttttccgtg aaaacggagc tgaacaatag gctgttccca   2520
tgtagccccc tggcctctgt gccttctttt gattatgttt tttaaaatat ttatctgatt   2580
aagttgtcta aacaatgctg atttggtgac caactgtcac tcattgctga gcctctgctc   2640
cccaggggag ttgtgtctgt aatcgcccta ctattcagtg gcgagaaata aagtttgctt   2700
agaaaagaaa catggtctcc ttcttggaat taattctgca tctgcctctt cttgtgggtg   2760
ggaagaagct ccctaagtcc tctctccaca ggctttaaga tccctcggac ccagtcccat   2820
ccttagactc ctagggccct ggagacccta cataaacaaa gcccaacaga atattcccca   2880
tcccccagga aacaagagcc tgaacctaat tacctctccc tcagggcatg ggaatttcca   2940
actctgggaa ttccaatcct tgctgggaaa atcctgcagc tcaggtgaga tttccggctg   3000
ttgcagctgg ccagcagtcc ggagagagct ggagaggagc cgcattctca ggtacctgaa   3060
tcacacattt aaatcggtcc gcgtaccgcg ccggcctccg cgccgggttt tggcgcctcc   3120
cgcgggcgcc cccctcctca cggcgagcgc tgccacgtca gacgaagggc gcagcgagcg   3180
tcctgatcct tccgcccgga cgctcaggac agcggcccgc tgctcataag actcggcctt   3240
agaaccccag tatcagcaga aggacatttt aggacgggac ttgggtgact ctagggcact   3300
ggttttcttt ccagagagcg gaacaggcga ggaaaagtag tcccttctcg gcgattctgc   3360
```

-continued

```
ggagggatct ccgtggggcg gtgaacgccg atgattatat aaggacgcgc cgggtgtggc   3420
acagctagtt ccgtcgcagc cgggatttgg gtcgcggttc ttgtttgtgg atcgctgtga   3480
tcgtcacttg gtgagtagcg ggctgctggg ctgggtacgt gcgctcgggg ttggcgagtg   3540
tgttttgtga agttttttag gcaccttttg aaatgtaatc atttgggtca atatgtaatt   3600
ttcagtgtta gactagtaaa ttgtccgcta aattctggcc gtttttggct tttttgttag   3660
acgagctagc gccgccacca tgggccctaa aaagaagcgt aaagtcgccc ccccgaccga   3720
tgtcagcctg gggggacgagc tccacttaga cggcgaggac gtggcgatgg cgcatgccga   3780
cgcgctagac gatttcgatc tggacatgtt gggggacggg gattccccgg gtccgggatt   3840
tacccccccac gactccgccc cctacggcgc tctggatatg gccgacttcg agtttgagca   3900
gatgtttacc gatgcccttg gaattgacga gtacggtggg gaattcgaga tgcctgtgga   3960
caggatcctg gaggcagagc ttgctgtgga acagaagagt gaccagggcg ttgagggtcc   4020
tgggggaacc gggggtagcg gcagcagccc aaatgaccct gtgactaaca tctgtcaggc   4080
agctgacaaa cagctattca cgcttgttga gtgggcgaag aggatcccac acttttcctc   4140
cttgcctctg gatgatcagg tcatattgct gcgggcaggc tggaatgaac tcctcattgc   4200
ctccttttca caccgatcca ttgatgttcg agatggcatc ctccttgcca caggtcttca   4260
cgtgcaccgc aactcagccc attcagcagg agtaggagcc atctttgatc gggtgctgac   4320
agagctagtg tccaaaatgc gtgacatgag gatggacaag acagagcttg gctgcctgag   4380
ggcaatcatt ctgtttaatc cagaggtgag ggtttgaaa tccgcccagg aagttgaact   4440
tctacgtgaa aaagtatatg ccgctttgga agaatatact agaacaacac atcccgatga   4500
accaggaaga tttgcaaaac ttttgcttcg tctgccttct ttacgttcca taggccttaa   4560
gtgtttggag catttgtttt tctttcgcct tattggagat gttccaattg atacgttcct   4620
gatggagatg cttgaatcac cttctgattc ataatctagc ctagcccccc tctccctccc   4680
ccccccctaa cgttactggc cgaagccgct tggaataagg ccggtgtgcg tttgtctata   4740
tgttattttc caccatattg ccgtcttttg gcaatgtgag ggcccggaaa cctggccctg   4800
tcttcttgac gagcattcct aggggtcttt cccctctcgc caaaggaatg caaggtctgt   4860
tgaatgtcgt gaaggaagca gttcctctgg aagcttcttg aagacaaaca acgtctgtag   4920
cgaccctttg caggcagcgg aacccccccac ctggcgacag gtgcctctgc ggccaaaagc   4980
cacgtgtata agatacacct gcaaaggcgg cacaacccca gtgccacgtt gtgagttgga   5040
tagttgtgga aagagtcaaa tggctctcct caagcgtatt caacaagggg ctgaaggatg   5100
cccagaaggt accccattgt atgggatctg atctggggcc tcggtgcaca tgctttacat   5160
gtgtttagtc gaggttaaaa aacgtctagg ccccccgaac cacggggacg tggttttcct   5220
ttgaaaaaca cgatctctag gcgccaccat gaagctactg tcttctatcg aacaagcatg   5280
cgatatttgc cgacttaaaa agctcaagtg ctccaaagaa aaaccgaagt gcgccaagtg   5340
tctgaagaac aactgggagt gtcgctactc tcccaaaacc aaaaggtctc cgctgactag   5400
ggcacatctg acagaagtgg aatcaaggct agaaagactg gaacagctat ttctactgat   5460
ttttcctcga gaagaccttg acatgatttt gaaaatggat tctttacagg atataaaagc   5520
attgttaaca ggattatttg tacaagataa tgtgaataaa gatgccgtca cagatagatt   5580
ggcttcagtg gagactgata tgcctctaac attgagacag catagaataa gtgcgacatc   5640
atcatcggaa gagagtagta acaaaggtca aagacagttg actgtatcgc cggaattccc   5700
ggggatccgg cctgagtgcg tagtacccga gactcagtgc gccatgaagc ggaaagagaa   5760
```

```
gaaagcacag aaggagaagg acaaactgcc tgtcagcacg acgacggtgg acgaccacat   5820
gccgcccatt atgcagtgtg aacctccacc tcctgaagca gcaaggattc acgaagtggt   5880
cccaaggttt ctctccgaca agctgttggt gacaaaccgg cagaaaaaca tcccccagtt   5940
gacagccaac cagcagttcc ttatcgccag gctcatctgg taccaggacg ggtacgagca   6000
gccttctgat gaagatttga agaggattac gcagacgtgg cagcaagcgg acgatgaaaa   6060
cgaagagtcg gacactccct tccgccagat cacagagatg actatcctca cggtccaact   6120
tatcgtggag ttcgcgaagg gattgccagg gttcgccaag atctcgcagc ctgatcaaat   6180
tacgctgctt aaggcttgct caagtgaggt aatgatgctc cgagtcgcgc gacgatacga   6240
tgcggcctca gacagtattc tgttcgcgaa caaccaagcg tacactcgcg acaactaccg   6300
caaggctggc atggccgagg tcatcgagga tctactgcac ttctgccggt gcatgtactc   6360
tatggcgttg gacaacatcc attacgcgct gctcacggct gtcgtcatct tttctgaccg   6420
gccagggttg gagcagccgc aactggtgga agagatccag cggtactacc tgaatacgct   6480
ccgcatctat atcctgaacc agctgagcgg gtcggcgcgt tcgtccgtca tatacggcaa   6540
gatcctctca atcctctctg agctacgcac gctcggcatg caaaactcca acatgtgcat   6600
ctccctcaag ctcaagaaca gaaagctgcc gcctttcctc gaggagatct gggatgtggc   6660
ggacatgtcg cacacccaac cgccgcctat cctcgagtcc cccacgaatc tctaggcggc   6720
ctctagagcg gccgccaccg cggggagatc cagacatgat aagatacatt gatgagtttg   6780
gacaaaccac aactagaatg cagtgaaaaa aatgctttat ttgtgaaatt tgtgatgcta   6840
ttgctttatt tgtaaccatt ataagctgca ataaacaagt taacaacaac aattgcattc   6900
attttatgtt tcaggttcag ggggaggtgt gggaggtttt ttaaagcaag taaaacctct   6960
acaaatgtgg tatggctgat tatgatccgg ctgcctcgcg cgtttcggtg atgacggtga   7020
aaacctctga cacatgcagc tcccggagac ggtcacagct tgtctgtaag cggatgccgg   7080
gagcagacaa gcccgtcagg gcgcgtcagc gggtgttggc gggtgtcggg gcgcagccat   7140
gaggtcgact ctagtccccg cggtggcaga tctggaaggt gctgaggtac gatgagaccc   7200
gcaccaggtg cagaccctgc gagtgtggcg gtaaacatat taggaaccag cctgtgatgc   7260
tggatgtgac cgaggagctg aggcccgatc acttggtgct ggcctgcacc cgcgctgagt   7320
ttggctctag cgatgaagat acagattgag gtactgaaat gtgtgggcgt ggcttaaggg   7380
tgggaaagaa tatataaggt gggggtctta tgtagttttg tatctgtttt gcagcagccg   7440
ccgccgccat gagcaccaac tcgtttgatg gaagcattgt gagctcatat ttgacaacgc   7500
gcatgccccc atgggccggg gtgcgtcaga atgtgatggg ctccagcatt gatggtcgcc   7560
ccgtcctgcc cgcaaactct actaccttga cctacgagac cgtgtctgga acgccgttgg   7620
agactgcagc ctccgccgcc gcttcagccg ctgcagccac cgcccgcggg attgtgactg   7680
actttgcttt cctgagcccg cttgcaagca gtgcagcttc ccgttcatcc gcccgcgatg   7740
acaagttgac ggctcttttg gcacaattgg attctttgac ccgggaactt aatgtcgttt   7800
ctcagcagct gttggatctg cgccagcagg tttctgccct gaaggcttcc tcccctccca   7860
atgcggttta aaacataaat aaaaaaccag actctgtttg gatttggatc aagcaagtgt   7920
cttgctgtct ttatttaggg gttttgcgcg cgcggtaggc ccgggaccag cggtctcggt   7980
cgttgagggt cctgtgtatt ttttccagga cgtggtaaag gtgactctgg atgttcagat   8040
acatgggcat aagcccgtct ctggggtgga ggtagcacca ctgcagagct tcatgctgcg   8100
```

gggtggtgtt gtagatgatc cagtcgtagc aggagcgctg ggcgtggtgc ctaaaaatgt 8160
ctttcagtag caagctgatt gccaggggca ggcccttggt gtaagtgttt acaaagcggt 8220
taagctggga tgggtgcata cgtggggata tgagatgcat cttggactgt atttttaggt 8280
tggctatgtt cccagccata tccctccggg gattcatgtt gtgcagaacc accagcacag 8340
tgtatccggt gcacttggga aatttgtcat gtagcttaga aggaaatgcg tggaagaact 8400
tggagacgcc cttgtgacct ccaagatttt ccatgcattc gtccataatg atggcaatgg 8460
gcccacgggc ggcggcctgg gcgaagatat ttctgggatc actaacgtca tagttgtgtt 8520
ccaggatgag atcgtcatag gccattttta caaagcgcgg gcggagggtg ccagactgcg 8580
gtataatggt tccatccggc ccaggggcgt agttaccctc acagatttgc atttcccacg 8640
ctttgagttc agatgggggg atcatgtcta cctgcggggc gatgaagaaa acggtttccg 8700
gggtagggga gatcagctgg gaagaaagca ggttcctgag cagctgcgac ttaccgcagc 8760
cggtgggccc gtaaatcaca cctattaccg gctgcaactg gtagttaaga gagctgcagc 8820
tgccgtcatc cctgagcagg ggggccactt cgttaagcat gtccctgact cgcatgtttt 8880
ccctgaccaa atccgccaga aggcgctcgc cgcccagcga tagcagttct tgcaaggaag 8940
caaagttttt caacggtttg agaccgtccg ccgtaggcat gcttttgagc gtttgaccaa 9000
gcagttccag gcggtcccac agctcggtca cctgctctac ggcatctcga tccagcatat 9060
ctcctcgttt cgcgggttgg ggcggctttc gctgtacggc agtagtcggt gctcgtccag 9120
acgggccagg gtcatgtctt tccacgggcg cagggtcctc gtcagcgtag tctgggtcac 9180
ggtgaagggg tgcgctccgg gctgcgcgct ggccagggtg cgcttgaggc tggtcctgct 9240
ggtgctgaag cgctgccggt cttcgccctg cgcgtcggcc aggtagcatt tgaccatggt 9300
gtcatagtcc agcccctccg cggcgtggcc cttggcgcgc agcttgccct tggaggaggc 9360
gccgcacgag gggcagtgca gacttttgag ggcgtagagc ttgggcgcga gaaataccga 9420
ttccggggag taggcatccg cgccgcaggc cccgcagacg gtctcgcatt ccacgagcca 9480
ggtgagctct ggccgttcgg ggtcaaaaac caggtttccc ccatgctttt tgatgcgttt 9540
cttacctctg gtttccatga gccggtgtcc acgctcggtg acgaaaaggc tgtccgtgtc 9600
cccgtataca gacttgagag gcctgtcctc gaccgatgcc cttgagagcc ttcaacccag 9660
tcagctcctt ccggtgggcg cggggcatga ctatcgtcgc cgcacttatg actgtcttct 9720
ttatcatgca actcgtagga caggtgccgg cagcgctctg ggtcattttc ggcgaggacc 9780
gctttcgctg gagcgcgacg atgatcggcc tgtcgcttgc ggtattcgga atcttgcacg 9840
ccctcgctca agccttcgtc actggtcccg ccaccaaacg tttcggcgag aagcaggcca 9900
ttatcgccgg catggcggcc gacgcgctgg gctacgtctt gctggcgttc gcgacgcgag 9960
gctggatggc cttccccatt atgattcttc tcgcttccgg cggcatcggg atgcccgcgt 10020
tgcaggccat gctgtccagg caggtagatg acgaccatca gggacagctt caaggccagc 10080
aaaaggccag gaaccgtaaa aaggccgcgt tgctggcgtt tttccatagg ctccgccccc 10140
ctgacgagca tcacaaaaat cgacgctcaa gtcagaggtg gcgaaacccg acaggactat 10200
aaagatacca ggcgtttccc cctggaagct ccctcgtgcg ctctcctgtt ccgaccctgc 10260
cgcttaccgg atacctgtcc gcctttctcc cttcgggaag cgtggcgctt tctcatagct 10320
cacgctgtag gtatctcagt tcggtgtagg tcgttcgctc caagctgggc tgtgtgcacg 10380
aaccccccgt tcagcccgac cgctgcgcct tatccggtaa ctatcgtctt gagtccaacc 10440
cggtaagaca cgacttatcg ccactggcag cagccactgg taacaggatt agcagagcga 10500
ggtatgtagg cggtgctaca gagttcttga agtggtggcc taactacggc tacactagaa 10560
ggacagtatt tggtatctgc gctctgctga agccagttac cttcggaaaa agagttggta 10620
gctcttgatc cggcaaacaa accaccgctg gtagcggtgg tttttttgtt tgcaagcagc 10680
agattacgcg cagaaaaaaa ggatctcaag aagatccttt gatcttttct acggggtctg 10740
acgctcagtg gaacgaaaac tcacgttaag ggattttggt catgagatta tcaaaaagga 10800
tcttcaccta gatcctttta aattaaaaat gaagttttaa atcaatctaa agtatatatg 10860
agtaaacttg gtctgacagt taccaatgct taatcagtga ggcacctatc tcagcgatct 10920
gtctatttcg ttcatccata gttgcctgac tccccgtcgt gtagataact acgatacggg 10980
agggcttacc atctggcccc agtgctgcaa tgataccgcg agacccacgc tcaccggctc 11040
cagatttatc agcaataaac cagccagccg gaagggccga gcgcagaagt ggtcctgcaa 11100
ctttatccgc ctccatccag tctattaatt gttgccggga agctagagta agtagttcgc 11160
cagttaatag tttgcgcaac gttgttgcca ttgctgcagg catcgtggtg tcacgctcgt 11220
cgtttggtat ggcttcattc agctccggtt cccaacgatc aaggcgagtt acatgatccc 11280
ccatgttgtg caaaaaagcg gttagctcct tcggtcctcc gatcgttgtc agaagtaagt 11340
tggccgcagt gttatcactc atggttatgg cagcactgca taattctctt actgtcatgc 11400
catccgtaag atgcttttct gtgactggtg agtactcaac caagtcattc tgagaatagt 11460
gtatgcggcg accgagttgc tcttgcccgg cgtcaacacg ggataatacc gcgccacata 11520
gcagaacttt aaaagtgctc atcattggaa aacgttcttc ggggcgaaaa ctctcaagga 11580
tcttaccgct gttgagatcc agttcgatgt aacccactcg tgcacccaac tgatcttcag 11640
catcttttac tttcaccagc gtttctgggt gagcaaaaac aggaaggcaa aatgccgcaa 11700
aaaagggaat aagggcgaca cggaaatgtt gaatactcat actcttcctt tttcaatatt 11760
attgaagcat ttatcagggt tattgtctca tgagcggata catatttgaa tgtatttaga 11820
aaaa 11824

<210> SEQ ID NO 60
<211> LENGTH: 11780
<212> TYPE: DNA
<213> ORGANISM: Artificial Sequence
<220> FEATURE:
<223> OTHER INFORMATION: PolyDNA_from_VVN-43534

<400> SEQUENCE: 60
taaacaaata ggggttccgc gcacatttcc ccgaaaagtg ccacctgacg tctaagaaac 60
cattattatc atgacattaa cctataaaaa taggcgtatc acgaggccct ttcgtcttca 120
attaattaag ctagcatcat caataatata ccttattttg gattgaagcc aatatgataa 180
tgagggggtg gagtttgtga cgtggcgcgg ggcgtgggaa cggggcgggt gacgtagtag 240
tgtggcggaa gtgtgatgtt gcaagtgtgg cggaacacat gtaagcgacg gatgtggcaa 300
aagtgacgtt tttggtgtgc gccggtgtac acaggaagtg acaattttcg cgcggtttta 360
ggcggatgtt gtagtaaatt tgggcgtaac cgagtaagat ttggccattt tcgcgggaaa 420
actgaataag aggaagtgaa atctgaataa ttttgtgtta ctcatagcgc gtaatatttg 480
tctagggaga tccggtaccg gcgcgcgcgc cgtttggccg cctcgagtct agagatccgg 540
tgagtattag gcgcgcacca ggtgccgcaa taaaatatct ttattttcat tacatctgtg 600
tgttggtttt ttgtgtgaat cgatagtact aacatacgct ctccatcaaa acaaaacgaa 660

-continued

```
acaaaacaaa ctagcaaaat aggctgtccc cagtgcaagt gcaggtgcca gaacatttct    720
ctatcgataa tgcaggtcgg agtactgtcc tccgagcgga gtactgtcct ccgagcggag    780
tactgtcctc cgagcggagt actgtcctcc gagcggagta ctgtcctccg agcggagtac    840
tgtcctccga gcggagactc ttcgaaggaa gaggggcggg gtcgatcgac cccgcccctc    900
ttccttcgaa ggaagagggg cggggtcgaa gacctagagg gtatataatg ggtgccttag    960
ctggtgtgtg agctcatctt cctgtagatc acgcgtctcc ctcagcaagg acagcagagg   1020
accagctaag agggagagaa gcaactacag acccccccctg aaaacaaccc tcagacgcca   1080
catcccctga caagctgcca ggcaggttct cttcctctca catactgacc cacggctcca   1140
ccctctctcc cctggaaagg acaccatgag cactgaaagc atgatccggg acgtggagct   1200
ggccgaggag gcgctcccca agaagacagg ggggccccag ggctccaggc ggtgcttgtt   1260
cctcagcctc ttctccttcc tgatcgtggc aggcgccacc acgctcttct gcctgctgca   1320
ctttggagtg atcggccccc agagggaaga gttccccagg gacctctctc taatcagccc   1380
tctggcccag gcagtcagat catcttctcg aaccccgagt gacaagcctg tagcccatgt   1440
tgtagcaaac cctcaagctg aggggcagct ccagtggctg aaccgccggg ccaatgccct   1500
cctggccaat ggcgtggagc tgagagataa ccagctggtg gtgccatcag agggcctgta   1560
cctcatctac tcccaggtcc tcttcaaggg ccaaggctgc ccctccaccc atgtgctcct   1620
cacccacacc atcagccgca tcgccgtctc ctaccagacc aaggtcaacc tcctctctgc   1680
catcaagagc ccctgccaga gggagacccc agagggggct gaggccaagc cctggtatga   1740
gcccatctat ctgggagggg tcttccagct ggagaagggt gaccgactca gcgctgagat   1800
caatcggccc gactatctcg actttgccga gtctgggcag gtctactttg ggatcattgc   1860
cctgtgagga ggacgaacat ccaaccttcc caaacgcctc ccctgcccca atccctttat   1920
taccccctcc ttcagacacc ctcaacctct tctggctcaa aaagagaatt gggggcttag   1980
ggtcggaacc caagcttaga actttaagca acaagaccac cacttcgaaa cctgggattc   2040
aggaatgtgt ggcctgcaca gtgaagtgct ggcaaccact aagaattcaa actggggcct   2100
ccagaactca ctggggccta cagctttgat ccctgacatc tggaatctgg agaccaggga   2160
gcctttggtt ctggccagaa tgctgcagga cttgagaaga cctcacctag aaattgacac   2220
aagtggacct taggccttcc tctctccaga tgtttccaga cttccttgag acacggagcc   2280
cagccctccc catggagcca gctccctcta tttatgtttg cacttgtgat tatttattat   2340
ttatttatta tttatttatt tacagatgaa tgtatttatt tgggagaccg gggtatcctg   2400
ggggacccaa tgtaggagct gccttggctc agacatgttt tccgtgaaaa cggagctgaa   2460
caataggctg ttcccatgta gcccccctggc ctctgtgcct tcttttgatt atgtttttta   2520
aaatatttat ctgattaagt tgtctaaaca atgctgattt ggtgaccaac tgtcactcat   2580
tgctgagcct ctgctcccca ggggagttgt gtctgtaatc gccctactat tcagtggcga   2640
gaaataaagt ttgcttagaa aagaaacatg gtctccttct tggaattaat tctgcatctg   2700
cctcttcttg tgggtgggaa gaagctccct aagtcctctc tccacaggct ttaagatccc   2760
tcggacccag tcccatcctt agactcctag ggccctggag accctacata aacaaagccc   2820
aacagaatat tccccatccc ccaggaaaca agagcctgaa cctaattacc tctccctcag   2880
ggcatgggaa tttccaactc tgggaattcc aatccttgct gggaaaatcc tgcagctcag   2940
gtgagatttc cggctgttgc agctggccag cagtccggag agagctggag aggagccgca   3000
ttctcaggta cctgaatcac acatttaaat cggtccgcgt accgcgccgg cctccgcgcc   3060
```

-continued

```
gggttttggc gcctcccgcg ggcgcccccc tcctcacggc gagcgctgcc acgtcagacg   3120
aagggcgcag cgagcgtcct gatccttccg cccggacgct caggacagcg gcccgctgct   3180
cataagactc ggccttagaa ccccagtatc agcagaagga cattttagga cgggacttgg   3240
gtgactctag ggcactggtt ttctttccag agagcggaac aggcgaggaa aagtagtccc   3300
ttctcggcga ttctgcggag ggatctccgt ggggcggtga acgccgatga ttatataagg   3360
acgcgccggg tgtggcacag ctagttccgt cgcagccggg atttgggtcg cggttcttgt   3420
ttgtggatcg ctgtgatcgt cacttggtga gtagcgggct gctgggctgg gtacgtgcgc   3480
tcggggttgg cgagtgtgtt ttgtgaagtt ttttaggcac cttttgaaat gtaatcattt   3540
gggtcaatat gtaattttca gtgttagact agtaaattgt ccgctaaatt ctggccgttt   3600
ttggcttttt tgttagacga gctagcgccg ccaccatggg ccctaaaaag aagcgtaaag   3660
tcgccccccc gaccgatgtc agcctggggg acgagctcca cttagacggc gaggacgtgg   3720
cgatggcgca tgccgacgcg ctagacgatt tcgatctgga catgttgggg gacggggatt   3780
ccccgggtcc gggatttacc ccccacgact ccgcccccta cggcgctctg gatatggccg   3840
acttcgagtt tgagcagatg tttaccgatg cccttggaat tgacgagtac ggtggggaat   3900
tcgagatgcc tgtggacagg atcctggagg cagagcttgc tgtggaacag aagagtgacc   3960
agggcgttga gggtcctggg ggaaccgggg gtagcggcag cagcccaaat gaccctgtga   4020
ctaacatctg tcaggcagct gacaaacagc tattcacgct tgttgagtgg gcgaagagga   4080
tcccacactt ttcctccttg cctctggatg atcaggtcat attgctgcgg gcaggctgga   4140
atgaactcct cattgcctcc ttttcacacc gatccattga tgttcgagat ggcatcctcc   4200
ttgccacagg tcttcacgtg caccgcaact cagcccattc agcaggagta ggagccatct   4260
ttgatcgggt gctgacagag ctagtgtcca aaatgcgtga catgaggatg gacaagacag   4320
agcttggctg cctgagggca atcattctgt ttaatccaga ggtgaggggt ttgaaatccg   4380
cccaggaagt tgaacttcta cgtgaaaaag tatatgccgc tttggaagaa tatactagaa   4440
caacacatcc cgatgaacca ggaagatttg caaaactttt gcttcgtctg ccttctttac   4500
gttccatagg ccttaagtgt ttggagcatt tgtttttctt tcgccttatt ggagatgttc   4560
caattgatac gttcctgatg gagatgcttg aatcaccttc tgattcataa tctagcctag   4620
cccccctctc cctccccccc ccctaacgtt actggccgaa gccgcttgga ataaggccgg   4680
tgtgcgtttg tctatatgtt attttccacc atattgccgt cttttggcaa tgtgagggcc   4740
cggaaacctg gccctgtctt cttgacgagc attcctaggg gtctttcccc tctcgccaaa   4800
ggaatgcaag gtctgttgaa tgtcgtgaag gaagcagttc ctctggaagc ttcttgaaga   4860
caaacaacgt ctgtagcgac cctttgcagg cagcggaacc ccccacctgg cgacaggtgc   4920
ctctgcggcc aaaagccacg tgtataagat acacctgcaa aggcggcaca accccagtgc   4980
cacgttgtga gttggatagt tgtggaaaga gtcaaatggc tctcctcaag cgtattcaac   5040
aaggggctga aggatgccca gaaggtaccc cattgtatgg gatctgatct ggggcctcgg   5100
tgcacatgct ttacatgtgt ttagtcgagg ttaaaaaacg tctaggcccc ccgaaccacg   5160
gggacgtggt tttcctttga aaaacacgat ctctaggcgc caccatgaag ctactgtctt   5220
ctatcgaaca agcatgcgat atttgccgac ttaaaaagct caagtgctcc aaagaaaaac   5280
cgaagtgcgc caagtgtctg aagaacaact gggagtgtcg ctactctccc aaaaccaaaa   5340
ggtctccgct gactagggca catctgacag aagtggaatc aaggctagaa agactggaac   5400
```

-continued

```
agctatttct actgattttt cctcgagaag accttgacat gattttgaaa atggattctt   5460
tacaggatat aaaagcattg ttaacaggat tatttgtaca agataatgtg aataaagatg   5520
ccgtcacaga tagattggct tcagtggaga ctgatatgcc tctaacattg agacagcata   5580
gaataagtgc gacatcatca tcggaagaga gtagtaacaa aggtcaaaga cagttgactg   5640
tatcgccgga attcccgggg atccggcctg agtgcgtagt acccgagact cagtgcgcca   5700
tgaagcggaa agagaagaaa gcacagaagg agaaggacaa actgcctgtc agcacgacga   5760
cggtggacga ccacatgccg cccattatgc agtgtgaacc tccacctcct gaagcagcaa   5820
ggattcacga agtggtccca aggtttctct ccgacaagct gttggtgaca aaccggcaga   5880
aaaacatccc ccagttgaca gccaaccagc agttccttat cgccaggctc atctggtacc   5940
aggacgggta cgagcagcct tctgatgaag atttgaagag gattacgcag acgtggcagc   6000
aagcggacga tgaaaacgaa gagtcggaca ctcccttccg ccagatcaca gagatgacta   6060
tcctcacggt ccaacttatc gtggagttcg cgaagggatt gccagggttc gccaagatct   6120
cgcagcctga tcaaattacg ctgcttaagg cttgctcaag tgaggtaatg atgctccgag   6180
tcgcgcgacg atacgatgcg gcctcagaca gtattctgtt cgcgaacaac caagcgtaca   6240
ctcgcgacaa ctaccgcaag gctggcatgg ccgaggtcat cgaggatcta ctgcacttct   6300
gccggtgcat gtactctatg gcgttggaca acatccatta cgcgctgctc acggctgtcg   6360
tcatcttttc tgaccggcca gggttggagc agccgcaact ggtggaagag atccagcggt   6420
actacctgaa tacgctccgc atctatatcc tgaaccagct gagcgggtcg gcgcgttcgt   6480
ccgtcatata cggcaagatc ctctcaatcc tctctgagct acgcacgctc ggcatgcaaa   6540
actccaacat gtgcatctcc ctcaagctca agaacagaaa gctgccgcct ttcctcgagg   6600
agatctggga tgtggcggac atgtcgcaca cccaaccgcc gcctatcctc gagtccccca   6660
cgaatctcta ggcggcctct agagcggccg ccaccgcggg gagatccaga catgataaga   6720
tacattgatg agtttggaca aaccacaact agaatgcagt gaaaaaaatg ctttatttgt   6780
gaaatttgtg atgctattgc tttatttgta accattataa gctgcaataa acaagttaac   6840
aacaacaatt gcattcattt tatgtttcag gttcaggggg aggtgtggga ggttttttaa   6900
agcaagtaaa acctctacaa atgtggtatg gctgattatg atccggctgc ctcgcgcgtt   6960
tcggtgatga cggtgaaaac ctctgacaca tgcagctccc ggagacggtc acagcttgtc   7020
tgtaagcgga tgccgggagc agacaagccc gtcagggcgc gtcagcgggt gttggcgggt   7080
gtcggggcgc agccatgagg tcgactctag tccccgcggt ggcagatctg gaaggtgctg   7140
aggtacgatg agacccgcac caggtgcaga ccctgcgagt gtggcggtaa acatattagg   7200
aaccagcctg tgatgctgga tgtgaccgag gagctgaggc ccgatcactt ggtgctggcc   7260
tgcacccgcg ctgagtttgg ctctagcgat gaagatacag attgaggtac tgaaatgtgt   7320
gggcgtggct taagggtggg aaagaatata taaggtgggg gtcttatgta gttttgtatc   7380
tgttttgcag cagccgccgc cgccatgagc accaactcgt ttgatggaag cattgtgagc   7440
tcatatttga caacgcgcat gcccccatgg gccggggtgc gtcagaatgt gatgggctcc   7500
agcattgatg gtcgccccgt cctgcccgca aactctacta ccttgaccta cgagaccgtg   7560
tctggaacgc cgttggagac tgcagcctcc gccgccgctt cagccgctgc agccaccgcc   7620
cgcgggattg tgactgactt tgctttcctg agcccgcttg caagcagtgc agcttcccgt   7680
tcatccgccc gcgatgacaa gttgacggct cttttggcac aattggattc tttgacccgg   7740
gaacttaatg tcgtttctca gcagctgttg gatctgcgcc agcaggtttc tgccctgaag   7800
```

gcttcctccc ctcccaatgc ggtttaaaac ataaataaaa aaccagactc tgtttggatt 7860
tggatcaagc aagtgtcttg ctgtctttat ttaggggttt tgcgcgcgcg gtaggcccgg 7920
gaccagcggt ctcggtcgtt gagggtcctg tgtatttttt ccaggacgtg gtaaaggtga 7980
ctctggatgt tcagatacat gggcataagc ccgtctctgg ggtggaggta gcaccactgc 8040
agagcttcat gctgcggggt ggtgttgtag atgatccagt cgtagcagga gcgctgggcg 8100
tggtgcctaa aaatgtcttt cagtagcaag ctgattgcca ggggcaggcc cttggtgtaa 8160
gtgtttacaa agcggttaag ctgggatggg tgcatacgtg gggatatgag atgcatcttg 8220
gactgtattt ttaggttggc tatgttccca gccatatccc tccggggatt catgttgtgc 8280
agaaccacca gcacagtgta tccggtgcac ttgggaaatt tgtcatgtag cttagaagga 8340
aatgcgtgga agaacttgga gacgcccttg tgacctccaa gattttccat gcattcgtcc 8400
ataatgatgg caatgggccc acgggcggcg gcctgggcga agatatttct gggatcacta 8460
acgtcatagt tgtgttccag gatgagatcg tcataggcca tttttacaaa gcgcgggcgg 8520
agggtgccag actgcggtat aatggttcca tccggcccag gggcgtagtt accctcacag 8580
atttgcattt cccacgcttt gagttcagat ggggggatca tgtctacctg cggggcgatg 8640
aagaaaacgg tttccggggt aggggagatc agctgggaag aaagcaggtt cctgagcagc 8700
tgcgacttac cgcagccggt gggcccgtaa atcacaccta ttaccggctg caactggtag 8760
ttaagagagc tgcagctgcc gtcatccctg agcagggggg ccacttcgtt aagcatgtcc 8820
ctgactcgca tgttttccct gaccaaatcc gccagaaggc gctcgccgcc cagcgatagc 8880
agttcttgca aggaagcaaa gtttttcaac ggtttgagac cgtccgccgt aggcatgctt 8940
ttgagcgttt gaccaagcag ttccaggcgg tcccacagct cggtcacctg ctctacggca 9000
tctcgatcca gcatatctcc tcgtttcgcg ggttggggcg gctttcgctg tacggcagta 9060
gtcggtgctc gtccagacgg gccagggtca tgtctttcca cgggcgcagg gtcctcgtca 9120
gcgtagtctg ggtcacggtg aaggggtgcg ctccgggctg cgcgctggcc agggtgcgct 9180
tgaggctggt cctgctggtg ctgaagcgct gccggtcttc gccctgcgcg tcggccaggt 9240
agcatttgac catggtgtca tagtccagcc cctccgcggc gtggcccttg gcgcgcagct 9300
tgcccttgga ggaggcgccg cacgaggggc agtgcagact tttgagggcg tagagcttgg 9360
gcgcgagaaa taccgattcc ggggagtagg catccgcgcc gcaggccccg cagacggtct 9420
cgcattccac gagccaggtg agctctggcc gttcggggtc aaaaaccagg tttcccccat 9480
gctttttgat gcgtttctta cctctggttt ccatgagccg gtgtccacgc tcggtgacga 9540
aaaggctgtc cgtgtccccg tatacagact tgagaggcct gtcctcgacc gatgcccttg 9600
agagccttca acccagtcag ctccttccgg tgggcgcggg gcatgactat cgtcgccgca 9660
cttatgactg tcttctttat catgcaactc gtaggacagg tgccggcagc gctctgggtc 9720
attttcggcg aggaccgctt tcgctggagc gcgacgatga tcggcctgtc gcttgcggta 9780
ttcggaatct tgcacgccct cgctcaagcc ttcgtcactg gtcccgccac caaacgtttc 9840
ggcgagaagc aggccattat cgccggcatg gcggccgacg cgctgggcta cgtcttgctg 9900
gcgttcgcga cgcgaggctg gatggccttc cccattatga ttcttctcgc ttccggcggc 9960
atcgggatgc ccgcgttgca ggccatgctg tccaggcagg tagatgacga ccatcaggga 10020
cagcttcaag gccagcaaaa ggccaggaac cgtaaaaagg ccgcgttgct ggcgtttttc 10080
cataggctcc gcccccctga cgagcatcac aaaaatcgac gctcaagtca gaggtggcga 10140

```
aacccgacag gactataaag ataccaggcg tttccccctg gaagctccct cgtgcgctct  10200

cctgttccga ccctgccgct taccggatac ctgtccgcct ttctcccttc gggaagcgtg  10260

gcgctttctc atagctcacg ctgtaggtat ctcagttcgg tgtaggtcgt tcgctccaag  10320

ctgggctgtg tgcacgaacc ccccgttcag cccgaccgct gcgccttatc cggtaactat  10380

cgtcttgagt ccaacccggt aagacacgac ttatcgccac tggcagcagc cactggtaac  10440

aggattagca gagcgaggta tgtaggcggt gctacagagt tcttgaagtg gtggcctaac  10500

tacggctaca ctagaaggac agtatttggt atctgcgctc tgctgaagcc agttaccttc  10560

ggaaaaagag ttggtagctc ttgatccggc aaacaaacca ccgctggtag cggtggtttt  10620

tttgtttgca agcagcagat tacgcgcaga aaaaaaggat ctcaagaaga tcctttgatc  10680

ttttctacgg ggtctgacgc tcagtggaac gaaaactcac gttaagggat tttggtcatg  10740

agattatcaa aaaggatctt cacctagatc cttttaaatt aaaaatgaag ttttaaatca  10800

atctaaagta tatatgagta aacttggtct gacagttacc aatgcttaat cagtgaggca  10860

cctatctcag cgatctgtct atttcgttca tccatagttg cctgactccc cgtcgtgtag  10920

ataactacga tacgggaggg cttaccatct ggccccagtg ctgcaatgat accgcgagac  10980

ccacgctcac cggctccaga tttatcagca ataaaccagc cagccggaag ggccgagcgc  11040

agaagtggtc ctgcaacttt atccgcctcc atccagtcta ttaattgttg ccgggaagct  11100

agagtaagta gttcgccagt taatagtttg cgcaacgttg ttgccattgc tgcaggcatc  11160

gtggtgtcac gctcgtcgtt tggtatggct tcattcagct ccggttccca acgatcaagg  11220

cgagttacat gatcccccat gttgtgcaaa aaagcggtta gctccttcgg tcctccgatc  11280

gttgtcagaa gtaagttggc cgcagtgtta tcactcatgg ttatggcagc actgcataat  11340

tctcttactg tcatgccatc cgtaagatgc ttttctgtga ctggtgagta ctcaaccaag  11400

tcattctgag aatagtgtat gcggcgaccg agttgctctt gcccggcgtc aacacgggat  11460

aataccgcgc cacatagcag aactttaaaa gtgctcatca ttggaaaacg ttcttcgggg  11520

cgaaaactct caaggatctt accgctgttg agatccagtt cgatgtaacc cactcgtgca  11580

cccaactgat cttcagcatc ttttactttc accagcgttt ctgggtgagc aaaaacagga  11640

aggcaaaatg ccgcaaaaaa gggaataagg gcgacacgga aatgttgaat actcatactc  11700

ttcctttttc aatattattg aagcatttat cagggttatt gtctcatgag cggatacata  11760

tttgaatgta tttagaaaaa                                              11780
```

<210> SEQ ID NO 61
<211> LENGTH: 12196
<212> TYPE: DNA
<213> ORGANISM: Artificial Sequence
<220> FEATURE:
<223> OTHER INFORMATION: Ad-RTS-hIL-12 is VVN2823

<400> SEQUENCE: 61

```
taaacaaata ggggttccgc gcacatttcc ccgaaaagtg ccacctgacg tctaagaaac     60

cattattatc atgacattaa cctataaaaa taggcgtatc acgaggccct ttcgtcttca    120

attaattaag ctagcatcat caataatata ccttattttg gattgaagcc aatatgataa    180

tgaggggggtg gagtttgtga cgtggcgcgg ggcgtgggaa cggggcgggt gacgtagtag    240

tgtggcggaa gtgtgatgtt gcaagtgtgg cggaacacat gtaagcgacg gatgtggcaa    300

aagtgacgtt tttggtgtgc gccggtgtac acaggaagtg acaattttcg cgcggtttta    360

ggcggatgtt gtagtaaatt tgggcgtaac cgagtaagat ttggccattt tcgcgggaaa    420
```

```
actgaataag aggaagtgaa atctgaataa ttttgtgtta ctcatagcgc gtaatatttg    480
tctagggaga tccggtaccg gcgcgcgcgc cgtttggccg cctcgagtct agagatccgg    540
tgagtattag gcgcgcacca ggtgccgcaa taaaatatct ttattttcat tacatctgtg    600
tgttggtttt ttgtgtgaat cgatagtact aacatacgct ctccatcaaa acaaaacgaa    660
acaaaacaaa ctagcaaaat aggctgtccc cagtgcaagt gcaggtgcca gaacatttct    720
ctatcgataa tgcaggtcgg agtactgtcc tccgagcgga gtactgtcct ccgagcggag    780
tactgtcctc cgagcggagt actgtcctcc gagcggagta ctgtcctccg agcggagtac    840
tgtcctccga gcggagactc ttcgaaggaa gaggggcggg gtcgatcgac cccgcccctc    900
ttccttcgaa ggaagagggg cggggtcgaa gacctagagg gtatataatg ggtgccttag    960
ctggtgtgtg agctcatctt cctgtagatc acgcgtgcca ccatgggtca ccagcagttg   1020
gtcatctctt ggttttccct ggtttttctg gcatctcccc tcgtggccat atgggaactg   1080
aagaaagatg tttatgtcgt agaattggat tggtatccgg atgcccctgg agaaatggtg   1140
gtcctcacct gtgacacccc tgaagaagat ggtatcacct ggaccttgga ccagagcagt   1200
gaggtcttag gctctggcaa aaccctgacc atccaagtca aagagtttgg agatgctggc   1260
cagtacacct gtcacaaagg aggcgaggtt ctaagccatt cgctcctgct gcttcacaaa   1320
aaggaagatg gaatttggtc cactgatatt ttaaaggacc agaaagaacc caaaaataag   1380
acctttctaa gatgcgaggc caagaattat tctggacgtt tcacctgctg gtggctgacg   1440
acaatcagta ctgatttgac attcagtgtc aaaagcagca gaggctcttc tgacccccaa   1500
ggggtgacgt gcggagctgc tacactctct gcagagagag tcagagggga caacaaggag   1560
tatgagtact cagtggagtg ccaggaggac agtgcctgcc cagctgctga ggagagtctg   1620
cccattgagg tcatggtgga tgccgttcac aagctcaagt atgaaaacta caccagcagc   1680
ttcttcatca gggacatcat caaacctgac ccacccaaga acttgcagct gaagccatta   1740
aagaattctc ggcaggtgga ggtcagctgg gagtaccctg acacctggag tactccacat   1800
tcctacttct ccctgacatt ctgcgttcag gtccagggca agagcaagag agaaaagaaa   1860
gatagagtct tcacggacaa gacctcagcc acggtcatct gccgcaaaaa tgccagcatt   1920
agcgtgcggg cccaggaccg ctactatagc tcatcttgga gcgaatgggc atctgtgccc   1980
tgcagttagg ttgggcgagc tcgaattcat tgatcccccg ggctgcagga attcgatatc   2040
aagctcggga tccgaattcc gccccccccc cccccccccc cctaacgtta ctggccgaag   2100
ccgcttggaa taaggccggt gtgcgtttgt ctatatgtta ttttccacca tattgccgtc   2160
ttttggcaat gtgagggccc ggaaacctgg ccctgtcttc ttgacgagca ttcctagggg   2220
tctttcccct ctcgccaaag gaatgcaagg tctgttgaat gtcgtgaagg aagcagttcc   2280
tctggaagct tcttgaagac aaacaacgtc tgtagcgacc ctttgcaggc agcggaaccc   2340
cccacctggc gacaggtgcc tctgcggcca aaagccacgt gtataagata cacctgcaaa   2400
ggcggcacaa ccccagtgcc acgttgtgag ttggatagtt gtggaaagag tcaaatggct   2460
ctcctcaagc gtattcaaca aggggctgaa ggatgcccag aaggtacccc attgtatggg   2520
atctgatctg gggcctcggt gcacatgctt tacatgtgtt tagtcgaggt taaaaaaacg   2580
tctaggcccc ccgaaccacg gggacgtggt tttcctttga aaaacacgat gataatatgg   2640
ccacaaccat gggtccagcg cgcagcctcc tccttgtggc taccctggtc ctcctggacc   2700
acctcagttt ggccagaaac ctccccgtgg ccactccaga cccaggaatg ttcccatgcc   2760
```

```
ttcaccactc ccaaaacctg ctgagggccg tcagcaacat gctccagaag gccagacaaa   2820
ctctagaatt ttacccttgc acttctgaag agattgatca tgaagatatc acaaaagata   2880
aaaccagcac agtggaggcc tgtttaccat tggaattaac caagaatgag agttgcctaa   2940
attccagaga gacctctttc ataactaatg ggagttgcct ggcctccaga aagacctctt   3000
ttatgatggc cctgtgcctt agtagtattt atgaagactt gaagatgtac caggtggagt   3060
tcaagaccat gaatgcaaag cttctgatgg atcctaagag gcagatcttt ctagatcaaa   3120
acatgctggc agttattgat gagctgatgc aggccctgaa tttcaacagt gagactgtgc   3180
cacaaaaatc ctcccttgaa gaaccggatt tttataaaac taaaatcaag ctctgcatac   3240
ttcttcatgc tttcagaatt cgggcagtga ctattgatag agtgatgagc tatctgaatg   3300
cttcctaacg tacgtcgaca tcgagaactt gtttattgca gcttataatg gttacaaata   3360
aagcaatagc atcacaaatt tcacaaataa agcatttttt tcactgcatt ctagttgtgg   3420
tttgtccaaa ctcatcaatg tatcttatca tgtctgggcg cgccggcctc cgcgccgggt   3480
tttggcgcct cccgcgggcg ccccccctcct cacggcgagc gctgccacgt cagacgaagg   3540
gcgcagcgag cgtcctgatc cttccgcccg gacgctcagg acagcggccc gctgctcata   3600
agactcggcc ttagaacccc agtatcagca gaaggacatt ttaggacggg acttgggtga   3660
ctctagggca ctggttttct ttccagagag cggaacaggc gaggaaaagt agtcccttct   3720
cggcgattct gcggagggat ctccgtgggg cggtgaacgc cgatgattat ataaggacgc   3780
gccgggtgtg gcacagctag ttccgtcgca gccgggattt gggtcgcggt tcttgtttgt   3840
ggatcgctgt gatcgtcact tggtgagtag cgggctgctg ggctgggtac gtgcgctcgg   3900
ggttggcgag tgtgttttgt gaagtttttt aggcaccttt tgaaatgtaa tcatttgggt   3960
caatatgtaa ttttcagtgt tagactagta aattgtccgc taaattctgg ccgtttttgg   4020
ctttttttgtt agacgagcta gcgccgccac catgggccct aaaaagaagc gtaaagtcgc   4080
ccccccgacc gatgtcagcc tgggggacga gctccactta gacggcgagg acgtggcgat   4140
ggcgcatgcc gacgcgctag acgatttcga tctggacatg ttgggggacg gggattcccc   4200
gggtccggga tttacccccc acgactccgc cccctacggc gctctggata tggccgactt   4260
cgagtttgag cagatgttta ccgatgccct tggaattgac gagtacggtg gggaattcga   4320
gatgcctgtg gacaggatcc tggaggcaga gcttgctgtg gaacagaaga gtgaccaggg   4380
cgttgagggt cctgggggaa ccgggggtag cggcagcagc ccaaatgacc ctgtgactaa   4440
catctgtcag gcagctgaca aacagctatt cacgcttgtt gagtgggcga agaggatccc   4500
acacttttcc tccttgcctc tggatgatca ggtcatattg ctgcgggcag gctggaatga   4560
actcctcatt gcctcctttt cacaccgatc cattgatgtt cgagatggca tcctccttgc   4620
cacaggtctt cacgtgcacc gcaactcagc ccattcagca ggagtaggag ccatctttga   4680
tcgggtgctg acagagctag tgtccaaaat gcgtgacatg aggatggaca agacagagct   4740
tggctgcctg agggcaatca ttctgtttaa tccagaggtg aggggtttga aatccgccca   4800
ggaagttgaa cttctacgtg aaaaagtata tgccgctttg gaagaatata ctagaacaac   4860
acatcccgat gaaccaggaa gatttgcaaa acttttgctt cgtctgcctt ctttacgttc   4920
cataggcctt aagtgtttgg agcatttgtt tttctttcgc cttattggag atgttccaat   4980
tgatacgttc ctgatggaga tgcttgaatc accttctgat tcataatcta gcctagcccc   5040
cctctccctc cccccccct aacgttactg gccgaagccg cttggaataa ggccggtgtg   5100
cgtttgtcta tatgttattt tccaccatat tgccgtcttt tggcaatgtg agggcccgga   5160
```

aacctggccc tgtcttcttg acgagcattc ctaggggtct ttcccctctc gccaaaggaa 5220
tgcaaggtct gttgaatgtc gtgaaggaag cagttcctct ggaagcttct tgaagacaaa 5280
caacgtctgt agcgaccctt tgcaggcagc ggaacccccc acctggcgac aggtgcctct 5340
gcggccaaaa gccacgtgta taagatacac ctgcaaaggc ggcacaaccc cagtgccacg 5400
ttgtgagttg gatagttgtg gaaagagtca aatggctctc ctcaagcgta ttcaacaagg 5460
ggctgaagga tgcccagaag gtaccccatt gtatgggatc tgatctgggg cctcggtgca 5520
catgctttac atgtgtttag tcgaggttaa aaaacgtcta ggccccccga accacgggga 5580
cgtggttttc ctttgaaaaa cacgatctct aggcgccacc atgaagctac tgtcttctat 5640
cgaacaagca tgcgatattt gccgacttaa aaagctcaag tgctccaaag aaaaaccgaa 5700
gtgcgccaag tgtctgaaga acaactggga gtgtcgctac tctcccaaaa ccaaaaggtc 5760
tccgctgact agggcacatc tgacagaagt ggaatcaagg ctagaaagac tggaacagct 5820
atttctactg atttttcctc gagaagacct tgacatgatt ttgaaaatgg attctttaca 5880
ggatataaaa gcattgttaa caggattatt tgtacaagat aatgtgaata aagatgccgt 5940
cacagataga ttggcttcag tggagactga tatgcctcta acattgagac agcatagaat 6000
aagtgcgaca tcatcatcgg aagagagtag taacaaaggt caaagacagt tgactgtatc 6060
gccggaattc ccggggatcc ggcctgagtg cgtagtaccc gagactcagt gcgccatgaa 6120
gcggaaagag aagaaagcac agaaggagaa ggacaaactg cctgtcagca cgacgacggt 6180
ggacgaccac atgccgccca ttatgcagtg tgaacctcca cctcctgaag cagcaaggat 6240
tcacgaagtg gtcccaaggt ttctctccga caagctgttg gtgacaaacc ggcagaaaaa 6300
catcccccag ttgacagcca accagcagtt ccttatcgcc aggctcatct ggtaccagga 6360
cgggtacgag cagccttctg atgaagattt gaagaggatt acgcagacgt ggcagcaagc 6420
ggacgatgaa aacgaagagt cggacactcc cttccgccag atcacagaga tgactatcct 6480
cacggtccaa cttatcgtgg agttcgcgaa gggattgcca gggttcgcca agatctcgca 6540
gcctgatcaa attacgctgc ttaaggcttg ctcaagtgag gtaatgatgc tccgagtcgc 6600
gcgacgatac gatgcggcct cagacagtat tctgttcgcg aacaaccaag cgtacactcg 6660
cgacaactac cgcaaggctg gcatggccga ggtcatcgag gatctactgc acttctgccg 6720
gtgcatgtac tctatggcgt tggacaacat ccattacgcg ctgctcacgg ctgtcgtcat 6780
cttttctgac cggccagggt tggagcagcc gcaactggtg gaagagatcc agcggtacta 6840
cctgaatacg ctccgcatct atatcctgaa ccagctgagc gggtcggcgc gttcgtccgt 6900
catatacggc aagatcctct caatcctctc tgagctacgc acgctcggca tgcaaaactc 6960
caacatgtgc atctccctca agctcaagaa cagaaagctg ccgcctttcc tcgaggagat 7020
ctgggatgtg gcggacatgt cgcacaccca accgccgcct atcctcgagt cccccacgaa 7080
tctctaggcg gcctctagag cggccgccac cgcggggaga tccagacatg ataagataca 7140
ttgatgagtt tggacaaacc acaactagaa tgcagtgaaa aaaatgcttt atttgtgaaa 7200
tttgtgatgc tattgcttta tttgtaacca ttataagctg caataaacaa gttaacaaca 7260
acaattgcat tcattttatg tttcaggttc agggggaggt gtgggaggtt ttttaaagca 7320
agtaaaacct ctacaaatgt ggtatggctg attatgatcc ggctgcctcg cgcgtttcgg 7380
tgatgacggt gaaaacctct gacacatgca gctcccggag acggtcacag cttgtctgta 7440
agcggatgcc gggagcagac aagcccgtca gggcgcgtca gcgggtgttg gcgggtgtcg 7500

-continued

```
gggcgcagcc atgaggtcga ctctagtccc cgcggtggca gatctggaag gtgctgaggt   7560
acgatgagac ccgcaccagg tgcagaccct gcgagtgtgg cggtaaacat attaggaacc   7620
agcctgtgat gctggatgtg accgaggagc tgaggcccga tcacttggtg ctggcctgca   7680
cccgcgctga gtttggctct agcgatgaag atacagattg aggtactgaa atgtgtgggc   7740
gtggcttaag ggtgggaaag aatatataag gtgggggtct tatgtagttt tgtatctgtt   7800
ttgcagcagc cgccgccgcc atgagcacca actcgtttga tggaagcatt gtgagctcat   7860
atttgacaac gcgcatgccc ccatgggccg gggtgcgtca gaatgtgatg ggctccagca   7920
ttgatggtcg ccccgtcctg cccgcaaact ctactacctt gacctacgag accgtgtctg   7980
gaacgccgtt ggagactgca gcctccgccg ccgcttcagc cgctgcagcc accgcccgcg   8040
ggattgtgac tgactttgct ttcctgagcc cgcttgcaag cagtgcagct tcccgttcat   8100
ccgcccgcga tgacaagttg acggctcttt tggcacaatt ggattctttg acccgggaac   8160
ttaatgtcgt ttctcagcag ctgttggatc tgcgccagca ggtttctgcc ctgaaggctt   8220
cctcccctcc caatgcggtt taaaacataa ataaaaaacc agactctgtt tggatttgga   8280
tcaagcaagt gtcttgctgt ctttatttag gggttttgcg cgcgcggtag gcccgggacc   8340
agcggtctcg gtcgttgagg gtcctgtgta tttttttccag gacgtggtaa aggtgactct   8400
ggatgttcag atacatgggc ataagcccgt ctctggggtg gaggtagcac cactgcagag   8460
cttcatgctg cggggtggtg ttgtagatga tccagtcgta gcaggagcgc tgggcgtggt   8520
gcctaaaaat gtctttcagt agcaagctga ttgccagggg caggcccttg gtgtaagtgt   8580
ttacaaagcg gttaagctgg gatgggtgca tacgtgggga tatgagatgc atcttggact   8640
gtatttttag gttggctatg ttcccagcca tatccctccg ggattcatg ttgtgcagaa   8700
ccaccagcac agtgtatccg gtgcacttgg gaaatttgtc atgtagctta gaaggaaatg   8760
cgtggaagaa cttggagacg cccttgtgac ctccaagatt ttccatgcat tcgtccataa   8820
tgatggcaat gggcccacgg gcggcggcct gggcgaagat atttctggga tcactaacgt   8880
catagttgtg ttccaggatg agatcgtcat aggccatttt tacaaagcgc gggcggaggg   8940
tgccagactg cggtataatg gttccatccg gcccaggggc gtagttaccc tcacagattt   9000
gcatttccca cgctttgagt tcagatgggg ggatcatgtc tacctgcggg gcgatgaaga   9060
aaacggtttc cggggtaggg gagatcagct gggaagaaag caggttcctg agcagctgcg   9120
acttaccgca gccggtgggc ccgtaaatca cacctattac cggctgcaac tggtagttaa   9180
gagagctgca gctgccgtca tccctgagca ggggggccac ttcgttaagc atgtccctga   9240
ctcgcatgtt ttccctgacc aaatccgcca gaaggcgctc gccgcccagc gatagcagtt   9300
cttgcaagga agcaaagttt ttcaacggtt tgagaccgtc cgccgtaggc atgcttttga   9360
gcgtttgacc aagcagttcc aggcggtccc acagctcggt cacctgctct acggcatctc   9420
gatccagcat atctcctcgt ttcgcgggtt ggggcggctt tcgctgtacg gcagtagtcg   9480
gtgctcgtcc agacgggcca gggtcatgtc tttccacggg cgcagggtcc tcgtcagcgt   9540
agtctgggtc acggtgaagg ggtgcgctcc gggctgcgcg ctggccaggg tgcgcttgag   9600
gctggtcctg ctggtgctga agcgctgccg gtcttcgccc tgcgcgtcgg ccaggtagca   9660
tttgaccatg gtgtcatagt ccagcccctc cgcggcgtgg cccttggcgc gcagcttgcc   9720
cttggaggag gcgccgcacg aggggcagtg cagacttttg agggcgtaga gcttgggcgc   9780
gagaaatacc gattccgggg agtaggcatc cgcgccgcag gccccgcaga cggtctcgca   9840
ttccacgagc caggtgagct ctggccgttc ggggtcaaaa accaggtttc ccccatgctt   9900
```

-continued

```
tttgatgcgt ttcttacctc tggtttccat gagccggtgt ccacgctcgg tgacgaaaag   9960
gctgtccgtg tccccgtata cagacttgag aggcctgtcc tcgaccgatg cccttgagag  10020
ccttcaaccc agtcagctcc ttccggtggg cgcggggcat gactatcgtc gccgcactta  10080
tgactgtctt ctttatcatg caactcgtag gacaggtgcc ggcagcgctc tgggtcattt  10140
tcggcgagga ccgctttcgc tggagcgcga cgatgatcgg cctgtcgctt gcggtattcg  10200
gaatcttgca cgccctcgct caagccttcg tcactggtcc cgccaccaaa cgtttcggcg  10260
agaagcaggc cattatcgcc ggcatggcgg ccgacgcgct gggctacgtc ttgctggcgt  10320
tcgcgacgcg aggctggatg gccttcccca ttatgattct tctcgcttcc ggcggcatcg  10380
ggatgcccgc gttgcaggcc atgctgtcca ggcaggtaga tgacgaccat cagggacagc  10440
ttcaaggcca gcaaaaggcc aggaaccgta aaaaggccgc gttgctggcg tttttccata  10500
ggctccgccc ccctgacgag catcacaaaa atcgacgctc aagtcagagg tggcgaaacc  10560
cgacaggact ataaagatac caggcgtttc cccctggaag ctccctcgtg cgctctcctg  10620
ttccgaccct gccgcttacc ggatacctgt ccgcctttct cccttcggga agcgtggcgc  10680
tttctcatag ctcacgctgt aggtatctca gttcggtgta ggtcgttcgc tccaagctgg  10740
gctgtgtgca cgaacccccc gttcagcccg accgctgcgc cttatccggt aactatcgtc  10800
ttgagtccaa cccggtaaga cacgacttat cgccactggc agcagccact ggtaacagga  10860
ttagcagagc gaggtatgta ggcggtgcta cagagttctt gaagtggtgg cctaactacg  10920
gctacactag aaggacagta tttggtatct gcgctctgct gaagccagtt accttcggaa  10980
aaagagttgg tagctcttga tccggcaaac aaaccaccgc tggtagcggt ggtttttttg  11040
tttgcaagca gcagattacg cgcagaaaaa aaggatctca agaagatcct ttgatctttt  11100
ctacggggtc tgacgctcag tggaacgaaa actcacgtta agggattttg gtcatgagat  11160
tatcaaaaag gatcttcacc tagatccttt taaattaaaa atgaagtttt aaatcaatct  11220
aaagtatata tgagtaaact tggtctgaca gttaccaatg cttaatcagt gaggcaccta  11280
tctcagcgat ctgtctattt cgttcatcca tagttgcctg actccccgtc gtgtagataa  11340
ctacgatacg ggagggctta ccatctggcc ccagtgctgc aatgataccg cgagacccac  11400
gctcaccggc tccagattta tcagcaataa accagccagc cggaagggcc gagcgcagaa  11460
gtggtcctgc aactttatcc gcctccatcc agtctattaa ttgttgccgg gaagctagag  11520
taagtagttc gccagttaat agtttgcgca acgttgttgc cattgctgca ggcatcgtgg  11580
tgtcacgctc gtcgtttggt atggcttcat tcagctccgg ttcccaacga tcaaggcgag  11640
ttacatgatc ccccatgttg tgcaaaaaag cggttagctc cttcggtcct ccgatcgttg  11700
tcagaagtaa gttggccgca gtgttatcac tcatggttat ggcagcactg cataattctc  11760
ttactgtcat gccatccgta agatgctttt ctgtgactgg tgagtactca accaagtcat  11820
tctgagaata gtgtatgcgg cgaccgagtt gctcttgccc ggcgtcaaca cgggataata  11880
ccgcgccaca tagcagaact ttaaaagtgc tcatcattgg aaaacgttct tcggggcgaa  11940
aactctcaag gatcttaccg ctgttgagat ccagttcgat gtaacccact cgtgcaccca  12000
actgatcttc agcatctttt actttcacca gcgtttctgg gtgagcaaaa acaggaaggc  12060
aaaatgccgc aaaaaaggga ataagggcga cacggaaatg ttgaatactc atactcttcc  12120
tttttcaata ttattgaagc atttatcagg gttattgtct catgagcgga tacatatttg  12180
aatgtattta gaaaaa                                                  12196
```

<210> SEQ ID NO 62
<211> LENGTH: 12166
<212> TYPE: DNA
<213> ORGANISM: Artificial Sequence
<220> FEATURE:
<223> OTHER INFORMATION: Ad-RTS-mIL-12 is VVN2539

<400> SEQUENCE: 62
taaacaaata ggggttccgc gcacatttcc ccgaaaagtg ccacctgacg tctaagaaac 60
cattattatc atgacattaa cctataaaaa taggcgtatc acgaggccct ttcgtcttca 120
agaaaattaa ttaagctagc atcatcaata atataccta ttttggattg aagccaatat 180
gataatgagg gggtggagtt tgtgacgtgg cgcggggcgt gggaacgggg cgggtgacgt 240
agtagtgtgg cggaagtgtg atgttgcaag tgtggcggaa cacatgtaag cgacggatgt 300
ggcaaaagtg acgtttttgg tgtgcgccgg tgtacacagg aagtgacaat tttcgcgcgg 360
ttttaggcgg atgttgtagt aaatttgggc gtaaccgagt aagatttggc cattttcgcg 420
ggaaaactga ataagaggaa gtgaaatctg aataattttg tgttactcat agcgcgtaat 480
atttgtctag ggagatccgg taccggcgcg cgcgccgttt ggccgcctcg agtctagaga 540
tccggtgagt gattaggcgc gcaccaggtg ccgcaataaa atatctttat tttcattaca 600
tctgtgtgtt ggtttttgt gtgaatcgat agtactaaca tacgctctcc atcaaaacaa 660
aacgaaacaa aacaaactag caaaataggc tgtccccagt gcaagtgcag gtgccagaac 720
atttctctat cgataatgca ggtcggagta ctgtcctccg agcggagtac tgtcctccga 780
gcggagtact gtcctccgag cggagtactg tcctccgagc ggagtactgt cctccgagcg 840
gagtactgtc ctccgagcgg agactcttcg aaggaagagg ggcggggtcg atcgaccccg 900
cccctcttcc ttcgaaggaa gaggggcggg gtcgaagacc tagagggtat ataatgggtg 960
ccttagctgg tgtgtgagct catcttcctg tagatcacgc gtgccaccat gtgtcctcag 1020
aagctaacca tctcctggtt tgccatcgtt ttgctggtgt ctccactcat ggccatgtgg 1080
gagctggaga aagacgttta tgttgtagag gtggactgga ctcccgatgc ccctggagaa 1140
acagtgaacc tcacctgtga cacgcctgaa gaagatgaca tcacctggac ctcagaccag 1200
agacatggag tcataggctc tggaaagacc ctgaccatca ctgtcaaaga gtttctagat 1260
gctggccagt acacctgcca caaaggaggc gagactctga gccactcaca tctgctgctc 1320
cacaagaagg aaaatggaat ttggtccact gaaattttaa aaaatttcaa aaacaagact 1380
ttcctgaagt gtgaagcacc aaattactcc ggacggttca cgtgctcatg gctggtgcaa 1440
agaaacatgg acttgaagtt caacatcaag agcagtagca gtcccccga ctctcgggca 1500 gtgacatgtg gaatggcgtc tctgtctgca gagaaggtca cactggacca aagggactat 1560
gagaagtatt cagtgtcctg ccaggaggat gtcacctgcc caactgccga ggagaccctg 1620
cccattgaac tggcgttgga agcacggcag cagaataaat atgagaacta cagcaccagc 1680
ttcttcatca gggacatcat caaaccagac ccgcccaaga acttgcagat gaagcctttg 1740
aagaactcac aggtggaggt cagctgggag taccctgact cctggagcac tccccattcc 1800
tacttctccc tcaagttctt tgttcgaatc cagcgcaaga aagaaaagat gaaggagaca 1860
gaggaggggt gtaaccagaa aggtgcgttc ctcgtagaga agacatctac cgaagtccaa 1920
tgcaaaggcg ggaatgtctg cgtgcaagct caggatcgct attacaattc ctcatgcagc 1980
aagtgggcat gtgttccctg cagggtccga tcctaggatg caacggatcc gaattccgcc 2040
cccctctccc tcccccccc ctaacgttac tggccgaagc cgcttggaat aaggccggtg 2100

-continued

```
tgcgtttgtc tatatgttat tttccaccat attgccgtct tttggcaatg tgagggcccg   2160
gaaacctggc cctgtcttct tgacgagcat tcctaggggt ctttcccctc tcgccaaagg   2220
aatgcaaggt ctgttgaatg tcgtgaagga agcagttcct ctggaagctt cttgaagaca   2280
aacaacgtct gtagcgaccc tttgcaggca gcggaacccc ccacctggcg acaggtgcct   2340
ctgcggccaa aagccacgtg tataagatac acctgcaaag gcggcacaac cccagtgcca   2400
cgttgtgagt tggatagttg tggaaagagt caaatggctc tcctcaagcg tattcaacaa   2460
ggggctgaag gatgcccaga aggtacccca ttgtatggga tctgatctgg ggcctcggtg   2520
cacatgcttt acatgtgttt agtcgaggtt aaaaaaacgt ctaggccccc cgaaccacgg   2580
ggacgtggtt ttcctttgaa aaacacgatg ataatatggc cacaaccatg ggtcaatcac   2640
gctacctcct ctttttggcc acccttgccc tcctaaacca cctcagtttg gccagggtca   2700
ttccagtctc tggacctgcc aggtgtctta gccagtcccg aaacctgctg aagaccacag   2760
atgacatggt gaagacggcc agagaaaagc tgaaacatta ttcctgcact gctgaagaca   2820
tcgatcatga agacatcaca cgggaccaaa ccagcacatt gaagacctgt ttaccactgg   2880
aactacacaa gaacgagagt tgcctggcta ctagagagac ttcttccaca acaagaggga   2940
gctgcctgcc cccacagaag acgtctttga tgatgaccct gtgccttggt agcatctatg   3000
aggacttgaa gatgtaccag acagagttcc aggccatcaa cgcagcactt cagaatcaca   3060
accatcagca gatcattcta gacaagggca tgctggtggc catcgatgag ctgatgcagt   3120
ctctgaatca taatggcgag actctgcgcc agaaacctcc tgtgggagaa gcagaccctt   3180
acagagtgaa aatgaagctc tgcatcctgc ttcacgcctt cagcacccgc gtcgtgacca   3240
tcaacagggt gatgggctat ctgagctccg cctgagtcga catcgagaac ttgtttattg   3300
cagcttataa tggttacaaa taaagcaata gcatcacaaa tttcacaaat aaagcatttt   3360
tttcactgca ttctagttgt ggtttgtcca aactcatcaa tgtatcttat catgtctggc   3420
gcgccggcct ccgcgccggg ttttggcgcc tcccgcgggc gcccccctcc tcacggcgag   3480
cgctgccacg tcagacgaag ggcgcaggag cgtcctgatc cttccgcccg gacgctcagg   3540
acagcggccc gctgctcata agactcggcc ttagaacccc agtatcagca gaaggacatt   3600
ttaggacggg acttgggtga ctctagggca ctggttttct ttccagagag cggaacaggc   3660
gaggaaaagt agtcccttct cggcgattct gcggagggat ctccgtgggg cggtgaacgc   3720
cgatgattat ataaggacgc gccgggtgtg gcacagctag ttccgtcgca gccgggattt   3780
gggtcgcggt tcttgtttgt ggatcgctgt gatcgtcact tggtgagtag cgggctgctg   3840
ggctgggtac gtgcgctcgg ggttggcgag tgtgttttgt gaagtttttt aggcaccttt   3900
tgaaatgtaa tcatttgggt caatatgtaa ttttcagtgt tagactagta aattgtccgc   3960
taaattctgg ccgtttttgg ctttttttgtt agacgagcta gcgccgccac catgggccct   4020
aaaaagaagc gtaaagtcgc ccccccgacc gatgtcagcc tgggggacga gctccactta   4080
gacggcgagg acgtggcgat ggcgcatgcc gacgcgctag acgatttcga tctggacatg   4140
ttgggggacg gggattcccc ggggccggga tttacccccc acgactccgc cccctacggc   4200
gctctggata tggccgactt cgagtttgag cagatgttta ccgatgccct tggaattgac   4260
gagtacggtg gggaattcga gatgcctgtg gacaggatcc tggaggcaga gcttgctgtg   4320
gaacagaaga gtgaccaggg cgttgagggt cctgggggaa ccgggggtag cggcagcagc   4380
ccaaatgacc ctgtgactaa catctgtcag gcagctgaca aacagctatt cacgcttgtt   4440
```

```
gagtgggcga agaggatccc acacttttcc tccttgcctc tggatgatca ggtcatattg   4500
ctgcgggcag gctggaatga actcctcatt gcctcctttt cacaccgatc cattgatgtt   4560
cgagatggca tcctccttgc cacaggtctt cacgtgcacc gcaactcagc ccattcagca   4620
ggagtaggag ccatctttga tcgggtgctg acagagctag tgtccaaaat gcgtgacatg   4680
aggatggaca agacagagct tggctgcctg agggcaatca ttctgtttaa tccagaggtg   4740
aggggtttga aatccgccca ggaagttgaa cttctacgtg aaaaagtata tgccgctttg   4800
gaagaatata ctagaacaac acatcccgat gaaccaggaa gatttgcaaa acttttgctt   4860
cgtctgcctt ctttacgttc cataggcctt aagtgtttgg agcatttgtt tttctttcgc   4920
cttattggag atgttccaat tgatacgttc ctgatggaga tgcttgaatc accttctgat   4980
tcataatcta gcggccctag cccccctctc cctccccccc ccctaacgtt actggccgaa   5040
gccgcttgga ataaggccgg tgtgcgtttg tctatatgtt attttccacc atattgccgt   5100
cttttggcaa tgtgagggcc cggaaacctg gccctgtctt cttgacgagc attcctaggg   5160
gtctttcccc tctcgccaaa ggaatgcaag gtctgttgaa tgtcgtgaag gaagcagttc   5220
ctctggaagc ttcttgaaga caaacaacgt ctgtagcgac cctttgcagg cagcggaacc   5280
ccccacctgg cgacaggtgc ctctgcggcc aaaagccacg tgtataagat acacctgcaa   5340
aggcggcaca accccagtgc cacgttgtga gttggatagt tgtggaaaga gtcaaatggc   5400
tctcctcaag cgtattcaac aaggggctga aggatgccca gaaggtaccc cattgtatgg   5460
gatctgatct ggggcctcgg tgcacatgct ttacatgtgt ttagtcgagg ttaaaaaacg   5520
tctaggcccc ccgaaccacg gggacgtggt tttcctttga aaaacacgat ctctagggcc   5580
gcgccaccat gaagctactg tcttctatcg aacaagcatg cgatatttgc cgacttaaaa   5640
agctcaagtg ctccaaagaa aaaccgaagt gcgccaagtg tctgaagaac aactgggagt   5700
gtcgctactc tcccaaaacc aaaaggtctc cgctgactag ggcacatctg acagaagtgg   5760
aatcaaggct agaaagactg gaacagctat ttctactgat tttcctcga gaagaccttg   5820
acatgatttt gaaaatggat tctttacagg atataaaagc attgttaaca ggattatttg   5880
tacaagataa tgtgaataaa gatgccgtca cagatagatt ggcttcagtg gagactgata   5940
tgcctctaac attgagacag catagaataa gtgcgacatc atcatcggaa gagagtagta   6000
acaaaggtca aagacagttg actgtatcgc cggaattccc ggggatccgg cctgagtgcg   6060
tagtacccga gactcagtgc gccatgaagc ggaaagagaa gaaagcacag aaggagaagg   6120
acaaactgcc tgtcagcacg acgacggtgg acgaccacat gccgcccatt atgcagtgtg   6180
aacctccacc tcctgaagca gcaaggattc acgaagtggt cccaaggttt ctctccgaca   6240
agctgttgga gacaaaccgg cagaaaaaca tcccccagtt gacagccaac cagcagttcc   6300
ttatcgccag gctcatctgg taccaggacg ggtacgagca gccttctgat gaagatttga   6360
agaggattac gcagacgtgg cagcaagcgg acgatgaaaa cgaagagtcg gacactccct   6420
tccgccagat cacagagatg actatcctca cggtccaact tatcgtggag ttcgcgaagg   6480
gattgccagg gttcgccaag atctcgcagc ctgatcaaat tacgctgctt aaggcttgct   6540
caagtgaggt aatgatgctc cgagtcgcgc gacgatacga tgcggcctca gacagtattc   6600
tgttcgcgaa caaccaagcg tacactcgcg acaactaccg caaggctggc atggccgagg   6660
tcatcgagga tctactgcac ttctgccggt gcatgtactc tatggcgttg gacaacatcc   6720
attacgcgct gctcacggct gtcgtcatct tttctgaccg gccagggttg gagcagccgc   6780
aactggtgga agagatccag cggtactacc tgaatacgct ccgcatctat atcctgaacc   6840
```

agctgagcgg gtcggcgcgt tcgtccgtca tatacggcaa gatcctctca atcctctctg 6900
agctacgcac gctcggcatg caaaactcca acatgtgcat ctccctcaag ctcaagaaca 6960
gaaagctgcc gcctttcctc gaggagatct gggatgtggc ggacatgtcg cacacccaac 7020
cgccgcctat cctcgagtcc cccacgaatc tctaggcggc ctctagagcg gccgccaccg 7080
cggggagatc cagacatgat aagatacatt gatgagtttg gacaaaccac aactagaatg 7140
cagtgaaaaa aatgctttat ttgtgaaatt tgtgatgcta ttgctttatt tgtaaccatt 7200
ataagctgca ataaacaagt taacaacaac aattgcattc attttatgtt tcaggttcag 7260
ggggaggtgt gggaggtttt ttaaagcaag taaaacctct acaaatgtgg tatggctgat 7320
tatgatcccg gctgcctcgc gcgtttcggt gatgacggtg aaaacctctt gacacatgca 7380
gctcccggag acggtcacag cttgtctgta agcggatgcc gggagcagac aagcccgtca 7440
gggcgcgtca gcgggtgttg gcgggtgtcg gggcgcagcc atgaggtcga ctctagtccc 7500
cgcggtggca gatctggaag gtgctgaggt acgatgagac ccgcaccagg tgcagaccct 7560
gcgagtgtgg cggtaaacat attaggaacc agcctgtgat gctggatgtg accgaggagc 7620
tgaggcccga tcacttggtg ctggcctgca cccgcgctga gtttggctct agcgatgaag 7680
atacagattg aggtactgaa atgtgtgggc gtggcttaag ggtgggaaag aatatataag 7740
gtgggggtct tatgtagttt tgtatctgtt ttgcagcagc cgccgccgcc atgagcacca 7800
actcgtttga tggaagcatt gtgagctcat atttgacaac gcgcatgccc ccatgggccg 7860
gggtgcgtca gaatgtgatg ggctccagca ttgatggtcg ccccgtcctg cccgcaaact 7920
ctactacctt gacctacgag accgtgtctg gaacgccgtt ggagactgca gcctccgccg 7980
ccgcttcagc cgctgcagcc accgcccgcg ggattgtgac tgactttgct ttcctgagcc 8040
cgcttgcaag cagtgcagct tcccgttcat ccgcccgcga tgacaagttg acggctcttt 8100
tggcacaatt ggattctttg acccgggaac ttaatgtcgt ttctcagcag ctgttggatc 8160
tgcgccagca ggtttctgcc ctgaaggctt cctcccctcc caatgcggtt taaaacataa 8220
ataaaaaacc agactctgtt tggatttgga tcaagcaagt gtcttgctgt ctttatttag 8280
gggttttgcg cgcgcggtag gcccgggacc agcggtctcg gtcgttgagg gtcctgtgta 8340 tttttccag gacgtggtaa aggtgactct ggatgttcag atacatgggc ataagcccgt 8400
ctctggggtg gaggtagcac cactgcagag cttcatgctg cggggtggtg ttgtagatga 8460
tccagtcgta gcaggagcgc tgggcgtggt gcctaaaaat gtctttcagt agcaagctga 8520
ttgccagggg caggcccttg gtgtaagtgt ttacaaagcg gttaagctgg gatgggtgca 8580
tacgtgggga tatgagatgc atcttggact gtatttttag gttggctatg ttcccagcca 8640
tatccctccg ggattcatg ttgtgcagaa ccaccagcac agtgtatccg gtgcacttgg 8700
gaaatttgtc atgtagctta gaaggaaatg cgtggaagaa cttggagacg cccttgtgac 8760
ctccaagatt ttccatgcat tcgtccataa tgatggcaat gggcccacgg gcggcggcct 8820
gggcgaagat atttctggga tcactaacgt catagttgtg ttccaggatg agatcgtcat 8880
aggccatttt tacaaagcgc gggcggaggg tgccagactg cggtataatg gttccatccg 8940
gcccaggggc gtagttaccc tcacagattt gcatttccca cgctttgagt tcagatgggg 9000
ggatcatgtc tacctgcggg gcgatgaaga aaacggtttc cggggtaggg gagatcagct 9060
gggaagaaag caggttcctg agcagctgcg acttaccgca gccggtgggc ccgtaaatca 9120
cacctattac cgggtgcaac tggtagttaa gagagctgca gctgccgtca tccctgagca 9180

-continued gggggggccac ttcgttaagc atgtccctga ctcgcatgtt ttccctgacc aaatccgcca 9240
gaaggcgctc gccgcccagc gatagcagtt cttgcaagga agcaaagttt ttcaacggtt 9300
tgagaccgtc cgccgtaggc atgcttttga gcgtttgacc aagcagttcc aggcggtccc 9360
acagctcggt cacctgctct acggcatctc gatccagcat atctcctcgt ttcgcgggtt 9420
ggggcggctt tcgctgtacg gcagtagtcg gtgctcgtcc agacgggcca gggtcatgtc 9480
tttccacggg cgcagggtcc tcgtcagcgt agtctgggtc acggtgaagg ggtgcgctcc 9540
gggctgcgcg ctggccaggg tgcgcttgag gctggtcctg ctggtgctga agcgctgccg 9600
gtcttcgccc tgcgcgtcgg ccaggtagca tttgaccatg gtgtcatagt ccagcccctc 9660
cgcggcgtgg cccttggcgc gcagcttgcc cttggaggag gcgccgcacg aggggcagtg 9720
cagacttttg agggcgtaga gcttgggcgc gagaaatacc gattccgggg agtaggcatc 9780
cgcgccgcag gccccgcaga cggtctcgca ttccacgagc caggtgagct ctggccgttc 9840
ggggtcaaaa accaggtttc ccccatgctt tttgatgcgt ttcttacctc tggtttccat 9900
gagccggtgt ccacgctcgg tgacgaaaag gctgtccgtg tccccgtata cagacttgag 9960
aggcctgtcc tcgaccgatg cccttgagag ccttcaaccc agtcagctcc ttccggtggg 10020
cgcggggcat gactatcgtc gccgcactta tgactgtctt ctttatcatg caactcgtag 10080
gacaggtgcc ggcagcgctc tgggtcattt tcggcgagga ccgctttcgc tggagcgcga 10140
cgatgatcgg cctgtcgctt gcggtattcg gaatcttgca cgccctcgct caagccttcg 10200
tcactggtcc cgccaccaaa cgtttcggcg agaagcaggc cattatcgcc ggcatggcgg 10260
ccgacgcgct gggctacgtc ttgctggcgt tcgcgacgcg aggctggatg gccttcccca 10320
ttatgattct tctcgcttcc ggcggcatcg ggatgcccgc gttgcaggcc atgctgtcca 10380
ggcaggtaga tgacgaccat cagggacagc ttcaaggcca gcaaaaggcc aggaaccgta 10440
aaaaggccgc gttgctggcg tttttccata ggctccgccc ccctgacgag catcacaaaa 10500
atcgacgctc aagtcagagg tggcgaaacc cgacaggact ataaagatac caggcgtttc 10560
cccctggaag ctccctcgtg cgctctcctg ttccgaccct gccgcttacc ggatacctgt 10620
ccgcctttct cccttcggga agcgtggcgc tttctcatag ctcacgctgt aggtatctca 10680
gttcggtgta ggtcgttcgc tccaagctgg gctgtgtgca cgaacccccc gttcagcccg 10740
accgctgcgc cttatccggt aactatcgtc ttgagtccaa cccggtaaga cacgacttat 10800
cgccactggc agcagccact ggtaacagga ttagcagagc gaggtatgta ggcggtgcta 10860
cagagttctt gaagtggtgg cctaactacg gctacactag aaggacagta tttggtatct 10920
gcgctctgct gaagccagtt accttcggaa aaagagttgg tagctcttga tccggcaaac 10980
aaaccaccgc tggtagcggt ggtttttttg tttgcaagca gcagattacg cgcagaaaaa 11040
aaggatctca agaagatcct ttgatctttt ctacggggtc tgacgctcag tggaacgaaa 11100
actcacgtta agggattttg gtcatgagat tatcaaaaag gatcttcacc tagatccttt 11160
taaattaaaa atgaagtttt aaatcaatct aaagtatata tgagtaaact tggtctgaca 11220
gttaccaatg cttaatcagt gaggcaccta tctcagcgat ctgtctattt cgttcatcca 11280
tagttgcctg actccccgtc gtgtagataa ctacgatacg ggagggctta ccatctggcc 11340
ccagtgctgc aatgataccg cgagacccac gctcaccggc tccagattta tcagcaataa 11400
accagccagc cggaagggcc gagcgcagaa gtggtcctgc aactttatcc gcctccatcc 11460
agtctattaa ttgttgccgg gaagctagag taagtagttc gccagttaat agtttgcgca 11520
acgttgttgc cattgctgca ggcatcgtgg tgtcacgctc gtcgtttggt atggcttcat 11580

-continued tcagctccgg ttcccaacga tcaaggcgag ttacatgatc ccccatgttg tgcaaaaaag 11640
cggttagctc cttcggtcct ccgatcgttg tcagaagtaa gttggccgca gtgttatcac 11700
tcatggttat ggcagcactg cataattctc ttactgtcat gccatccgta agatgctttt 11760
ctgtgactgg tgagtactca accaagtcat tctgagaata gtgtatgcgg cgaccgagtt 11820
gctcttgccc ggcgtcaaca cgggataata ccgcgccaca tagcagaact ttaaaagtgc 11880
tcatcattgg aaaacgttct tcggggcgaa aactctcaag gatcttaccg ctgttgagat 11940
ccagttcgat gtaacccact cgtgcaccca actgatcttc agcatctttt actttcacca 12000
gcgtttctgg gtgagcaaaa acaggaaggc aaaatgccgc aaaaaaggga ataagggcga 12060
cacggaaatg ttgaatactc atactcttcc tttttcaata ttattgaagc atttatcagg 12120
gttattgtct catgagcgga tacatatttg aatgtattta gaaaaa 12166

<210> SEQ ID NO 63
<211> LENGTH: 193
<212> TYPE: PRT
<213> ORGANISM: Homo sapiens

<400> SEQUENCE: 63

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 64
<211> LENGTH: 240
<212> TYPE: PRT
<213> ORGANISM: Choristoneura fumiferana

<400> SEQUENCE: 64

```
Leu Thr Ala Asn Gln Gln Phe Leu Ile Ala Arg Leu Ile Trp Tyr Gln
1               5                   10                  15

Asp Gly Tyr Glu Gln Pro Ser Asp Glu Asp Leu Lys Arg Ile Thr Gln
```

```
            20                  25                  30

Thr Trp Gln Gln Ala Asp Asp Glu Asn Glu Glu Ser Asp Thr Pro Phe
        35                  40                  45

Arg Gln Ile Thr Glu Met Thr Ile Leu Thr Val Gln Leu Ile Val Glu
    50                  55                  60

Phe Ala Lys Gly Leu Pro Gly Phe Ala Lys Ile Ser Gln Pro Asp Gln
65                  70                  75                  80

Ile Thr Leu Leu Lys Ala Cys Ser Ser Glu Val Met Met Leu Arg Val
                85                  90                  95

Ala Arg Arg Tyr Asp Ala Ala Ser Asp Ser Val Leu Phe Ala Asn Asn
            100                 105                 110

Gln Ala Tyr Thr Arg Asp Asn Tyr Arg Lys Ala Gly Met Ala Tyr Val
        115                 120                 125

Ile Glu Asp Leu Leu His Phe Cys Arg Cys Met Tyr Ser Met Ala Leu
    130                 135                 140

Asp Asn Ile His Tyr Ala Leu Leu Thr Ala Val Val Ile Phe Ser Asp
145                 150                 155                 160

Arg Pro Gly Leu Glu Gln Pro Gln Leu Val Glu Glu Ile Gln Arg Tyr
                165                 170                 175

Tyr Leu Asn Thr Leu Arg Ile Tyr Ile Leu Asn Gln Leu Ser Gly Ser
            180                 185                 190

Ala Arg Ser Ser Val Ile Tyr Gly Lys Ile Leu Ser Ile Leu Ser Glu
        195                 200                 205

Leu Arg Thr Leu Gly Met Gln Asn Ser Asn Met Cys Ile Ser Leu Lys
    210                 215                 220

Leu Lys Asn Arg Lys Leu Pro Pro Phe Leu Glu Glu Ile Trp Asp Val
225                 230                 235                 240
```

```
<210> SEQ ID NO 65
<211> LENGTH: 582
<212> TYPE: DNA
<213> ORGANISM: Homo sapiens
<220> FEATURE:
<221> NAME/KEY: misc_feature
<222> LOCATION: (1)..(582)
<223> OTHER INFORMATION: human erythropoietn expression vector (contains
      signal peptide and stop codon)

<400> SEQUENCE: 65

atgggagtgc atgagtgtcc cgcttggctc tggctcctgc tgtccctcct gtccctgcct     60

ctgggactgc ctgtgctcgg agcccccccc agactgatct gcgacagcag agtgctggag    120

agatacctgt tggaggccaa ggaagccgag aacatcacca ccggctgcgc cgagcactgc    180

tccctgaacg agaacatcac cgtgcccgac accaaggtga acttctacgc ctggaagcgc    240

atggaggtgg gccagcaggc cgtggaggtg tggcagggcc tggccctgct gtccgaggcc    300

gtgctgagag gccaggccct gctggtgaac agcagccagc cctgggagcc cctgcaactg    360

cacgttgaca aggccgtgag cggcctgaga agcctgacca ccctgctgag agccctgggc    420

gctcagaagg aggccatcag cccccccgac gccgccagcg ccgcccccct gagaaccatc    480

accgccgaca ccttcagaaa gctgttcaga gtgtacagca acttcctgag aggcaagctg    540

aagctgtaca ccggcgaggc ttgcagaacc ggcgacagat ga                       582


<210> SEQ ID NO 66
<211> LENGTH: 2300
<212> TYPE: DNA
<213> ORGANISM: Homo sapiens
```

<220> FEATURE:
<221> NAME/KEY: misc_feature
<222> LOCATION: (1)..(2300)
<223> OTHER INFORMATION: human myelin basic protein

<400> SEQUENCE: 66

```
ggacaacacc ttcaaagaca ggccctctga gtccgacgag ctccagacca tccaagaaga     60
cagtgcagcc acctccgaga gcctggatgt gatggcgtca cagaagagac cctcccagag    120
gcacggatcc aagtacctgg ccacagcaag taccatggac catgccaggc atggcttcct    180
cccaaggcac agagacacgg gcatccttga ctccatcggg cgcttctttg gcggtgacag    240
gggtgcgccc aagcggggct ctggcaaggt accctggcta aagccgggcc ggagccctct    300
gccctctcat gcccgcagcc agcctgggct gtgcaacatg tacaaggact cacaccaccc    360
ggcaagaact gctcactacg gctccctgcc ccagaagtca cacggccgga cccaagatga    420
aaaccccgta gtccacttct tcaagaacat tgtgacgcct cgcacaccac ccccgtcgca    480
gggaaagggg agaggactgt ccctgagcag atttagctgg ggggccgaag gccagagacc    540
aggatttggc tacggaggca gagcgtccga ctataaatcg gctcacaagg gattcaaggg    600
agtcgatgcc cagggcacgc tttccaaaat ttttaagctg ggaggaagag atagtcgctc    660
tggatcaccc atggctagac gctgaaaacc cacctggttc cggaatcctg tcctcagctt    720
cttaatataa ctgccttaaa actttaatcc cacttgcccc tgttacctaa ttagagcaga    780
tgacccctcc cctaatgcct gcggagttgt gcacgtagta gggtcaggcc acggcagcct    840
accggcaatt tccggccaac agttaaatga gaacatgaaa acagaaaacg gttaaaactg    900
tccctttctg tgtgaagatc acgttccttc ccccgcaatg tgcccccaga cgcacgtggg    960
tcttcagggg gccaggtgca cagacgtccc tccacgttca cccctccacc cttggacttt   1020
cttttcgccg tggctgcggc acccttgcgc ttttgctggt cactgccatg gaggcacaca   1080
gctgcagaga cagagaggac gtgggcggca gagaggactg ttgacatcca agcttccttt   1140
gttttttttt cctgtccttc tctcacctcc taaagtagac ttcatttttc ctaacaggat   1200
tagacagtca aggagtggct tactacatgt gggagctttt ggtatgtgac atgcgggctg   1260
ggcagctgtt agagtccaac gtggggcagc acagagaggg ggccacctcc ccaggccgtg   1320
gctgcccaca caccccaatt agctgaattc gcgtgtggca gagggaggaa aaggaggcaa   1380
acgtgggctg ggcaatggcc tcacatagga aacagggtct tcctggagat ttggtgatgg   1440
agatgtcaag caggtggcct ctggacgtca ccgttgccct gcatggtggc cccagagcag   1500
cctctatgaa caacctcgtt tccaaaccac agcccacagc cggagagtcc aggaagactt   1560
gcgcactcag agcagaaggg taggagtcct ctagacagcc tcgcagccgc gccagtcgcc   1620
catagacact ggctgtgacc gggcgtgctg gcagcggcag tgcacagtgg ccagcactaa   1680
ccctccctga gaagataacc ggctcattca cttcctccca gaagacgcgt ggtagcgagt   1740
aggcacaggc gtgcacctgc tcccgaatta ctcaccgaga cacacgggct gagcagacgg   1800
ccccgtggat ggagacaaag agctcttctg accatatcct tcttaacacc cgctggcatc   1860
tcctttcgcg cctccctccc taacctactg acccaccttt tgattttagc gcacctgtga   1920
ttgataggcc ttccaaagag tcccacgctg gcatcaccct ccccgaggac ggagatgagg   1980
agtagtcagc gtgatgccaa aacgcgtctt cttaatccaa ttctaattct gaatgtttcg   2040
tgtgggctta ataccatgtc tattaatata tagcctcgat gatgagagag ttacaaagaa   2100
caaaactcca gacacaaacc tccaaatttt tcagcagaag cactctgcgt cgctgagctg   2160
```

-continued

```
aggtcggctc tgcgatccat acgtggccgc acccacacag cacgtgctgt gacgatggct   2220

gaacggaaag tgtacactgt tcctgaatat tgaaataaaa caataaactt ttaatggtaa   2280

aaaaaaaaaa aaaaaaaaaa                                               2300
```

VECTORS CONDITIONALLY EXPRESSING THERAPEUTIC PROTEINS, HOST CELLS COMPRISING THE VECTORS, AND USES THEREOF

BACKGROUND OF THE INVENTION

Field of the Invention

This invention relates to the field of gene therapy for the treatment of diseases and disorders, for example, cancer, lysosomal storage disorders, ocular diseases, liver diseases, or infectious diseases. In one embodiment, the invention provides the engineering of immune cells or therapy support cells (TSC) to express one or more therapeutic proteins (e.g., immunomodulators) and use of the cells as therapeutics. In another embodiment, the invention includes a vector, e.g., adenovirus, for conditional expression of therapeutic proteins (e.g., immunodulators) disclosed herein, e.g., IL-12, TNF-alpha and methods of using such vectors.

Background

Interleukin-12 (IL-12) is a member of the type I cytokine family involved in contributing to a number of biological processes including, but not limited to, protective immune response and suppression of tumorigenesis (Abdi et al., 2006; Adorini, 1999; Adorini, 2001; Adorini et al., 2002; Adorini et al., 1996; Akhtar et al., 2004; Akiyama et al., 2000; Al-Mohanna et al., 2002; Aliberti et al., 1996; Allavena et al., 1994; Alli and Khar, 2004; Alzona et al., 1996; Amemiya et al., 2006; Araujo et al., 2001; Arulanandam et al., 1999; Athie et al., 2000; Athie-Morales et al., 2004; Bertagnolli et al., 1992; Bhardwaj et al., 1996; Biedermann et al., 2006; Brunda and Gately, 1994; Buchanan et al., 1995; Romani et al., 1997; Rothe et al., 1996; Satoskar et al., 2000; Schopf et al., 1999; Thomas et al., 2000; Tsung et al., 1997; Wolf et al., 1994; Yuminamochi et al., 2007). A growing body of evidence suggests that IL-12 may be a promising target to control human diseases (e.g., cancer).

Despite the fact that IL-12 remains promising as a cancer therapeutic agent based on its potent supportive activity on Type-1 anti-tumor NK cells, $CD^+$ T cells and $CD8^+$ T cells (Trinchieri, 2003), the reported toxicity of recombinant human IL-12 (rhIL-12) in patients (Atkins et al., 1997), together with limited sources of GMP-grade rhIL-12 for clinical application, have prevented successful IL-12-based therapeutic approaches. Thus it seems reasonable that gene therapy approaches may represent safer, more tenable treatment options. Indeed, phase I clinical trials implementing intra- or peri-tumoral delivery of recombinant viral—(Sangro et al., 2004; Triozzi et al., 2005) or plasmid-based IL-12 cDNA (Heinzerling et al., 2005), or IL-12 gene modified autologous fibroblasts (Kang et al., 2001) have been found safe and well-tolerated.

However, objective clinical responses in patients with melanoma or a diverse range of carcinomas receiving these gene therapies have been rare, variable, transient and largely focused at the site of treatment (Heinzerling et al., 2005; Kang et al., 2001; Sangro et al., 2004; Triozzi et al., 2005). In cases where disease resolution was partial or complete, increased frequencies of tumor-infiltrating lymphocytes (Heinzerling et al., 2005; Sangro et al., 2004) and elevated levels of circulating tumor-specific $CD8^+$ T cells (Heinzerling et al., 2005) have been noted, consistent with the improved cross-priming of antigen-specific T cells in these patients.

Since the cross-priming of specific T cells is best accomplished by dendritic cells (DC) that serve as a natural but regulated source of IL-12 (Berard et al., 2000), recent reports of the superior pre-clinical efficacy of DC-based IL-12 gene therapy have been of great interest (Satoh et al., 2002; Tatsumi et al., 2003; Yamanaka et al., 2002). For example, it was shown that intratumoral (i.t.) injection of DC engineered to produce IL-12p70 (via recombinant adenovirus infection) results in the dramatically improved cross-priming of a broadly-reactive, tumor-specific $CD8^+$ T cell repertoire in concert with tumor rejection in murine models (Tatsumi et al., 2003). Given the previous use of a recombinant adenovirus encoding mIL-12 under a CMV-based promoter (rAd.cIL12, (Tatsumi et al., 2003)), engineered DC production of IL-12 was constitutive, hence the immunologic impact of this cytokine early within the tumor lesion and later within tumor-draining lymph nodes could not be resolved with regards to therapeutic outcome. Thus, a need exists for DC engineered for conditional expression of IL-12 for the purpose of regulating both the level of transgene expression and the timing of the transgene activation. The invention provides a promising therapeutic outcome for the use of such cells.

Many of the therapeutic proteins currently under investigation in pre-clinical or clinical trials do not exhibit harmful side effects when present in a patient prior to expression of the nucleic acid sequence in the host cell of the patient or the proper physiologic context. Some proteins, however, such as tumor necrosis factor (TNF), cause adverse effects when expressed outside the normal physiologic tissues or context (e.g., exposed to non-target tissues). Systemic or even local administration of this protein is extremely toxic to many non-tumor cell types, potentiating anaphylaxis and cachexia. In addition, prolonged exposure to TNF-alpha may yield profoundly different cellular responses than acute stimulations. For these reasons, safe and effective TNF-alpha therapies against cancer have remained elusive.

In view of the problems associated with gene expression of genes through vector compositions containing the protein encoded by the nucleic acid sequence of interest in, there remains a need for an improved transfer vector compositions to be used for direct injection or for use in cell based therapies.

Lysosomal storage diseases (LSDs) represent a class of inherited genetic disorders that can currently be treated only by protein therapeutics, in the form of enzyme replacement therapy.

LSDs are a class of 49 genetically inherited disorders characterized by a deficiency of one or more lysosomal enzymes that causes accumulation of undigested macromolecules inside the lysosome. Accumulation of these waste products causes lysosomes within cells to enlarge, leading to cell damage and degeneration. Accumulated damage in organs and tissues results in progressive deterioration in physical and/or mental state, and eventually death. Diagnosis is typically made in infancy. The severity of the individual disease is variable and correlated to the amount of residual enzyme activity produced by the defective gene.

The incidence of LSDs is about 1 in 5000 persons (130,000 cases worldwide). Severity is variable and is correlated to the amount of residual enzyme activity produced by the defective gene. Severely affected patients may live only into their teens, while less severely affected patients may survive into adulthood.

Enzyme replacement therapy is the only method available to treat LSDs. Therapy consists of systemic infusion of active proteins that target to lysosomes and break down accumulating waste molecules. Examples of LSD protein therapeutics include Fabrazyme (Genzyme) for Fabry Disease, Elaprase (Shire) for MPSII, and Myozome (Genzyme) for Pompe Disease, and Cerezyme (Genzyme) for Gaucher Disease.

Enzyme replacement therapy is accompanied by certain drawbacks, such as the requirement for post-translational protein modifications, the replacement enzymes exhibit short half lives in vivo, and patients develop an immune response to the replacement enzymes. Therefore, there remains a need in the art for and alternative to enzyme replacement therapy to treat lysosomal storage disease.

SUMMARY OF THE INVENTION

The invention provides a recombinant vector encoding protein(s) having the function(s) of one or more therapeutic proteins (e.g., immunomodulators), under the control of one or more promoters. In one embodiment, the one or more promoters are conditional. In another embodiment, the one or more promoters are constitutive. In another embodiment, the vector is an adenovirus vector encoding the protein(s) driven off a promoter that can be conditionally, activated by provision of a soluble small molecule ligand such as diacylhydrazines (e.g., RG-115819, RG-115830 or RG-115932). This vector allows for the control of expression of the protein(s) from immune cells, TSC and from direct injection of the vectors comprising therapeutic proteins (e.g., immunomodulators).

In one embodiment, the invention provides a vector for conditionally expressing protein(s) having the function(s) of one or more therapeutic proteins (e.g., immunomodulators) comprising a polynucleotide encoding a gene switch, wherein said polynucleotide encoding a gene switch comprises (1) at least one transcription factor sequence operably linked to a promoter, wherein said at least one transcription factor sequence encodes a ligand-dependent transcription factor, and (2) a polynucleotide encoding one or more proteins having the function of a therapeutic protein (e.g., immunomodulator) linked to a promoter which is activated by said ligand-dependent transcription factor. In one embodiment, the therapeutic protein (e.g., immunomodulator) is selected from IL-1, IL-2, IL-3, IL-4, IL-5, IL-7, IL-8, IL-9, IL-10R DN or a subunit thereof, IL-15, IL-18, IL-21, IL-23, IL-24, IL-27, GM-CSF, IFN-alpha, IFN-gamma, CCL3 (MIP-1a), CCL5 (RANTES), CCL7 (MCP3), XCL1 (lymphotactin), CXCL1 (MGSA-alpha), CCR7, CCL19 (MIP-3b), CXCL9 (MIG), CXCL10 (IP-10), CXCL12 (SDF-1), CCL21 (6Ckine), OX40L, 4-1BBL, CD40, CD70, GITRL, LIGHT, b-Defensin, HMGB1, Flt3L, IFN-beta, TNF-alpha, dnFADD, TGF-alpha, PD-L1RNAi, a PD-L1 antisense oligonucleotide, TGFbRII DN, ICOS-L, S100, CD40L, p53, survivin, p53-survivin fusion, MAGE3, PSA and PSMA.

In another embodiment, the invention provides a vector for expressing protein(s) having the function(s) of one or more therapeutic proteins (e.g., immunomodulators) and a protein having the function of IL-12, comprising a polynucleotide encoding a gene switch, wherein said polynucleotide comprises (1) at least one transcription factor sequence operably linked to a promoter, wherein said at least one transcription factor sequence encodes a ligand-dependent transcription factor, (2) a polynucleotide encoding said protein(s) having the function(s) of the one or more therapeutic proteins (e.g., immunomodulators), and (3) a polynucleotide encoding a protein having the function of the IL-12; wherein at least one polynucleotide of (2) and (3) are linked to the promoter which is activated by the ligand-dependent transcription factor.

In some embodiments, the vector of the invention conditionally expresses TNF-alpha. In certain embodiments, the vector, e.g., adenoviral vector, conditionally expressing one or more proteins having the function of a therapeutic protein (e.g., immunomodulator), e.g., TNF-alpha, further comprises a nucleic acid sequence encoding a signal peptide. The signal peptide can be codon-optimized. In other embodiments, the vector further comprises 5' untranslated region (UTR), 3' regulatory region, or both and improves protein expression and/or overall yield.

The invention further provides a method of producing a population of cells, e.g., immune cells or TSC, expressing protein(s) having the function of one or more therapeutic proteins (e.g., immunomodulators), by modifying (e.g., transfecting, electroporating, etc.) the cells with a recombinant vector conditionally expressing protein(s) having the function(s) of the one or more therapeutic proteins (e.g., immunomodulators), wherein the vector comprises a polynucleotide encoding a gene switch, wherein said polynucleotide comprises (1) at least one transcription factor sequence operably linked to a promoter, wherein said at least one transcription factor sequence encodes a ligand-dependent transcription factor, and (2) a polynucleotide encoding one or more proteins having the function of a therapeutic protein (e.g., immunomodulator) modulator linked to a promoter which is activated by said ligand-dependent transcription factor.

In another embodiment, the invention provides a method of producing a population of cells, e.g., immune cells or TSC, expressing proteins having the function(s) of one or more therapeutic proteins (e.g., immunomodulators) and a protein having the function of IL-12, by modifying the cells with a recombinant vector comprising a polynucleotide encoding a gene switch, wherein said polynucleotide comprises (1) at least one transcription factor sequence operably linked to a promoter, wherein said at least one transcription factor sequence encodes a ligand-dependent transcription factor, (2) a polynucleotide encoding said protein(s) having the function(s) of the one or more therapeutic proteins (e.g., immunomodulators), and (3) a polynucleotide encoding a protein having the function of the IL-12; wherein at least one polynucleotide of (2) and (3) are linked to the promoter which is activated by said ligand-dependent transcription factor.

In some embodiments, the invention provides a method of increasing expression of a therapeutic protein (e.g., immunomodulator), e.g., TNF-alpha, mRNA expression, or protein expression comprising generating the vector conditionally expressing one or more proteins having the function of a therapeutic protein (e.g., immunomodulator) and one or more regulatory sequence, wherein said one or more regulatory sequence improves expression of the therapeutic proteins (e.g., immunomodulators), e.g., TNF-alpha.

The invention further provides a population of cells, e.g., immune cells or TSC, expressing protein(s) having the function of one or more therapeutic proteins (e.g., immunomodulators), which has been modified (e.g., transfected, electroporated, etc.) with a recombinant vector conditionally the expressing protein(s) having the function(s) of the one or more therapeutic proteins (e.g., immunomodulators), wherein the vector comprises a polynucleotide encoding a gene switch, wherein said polynucleotide comprises (1) at least one transcription factor sequence operably linked to a promoter, wherein said at least one transcription factor sequence encodes a ligand-dependent transcription factor, and (2) a polynucleotide encoding one or more proteins having the function of a therapeutic protein (e.g., immunomodulator) linked to the promoter which is activated by said ligand-dependent transcription factor.

In another embodiment, the invention provides a population of cells, e.g., immune cells or TSC, expressing proteins having the function(s) of one or more therapeutic proteins (e.g., immunomodulators) and a protein having the function of IL-12, which has been modified with a recombinant vector comprising a polynucleotide encoding a gene switch, wherein said polynucleotide comprises (1) at least one transcription factor sequence operably linked to a promoter, wherein said at least one transcription factor sequence encodes a ligand-dependent transcription factor, (2) a polynucleotide encoding said protein(s) having the function(s) of the one or more therapeutic proteins (e.g., immunomodulators) and (3) a polynucleotide encoding a protein having the function of the IL-12; wherein at least one polynucleotide of (2) and (3) are linked to a promoter which is activated by said ligand-dependent transcription factor.

In another embodiment, the invention provides a composition comprising two or more populations of cells of the present invention, e.g., immune cells or TSC, wherein each population of cells in the composition expresses one or more therapeutic proteins (e.g., immunomodulators) that are different from the one or more therapeutic proteins (e.g., immunomodulators) expressed in the other population(s) of cells in the composition. In one embodiment, the composition contains two populations of cells. In another embodiment, the composition contains more than two populations of cells. In another embodiment, the composition contains three populations of cells. In another embodiment, the composition contains four populations of cells.

In another embodiment, the invention provides an in vitro engineered cell, e.g., immune cell or TSC, comprising a vector comprising a polynucleotide encoding a gene switch, wherein said polynucleotide comprises (1) at least one transcription factor sequence operably linked to a promoter, wherein said at least one transcription factor sequence encodes a ligand-dependent transcription factor, and (2) a polynucleotide encoding a protein having the function of a therapeutic protein (e.g., immunomodulator) linked to a promoter which is activated by said ligand-dependent transcription factor. In another embodiment, the invention provides an in vitro engineered cell, e.g., immune cell or TSC, comprising a vector comprising a polynucleotide encoding a gene switch, wherein said polynucleotide comprises (1) at least one transcription factor sequence operably linked to a promoter, wherein said at least one transcription factor sequence encodes a ligand-dependent transcription factor, (2) a polynucleotide encoding a protein having the function of a therapeutic protein (e.g., immunomodulator), and (3) a polynucleotide encoding a protein having the function of IL-12; wherein at least one polynucleotide of (2) and (3) are linked to a promoter which is activated by said ligand-dependent transcription factor.

In another embodiment, the invention provides a composition comprising two or more populations of in vitro engineered cells, e.g., immune cells or TSCs, of the present invention, wherein each of the populations of in vitro engineered cells in the composition comprises a vector comprising a polynucleotide encoding a gene switch, wherein said polynucleotide comprises (1) at least one transcription factor sequence operably linked to a promoter, wherein said at least one transcription factor sequence encodes a ligand-dependent transcription factor, and (2) a polynucleotide encoding a protein having the function of a therapeutic protein (e.g., immunomodulator) linked to a promoter which is activated by said ligand-dependent transcription factor, and wherein each population of in vitro engineered cells in the composition expresses one or more therapeutic proteins (e.g., immunomodulators) that are different from the one or more therapeutic proteins (e.g., immunomodulators) expressed in the other population(s) of in vitro engineered cell in the composition. In one embodiment, the invention provides a composition comprising two or more populations of in vitro engineered cells, e.g., immune cell or TSC, each of said populations of cells comprising a vector comprising a polynucleotide encoding a gene switch, wherein said polynucleotide comprises (1) at least one transcription factor sequence operably linked to a promoter, wherein said at least one transcription factor sequence encodes a ligand-dependent transcription factor, (2) a polynucleotide encoding a protein having the function of a therapeutic protein (e.g., immunomodulator), and (3) a polynucleotide encoding a protein having the function of IL-12; wherein at least one polynucleotide of (2) and (3) are linked to a promoter which is activated by said ligand-dependent transcription factor. In one embodiment, the composition contains two populations of in vitro engineered cells. In another embodiment, the composition contains more than two populations of in vitro engineered cells. In another embodiment, the composition contains three populations of in vitro engineered cells. In another embodiment, the composition contains four populations of in vitro engineered cells.

The invention also provides a pharmaceutical composition comprising a population of cells, e.g., immune cells or TSC, as described herein or a composition suitable for direct injection of the expression vectors absent a population of cells, i.e., directly injected.

In one embodiment, the polynucleotide coding for the one or more proteins having the functions of the immunomodulator is under control of the promoter of the gene switch and the polynucleotide coding for a protein having the function of IL-12 is under control of a constitutive promoter. In another embodiment, both the polynucleotide coding for protein(s) having the functions of the therapeutic proteins (e.g., immunomodulators) and the polynucleotide coding for a protein having the function of IL-12 are both under control of a multicistronic promoter of the gene switch. In another embodiment, the polynucleotide coding for a protein(s) having the function of the therapeutic proteins (e.g., immunomodulators) is under control of the promoter of the gene switch and the polynucleotide coding for a protein having the function of IL-12 is under control of a conditional promoter which is different than the gene switch promoter. In a further embodiment, the gene regulation system for the polynucleotide coding for the protein(s) having the function of the therapeutic proteins (e.g., immunomodulators) and the gene regulation system for the polynucleotide having the function of IL-12 are orthogonal. In a further embodiment, the gene regulation system for each polynucleotide coding for each protein is orthogonal.

In one embodiment, the invention also provides a treatment of cancer, such as, but not limited to, melanoma tumors, glioma tumors, renal cancer, and prostate cancers, as well as the cancers listed herein in Table 1. IL-12 gene therapy has demonstrated anti-tumor efficacy in animal model studies when applied as a recombinant cDNA vector (Faure et al., 1998; Sangro et al., 2005), but even more so, when applied in the context of gene-modified DC (Satoh et al., 2002; Svane et al., 1999; Tatsumi et al., 2003; Yamanaka et al., 2002). To date, however, human phase I trials of IL-12 gene therapy implementing plasmids or viral vectors have failed to achieve durable, objective clinical responses in the cancer setting (Heinzerling et al., 2005; Kang et al., 2001; Sangro et al., 2004; Triozzi et al., 2005) gene therapy as described herein provides a promising therapeutic modality.

In one embodiment, the invention provides a method for treating a tumor in a mammal, comprising the steps of:

(a) administering intratumorally to tumor microenvironments, in the area surrounding the tumor, or systemically a population of immune cells, TSCs or vectors of the invention (or a combination thereof), which are in vitro engineered to conditionally express one or more proteins having the function of a therapeutic protein (e.g., immunomodulator); and (b) administering to said mammal a therapeutically effective amount of an activating ligand;

thereby inducing expression of a protein having the function of the therapeutic protein (e.g., immunomodulator) and treating said tumor.

In one embodiment, the invention provides a method for treating a tumor in a mammal, comprising the steps of:

(a) administering intratumorally to tumor microenvironments a population of immune cells or TSC, which are in vitro engineered to conditionally express one or more proteins having the function of a therapeutic protein (e.g., immunomodulator); and (b) administering to said mammal a therapeutically effective amount of an activating ligand;

thereby inducing expression of a protein having the function of the therapeutic proteins (e.g., immunomodulators) and treating said tumor.

In another embodiment, the invention provides a method for treating a tumor in a mammal, comprising the steps of:

(a) administering intratumorally to tumor microenvironments two or more populations of immune cells or TSCs, which are in vitro engineered to conditionally express one or more proteins having the function of a therapeutic protein (e.g., immunomodulator), wherein each population of immune cells or TSCs expresses a different set of one or more therapeutic proteins (e.g., immunomodulators); and (b) administering to said mammal a therapeutically effective amount of one or more activating ligands;

thereby inducing expression of proteins having the function of the therapeutic proteins (e.g., immunomodulators) and treating said tumor.

In another embodiment, the invention provides a method for treating a tumor in a mammal, comprising the steps of:

(a) administering intratumorally to tumor microenvironments a population of an immune cells or TSC, which are in vitro engineered to conditionally express one or more proteins having the function of a therapeutic protein (e.g., immunomodulator) and a protein having the function of IL-12, wherein at least one of the proteins having the function of the therapeutic protein (e.g., immunomodulator) or IL-12 is under control of a conditional promoter that is activated by a ligand; and (b) administering to said mammal a therapeutically effective amount of the activating ligand;

thereby inducing expression of a protein having the function of the therapeutic protein (e.g., immunomodulator) and/or the protein having the function of IL-12 and treating said tumor.

In another embodiment, the invention provides a method for treating a tumor in a mammal, comprising the steps of:

(a) administering intratumorally to tumor microenvironments two or more populations of an immune cells or TSCs, which are in vitro engineered to conditionally express one or more proteins having the function of a therapeutic protein (e.g., immunomodulator) and a protein having the function of IL-12, wherein each population of immune cells or TSCs expresses a different set of one or more proteins having the function of a therapeutic protein (e.g., immunomodulator), wherein at least one of the proteins having the function of the therapeutic protein (e.g., immunomodulator) or IL-12 is under control of a conditional promoter that is activated by a ligand; and (b) administering to said mammal a therapeutically effective amount of one or more activating ligands;

thereby inducing expression of a protein having the function of the therapeutic proteins (e.g., immunomodulator) and/or the protein having the function of IL-12 and treating said tumor.

In another embodiment, the invention provides a method for treating a disease or disorder in a mammal, comprising the steps of:

(a) administering to said mammal a population of modified cells, which are modified to conditionally express one or more proteins having the function of an therapeutic protein (e.g., immunomodulator); and (b) administering to said mammal a therapeutically effective amount of an activating ligand;

thereby inducing expression of a protein having the function of the therapeutic protein (e.g., immunomodulator) and treating said disease or disorder.

In another embodiment, the invention provides a method for treating a disease or disorder in a mammal, comprising the steps of:

(a) administering to said mammal two or more populations of modified cells, which are modified to conditionally express one or more proteins having the function of a therapeutic protein (e.g., immunomodulator), wherein each population of modified cells expresses a different set of one or more therapeutic proteins (e.g., immunomodulators); and (b) administering to said mammal a therapeutically effective amount of one or more activating ligands;

thereby inducing expression of proteins having the function of the therapeutic proteins (e.g., immunomodulators) and treating said disease or disorder.

In another embodiment, the invention provides a method for treating a disease or disorder in a mammal, comprising the steps of:

(a) administering to said mammal a population of a modified cells, which are modified to conditionally express one or more proteins having the function of a therapeutic protein (e.g., immunomodulator) and a protein having the function of IL-12, wherein at least one of the proteins having the function of the therapeutic protein (e.g., immunomodulator) or IL-12 is under control of a conditional promoter that is activated by a ligand; and (b) administering to said mammal a therapeutically effective amount of the activating ligand;

thereby inducing expression of a protein having the function of the therapeutic protein (e.g., immunomodulator) and/or the protein having the function of IL-12 and treating said disease or disorder.

In another embodiment, the invention provides a method for treating a disease or disorder in a mammal, comprising the steps of:

(a) administering to said mammal two or more populations of modified cells, which are modified to conditionally express one or more proteins having the function of a therapeutic protein (e.g., immunomodulator) and a protein having the function of IL-12, wherein each population of modified cells expresses a different set of one or more proteins having the function of a therapeutic protein (e.g., immunomodulator), wherein at least one of the proteins having the function of the therapeutic protein (e.g., immunomodulator) or IL-12 is under control of a conditional promoter that is activated by a ligand; and (b) administering to said mammal a therapeutically effective amount of one or more activating ligands;

thereby inducing expression of a protein having the function of the therapeutic proteins (e.g., immunomodulators) and/or the protein having the function of IL-12 and treating said disease or disorder.

The invention also provides a method for determining the efficacy of engineered cell-, e.g., immune cell- or TSC-, based therapy by measuring the level of expression or activity of IFN-gamma in a patient before the start of therapy, thereby generating a control level, followed by the administration of cells engineered to express one or more proteins having the functions of a therapeutic protein (e.g., immunomodulator) and optionally a protein having the function of IL-12, administering an effective amount of an activating ligand, and then measuring the level of expression of IFN-gamma to generate a test level, and comparing the control level to the test level to determine if the therapeutic regime is effective.

Further included is a method of treating a tumor, reducing a tumor size, or preventing a tumor formation in a mammal in need thereof comprising (a) administering a therapeutically effective amount of the vector conditionallly expressing at least one therapeutic protein (e.g., immunomodulator), e.g., IL-12, TNF-alpha, in said mammal, (b) administering to said mammal a therapeutically effective amount of one or more activating ligand, wherein said activating ligand activates expression of the protein having the function of the therapeutic protein (e.g., immunomodulator), thereby inducing expression of the protein having the function of the therapeutic protein (e.g., immunomodulator) and treating said tumor.

In one embodiment, the invention provides a method for determining the efficacy of an in vitro engineered cell-, e.g., immune cell- or TSC-, based therapeutic regime in a patient comprising:

(a) measuring the level of expression or the level of activity or both of interferongamma (IFN-gamma) in a first biological sample obtained from said patient in need thereof before administration of the in vitro engineered cells, thereby generating a control level;

(b) administering to a patient in need thereof the in vitro engineered cells engineered to conditionally express one or more proteins having the functions of a therapeutic protein (e.g., immunomodulator) and optionally a protein having the function of IL-12;

(c) administering to said patient in need thereof an effective amount of an activating ligand;

(d) measuring the level of expression or the level of activity or both of IFN-gamma in a second biological sample obtained from said patient in need thereof following administration of in vitro engineered immune cells and activating ligand, thereby generating a test level; and (e) comparing the control level to the test level of IFN-gamma, wherein an increase in the test level of expression, activity or both of IFN-gamma relative to the control level indicates that the therapeutic regime is effective in said patient in need thereof.

In one embodiment, the invention provides a method for treating a tumor, reducing a tumor size, or preventing a tumor formation in a mammal in need thereof, comprising: (a) administering intratumorally to tumor microenvironments a vector for conditionally expressing protein(s) having the function(s) of one or more therapeutic proteins (e.g., immunomodulators), the vector comprising a polynucleotide encoding a gene switch, wherein the polynucleotide comprises (1) at least one transcription factor sequence which is operably linked to a promoter, wherein the at least one transcription factor sequence encodes a ligand-dependent transcription factor, and (2) a polynucleotide encoding one or more proteins having the function of a therapeutic protein (e.g., immunomodulator) operably linked to a promoter which is activated by the ligand-dependent transcription factor, wherein the one or more therapeutic proteins (e.g., immunomodulators) are selected from IL-1, IL-2, IL-3, IL-4, IL-5, IL-7, IL-8, IL-9, IL-10R DN or a subunit thereof, IL-15, IL-18, IL-21, IL-23, IL-24, IL-27, GM-CSF, IFN-alpha, IFN-gamma, IFN-alpha 1, IFN alpha 2, IL-15-R-alpha, CCL3 (MIP-1a), CCL5 (RANTES), CCL7 (MCP3), XCL1 (lymphotactin), CXCL1 (MGSA-alpha), CCR7, CCL19 (MIP-3b), CXCL9 (MIG), CXCL10 (IP-10), CXCL12 (SDF-1), CCL21 (6Ckine), OX40L, 4-1BBL, CD40, CD70, GITRL, LIGHT, b-Defensin, HMGB1, Flt3L, IFN-beta, TNF-alpha, dnFADD, BCG, TGF-alpha, PD-L1 RNAi, a PD-L1 antisense oligonucleotide, TGFbRII DN, ICOS-L, S100, CD40L, OX40L, p53, survivin, p53-survivin fusion, MAGE3, PSA and PSMA, wherein the vector is not contained within a cell; and (b) administering to the mammal a therapeutically effective amount of one or more activating ligands; thereby inducing expression of the one or more proteins having the functions of the therapeutic protein (e.g., immunomodulator) and treating the tumor.

The present invention also provides a method for treating a disease in a mammal in need thereof, comprising: (a) administering to said mammal a vector for conditionally expressing protein(s), said vector comprising a polynucleotide encoding a gene switch, wherein said polynucleotide comprises (1) at least one transcription factor sequence which is operably linked to a promoter, wherein said at least one transcription factor sequence encodes a ligand-dependent transcription factor, and (2) a polynucleotide encoding one or more proteins operably linked to a promoter which is activated by said ligand-dependent transcription factor, wherein said vector is not contained within a cell; and (b) administering to said non-human animal a therapeutically effective amount of one or more activating ligands; thereby inducing expression of the one or more proteins and treating said disease.

The present invention also provides a method for treating a lysosomal storage disorder in a mammal in need thereof, comprising: (a) administering to said mammal a vector for conditionally expressing one or more protein(s), said vector comprising a polynucleotide encoding a gene switch, wherein said polynucleotide comprises (1) at least one transcription factor sequence which is operably linked to a promoter, wherein said at least one transcription factor sequence encodes a ligand-dependent transcription factor, and (2) a polynucleotide encoding one or more proteins operably linked to a promoter which is activated by said ligand-dependent transcription factor, wherein said vector is not contained within a cell prior to in vivo administration; and (b) administering to said mammal a therapeutically effective amount of one or more activating ligands; thereby inducing expression of the one or more proteins and treating said lysosomal storage disorder.

The present invention also provides a method for treating a liver disease in a mammal in need thereof, comprising: (a) administering to said mammal a vector for conditionally expressing protein(s), said vector comprising a polynucleotide encoding a gene switch, wherein said polynucleotide comprises (1) at least one transcription factor sequence which is operably linked to a promoter, wherein said at least one transcription factor sequence encodes a ligand-dependent transcription factor, and (2) a polynucleotide encoding one or more proteins operably linked to a promoter which is activated by said ligand-dependent transcription factor, wherein said vector is not contained within a cell prior to in vivo administration; and (b) administering to said non-human animal a therapeutically effective amount of one or more activating ligands; thereby inducing expression of the one or more proteins and treating said liver disease.

DETAILED DESCRIPTION OF DRAWINGS

FIG. 10 shows a summary chart for translation, post-transcriptional, translation, and post-translation processes.

Figure 31:
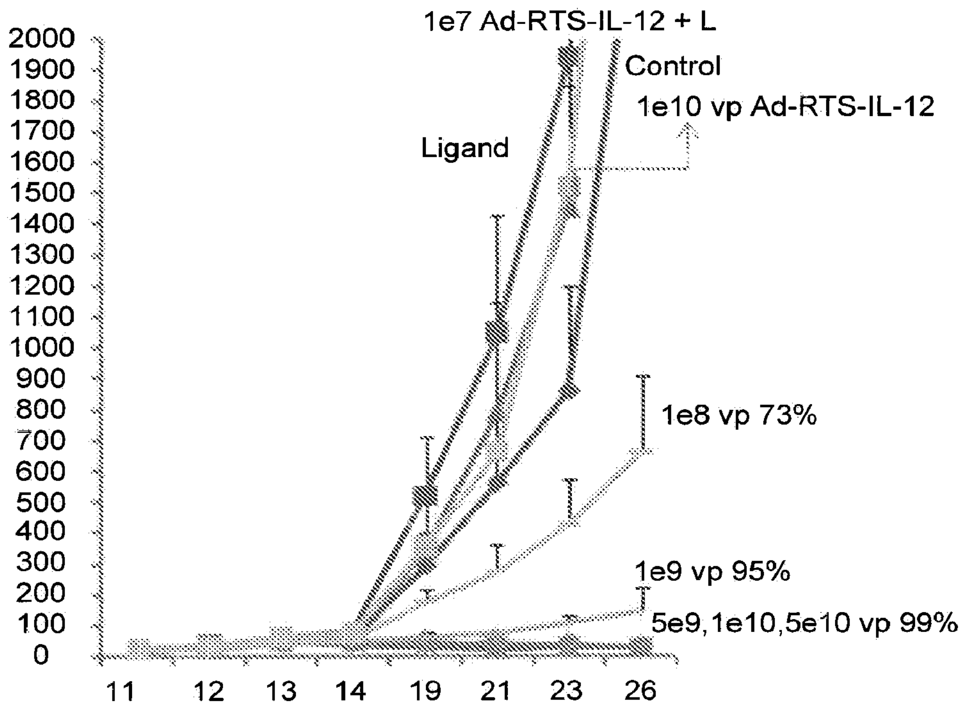

FIG. 31 is a line graph that shows Ad-RTS-IL-12 dose response study in the mouse B16F0 melanoma model. Mice were treated on day 12 with a single injection of Ad-RTS-IL-12 at doses of 1ee7; 1ee8; 1ee9; 5ee9; 1ee10; 5ee10 viral particles (vp)) and ligand was delivered using chow starting on day 11. The x-axis shows days post tumor cell inoculation and y-axis indicates tumor volume. Dose levels showed substantial anti-tumor effect. The % tumor reduction compared to control is indicated.

Figure 32:
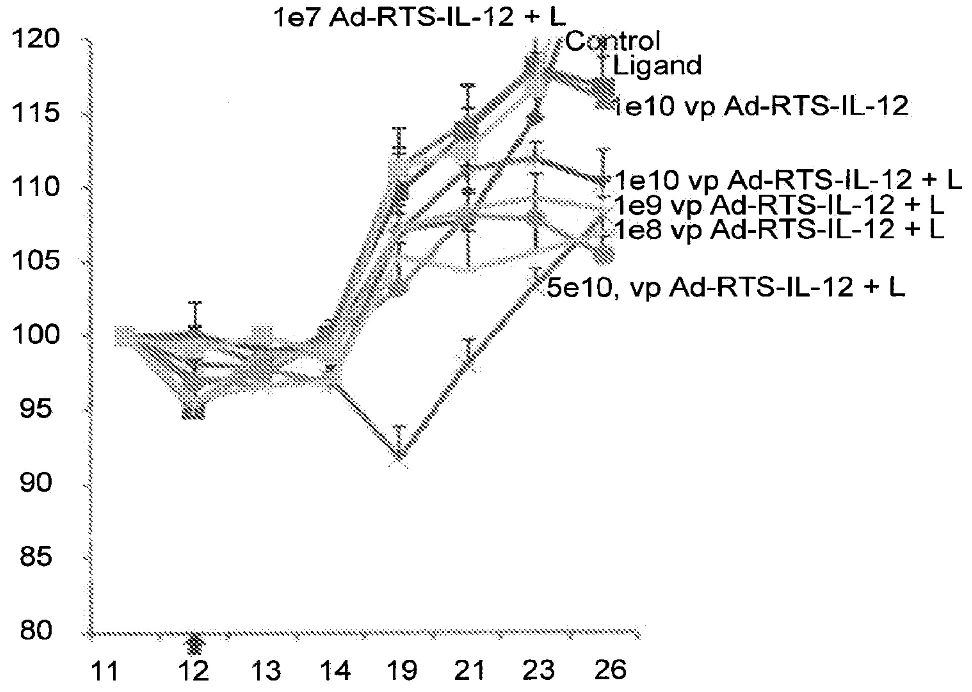

FIG. 32 is a line graph that shows body weight changes over the course of the study. The changes are shown as % body weight on y-axis.

Figure 33B:
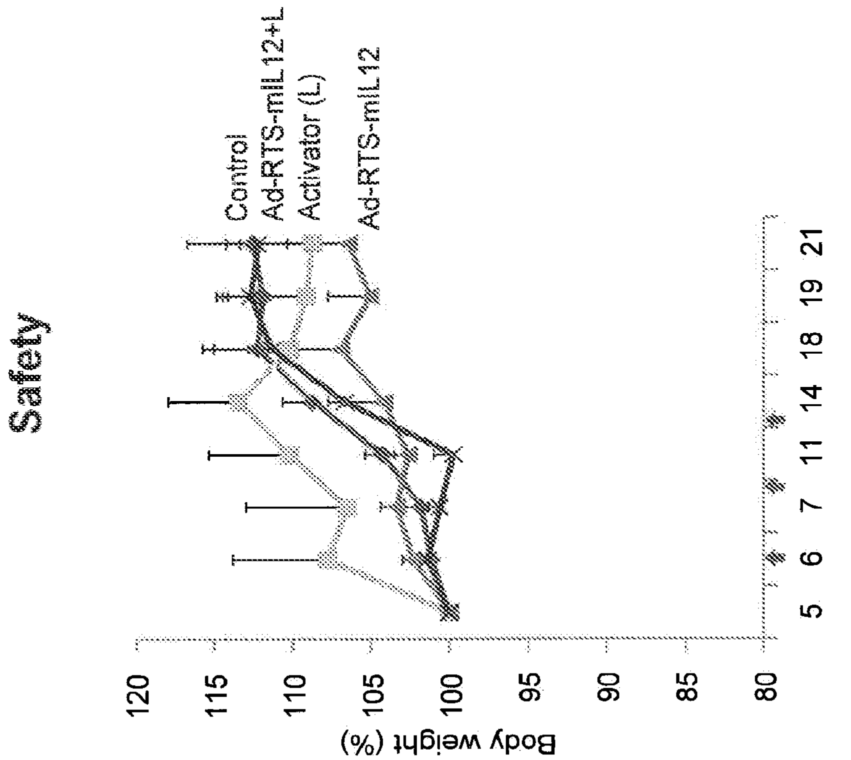
Figure 33A:
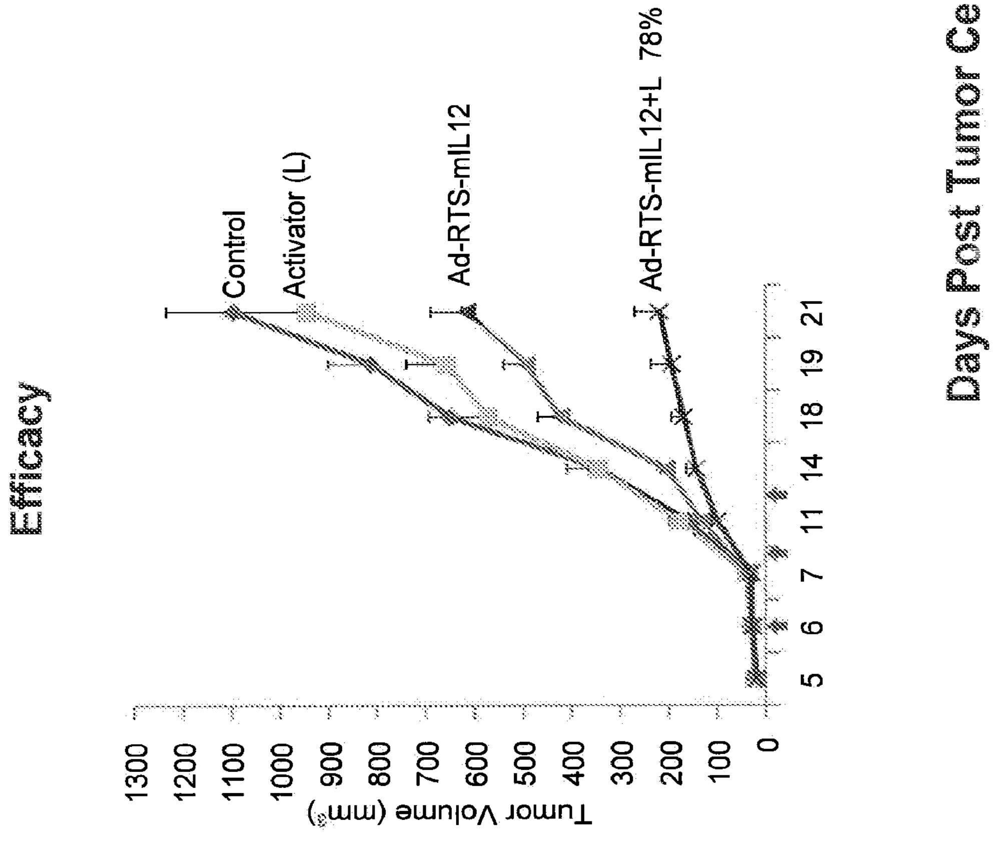

FIGS. 33A and 33B are line graphs that show the anti-tumor activity (FIG. 33A) and safety (FIG. 33B) of Ad-RTS-mIL12 in the Lewis mouse lung carcinoma (LLC) model. Lewis lung tumor was grown subcutaneousely in immuno-competent C57b/6 mice. When the tumor reached desirable size, the treatment was initiated. Animals received a single dose of AdRTS-mIL12 (1e10 vp) on Day 6, 9, 13 post tumor cell inoculation. Ad-RTS-mIL12 with activator displayed marked anti-tumor activity relative to control animals. No major toxicity was noticed.

Figure 34B:
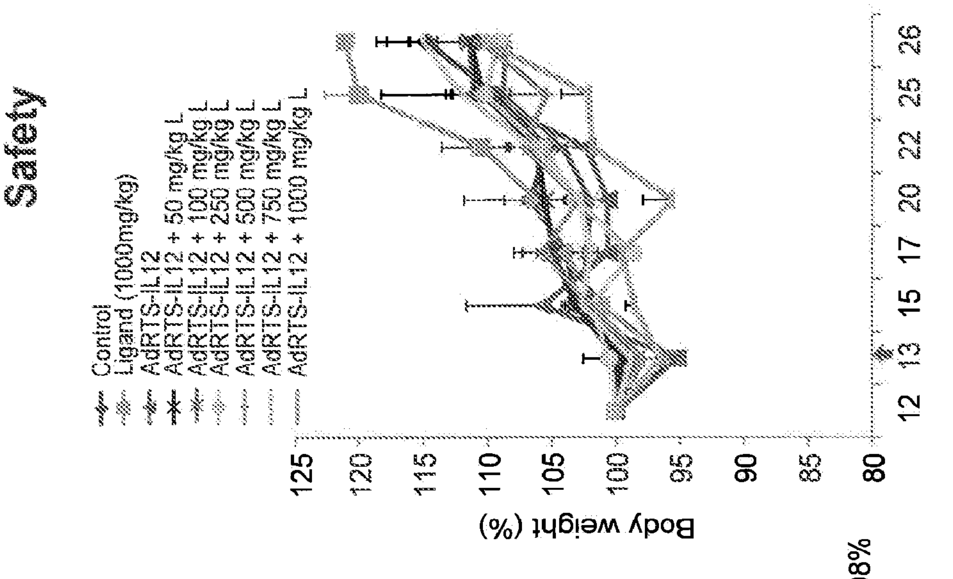
Figure 34A:
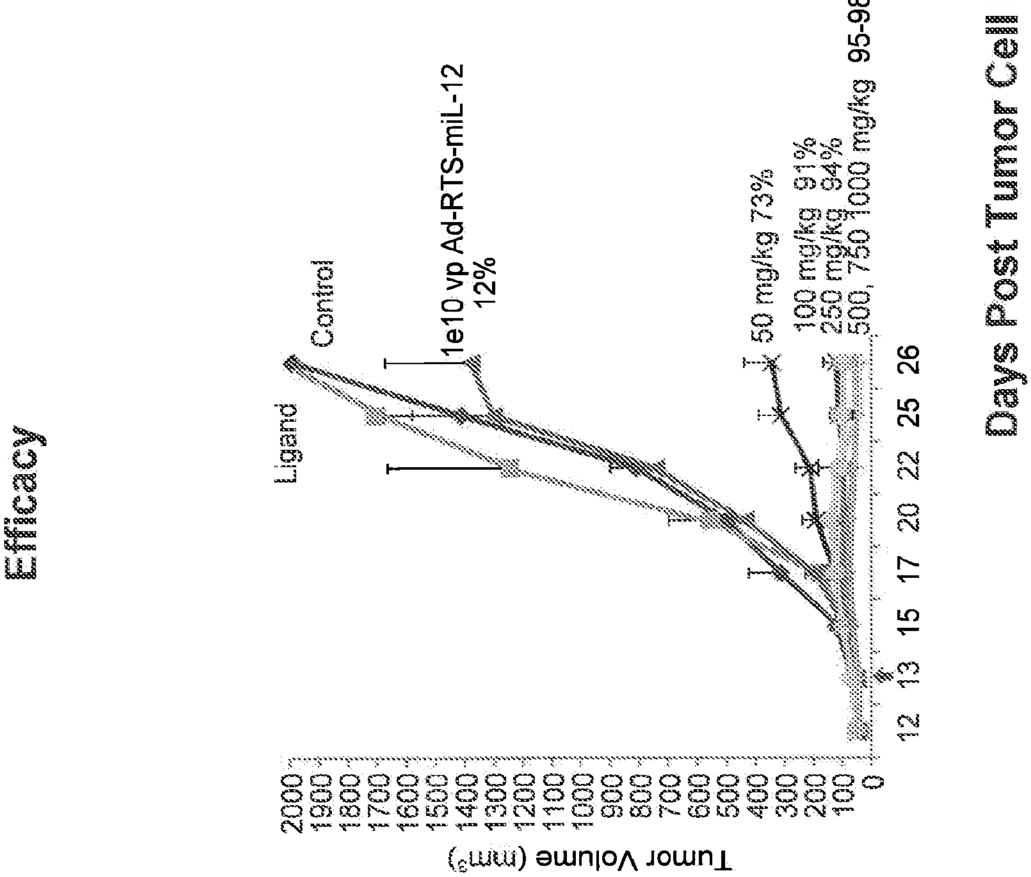

FIGS. 34A and 34B are line graphs that show efficacy (FIG. 34A) and safety (FIG. 34B) in a mouse melanoma (B16F0) model in which animals were treated with AdRTS-mIL12. Tumor was developed s.c. on the flank of C57b/6 mice. A single dose of Ad-RTS-mIL12 (1e10 vp) administered intratumorally (i.t.) on Day 13 post cell inoculation (arrow). The activator ligand (50, 100, 250, 500, 750 and 1000 mg/kg) was given 24 hr prior to vector injection until end of experiment. The tumor growth inhibition was indicated as percentage and compared to control animals. Ad-RTS-IL12 showed therapeutic benefit with broad activator dose window. The treatment was well tolerated.

Figures 35A, 35B:
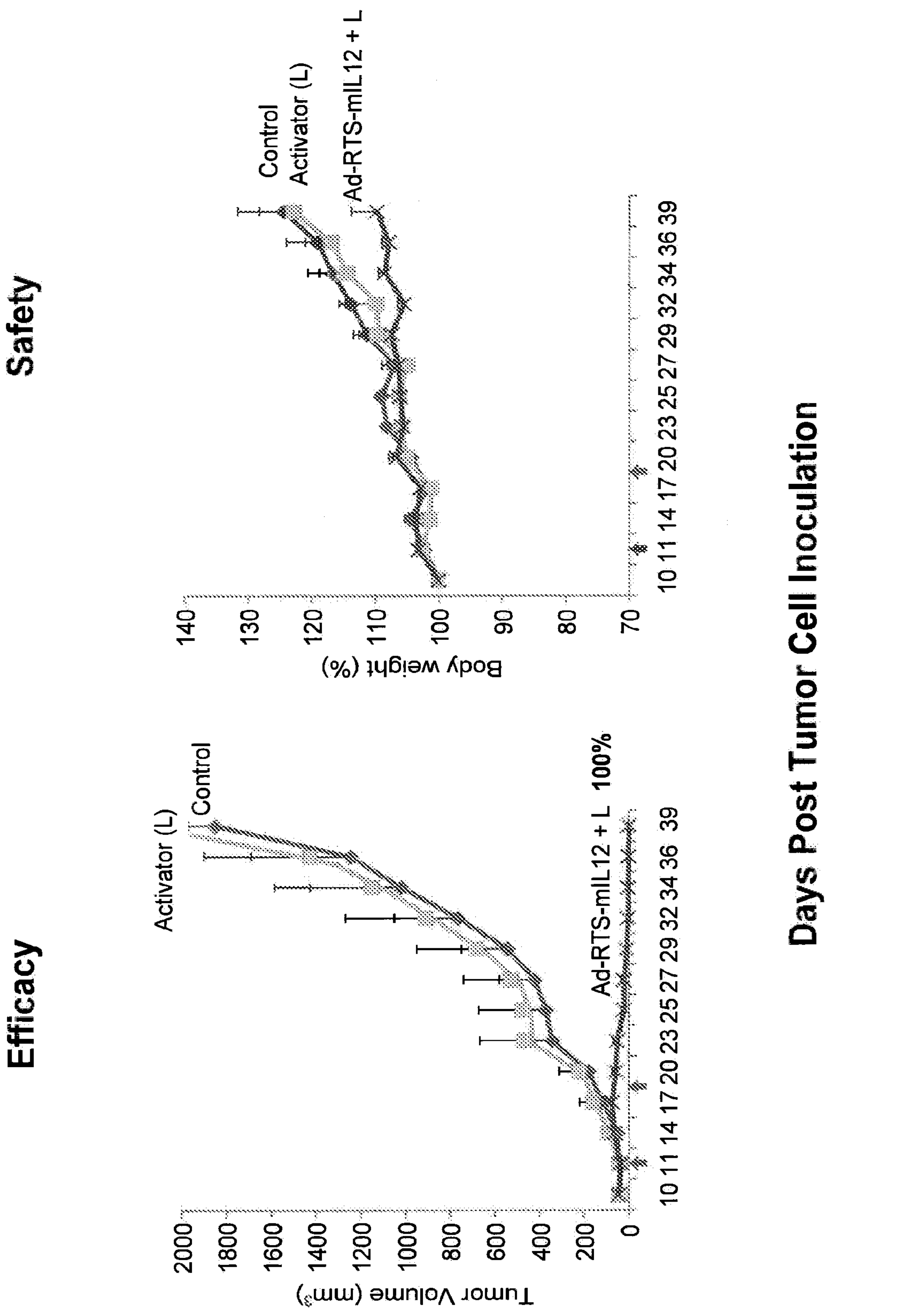

FIGS. 35A and 35B are line graphs that show efficacy (FIG. 35A) and safety (FIG. 35B) of Ad-RTS-mIL12 in a mouse colon cancer (CT26Luc) model. Murine colon tumor was grown subcutaneously on the flank region of Balb/C mice. Animals were treated intratumorally (i.t.) twice with of Ad-RTS-mIL12 at a dose level of 1e10 vp/100 ul on day 11 and 18 post cell inoculation (arrow). Activator was started 24 hr prior to vector injection. Tumor volume and body weight were monitored throughout the experiment. Treatment with Ad-RTS-mIL12 led to outstanding tumor growth inhibition (100%) relative to control animals. Notably, all the animals treated with Ad-RTS-mIL12 plus activators were tumor free.

Figures 36A, 36B:
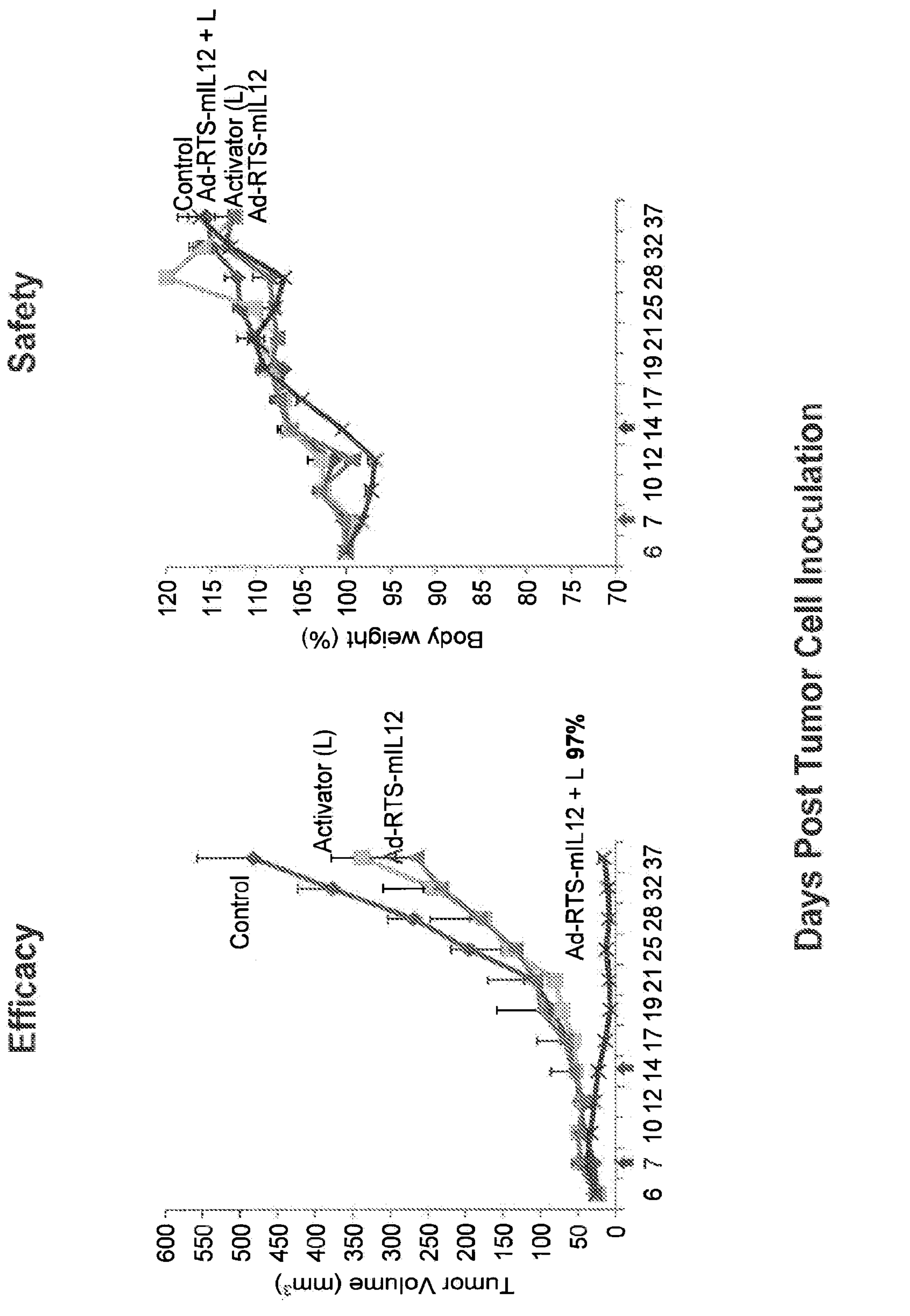

FIGS. 36A and 36B are line graphs that show efficacy (FIG. 36A) and safety (FIG. 36B) Efficacy of Ad-RTS-mIL12 in a pancreatic cancer (PAN02) model. Subcutaneous PAN02 tumor bearing mice were treated intratumorally (i.t.) with a single dose of Ad-RTS-mIL12 at a dose level of 1e10 vp/100 ul on Day 7 and 14 (arrow) post tumor cell inoculation. The activator chow was supplied to animals a day before vector administration until end of experiment. The control or vector alone group received normal rodent chow only. The result suggests the Ad-RTS-IL12 displays significant antitumor activity (97%) relative to control animals. No major body weight changes were found as a result of Ad-RTS-IL12 therapy.

Figure 37:
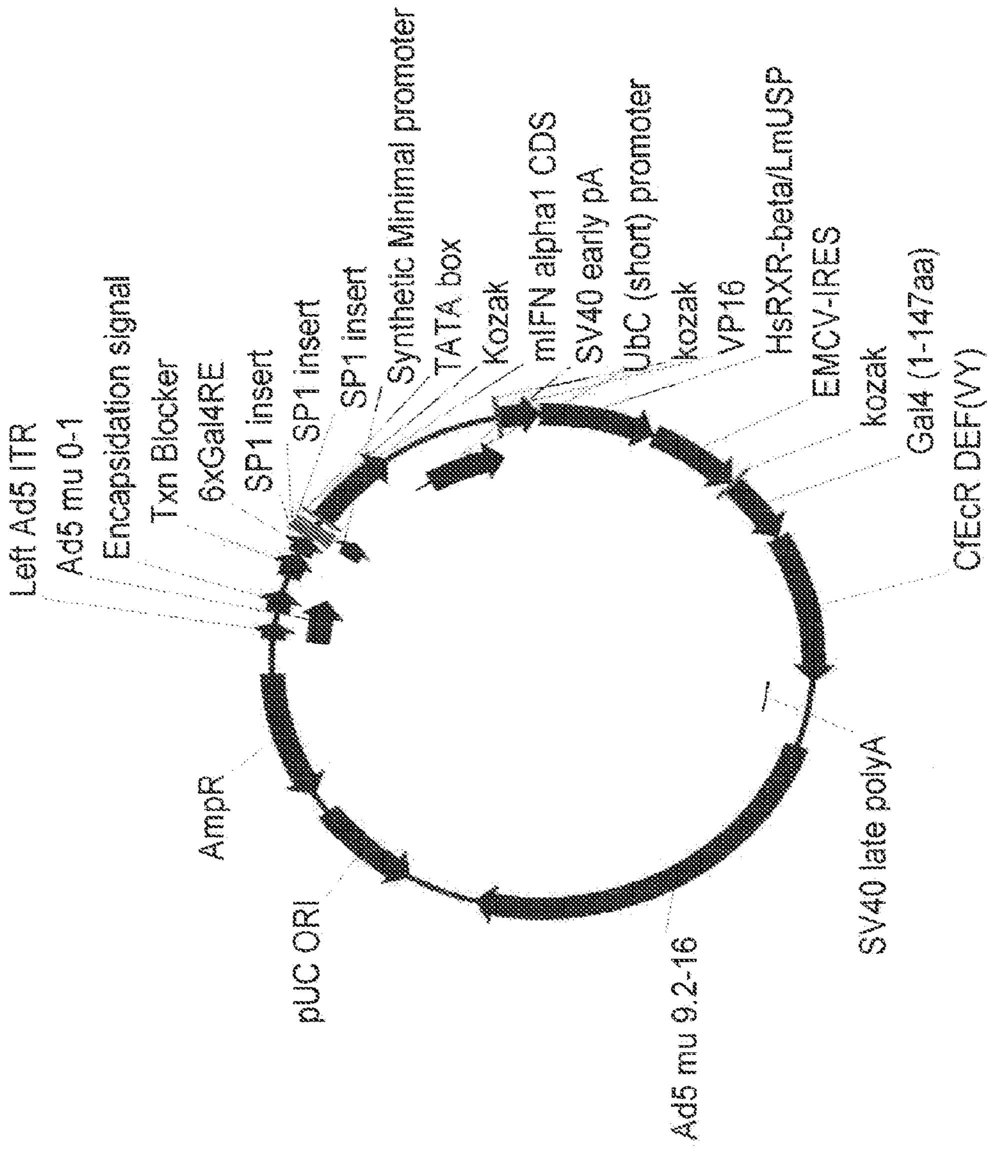

FIG. 37 is a vector map for AD-RTS-mIFN alpha.

Figure 38:
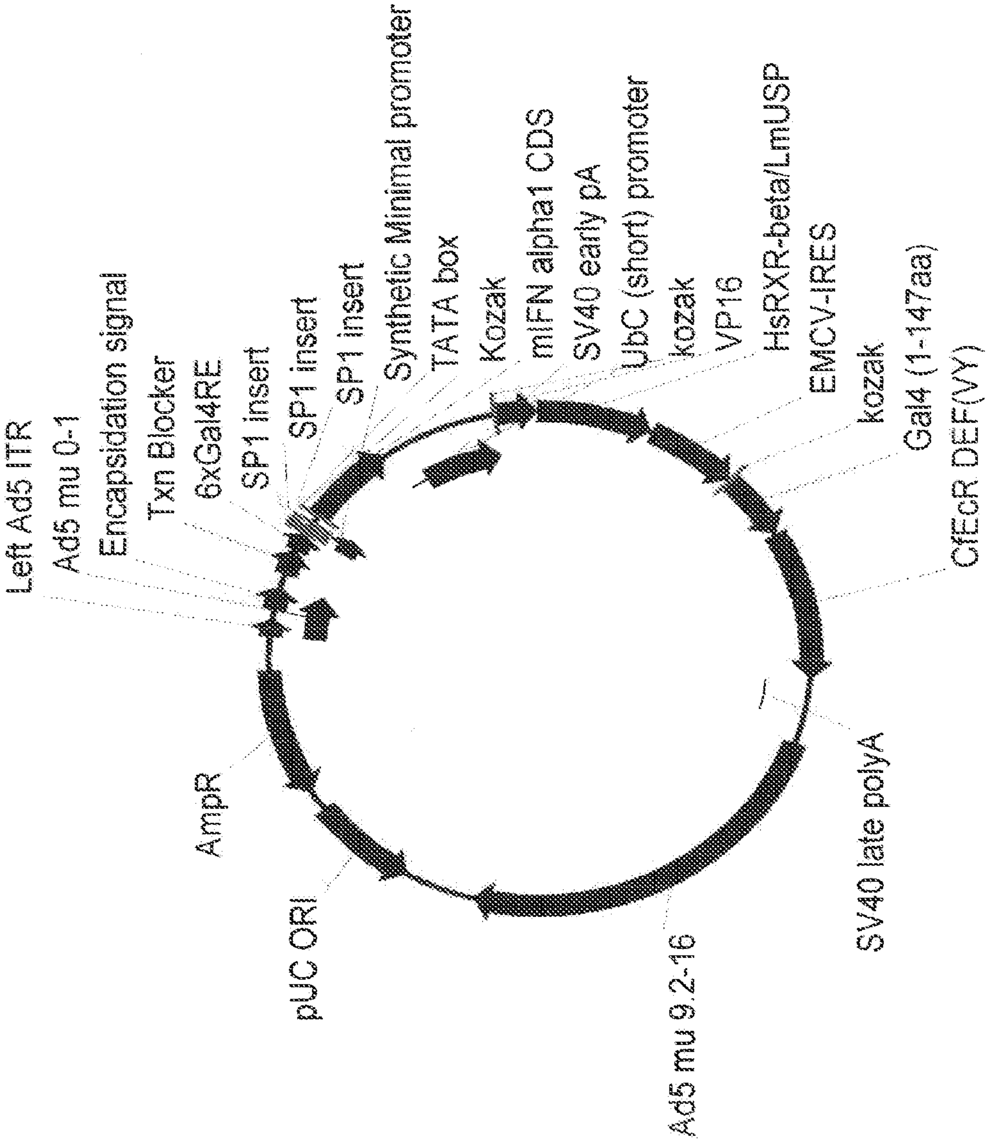

FIG. 38 is a vector map for AD-RTS-mTNF alpha.

Figure 39A:
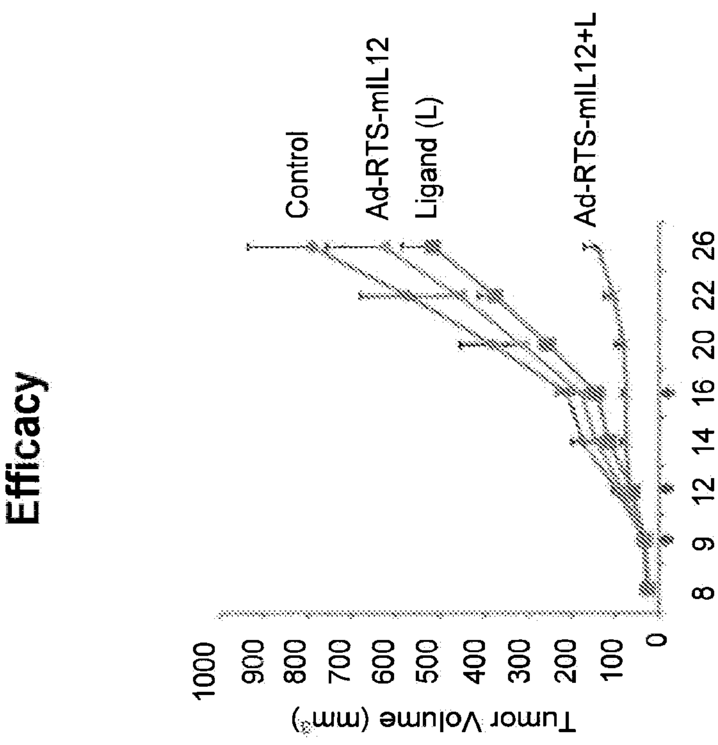
Figure 39B:
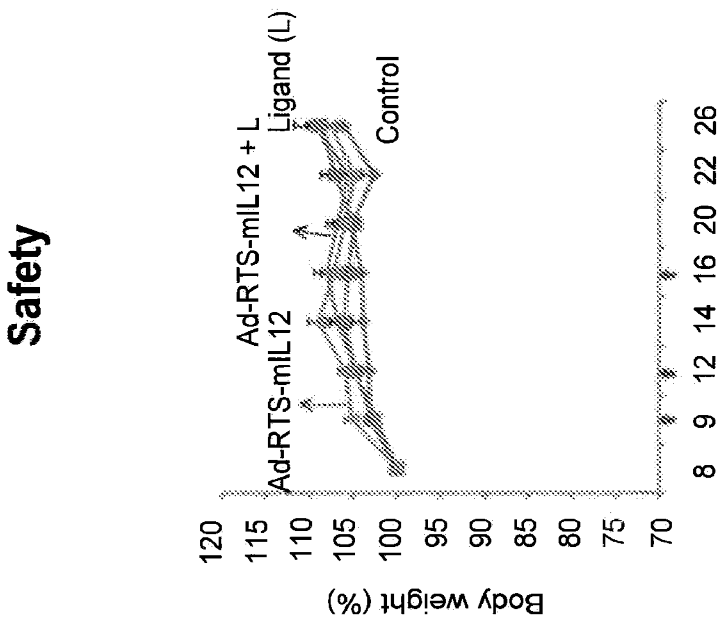

FIGS. 39A and 39B are line graphs that show efficacy (FIG. 39A) and safety (FIG. 39B) of Ad-RTS-mIL12 in a breast cancer (4T1) model. The 4T1 tumors were grown subcutaneously (s.c.) on the flank of BALB/C mice. The tumor bearing mice were randomized into four groups with 5 animals each; control no treatment, the activator ligand (L) alone, Ad-RTS-mIL12 alone and Ad-RTS-mIL12 with activator ligand. A single injection of Ad-RTS-mIL12 was given intratumorally (i.t.) at a dose level of 1e10 v.p./100 $\mu$l PBS at three different time points (arrow). The activator ligand was given to mice through chow 24 hr prior to vector injection until end of experiment. Tumor sizes (volume) and body weights (%) are shown as mean±SE. The animals with no treatment (control) had rapid tumor growth. Treatment with activator ligand alone or three doses of Ad-RTS-mIL12 without activator ligand had slight tumor growth inhibition of 22% and 35% respectively relative to control. Notably, the treatment with Ad-RTS-IL12 plus activator ligand led to significant tumor growth inhibition of 82% compared with control animals with no treatment. No major body weight loss was found in any treatment.

Figure 40:
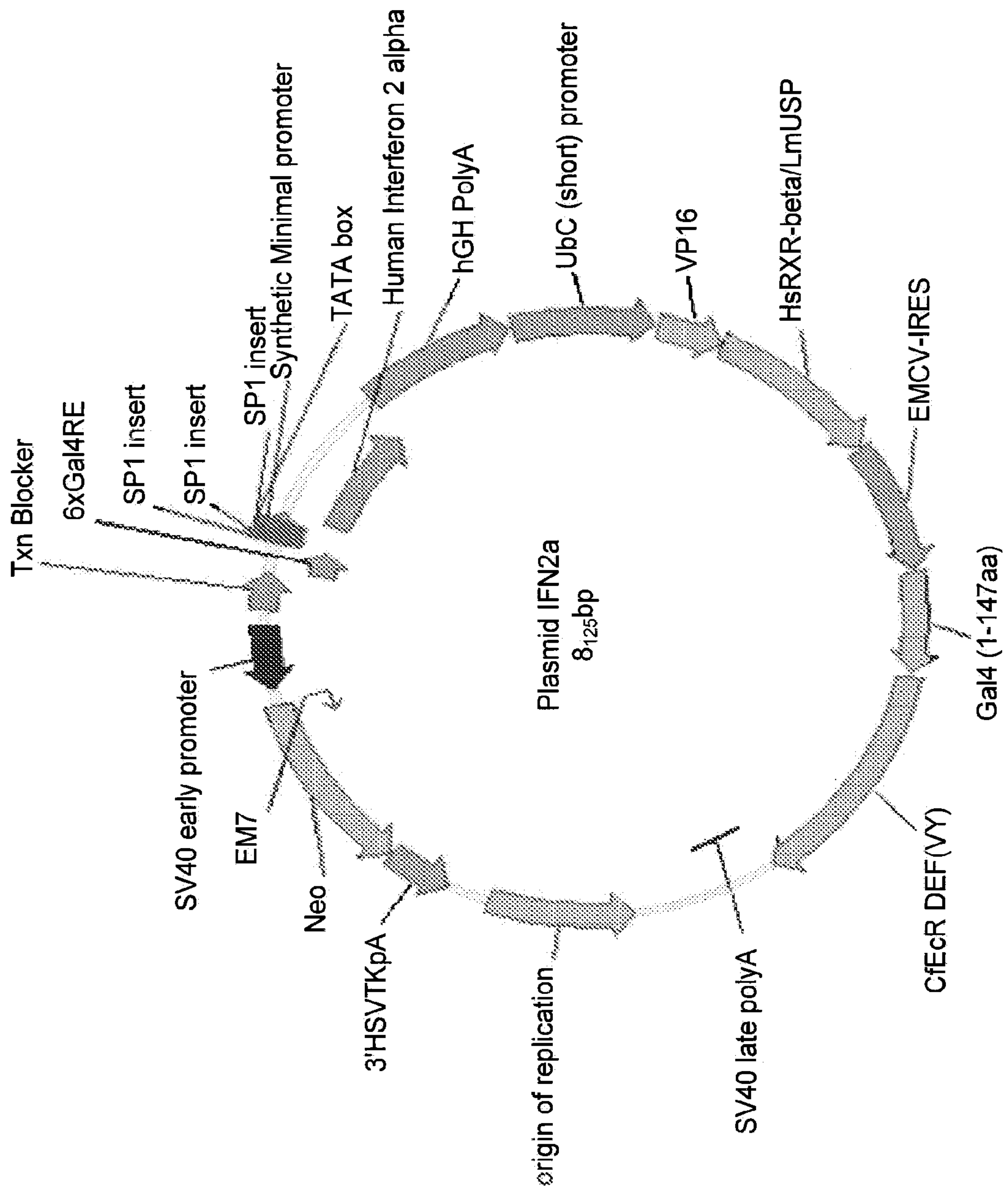

FIG. 40 is a vector map for Interferon alpha-2a.

DETAILED DESCRIPTION OF SEQUENCES

Therapeutic Proteins

Cytokines

The polynucleotide sequences of interleukin 1 (IL-1), which are cytokines important for inflammatory response against infection, are available from public databases as accession numbers M28983 (human IL-1$\alpha$); M15330 (human IL-1$\beta$); AF201830 (human IL-1$\delta$); AF201831 (human IL-1$\varepsilon$); AF201832 (human IL-1$\xi$); AF201833 (human IL-1$\eta$); NM_010554 (mouse IL-1$\alpha$); NM_008361 (mouse IL-1$\beta$); NM_019451 (mouse L-1$\delta$); □ NM_019450 (mouse IL-1f6); NM_027163 (mouse IL-1f8); NM_153511 (mouse IL-1f9); NM_204524 (chicken IL-1$\beta$); NM_017019 (rat IL-1$\alpha$); and NM_031512 (rat IL-1$\beta$), sequences of which are incorporated by reference herein.

The amino acid sequences of interleukin 1 (IL-1) are available from public databases as accession numbers AAA59134 (human IL-1$\alpha$); AAA59135 (human IL-1$\beta$); AAF25210 (human IL-1$\delta$); AAF25211 (human IL-1$\varepsilon$); AAF25212 (human IL-1$\zeta$); AAF25213 (human IL-1$\eta$); NP_034684 (mouse IL-1$\alpha$); NP_032387 (mouse IL-1$\beta$); NP_062324 (mouse L-1$\delta$); □□NP_062323 (mouse IL-1f6); NP_081439 (mouse IL-1f8); NP_705731 (mouse IL-1f9); NP_989855 (chicken IL-1$\beta$); NP_058715 (rat IL-1$\alpha$); and NP_113700 (rat IL-1$\beta$), sequences of which are incorporated by reference herein. Laurent et al., *Psychiatr. Genet.* 7: 103 (1997) identified polymorphic mutations in human interleukin-1 beta gene.

The polynucleotide sequences of interleukin 2 (IL-2), which belongs to a family of cytokines, including IL-4, IL-7, IL-9, IL-15, and IL-21, are available from public databases as accession numbers U25676 (human); NM_008366 (mouse); NM_204153 (chicken); and NM_053836 (rat), sequences of which are incorporated by reference herein.

The amino acid sequences of interleukin 2 (IL-2) are available from public databases as accession numbers AAA70092 (human); NP_032392 (mouse); NP_989484 (chicken); and NP_446288 (rat), sequences of which are incorporated by reference herein.

Liu et al., *Appl. Biochem. Biotechnol.* 133: 77 (2006) generated mutant human IL2, and Lorberboum et al., *J. Biol. Chem.* 265: 16311 (1990) describes generation of chimeric IL-2.

The polynucleotide sequences of interleukin 4 (IL-4), which is a cytokine that induces differentiation of naïve helper T cells to Th2 cells, are available from public databases as accession numbers M23442 (human); NM_021283 (mouse); NM_001007079 (chicken); and NM_201270 (rat), sequences of which are incorporated by reference herein.

The amino acid sequences of interleukin 4 (IL-4) are available from public databases as accession numbers AAA59150 (human); NP_067258 (mouse); NP_001007080 (chicken); and NP_958427 (rat), sequences of which are incorporated by reference herein.

Kawashima et al., *J. Med. Genet.* 35: 502 (1998) describes polymorphisms in IL-4 gene, that are associated with atopic dermatitis.

Interleukin 7 (IL-7) is a cytokine important for B and T cell development. The polynucleotide sequences of IL-7 are available from public databases as accession numbers J04156 (human); NM_008371 (mouse); NM_001037833 (chicken); and NM_013110 (rat), sequences of which are incorporated by reference herein.

The amino acid sequences of interleukin 7 (IL-7) are available from public databases as accession numbers AAA59156 (human); NP_032397 (mouse); NP_001032922 (chicken); and NP_037242 (rat), sequences of which are incorporated by reference herein.

Feng et al., *Genetics* 175:545 (2007) have identified point mutations in IL-7 that results in functional deficiency.

Interleukin 9 (IL-9) is a cytokine produced by T-cells and is a regulator of hematopoietic cells. The polynucleotide sequences of IL-9 are available from public databases as accession numbers NM_000590 (human); NM_008373 (mouse); NM_001037825 (chicken); and NM_001105747 (rat), sequences of which are incorporated by reference herein.

The amino acid sequences of interleukin 9 (IL-9) are available from public databases as accession numbers NP_000581 (human); NP_032399 (mouse); NP_001032914 (chicken); and NP_001099217 (rat), sequences of which are incorporated by reference herein.

IL-12 is a cytokine that can act as a growth factor for activated T and NK cells, enhance the lytic activity of NK/lymphokine-activated Killer cells, and stimulate the production of IFN-gamma by resting peripheral blood mononuclear cells (PBMC). The polynucleotide sequences of IL-12 are available from public databases as accession numbers NM_000882 (human IL12A); NM_002187 (human IL12B); NM_008351 (mouse IL12a); NM_008352 (mouse IL12b); NM_213588 (chicken IL12A); NM_213571 (chicken IL12B); NM_053390 (rat IL12a); and NM_022611 (rat IL12b), sequences of which are incorporated by reference herein.

The amino acid sequences of interleukin 12 (IL-12) are available from public databases as accession numbers NP 000873 (human IL12A); NP_002178 (human IL12B); NP 032377 (mouse IL12a); NP_032378 (mouse IL12b); NP_998753 (chicken IL12A); NP 998736 (chicken IL12B); NP_445842 (rat IL12a); and NP_072133 (rat IL12b), sequences of which are incorporated by reference herein.

Interleukin 15 (IL-15) is a cytokine that regulates T and natural killer cell activation and proliferation. The polynucleotide sequences of IL-15 are available from public databases as accession numbers U14407 (human); NM_008357 (mouse); EU334509 (chicken); and AF015719 (rat), sequences of which are incorporated by reference herein.

The amino acid sequences of interleukin 15 (IL-15) are available from public databases as accession numbers AAA21551 (human); NP 032383 (mouse); ABY55312 (chicken); and AAB94536 (rat), sequences of which are incorporated by reference herein.

Interleukin 18 (IL-18), a cytokine produced by macrophage that together with interleukin 12 induces cell-mediated immunity following infection with microbial products. The polynucleotide sequences of IL-18 are available from public databases as accession numbers U90434 (human); NM_008360 (mouse); EU747333 (chicken); and AY258448 (rat), sequences of which are incorporated by reference herein.

The amino acid sequences of interleukin 18 (IL-18) are available from public databases as accession numbers AAB50010 (human); NP_032386 (mouse); ACE79188 (chicken); and AAP14669 (rat), sequences of which are incorporated by reference herein.

The polynucleotide sequences of interleukin 21 (IL-21), which is a cytokine that has a potent regulatory effects on cells of the immune system, including natural killer cells and cytotoxic T cells by inducing cell proliferation, are available from public databases as accession numbers AF254069 (human); NM_021782 (mouse); NM_001024835 (chicken); and NM_001108943 (rat), sequences of which are incorporated by reference herein.

The amino acid sequences of interleukin 21 (IL-21) are available from public databases as accession numbers, AAG29348 (human); NP_068554 (mouse); NP_001020006 (chicken); and NP_001102413 (rat), sequences of which are incorporated by reference herein.

Interleukin 27 (IL-27) is a cytokine that plays important function in regulating the activity of B and T lymphocytes. The polynucleotide sequences of IL-27 are available from public databases as accession numbers AY099296 (human); NM_145636 (mouse); and XM_344962 (rat), sequences of which are incorporated by reference herein.

The amino acid sequences of interleukin 27 (IL-27) are available from public databases as accession numbers AAM34498 (human); NP_663611 (mouse); and XP_344963 (rat), sequences of which are incorporated by reference herein.

The polynucleotide sequences of interferon beta 1 (IFNB1), which is a member of group of interferon proteins that bind to specific cell surface receptors (IFNAR), and stimulates both macrophages and natural killer (NK) cells to elicit an anti-viral response, are available from public databases as accession numbers NM_002176 (human); NM_010510 (mouse); NM_001024836 (chicken); and NM_019127 (rat), sequences of which are incorporated by reference herein.

The amino acid sequences of interferon beta 1 (IFNB1) are available from public databases as accession numbers NP_002167 (human); NP_034640 (mouse); NP_001020007 (chicken); and NP_062000 (rat), sequences of which are incorporated by reference herein.

Interferon gamma (IFN-gamma) is a soluble cytokine that is the only Type II interferon and has antiviral, immunoregulatory, and anti-tumor activity. The polynucleotide sequences of IFN-gamma are available from public databases as accession numbers NM_000619 (human); NM_008337 (mouse); and NM_138880 (rat), sequences of which are incorporated by reference herein.

The amino acid sequences of interferon gamma (IFN-gamma) are available from public databases as accession numbers NP_000610 (human); NP_032363 (mouse); and NP_620235 (rat) sequences of which are incorporated by reference herein.

The polynucleotide sequences of tumor necrosis factor (TNF-alpha), which is a multifunctional proinflammatory cytokine secreted predominantly by monocytes/macrophages that has effects on lipid metabolism, coagulation, insulin resistance, and endothelial function, are available from public databases as accession numbers X02910 (human); NM_013693 (mouse); and BC107671 (rat), sequences of which are incorporated by reference herein.

The amino acid sequences of TNF-alpha are available from public databases as accession numbers CAA26669 (human); NP_038721 (mouse); and AAI07672 (rat), sequences of which are incorporated by reference herein.

Human TNF-alpha (abbreviated herein as hTNF-alpha, or simply hTNF) is a human cytokine that exists as a 17 kD soluble form (sTNF-alpha) and a 26 kD membrane associated form (tmTNF-alpha), the biologically active form of which is composed of a trimer of noncovalently bound 17 kD molecules. The structure of hTNF-alpha is described for example, in Pennica, D., et al. (1984) *Nature* 312:724-729; Davis, J. M., et al. (1987) *Biochemistry* 26:1322-1326; and Jones, E. Y., et al. (1989) *Nature* 338:225-228. TNF-alpha may bind to TNF-receptor type 1 (TNFR-1) or TNF-receptor type 2 (TNFR-2) and is involved in regulating immune cells, inducing apoptosis or inflammation, or inhibiting tumorigenesis or viral replication. The cell signaling cascades produced by TNF/TNFR binding are described, e.g., in Wajant, H., et al. (2003) *Cell Death Differ.* 10(1): 45-65 or Chen, G., et al. (2002) *Science* 296: 1634-5.

The full-length human TNF-alpha polypeptide consists of a cytoplasmic domain, a transmembrane domain, and an extracellular domain. A polypeptide sequence of 233aa was reported as a human TNF-alpha polypeptide sequence and is designated herein as SEQ ID NO: 37, which has a cytoplasmic domain of amino acids 1-35 of SEQ ID NO: 37, a transmembrane domain of amino acids 36-56 of SEQ ID NO: 37, and an extracellular domain of amino acids 57-233 of SEQ ID NO: 37. SEQ ID NO: 37 is a nucleotide sequence encoding SEQ ID NO: 35 or 36. Variants of human TNF-alpha include, but are not limited to, the polypeptides with one or more of the following mutations: L105S, R108W, L112F, A160V, S162F, V167A, E222K, F63S, PSD84-86VNR, or E183R.

Chemokines

Chemokine (C motif) ligand 1 (XCL1, also known as Lymphotactin) is chemotactic for CD4+ and CD8+ T cells but not for monocytes, and induces a rise in intracellular calcium in peripheral blood lymphocytes. The polynucleotide sequences of XCL1 are available from public databases as accession numbers NM_002995 (human); NM_008510 (mouse); and NM_134361 (rat), sequences of which are incorporated by reference herein.

The amino acid sequences of XCL1 are available from public databases as accession numbers NP 002986 (human); NP_032536 (mouse); and NP 599188 (rat), sequences of which are incorporated by reference herein. U.S. Pat. No. 6,022,534 discloses lymphotactin and use to either attract cytotoxic T cells and/or NK cells, and/or to induce proliferation or resident cells. Methods for isolation and usage of an antilymphotactin antibody, and XCL1 fusion protein are also disclosed.

The polynucleotide sequences of CC chemokine ligand 3 (CCL3), also known as macrophage inflammatory protein-1 (MIP-1), which is a so-called monokine (a type of cytokine produced primarily by monocytes and macrophages) that is involved in the acute inflammatory state in the recruitment and activation of polymorphonuclear leukocytes, are available from public databases as accession numbers NM_002983 (human); NM_011337 (mouse); and NM_013025 (rat), sequences of which are incorporated by reference herein.

The amino acid sequences of CCL3 are available from public databases as accession numbers NP_002974 (human); NP_035467 (mouse); and NP_037157 (rat), sequences of which are incorporated by reference herein.

The polynucleotide sequences of CCL5 (RANTES), which is a proinflammatory cytokine involved in inflammation and asthma, are available from public databases as accession numbers AF043341 (human); NM_013653 (mouse); and NM_031116 (rat), sequences of which are incorporated by reference herein.

The amino acid sequences of CCL5 are available from public databases as accession numbers AAC03541 (human); NP_038681 (mouse); and NP_112378 (rat), sequences of which are incorporated by reference herein.

The polynucleotide sequences of CC chemokine ligand 7 (CCL7), which is a chemokine involved in macrophage recruitment during inflammation and cancer invasion, are available from public databases as accession numbers NM_006273 (human); NM_013654 (mouse); and NM_001007612 (rat), sequences of which are incorporated by reference herein.

The amino acid sequences of CCL7 are available from public databases as accession numbers NP_006264 (human); NP_038682 (mouse); and NP 001007613 (rat), sequences of which are incorporated by reference herein.

Chemokine (CXC motif) ligand 9 (CXCL9, also known as MIG) is a T-cell chemoattractant inducible by gamma interferon. The polynucleotide sequences of CXCL9 are available from public databases as accession numbers NM_002416 (human); NM_0108599 (mouse); and NM_145672 (rat), sequences of which are incorporated by reference herein.

The amino acid sequences of CXCL9 are available from public databases as accession numbers NP_002407 (human); NP_032625 (mouse); and NP 663705 (rat), sequences of which are incorporated by reference herein.

Chemokine (C-X-C motif) ligand 10 (CXCL10) is a small cytokine with roles in chemoattraction for cells in the immune system, adhesion of T cells to endothelial cells, anti-tumor activity and angiogenesis. The polynucleotide sequences of CXCL10 are available from public databases as accession numbers X02530 (human); NM_021274 (mouse); and BC058444 (rat), sequences of which are incorporated by reference herein.

The amino acid sequences of chemokine (C-X-C motif) ligand 10 (CXCL10) are available from public databases as accession numbers CAA26370 (human); NP_067249 (mouse); and AAH58444 (rat), sequences of which are incorporated by reference herein.

Chemokine (C-X-C motif) ligand 12 (CXCL12), also known as stromal cell-derived factor 1 (SDF-1), is a small cytokine that belong to the intercrine family, members of which activate leukocytes and are often induced by proinflammatory stimuli such as LPS, TNF or IL1. The polynucleotide sequences of CXCL12 are available from public databases as accession numbers NM_000609 (human); NM_001012477 (mouse); NM_204510 (chicken); and NM_001033883 (rat), sequences of which are incorporated by reference herein.

The amino acid sequences of CXCL12 are available from public databases as accession numbers NP_000600 (human); NP_001012495 (mouse); NP_989841 (chicken); and NP_001029055 (rat), sequences of which are incorporated by reference herein.

Hansson et al., *Microbes and Infection* 8:841 (2006) discusses that interaction between chemokine (C-C motif) receptor 7 (CCR7) and chemokine (C-C motif) ligand 19 (CCL19, also known as MIP-3β) is crucial for the generation of primary immune responses. The polynucleotide sequences of CCR7 are available from public databases as accession numbers NM_001838 (human); and NM_007719 (mouse), sequences of which are incorporated by reference herein.

The amino acid sequences of CCR7 are available from public databases as accession numbers NP_001829 (human); and NP_031745 (mouse), sequences of which are incorporated by reference herein.

The polynucleotide sequences of CCL19 are available from public databases as accession numbers NM_006274 (human); and NM_011888 (mouse), sequences of which are incorporated by reference herein.

The amino acid sequences of CCL19 are available from public databases as accession numbers NP_006265 (human); and NP_036018 (mouse), sequences of which are incorporated by reference herein.

The polynucleotide sequences of CC chemokine ligand 21 (CCL21), a well established ligand for CCR7 which is necessary for CD4+ but not CD8+ T cells to reach their steady state 'set point', and perturbations in the expression of CCL21 may alter susceptibility to autoimmunity, are available from public databases as accession numbers AB002409 (human); NM_011335 (mouse CCL21a); NM_011124 (mouse CCL21b); and NM_023052 (mouse CCL21c); sequences of which are incorporated by reference herein.

The amino acid sequences of CCL21 are available from public databases as accession numbers BAA21817 (human); NP_035465 (mouse CCL21a); NP_035254 (mouse CCL21b); and NP_075539 (mouse CCL21c), sequences of which are incorporated by reference herein.

Interleukin-8 (IL-8), is a chemokine, also called neutrophil-activating peptide-1 or SCYB8, is a tissue-derived peptide secreted by several types of cells in response to inflammatory stimuli. U.S. Pat. Nos. 6,133,426 and 6,177,980 disclose amino acid and polynucleotide sequences of humanized anti-IL-8 antibodies. The polynucleotide sequence of human IL-8 is available from public database as accession number NM_000584, sequence of which is incorporated by reference herein.

The amino acid sequence of human IL-8 is available from public database as accession number NP_000575, sequence of which is incorporated by reference herein.

Growth Factors

Granulocyte/macrophage colony-stimulating factor (GM-CSF) is a cytokine that functions as a white blood cell growth factor, stimulates stems cells to produce granulocytes (neutrophils, eosinophils, and basophils) and monocytes. The polynucleotide sequences of GM-CSF are available from public databases as accession numbers M11734 (human); NM_009969 (mouse); EU520303 (chicken); NM_001037660 (rat Csf2ra); and NM_133555 (rat Csf2rb), sequences of which are incorporated by reference herein.

The amino acid sequences of granulocyte/macrophage colony-stimulating factor (GM-CSF) are available from public databases as accession numbers AAA52122 (human); NP_034099 (mouse); ACB11534 (chicken); NP_001032749 (rat Csf2ra); and NP_598239 (Csf2rb), sequences of which are incorporated by reference herein.

The polynucleotide sequences of FMS-related tyrosine kinase ligand (FLT3/FLK2 ligand, Flt3L), which may function as a growth factor receptor on hematopoietic stem cells or progenitor cells or both, are available from public databases as accession numbers U04806 (human); and NM_013520 (mouse), sequences of which are incorporated by reference herein.

The amino acid sequences of FLT3/FLK2 ligand (Flt3L) are available from public databases as accession numbers AAA17999 (human); and NP_038548 (mouse), sequences of which are incorporated by reference herein.

The polynucleotide sequence of transforming growth factor, alpha (TGF-alpha), which is upregulated in some human cancers can reversibly confer the transformed phenotype on cultured cells, is available from public databases as accession numbers NM_001099691 (human); NM_031199 (mouse); NM_001001614 (chicken); and NM_012671 (rat), sequences of which are incorporated by reference herein.

The amino acid sequences of TGF-alpha is available from public databases as accession numbers NP 001093161 (human); NP_112476 (mouse); NP_001001614 (chicken); and NP_036803 (rat), sequences of which are incorporated by reference herein.

Adjuvants

Beta-defensins are antimicrobial peptides implicated in innate immune response against many Gram-negative and Gram-positive bacteria, fungi and viruses. The polynucleotide sequences of beta-defensins are available from public databases as accession numbers X92744 (human hBD-1); AJ000152 (human hBD-2); AF217245 (human beta defensin-3); AJ314835 (human beta defensin-4); AB089180 (human hBD-5); AY122466 (human defensin beta 106, DEFB106); AF540979 (human beta defensin 107, DEFB107); AF529416 (human beta defensin, DEFB108); DQ012014 (human beta defensin 110, DEFB110); DQ012015 (human beta defensin 111, DEFB111); DQ012016 (human beta defensin 112, DEFB112); DQ012017 (human beta defensin 113, DEFB113); DQ012018 (human beta defensin 114, DEFB114); DQ012019 (human beta defensin 115, DEFB115); DQ012020 (human beta defensin 116, DEFB116); DQ012021 (human beta defensin 117, DEFB117); NM_007843 (mouse defensin beta 1); NM_010030 (mouse defensin beta 2, Defb2); NM_013756 (mouse defensin beta 3, Defb3); NM_019728 (mouse defensin beta 4, Defb4); NM_030734 (mouse defensin beta 5, Defb5); NM_054074 (mouse defensin beta 6, Defb6); NM_139220 (mouse defensin beta 7); NM_153108 (mouse defensin beta 8, Defb8); NM_139219 (mouse defensin beta 9, Defb9); and NM_139225 (mouse defensin beta 10, Defb10); sequences of which are incorporated by reference herein.

The amino acid sequences of beta-defensins are available from public databases as accession numbers CAA63405 (human hBD-1); CAB65126 (human hBD-2); AAF73853 (human beta defensin-3); CAC85520 (human beta defensin-4); BAC10630 (human hBD-5); AAM93908 (human defensin beta 106, DEFB106); AAN33115 (human beta defensin 107, DEFB107); AAQ09525 (human beta defensin, DEFB108); AAY59750 (human beta defensin 110, DEFB110); AAY59751 (human beta defensin 111, DEFB111); AAY59752 (human beta defensin 112, DEFB112); AAY59753 (human beta defensin 113, DEFB113); AAY59754 (human beta defensin 114, DEFB114); AAY59755 (human beta defensin 115, DEFB115); AAY59756 (human beta defensin 116, DEFB116); AAY59757 (human beta defensin 117, DEFB117); NP_031869 (mouse defenin beta 1); NP_034160 (mouse defensin beta 2, Defb2); NP_038784 (mouse defensin beta 3, Defb3); NP_062702 (mouse defensin beta 4, Defb4); NP_109659 (mouse defensin beta 5, Defb5); NP_473415 (mouse defensin beta 6, Defb6); NP_631966 (mouse defensin beta 7, Defb7); NP_694748 (mouse defensin beta 8, Defb8); NP_631965 (mouse defensin beta 9, Defb9); and NP_0.631971 (mouse defensin beta 10, Defb10), sequences of which are incorporated by reference herein. See also U.S. Pat. No. 5,242,902 for additional human and rat defensin peptide sequences.

High-mobility group box-1 (HMGB1) proteins are non-histone chromosomal proteins that function as cytokines, mediating local and systemic responses to necrotic cell death and cancer, invasion by pathogens, trauma, and sepsis. The polynucleotide sequences of HMGB1 proteins are available from public databases as accession numbers NM_002128 (human); NM_010439 (mouse); NM_204902 (chicken); and NM_012963 (rat), sequences of which are incorporated by reference herein.

The amino acid sequences of high-mobility group box-1 (HMGB1) are available from public databases as accession numbers NP_002119 (human); NP 034569 (mouse); NP 990233 (chicken); and NP_037095 (rat), sequences of which are incorporated by reference herein.

Phagocytic S100 proteins mediate inflammatory responses and recruit inflammatory cells to sites of tissue damage, and are members of Damage-associated molecular pattern (DAMP) molecules that are important for innate immunity. See Foell et al., *J. Leukocyte Biol.* 81:1 (2006). The polynucleotide sequences of S100 proteins are available from public databases as accession numbers BC014392 (human S100 A1); BC002829 (human S100 A2); BC012893 (human S100 A3); BC016300 (human S100 A4); Z18954 (human S100D); BC001431 (human S100 A6); BC 034687 (human S100 A7); BC005928 (human S100 A8); BC047681 (human S100 A9); BC015973 (human S100 A10); D38583 (human clagizzarin); NM_011309 (mouse S100al); NM_009115 (mouse S100b); NM_013650 (mouse S100a8); NM_009114 (mouse S100a9); NM_011310 (mouse S100a3); NM_011311 (mouse S100a4); and NM_011312 (mouse S100a5), sequences of which are incorporated by reference herein.

The amino acid sequences of S100 proteins are available from public databases as accession numbers AAH14392 (human S100 A1); AAH02829 (human S100 A2); AAH12893 (human S100 A3); AAH16300 (human S100 A4); CAA79479 (human S100D); AAH01431 (human S100 A6); AAH34687 (human S100 A7); AAH05928 (human S100 A8); AAH47681 (human S100 A9); AAH15973 (human S100 A10); BAA07597 (human clagizzarin); NP_035439 (mouse S100al); NP 033141 (mouse S100b); NP_038678 (mouse S100a8); NP 033140 (mouse S100a9); NP_035440 (mouse S100a3); NP_035441 (mouse S100a4); and NP 035442 (mouse S100a5), sequences of which are incorporated by reference herein.

Mannan, a plant polysaccharide, that is a polymer of the sugar mannose, is useful for generation of an immune response. U.S. Pat. No. 5,807,559, discloses immunogenic conjugates of Mannan that may be useful for generating T cell immunity against tumor-associated carbohydrate structures or against carbohydrate structures expressed on infectious agents and/or infected host cells. U.S. Pat. No. 5,773, 425 discloses use of mannan to relieve symptoms and/or cure viral diseases and to enhance immune response.

Bacille Calmette-Guerin (BCG), live attenuated *Mycobacterium* species, are used as vaccine against to prevent severe and fatal tuberculosis. U.S. Pat. No. 7,393,541 discloses generation of an adjuvant vaccine for producing an in vivo T-cell mediated immune response to a *mycobacterium* in a mammalian subject. See also Hubbard and Collins, *Infect. Immun.* 59(2): 570. U.S. Pat. No. 5,292,513 discloses a method for priming macrophages in vivo in patients in need of enhanced bactericidal and anti-viral activity with heat killed BCG. The complete genome sequence of BCG is available from public databases as accession number NC_008769 (*M. bovis* BCG str. Pasteur 1173P2, complete genome).

Bacterial lipopolysaccharides (LPS) are endotoxins that induces a strong immune response upon infection with Gram-negative bacteria. U.S. Pat. No. 4,148,877 discloses fractionation of LPS from bacterial culture and use the fraction as a drug to induce resistance to bacterial infection. U.S. Pat. No. 5,292,513 discloses a method for priming macrophages in vivo in patients in need of enhanced bactericidal and anti-viral activity with LPS.

Co-Stimulatory Molecules (Positive)

OX40 ligand (OX40L) belongs to tumor necrosis factor (ligand) superfamily member 4 (Tnfsf4), is expressed on dendritic cells and promotes Th2 cell differentiation. The polynucleotide sequences of OX40 ligand are available from public databases as accession numbers X79929 (human); U12763 (mouse); and AF037067 (rat), sequences of which are incorporated by reference herein.

The amino acid sequences of OX40 ligand (OX40L) are available from public databases as accession numbers CAA56284 (human); AAA21871 (mouse); and AAC67236 (rat), sequences of which are incorporated by reference herein.

The 4-1BB ligand (4-1BBL) belongs to tumor necrosis factor (ligand) superfamily member 9 (Tnfsf9), which is a type 2 transmembrane glycoprotein and is expressed on activated T lymphocytes. The polynucleotide sequences of 4-1BBL are available from public databases as accession numbers NM_003811 (human); NM_009404 (mouse); and AY332409 (rat), sequences of which are incorporated by reference herein.

The amino acid sequences of 4-1BB ligand (4-1BBL) are available from public databases as accession numbers NP_003802 (human); NP_033430 (mouse); and AAQ01228 (rat), sequences of which are incorporated by reference herein.

The CD40 protein belongs to the tumor necrosis factor receptor superfamily member 5, is essential in mediating a broad variety of immune and inflammatory responses including T cell-dependent immunoglobulin class switching, memory B cell development, and germinal center formation. The polynucleotide sequences of CD40 proteins are available from public databases as accession numbers X60592 (human); NM_170701 (mouse); NM_204665 (chicken); and NM_134360 (rat), sequences of which are incorporated by reference herein.

The amino acid sequences of CD40 proteins are available from public databases as accession numbers CAA43045 (human); NP_733802 (mouse); NP_989996 (chicken); and NP_599187 (rat), sequences of which are incorporated by reference herein.

CD40L (CD40 ligand, or CD154) is primarily expressed on activated T cells and is a member of the TNF superfamily of molecules. It binds to CD40 on antigen-presenting cells. CD40L plays the role of a costimulatory molecule and induces activation in antigen-presenting cells in associate with T cell receptor stimulation my MHC molecules on the antigen-presenting cells. CD40L has three binding partners: CD40, $\alpha5\beta1$ integrin and $\alpha IIb\beta3$. The CD40L sequences are available from public databases as accession numbers NM_000074 and MP_000065 (human) and NM_011616 and NP_035746 (mouse).

The glucocorticoid-induced tumor necrosis factor receptor family-related protein (GITR) can evoke effective tumor immunity via T cell stimulation. Administration of anti-GITR monoclonal antibody (mAb) can provoke potent tumor-specific immunity and eradicated established tumors without eliciting overt autoimmune disease. See Ko et al., *J. Exp. Med.* 7: 885 (2005). U.S. Pat. No. 6,503,184 B1 discloses an Anti-GITR antibody.

The polynucleotide sequences of GITR ligand (GITRL) are available from public databases as accession numbers AY358868 (human); and AY359852 (mouse), sequences of which are incorporated by reference herein.

The amino acid sequences of GITR ligand (GITRL) are available from public databases as accession numbers AAQ89227 (human); and AAQ55265 (mouse), sequences of which are incorporated by reference herein.

Herpes virus entry mediator (HVEM) binding ligand (HSVgD), also referred to as p30, or LIGHT is a TNF family member involved in co-stimulation of T cells. LIGHT has two receptors, herpes virus entry mediator (HVEM) and lymphotoxin-β receptor (LT-βR). Being a ligand for HVEM, HSVgD activates T cells by acting as a costimulatory factor to T cells that results in T cell proliferation and cytokine secretion. See U.S. Pat. No. 7,118,742 for polynucleotide and amino acid sequences of LIGHT. U.S. Pat. No. 5,654,174 describes a variant gD protein with deletion of carboxy terminal residues.

CD70 is a cytokine that binds to CD27. It plays a role in T-cell activation. Induces the proliferation of costimulated T-cells and enhances the generation of cytolytic T-cells. The polynucleotide sequences of CD70 are available from public databases as accession numbers NM_001252 (human); NM_011617 (mouse); and NM_001106878 (rat), sequences of which are incorporated by reference herein.

The amino acid sequences of CD70 are available from public databases as accession numbers NP_001243 (human); NP_035747 (mouse); and NP_001100348 (rat), sequences of which are incorporated by reference herein.

ICOS-L is a ligand for the T-cell-specific cell surface receptor ICOS and acts as a costimulatory signal for T-cell proliferation and cytokine secretion. ICOS-L also induces B-cell proliferation and differentiation into plasma cells. ICOS-L could play an important role in mediating local tissue responses to inflammatory conditions, as well as in modulating the secondary immune response by co-stimulating memory T-cell function. The polynucleotide sequences of ICOS-L are available from public databases as accession numbers NM_015259 (human); and NM_015790 (mouse), sequences of which are incorporated by reference herein.

The amino acid sequences of ICOS-L are available from public databases as accession numbers NP_056074 (human); and NP_056605 (mouse), sequences of which are incorporated by reference herein.

PD-L1 (also known as CD274) protein is expressed in activated monocytes, T and B cells. PD-L1 is upregulated in monocytes upon treatment with IFN-gamma, and in dendritic cells and keratinocytes upon treatment with IFN-gamma, together with other activators. The polynucleotide sequences of PD-L1 proteins are available from public databases as accession numbers NM_014143 (human); and NM_021893 (mouse), sequences of which are incorporated by reference herein.

The amino acid sequences of PD-L1 proteins are available from public databases as accession numbers NP_054862 (human); and NP_068693 (mouse), sequences of which are incorporated by reference herein.

Co-Stimulatory Molecule (Negative)

Cytotoxic T lymphocyte-associated 4 (CTLA4) is a member of the immunoglobulin superfamily and is a costimulatory molecule expressed in activated T cells. U.S. Pat. Nos. 7,034,121 and 6,984,720 disclose methods of preparation and usage of antibodies against CTLA4. U.S. Pat. No. 6,984,720 also discloses amino acid sequences of heavy and light chain of anti-CTLA4 antibody.

PD-1 molecules are members of the immunoglobulin gene superfamily, which binds to PD-1 ligand (PD-L1). Binding of a PD-1 receptor on a T-cell by PD-L1 transmits a costimulatory signal to the cell, which prevents the cells from progressing through the cell cycle, and increases T cell proliferation. Inhibition of an interaction between PD-L1 and receptor on the T cell with an anti-PD-L1 antibody results in the down regulation of the immune response termed as immune cell energy. U.S. Pat. No. 7,029,674 discloses methods of preparation and sequence of anti-PD-L1 antibody.

PD-L2 is primarily known as a ligand for PD-1 (or the human homologue PDCD1). However, PD-12 has been reported to be involved in the costimulatory signal, essential for T lymphocyte proliferation and IFN-gamma production in a PDCD1-independent manner. Interaction with PDCD1 inhibit T-cell proliferation by blocking cell cycle progression, and cytokine production. Yamazaki et al., *J. of Immunol.* 169: 5538 (2002) and Ansari et al., *J Exp. Med.* 198: 63 (2003) describe preparation of anti-PD-L2 monoclonal antibodies.

Counter Immune Suppressants (Tolerance Inhibitors)

Transforming growth factor-beta (TGF-β) is a multifunctional protein that regulates cell proliferation and differentiation, by interacting with one of the two transmembrane serine/threonine kinase receptors, type I and type II. See Chen et al., *Science* 28: 1335 (1993). TGF receptor type II (TGFR2) phosphorylate and activate type I receptors which autophosphorylate, then bind and activate SMAD transcriptional regulators. Lynch M A et al., *Cancer Res.* 58: 4227 (1998) describes mutations in the transforming growth factor β receptor type II gene (TGFBR2) that are associated with human ovarian carcinomas. Brand et al., *J. Biol. Chem.* 268:11500-11503 (1993) describes that deletion of predicted serine/theronine kinase cytoplasmic domain (nucleotides 1172-2036 of TGFβR2 cDNA H2-3FF, available from public databases as accession number M85079 and amino acid sequence available as accession number AAA61164) impairs the all three TGF-β (1, 2 and 3) dependent gene expressions. TGF-3 is produced in most human tumors and inhibits tumor antigen-specific cellular immunity. Foster et al., *J. Immunother.* 31:500 (2008) describes that expression of dominant negative TGFβR2 in cytotoxic T lymphocytes can lead to resistance to the inhibitory effects of TGF-β.

TGFβ acts synergistically with TGFα in inducing transformation. It also acts as a negative autocrine growth factor. Dysregulation of TGFβ activation and signaling may result in apoptosis. Ziyadeh et al., *Proc. Natl. Acad. Sci.* 97: 8015 (2000) describes that administration of anti-TGFβ antibody can prevent renal insufficiency and glomerulosclerosis in the db/db mouse, a model of type II diabetes that develops overt nephropathy. Methods of generation and use of TGFβ monoclonal antibodies are described in U.S. Pat. No. 6,419,928. Barcellos-Hoff et al., *Am J. Pathol.* 147:5 (1995) also describes a method for generation of TGFβ antibody. Amino acid and nucleotide sequences for TGFβ fusion protein constructs are described in U.S. Pat. No. 6,756,215.

IL-10 is a cytokine produced by activated Th2 cells, B cells, keratinocytes, monocytes, and macrophages. IL-10 inhibits the synthesis of a number of cytokines, including IFN-gamma, IL-2, IL-3, TNF and GM-CSF produced by activated macrophages and by helper T-cells. IL-10 is useful in promoting growth and differentiation of activated human B cells, inhibiting Th1 responses to prevent transplant rejection and T cell-mediated autoimmune diseases. O'Farrell et al., *EMBO J* 17:1006 (1998); Kanbayashi et al., *Cell Immunol.* 171:153 (1996); Fukushima et al., *Br. J, Ophthalmol.* 90:1535 (2006); and van Lent et al., *Ann. Rheum. Dis.* 66:334 (2007) describe the preparation of anti-IL10 antibodies. U.S. Pat. No. 7,326,567 discloses polynucleotide sequence of IL-10 antibody. U.S. Pat. No. 5,837,232 discloses a method to treat a B-cell mediated autoimmune disorder with anti-IL-10 antibodies.

Suppressor of cytokine signaling (SOCS) family proteins form part of a classical negative feedback system that regulates cytokine signal transduction. Alexander et al. *Cell* 98: 597 (1999) describes that suppressor of cytokine signaling 1 (SOCS 1) is a critical inhibitor of interferon-gamma signaling and prevents the potentially fatal neonatal actions of this cytokine. Hilton et al., *Proc. Natl. Acad. Sci. USA* 95:114 (1999) discusses that SOCS1 is involved in negative regulation of cytokines that signal through the JAK/STAT3 pathway. Ohya et al. *J. Biol. Chem.* 272: 27178 (1997) describes that SOCS proteins appear to be a major regulator of signaling by interleukin 6 (IL-6) and leukemia inhibitory factor (LIF). U.S. Pat. No. 6,534,277 discloses a method for the preparation and use of anti-SOCS1 antibody, where a nucleic acid sequence encoding SOCS1 antibody is introduced into cells such that the antibody is expressed by the cells or their progeny, and the recombinant cells are then administered in vivo for therapeutic effect. U.S. Pat. Nos. 6,323,317 and 7,049,418 also disclose anti-SOCS1 antibodies.

TGF-α is a mitogenic polypeptide that is able to bind to the EGF receptor and to act synergistically with TGF-β to promote anchorage-independent cell proliferation in soft agar. Ellis et al., *N. Engl. J. Med* 317:158 (1987) describes that TGF-α plays a role in certain paraneoplastic manifestations of melanoma. U.S. Pat. No. 4,742,003 and Xian et al., *The J. of Histochem. & Cytochem.* 47:949 (1999) describe methods of preparation of Anti-TGF-α antibodies.

Both tumor necrosis factor receptor (TNFR1) and Fas contain cytoplasmic Fas-associated protein with death domain (FADD), which is essential for Fas and TNF-induced signaling for programmed cell death (apoptosis) and receptor oligomerization. A mammalian protein designated FADD having the ability to bind the cytoplasmic region or domain of the Fas receptor and inhibits FAS mediated apoptosis has been identified. The polynucleotide sequence of FADD is available from public database as accession number U24231, and the amino acid sequence as accession number AAA86517, which are incorporated by reference herein. A FADD fragment or nucleic acid encoding it which is a dominant negative inhibitor of functionally intact native FADD is described in U.S. Pat. No. 6,562,797 B 1.

p53 (also known as protein 53 or tumor protein 53), is a tumor suppressor protein that in humans is encoded by the TP53 gene. p53 is important in multicellular organisms, where it regulates the cell cycle and thus functions as a tumor suppressor that is involved in preventing cancer. Amino acid and polynucleotide sequences for p53 are available as accession numbers NM_00546 and NP 000537 (human) and NM_011640 and NP_035770 (mouse).

Survivin is a member of the inhibitor of apoptosis family. The survivin protein functions to inhibit caspase activation, thereby leading to negative regulation of apoptosis or programmed cell death. This has been shown by disruption of survivin induction pathways leading to increase in apoptosis and decrease in tumour growth. The survivin protein is expressed highly in most human tumours and fetal tissue, but is completely absent in terminally differentiated cells. This fact therefore makes survivin an ideal target for cancer therapy as cancer cells are targeted while normal cells are left alone. Survivin expression is also highly regulated by the cell cycle and is only expressed in the G2-M phase. It is known that survivin localizes to the mitotic spindle by interaction with tubulin during mitosis and may play a contributing role in regulating mitosis. Rregulation of survivin appears seems to be linked to the p53 protein. Amino acid and polynucleotide sequences for p53 are available as accession numbers NM_001012270 and NP_001012270 (human) and NM_001012273 and NP_001012273 (mouse).

The melanoma-associated antigen-3 (MAGE3) amino acid sequence is found as accession number P43357-1 (UniParc).

Prostate-specific antigen (PSA) is a protein produced by the cells of the prostate gland. PSA is present in small quantities in the serum of men with healthy prostates, but is often elevated in the presence of prostate cancer and in other prostate disorders.

Prostate specific membrane antigen (PSMA) is a type 2 integral membrane glycoprotein found in prostate tissues and a few other tissues. It is a possible therapeutic target for prostate cancer.

DESCRIPTION OF SEQUENCE LISTING

SEQ ID NO: 1 is a polynucleotide sequence of a construct coding for mIL-12 and m-IL21.

SEQ ID NO: 2 is a polynucleotide sequence of a construct coding for hIL-12 and hIL-21.

SEQ ID NO: 3 is a polynucleotide sequence of a construct coding for mIL-21 and mIL-15.

SEQ ID NO: 4 is a polynucleotide sequence of a construct coding for mIL-12.

SEQ ID NO: 5 is a polynucleotide sequence of a construct coding for hIL-21 and hIL-15.

SEQ ID NO: 6 is a polynucleotide sequence of a construct coding for hIL-21.

SEQ ID NO: 7 is a polynucleotide sequence of a construct coding for mIL-21.

SEQ ID NO: 8 is a polynucleotide sequence of a construct coding for hIL-21.

SEQ ID NO: 9 is a polynucleotide sequence coding for mIL-21.

SEQ ID NO: 10 is an amino acid sequence of mIL-21.

SEQ ID NO: 11 is a polynucleotide sequence coding for mIL-15.

SEQ ID NO: 12 is an amino acid sequence of mIL-15.

SEQ ID NO: 13 is a polynucleotide sequence coding for mp40 of mIL-12.

SEQ ID NO: 14 is the amino acid sequence of mp40 of mIL-12.

SEQ ID NO: 15 is a polynucleotide sequence coding for mp35 of mIL-12.

SEQ ID NO: 16 is the amino acid sequence of mp35 of mIL-12.

SEQ ID NO: 17 is a polynucleotide sequence coding for hIL-21.

SEQ ID NO: 18 is the amino acid sequence of hIL-21.

SEQ ID NO: 19 is a polynucleotide sequence coding for hIL-15.

SEQ ID NO: 20 is the amino acid sequence of hIL-15.

SEQ ID NO: 21 is a polynucleotide sequence coding for p40 of hIL-12.

SEQ ID NO: 22 is the amino acid sequence of p40 of hIL-12.

SEQ ID NO: 23 is a polynucleotide sequence coding for p35 of hIL-12.

SEQ ID NO: 24 is the amino acid sequence of p35 of hIL-12.

SEQ ID NO: 25 is a nucleic acid sequence of an ecdysone response element found in *Drosophila.*

SEQ ID NO: 26 is a nucleic acid sequence of an ecdysone response element found in *Drosophila melanogaster*.

SEQ ID NO: 27 is a nucleic acid sequence of an ecdysone response element found in *Drosophila melanogaster*.

SEQ ID NO: 28 is a restriction site of a homing endonuclease (HE) enzyme (I-Scel)

SEQ ID NO: 29 is a DNA sequence of adenovirus vector comprising human IL-12 coding sequence: Ad-RTS-hIL-12 (SP1-RheolL-12).

SEQ ID NO: 30 is a nucleic acid sequence of human TNF wild-type 5'UTR.

SEQ ID NO: 31 is a nucleic acid sequence of 5U2 5'UTR.

SEQ ID NO: 32 is a codon-optimized nucleic acid sequence encoding IL-2 signal peptide.

SEQ ID NO: 33 is a wild-type nucleic acid sequence encoding human TNF-alpha signal peptide.

SEQ ID NO: 34 is a codon-optimized nucleotide sequence encoding human TNF-alpha signal peptide.

SEQ ID NO: 35 is a wild-type nucleic acid sequence encoding human TNF-alpha.

SEQ ID NO: 36 is a codon-optimized nucleic acid sequence encoding human TNF-alpha.

SEQ ID NO: 37 is an amino acid sequence of human TNF-alpha.

SEQ ID NO: 38 is a nucleic acid sequence of 3' regulatory region comprising a nucleotide sequence encoding a SV40 polyadenylation signal.

SEQ ID NO: 39 is a nucleic acid sequence of 3' regulatory region comprising a nucleotide sequence encoding a human growth hormone polyadenylation signal.

SEQ ID NO: 40 is a nucleic acid sequence comprising wild-type human TNF-alpha 3'UTR.

SEQ ID NO: 41 is a nucleic acid sequence of human TNF-alpha 3' UTR AtoC mutant.

SEQ ID NO: 42 is a nucleic acid sequence of human GAST 3'UTR.

SEQ ID NO: 43 is a nucleic acid sequence of synthetic 3' regulatory region.

SEQ ID NO: 44 is a nucleic acid sequence of human GAPDH 5'UTR.

SEQ ID NO: 45 is a wild-type nucleic acid sequence of insuline SP.

SEQ ID NO: 46 is a wild-type nucleic acid sequence encoding human FGF-19 signal peptide.

SEQ ID NO: 47 is a nucleic acid sequence of Vector 43318.

SEQ ID NO: 48 is a nucleic acid sequence of Vector 43319.

SEQ ID NO: 49 is a nucleic acid sequence of Vector 43320.

SEQ ID NO: 50 is a nucleic acid sequence of Vector 43321.

SEQ ID NO: 51 is a nucleic acid sequence of Vector 43322.

SEQ ID NO: 52 is a nucleic acid sequence of Vector 43323.

SEQ ID NO: 53 is a nucleic acid sequence of Vector 43324.

SEQ ID NO: 54 is a nucleic acid sequence of Vector 43325.

SEQ ID NO: 55 is a nucleic acid sequence of Vector 43326.

SEQ ID NO: 56 is a nucleic acid sequence of Vector 43327.

SEQ ID NO: 57 is a nucleic acid sequence of Vector 43328.

SEQ ID NO: 58 is a nucleic acid sequence of Vector 43329.

SEQ ID NO: 59 is a nucleic acid sequence of Vector 43533.

SEQ ID NO: 60 is a nucleic acid sequence of Vector 43534.

SEQ ID NO: 61 is a nucleic acid sequence of Vector VVN2823 (Ad-RTS-hIL-12).

SEQ ID NO: 62 is a nucleic acid sequence of Vector VVN2539 (Ad-RTS-mIL-12).

DETAILED DESCRIPTION OF INVENTION

Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference and understanding, and the inclusion of such definitions herein should not necessarily be construed to mean a substantial difference over what is generally understood in the art. Commonly understood definitions of molecular biology terms and/or methods and/or protocols can be found in Rieger et al., Glossary of Genetics: Classical and Molecular, 5th edition, Springer-Verlag: New York, 1991; Lewin, Genes V, Oxford University Press: New York, 1994; Sambrook et al., Molecular Cloning, A Laboratory Manual (3d ed. 2001) and Ausubel et al., Current Protocols in Molecular Biology (1994). As appropriate, procedures involving the use of commercially available kits and/or reagents are generally carried out in accordance with manufacturer's guidance and/or protocols and/or parameters unless otherwise noted.

The term "isolated" for the purposes of the invention designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

The term "purified," as applied to biological materials does not require the material to be present in a form exhibiting absolute purity, exclusive of the presence of other compounds. It is rather a relative definition.

"Nucleic acid," "nucleic acid molecule," "oligonucleotide," "nucleotide," and "polynucleotide" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, plasmid DNA, synthetic DNA, and semi-synthetic DNA.

The term "fragment," as applied to polynucleotide sequences, refers to a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000, 1500, 2000, 3000, 4000, 5000, or more consecutive nucleotides of a nucleic acid according to the invention.

As used herein, an "isolated nucleic acid fragment" refers to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to a polynucleotide comprising nucleotides that encode a functional molecule, including functional molecules produced by transcription only (e.g., a bioactive RNA species) or by transcription and translation (e.g., a polypeptide). The term "gene" encompasses cDNA and genomic DNA nucleic acids. "Gene" also refers to a nucleic acid fragment that expresses a specific RNA, protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism, A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. For example, the interleukin-12 (IL-12) gene encodes the IL-12 protein. IL-12 is a heterodimer of a 35-kD subunit (p35) and a 40-kD subunit (p40) linked through a disulfide linkage to make fully functional IL-12p70. The IL-12 gene encodes both the p35 and p40 subunits.

"Heterologous DNA" refers to DNA not naturally located in the cell, or in a chromosomal site of the cell. The heterologous DNA may include a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook et al. in Molecular Cloning: A Laboratory Manual, Second Edition, Cold Spring Harbor Laboratory Press, Cold Spring Harbor (1989), particularly Chapter 11 and Table 11.1 therein). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the invention also includes isolated nucleic acid fragments that are complementary to the complete sequences as disclosed or used herein as well as those substantially similar nucleic acid sequences.

In one embodiment of the invention, polynucleotides are detected by employing hybridization conditions comprising a hybridization step at $T_m$ of 55° C., and utilizing conditions as set forth above. In other embodiments, the $T_m$ is 60° C., 63° C., or 65° C.

Post-hybridization washes also determine stringency conditions. One set of conditions uses a series of washes starting with 6×SSC, 0.5% SDS at room temperature for 15 minutes (min), then repeated with 2×SSC, 0.5% SDS at 45° C. for 30 min, and then repeated twice with 0.2×SSC, 0.5% SDS at 50° C. for 30 min. One set of stringent conditions uses higher temperatures in which the washes are identical to those above except for the temperature of the final two 30 min washes in 0.2×SSC, 0.5% SDS is increased to 60° C. Another set of highly stringent conditions uses two final washes in 0.1×SSC, 0.1% SDS at 65° C.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In one embodiment of the invention, polynucleotides are detected by employing hybridization conditions comprising a hybridization step in less than 500 mM salt and at least 37° C., and a washing step in 2×SSPE at a temperature of at least 63° C. In another embodiment, the hybridization conditions comprise less than 200 mM salt and at least 37° C. for the hybridization step. In a further embodiment, the hybridization conditions comprise 2×SSPE and 63° C. for both the hybridization and washing steps.

In another embodiment, the length for a hybridizable nucleic acid is at least about 10 nucleotides. Preferably a minimum length for a hybridizable nucleic acid is at least about 15 nucleotides; e.g., at least about 20 nucleotides; e.g., at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a short nucleic acid that is hybridizable to a genomic DNA molecule, a cDNA molecule, a plasmid DNA or an mRNA molecule. Oligonucleotides can be labeled, e.g., with $^{32}$P-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, for DNA sequencing, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" refers to an oligonucleotide that hybridizes to a target nucleic acid sequence to create a double stranded nucleic acid region that can serve as an initiation point for DNA synthesis under suitable conditions. Such primers may be used in a polymerase chain reaction or for DNA sequencing.

"Polymerase chain reaction" is abbreviated PCR and refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and refers to an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" or "coding region" refers to a double-stranded DNA sequence that encodes a polypeptide and can be transcribed and translated into a polypeptide in a cell, ex vivo, in vitro or in vivo when placed under the control of suitable regulatory sequences. "Suitable regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in an eukaryotic cell, a polyadenylation signal and transcription termination sequence will usually be located 3' to the coding sequence.

"Open reading frame" is abbreviated ORF and refers to a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (← →) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→ ←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→ →) or (5'→3'5'→3').

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to a reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" are used interchangeably and refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes both viral and nonviral vehicles for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. Another example of vectors that are useful in the invention is the ULTRAVECTOR® Production System (Intrexon Corp., Blacksburg, Va.) as described in WO 2007/038276. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include, but are not limited to, retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" refers to a "replicon," which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector"). Cloning vectors may comprise one or more sequences that can be used for selection of cells comprising the vector and/or one or more multiple cloning sites for insertion of sequences of interest.

The term "expression vector" refers to a vector, plasmid or vehicle designed to enable the expression of an inserted nucleic acid sequence. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving expression of these genes can be used in an expression vector, including but not limited to, viral promoters, bacterial promoters, animal promoters, mammalian promoters, synthetic promoters, constitutive promoters, tissue specific promoters, pathogenesis or disease related promoters, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-, seed specific-, pollen specific-, ovary specific-, cauliflower mosaic virus 35S, CMV 35S minimal, cassava vein mosaic virus (CsVMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art including, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Vectors may be introduced into the desired host cells by methods known in the art, e.g., transfection, electroporation, microinjection, transduction, cell fusion, DEAE dextran, calciuimr phosphate precipitation, lipofection (lysosome fusion), use of a gene gun, or a DNA vector transporter (see, e.g., Wu et al., *J Biol. Chem.* 267:963 (1992); Wu et al., *J. Biol. Chem.* 263:14621 (1988); and Hartmut et al., Canadian Patent Application No. 2,012,311).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Felgner et al., *Proc. Natl. Acad Sci. USA.* 84:7413 (1987); Mackey et al., Proc. Natl. Acad Sci. USA 85:8027 (1988); and Ulmer et al., *Science* 259:1745 (1993)). The use of cationic lipids may promote encapsulation of negatively charged nucleic acids, and also promote fusion with negatively charged cell membranes (Felgner et al., *Science* 337:387 (1989)). Particularly useful lipid compounds and compositions for transfer of nucleic acids are described in WO95/18863, WO96/17823 and U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey et al. 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., *Hum. Gene Ther.* 3:147 (1992); and Wu et al., *J. Biol. Chem.* 262:4429 (1987)).

The term “transfection” refers to the uptake of exogenous or heterologous RNA or DNA by a cell. A cell has been “transfected” by exogenous or heterologous RNA or DNA when such RNA or DNA has been introduced inside the cell. A cell has been “transformed” by exogenous or heterologous RNA or DNA when the transfected RNA or DNA effects a phenotypic change. The transforming RNA or DNA can be integrated (covalently linked) into chromosomal DNA making up the genome of the cell.

“Transformation” refers to the transfer of a nucleic acid fragment into the genome of a host organism, resulting in genetically stable inheritance. Host organisms containing the transformed nucleic acid fragments are referred to as “transgenic” or “recombinant” or “transformed” organisms.

In addition, the recombinant vector comprising a polynucleotide according to the invention may include one or more origins for replication in the cellular hosts in which their amplification or their expression is sought, markers or selectable markers.

The term “selectable marker” refers to an identifying factor, usually an antibiotic or chemical resistance gene, that is able to be selected for based upon the marker gene’s effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term “reporter gene” refers to a nucleic acid encoding an identifying factor that is able to be identified based upon the reporter gene’s effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

“Promoter” and “promoter sequence” are used interchangeably and refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as “constitutive promoters.” Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is farther recognized that since in most cases the exact boundaries of regulatory sequences have not been completely defined, DNA fragments of different lengths may have identical promoter activity.

In any of the vectors of the present invention, the vector optionally comprises a promoter disclosed herein. In one embodiment, the promoter is a promoter listed in Table 1 herein.

In any of the vectors of the present invention, the vector optionally comprises a tissue-specific promoter. In one embodiment, the tissue-specific promoter is a tissue specific promoter disclosed herein. In another embodiment, the tissue-specific promoter is a tissue specific promoter listed in Table 2 herein.

The promoter sequence is typically bounded at its 3' terminus by the transcription initiation site and extends upstream (5' direction) to include the minimum number of bases or elements necessary to initiate transcription at levels detectable above background. Within the promoter sequence is found a transcription initiation site (conveniently defined for example, by mapping with nuclease Si), as well as protein binding domains (consensus sequences) responsible for the binding of RNA polymerase.

"Therapeutic switch promoter" ("TSP") refers to a promoter that controls expression of a gene switch component. Gene switches and their various components are described in detail elsewhere herein. In certain embodiments a TSP is constitutive, i.e., continuously active. A constitutive TSP may be either constitutive-ubiquitous (i.e., generally functions, without the need for additional factors or regulators, in any tissue or cell) or constitutive-tissue or cell specific (i.e., generally functions, without the need for additional factors or regulators, in a specific tissue type or cell type). In certain embodiments a TSP of the invention is activated under conditions associated with a disease, disorder, or condition. In certain embodiments of the invention where two or more TSPs are involved the promoters may be a combination of constitutive and activatable promoters. As used herein, a "promoter activated under conditions associated with a disease, disorder, or condition" includes, without limitation, disease-specific promoters, promoters responsive to particular physiological, developmental, differentiation, or pathological conditions, promoters responsive to specific biological molecules, and promoters specific for a particular tissue or cell type associated with the disease, disorder, or condition, e.g. tumor tissue or malignant cells. TSPs can comprise the sequence of naturally occurring promoters, modified sequences derived from naturally occurring promoters, or synthetic sequences (e.g., insertion of a response element into a minimal promoter sequence to alter the responsiveness of the promoter).

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" refer to DNA regulatory sequences, such as promoters, enhancers, terminators, and the like, that provide for the expression of a coding sequence in a host cell. In eukaryotic cells, polyadenylation signals are control sequences.

The term "response element" refers to one or more cis-acting DNA elements which confer responsiveness on a promoter mediated through interaction with the DNA-binding domains of a transcription factor. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element is incorporated. The DNA binding domain of the transcription factor binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (SEQ ID NO: 25) (see Cherbas et. al., *Genes Dev.* 5:120 (1991)); AGGTCAN$_{(n)}$AGGTCA, where N$_{(n)}$ can be one or more spacer nucleotides (SEQ ID NO: 26) (see D'Avino et al., *Mol. Cell. Endocrinol.* 113:1 (1995)); and GGGTTGAATGAATTT (SEQ ID NO: 27) (see Antoniewski et al., *Mol. Cell Biol.* 14:4465 (1994)).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein refers to the transcription and stable accumulation of sense (mRNA) or antisense RNA derived from a nucleic acid or polynucleotide. Expression may also refer to translation of mRNA into a protein or polypeptide.

The terms "cassette," "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and a ligand-dependent transcription factor-based system which, in the presence of one or more ligands, modulates the expression of a gene into which the response element and promoter are incorporated. The term "a polynucleotide encoding a gene switch" refers to the combination of a response element associated with a promoter, and a polynucleotide encoding a ligand-dependent transcription factor-based system which, in the presence of one or more ligands, modulates the expression of a gene into which the response element and promoter are incorporated.

The therapeutic switch promoters of the invention may be any promoter that is useful for treating, ameliorating, or preventing a specific disease, disorder, or condition. Examples include, without limitation, promoters of genes that exhibit increased expression only during a specific disease, disorder, or condition and promoters of genes that exhibit increased expression under specific cell conditions (e.g., proliferation, apoptosis, change in pH, oxidation state, oxygen level). In some embodiments where the gene switch comprises more than one transcription factor sequence, the specificity of the therapeutic methods can be increased by combining a disease- or condition-specific promoter with a tissue- or cell type-specific promoter to limit the tissues in which the therapeutic product is expressed. Thus, tissue- or cell type-specific promoters are encompassed within the definition of therapeutic switch promoter.

As an example of disease-specific promoters, useful promoters for treating cancer include the promoters of oncogenes. Examples of classes of oncogenes include, but are not limited to, growth factors, growth factor receptors, protein kinases, programmed cell death regulators and transcription factors. Specific examples of oncogenes include, but are not limited to, sls, erb B, erb B-2, ras, abl, myc and bcl-2 and TERT. Examples of other cancer-related genes include tumor associated antigen genes and other genes that are overexpressed in neoplastic cells (e.g., MAGE-1, carcinoembryonic antigen, tyrosinase, prostate specific antigen, prostate specific membrane antigen, p53, MUC-1, MUC-2, MUC-4, HER-2/neu, T/Tn, MART-1, gp100, GM2, Tn, sTn, and Thompson-Friedenreich antigen (TF)).

Examples of promoter sequences and other regulatory elements (e.g., enhancers) that are known in the art and are useful as therapeutic switch promoters in the present invention are disclosed in the references listed in Tables 1 and 2, along with the disease/disorder (Table 1) or tissue specificity (Table 2) associated with each promoter. The promoter sequences disclosed in these references are herein incorporated by reference in their entirety.

The polynucleotide encoding any of the proteins listed in Table 1 may also be expressed using a vector of the present invention with a promoter that is not a therapeutic promoter.

TABLE 1

| Promoter Sequence | Disease/Disorder | Patent/Published Application No. |
|---|---|---|
| Her-2/neu (ERBB2/c-erbB-2) | cancer | 5,518,885 |
| Osteocalcin | calcified tumors | 5,772,993 |
| stromelysin-1 | cancer | 5,824,794 |
| prostate specific antigen | prostate cancer | 5,919,652 |
| human sodium-iodide symporter | thyroid carcinoma | 6,015,376 |
| H19, IF-1, IGF-2 | cancer | 6,306,833 |
| thymosin β15 | breast, pancreatic, prostate cancer | 6,489,463 |
| T cell factor | cancer | 6,608,037 |
| cartilage-derived retinoic acid-sensitive protein | chondrosarcoma, mammary tumor | 6,610,509 |
| Insulin | pancreatic cancer | 6,716,824 |
| PEG-3 | cancer | 6,737,523 |

TABLE 1-continued

| Promoter Sequence | Disease/Disorder | Patent/Published Application No. |
|---|---|---|
| telomerase reverse transcriptase | cancer | 6,777,203 |
| melanoma differentiation associated gene-7 | cancer | 6,841,362 |
| Prostasin | cancer | 6,864,093 |
| telomerase catalytic subunit; cyclin-A | cancer | 6,936,595 |
| midkine; c-erbB-2 | cancer | 7,030,099 |
| prostate-specific membrane antigen | prostate cancer | 7,037,647 |
| p51 | cancer | 7,038,028 |
| telomerase RNA | cancer | 7,084,267 |
| prostatic acid phosphatase | prostate cancer | 7,094,533 |
| $PCA3_{dd3}$ | prostate cancer | 7,138,235 |
| DF3/MUC1 | cancer | 7,247,297 |
| hex II | cancer | 2001/0011128 |
| cyclooxygenase-2 | cancer | 2002/0107219 |
| super PSA | prostate cancer | 2003/0078224 |
| skp2 | cancer | 2003/0109481 |
| PRL-3 | metastatic colon cancer | 2004/0126785 |
| CA125/M17S2 | ovarian cancer | 2004/0126824 |
| IAI.3B | ovarian cancer | 2005/0031591 |
| CRG-L2 | liver cancer | 2005/0124068 |
| TRPM4 | prostate cancer | 2006/0188990 |
| RTVP | glioma | 2006/0216731 |
| TARP | prostate cancer, breast cancer | 2007/0032439 |
| telomere reverse transcriptase | cancer | 2007/0059287 |
| A4 amyloid protein | Alzheimer's disease | 5,151,508 |
| amyloid β-protein precursor | Alzheimer's disease | 5,643,726 |
| precursor of the Alzheimer's Disease A4 amyloid protein | Alzheimer's disease | 5,853,985 |
| neuropeptide FF | CNS disorders | 6,320,038 |
| endoplasmic reticulum stress elements | stress | 7,049,132 |
| urocortin II | psychopathologies | 7,087,385 |
| tyrosine hydroxylase | neurological disorders | 7,195,910 |
| complement factor 3; serum amyloid A3 | inflammation | 5,851,822 |
| tissue inhibitor of metalloproteinase-3 (TIMP-3) | rheumatism, cancer, autoimmune disease, inflammation | 5,854,019 |
| p75 tumor necrosis factor receptor | autoimmune disease | 5,959,094 |
| tumor necrosis factor-α | inflammation | 6,537,784 |
| peroxisome proliferator activated receptor/IIA-1 nonpancreatic secreted phospholipase A2 | inflammation | 6,870,044 |
| SOCS-3 | growth disorders, autoimmune disease, inflammation | 2002/0174448 |
| SR-BI | lipid disorders | 5,965,790 |
| Ob | obesity | 5,698,389 |
| site-1 protease | obesity, diabetes | 7,045,294 |
| TIGR | glaucoma | 7,138,511 |
| VL30 | anoxia | 5,681,706 |
| excitatory amino acid transporter-2 | nervous system ischemia | 2004/0171108 |
| MDTS9 | renal failure | 2006/0014931 |
| LIM, pyrroline 5-carboxylate reductase, SIM2 | prostate disorders | 2006/0134688 |
| Bax | apoptosis | 5,744,310 |
| Fas | apoptosis | 5,888,764 |
| bbc3 | apoptosis | 7,202,024 |
| PINK-1 | PI-3 kinase/Akt pathway disorders | 2006/0228776 |

TABLE 2

| Promoter Sequence | Tissue Specificity | Patent/Published Application No. |
|---|---|---|
| troponin T | skeletal muscle | 5,266,488 |
| myoD | muscle | 5,352,595 |
| Actin | muscle | 5,374,544 |
| smooth muscle 22α | arterial smooth muscle | 5,837,534 |
| Utrophin | muscle | 5,972,609 |
| Myostatin | muscle | 6,284,882 |
| smooth muscle myosin heavy chain | smooth muscle | 6,780,610 |
| cardiac ankyrin repeat protein | cardiac muscle | 7,193,075 |
| MLP | muscle | 2002/0042057 |
| Smoothelin | smooth muscle | 2003/0157494 |
| MYBPC3 | cardiomyocytes | 2004/0175699 |
| Tα1 α-tubulin | neurons | 5,661,032 |
| intercellular adhesion molecule-4 (ICAM-4) | neurons | 5,753,502 |
| γ-aminobutyric acid type A receptor β1 subunit | hippocampus | 6,066,726 |
| neuronal nicotinic acetylcholine receptor β2-subunit | neurons | 6,177,242 |
| presenilin-1 | neurons | 6,255,473 |
| calcium-calmodulin-dependent kinase IIα | forebrain | 6,509,190 |
| $CRF_{2a}$ receptor | brain | 7,071,323 |
| nerve growth factor | neurons | 2003/159159 |
| GLP-2 receptor | gut, brain | 2002/0045173 |
| type I transglutaminase | keratinocytes | 5,643,746 |
| K14 | keratinocytes | 6,596,515 |
| stearoyl-CoA desaturase | skin | 2002/0151018 |
| Megsin | renal cells | 6,790,617 |
| Prolactin | pituitary | 5,082,779 |
| GDF-9 | ovary, testes, hypothalamus, pituitary, placenta | 7,227,013 |
| PSP94 | prostate | 2003/0110522 |
| NRL; NGAL | mammary gland | 5,773,290 |
| long whey acidic protein | mammary gland | 5,831,141 |
| mammary associated amyloid A | mammary ductal epithelial cells | 2005/0107315 |
| endothelin-1 | endothelial cells | 5,288,846 |
| Serglycin | hematopoietic cells | 5,340,739 |
| platelet-endothelial cell adhesion molecule-1 (PECAM-1) | platelets, leukocytes, endothelial cells | 5,668,012 |
| Tie receptor tyrosine kinase | endothelial cells, bone marrow | 5,877,020 |
| KDR/flk-1 | endothelial cells | 5,888,765 |
| Endoglin | endothelial cells | 6,103,527 |
| CCR5 | myeloid and lymphoid cells | 6,383,746 |
| CD11d | myeloid cells | 6,881,834 |
| platelet glycoprotein IIb | hematopoietic cells | 6,884,616 |
| preproendothelin-1 | endothelial cells | 7,067,649 |
| interleukin-18 binding protein | mononuclear cells | 2006/0239984 |
| CD34 | hematopoietic stem cells | 5,556,954 |
| Tec tyrosine kinase | hematopoietic stem cells, liver | 6,225,459 |

Other genes that exhibit changes in expression levels during specific diseases or disorders and therefore may provide promoters that are useful in the present invention include, without limitation, the genes (along with the associated disease/disorder) listed in Table 3.

TABLE 3

| Gene | Disease/Disorder | Patent/ Published Application No. |
|---|---|---|
| MLH1, MSH2, MSH6, PMS1, APC | Colorectal cancer | 7,148,016 |
| LEF-1 | Colon cancer | 2002/0169300 |
| $F_2$ receptor | Colon cancer | 2002/0187502 |
| TGF-β type II receptor | Colon cancer | 2004/0038284 |
| EYA4 | Colon cancer | 2005/0003463 |
| PCA3 | Prostate cancer | 7,138,235 |
| K2 | Prostate cancer | 6,303,361 |
| PROST 03 | Prostate cancer metastases | 2002/0009455 |
| PCAM-1 | Prostate cancer | 2002/0042062 |
| PCADM-1 | Prostate cancer | 2003/0100033 |
| $PCA3_{dd3}$ | Prostate cancer | 2003/0165850 |
| PCAV | Prostate cancer | 2006/0275747 |
| PAcP | Androgen-insensitive prostate cancer | 2006/0294615 |
| SEQ ID NO: 1 of the patent 5,866,329, incorporated by reference herein | Liver cancer | 5,866,329 |
| SEQ ID NOS: 1, 3 of the U.S. patent application publication 2002/0115094, incorporated by reference herein | Hepatocellular cancer | 2002/0115094 |
| SEQ ID NO: 1 of the patent U.S. application publication 2005/0037372, incorporated by reference herein | Hepatocellular carcinoma | 2005/0037372 |
| $ATB_0$ | Hepatocellular carcinoma | 2006/0280725 |
| SEQ ID NOS: 1, 3 of the U.S. patent application publication 2007/0042420 | Liver cancer | 2007/0042420 |
| CSA-1 | Chondrosarcoma | 2001/0016649 |
| SEQ ID NOS: 1-15 of the U.S. patent application publication 2001/0016651, incorporated by reference herein | Pancreatic cancer | 2001/0016651 |
| SEQ ID NOS: 1-15 of the U.S. patent application publication 2003/0212264, incorporated by reference herein | Pancreatic cancer | 2003/0212264 |
| SYG972 | Breast cancer | 2002/0055107 |
| Urb-ctf | Breast cancer | 2003/0143546 |
| BCU399 | Breast cancer | 2003/0180728 |
| TBX2 | Breast cancer | 2004/0029185 |
| Cyr61 | Breast cancer | 2004/0086504 |
| DIAPH3 | Breast cancer | 2005/0054826 |
| SEQ ID NOS: 1-24 of the U.S. patent application publication 2007/0134669, incorporated by reference herein | Breast cancer | 2007/0134669 |
| Human aspartyl (asparaginyl) beta-hydroxylase | CNS cancer | 2002/0102263 |
| BEHAB | CNS cancer | 2003/0068661 |
| IL-8 | Kaposi's Sarcoma | 2003/0096781 |
| SEQ ID NOS: 1-278 of the U.S. patent application publication 2002/0198362, incorporated by reference herein | Hematological cancers | 2002/0198362 |
| BLSA | B-cell cancer | 2003/0147887 |
| BP1 | Leukemia | 2003/0171273 |
| DAP-kinase, HOXA9 | Non-small cell lung cancer | 2003/0224509 |
| ARP | Clear cell renal carcinoma, inflammatory disorders | 2004/0010119 |
| Nbk | Renal cancer | 2005/0053931 |
| CD43 | Ovarian cancer | 2006/0216231 |
| SEQ ID NOS: 1-84 of the U.S. patent application publication 2007/0054268, | Ovarian cancer | 2007/0054268 |

TABLE 3-continued

| Gene | Disease/Disorder | Patent/ Published Application No. |
|---|---|---|
| incorporated by reference herein | | |
| β7-hcG, β6-hCG, β6e-hCG, β5-hCG, β8-hcG, β3-hCG | Uterine tumors | 2006/0292567 |
| MTA1s | Hormone insensitive cancer | 2006/0204957 |
| Old-35, Old-64 | Tumor proliferation | 2003/0099660 |
| LAGE-1 | Cancer | 6,794,131 |
| CIF150/hTAF$_{II}$150 | Cancer | 6,174,679 |
| P65 oncofetal protein | Cancer | 5,773,215 |
| Telomerase | Cancer | 2002/0025518 |
| CYP1B1 | Cancer | 2002/0052013 |
| 14-3-3σ | Cancer | 2002/0102245 |
| NES1 | Cancer | 2002/0106367 |
| CAR-1 | Cancer | 2002/0119541 |
| HMGI, MAG | Cancer | 2002/0120120 |
| ELL2 | Cancer | 2002/0132329 |
| Ephrin B2 | Cancer | 2002/0136726 |
| WAF1 | Cancer | 2002/0142442 |
| CIF130 | Cancer | 2002/0143154 |
| C35 | Cancer | 2002/0155447 |
| BMP2 | Cancer | 2002/0159986 |
| BUB3 | Cancer | 2002/0160403 |
| Polymerase kappa | Cancer | 2003/0017573 |
| EAG1, EAG2 | Cancer | 2003/0040476 |
| SEQ ID NOS: 18, 20, 22 of the U.S. patent application publication 2003/0044813, incorporated by reference herein | Cancer | 2003/0044813 |
| HMG I | Cancer | 2003/0051260 |
| HLTF | Cancer | 2003/0082526 |
| Barx2 | Cancer | 2003/0087243 |
| SEQ ID NOS: 18, 20, 22, 32, 34, 36 of the U.S. patent application publication 2003/0108920, incorporated by reference herein | Cancer | 2003/0108920 |
| Cables | Cancer | 2003/0109443 |
| Pp 32r1 | Cancer | 2003/0129631 |
| BMP4 | Cancer | 2003/0134790 |
| TS10q23.3 | Cancer | 2003/0139324 |
| Nuclear spindle-associating protein | Cancer | 2003/0157072 |
| PFTAIRE | Cancer | 2003/0166217 |
| SEMA3B | Cancer | 2003/0166557 |
| MOGp | Cancer, multiple sclerosis, inflammatory disease | 2003/0166898 |
| Fortilin | Cancer | 2003/0172388 |
| SEQ ID NO: 1 of the U.S. patent application publication 2003/0215833, incorporated by reference herein | Cancer | 2003/0215833 |
| IGFBP-3 | Cancer | 2004/0005294 |
| Polyhomeotic 2 | Cancer | 2004/0006210 |
| PNQALRE | Cancer | 2004/0077009 |
| SEQ ID NOS: 1, 3 of the U.S. patent application publication 2004/0086916, incorporated by reference herein | Cancer | 2004/0086916 |
| SCN5A | Cancer | 2004/0146877 |
| miR15, miR16 | Cancer | 2004/0152112 |
| Headpin | Cancer | 2004/0180371 |
| PAOh1/SMO | Cancer | 2004/0229241 |
| Hippo, Mst2 | Cancer | 2005/0053592 |
| PSMA-like | Cancer, neurological disorders | 2005/0064504 |
| JAB1 | Cancer | 2005/0069918 |
| NF-AT | Cancer | 2005/0079496 |
| P28ING5 | Cancer | 2005/0097626 |
| MTG16 | Cancer | 2005/0107313 |
| ErbB-2 | Cancer | 2005/0123538 |

TABLE 3-continued

| Gene | Disease/Disorder | Patent/ Published Application No. |
|---|---|---|
| HDAC9 | Cancer | 2005/0130146 |
| GPBP | Cancer | 2005/0130227 |
| MG20 | Cancer | 2005/0153352 |
| KLF6 | Cancer | 2005/0181374 |
| ARTS1 | Cancer | 2005/0266443 |
| Dock 3 | Cancer | 2006/0041111 |
| Annexin 8 | Cancer | 2006/0052320 |
| MH15 | Cancer | 2006/0068411 |
| DELTA-N p73 | Cancer | 2006/0088825 |
| RapR6 | Cancer | 2006/099676 |
| StarD10 | Cancer | 2006/0148032 |
| Ciz1 | Cancer | 2006/0155113 |
| HUJ1 | Cancer | 2006/0194235 |
| RapR7 | Cancer | 2006/0240021 |
| A34 | Cancer | 2006/0292154 |
| Sef | Cancer | 2006/0293240 |
| Killin | Cancer | 2007/0072218 |
| SGA-1M | Cancer | 2007/0128593 |
| TGFβ Type II receptor | Cancer | 2062/0064786 |
| GCA-associated genes | Giant cell arteritis | 6,743,903 |
| PRV-1 | Polycythemia vera | 6,686,153 |
| SEQ ID NOS: 2, 4 of the U.S. patent 5,948,637, incorporated by reference herein | Ischemia | 5,948,637 |
| Vezf1 | Vascular disorders | 2002/0023277 |
| MLP | Dilatative cardiomyopathy | 2002/0042057 |
| VEGI | Pathological angiogenesis | 2002/0111325 |
| PRO256 | Cardiovascular disorders | 2002/0123091 |
| AOP2 | Atherosclerosis | 2002/0142417 |
| Remodelin | Arterial restenosis, fibrosis | 2002/0161211 |
| Phosphodiesterase 4D | Stroke | 2003/0054531 |
| Prostaglandin receptor subtype EP3 | Peripheral arterial occlusive disease | 2003/0157599 |
| CARP | Heart disorders | 2004/0014706 |
| HOP | Congenital heart disease | 2004/0029158 |
| SEQ ID NOS: 1-4 of the U.S. patent application publication 2004/0087784, incorporated by reference herein | Apoplexy | 2004/0087784 |
| PLTP | Atherosclerosis, vascular disease, hypercholesterolemia, Tangier's disease, familial HDL deficiency disease | 2006/0252787 |
| SEQ ID NOS: 1, 3-8, 15, 16 of the U.S. patent application publication 2007/0160996, incorporated by reference herein | Thrombosis | 2007/0160996 |
| UCP-2 | Stroke | 2002/0172958 |
| FLJ11011 | Fanconi's Anemia | 2006/0070134 |
| Codanin-1 | Anemia | 2006/0154331 |
| SEQ ID NOS: 1, 6, 8 of the U.S. patent 5,763,591, incorporated by reference herein | Insulin-dependent diabetes mellitus | 5,763,591 |
| Resistin | Type II diabetes | 2002/0161210 |
| Archipelin | Diabetes | 2003/0202976 |
| SEQ ID NOS: 2, 7, 16, 27 of the U.S. patent application publication 2004/0053397, incorporated by reference herein | Diabetes, hyperlipidemia | 2004/0053397 |
| Neuronatin | Metabolic disorders | 2004/0259777 |
| Ncb5or | Diabetes | 2005/0031605 |
| 7B2 | Endocrine disorders | 2005/0086709 |
| PTHrP, PEX | Metabolic bone diseases | 2005/0113303 |

TABLE 3-continued

| Gene | Disease/Disorder | Patent/ Published Application No. |
|---|---|---|
| KChIP1 | Type II diabetes | 2005/0196784 |
| SLIT-3 | Type II diabetes | 2006/0141462 |
| CX3CR1 | Type II diabetes | 2006/0160076 |
| SMAP-2 | Diabetes | 2006/0210974 |
| SEQ ID NOS: 2, 8, 12, 16, 22, 26, 28, 32 of the U.S. patent application publication 2006/0228706, incorporated by reference herein | Type II diabetes | 2006/0228706 |
| IC-RFX | Diabetes | 2006/0264611 |
| E2IG4 | Diabetes, insulin resistance, obesity | 2007/0036787 |
| SEQ ID NOS: 2, 8, 10, 14, 18, 24, 26, 30, 34, 38, 44, 50, 54, 60, 62, 68, 74, 80, 86, 92, 98, 104, 110 of the U.S. patent application publication 2007/0122802, incorporated by reference herein | Diabetes | 2007/0122802 |
| UCP2 | Body weight disorders | 2002/0127600 |
| Ob receptor | Body weight disorders | 2002/0182676 |
| Ob | Bodyweight disorders | 2004/0214214 |
| Dp1 | Neurodegenerative disorders | 2001/0021771 |
| NRG-1 | Schizophrenia | 2002/0045577 |
| Synapsin III | Schizophrenia | 2002/0064811 |
| NRG1AG1 | Schizophrenia | 2002/0094954 |
| AL-2 | Neuronal disorders | 2002/0142444 |
| Proline dehydrogenase | Bipolar disorder, major depressive disorder, schizophrenia, obsessive compulsive disorder | 2002/0193581 |
| MNR2 | Chronic neurodegenerative disease | 2002/0197678 |
| ATM | Ataxia-telangiectasia | 2004/0029198 |
| Ho-1 | Dementing diseases | 2004/0033563 |
| CON202 | Schizophrenia | 2004/0091928 |
| Ataxin-1 | Neurodegenerative disorders | 2004/0177388 |
| NR3B | Motor neuron disorders | 2005/0153287 |
| NIPA-1 | Hereditary spastic paraplegia | 2005/0164228 |
| DEPP, adrenomedullin, csdA | Schizophrenia | 2005/0227233 |
| Inf-20 | Neurodegenerative diseases | 2006/0079675 |
| EOPA | Brain development and degeneration disorders | 2007/0031830 |
| SERT | Autism | 2007/0037194 |
| FRP-1 | Glaucoma | 2002/0049177 |
| Serum amyloid A | Glaucoma | 2005/0153927 |
| BMP2 | Osteoporosis | 2002/0072066 |
| BMPR1A | Juvenile polyposis | 2003/0072758 |
| ACLP | Gastroschisis | 2003/0084464 |
| Resistin-like molecule β | Familial adenomatous polyposis, diabetes, insulin resistance, colon cancer, inflammatory bowel disorder | 2003/0138826 |
| Dlg5 | Inflammatory bowel disease | 2006/0100132 |
| SEQ ID NOS: 1-82 of the U.S. patent application publication 2002/0119452, incorporated by reference herein | Osteoarthritis | 2002/0119452 |
| TRANCE | Immune system disorders | 2003/0185820 |
| Matrilin-3 | Osteoarthritis | 2003/0203380 |
| Synoviolin | Rheumatoid arthritis | 2004/0152871 |
| SEQ ID NOS: 9, 35 of the U.S. patent application publication 2007/0028314, incorporated by reference herein | Osteoarthritis | 2007/0028314 |
| HIV LTR | HIV infection | 5,627,023 |
| SHIVA | HIV infection | 2004/0197770 |
| EBI 1, EBI 2, EBI 3 | Epstein Barr virus infection | 2002/0040133 |
| NM23 family | Skin/intestinal disorders | 2002/0034741 |
| SEQ ID NO: 1 of the U.S. patent application publication 2002/0169127, incorporated by reference herein | Psoriasis | 2002/0169127 |
| Eps8 | Skin disorders wound healing | 2003/0180302 |
| Beta-10 | Thyroid gland pathology | 2002/0015981 |
| SEQ ID NO: 2 of the U.S. patent application publication 2003/0207403, incorporated by reference herein | Thyroid conditions | 2003/0207403 |
| SEQ ID NO: 3 of the U.S. patent application publication 2007/0020275, incorporated by reference herein | Thyroid disorders | 2007/0020275 |
| Hair follicle growth factor | Alopecia | 2003/0036174 |
| Comeodesrnosin | Alopecia | 2003/0211065 |
| GCR9 | Asthma, lymphoma, leukemia | 2003/0166150 |
| SEQ ID NO: 1-71 of the U.S. patent application publication 2004/0002084, incorporated by reference herein | Asthma | 2004/0002084 |
| Bg | Chediak-Higashi syndrome | 2002/0115144 |
| SEQ ID NOS: 1-16 of the U.S. patent application publication 2002/0127555, incorporated by reference herein | Endometriosis | 2002/0127555 |
| GF23 | Hypophosphatemic disorders | 2005/0156014 |
| BBSR | Bardet-Biedl syndrome | 2003/0152963 |
| MIC-1 | Fetal abnormalities, cancer, inflammatory disorders, miscarriage, premature birth | 2004/0053325 |
| MIA-2 | Liver damage | 2004/0076965 |
| IL-17B | Cartilage degenerative disorders | 2004/0171109 |
| Formylglycine generating enzyme | Multiple sulfatase deficiency | 2004/0229250 |
| LPLA2 | Pulmonary alveolar proteinosis | 2006/0008455 |
| CXCL1O | Respiratory illnesses | 2006/0040329 |
| SEQ ID NOS: 1, 2 of the U.S. patent application publication 2006/0140945, incorporated by reference herein | Nephropathy | 2006/0140945 |
| HFE2A | Iron metabolism disease | 2007/0166711 |

Once a gene with an expression pattern that is modulated during a disease, disorder, or condition is identified, the promoter of the gene may be used in the gene switch of the invention. The sequence of many genes, including the promoter region, is known in the art and available in public databases, e.g., GenBank. Thus, once an appropriate gene is identified, the promoter sequence can be readily identified and obtained. Another aspect of the present invention is directed towards identifying suitable genes whose promoter can be isolated and placed into a gene switch. The identity of the gene, therefore, may not be critical to specific embodiments of the present invention, provided the promoter can be isolated and used in subsequent settings or environments. The current invention thus includes the use of promoters from genes that are yet to be identified. Once suitable genes are identified, it is a matter of routine skill or experimentation to determine the genetic sequences needed for promoter function. Indeed, several commercial protocols exist to aid in the determination of the promoter region of genes of interest. By way of example, Ding et al. recently elucidated the promoter sequence of the novel Sprouty4 gene (*Am. J Physiol. Lung Cell. Mol. Physiol.* 287: L52 (2004), which is incorporated by reference) by progressively deleting the 5'-flanking sequence of the human Sprouty4 gene. Briefly, once the transcription initiation site was determined, PCR fragments were generated using common PCR primers to clone segments of the 5'-flanking segment in a unidirectional manner. The generated segments were cloned into a luciferase reporter vector and luciferase activity was measured to determine the promoter region of the human Sprouty4 gene, Another example of a protocol for acquiring and validating gene promoters includes the following steps: (1) acquire diseased and non-diseased cell/tissue samples of similar/same tissue type; (2) isolate total RNA or mRNA from the samples; (3) perform differential microarray analysis of diseased and non-diseased RNA; (4) identify candidate disease-specific transcripts; (5) identify genomic sequences associated with the disease-specific transcripts; (6) acquire or synthesize DNA sequence upstream and downstream of the predicted transcription start site of the disease-specific transcript; (7) design and produce promoter reporter vectors using different lengths of DNA from step 6; and (8) test promoter reporter vectors in diseased and non-diseased cells/tissues, as well as in unrelated cells/tissues.

The source of the promoter that is inserted into the gene switch can be natural or synthetic, and the source of the promoter should not limit the scope of the invention described herein. In other words, the promoter may be directly cloned from cells, or the promoter may have been previously cloned from a different source, or the promoter may have been synthesized.

Gene Switch Systems

The gene switch may be any gene switch that regulates gene expression by addition or removal of a specific ligand. In one embodiment, the gene switch is one in which the level of gene expression is dependent on the level of ligand that is present. Examples of ligand-dependent transcription factor complexes that may be used in the gene switches of the invention include, without limitation, members of the nuclear receptor superfamily activated by their respective ligands (e.g., glucocorticoid, estrogen, progestin, retinoid, ecdysone, and analogs and minetics thereof) and rTTA activated by tetracycline. In one aspect of the invention, the gene switch is an EcR-based gene switch. Examples of such systems include, without limitation, the systems described in U.S. Pat. Nos. 6,258,603, 7,045,315, U.S. Published Patent Application Nos. 2006/0014711, 2007/0161086, and International Published Application No. WO 01/70816. Examples of chimeric ecdysone receptor systems are described in U.S. Pat. No. 7,091,038, U.S. Published Patent Application Nos. 2002/0110861, 2004/0033600, 2004/0096942, 2005/0266457, and 2006/0100416, and International Published Application Nos. WO 01/70816, WO 02/066612, WO 02/066613, WO 02/066614, WO 02/066615, WO 02/29075, and WO 2005/108617, each of which is incorporated by reference in its entirety. An example of a non-steroidal ecdysone agonist-regulated system is the RheoSwitch® Mammalian Inducible Expression System (New England Biolabs, Ipswich, Mass.). In another aspect of the invention, the gene switch is based on heterodimerization of FK506 binding protein (FKBP) with FKBP rapamycin associated protein (FRAP) and is regulated through rapamycin or its non-immunosuppressive analogs. Examples of such systems, include, without limitation, the ARGENT™ Transcriptional Technology (ARIAD Pharmaceuticals, Cambridge, Mass.) and the systems described in U.S. Pat. Nos. 6,015,709, 6,117,680, 6,479,653, 6,187,757, and 6,649,595.

In one embodiment, the gene switch comprises a single transcription factor sequence encoding a ligand-dependent transcription factor complex under the control of a therapeutic switch promoter. The transcription factor sequence may encode a ligand-dependent transcription factor complex that is a naturally occurring or an artificial ligand-dependent transcription factor complex. An artificial transcription factor is one in which the natural sequence of the transcription factor has been altered, e.g., by mutation of the sequence or by the combining of domains from different transcription factors. In one embodiment, the transcription factor comprises a Group H nuclear receptor ligand binding domain. In one embodiment, the Group H nuclear receptor ligand binding domain is from an ecdysone receptor, a ubiquitous receptor (UR), an orphan receptor 1 (OR-1), a steroid hormone nuclear receptor 1 (NER-1), a retinoid X receptor interacting protein-15 (RIP-15), a liver X receptor β (LXRβ), a steroid hormone receptor like protein (RLD-1), a liver X receptor (LXR), a liver X receptor α (LXRα), a farnesoid X receptor (FXR), a receptor interacting protein 14 (RIP-14), or a farnesol receptor (HRR-1). In another embodiment, the Group H nuclear receptor LBD is from an ecdysone receptor.

A. Ecdysone-Based Gene Switch

The EcR and the other Group H nuclear receptors are members of the nuclear receptor superfamily wherein all members are generally characterized by the presence of an amino-terminal transactivation domain (AD, also referred to interchangeably as "TA" or "TD"), optionally fused to a heterodimerization partner (HP) to form a coactivation protein (CAP), a DNA binding domain (DBD), and a LBD fused to the DBD via a hinge region to form a ligand-dependent transcription factor (LTF). As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, Science 240:889 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The following polypeptide sequence was reported as a polypeptide sequence of Ecdysone receptor (Ecdysteroid receptor) (20-hydroxy-ecdysone receptor) (20E receptor) (EcRH) (Nuclear receptor subfamily 1 group H member 1) and has the accession number P34021 in Genbank.

```
Ecdysone receptor (878aa) from Drosophila melanogaster (Fruit fly)
                                                  (SEQ ID NO: 5)
  1  mkrrwsnngg fmrlpeesss evtsssnglv lpsgvnmsps sldshdycdq dlwlcgnesg

 61  sfggsnghgl sqqqqsvitl amhgcsstlp aqttiiping nangnggstn gqyvpgatnl

121  galangmlng gfngmqqqiq nghglinstt pstpttplhl qqnlggaggg giggmgilhh

181  angtpnglig vvgggggvgl gvggggvggl gmqhtprsds vnsissgrdd lspssslngy

241  sanescdakk skkgpaprvq eelclvcgdr asgyhynalt cegckgffrr svtksavycc

301  kfgracemdm ymrrkcqecr lkkclavgmr pecvvpenqc amkrrekkaq kekdkmttsp

361  ssqhggngsl asgggqdfvk keildlmtce ppqhatipll pdeilakcqa rnipsltynq

421  laviykliwy qdgyeqpsee dlrrimsqpd enesqtdvsf rhiteitilt vqlivefakg

481  lpaftkipqe dqitllkacs sevmmlrmar rydhssdsif fannrsytrd sykmagmadn

541  iedllhfcrq mfsmkvdnve yalltaivif sdrpglekaq lveaiqsyyi dtlriyilnr

601  hcgdsmslvf yakllsilte lrtlgnqnae mcfslklknr klpkfleeiw dvhaippsvq

661  shlqitqeen erleraermr asvggaitag idcdsastsa aaaaaqhqpq pqpqpqpssl

721  tqndsqhqtq pqlqpqlppq lqgqlqpqlq pqlqtqlqpq iqpqpqllpv sapvpasvta

781  pgslsavsts seymggsaai gpitpattss itaavtasst tsavpmgngv gvgvgvggnv

841  smyanaqtam almgvalhsh qeqliggvav ksehstta
```

The DBD is characterized by the presence of two cysteine zinc fingers between which are two amino acid motifs, the P-box and the D-box, which confer specificity for response elements. These domains may be either native, modified, or chimeras of different domains of heterologous receptor proteins. The EcR, like a subset of the nuclear receptor family, also possesses less well-defined regions responsible for heterodimerization properties. Because the domains of nuclear receptors are modular in nature, the LBD, DBD, and AD may be interchanged.

In another embodiment, the transcription factor comprises a AD, a DBD that recognizes a response element associated with the therapeutic protein or therapeutic polynucleotide whose expression is to be modulated; and a Group H nuclear receptor LBD. In certain embodiments, the Group H nuclear receptor LBD comprises a substitution mutation.

Figure 2:
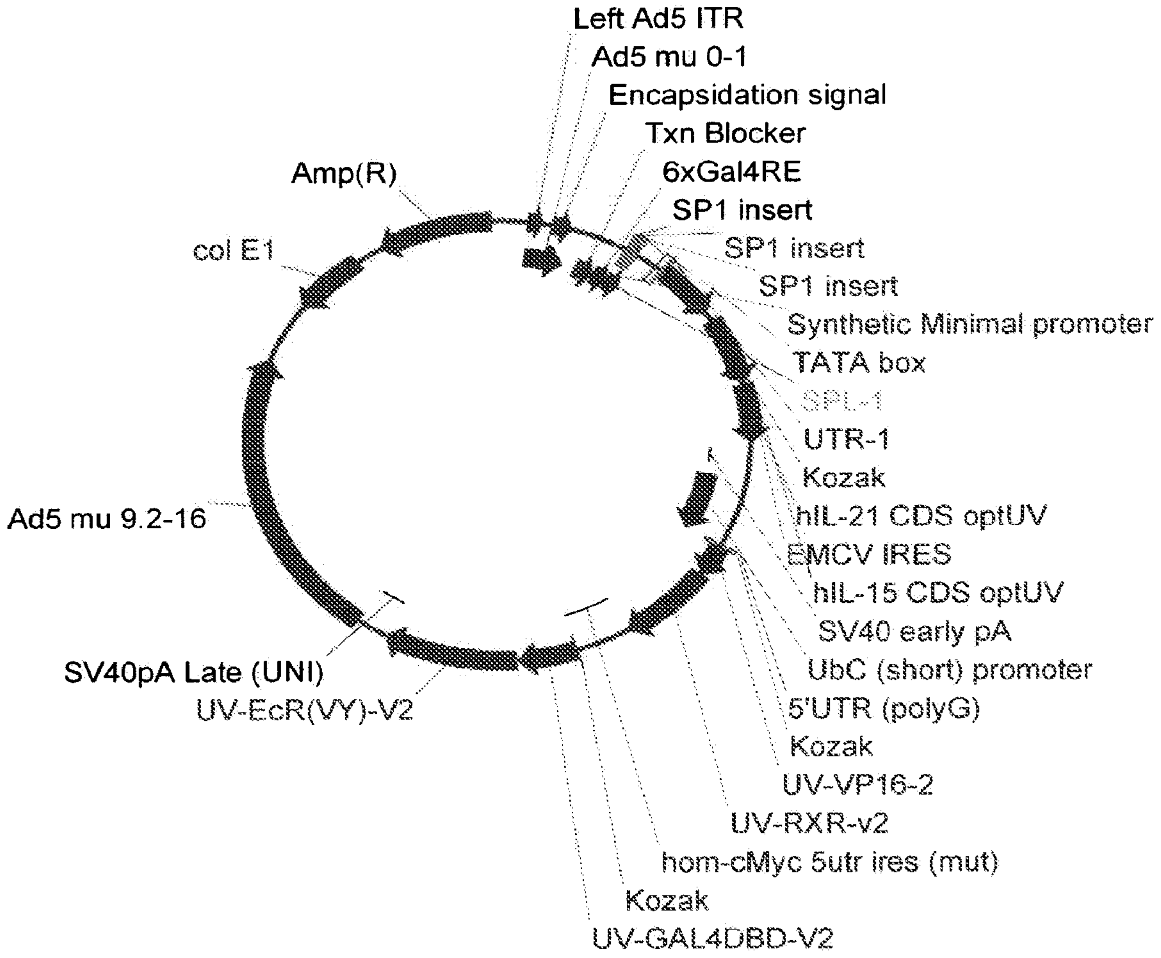
FIG. 2 shows a plasmid map for a regulated promoter expression system for a bicistronic transcript encoding hIL-21 and hIL-15.

In another embodiment, the gene switch comprises a first transcription factor sequence, e.g., a CAP, under the control of a first therapeutic switch promoter (TSP-1) and a second transcription factor sequence, e.g., a LTF, under the control of a second therapeutic switch promoter (TSP-2), wherein the proteins encoded by said first transcription factor sequence and said second transcription factor sequence interact to form a protein complex (LDTFC), i.e., a "dual switch"- or "two-hybrid"-based gene switch. The first and second TSPs may be the same or different. In this embodiment, the presence of two different TSPs in the gene switch that are required for therapeutic molecule expression enhances the specificity of the therapeutic method (see FIG. 2). FIG. 2 also demonstrates the ability to modify the therapeutic gene switch to treat any disease, disorder, or condition simply by inserting the appropriate TSPs.

Figure 1:
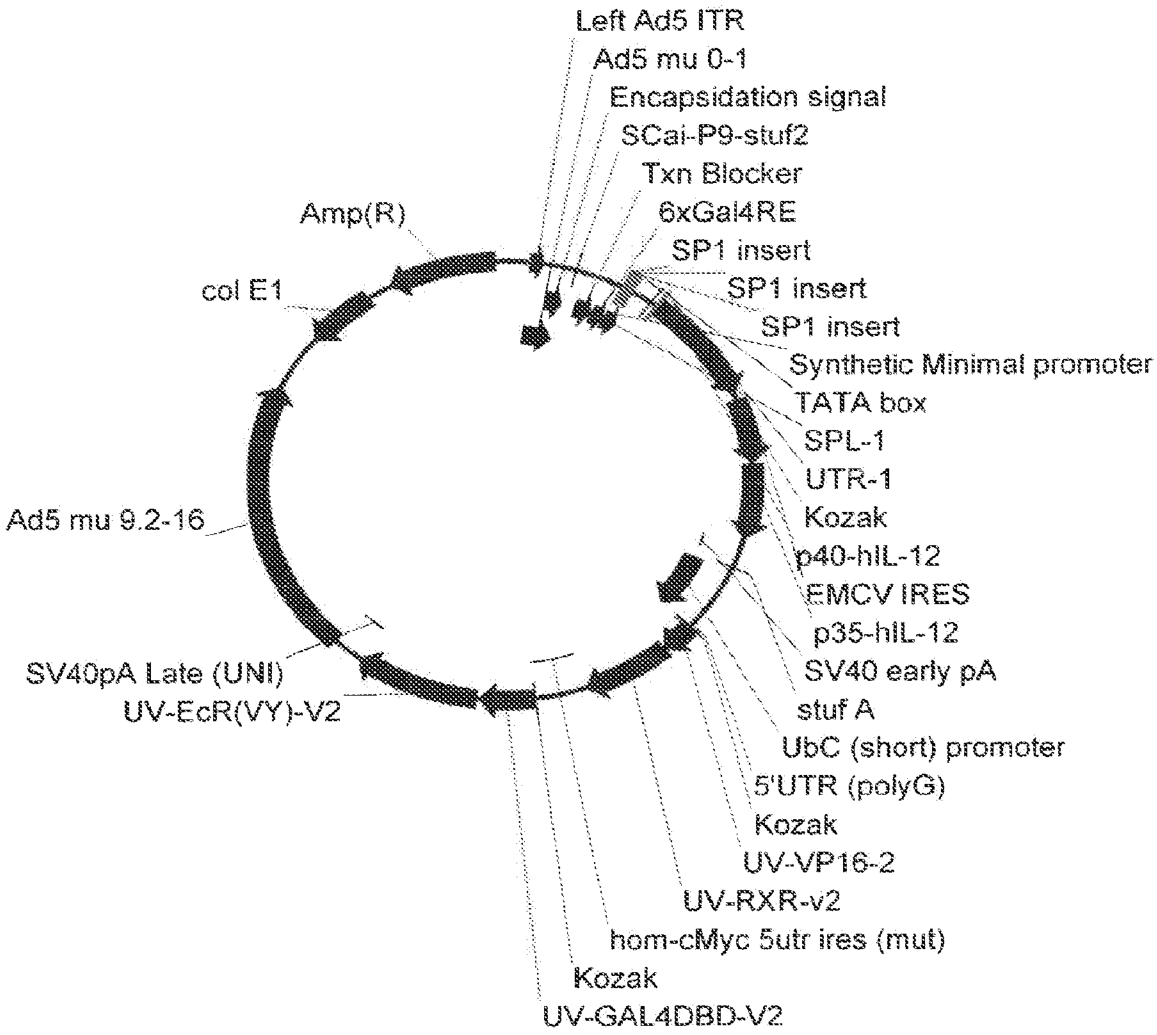
FIG. 1 shows a plasmid map for a regulated promoter expression system for a bicistronic transcript encoding hIL-12.

In a further embodiment, both the first and the second transcription factor sequence, e.g., a CAP or a LTF, are under the control of a single therapeutic switch promoter (e.g. TSP-1 in FIG. 1). Activation of this promoter will generate both CAP and LTF with a single open reading frame. This can be achieved with the use of a transcriptional linker such as an IRES (internal ribosomal entry site). In this embodiment, both portions of the ligand-dependent transcription factor complex are synthesized upon activation of TSP-1. TSP-1 can be a constitutive promoter or only activated under conditions associated with the disease, disorder, or condition.

Figure 4:
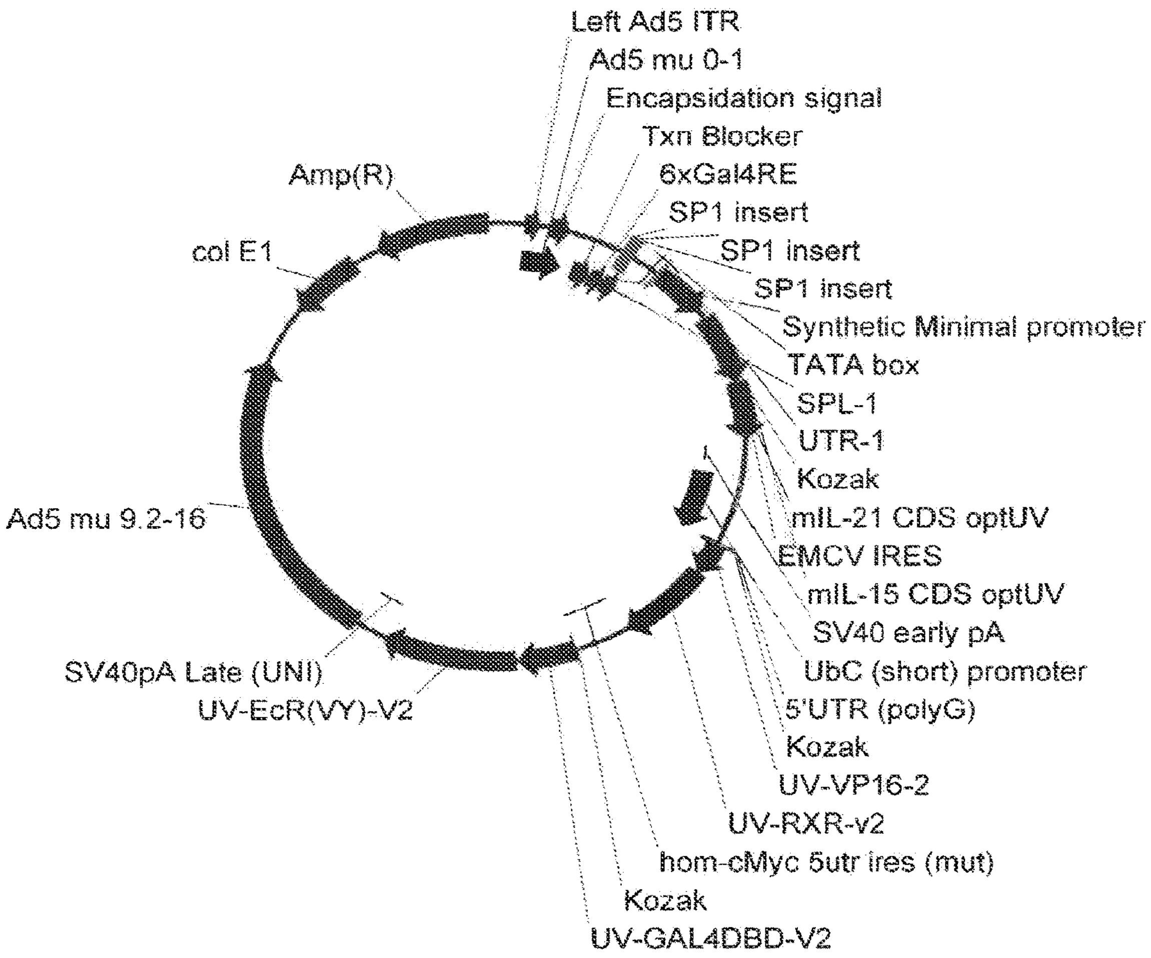
FIG. 4 shows a plasmid map for a regulated promoter expression system for a bicistronic transcript encoding mIL-21 and mIL-15.
Figure 5:
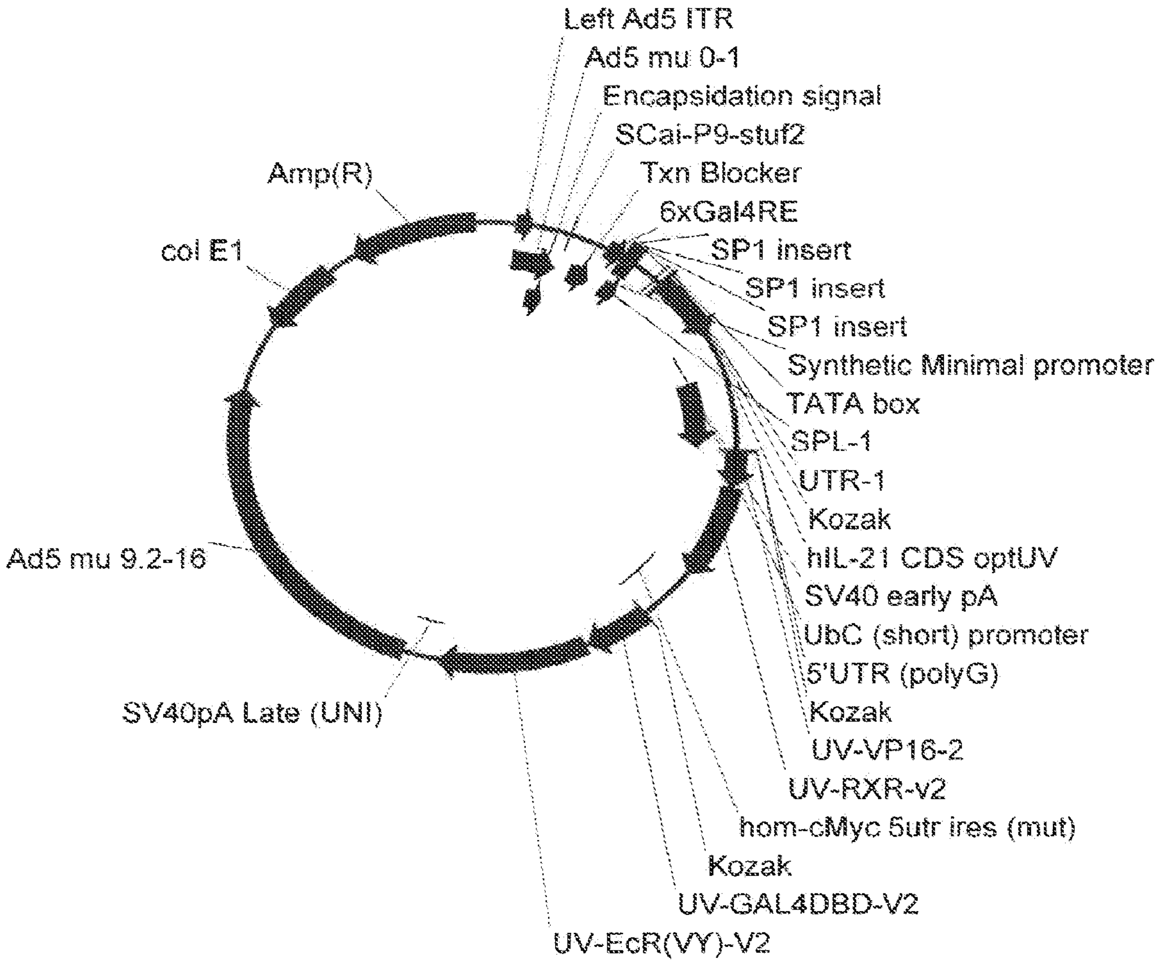
FIG. 5 shows a plasmid map for a regulated promoter expression system for hIL-21.
Figure 6:
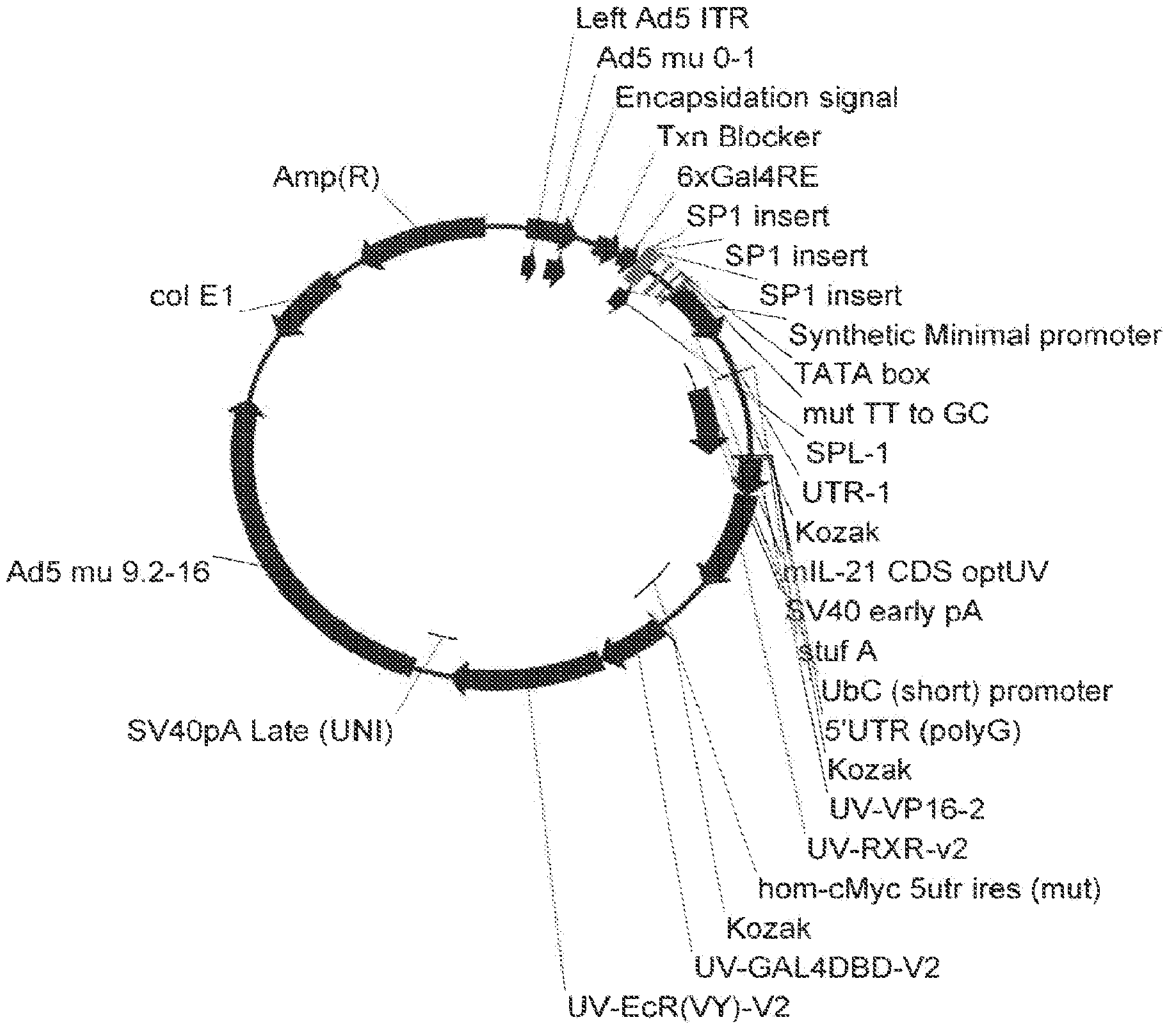
FIG. 6 shows a plasmid map for a regulated promoter expression system for mIL-21.

In a further embodiment, one transcription factor sequence, e.g. a LTF, is under the control of a therapeutic switch promoter only activated under conditions associated with the disease, disorder, or condition (e.g., TSP-2 or TSP-3 in FIG. 4) and the other transcription factor sequence, e.g., CAP, is under the control of a constitutive therapeutic switch promoter (e.g., TSP-1 in FIG. 4). In this embodiment, one portion of the ligand-dependent transcription factor complex is constitutively present while the second portion will only be synthesized under conditions associated with the disease, disorder, or condition.

Figure 3:
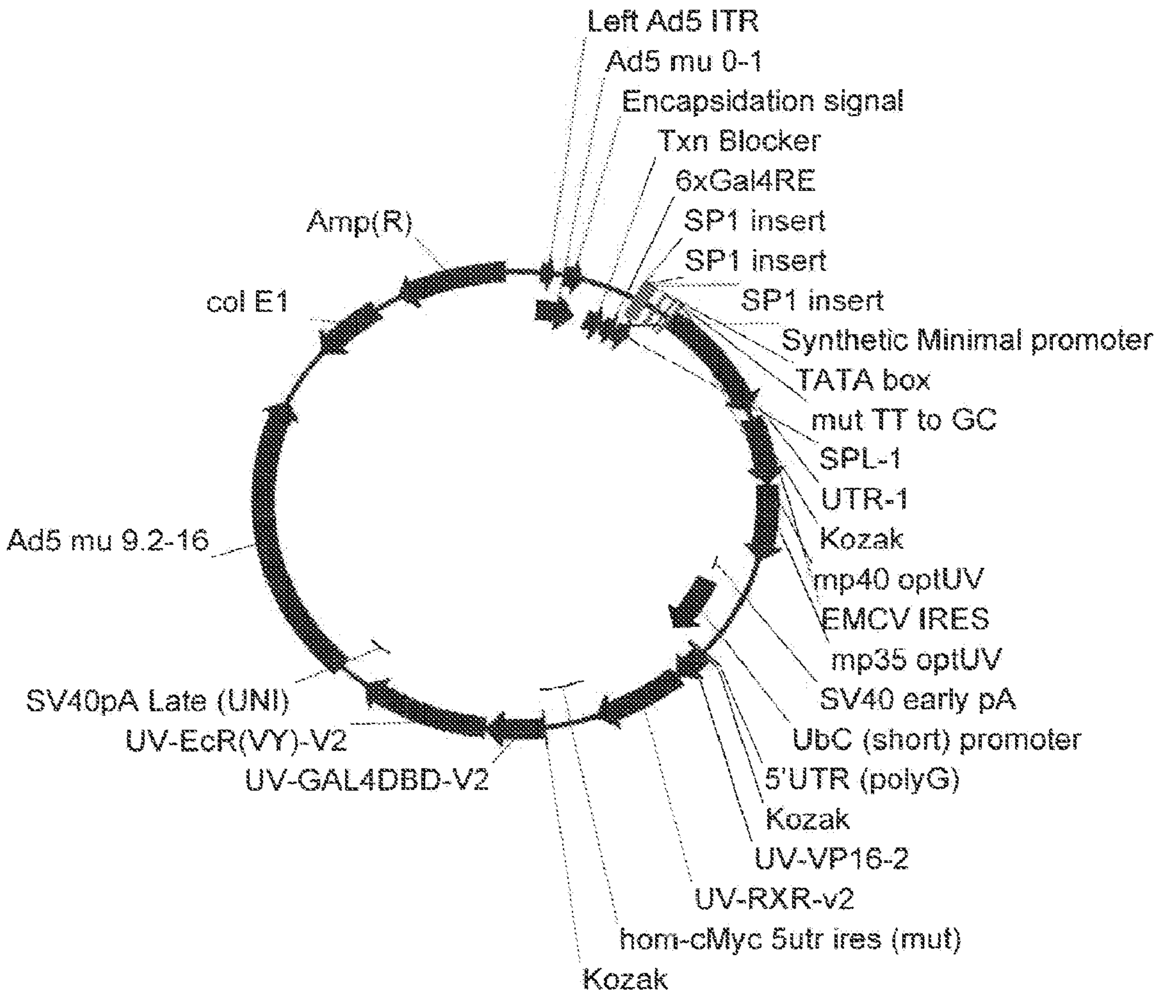
FIG. 3 shows a plasmid map for a regulated promoter expression system for a bicistronic transcript encoding mIL-12.

In another embodiment, one transcription factor sequence, e.g., CAP, is under the control of a first TSP (e.g., TSP-1 in FIG. 3) and two or more different second transcription factor sequences, e.g., LTF-1 and LTF-2 are under the control of different TSPs (e.g., TSP-2 and TSP-3 in FIG. 3). In this embodiment, each of the LTFs may have a different DBD that recognizes a different factor-regulated promoter sequence (e.g., DBD-A binds to a response element associated with factor-regulated promoter-1 (FRP-1) and DBD-B binds to a response element associated with factor-regulated promoter-2 (FRP-2). Each of the factor-regulated promoters may be operably linked to a different therapeutic gene. In this manner, multiple treatments may be provided simultaneously.

In one embodiment, the first transcription factor sequence encodes a polypeptide comprising a AD, a DBD that recognizes a response element associated with the therapeutic product sequence whose expression is to be modulated; and a Group H nuclear receptor LBD, and the second transcription factor sequence encodes a transcription factor comprising a nuclear receptor LBD selected from a vertebrate retinoid X receptor (RXR), an invertebrate RXR, an ultraspiracle protein (USP), or a chimeric nuclear receptor comprising at least two different nuclear receptor ligand binding domain polypeptide fragments selected from a vertebrate RXR, an invertebrate RXR, and a USP (see WO 01/70816 A2 and US 2004/0096942 A1). The "partner" nuclear receptor ligand binding domain may further comprise a truncation mutation, a deletion mutation, a substitution mutation, or another modification.

In another embodiment, the gene switch comprises a first transcription factor sequence encoding a first polypeptide comprising a nuclear receptor LBD and a DBD that recognizes a response element associated with the therapeutic product sequence whose expression is to be modulated, and a second transcription factor sequence encoding a second polypeptide comprising an AD and a nuclear receptor LBD, wherein one of the nuclear receptor LBDs is a Group H nuclear receptor LBD. In one embodiment, the first polypeptide is substantially free of an AD and the second polypeptide is substantially free of a DBD. For purposes of the invention, "substantially free" means that the protein in question does not contain a sufficient sequence of the domain in question to provide activation or binding activity.

In another aspect of the invention, the first transcription factor sequence encodes a protein comprising a heterodimerization partner and an AD (a "CAP") and the second transcription factor sequence encodes a protein comprising a DBD and a LBD (a "LTF").

When only one nuclear receptor LBD is a Group H LBD, the other nuclear receptor LBD may be from any other nuclear receptor that forms a dimer with the Group H LBD. For example, when the Group H nuclear receptor LBD is an EcR LBD, the other nuclear receptor LBD "partner" may be from an EcR, a vertebrate RXR, an invertebrate RXR, an ultraspiracle protein (USP), or a chimeric nuclear receptor comprising at least two different nuclear receptor LBD polypeptide fragments selected from a vertebrate RXR, an invertebrate RXR, or a USP (see WO 01/70816 A2, International Patent Application No. PCT/US02/05235 and US 2004/0096942 A1, incorporated herein by reference in their entirety). The "partner" nuclear receptor ligand binding domain may further comprise a truncation mutation, a deletion mutation, a substitution mutation, or another modification.

In one embodiment, the vertebrate RXR LBD is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

In one embodiment, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), an ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

In one embodiment, the chimeric RXR LBD comprises at least two polypeptide fragments selected from a vertebrate species RXR polypeptide fragment, an invertebrate species RXR polypeptide fragment, or a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment. Such chimeric RXR LBDs are disclosed, for example, in WO 2002/066614.

In one embodiment, the chimeric RXR ligand binding domain comprises at least one vertebrate species RXR polypeptide fragment and one invertebrate species RXR polypeptide fragment, In another embodiment, the chimeric RXR ligand binding domain comprises at least one vertebrate species RXR polypeptide fragment and one non-Dipteran/non-Lepidopteran invertebrate species RXR homolog polypeptide fragment.

The ligand, when combined with the LBD of the nuclear receptor(s), which in turn are bound to the response element of a FRP associated with a therapeutic product sequence, provides external temporal regulation of expression of the therapeutic product sequence. The binding mechanism or the order in which the various components of this invention bind to each other, that is, for example, ligand to LBD, DBD to response element, AD to promoter, etc., is not critical.

In a specific example, binding of the ligand to the LBD of a Group H nuclear receptor and its nuclear receptor LBD partner enables expression of the therapeutic product sequence. This mechanism does not exclude the potential for ligand binding to the Group H nuclear receptor (GHNR) or its partner, and the resulting formation of active homodimer complexes (e.g. GHNR+GHNR or partner+partner). Preferably, one or more of the receptor domains is varied producing a hybrid gene switch. Typically, one or more of the three domains, DBD, LBD, and AD, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988)) or LexA protein from *Escherichia coli* (see Brent et al., *Cell* 43:729 (1985)), or synthetic response elements specific for targeted interactions with proteins designed, modified, and selected for such specific interactions (see, for example, Kim et al., *Proc. Natl. Acad Sci. USA,* 94:3616 (1997)) to accommodate hybrid receptors. Another advantage of two-hybrid systems is that they allow choice of a promoter used to drive the gene expression according to a desired end result. Such double control may be particularly important in areas of gene therapy, especially when cytotoxic proteins are produced, because both the timing of expression as well as the cells wherein expression occurs may be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

The DNA binding domain of the first hybrid protein binds, in the presence or absence of a ligand, to the DNA sequence of a response element to initiate or suppress transcription of downstream gene(s) under the regulation of this response element.

The functional LDTFC, e.g., an EcR complex, may also include additional protein(s) such as immunophilins. Additional members of the nuclear receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., *Curr. Opin. Cell Biol.* 9:222 (1997)). Also, protein cofactors generally known as corepressors (also known as repressors, silencers, or silencing mediators) may be required to effectively inhibit transcriptional activation in the absence of ligand. These corepressors may interact with the unliganded EcR to silence the activity at the response element. Current evidence suggests that the binding of ligand changes the conformation of the receptor, which results in release of the corepressor and recruitment of the above described coactivators, thereby abolishing their silencing activity. Examples of corepressors include N—CoR and SMRT (for review, see Horwitz et al., *Mol Endocrinol.* 10:1167 (1996)). These cofactors may either be endogenous within the cell or organism, or may be added exogenously as transgenes to be expressed in either a regulated or unregulated fashion.

B. Rapamycin Based Gene Switch

The present invention further provides a gene switch system which utilizes FK506 binding protein as the ligand-dependent transcription factor complex and rapamycin as the ligand. In one embodiment, the construct encoding the gene switch comprises (a) a first polynucleotide encoding a first chimeric protein which binds to rapamycin or an analog thereof and which comprises at least one FK506-binding protein (FKBP) domain and at least one protein domain heterologous thereto, wherein the FKBP domain comprises a peptide sequence selected from:
  (1) a naturally occurring FKBP
  (2) a variant of a naturally occurring FKBP in which up to 10 amino acid residues have been deleted, inserted, or replaced with substitute amino acids, and
  (3) an FKBP encoded by a DNA sequence which selectively hybridizes to a DNA sequence encoding an FKBP of (1) or (2);
(b) a second polynucleotide encoding a second chimeric protein which forms a complex with both (a) rapamycin or a rapamycin analog and (b) the first chimeric protein, and which comprises at least one FKBP:rapamycin binding (FRB) domain and at least one protein domain heterologous thereto, wherein the FRB domain comprises a peptide sequence selected from:
  (4) a naturally occurring FRB domain,
  (5) a variant of a naturally occurring FRB domain in which up to 10 amino acid residues have been deleted, inserted, or replaced with substitute amino acids, and
  (6) an FRB domain encoded by a DNA sequence which selectively hybridizes to a DNA sequence encoding an FRB of (4) or (5).

In this gene switch system, each of the first polynucleotide and the second polynucleotide are under the control of one or more therapeutic switch promoters as described elsewhere herein. Furthermore, in certain embodiments, at least one protein domain heterologous to the FKBP and/or FRB domains in the first and second chimeric protein may be one or more "action" or "effector" domains. Effector domains may be selected from a wide variety of protein domains including DNA binding domains, transcription activation domains, cellular localization domains and signaling domains (i.e., domains which are capable upon clustering or multimerization, of triggering cell growth, proliferation, differentiation, apoptosis, gene transcription, etc.).

In certain embodiments, one fusion protein contains at least one DNA binding domain (e.g., a GAL4 or ZFHD1 DNA-binding domain) and another fusion protein contains at least one transcription activation domain (e.g., a VP16 or p65 transcription activation domain). Ligand-mediated association of the fusion proteins represents the formation of a transcription factor complex and leads to initiation of transcription of a target gene linked to a DNA sequence recognized by (i.e., capable of binding with) the DNA-binding domain on one of the fusion proteins. Information regarding the gene expression system as well as the ligand is disclosed in U.S. Pat. Nos. 6,187,757 B1, 6,649,595 B1, 6,509,152 B1, 6,479,653 B1, and 6,117,680 B1.

In other embodiments, the present invention provides a gene switch system which comprises polynucleotides encoding two fusion proteins which self-aggregate in the absence of a ligand, wherein (a) the first fusion protein comprises a conditional aggregation domain which binds to a selected ligand and a transcription activation domain, and (b) the second fusion protein comprising a conditional aggregation domain which binds to a selected ligand and a DNA binding domain, and (c) in the absence of ligand, the cells express a gene operably linked to regulatory DNA to which said DNA binding domain binds. Modified cells comprising the gene switch system are expanded in the presence of the ligand in an amount sufficient for repression of the gene. Ligand removal induces expression of the encoded protein that causes cell death. The nucleic acids encoding the two fusion proteins are under the control of at least one conditional promoter. The gene expression system utilizing conditional aggregation domains is disclosed in U.S. Publication No. 2002/0048792.

C. Procaryotic Repressor/Operator Based Gene Switch System

In one embodiment, the present invention provides gene switch system comprising (a) a first polynucleotide coding for a transactivator fusion protein comprising a prokaryotic tetracycline ("tet") repressor and a eucaryotic transcriptional activator protein domain; and (b) a second polynucleotide coding for a therapeutic protein or therapeutic polypeptide, wherein said second polynucleotide is operably linked to a minimal promoter and at least one tet operator sequence. The first polynucleotide coding for a transactivator fusion protein may comprise therapeutic switch promoter as described elsewhere herein. The expression of the lethal protein is up-regulated in the absence of tetracycline. (see, e.g., Gossen et al. (1992) *Proc. Natl. Acad. Sci.* 89: 5547-5551; Gossen et al. (1993) *TIBS* 18: 471-475; Furth et al. (1994) *Proc. Natl. Acad Sci.* 91: 9302-9306; and Shockett et al. (1995) *Proc. Natl. Acad Sci.* 92: 6522-6526). The TetO expression system is disclosed in U.S. Pat. No. 5,464,758 B1.

In another embodiment, the gene switch system comprises the lactose ("Lac") repressor-operator systems from the bacterium *Escherichia coli*. The gene switch system of the present invention may also comprise (a) a first polynucleotide coding for a transactivator fusion protein comprising a prokaryotic lac I repressor and a eucaryotic transcriptional activator protein domain; and (b) a second polynucleotide coding for a therapeutic protein or therapeutic polypeptide, wherein said second polynucleotide is operably linked to a therapeutic switch promoter. In the Lac system, a lac operon is inactivated in the absence of lactose, or synthetic analogs such as isopropyl-b-D-thiogalactoside.

Additional gene switch systems include those described in the following: U.S. Pat. No. 7,091,038; WO2004078924; EP1266015; US20010044151; US20020110861; US20020119521; US20040033600; US20040197861; US20040235097; US20060020146; US20040049437; US20040096942; US20050228016; US20050266457; US20060100416; WO2001/70816; WO2002/29075; WO2002/066612; WO2002/066613; WO2002/066614; WO2002/066615; WO2005/108617; U.S. Pat. No. 6,258,603; US20050209283; US20050228016; US20060020146; EP0965644; U.S. Pat. Nos. 7,304,162; 7,304,161; MX234742; KR10-0563143; AU765306; AU2002-248500; and AU2002-306550.

D. Combination of the Gene Switch Systems

The present invention provides nucleic acid compositions, modified cells, and bioreactors comprising two or more gene switch systems comprising different ligand-dependent transcription factor complexes which are activated by an effective amount of one or more ligands, wherein the two or more gene switch systems comprise a first gene switch and a second gene switch, both of which selectively induce expression of one or more therapeutic polypeptides or therapeutic polynucleotides, upon binding to one or more ligands. Within the scope of the present invention are any numbers of and/or combinations of gene switch systems.

In one embodiment, the present invention provides a nucleic acid composition comprising:

a. a first gene switch system which comprises:
  i. a first gene expression cassette comprising a polynucleotide encoding a first hybrid polypeptide which comprises:
    1. a transactivation domain, which activates a factor-regulated promoter operably associated with a polynucleotide encoding a therapeutic polypeptide or therapeutic polynucleotide; and
    2. a heterodimer partner domain,
  ii. a second gene expression cassette comprising a polynucleotide encoding a second hybrid polypeptide which comprises:
    1. a DNA-binding domain, which recognizes a factor-regulated promoter operably associated with a polynucleotide encoding a therapeutic polypeptide or therapeutic polynucleotide; and
    2. a ligand binding domain; and
  iii. a third gene expression cassette comprising a polynucleotide encoding a therapeutic polypeptide or therapeutic polynucleotide comprising:
    1. a factor-regulated promoter, which is activated by the transactivation domain of the second hybrid polypeptide; and,
    2. a polynucleotide encoding a therapeutic polypeptide or therapeutic polynucleotide, and b. a second gene expression system which comprises:
  i. a first gene expression cassette comprising a polynucleotide encoding a first hybrid polypeptide which comprises:
    1. a transactivation domain, which activates a factor-regulated promoter operably associated with a polynucleotide encoding a therapeutic polypeptide or therapeutic polynucleotide; and
    2. a heterodimer partner domain,
  ii. a second gene expression cassette comprising a polynucleotide encoding a second hybrid polypeptide which comprises:
    1. a DNA-binding domain, which recognizes a factor-regulated promoter operably associated with a polynucleotide encoding a therapeutic polypeptide or therapeutic polynucleotide; and
    2. a ligand binding domain; and
  iii. a third gene expression cassette comprising a polynucleotide encoding a therapeutic polypeptide or therapeutic polynucleotide comprising:
    1. a factor-regulated promoter, which is activated by the transactivation domain of the second hybrid polypeptide; and,
    2. a polynucleotide encoding a therapeutic polypeptide or therapeutic polynucleotide.

The multiple inducible gene expression systems provide for expression of a given therapeutic polynucleotide or therapeutic polypeptide under conditions associated with different diseases, disorders or conditions, or expression of multiple therapeutic polypeptides or therapeutic polynucleotides either under the same conditions associated with the same disease disorder or condition, or under different conditions associated with different diseases, disorders, or conditions.

In certain embodiments, the combination of two or more gene switch systems may be (1) a dual-switch ecdysone receptor based gene expression system and (2) a single-switch ecdysone receptor based gene switch. In other embodiments, the combination may be (1) an single- or dual-switch ecdysone receptor based gene switch and (2) a rapamycin based gene switch. Alternatively, the combination of gene switch systems may be two identical rapamycin based gene switch systems disclosed above. Any possible combinations of the gene switch systems are within the scope of the invention. Examples of dual-switch ecdysone systems can be found, for example, in WO 2002/29075 and US 2002/0110861.

Ligands

As used herein, the term "ligand," as applied to LDTFC-based gene switches e.g., EcD complex based gene switches, describes small and soluble molecules having the capability of activating a gene switch to stimulate expression of a polypeptide encoded therein. The ligand for a ligand-dependent transcription factor complex of the invention binds to the protein complex comprising one or more of the ligand binding domain, the heterodimer partner domain, the DNA binding domain, and the transactivation domain. The choice of ligand to activate the ligand-dependent transcription factor complex depends on the type of the gene switch utilized.

Examples of ligands include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; amidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, famesol, bile acids, 1,1-biphosphonate esters, juvenile hormone III, and the like. Examples of diacylhydrazine ligands useful in the present invention include RG-115819 (3,5-Dimethyl-benzoic acid N-(1-ethyl-2,2-dimethyl-propyl)-N'-(2-methyl-3-methoxybenzoyl)-hydrazide), RG-115932 ((R)-3,5-Dimethyl-benzoic acid N-(1-tert-butyl-butyl)N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See, e.g., U.S. patent application Ser. No. 12/155,111, and PCT Appl. No. PCT/US2008/006757, both of which are incorporated herein by reference in their entireties.

For example, a ligand for the edysone receptor based gene switch may be selected from any suitable ligands. Both naturally occurring ecdysone or ecdyson analogs (e.g., 20-hydroxyecdysone, muristerone A, ponasterone A, ponasterone B, ponasterone C, 26-iodoponasterone A, inokosterone or 26-mesylinokosterone) and non-steroid inducers may be used as a ligand for gene switch of the present invention. U.S. Pat. No. 6,379,945 BI, describes an insect steroid receptor isolated from *Heliothis virescens* ("HEcR") which is capable of acting as a gene switch responsive to both steroid and certain non-steroidal inducers. Non-steroidal inducers have a distinct advantage over steroids, in this and many other systems which are responsive to both steroids and non-steroid inducers, for a number of reasons including, for example: lower manufacturing cost, metabolic stability, absence from insects, plants, or mammals, and environmental acceptability. U.S. Pat. No. 6,379,945 B1 describes the utility of two dibenzoylhydrazines, 1,2-dibenzoyl-1-tert-butyl-hydrazine and tebufenozide (N-(4-ethylbenzoyl)-N'-(3,5-dimethylbenzoyl)-N'-tert-butyl-hydrazine) as ligands for an ecdysone-based gene switch. Also included in the present invention as a ligand are other dibenzoylhydrazines, such as those disclosed in U.S. Pat. No. 5,117,057 B1. Use of tebufenozide as a chemical ligand for the ecdysone receptor from *Drosophila melanogaster* is also disclosed in U.S. Pat. No. 6,147,282. Additional, non-limiting examples of ecdysone ligands are 3,5-di-tert-butyl-4-hydroxy-N-isobutyl-benzamide, 8-O-acetylharpagide, a 1,2-diacyl hydrazine, an N'-substituted-N,N'-disubstituted hydrazine, a dibenzoylalkyl cyanohydrazine, an N-substituted-N-alkyl-N,N-diaroyl hydrazine, an N-substituted-N-acyl-N-alkyl, carbonyl hydrazine or an N-aroyl-N'-alkylN'-aroyl hydrazine. (See U.S. Pat. No. 6,723,531).

In one embodiment, the ligand for an ecdysone based gene switch system is a diacylhydrazine ligand or chiral diacylhydrazine ligand. The ligand used in the gene switch system may be compounds of Formula I Formula I

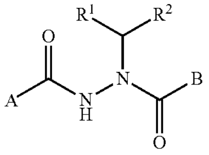

wherein

A is alkoxy, arylalkyloxy or aryloxy;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

or pharmaceutically acceptable salts, hydrates, crystalline forms or amorphous forms thereof.

In another embodiment, the ligand may be enantiomerically enriched compounds of Formula II Formula II

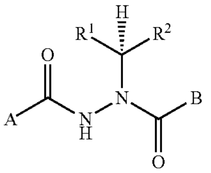

wherein

A is alkoxy, arylalkyloxy, aryloxy, arylalkyl, optionally substituted aryl or optionally substituted heteroaryl;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

with the proviso that $R^1$ does not equal $R^2$;

wherein the absolute configuration at the asymmetric carbon atom bearing $R^1$ and $R^2$ is predominantly S;

or pharmaceutically acceptable salts, hydrates, crystalline forms or amorphous forms thereof.

In certain embodiments, the ligand may be enantiomerically enriched compounds of Formula III Formula III

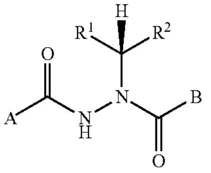

wherein

A is alkoxy, arylalkyloxy, aryloxy, arylalkyl, optionally substituted aryl or optionally substituted heteroaryl;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

with the proviso that $R^1$ does not equal $R^2$;

wherein the absolute configuration at the asymmetric carbon atom bearing $R^1$ and $R^2$ is predominantly R;

or pharmaceutically acceptable salts, hydrates, crystalline forms or amorphous forms thereof.

In one embodiment, a ligand may be (R)-3,5-dimethyl-benzoic acid N-(1-tertbutyl-butyl)-N'-(2-ethyl-3-methoxy-benzoyl)-hydrazide having an enantiomeric excess of at least 95% or a pharmaceutically acceptable salt, hydrate, crystalline form or amorphous form thereof.

The diacylhydrazine ligands of Formula I and chiral diacylhydrazine ligands of Formula II or III, when used with an ecdysone-based gene switch system, provide the means for external temporal regulation of expression of a therapeutic polypeptide or therapeutic polynucleotide of the present invention. See U.S. application Ser. No. 12/155,111, filed May 29, 2008, which is fully incorporated by reference herein.

The ligands used in the present invention may form salts. The term "salt(s)" as used herein denotes acidic and/or basic salts formed with inorganic and/or organic acids and bases. In addition, when a compound of Formula I, II or III contains both a basic moiety and an acidic moiety, zwitterions ("inner salts") may be formed and are included within the term "salt(s)" as used herein. Pharmaceutically acceptable (i.e., non-toxic, physiologically acceptable) salts are used, although other salts are also useful, e.g., in isolation or purification steps which may be employed during preparation. Salts of the compounds of Formula I, II or III may be formed, for example, by reacting a compound with an amount of acid or base, such as an equivalent amount, in a medium such as one in which the salt precipitates or in an aqueous medium followed by lyophilization.

The ligands which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The ligands which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Non-limiting examples of the ligands for the inducible gene expression system utilizing the FK506 binding domain are FK506, Cyclosporin A, or Rapamycin. FK506, rapamycin, and their analogs are disclosed in U.S. Pat. Nos. 6,649,595 B2 and 6,187,757. See also U.S. Pat. Nos. 7,276,498 and 7,273,874.

The ligands described herein may be administered alone or as part of a pharmaceutical composition comprising a pharmaceutically acceptable carrier. In one embodiment, the pharmaceutical composition are in the form of solutions, suspensions, tablets, capsules, ointments, elixirs, or injectable compositions.

In one embodiment, the vector and methods of the present invention can be used to express a polynucleotide that encodes a protein including, but not limited to, a cytokine, an immunomodulator, a clotting factor, an antibody or a fragment of an antibody, a tumor necrosis factor receptor (TNFR), such as Ertanercept, an erythropoietin, alpha-1 antitrypsin, an interferon (IFN), interferon alpha, interferon beta, interferon gamma, interferon-beta-1a, interferon-beta-1b, Factor VII, Factor VIII, Factor IX, antithrombin III, a hepatitis B virus protein, a hormone, for example, a growth hormone (GH), human growth hormone (hGH), parathyroid hormone (PH), thyroid stimulating hormone (TSH), GCSF or fragment thereof, GM-CSF or a fragment thereof.

In one embodiment, the polynucleotide encoding an antibody encodes a monoclonal antibody.

In another embodiment, the vector and methods of the present invention can be used to express nucleic acid as a vaccine. The present invention also provides a vaccine composition comprising a vector or expression system of the present invention. In another embodiment, the vaccine composition comprises an adjuvant.

The term "ecdysone receptor-based," with respect to a gene switch, refers to a gene switch comprising at least a functional part of a naturally occurring or synthetic ecdysone receptor ligand binding domain and which regulates gene expression in response to a ligand that binds to the ecdysone receptor ligand binding domain. Examples of ecdysone-responsive systems are described in U.S. Pat. Nos. 7,091,038 and 6,258,603. In one embodiment, the system is the RheoSwitch® Therapeutic System (RTS), which contains two fusion proteins, the DEF domains of a mutagenized ecdysone receptor (EcR) fused with a Gal4 DNA binding domain and the EF domains of a chimeric RXR fused with a VP16 transcription activation domain, expressed under a constitutive promoter as illustrated in FIG. 1.

The terms "modulate" and "modulates" mean to induce, reduce or inhibit nucleic acid or gene expression, resulting in the respective induction, reduction or inhibition of protein or polypeptide production.

The polynucleotides or vectors according to the invention may further comprise at least one promoter suitable for driving expression of a gene in a host cell.

Enhancers that may be used in embodiments of the invention include but are not limited to: an SV40 enhancer, a cytomegalovirus (CMV) enhancer, an elongation factor 1 (EF 1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In one embodiment of the invention, the termination control region may be comprised or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" refers to a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" refers to a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

"Polypeptide," "peptide" and "protein" are used interchangeably and refer to a polymeric compound comprised of covalently linked amino acid residues.

An "isolated polypeptide," "isolated peptide" or "isolated protein" refer to a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one wild-type or naturally occurring amino acid with a different amino acid relative to the wild-type or naturally occurring polypeptide. A substitution mutant polypeptide may comprise only one wild-type or naturally occurring amino acid substitution and may be referred to as a "point mutant" or a "single point mutant" polypeptide. Alternatively, a substitution mutant polypeptide may comprise a substitution of two or more wild-type or naturally occurring amino acids with two or more amino acids relative to the wild-type or naturally occurring polypeptide. According to the invention, a Group H nuclear receptor ligand binding domain polypeptide comprising a substitution mutation comprises a substitution of at least one wild-type or naturally occurring amino acid with a different amino acid relative to the wild-type or naturally occurring Group H nuclear receptor ligand binding domain polypeptide.

When the substitution mutant polypeptide comprises a substitution of two or more wild-type or naturally occurring amino acids, this substitution may comprise either an equivalent number of wild-type or naturally occurring amino acids deleted for the substitution, i.e., 2 wild-type or naturally occurring amino acids replaced with 2 non-wild-type or non-naturally occurring amino acids, or a non-equivalent number of wild-type amino acids deleted for the substitution, i.e., 2 wild-type amino acids replaced with 1 non-wild-type amino acid (a substitution+deletion mutation), or 2 wild-type amino acids replaced with 3 non-wild-type amino acids (a substitution+insertion mutation).

Substitution mutants may be described using an abbreviated nomenclature system to indicate the amino acid residue and number replaced within the reference polypeptide sequence and the new substituted amino acid residue. For example, a substitution mutant in which the twentieth ($20^{th}$) amino acid residue of a polypeptide is substituted may be abbreviated as "x20z", wherein "x" is the amino acid to be replaced, "20" is the amino acid residue position or number within the polypeptide, and "z" is the new substituted amino acid. Therefore, a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide.

A substitution mutation may be made by any technique for mutagenesis known in the art, including but not limited to, in vitro site-directed mutagenesis (Hutchinson et al., *J. Biol. Chem.* 253:6551 (1978); Zoller et al., DNA 3:479 (1984); Oliphant et al., *Gene* 44:177 (1986); Hutchinson et al., *Proc. Natl. Acad. Sci. USA* 83:710 (1986)), use of TAB® linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

The term "fragment," as applied to a polypeptide, refers to a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 or more amino acids.

A "variant" of a polypeptide or protein refers to any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. In one embodiment, a variant polypeptide comprises at least about 14 amino acids.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., *Cell* 50:667 (1987)). Such proteins (and their encoding genes) have sequence homology, as reflected by their high degree of sequence similarity. However, in common usage and in the application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., *Cell* 50:667 (1987)). In one embodiment, two DNA sequences are "substantially homologous" or "substantially similar" when at least about 50% (e.g., at least about 75%, 90%, or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art (see e.g., Sambrook et al., 1989, supra).

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the invention are those nucleic acid fragments whose DNA sequences are at least about 70%, 80%, 90% or 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403 (1993)); available at ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers.

Accordingly, a "substantial portion" of a nucleotide sequence comprises enough of the sequence to specifically identify and/or isolate a nucleic acid fragment comprising the sequence.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); Computer Analysis of Sequence Data, Part I (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using sequence analysis software such as the Megalign program of the LASERGENE bioinformatics computing suite (DNASTAR Inc., Madison, Wis.). Multiple alignment of the sequences may be performed using the Clustal method of alignment (Higgins et al., *CABIOS*. 5:151 (1989)) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software includes, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403 (1990)), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentiality of the actual modulation. Preferably, modulation of each individually operable gene regulation system effects a change in gene expression at least 2-fold greater than all other operable systems in the cell, tissue, or organism, e.g., at least 5-fold, 10-fold, 100-fold, or 500-fold greater. Ideally, modulation of each of the given systems by its respective ligand at a chosen concentration results in a measurable change in the magnitude of expression of the gene of that system and no measurable change in expression of all other systems operable in the cell, tissue, or organism. In such cases the multiple inducible gene regulation system is said to be "fully orthogonal." Useful orthogonal ligands and orthogonal receptor-based gene expression systems are described in US 2002/0110861 A1.

The term "exogenous gene" means a gene foreign to the subject, that is, a gene which is introduced into the subject through a transformation process, an unmutated version of an endogenous mutated gene or a mutated version of an endogenous unmutated gene. The method of transformation is not critical to this invention and may be any method suitable for the subject known to those in the art. Exogenous genes can be either natural or synthetic genes which are introduced into the subject in the form of DNA or RNA which may function through a DNA intermediate such as by reverse transcriptase. Such genes can be introduced into target cells, directly introduced into the subject, or indirectly introduced by the transfer of transformed cells into the subject.

The term "therapeutic product" refers to a therapeutic polypeptide or therapeutic polynucleotide which imparts a beneficial function to the host cell in which such product is expressed. Therapeutic polypeptides may include, without limitation, peptides as small as three amino acids in length, single- or multiple-chain proteins, and fusion proteins. Therapeutic polynucleotides may include, without limitation, antisense oligonucleotides, small interfering RNAs, ribozymes, and RNA external guide sequences. The therapeutic product may comprise a naturally occurring sequence, a synthetic sequence or a combination of natural and synthetic sequences, The term "ligand-dependent transcription factor complex" or "LDTFC" refers to a transcription factor comprising one or more protein subunits, which complex can regulate gene expression driven by a "factor-regulated promoter" as defined herein. A model LDTFC is an "ecdysone receptor complex" generally refers to a heterodimeric protein complex having at least two members of the nuclear receptor family, ecdysone receptor ("EcR") and ultraspiracle ("USP") proteins (see Yao et al., *Nature* 366:476 (1993)); Yao et al., *Cell* 71:63 (1992)). A functional LDTFC such as an EcR complex may also include additional protein(s) such as immunophilins. Additional members of the nuclear receptor family of proteins, known as transcriptional factors (such as DHR38, betaFTZ-1 or other insect homologs), may also be ligand dependent or independent partners for EcR and/or USP. A LDTFC such as an EcR complex can also be a heterodimer of EcR protein and the vertebrate homolog of ultraspiracle protein, retinoic acid-X-receptor ("RXR") protein or a chimera of USP and RXR. The terms "LDTFC" and "EcR complex" also encompass homodimer complexes of the EcR protein or USP, as well as single polypeptides or trimers, tetramer, and other multimers serving the same function.

A LDTFC such as an EcR complex can be activated by an active ecdysteroid or non-steroidal ligand bound to one of the proteins of the complex, inclusive of EcR, but not excluding other proteins of the complex. A LDTFC such as an EcR complex includes proteins which are members of the nuclear receptor superfamily wherein all members are characterized by the presence of one or more polypeptide subunits comprising an amino-terminal transactivation domain ("AD," "TD," or "TA," used interchangeably herein), a DNA binding domain ("DBD"), and a ligand binding domain ("LBD"). The AD may be present as a fusion with a "heterodimerization partner" or "HP." A fusion protein comprising an AD and HP of the invention is referred to herein as a "coactivation protein" or "CAP." The DBD and LBD may be expressed as a fusion protein, referred to herein as a "ligand-inducible transcription factor ("LTF"). The fusion partners may be separated by a linker, e.g., a hinge region. Some members of the LTF family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The DNA sequences making up the exogenous gene, the response element, and the LDTFC, e.g., EcR complex, may be incorporated into archaebacteria, procaryotic cells such as *Escherichia coli, Bacillus subtilis*, or other enterobacteria, or eucaryotic cells such as plant or animal cells. However, because many of the proteins expressed by the gene are processed incorrectly in bacteria, eucaryotic cells are preferred. The cells may be in the form of single cells or multicellular organisms. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands of this invention for the EcR. As a result, they are "substantially insensitive" to the ligands of this invention. Thus, the ligands useful in this invention will have negligible physiological or other effects on transformed cells, or the whole organism. Therefore, cells can grow and express the desired product, substantially unaffected by the presence of the ligand itself.

The term "ecdysone receptor complex" generally refers to a heterodimeric protein complex having at least two members of the nuclear receptor family, ecdysone receptor ("EcR") and ultraspiracle ("USP") proteins (see Yao et al., *Nature* 366:476 (1993)); Yao et al., *Cell* 71:63 (1992)). The functional EcR complex may also include additional protein(s) such as immunophilins. Additional members of the nuclear receptor family of proteins, known as transcriptional factors (such as DHR38, betaFTZ-1 or other insect homologs), may also be ligand dependent or independent partners for EcR and/or USP. The EcR complex can also be a heterodimer of EcR protein and the vertebrate homolog of ultraspiracle protein, retinoic acid-X-receptor ("RXR") protein or a chimera of USP and RXR. The term EcR complex also encompasses homodimer complexes of the EcR protein or USP.

An EcR complex can be activated by an active ecdysteroid or non-steroidal ligand bound to one of the proteins of the complex, inclusive of EcR, but not excluding other proteins of the complex. As used herein, the term "ligand," as applied to EcR-based gene switches, describes small and soluble molecules having the capability of activating a gene switch to stimulate expression of a polypeptide encoded therein. Examples of ligands include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; amidoketones such as those described in U.S. Published Application No. 2004/0049037; and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, famesol, bile acids, 1,1-biphosphonate esters, juvenile hormone III, and the like. Examples of diacylhydrazine ligands useful in the invention include RG-115819 (3,5-Dimethyl-benzoic acid N-(1-ethyl-2,2-dimethyl-propyl)-N'-(2-methyl-3-methoxy-benzoyl)hydrazide), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See U.S. application Ser. No. 12/155,111, filed May 29, 2008, and PCT/US2008/006757 filed May 29, 2008, for additional diacylhydrazines that are useful in the practice of the invention.

The EcR complex includes proteins which are members of the nuclear receptor superfamily wherein all members are characterized by the presence of an amino-terminal transactivation domain ("TA"), a DNA binding domain ("DBD"), and a ligand binding domain ("LBD") separated by a hinge region. Some members of the family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The DNA sequences making up the exogenous gene, the response element, and the EcR complex may be incorporated into archaebacteria, procaryotic cells such as *Escherichia coli, Bacillus subtilis*, or other enterobacteria, or eucaryotic cells such as plant or animal cells. However, because many of the proteins expressed by the gene are processed incorrectly in bacteria, eucaryotic cells are preferred. The cells may be in the form of single cells or multicellular organisms. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands of this invention for the EcR. As a result, they are "substantially insensitive" to the ligands of this invention. Thus, the ligands useful in this invention will have negligible physiological or other effects on transformed cells, or the whole organism. Therefore, cells can grow and express the desired product, substantially unaffected by the presence of the ligand itself.

EcR ligands, when used with the EcR complex which in turn is bound to the response element linked to an exogenous gene (e.g., IL-12), provide the means for external temporal regulation of expression of the exogenous gene. The order in which the various components bind to each other, that is, ligand to receptor complex and receptor complex to response element, is not critical. Typically, modulation of expression of the exogenous gene is in response to the binding of the EcR complex to a specific control, or regulatory, DNA element. The EcR protein, like other members of the nuclear receptor family, possesses at least three domains, a transactivation domain, a DNA binding domain, and a ligand binding domain. This receptor, like a subset of the nuclear receptor family, also possesses less well-defined regions responsible for heterodimerization properties. Binding of the ligand to the ligand binding domain of EcR protein, after heterodimerization with USP or RXR protein, enables the DNA binding domains of the heterodimeric proteins to bind to the response element in an activated form, thus resulting in expression or suppression of the exogenous gene. This mechanism does not exclude the potential for ligand binding to either EcR or USP, and the resulting formation of active homodimer complexes (e.g., EcR+EcR or USP+USP). In one embodiment, one or more of the receptor domains can be varied producing a chimeric gene switch. Typically, one or more of the three domains may be chosen from a source different than the source of the other domains so that the chimeric receptor is optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988) or LexA protein from *E. coli* (see Brent et al., Cell 43:729 (1985)) to accommodate chimeric EcR complexes. Another advantage of chimeric systems is that they allow choice of a promoter used to drive the exogenous gene according to a desired end result. Such double control can be particularly important in areas of gene therapy, especially when cytotoxic proteins are produced, because both the timing of expression as well as the cells wherein expression occurs can be controlled. When exogenous genes, operatively linked to a suitable promoter, are introduced into the cells of the subject, expression of the exogenous genes is controlled by the presence of the ligand of this invention. Promoters may be constitutively or inducibly regulated or may be tissue-specific (that is, expressed only in a particular type of cell) or specific to certain developmental stages of the organism.

In certain embodiments, the therapeutic switch promoter described in the methods is constitutive. In certain embodiments, the therapeutic switch promoter is activated under conditions associated with a disease, disorder, or condition, e.g., the promoter is activated in response to a disease, in response to a particular physiological, developmental, differentiation, or pathological condition, and/or in response to one or more specific biological molecules; and/or the promoter is activated in particular tissue or cell types. In certain embodiments, the disease, disorder, or condition is responsive to the therapeutic polypeptide or polynucleotide. For example in certain non-limiting embodiments the therapeutic polynucleotide or polypeptide is useful to treat, prevent, ameliorate, reduce symptoms, prevent progression, or cure the disease, disorder or condition, but need not accomplish any one or all of these things. In certain embodiments, the first and second polynucleotides are introduced so as to permit expression of the ligand-dependent transcription factor complex under conditions associated with a disease, disorder or condition. In one embodiment, the therapeutic methods are carried out such that the therapeutic polypeptide or therapeutic polynucleotide is expressed and disseminated through the subject at a level sufficient to treat, ameliorate, or prevent said disease, disorder, or condition. As used herein, "disseminated" means that the polypeptide is expressed and released from the modified cell sufficiently to have an effect or activity in the subject. Dissemination may be systemic, local or anything in between. For example, the therapeutic polypeptide or therapeutic polynucleotide might be systemically disseminated through the bloodstream or lymph system. Alternatively, the therapeutic polypeptide or therapeutic polynucleotide might be disseminated locally in a tissue or organ to be treated.

Numerous genomic and cDNA nucleic acid sequences coding for a variety of polypeptides, such as transcription factors and reporter proteins, are well known in the art. Those skilled in the art have access to nucleic acid sequence information for virtually all known genes and can either obtain the nucleic acid molecule directly from a public depository, the institution that published the sequence, or employ routine methods to prepare the molecule. See for example the description of the sequence accession numbers, infra.

The gene switch may be any gene switch system that regulates gene expression by addition or removal of a specific ligand. In one embodiment, the gene switch is one in which the level of gene expression is dependent on the level of ligand that is present. Examples of ligand-dependent transcription factors that may be used in the gene switches of the invention include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. In one aspect of the invention, the gene switch is an EcR-based gene switch. Examples of such systems include, without limitation, the systems described in U.S. Pat. Nos. 6,258,603, 7,045,315, U.S. Published Patent Application Nos. 2006/0014711, 2007/0161086, and International Published Application No. WO 01/70816. Examples of chimeric ecdysone receptor systems are described in U.S. Pat. No. 7,091,038, U.S. Published Patent Application Nos. 2002/0110861, 2004/0033600, 2004/0096942, 2005/0266457, and 2006/0100416, and International Published Application Nos. WO 01/70816, WO 02/066612, WO 02/066613, WO 02/066614, WO 02/066615, WO 02/29075, and WO 2005/108617. An example of a non-steroidal ecdysone agonist-regulated system is the RheoSwitch® Mammalian Inducible Expression System (New England Biolabs, Ipswich, Mass.).

In one embodiment, a polynucleotide encoding the gene switch comprises a single transcription factor sequence encoding a ligand-dependent transcription factor under the control of a promoter. The transcription factor sequence may encode a ligand-dependent transcription factor that is a naturally occurring or an artificial transcription factor. An artificial transcription factor is one in which the natural sequence of the transcription factor has been altered, e.g., by mutation of the sequence or by the combining of domains from different transcription factors. In one embodiment, the transcription factor comprises a Group H nuclear receptor ligand binding domain (LBD). In one embodiment, the Group H nuclear receptor LBD is from an EcR, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, or a farnesol receptor. In another embodiment, the Group H nuclear receptor LBD is from an ecdysone receptor.

The EcR and the other Group H nuclear receptors are members of the nuclear receptor superfamily wherein all members are generally characterized by the presence of an amino-terminal transactivation domain (TD), a DNA binding domain (DBD), and a LBD separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, Science 240:889 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for response elements. These domains may be either native, modified, or chimeras of different domains of heterologous receptor proteins. The EcR, like a subset of the nuclear receptor family, also possesses less well-defined regions responsible for heterodimerization properties. Because the domains of nuclear receptors are modular in nature, the LBD, DBD, and TD may be interchanged.

In another embodiment, the transcription factor comprises a TD, a DBD that recognizes a response element associated with the exogenous gene whose expression is to be modulated; and a Group H nuclear receptor LBD. In certain embodiments, the Group H nuclear receptor LBD comprises a substitution mutation.

In another embodiment, a polynucleotide encoding the gene switch comprises a first transcription factor sequence under the control of a first promoter and a second transcription factor sequence under the control of a second promoter, wherein the proteins encoded by said first transcription factor sequence and said second transcription factor sequence interact to form a protein complex which functions as a ligand-dependent transcription factor, i.e., a "dual switch"- or "two-hybrid"-based gene switch. The first and second promoters may be the same or different.

In certain embodiments, the polynucleotide encoding a gene switch comprises a first transcription factor sequence and a second transcription factor sequence under the control of a promoter, wherein the proteins encoded by said first transcription factor sequence and said second transcription factor sequence interact to form a protein complex which functions as a ligand-dependent transcription factor, i.e., a "single gene switch". The first transcription factor sequence and a second transcription factor sequence may be connected by an internal ribosomal entry site (IRES). The IRES may be an EMCV IRES.

In one embodiment, the first transcription factor sequence encodes a polypeptide comprising a TD, a DBD that recognizes a response element associated with the exogenous gene whose expression is to be modulated; and a Group H nuclear receptor LBD, and the second transcription factor sequence encodes a transcription factor comprising a nuclear receptor LBD selected from a vertebrate RXR LBD, an invertebrate RXR LBD, an ultraspiracle protein LBD, and a chimeric LBD comprising two polypeptide fragments, wherein the first polypeptide fragment is from a vertebrate RXR LBD, an invertebrate RXR LBD, or an ultraspiracle protein LBD, and the second polypeptide fragment is from a different vertebrate RXR LBD, invertebrate RXR LBD, or ultraspiracle protein LBD.

In another embodiment, the gene switch comprises a first transcription factor sequence encoding a first polypeptide comprising a nuclear receptor LBD and a DBD that recognizes a response element associated with the exogenous gene whose expression is to be modulated, and a second transcription factor sequence encoding a second polypeptide comprising a TD and a nuclear receptor LBD, wherein one of the nuclear receptor LBDs is a Group H nuclear receptor LBD. In one embodiment, the first polypeptide is substantially free of a TD and the second polypeptide is substantially free of a DBD. For purposes of the invention, "substantially free" means that the protein in question does not contain a sufficient sequence of the domain in question to provide activation or binding activity.

In another aspect of the invention, the first transcription factor sequence encodes a protein comprising a heterodimer partner and a TD and the second transcription factor sequence encodes a protein comprising a DBD and a LBD.

When only one nuclear receptor LBD is a Group H LBD, the other nuclear receptor LBD may be from any other nuclear receptor that forms a dimer with the Group H LBD. For example, when the Group H nuclear receptor LBD is an EcR LBD, the other nuclear receptor LBD "partner" may be from an EcR, a vertebrate RXR, an invertebrate RXR, an ultraspiracle protein (USP), or a chimeric nuclear receptor comprising at least two different nuclear receptor LBD polypeptide fragments selected from a vertebrate RXR, an invertebrate RXR, and a USP (see WO 01/70816 A2, International Patent Application No. PCT/US02/05235 and US 2004/0096942 A1). The "partner" nuclear receptor ligand binding domain may further comprise a truncation mutation, a deletion mutation, a substitution mutation, or another modification.

In one embodiment, the vertebrate RXR LBD is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

In one embodiment, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), an ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

In one embodiment, the chimeric RXR LBD comprises at least two polypeptide fragments selected from a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the invention may comprise at least two different species RXR polypeptide fragments, or when the species is the same, the two or more polypeptide fragments may be from two or more different isoforms of the species RXR polypeptide fragment.

In one embodiment, the chimeric RXR ligand binding domain comprises at least one vertebrate species RXR polypeptide fragment and one invertebrate species RXR polypeptide fragment.

In another embodiment, the chimeric RXR ligand binding domain comprises at least one vertebrate species RXR polypeptide fragment and one non-Dipteran/non-Lepidopteran invertebrate species RXR homolog polypeptide fragment.

The ligand, when combined with the LBD of the nuclear receptor(s), which in turn are bound to the response element linked to the exogenous gene, provides external temporal regulation of expression of the exogenous gene. The binding mechanism or the order in which the various components of this invention bind to each other, that is, for example, ligand to LBD, DBD to response element, TD to promoter, etc., is not critical.

In a specific example, binding of the ligand to the LBD of a Group H nuclear receptor and its nuclear receptor LBD partner enables expression of the exogenous gene. This mechanism does not exclude the potential for ligand binding to the Group H nuclear receptor (GHNR) or its partner, and the resulting formation of active homodimer complexes (e.g., GHNR+GHNR or partner+partner). Preferably, one or more of the receptor domains is varied producing a hybrid gene switch. Typically, one or more of the three domains, DBD, LBD, and TD, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988)) or LexA protein from *Escherichia coli* (see Brent et al., *Cell* 43:729 (1985)), or synthetic response elements specific for targeted interactions with proteins designed, modified, and selected for such specific interactions (see, for example, Kim et al., *Proc. Natl. Acad. Sci. USA,* 94:3616 (1997)) to accommodate hybrid receptors.

The functional EcR complex may also include additional protein(s) such as immunophilins. Additional members of the nuclear receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., *Curr. Opin. Cell Biol.* 9:222 (1997)). Also, protein cofactors generally known as corepressors (also known as repressors, silencers, or silencing mediators) may be required to effectively inhibit transcriptional activation in the absence of ligand. These corepressors may interact with the unliganded EcR to silence the activity at the response element. Current evidence suggests that the binding of ligand changes the conformation of the receptor, which results in release of the corepressor and recruitment of the above described coactivators, thereby abolishing their silencing activity. Examples of corepressors include N—CoR and SMRT (for review, see Horwitz et al., *Mol Endocrinol.* 10:1167 (1996)). These cofactors may either be endogenous within the cell or organism, or may be added exogenously as transgenes to be expressed in either a regulated or unregulated fashion.

The exogenous gene is operably linked to a promoter comprising at least one response element that is recognized by the DBD of the ligand-dependent transcription factor encoded by the gene switch. In one embodiment, the promoter comprises 1, 2, 3, 4, 5, 6, 7, 8, 9, 10, or more copies of the response element. Promoters comprising the desired response elements may be naturally occurring promoters or artificial promoters created using techniques that are well known in the art, e.g., one or more response elements operably linked to a minimal promoter.

A gene encoding an immunomodulator, e.g., IL-12, TNF-alpha, signal peptides, or any transcription factors herein can also be codon-optimized. In one embodiment, a coding region of an immunomodulator, e.g., IL-12, TNF-alpha, a signal peptide, or a transcription factor is codon-optimized for expression in human. As appreciated by one of ordinary skill in the art, various nucleic acid coding regions will encode the same polypeptide due to the redundancy of the genetic code. Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 4. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the polypeptides encoded by the DNA.

TABLE 4

The Standard Genetic Code

| | T | C | A | G |
|---|---|---|---|---|
| T | TTT Phe(F) | TCT Ser(S) | TAT Tyr(Y) | TGT Cys(C) |
| | TTC " | TCC " | TAC " | TGC " |
| | TTA Leu(L) | TCA " | TAA **Ter** | TGA **Ter** |
| | TTG " | TCG " | TAG **Ter** | TGG Trp(W) |
| C | CTT Leu(L) | CCT Pro(P) | CAT His(H) | CGT Arg(R) |
| | CTC " | CCC " | CAC " | CGC " |
| | CTA " | CCA " | CAA Gln(Q) | CGA " |
| | CTG " | CCG " | CAG " | CGG " |
| A | ATT Ile(I) | ACT Thr(T) | AAT Asn(N) | AGT Ser(S) |
| | ATC " | ACC " | AAC " | AGC " |
| | ATA " | ACA " | AAA Lys(K) | AGA Arg(R) |
| | **ATG** Met(M) | ACG " | AAG " | AGG " |
| G | GTT Val(V) | GCT Ala(A) | GAT Asp(D) | GGT Gly(G) |
| | GTC " | GCC " | GAC " | GGC " |
| | GTA " | GCA " | GAA Glu(E) | GGA " |
| | GTG " | GCG " | GAG " | GGG " |

It is to be appreciated that any polynucleotide that encodes a polypeptide in accordance with the invention falls within the scope of this invention, regardless of the codons used.

Many organisms display a bias for use of particular codons to code for insertion of a particular amino acid in a growing polypeptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

The polynucleotides are prepared by incorporating codons preferred for use in the genes of a given species into the DNA sequence.

Given the large number of gene sequences available for a wide variety of animal, plant and microbial species, it is possible to calculate the relative frequencies of codon usage. Codon usage tables are readily available, for example, at the "Codon Usage Database" available at http://www.kazusa.or.jp/codon/ (visited May 30, 2006), and these tables can be adapted in a number of ways. See Nakamura, Y., et al., "Codon usage tabulated from the international DNA sequence databases: status for the year 2000" *Nucl. Acids Res.* 28:292 (2000). Codon usage tables for humans calculated from GenBank Release 151.0, are reproduced below as Table 5 (from http://www.kazusa.or.ip/codon/ supra). These tables use mRNA nomenclature, and so instead of thymine (T) which is found in DNA, the tables use uracil (U) which is found in RNA. The tables have been adapted so that frequencies are calculated for each amino acid, rather than for all 64 codons.

TABLE 5

Codon Usage Table for Human Genes (*Homo sapiens*)

| Amino Acid | Codon | Frequency of Usage |
|---|---|---|
| Phe | UUU | 0.4525 |
| | UUC | 0.5475 |
| Leu | UUA | 0.0728 |
| | UUG | 0.1266 |
| | CUU | 0.1287 |
| | CUC | 0.1956 |
| | CUA | 0.0700 |
| | CUG | 0.4062 |
| Ile | AUU | 0.3554 |
| | AUC | 0.4850 |
| | AUA | 0.1596 |
| Met | AUG | 1.0000 |
| Val | GUU | 0.1773 |
| | GUC | 0.2380 |
| | GUA | 0.1137 |
| | GUG | 0.4710 |
| Ser | UCU | 0.1840 |
| | UCC | 0.2191 |
| | UCA | 0.1472 |
| | UCG | 0.0565 |
| | AGU | 0.1499 |
| | AGC | 0.2433 |
| Pro | CCU | 0.2834 |
| | CCC | 0.3281 |
| | CCA | 0.2736 |
| | CCG | 0.1149 |
| Thr | ACU | 0.2419 |
| | ACC | 0.3624 |
| | ACA | 0.2787 |
| | ACG | 0.1171 |
| Ala | GCU | 0.2637 |
| | GCC | 0.4037 |
| | GCA | 0.2255 |
| | GCG | 0.1071 |
| Tyr | UAU | 0.4347 |
| | UAC | 0.5653 |

TABLE 5-continued

Codon Usage Table for Human Genes (*Homo sapiens*)

| Amino Acid | Codon | Frequency of Usage |
|---|---|---|
| His | CAU | 0.4113 |
| | CAC | 0.5887 |
| Gln | CAA | 0.2541 |
| | CAG | 0.7459 |
| Asn | AAU | 0.4614 |
| | AAC | 0.5386 |
| Lys | AAA | 0.4212 |
| | AAG | 0.5788 |
| Asp | GAU | 0.4613 |
| | GAC | 0.5387 |
| Glu | GAA | 0.4161 |
| | GAG | 0.5839 |
| Cys | UGU | 0.4468 |
| | UGC | 0.5532 |
| Trp | UGG | 1.0000 |
| Arg | CGU | 0.0830 |
| | CGC | 0.1927 |
| | CGA | 0.1120 |
| | CGG | 0.2092 |
| | AGA | 0.2021 |
| | AUG | 0.2011 |
| Gly | GGU | 0.1632 |
| | GGC | 0.3438 |
| | GGA | 0.2459 |
| | GGG | 0.2471 |

By utilizing these or similar tables, one of ordinary skill in the art can apply the frequencies to any given polypeptide sequence, and produce a nucleic acid fragment of a codon-optimized coding region which encodes the polypeptide, but which uses codons optimal for a given species.

A number of options are available for synthesizing codon-optimized coding regions designed by any of the methods described above, using standard and routine molecular biological manipulations well known to those of ordinary skill in the art.

In one embodiment, the coding region encoding the immunomodulator, e.g., TNF-alpha, in the vector of the invention is codon-optimized. In another embodiment, the coding region is codon-optimized for expression in human. In a particular embodiment, TNF-alpha in the invention is encoded by a codon-optimized nucleic acid sequence.

To introduce the polynucleotides into the cells in vivo or ex vivo, a vector can be used. The vector may be, for example, a plasmid vector or a single- or double-stranded RNA or DNA viral vector. Such vectors may be introduced into cells of a subject in need thereof, e.g., mammal, by well-known techniques for introducing DNA and RNA into cells. Viral vectors may be replication competent or replication defective. In the latter case, viral propagation generally will occur only in complementing host cells. As used herein, the term "host cell" or "host" is used to mean a cell of the invention that is harboring one or more polynucleotides of the invention.

Thus, at a minimum, the vectors must include the polynucleotides of the invention. Other components of the vector may include, but are not limited to, selectable markers, chromatin modification domains, additional promoters driving expression of other polypeptides that may also be present on the vector (e.g., a lethal polypeptide), genomic integration sites, recombination sites, and molecular insertion pivots. The vectors may comprise any number of these additional elements, either within or not within the polynucleotides, such that the vector can be tailored to the specific goals of the therapeutic methods desired.

In one embodiment of the invention, the vectors that are introduced into the cells further comprise a "selectable marker gene" which, when expressed, indicates that the gene switch construct of the invention has been integrated into the genome of the host cell. In this manner, the selector gene can be a positive marker for the genome integration. While not critical to the methods of the invention, the presence of a selectable marker gene allows the practitioner to select for a population of live cells where the vector construct has been integrated into the genome of the cells. Thus, certain embodiments of the invention comprise selecting cells where the vector has successfully been integrated. As used herein, the term "select" or variations thereof, when used in conjunction with cells, is intended to mean standard, well-known methods for choosing cells with a specific genetic make-up or phenotype. Typical methods include, but are not limited to, culturing cells in the presence of antibiotics, such as G418, neomycin and ampicillin. Other examples of selectable marker genes include, but are not limited to, genes that confer resistance to dihydrofolate reductase, hygromycin, or mycophenolic acid. Other methods of selection include, but are not limited to, a selectable marker gene that allows for the use of thymidine kinase, hypoxanthine-guanine phosphoribosyltransferase or adenine phosphoribosyltransferase as selection agents. Cells comprising a vector construct comprising an antibiotic resistance gene or genes would then be capable of tolerating the antibiotic in culture. Likewise, cells not comprising a vector construct comprising an antibiotic resistance gene or genes would not be capable of tolerating the antibiotic in culture.

As used herein, a "chromatin modification domain" (CMD) refers to nucleotide sequences that interact with a variety of proteins associated with maintaining and/or altering chromatin structure, such as, but not limited to, DNA insulators. See Ciavatta et al., *Proc. Nat'l Acad. Sci. U.S.A.*, 103:9958 (2006). Examples of CMDs include, but are not limited to, the chicken β-globulin insulator and the chicken hypersensitive site 4 (cHS4). The use of different CMD sequences between one or more gene programs (i.e., a promoter, coding sequence, and 3' regulatory region), for example, can facilitate the use of the differential CMD DNA sequences as "mini homology arms" in combination with various microorganism or in vitro recombineering technologies to "swap" gene programs between existing multigenic and monogenic shuttle vectors. Other examples of chromatin modification domains are known in the art or can be readily identified.

Polynucleotide and nucleic acid coding regions in the vector of the invention can be associated with additional coding regions which encode secretory or signal peptides, which direct the secretion of an immunomodulator, e.g., TNF-alpha. According to the signal hypothesis, proteins secreted by mammalian cells have a signal peptide or secretory leader sequence which is cleaved from the mature protein once export of the growing protein chain across the rough endoplasmic reticulum has been initiated. Polypeptides secreted by vertebrate cells generally have a signal peptide fused to the N-terminus of the polypeptide, which is cleaved from the complete or "full length" polypeptide to produce a secreted or "mature" form of the polypeptide.

In one embodiment, a vector of the invention comprises a polynucleotide encoding a gene switch, wherein said polynucleotide comprises (1) at least one transcription factor sequence which is operably linked to a promoter, wherein said at least one transcription factor sequence encodes a ligand-dependent transcription factor, and (2) a polynucleotide encoding one or more proteins having the function of an immunomodulator operably linked to a promoter which is activated by said ligand-dependent transcription factor, wherein said polynucleotide encoding one or more proteins having the function of an immunomodulator further comprises a nucleic acid sequence encoding a signal peptide. In another embodiment, the signal peptide increase secretion of the immunomodulator, e.g., TNF-alpha, encoded by the vector compared to a vector comprising the immunomodulator's native signal peptide gene, e.g., TNF-alpha wild-type signal peptide gene. In particular, the signal peptide used in the invention can be codon-optimized. In a specific embodiment, the signal peptide is encoded by IL-2 wild-type signal peptide gene. In a further specific embodiment, the signal peptide is encoded by codon-optimized IL-2 signal peptide gene.

The vector of the invention can comprise various regulatory regions, for example, 5' untranslated region (5'UTR), 3' UTR, or both. The present invention is also directed to using various regulatory regions to induce improved secretion, protein translation, post-translation, mRNA transcription, or post-transcription process. As used herein, the "5' untranslated region" or "5'UTR" of a gene is to be understood as that part of a gene which is transcribed into a primary RNA transcript (pre-mRNA) and which part is located upstream of the coding sequence. The primary transcript is the initial RNA product, containing introns and exons, produced by transcription of DNA. Many primary transcripts must undergo RNA processing to form the physiologically active RNA species. The processing into a mature mRNA may comprise trimming of the ends, removal of introns, capping and/or cutting out of individual rRNA molecules from their precursor RNAs. The 5'UTR of an mRNA is thus that part of the mRNA which is not translated into protein and which is located upstream of the coding sequence. In a genomic sequence, the 5'UTR is typically defined as the region between the transcription initiation site and the start codon. The 5' untranslated regions (5'UTRs) of vertebrate mRNAs may be a few tens of bases to several hundred bases in length (Crowe et al., 2006 *BMC Genomics* 7:16). The 5'UTR used herein may occur naturally or be modified to contain one or more nucleic acid sequences not contiguous in nature (chimeric sequences), and/or may encompass substitutions, insertions, and deletions and combinations thereof. In one embodiment, the 5'UTR sequence is derived from the wildtype TNF-alpha sequence or 5U2 sequence. In another embodiment, the 5'UTR sequence is 5'UTR of 5U2. In some embodiments, the 5'UTR induces improved protein expression, e.g, mRNA transcription, pre-transcription, or post-transcription.

The 3' untranslated region (UTR) used in the invention refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor. Any suitable polyadenylation sequence can be used, including a synthetic optimized sequence, as well as the polyadenylation sequence of BGH (Bovine Growth Hormone), polyoma virus, TK (Thymidine Kinase), EBV (Epstein Barr Virus), and the papillomaviruses, including human papillomaviruses and BPV (Bovine Papilloma Virus). In a particular embodiment, a 3' regulatory region is the SV40e (human Sarcoma Virus-40) polyadenylation sequence. In another particular embodiment, a 3' regulatory region is the polyadenylation sequence of human growth hormone.

In certain embodiments, the signal peptide and/or the regulatory region alone or in combination can improve the protein secretion, transcription, or translation at least two fold, three fold, four fold, five fold, six fold, seven fold, eight fold, nine fold, 10 fold, 50 fold, 100 fold, 200 fold, 300 fold, 400 fold, or 500 fold compared to a control, which does not contain the signal peptide and/or the regulatory region. The secretion level of a protein, e.g., TNF-alpha, can be normalized to the protein expression encoded by a vector having a wild-type gene. In another specific embodiment of the present invention, the signal peptide and/or the regulatory region alone or in combination increase productivity of the immunomodulator, e.g., TNF-alpha, about 5% to about 10%, about 11% to about 20%, about 21% to about 30%, about 31% to about 40%, about 41% to about 50%, about 51% to about 60%, about 61% to about 70%, about 71% to about 80%, about 81% to about 90%, about 91% to about 100%, about 101% to about 149%, about 150% to about 199%, about 200% to about 299%, about 300% to about 499%, or about 500% to about 1000%. In a specific embodiment, the present invention comprises a vector conditionally expressing an immunomodulator, e.g., TNF-alpha, wherein said vector comprises 5' UTR of 5U2, a codon-optimized nucleic acid sequence encoding IL-2 signal peptide, a codon-optimized coding region encoding an immunomodulator, e.g., TNF-alpha, and a polyadenylation signal of SV40e or human growth hormone.

In a further embodiment, the vector of the invention comprises a polynucleotide sequence selected from the group consisting of SEQ ID NO: 47 (Vector 43318), SEQ ID NO: 48 (Vector 43319), SEQ ID NO: 49 (Vector 43320), SEQ ID NO: 50 (Vector 43321), SEQ ID NO: 51 (Vector 43322), SEQ ID) NO: 52 (Vector 43323), SEQ ID NO: 53 (Vector 43324), SEQ II) NO: 54 (Vector 43325), SEQ ID NO: 55 (Vector 43326), SEQ ID NO: 56 (Vector 43327), SEQ ID NO: 57 (Vector 43328), and SEQ ID) NO: 58 (Vector 43329). In a still specific embodiment, the vector comprises a polynucleotide sequence of SEQ II) NO: 52 (vector 43323) or SEQ ID NO: 58 (vector 43329).

Particular vectors for use with the invention are expression vectors that code for proteins or polynucleotides. Generally, such vectors comprise cis-acting control regions effective for expression in a host operatively linked to the polynucleotide to be expressed. Appropriate trans-acting factors are supplied by the host, supplied by a complementing vector or supplied by the vector itself upon introduction into the host, A great variety of expression vectors can be used to express proteins or polynucleotides. Such vectors include chromosomal, episomal and virus-derived vectors, e.g., vectors derived from bacterial plasmids, from bacteriophage, from yeast episomes, from yeast chromosomal elements, from viruses such as adeno-associated viruses, lentiviruses, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All may be used for expression in accordance with this aspect of the invention. Generally, any vector suitable to maintain, propagate or express polynucleotides or proteins in a host may be used for expression in this regard.

Suitable viral vectors used in the invention include, but not limited to, adenovirus-based vectors, retroviral vectors, herpes simplex virus (HSV)-based vectors, parvovirus-based vectors, e.g., adeno-associated virus (AAV)-based vectors, and AAV-adenoviral chimeric vectors. These viral vectors can be prepared using standard recombinant DNA techniques described in, for example, Sambrook et al., Molecular Cloning, a Laboratory Manual, 2d edition, Cold Spring Harbor Press, Cold Spring Harbor, N.Y. (1989), and Ausubel et al., Current Protocols in Molecular Biology, Greene Publishing Associates and John Wiley & Sons, New York, N.Y. (1994).

In one embodiment, a viral vector of the invention is an adenoviral vector. Adenovirus (Ad) is a 36 kb double-stranded DNA virus that efficiently transfers DNA in vivo to a variety of different target cell types. The adenoviral vector can be produced in high titers and can efficiently transfer DNA to replicating and non-replicating cells. The adenoviral vector genome can be generated using any species, strain, subtype, mixture of species, strains, or subtypes, or chimeric adenovirus as the source of vector DNA. Adenoviral stocks that can be employed as a source of adenovirus can be amplified from the adenoviral serotypes 1 through 51, which are currently available from the American Type Culture Collection (ATCC, Manassas, Va.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22-30, 32, 33, 36-39, and 42-47), subgroup E (serotype 4), subgroup F (serotypes 40 and 41), or any other adenoviral serotype. Given that the human adenovirus serotype 5 (Ad5) genome has been completely sequenced, the adenoviral vector of the invention is described herein with respect to the Ad5 serotype. The adenoviral vector can be any adenoviral vector capable of growth in a cell, which is in some significant part (although not necessarily substantially) derived from or based upon the genome of an adenovirus. The adenoviral vector can be based on the genome of any suitable wild-type adenovirus. In certain embodiments, the adenoviral vector is derived from the genome of a wild-type adenovirus of group C, especially of serotype 2 or 5. Adenoviral vectors are well known in the art and are described in, for example, U.S. Pat. Nos. 5,559,099, 5,712,136, 5,731,190, 5,837,511, 5,846,782, 5,851,806, 5,962,311, 5,965,541, 5,981,225, 5,994,106, 6,020,191, and 6,113,913, International Patent Applications WO 95/34671, WO 97/21826, and WO 00/00628, and Thomas Shenk, "Adenoviridae and their Replication," and M. S. Horwitz, "Adenoviruses," Chapters 67 and 68, respectively, in *Virology*, B. N. Fields et al., eds., 3d ed., Raven Press, Ltd., New York (1996).

In other embodiments, the adenoviral vector is replication-deficient. The term "replication-deficient" used herein means that the adenoviral vector comprises a genome that lacks at least one replication-essential gene function. A deficiency in a gene, gene function, or gene or genomic region, as used herein, is defined as a deletion of sufficient genetic material of the viral genome to impair or obliterate the function of the gene whose nucleic acid sequence was deleted in whole or in part. Replication-essential gene functions are those gene functions that are required for replication (i.e., propagation) of a replication-deficient adenoviral vector. Replication-essential gene functions are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., VA-RNA I and/or VA-RNA II). In still other embodiments, the replication-deficient adenoviral vector comprises an adenoviral genome deficient in at least one replication-essential gene function of one or more regions of an adenoviral genome (e.g., two or more regions of an adenoviral genome so as to result in a multiply replication-deficient adenoviral vector). The one or more regions of the adenoviral genome are selected from the group consisting of the E1, E2, and E4 regions. The replication-deficient adenoviral vector can comprise a deficiency in at least one replication-essential gene function of the E1 region (denoted an E1-deficient adenoviral vector), particularly a deficiency in a replication-essential gene function of each of the adenoviral E1A region and the adenoviral E1B region. In addition to such a deficiency in the E1 region, the recombinant adenovirus also can have a mutation in the major late promoter (MLP), as discussed in International Patent Application WO 00/00628. In a particular embodiment, the vector is deficient in at least one replication-essential gene function of the E1 region and at least part of the nonessential E3 region (e.g., an Xba I deletion of the E3 region) (denoted an E1/E3-deficient adenoviral vector).

In certain embodiments, the adenoviral vector is "multiply deficient," meaning that the adenoviral vector is deficient in one or more gene functions required for viral replication in each of two or more regions of the adenoviral genome. For example, the aforementioned E1-deficient or E1/E3-deficient adenoviral vector can be further deficient in at least one replication-essential gene function of the E4 region (denoted an E1/E4-deficient adenoviral vector). An adenoviral vector deleted of the entire E4 region can elicit a lower host immune response.

Alternatively, the adenoviral vector lacks replication-essential gene functions in all or part of the E1 region and all or part of the E2 region (denoted an E1/E2-deficient adenoviral vector). Adenoviral vectors lacking replication-essential gene functions in all or part of the E1 region, all or part of the E2 region, and all or part of the E3 region also are contemplated herein. If the adenoviral vector of the invention is deficient in a replication-essential gene function of the E2A region, the vector does not comprise a complete deletion of the E2A region, which is less than about 230 base pairs in length. Generally, the E2A region of the adenovirus codes for a DBP (DNA binding protein), a polypeptide required for DNA replication. DBP is composed of 473 to 529 amino acids depending on the viral serotype. It is believed that DBP is an asymmetric protein that exists as a prolate ellipsoid consisting of a globular Ct with an extended Nt domain. Studies indicate that the Ct domain is responsible for DBP's ability to bind to nucleic acids, bind to zinc, and function in DNA synthesis at the level of DNA chain elongation. However, the Nt domain is believed to function in late gene expression at both transcriptional and post-transcriptional levels, is responsible for efficient nuclear localization of the protein, and also may be involved in enhancement of its own expression. Deletions in the Nt domain between amino acids 2 to 38 have indicated that this region is important for DBP function (Brough et al., *Virology,* 196, 269-281 (1993)). While deletions in the E2A region coding for the Ct region of the DBP have no effect on viral replication, deletions in the E2A region which code for amino acids 2 to 38 of the Nt domain of the DBP impair viral replication. In one embodiment, the multiply replication-deficient adenoviral vector contains this portion of the E2A region of the adenoviral genome. In particular, for example, the desired portion of the E2A region to be retained is that portion of the E2A region of the adenoviral genome which is defined by the 5' end of the E2A region, specifically positions Ad5(23816) to Ad5(24032) of the E2A region of the adenoviral genome of serotype Ad5.

The adenoviral vector can be deficient in replication-essential gene functions of only the early regions of the adenoviral genome, only the late regions of the adenoviral genome, and both the early and late regions of the adenoviral genome. The adenoviral vector also can have essentially the entire adenoviral genome removed, in which case at least either the viral inverted terminal repeats (ITRs) and one or more promoters or the viral ITRs and a packaging signal are left intact (i.e., an adenoviral amplicon). The larger the region of the adenoviral genome that is removed, the larger the piece of exogenous nucleic acid sequence that can be inserted into the genome. For example, given that the adenoviral genome is 36 kb, by leaving the viral ITRs and one or more promoters intact, the exogenous insert capacity of the adenovirus is approximately 35 kb. Alternatively, a multiply deficient adenoviral vector that contains only an ITR and a packaging signal effectively allows insertion of an exogenous nucleic acid sequence of approximately 37-38 kb. Of course, the inclusion of a spacer element in any or all of the deficient adenoviral regions will decrease the capacity of the adenoviral vector for large inserts. Suitable replication-deficient adenoviral vectors, including multiply deficient adenoviral vectors, are disclosed in U.S. Pat. Nos. 5,851,806 and 5,994,106 and International Patent Applications WO 95/34671 and WO 97/21826. In one embodiment, the vector for use in the present inventive method is that described in International Patent Application PCT/US01/20536.

It should be appreciated that the deletion of different regions of the adenoviral vector can alter the immune response of the mammal. In particular, the deletion of different regions can reduce the inflammatory response generated by the adenoviral vector. Furthermore, the adenoviral vector's coat protein can be modified so as to decrease the adenoviral vector's ability or inability to be recognized by a neutralizing antibody directed against the wild-type coat protein, as described in International Patent Application WO 98/40509.

The adenoviral vector, when multiply replication-deficient, especially in replication-essential gene functions of the E1 and E4 regions, can include a spacer element to provide viral growth in a complementing cell line similar to that achieved by singly replication deficient adenoviral vectors, particularly an adenoviral vector comprising a deficiency in the E1 region. The spacer element can contain any sequence or sequences which are of the desired length. The spacer element sequence can be coding or non-coding and native or non-native with respect to the adenoviral genome, but does not restore the replication-essential function to the deficient region. In the absence of a spacer, production of fiber protein and/or viral growth of the multiply replication-deficient adenoviral vector is reduced by comparison to that of a singly replication-deficient adenoviral vector. However, inclusion of the spacer in at least one of the deficient adenoviral regions, preferably the E4 region, can counteract this decrease in fiber protein production and viral growth. The use of a spacer in an adenoviral vector is described in U.S. Pat. No. 5,851,806.

Construction of adenoviral vectors is well understood in the art. Adenoviral vectors can be constructed and/or purified using the methods set forth, for example, in U.S. Pat. No. 5,965,358 and International Patent Applications WO 98/56937, WO 99/15686, and WO 99/54441. The production of adenoviral gene transfer vectors is well known in the art, and involves using standard molecular biological techniques such as those described in, for example, Sambrook et al., supra, Watson et al., supra, Ausubel et al., supra, and in several of the other references mentioned herein.

Replication-deficient adenoviral vectors are typically produced in complementing cell lines that provide gene functions not present in the replication-deficient adenoviral vectors, but required for viral propagation, at appropriate levels in order to generate high titers of viral vector stock. In one embodiment, a cell line complements for at least one and/or all replication-essential gene functions not present in a replication-deficient adenovirus. The complementing cell line can complement for a deficiency in at least one replication-essential gene function encoded by the early regions, late regions, viral packaging regions, virus-associated RNA regions, or combinations thereof, including all adenoviral functions (e.g., to enable propagation of adenoviral amplicons, which comprise minimal adenoviral sequences, such as only inverted terminal repeats (ITRs) and the packaging signal or only ITRs and an adenoviral promoter). In another embodiment, the complementing cell line complements for a deficiency in at least one replication-essential gene function (e.g., two or more replication-essential gene functions) of the E1 region of the adenoviral genome, particularly a deficiency in a replication-essential gene function of each of the E1A and E1B regions. In addition, the complementing cell line can complement for a deficiency in at least one replication-essential gene function of the E2 (particularly as concerns the adenoviral DNA polymerase and terminal protein) and/or E4 regions of the adenoviral genome. Desirably, a cell that complements for a deficiency in the E4 region comprises the E4-ORF6 gene sequence and produces the E4-ORF6 protein. Such a cell desirably comprises at least ORF6 and no other ORF of the E4 region of the adenoviral genome. The cell line preferably is further characterized in that it contains the complementing genes in a non-overlapping fashion with the adenoviral vector, which minimizes, and practically eliminates, the possibility of the vector genome recombining with the cellular DNA. Accordingly, the presence of replication competent adenoviruses (RCA) is minimized if not avoided in the vector stock, which, therefore, is suitable for certain therapeutic purposes, especially gene therapy purposes. The lack of RCA in the vector stock avoids the replication of the adenoviral vector in non-complementing cells. The construction of complementing cell lines involves standard molecular biology and cell culture techniques, such as those described by Sambrook et al., supra, and Ausubel et al., supra. Complementing cell lines for producing the gene transfer vector (e.g., adenoviral vector) include, but are not limited to, 293 cells (described in, e.g., Graham et al., *J. Gen. Virol.,* 36, 59-72 (1977)), PER.C6 cells (described in, e.g., International Patent Application WO 97/00326, and U.S. Pat. Nos. 5,994,128 and 6,033,908), and 293-ORF6 cells (described in, e.g., International Patent Application WO 95/34671 and Brough et al., *J Virol.,* 71, 9206-9213 (1997)). The insertion of a nucleic acid sequence into the adenoviral genome (e.g., the E1 region of the adenoviral genome) can be facilitated by known methods, for example, by the introduction of a unique restriction site at a given position of the adenoviral genome.

Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. As such, long-term expression of a therapeutic factor(s) is achievable when using retrovirus. Retroviruses contemplated for use in gene therapy are relatively non-pathogenic, although pathogenic retroviruses exist. When employing pathogenic retroviruses, e.g., human immunodeficiency virus (HIV) or human T-cell lymphotrophic viruses (HTLV), care must be taken in altering the viral genome to eliminate toxicity to the host. A retroviral vector additionally can be manipulated to render the virus replication-deficient. As such, retroviral vectors are considered particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

An HSV-based viral vector is suitable for use as a gene transfer vector to introduce a nucleic acid into numerous cell types. The mature HSV virion consists of an enveloped icosahedral capsid with a viral genome consisting of a linear double-stranded DNA molecule that is 152 kb. Most replication-deficient HSV vectors contain a deletion to remove one or more intermediate-early genes to prevent replication. Advantages of the HSV vector are its ability to enter a latent stage that can result in long-term DNA expression and its large viral DNA genome that can accommodate exogenous DNA inserts of up to 25 kb. Of course, the ability of HSV to promote long-term production of exogenous protein is potentially disadvantageous in terms of short-term treatment regimens. However, one of ordinary skill in the art has the requisite understanding to determine the appropriate vector for a particular situation. HSV-based vectors are described in, for example, U.S. Pat. Nos. 5,837,532, 5,846,782, 5,849,572, and 5,804,413, and International Patent Applications WO 91/02788, WO 96/04394, WO 98/15637, and WO 99/06583.

AAV vectors are viral vectors of particular interest for use in gene therapy protocols. AAV is a DNA virus, which is not known to cause human disease. The AAV genome is comprised of two genes, rep and cap, flanked by inverted terminal repeats (ITRs), which contain recognition signals for DNA replication and packaging of the virus. AAV requires co-infection with a helper virus (i.e., an adenovirus or a herpes simplex virus), or expression of helper genes, for efficient replication. AAV can be propagated in a wide array of host cells including human, simian, and rodent cells, depending on the helper virus employed. An AAV vector used for administration of a nucleic acid sequence typically has approximately 96% of the parental genome deleted, such that only the ITRs remain. This eliminates immunologic or toxic side effects due to expression of viral genes. If desired, the AAV rep protein can be co-administered with the AAV vector to enable integration of the AAV vector into the host cell genome. Host cells comprising an integrated AAV genome show no change in cell growth or morphology (see, e.g., U.S. Pat. No. 4,797,368). As such, prolonged expression of therapeutic factors from AAV vectors can be useful in treating persistent and chronic diseases.

The polynucleotide sequence in the expression vector is operatively linked to appropriate expression control sequence(s) including, for instance, a promoter to direct mRNA transcription. Representatives of additional promoters include, but are not limited to, constitutive promoters and tissue specific or inducible promoters. Examples of constitutive eukaryotic promoters include, but are not limited to, the promoter of the mouse metallothionein I gene (Hamer et al., *J. Mol. Appl. Gen.* 1:273 (1982)); the TK promoter of Herpes virus (McKnight, Cell 31:355 (1982)); the SV40 early promoter (Benoist et al., *Nature* 290:304 (1981)); and the vaccinia virus promoter. Additional examples of the promoters that could be used to drive expression of a protein or polynucleotide include, but are not limited to, tissue-specific promoters and other endogenous promoters for specific proteins, such as the albumin promoter (hepatocytes), a proinsulin promoter (pancreatic beta cells) and the like. In general, expression constructs will contain sites for transcription, initiation and termination and, in the transcribed region, a ribosome binding site for translation. The coding portion of the mature transcripts expressed by the constructs may include a translation initiating AUG at the beginning and a termination codon (UAA, UGA or UAG) appropriately positioned at the end of the polypeptide to be translated.

In addition, the constructs may contain control regions that regulate, as well as engender expression. Generally, such regions will operate by controlling transcription, such as repressor binding sites and enhancers, among others.

Examples of eukaryotic vectors include, but are not limited to, pW-LNEO, pSV2CAT, pOG44, pXT1 and pSG available from Stratagene; pSVK3, pBPV, pMSG and pSVL available from Amersham Pharmacia Biotech; and pCMVDsRed2-express, pIRES2-DsRed2, pDsRed2-Mito, and pCMV-EGFP available from Clontech. Many other vectors are well-known and commercially available.

Particularly useful vectors, which comprise molecular insertion pivots for rapid insertion and removal of elements of gene programs, are described in United States Published Patent Application No. 2004/0185556, U.S. patent application Ser. No. 11/233,246 and International Published Application Nos. WO 2005/040336 and WO 2005/116231. An example of such vectors is the ULTRAVECTOR® Production System (Intrexon Corp., Blacksburg, Va.), as described in WO 2007/038276. As used herein, a "gene program" is a combination of genetic elements comprising a promoter (P), an expression sequence (E) and a 3' regulatory sequence (3), such that "PE3" is a gene program. The elements within the gene program can be easily swapped between molecular pivots that flank each of the elements of the gene program. A molecular pivot, as used herein, is defined as a polynucleotide comprising at least two non-variable rare or uncommon restriction sites arranged in a linear fashion. In one embodiment, the molecular pivot comprises at least three non-variable rare or uncommon restriction sites arranged in a linear fashion. Typically any one molecular pivot would not include a rare or uncommon restriction site of any other molecular pivot within the same gene program. Cognate sequences of greater than 6 nucleotides upon which a given restriction enzyme acts are referred to as "rare" restriction sites. There are, however, restriction sites of 6 bp that occur more infrequently than would be statistically predicted, and these sites and the endonucleases that cleave them are referred to as "uncommon" restriction sites. Examples of either rare or uncommon restriction enzymes include, but are not limited to, AsiS I, Pac I, Sbf I, Fse I, Asc I, Mlu I, SnaB I, Not I, Sal I, Swa I, Rsr II, BSiW I, Sfo I, Sgr AI, AflIII, Pvu I, Ngo MIV, Ase I, Flp I, Pme I, Sda I, Sgf I, Srf I, Nru I, Acl I, Cla I, Csp45 I, Age I, Bstl1107 I, BstB I, Hpa I, Aat II, EcoR V, Nhe 1, Spe I, Avi II, Avr II, Mfe I, Afe i, Fsp I, Kpn I, Sca I, BspE I, Nde I, Bfr I, Xho I, Pml I, ApaL I, Kas I, Xma I, BsrB 1, Nsi I, Sac II, Sac I, Blp I, PspoM I, Pci I, Stu I, Sph I, BamH I, Bsu36 I, Xba I, BbvC I, Bgl II, Nco I, Hind III, EcoR I, BsrG I and Sse8781 I.

The vector may also comprise restriction sites for a second class of restriction enzymes called homing endonuclease (HE) enzymes. HE enzymes have large, asymmetric restriction sites (12-40 base pairs), and their restriction sites are infrequent in nature. For example, the HE known as I-Scel has an 18 bp restriction site (5'TAGGGATAACAGGGTAAT3' (SEQ ID NO: 28)), predicted to occur only once in every $7\times10^{10}$ base pairs of random sequence. This rate of occurrence is equivalent to only one site in a genome that is 20 times the size of a mammalian genome. The rare nature of HE sites greatly increases the likelihood that a genetic engineer can cut a gene program without disrupting the integrity of the gene program if HE sites are included in appropriate locations in a cloning vector plasmid.

Selection of appropriate vectors and promoters for expression in a host cell is a well-known procedure, and the requisite techniques for vector construction and introduction into the host, as well as its expression in the host are routine skills in the art.

The introduction of the polynucleotides into the cells can be a transient transfection, stable transfection, or can be a locus-specific insertion of the vector. Transient and stable transfection of the vectors into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods in Molecular Biology (1986); Keown et al., 1990, Methods Enzymol. 185: 527-37; Sambrook et al., 2001, Molecular Cloning, A Laboratory Manual, Third Edition, Cold Spring Harbor Laboratory Press, N.Y. These stable transfection methods result in random insertion of the vector into the genome of the cell. Further, the copy number and orientation of the vectors are also, generally speaking, random.

In one embodiment of the invention, the vector is inserted into a bio-neutral site in the genome. A bio-neutral site is a site in the genome where insertion of the polynucleotides interferes very little, if any, with the normal function of the cell. Bioneutral sites may be analyzed using available bioinformatics. Many bio-neutral sites are known in the art, e.g., the ROSA-equivalent locus. Other bio-neutral sites may be identified using routine techniques well known in the art. Characterization of the genomic insertion site(s) is performed using methods known in the art. To control the location, copy number and/or orientation of the polynucleotides when introducing the vector into the cells, methods of locus-specific insertion may be used. Methods of locus-specific insertion are well-known in the art and include, but are not limited to, homologous recombination and recombinase-mediated genome insertion. Of course, if locus-specific insertion methods are to be used in the methods of the invention, the vectors may comprise elements that aid in this locus-specific insertion, such as, but not limited to, homologous recombination. For example, the vectors may comprise one, two, three, four or more genomic integration sites (GISs). As used herein, a "genomic integration site" is defined as a portion of the vector sequence which nucleotide sequence is identical or nearly identical to portions of the genome within the cells that allows for insertion of the vector in the genome. In particular, the vector may comprise two genomic insertion sites that flank at least the polynucleotides. Of course, the GISs may flank additional elements, or even all elements present on the vector.

In another embodiment, locus-specific insertion may be carried out by recombinase-site specific gene insertion. Briefly, bacterial recombinase enzymes, such as, but not limited to, PhiC31 integrase can act on "pseudo" recombination sites within the human genome. These pseudo recombination sites can be targets for locus-specific insertion using the recombinases. Recombinase-site specific gene insertion is described in Thyagarajan et al., *Mol. Cell Biol.* 21:3926 (2001). Other examples of recombinases and their respective sites that may be used for recombinase-site specific gene insertion include, but are not limited to, serine recombinases such as R4 and TP901-1 and recombinases described in WO 2006/083253.

In a further embodiment, the vector may comprise a chemo-resistance gene, e.g., the multidrug resistance gene mdr1, dihydrofolate reductase, or $O^6$-alkylguanine-DNA alkyltransferase. The chemo-resistance gene may be under the control of a constitutive (e.g., CMV) or inducible (e.g., RheoSwitch®) promoter. In this embodiment, if it is desired to treat a disease in a subject while maintaining the modified cells within the subject, a clinician may apply a chemotherapeutic agent to destroy diseased cells while the modified cells would be protected from the agent due to expression of a suitable chemo-resistance gene and may continue to be used for treatment, amelioration, or prevention of a disease or disorder. By placing the chemo-resistance gene under an inducible promoter, the unnecessary expression of the chemo-resistance gene can be avoided, yet it will still be available in case continued treatment is needed. If the modified cells themselves become diseased, they could still be destroyed by inducing expression of a lethal polypeptide as described below.

The methods of the invention are carried out by introducing the polynucleotides encoding the gene switch and the exogenous gene into cells of a subject. Any method known for introducing a polynucleotide into a cell known in the art, such as those described above, can be used.

When the polynucleotides are to be introduced into cells ex vivo, the cells may be obtained from a subject by any technique known in the art, including, but not limited to, biopsies, scrapings, and surgical tissue removal. The isolated cells may be cultured for a sufficient amount of time to allow the polynucleotides to be introduced into the cells, e.g., 2, 4, 6, 8, 10, 12, 18, 24, 36, 48, hours or more. Methods for culturing primary cells for short periods of time are well known in the art. For example, cells may be cultured in plates (e.g., in microwell plates) either attached or in suspension.

For ex vivo therapeutic methods, cells are isolated from a subject and cultured under conditions suitable for introducing the polynucleotides into the cells. Once the polynucleotides have been introduced into the cells, the cells are incubated for a sufficient period of time to allow the ligand-dependent transcription factor to be expressed, e.g., 0.5, 1, 2, 3, 4, 5, 6, 7, 8, 9, 10, 12, 18, or 24 hours or more. At some point after the introduction of the polynucleotides into the cells (either before or after significant levels of the ligand-dependent transcription factor is expressed), the cells are introduced back into the subject. Reintroduction may be carried out by any method known in the art, e.g., intravenous infusion or direct injection into a tissue or cavity. In one embodiment, the presence of the polynucleotides in the cells is determined prior to introducing the cells back into the subject. In another embodiment, cells containing the polynucleotides are selected (e.g., based on the presence of a selectable marker in the polynucleotides) and only those cells containing the polynucleotides are reintroduced into the subject. After the cells are reintroduced to the subject, ligand is administered to the subject to induce expression of the therapeutic polypeptide or therapeutic polynucleotide. In an alternative embodiment, the ligand may be added to the cells even before the cells are reintroduced to the subject such that the therapeutic polypeptide or therapeutic polynucleotide is expressed prior to reintroduction of the cells. The ligand may be administered by any suitable method, either systemically (e.g., orally, intravenously) or locally (e.g, intraperitoneally, intrathecally, intraventricularly, direct injection into the tissue or organ where the cells are reintroduced). The optimal timing of ligand administration can be determined for each type of cell and disease or disorder using only routine techniques.

The in vivo therapeutic methods of the invention involve direct in vivo introduction of the polynucleotides, e.g., adenoviral vector, into the cells of the subject. The polynucleotides may be introduced into the subject systemically or locally (e.g., at the site of the disease or disorder). Once the polynucleotides have been introduced to the subject, the ligand may be administered to induce expression of the therapeutic polypeptide or therapeutic polynucleotide. The ligand may be administered by any suitable method, either systemically (e.g., orally, intravenously) or locally (e.g., intraperitoneally, intrathecally, intraventricularly, direct injection into the tissue or organ where the disease or disorder is occurring). The optimal timing of ligand administration can be determined for each type of cell and disease or disorder using only routine techniques.

For in vivo use, the ligands described herein may be taken up in pharmaceutically acceptable carriers, such as, for example, solutions, suspensions, tablets, capsules, ointments, elixirs, and injectable compositions. Pharmaceutical compositions may contain from 0.01% to 99% by weight of the ligand. Compositions may be either in single or multiple dose forms. The amount of ligand in any particular pharmaceutical composition will depend upon the effective dose, that is, the dose required to elicit the desired gene expression or suppression.

Suitable routes of administering the pharmaceutical preparations include oral, rectal, topical (including dermal, buccal and sublingual), vaginal, parenteral (including subcutaneous, intramuscular, intravenous, intratumoral, intradermal, intrathecal and epidural), intravitreal, and by nasogastric tube. It will be understood by those skilled in the art that the route of administration will depend upon the condition being treated and may vary with factors such as the condition of the recipient.

As used herein, the term "rAD.RheoIL12" refers to an adenoviral polynucleotide vector harboring the IL-12 gene under the control of a gene switch of the RheoSwitch® Therapeutic System (RTS), which is capable of producing IL-12 protein in the presence of activating ligand. As used herein, the term "rAd.cIL12" refers to an adenoviral polynucleotide control vector containing the IL-12 gene under the control of a constitutive promoter.

As used herein, the term "IL-12p70" refers to IL-12 protein, which naturally has two subunits commonly referred to as p40 and p35. The term IL-12p70 encompasses fusion proteins comprising the two subunits of IL-12 (p40 and p35), wherein the fusion protein may include linker amino acids between subunits.

As used herein, the term "a protein having the function of an immunomodulator" refers to a protein that has at least 20% (e.g., at least 30%, 40%, 50%, 60%, 70%, 80% or 90%) of any bioactivity of an immunomodulator selected from IL-1, IL-2, IL-3, IL-4, IL5, IL-7, IL-8, IL-9, IL-10R or a subunit thereof. DN, IL-15, IL-18, IL-21, IL-23, IL-24, IL-27, GM-CSF, IFN-alpha, IFN-gamma, CCL3 (MIP-1a), CCL5 (RANTES), CCL7 (MCP3), XCL1 (lymphotactin), CXCL1 (MGSA-alpha), CCR7, CCL19 (MIP-3b), CXCL9 (MIG), CXCL10 (IP-10), CXCL12 (SDF-1), CCL21 (6Ckine), OX40L, 4-1BBL, CD40, CD70, GITRL, LIGHT, b-Defensin, HMGB1, Flt3L, IFN-beta, TNF-alpha, dnFADD, BCG, TGF-alpha, PD-L1, TGFbRII DN, ICOS-L and S100. Likewise, the term "a protein having the function of IL-12" refers to a protein that has at least 20% (e.g., at least 30%, 40%, 50%, 60%, 70%, 80% or 90%) of any bioactivity of human IL-12. The bioactivities of such immunomodulators are well known. See the following Table.

TABLE 6

Immunomodulators and their functions

| Immunomodulator | Function |
|---|---|
| | Cytokines |
| Interleukin-1 (IL-1) | IL-1 is a cytokine produced by activated macrophages. IL-1 stimulates thymocyte proliferation by inducing IL-2 release, B-cell maturation and proliferation, and fibroblast growth factor activity. IL-1 proteins are involved in the inflammatory response. |
| Interleukin-2 (IL-2) | IL-2 is a family of cytokines, that is produced by T-cells in response to antigenic or mitogenic stimulation, this protein is required for T-cell proliferation and other activities crucial to regulation of the immune response. IL-2 can stimulate B-cells, monocytes, lymphokine-activated killer cells, natural killer cells, and glioma cells. |
| Interleukin-3 (IL-3) | IL-3 stimulates the proliferation of hematopoietic pluripotent progenitor cells. It is secreted by activated T cells to support growth and differentiation of T cells from the bone marrow in an immune response. The combined intratumoral Ad-mIL-3 gene therapy in combination with radiation therapy was shown to significanth suppress tumor growth (Oh 2004). |
| Interleukin-4 (IL-4) | IL-4 is a cytokine that participates in at least several B-cell activation processes as well as of other cell types. It is a costimulator of DNA-synthesis. It induces the expression of class II MHC molecules on resting B-cells. It enhances both secretion and cell surface expression of IgE and IgG1. It also regulates the expression of the low affinity Fc receptor for IgE (CD23) on both lymphocytes and monocytes. |

TABLE 6-continued

| Immunomodulators and their functions | |
|---|---|
| Immunomodulator | Function |
| Interleukin-5 (IL-5) | IL-5 stimulates B cell growth and increase immunoglobulin secretion and induce tumor suppression (Nakashima 1993, Wu 1992). |
| Interleukin-7 (IL-7) | IL-7 is a cytokine that is a hematopoietic growth factor capable of stimulating the proliferation of lymphoid progenitors. It is important for proliferation during certain stages of B-cell maturation. |
| Interleukin-9 (IL-9) | IL-9 supports IL-2 independent and IL-4 independent growth of helper T-cells. |
| Interleukin-15 (IL-15) | IL-15 is a cytokine that stimulates the proliferation of T-lymphocytes. Stimulation by IL-15 requires interaction of IL-15 with components of IL-2R, including IL-2R beta and probably IL-2R gamma but not IL-2R alpha. |
| Interleukin-18 (IL-18) | IL-18 augments natural killer cell activity in spleen cells and stimulates interferon gamma production in T-helper type I cells. |
| Interleukin-21 (IL-21) | IL-21 is a cytokine with immunoregulatory activity. IL-21 may promote the transition between innate and adaptive immunity. |
| Interleukin-23 (IL-23) | IL-23 acts directly on DC to promote immunogenic presentation of tumor peptide and can I resulted in robust intratumoral CD8(+) and CD4(+) T-cell infiltration and induced a specific TH1-type response to the tumor in regional lymph nodes and spleen. (Hu 2006). |
| Interleukin-27 (IL-27) | IL-27 is a cytokine with pro- and anti-inflammatory properties, that can regulate T helper cell development, suppress T-cell proliferation, stimulate cytotoxic T cell activity, induce isotype switching in B-cells, and that has diverse effects on innate immune cells. |
| Intereukin-24 (IL-23) | IL-24 has been shown to suppress tumor growth (Susan 2004, Fisher 2003). |
| INF-alpha (IFNα) | IFN-alpha has anti-tumor function (Taqliaferri 2005). |
| Interferon beta 1 (IFNB1) | IFNB1 is a member of group of interferon proteins that bind to specific cell surface receptors (IFNAR), and stimulates both macrophages and natural killer (NK) cells to elicit an antiviral, antibacterial and anticancer activities. |
| Interferon gamma (IFN-gamma) | IFN-gamma is produced by lymphocytes activated by specific antigens or mitogens. IFN-gamma, in addition to having antiviral activity, has important immunoregulatory functions. It is a potent activator of macrophages, it has antiproliferative effects on transformed cells and it can potentiate the antiviral and antitumor effects of the type I interferons. |
| Tumor necrosis factor (TNF-alpha) | TNF-α is mainly secreted by macrophages and can induce cell death of certain tumor cell lines. It is a potent pyrogen, causing fever by direct action or by stimulation of interleukin-1 secretion. |
| | Chemokines |
| Chemokine (C motif) ligand 1 (XCL1) | Chemokine (C motif) ligand 1 (XCL1, also known as Lymphotactin) is chemotactic for CD4+ and CD8+ T cells but not for monocytes, and induces a rise in int-acellular calcium in peripheral blood lymphocytes. The combination of XCL1 with IL-2 and IL-12 can enhance immunotherapy and augment the antitumor response (Emtage 1999, Wang 2002). |
| CC chemokine ligand 3 (CCL3) | CC chemokine ligand 3 (CCL3), also known as macrophage inflammatory protein-1 (MIP-1), which is a so-called monokine (a type of cytokine produced primarily by monocytes and macrophages) that is involved in the acute inflammatory state in the recruitment and activation of polymorphonuclear leukocytes. |
| CCL5 (RANTES) | CCL5 (RANTES), is a chemoattractant for blood monocytes, memory T-helper cells and eosinophils. Causes the release of histamine from basophils and activates eosinophils. Binds to CCR1, CCR3, CCR4 and CCR5. One of the major HIV-suppressive factors produced by CD8+ T-cells. |
| CC chemokine ligand 7 (CCL7) | CCL7 is a chemotactic factor that attracts monocytes and eosinophils, but not neutrophils. CCL7 also augments monocyte anti-tumor activity. Also induces the release of gelatinase B. |
| Chemokine (CXC motif) ligand 9 (CXCL9) | CXCL9 is a cytokine that affects the growth, movement, or activation state of cells that participate in immune and inflammatory response. Chemotactic for activated T-cells. |
| Chemokine (C-X-C motif) ligand 10 (CXCL10) | Chemokine (C-X-C motif) ligand 10 (CXCL10) is a small cytokine with roles in chemoattraction for cells in the immune system, adhesion of T cells to endothelial cells, anti-tumor activity and angiogenesis. |
| Chemokine (C-X-C motif) ligand 12 (CXCL12) | Chemokine (C-X-C motif) ligand 12 (CXCL12), also known as stormal cell-derived factor 1 (SDF-1), is a small cytokine that belong to the intercrine family, members of which activate leukocytes and are often induced by proinflammatory stimuli such as LPS, TNF or IL1. |

TABLE 6-continued

| Immunomodulators and their functions | |
|---|---|
| Immunomodulator | Function |
| Chemokine (C-C motif) receptor 7 (CCR7) | CCR7 is the receptor for the MIP-3-beta chemokine. Probable mediator of EBV effects on B-lymphocytes or of normal lymphocyte functions. |
| Chemokine (C-C motif) ligand 19 (CCL19, also known as MIP-3β) | CCL19 plays a role not only in inflammatory and immunological responses but also in normal lymphocyte recirculation and homing. CCL19 has an important role in trafficking of T-cells in thymus, and T-cell and B-cell migration to secondary lymphoid organs. It specifically binds to chemokine receptor CCR7. |
| CC chemokine ligand 21 (CCL21) | CCL21 inhibits hemopoiesis and stimulates chemotaxis. CCL21 is chemotactic in vitro for thymocytes and activated T-cells, but not for B-cells, macrophages, or neutrophils. |
| Interleukin-8 (IL-8) | IL-8 is a chemotactic factor that attracts neutrophils, basophils, and T-cells, but not monocytes. It is also involved in neutrophil activation. It is released from several cell types in response to an inflammatory stimulus. |
| Growth Factors | |
| Granulocyte/macrophage colony-stimulating factor (GM-CSF) | GM-CSF is a cytokine that stimulates the growth and differentiation of hematopoietic precursor cells from various lineages, including granulocytes, macrophages, eosinophils and erythrocytes. |
| FMS-related tyrosine kinase ligand (FLT3/FLK2 ligand, Flt3L) | FMS-related tyrosine kinase ligand (FLT3/FLK2 ligand, Flt3L), which may function as a growth factor receptor on hematopoietic stem cells or progenitor cells or both. |
| TGFA | TGF alpha is a mitogenic polypeptide that is able to bind to the EGF receptor and to act synergistically with TGF beta to promote anchorage-independent cell proliferation in soft agar. |
| Adjuvants | |
| Beta-defensin | Beta-defensins are antimicrobial peptides implicated in innate immune response against many Gram-negative and Gram-positive bacteria, fungi and viruses. |
| High-mobility group box-1 (HMGB1) | High-mobility group box-1 (HMGB1) proteins are nonhistone chromosomal proteins that function as cytokines, mediating local and systemic responses to necrotic cell death and cancer, invasion by pathogens, trauma, and sepsis. |
| S100 | Phagocytic S100 proteins mediate inflammatory responses and recruit inflammatory cells to sites of tissue damage, and are members of Damage-associated molecular pattern (DAMP) molecules that are important for innate immunity. |
| Mannan | Mannan, a plant polysaccharide, that is a polymer of the sugar mannose, is useful for generation of a immune response. |
| Bacille Calmette-Guerin (BCG) | Bacille Calmette-Guerin (BCG), live attenuated Mycobacterium species, are used as vaccine against to prevent severe and fatal tuberculosis. |
| Bacterial lipopolysaccharides (LPS) | Bacterial lipopolysaccharides (LPS) are endotoxins that induces a strong immune response upon infection with Gram-negative bacteria. |
| Co-stimulatory Molecule (Postive) | |
| OX40 ligand | OX40 ligand (OX40L) belongs to tumor necrosis factor (ligand) superfamily member 4 (Tnfsf4), is expressed on dendritic cells and promotes Th2 cell differentiation. |
| 4-1BB ligand (4-1BBL) | 4-1BB ligand (4-1BBL) belongs to tumor necrosis factor (ligand) superfamily member 9 (Tnfsf9), which is a type 2 transmembrane glycoprotein and is expressed on activated T lymphocytes. 4-1BBL induces the proliferation of activated peripheral blood T-cells, and has a role in activation-induced cell death (AICD). |
| CD40 | The CD40 protein belongs to the tumor necrosis factor receptor superfamily member 5, is essential in mediating a broad variety of immune and inflammatory responses including T cell-dependent immunoglobulin class switching, memory B cell development, and germinal center formation. |
| Glucocorticoid-induced tumor necrosis factor receptor family-related protein (GITR) | GITR can evoke effective tumor immunity via T cell stimulation. Administration of anti-GITR monoclonal antibody (mAb) can provoke potent tumor-specific immunity and eradicated established tumors without eliciting overt autoimmune disease. |
| GITR Ligand (GITRL) | GITRL is the ligand for GITR. |
| CD70 | CD70 is a cytokine that binds to CD27. It plays a role in T-cell activation. Induces the proliferation of costimulated T-cells and enhances the generation of cytolytic T-cells. |
| LIGHT (HSVgD) | Herpes virus entry mediator (HVEM) binding ligand (HSVgD), also referred to as p30, or LIGHT is a TNF family member involved in co-stimulation of T cells. |

TABLE 6-continued

| Immunomodulators and their functions | |
|---|---|
| Immunomodulator | Function |
| PD-L1 (also known as CD274) | PD-L1 (also known as CD274) protein is expressed in activated monocytes, T and B cells. PD-L1 is upregulated in monocytes upon treatment with IFN-gamma, and in dendritic cells and keratinocytes upon treatment with IFN-gamma, together with other activators. |
| ICOS-L | ICOS-L is a ligand for the T-cell-specific cell surface receptor ICOS and acts as a costimulatory signal for T-cell proliferation and cytokine secretion; induces also B-cell proliferation and differentiation into plasma cells. |
| Co-stimulatory Molecule (Negative) | |
| Anti-CTLA4 | Cytotoxic T lymphocyte-associated 4 (CTLA4) is a member of the immunoglobulin superfamily and is a costimulatory molecule expressed in activated T cells. |
| Anti-PD-L1 | Binding of a PD-1 receptor on a T-cell by PD-L1 transmits a negative costimulatory signal to the cell, which prevents the cells to progress through the cell cycle, and increases T cell proliferation. Inhibition of an interaction between PD-L1 and receptor on the T cell with an anti-PD-L1 antibody results in the downregulation of the immune response termed as immune cell anergy. |
| Anti-PD-L2 | PD-L2 is involved in the costimulatory signal, essential for T lymphocyte proliferation and IFN-gamma production in a PDCD1-independent manner, but the ligand is known to primarily act through PD-1 resulting in anergic responses. |
| Counter Immune Suppressant (Tolerance Inhibitory) | |
| TGFR2DN | On ligand binding, TGFR2 forms a receptor complex consisting of two type II and two type I transmembrane serine/threonine kinases. Type II receptors phosphorylate and activate type I receptors which autophosphorylate, then bind and activate SMAD transcriptional regulators. Receptor for TGF-beta. Deletion of predicted serine/theronine kinase cytoplasmic domain (nucleotides 1172-2036 of TGβR2 cDNA H2-3FF, available from public databases as accession number M85079 and amino acid sequence available as accession number AAA61164) impairs the all three TGF-β (1, 2 and 3) dependent gene expressions. |
| Anti-TGFβ | TCFβ is a multifunctional peptide that controls proliferation, differentiation, and other functions in many cell types. TGFβ acts synergistically with TGFα in inducing transformation. It also acts as a negative autocrine growth factor. Dysregulation of TGFβ activation and signaling may result in apoptosis. administration of anti-TGFβ antibody can prevent renal insufficiency and glomerulosclerosis in the db/db mouse, a model of type II diabetes that develops overt nephropathy. |
| Anti-IL10 | IL-10 is a cytokine produced by activated Th2 cells, B cells, keratinocytes, monocytes, and macrophages. IL-10 is useful in promoting growth and differentiation of activated human B cells, inhibiting Th1 responses to prevent transplant rejection and T cell-mediated autoimmune diseases. |
| Anti-Suppressor of cytokine signaling1 (SOCS1) | Suppressor of cytokine signaling1 (SOCS1) is a critical inhibitor of interferon-gamma signaling and prevents the potentially fatal neonatal actions of this cytokine. |
| Anti-TGF-α | TGF-α is a mitogenic polypeptide that is able to bind to the EGF receptor and to act synergistically with TGF-β to promote anchorage-independent cell proliferation in soft agar. |
| Fas contain cytoplasmic Fas-associated protein with death domain (FADD) | FADD is essential for Fas and TNF-induced signaling for programmed cell death (apoptosis) and receptor oligomerization. |

The bioactivities of IL-12 are also well known and include, without limitation, differentiation of naive T cells into Th1 cells, stimulation of the growth and function of T cells, production of interferon-gamma (IFN-gamma) and tumor necrosis factor-alpha (TNF-α) from T and natural killer (NK) cells, reduction of IL-4 mediated suppression of IFN-gamma, enhancement of the cytotoxic activity of NK cells and $CD8^+$ cytotoxic T lymphocytes, stimulation of the expression of IL-12R-31 and IL-12R-132, facilitation of the presentation of tumor antigens through the upregulation of MHC I and II molecules, and anti-angiogenic activity. The term "a protein having the function of IL-12" encompasses mutants of a wild type IL-12 sequence, wherein the wild type sequence has been altering by one or more of addition, deletion, or substitution of amino acids, as well as non-IL-12 proteins that mimic one or more of the bioactivities of IL-12.

As used herein, the terms "activating" or "activate" refer to any measurable increase in cellular activity of a gene switch, resulting in expression of a gene of interest (e.g., selected from IL-1, IL-2, IL-3, IL-4, IL-5, IL-7, IL-8, IL-9, IL-10R or a subunit thereof DN, IL-15, IL-18, IL-21, IL-23, IL-24, IL-27, GM-CSF, IFN-alpha, IFN-gamma, CCL3

(MIP-1a), CCL5 (RANTES), CCL7 (MCP3), XCL1 (lymphotactin), CXCL1 (MGSA-alpha), CCR7, CCL19 (MIP-3b), CXCL9 (MIG), CXCL10 (IP-10), CXCL12 (SDF-1), CCL21 (6Ckine), OX40L, 4-1BBL, CD40, CD70, GITRL, LIGHT, b-Defensin, HMGB1, Flt3L, IFN-beta, TNF-alpha, dnFADD, TGF-alpha, PD-L1 RNAi, a PD-L1 antisense oligonucleotide, TGFbRII DN, ICOS-L and S100.

As used herein, the terms “treating” or “treatment” of a disease refer to executing a protocol, which may include administering one or more drugs or in vitro engineered cells to a mammal (human or non-human), in an effort to alleviate signs or symptoms of the disease. Thus, “treating” or “treatment” should not necessarily be construed to require complete alleviation of signs or symptoms, does not require a cure, and specifically includes protocols that have only marginal effect on the subject.

As used herein, “immune cells” include dendritic cells, macrophages, neurophils, mast cells, eosinophils, basophils, natural killer cells and lymphocytes (e.g., B and T cells).

As used herein, the terms “dendritic cells” and “DC” are interchangeably used.

As used herein, the term “therapy support cells” (TSC) are cells that can be modified (e.g., transfected, electroporated, etc.) with the vector of the invention to deliver the one or more proteins having the function of an immunomodulator and, optionally, a protein having the function of IL-12, to tumor microenvironments. Such TSC include, but are not limited to, stem cells, fibroblasts, endothelial cells and keratinocytes.

As used herein, the terms “in vitro engineered immune cells” or “in vitro engineered population of immune cells” or “a population of engineered immune cells” or “immune cells expressing an immunomodulator” or “immune cells expressing IL-12” refer to immune cells, e.g., dendritic cells, conditionally expressing an immunomodulator and/or IL-12 as the case may be under the control of a gene switch, which can be activated by an activating ligand.

As used herein, the terms “in vitro engineered TSC” or “in vitro engineered population of TSC” or “a population of engineered TSC” or “TSC expressing an immunomodulator” or “TSC expressing IL-12” refer to therapy support cells, e.g., stem cells, fibroblasts, endothelial cells and keratinocytes, conditionally expressing an immunomodulator and/or IL-12 as the case may be under the control of a gene switch, which can be activated by activating ligand.

As used herein, the term “modified cell” refers to cells which have been altered by a process including, but not limited to, transfection, electroporation, microinjection, transduction, cell fusion, DEAE dextran, calcium phosphate precipitation and lipofection (lysosome fusion).

As used herein, the terms “MOI” or “Multiplicity of Infection” refer to the average number of adenovirus particles that infect a single cell in a specific experiment (e.g., recombinant adenovirus or control adenovirus)

As used herein, the term “tumor” refers to all benign or malignant cell growth and proliferation either in vivo or in vitro, whether precancerous or cancerous cells and/or tissues.

In another embodiment, the vector and methods of the present invention can be used to treat disease.

In another embodiment, the vector and methods of the present invention can be used to treat a cancer. Non-limiting examples of cancers that can be treated according to the invention include breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, mesothelioma, osteogenic sarcoma, primary macroglobulinemia, and retinoblastoma, and the like. In another embodiment, the vector and methods of the present invention can be used to treat a metabolic-related disorder including, but not limited to, a disorder selected from the group consisting of dyslipidemia, atherosclerosis, insulin resistance, diabetes (e.g. diabetes type I, diabetes type II, MODY, and gestational diabetes), obesity, impaired glucose tolerance, atheromatous disease, hypertension, heart disease (which includes, but is not limited to, coronary heart disease, stroke, cardiac insufficiency, coronary insufficiency, and high blood pressure), hyperlipidemia, glucose intolerance, insulin resistance, hyperglycemia, hyperinsulinemia, metabolic syndrome X (or syndrome X, or insulin resistance syndrome, or Reaven's syndrome, or the metabolic cardiovascular risk syndrome), hypertension, chronic fatigue, accelerated aging, degenerative disease, endocrine deficiencies of aging, $G_m1$ gangliosidosis, Morquio-B disease, Krabbe's disease, Fabry's disease, Gaucher's disease, Tay-Sachs disease, Sandhoff disease, fucosidosis, disorders of carbohydrate metabolism (e.g. glycogen storage disease), disorders of amino acid metabolism (e.g. phenylketonuria, maple syrup urine disease, glutaric acidemia type 1), disorders of organic acid metabolism (e.g. alcaptonuria), disorders of fatty acid oxidation and mitochondrial metabolism (e.g. medium chain acyl dehydrogenase deficiency), disorders of porphyrin metabolism (e.g. acute intermittent porphyria), disorders of purine or pyrimidine metabolism (e.g. Lesch-Nyhan syndrome), disorders of steroid metabolism (e.g. congenital adrenal hyperplasia), disorders of mitochondrial function (e.g. Kearns-Sayre syndrome), and disorders of peroxisomal function (e.g. Zellweger syndrome).

In another embodiment, the vector and methods of the present invention can be used to treat an autoimmune disorder including, but not limited to, a disorder selected from the group consisting of Achlorhydra Autoimmune Active Chronic Hepatitis, Acute Disseminated Encephalomyelitis, Acute hemorrhagic leukoencephalitis, Addison's Disease, gammaglobulinemia, Agammaglobulinemia, Alopecia areata, Amyotrophic Lateral Sclerosis, Ankylosing Spondylitis, Anti-GBM/TBM Nephritis, Antiphospholipid syndrome, Antisynthetase syndrome, Arthritis, Atopic allergy, Atopic Dermatitis, Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaff's encephalitis, Blau syndrome, Bullous Pemphigoid, Castleman's disease, Chronic Fatigue Immune Dysfunction Syndrome, chronic inflammatory demyelinating polyneuropathy, Chronic recurrent multifocal ostomyelitis, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease, Cushing's Syndrome, Cutaneous leukocytoclastic angiitis, Dego's disease, Dermatitis herpetiformis, Dermatomyositis, Diabetes mellitus type 1, Diffuse cutaneous systemic sclerosis, Dressler's syndrome, Discoid lupus erythemratosus, eczema, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyositis, Fibrosing aveolitis, Gastritis, Gastrointestinal pemphigoid, Giant cell arteritis, Goodpasture's syndrome, Graves' disease, Guillain-Barré syndrome (GBS), Hashimoto's encephalitis, Hashimoto's thyroiditis, Hemoolytic anaemia, Henoch-Schonlein purpura, Herpes gestationis, Hughes syndrome (or Antiphospholipid syndrome), Hypogammnaglobulinemia, Idiopathic Inflammatory Demyelinating Diseases, Idiopathic pulmonary fibrosis, Idiopathic thrombocytopenic purpura, IgA nephropathy (or Berger's disease), inclusion body myositis, ory demyelinating polyneuopathy, Juvenile idiopathic arthritis, Juvenile rheumatoid arthritis, Lambert-Eaton myasthenic syndrome, Leukocytoclastic vasculitis, Lichen planus, Lichen sclerosus, Linear IgA disease (LAD), Lou Gehrig's Disease, Lupoid hepatitis, Lupus erythematosus, Majeed syndrome, Meniere's disease, Microscopic polyangiitis, Miller-Fisher syndrome, Mixed Connective Tissue Disease, Mucha-Habermann disease, Muckle-Wells syndrome, Multiple Myeloma, Myasthenia gravis, Myositis, Narcolepsy, Neuromyelitis optica (also Devic's Disease), Occular cicatricial pemphigoid, Ord thyroiditis, Palindromic rheumatism, PANDAS (Pediatric Autoimmune Neuropsychiatric Disorders Associated with *Streptococcus*), Paraneoplastic cerebellar degeneration, Paraneoplastic cerebellar degeneration, Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, psoriasis, psoriatic arthritis, Pyoderma gangrenosum, pure red cell aplasia, Rasmussen's encephalitis, Raynaud phenomenon, Relapsing polychondritis, Reiter's syndrome, Retroperitoneal fibrosis, Rheumatoid arthritis, Rheumatoid fever, Schmidt syndrome, Schnitzler syndrome, Scleritis, Sjögren's syndrome, Spondyloarthropathy, sticky blood syndrome, Still's Disease, Subacute bacterial endocarditis (SBE), Susac's syndrome, Sweet syndrome, Sydenham Chorea, Sympathetic ophthalmia, Takayasu's arteritis, Temporal arteritis, Tolosa-Hunt syndrome, Transverse Myelitis, Ulcerative Colitis, Undifferentiated connective tissue disease, Undifferentiated spondyloarthropathy, vasculitis, Wegener's granulomatosis, Wilson's syndrome, and Wiskott-Aldrich syndrome.

In another embodiment, vector and the methods of the present invention can be used to treat an ocular disorder that includes, but is not limited to, a disorder selected from the group consisting of glaucoma including Open Angle Glaucoma (e.g., Primary Open Angle Glaucoma, Pigmentary Glaucoma, and Exfoliative Glaucoma, Low Tension Glaucoma), Angle Closure Glaucoma (also known clinically as closed angle glaucoma, narrow angle glaucoma, pupillary block glaucoma, and ciliary block glaucoma) (e.g., Acute Angle Closure Glaucoma and Chronic Angle Closure Glaucoma), Aniridic Glaucoma, Congenital Glaucoma, Juvenile Glaucoma, Lens-Induced Glaucoma, Neovascular Glaucoma (e.g., using vectors composed of Vascular Endothelial Growth Factor (VEGF) decoy, Pigment Derived Growth Factor (PDGF), Endostatin, Angiostatin, or Angiopoetin-1), Post-Traumatic Glaucoma, Steroid-Induced Glaucoma, Sturge-Weber Syndrome Glaucoma, and Uveitis-Induced Glaucoma, diabetic retinopathy (e.g., using vectors composed of VEGF decoy, PDGF, Endostatin, Angiostatin, or Angiopoetin-1), macular degeneration (e.g. vectors composed of VEGF decoy, PDGF, Endostatin, Angiostatin, Angiopoetin-1, ATP Binding Casette Subfamily A Member 4), macular degeneration (e.g., using vectors composed of VEGF decoy, PDGF, Endostatin, Angiostatin, Angiopoetin-1, ATP Binding Casette Subfamily A Member 4), choroidal neovascularization, (e.g., using vectors composed of VEGF decoy, PDGF, Endostatin, Angiostatin, or Angiopoetin-1), vascular leak, and/or retinal edema, bacterial conjunctivitis, fungal conjunctivitis, viral conjunctivitis, uveitis, keratic precipitates, macular edema (e.g., using vectors composed of VEGF decoy, PDGF, Endostatin, Angiostatin, or Angiopoetin-1), inflammation response after intra-ocular lens implantation, uveitis syndromes (for example, chronic iridocyclitis or chronic endophthalmitis), retinal vasculitis (for example, as seen in rheumatoid arthritis, juvenile rheumatoid arthritis, systemic lupus erythymatosus, progressive systemic sclerosis, polyarteritis nodosa, Wegener's granulomatosis, temporal arteritis, Adamantiades Bechcet disease, Sjorgen's, relapsing polychondritis and HLA-B27 associated spondylitis), sarcoidosis, Eales disease, acute retinal necrosis, Vogt Koyanaki Harada syndrome, occular toxoplasmosis, radiation retinopathy, proliferative vitreoretinopathy, endophthalmitis, ocular glaucomas (for example, inflammatory glaucomas), optic neuritis, ischemic optic neuropathy (e.g. vectors composed of Allotopic NADH dehydrogenase Unit 4), thyroid associated orbitopathy, orbital pseudotumor, pigment dispersion syndrome (pigmentary glaucoma), scleritis, episcleritis choroidopathies (for example, "White-dot" syndromes including, but not limited to, acute multifocal posterior placoid), retinopathies (for example, cystoid macular edema, central serous choroidopathy and presumed ocular histoplasmosis syndrome (e.g., vectors composed of Glial Cell Derived Neurotropic Factor, Peripherin-2)), retinal vascular disease (for example, diabetic retinopathy, Coat's disease and retinal arterial macroaneurysm), retinal artery occlusions, retinal vein occlusions, retinopathy of prematurity, retinitis pigmentosa (e.g. vectors composed of Retinal Pigment Specific 65 kDa protein), familial exudative vitreoretinopathy (FEVR), idiopathic polypoidal choroidal vasculopathy, epiretinal macular membranes and cataracts.

In another embodiment, the vector and methods of the present invention can be used to treat a blood disorder that includes, but is not limited to, a blood disorder selected from the group consisting of anemia, bleeding and clotting disorders (e.g., disseminated intravascular coagulation (DIC), hemophilia, Henoch-Schonlien Purpura, hereditary hemorrhagic telangiectasia, thrombocytopenia (ITP, TTP), thrombophilia, Von Willebrand's disease), leukemias (e.g., acute lymphocytic leukemia, acute myelocytic leukemia, chronic lymphocytic leukemia, chronic myelocytic leukemia), lymphomas (e.g., Hodgkin lymphoma, non-Hodgkin lymphoma), myeloproliferative disorders (e.g., myelofibrosis, Polycythemia Vera, thrombocythemia), plasma cell disorders (e.g., macroglobulinemia, monoclonal gammopathies of undetermined significance, multiple lyeloma), spleen disorders, white blood cell disorders (e.g., basophilic disorder, eosinophilic disorder, lymphocytopenia, monocyte disorders, neutropenia, neutrophillic leukocytosis), thrombosis, deep vein thrombosis (DVT), hemochromatosis, menorrhagia, sickle cell disease, and thalassemia.

In another embodiment, the vector and methods of the present invention can be used to treat a neurological disorder that includes, but is not limited to, a neurological disorders selected from the group consisting of Gaucher disease, Parkinson's disease, Alzheimer's disease, amyotrophic lateral sclerosis (ALS), multiple sclerosis (MS), Huntington's disease, Fredrich's ataxia, Mild Cognitive Impairment, Cerebral Amyloid Angiopathy, Parkinsonism Disease, Lewy Body Disease, Frontotemporal Dementia (FTD) Multiple System Atrophy (MSA), Progressive Supranuclear Palsy, and movement disorders (including ataxia, cerebral palsy, choreoathetosis, dystonia, Tourette's syndrome, kernicterus) and tremor disorders, and leukodystrophies (including adrenoleukodystrophy, metachromatic leukodystrophy, Canavan disease, Alexander disease, Pelizaeus-Merzbacher disease), neuronal ceroid lipofucsinoses, ataxia telangectasia, Rett Syndrome, alpha.-synucleinopathy (e.g., Lewy Body Disease, Multiple System Atrophy, Hallervorden-Spatz disease, or Frontotemporal Dementia), Niemann-Pick Type C disease (NPCD), spinocerebellar ataxia Type 1, Type 2, and Type 3, and dentatorubral pallidoluysian atrophy (DRLPA).

In another embodiment, the vector and methods of the present invention can be used to treat a lung disorder that includes, but is not limited to, a lung disorder selected from the group consisting of asthma, atelectasis, bronchitis, COPD (chronic obstructive pulmonary disease), emphysema, Lung cancer, mesothelioma, pneumonia, asbestosis, Aspergilloma, Aspergillosis, Aspergillosis—acute invasive, bronchiectasis, bronchiolitis obliterans organizing pneumonia (BOOP), eosinophilic pneumonia, necrotizing pneumonia, ral effusion, pneumoconiosis, pneumothorax, pulmonary actinomycosis, monary alveolar proteinosis, pulmonary anthrax, pulmonary arteriovenous malformation, pulmonary fibrosis, pulmonary embolus, pulmonary histiocytosis X (eosinophilic granuloma), pulmonary hypertension, pulmonary edema, pulmonary hemorrhage, pulmonary nocardiosis, pulmonary tuberculosis, pulmonary veno-occlusive disease, rheumatoid lung disease, sarcoidosis, radiation fibrosis, hypersensitivity pneumonitis, acute respiratory distress syndrome (ARDS), infant respiratory distress syndrome, idiopathic pulmonary fibrosis, idiopathic interstitial pneumonia, lymphangioleiomyomatosis, pulmonary Langerhans' cell histiocytosis, pulmonary alveolar proteinosis, sinusitis, tonsillitis, otitis media, pharyngitis, laryngitis, Pulmonary hamartoma, pulmonary sequestration, congenital cystic adenomatoid malformation (CCAM), and cystic fibrosis.

In another embodiment, the vector and methods of the present invention can be used to treat a rheumatologic disorder that includes, but is not limited to, a rheumatic disorder selected from the group consisting of systemic lupus erythematosus, dermatomyositis, scleroderma, systemic necrotizing arteritis, cutaneous necrotizing venulitis, rheumatoid arthritis, Sjogren's Syndrome, Raynaud's phenomenon, Reiter's syndrome, arthritis, psoriatic arthritis, seronegative spondyloarthropathies, Sjogren's syndrome, systemic sclerosis, dermatomyositis/polymyositis, mixed connective tissue disease, and ankylosing spondylitis.

In another embodiment, the vector and methods of the present invention can be used to treat an infectious disease in a human that includes, but is not limited to, an infectious disease selected from the group consisting of fungal diseases such as dennatophytosis (e.g., trichophytosis, ringworm or tinea infections), athletes foot, paronychia, *pityriasis versicolor*, erythrasma, intertrigo, fungal diaper rash, *candida vulvitis, candida balanitis, otitis externa*, candidiasis (cutaneous and mucocutaneous), chronic mucocandidiasis (e.g. thrush and vaginal candidiasis), cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis, pneumocystosis, and fungemia, *Acinetobacter* infections, Actinomycosis, African sleeping sickness, AIDS (Acquired immune deficiency syndrome), Amebiasis, Anaplasmosis, Anthrax, *Arcanobacterium haemolyticum* infection, Argentine hemorrhagic fever, Ascariasis, Aspergillosis, atrovirus infection, Babesiosis, *Bacillus cereus* infection, Bacterial pneumonia, Bacterial vaginosis (BV), *Bacteroides* infection, Balantidiasis, *Baylisascaris* infection, BK virus infection, Black piedra, *Blastocystis hominis* infection, *Borrelia* infection, Botulism (and Infant botulism), Brazilian hemorrhagic fever, Brucellosis, *Burkholderia* infection, Buruli ulcer, Calcivirus infection (Norovirus and Sapovirus), Candidiasis, Cat-scratch disease, Cellulitis, Chagas Disease (American trypanosomiasis), Chancroid, Chickenpox, *Chlamydia*, Cholera, Chromoblastomycosis, Clonorchiasis, *Clostridium difficile*, Coccidioidomycosis, Colorado tick fever (CTF), Common cold (Acute viral rhinopharyngitis; *Acute coryza*), Creutzfeldt-Jakob disease (CJD), Cryptococcosis, Cryptosporidiosis, ous larva migrans (CLM), Dengue fever, Dientamoebiasis, Diphtheria, Diphyllobothriasis, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, *Erythema infectiosum, Exanthem subitum*, Fasciolopsiasis, Fasciolosis, Fatal familial insomnia (FFI), Filariasis, *Fusobacterium* infection, Gas gangrene (Clostridial myonecrosis), Geotrichosis, Gerstmann-Straiussler-Scheinker syndrome (GSS), Giardiasis Glanders, Gnathostomiasis, Gonorrhea, Granuloma inguinale (Donovanosis), Group A streptococcal infection, Group B streptococcal infection, *Haemophilus influenzae*, Hand, foot and mouth disease (HFMD), Hantavirus Pulmonary Syndrome (HPS) *Helicobacter pylori* infection, ic-uremic syndrome (HUS), Hemorrhagic fever with renal syndrome (HFRS), Hepatitis A, B, C, D, E, Herpes simplex, Histoplasmosis, Hookworm infection, n bocavirus infection, Human ewingii ehrlichiosis, Human granulocytic anaplasmosis (HGA), Human granulocytic anaplasmosis (HGA), Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Melioidosis (Whitmore's disease), Meningitis, Meningococcal disease, Metagonimiasis, Microsporidiosis, *Molluscum contagiosum* (MC), Mumps, Murine typhus (Endemic typhus), *Mycoplasma pneumonia*, Mycetoma, Myiasis, Neonatal conjunctivitis (*Ophthalmia neonatorum*), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis pneumonia* (PCP), Pneumonia, Poliomyelitis, Poliomyelitis, *Prevotella* infection, mary amoebic meningoencephalitis (PAM), Progressive multifocal leukoencephalopathy, Psittacosis, Q fever, Rabies, Rat-bite fever, Respiratory syncytial virus infection, Rhinosporidiosis, inovirus infection, Rickettsial infection, Rickettsialpox, Rift Valley fever (RVF), Rocky mountain spotted fever (RMSF), Rotavirus infection, Rubella, Salmonellosis, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, tanus (Lockjaw), *Tinea barbae* (Barber's itch), *Tinea capitis* (Ringworm of the Scalp), *Tinea corporis* (Ringworm of the Body), *Tinea cruris* (Jock itch), *Tinea manuum* (Ringworm of the Hand), *Tinea nigra, Tinea unguium* (Onychomycosis), *Tinea versicoor* (Pityriasis *versicolor*), Toxocariasis (Visceral Larva Migrans (VLM)), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, viral pneumonia, West Nile Fever, White piedra (Tinea blanca), *Yersinia pseudoluberculosis* infection, Yersiniosis, Yellow fever, and Zygomycosis.

In another embodiment, the vector and methods of the present invention can be used to treat one or more diseases in a mammal. In one aspect, the mammal is a human. In another aspect, the mammal is a non-human animal. One can readily contemplate a variety of diseases that can be treated using the teachings of the present invention. These diseases include, but are not limited to chronic renal disease, osteoarthritis, oncology, viral upper respiratory infection, feline plasma cell stomatitis, feline eosinophillic granulomas, feline leukemia virus infection, canine distemper infection, systemic fungal infections, cardiomyopathy, mucopolysaccharidosis VII, and infectious disease.

In one aspect, disease that is treated is an infectious diseases in an animal, and such infectious disease include, but are not limited to, Bovine respiratory disease, Porcine respiratory disease, Avian influenza, Avian infectious bronchitis, Bovine spongiform encephalopathy, Canine leishmaniasis, Chronic wasting disease, human immune deficiency virus (HIV), hepatitis, hepatitis A, hepatitis B, hepatitis C, Classical swine fever, *Echinococcus*, Enzootic pneumonia, FIP, Foot-and-mouth disease, Jaagsiekte, Maedi-Visna, Mastitis in animals, *Microsporum canis*, Orf (animal disease), Peste des petits ruminants, Pox diseases, Psittacine beak and feather disease, Rabies, Mediterranean fever (Brucellosis) or Bang's disease or undulant fever, Malta fever, contagious abortion, epizootic abortion, Salmonella food poisoning, enteric paratyphosis, Bacillary dysentery, Pseudotuberculosis, plague, pestilential fever, Tuberculosis, Vibrios, Circling disease, Weil's disease (Leptospirosis) or canicola fever, Hemorrhagic jaundice (Leptospira icterohaemorrhagiae), dairy worker fever (*L. hardjo*), Relapsing fever, tick-borne relapsing fever, spirochetal fever, vagabond fever, famine fever, Lyme arthritis, Bannworth's syndrome (lime disease), tick-borne meningopolyneuritis, erythema chronicum migrans, Vibriosis, Colibacteriosis, colitoxemia, white scours, gut edema of swine, enteric paratyphosis, Staphylococcal alimentary toxicosis, staphylococcal gastroenteritis, Canine Corona Virus (CCV) or canine parvovirus enteritis, feline infectious peritonitis virus, transmissible gastroenteritis (TGE) virus, Hagerman Redmouth Disease (ERMD), Infectious Hematopoietic necrosis (IHN), porcine *Actinobacillus* (*Haemophilus*) *pleuropneumonia*, Hansen's disease, Streptotrichosis, Mycotic Dermatitis of Sheep, Pseudoglanders, Whitmore's disease, Francis' disease, deerfly fever, rabbit fever, O'Hara disease, Streptobacillary fever, Haverhill fever, epidemic arthritic erythema, sodoku, Shipping or transport fever, hemorrhagic septicemia, Ornithosis, Parrot Fever, Chlamydiosis, North American blastomycosis, Chicago disease, Gilchrist's disease, Cat Scratch Fever, Benign Lymphoreticulosis, Benign nonbacterial Lymphadenitis, Bacillary Angiomatosis, Bacillary Peliosis Hepatis, Query fever, Balkan influenza, Balkan grippe, abattoir fever, Tick-borne fever, pneumorickettsiosis, American Tick Typhus, Tick-borne Typhus Fever, Vesicular Rickettsiosis, Kew Gardens Spotted Fever, Flea-borne Typhus Fever, Endemic Typhus Fever, Urban Typhus, Ringworm, Dermatophytosis, Tinea, Trichophytosis, Microsporosis, Jock Itch, Athlete's Foot, *Sporothrix schenckii*, dimorphic fungus, Cryptococcosis and histoplasmosis, Benign Epidermal Monkeypox, BEMP, Herpesvirus simiae, Simian B Disease, Venezuelan equine encephalitis, Type C lethargic encephalitis, Yellow fever, Black Vomit, hantavirus pulmonary syndrome, Korean Hemorrhagic Fever, Nephropathia Epidemica, Epidemic Hemorrhagic Fever, Hemorrhagic Nephrosonephritis, lymphocytic choriomeningitis, California encephalitis/La crosse encephalitis, African Hemorrhagic Fever, Green or Vervet Monkey Disease, Hydrophobia, Lyssa, Infectious hepatitis, Epidemic hepatitis, Epidemic jaundice, Rubeola, Morbilli, Swine and Equine Influenza, Fowl Plague, Newcastle disease, Piroplasmosis, toxoplasmosis, African Sleeping Sickness, Gambian Trypanosomiasis, Rhodesian Trypanosomiasis, Chagas's Disease, Chagas-Mazza Disease, South American Trypanosomiasis, *Entamoeba histolytica*, Balantidial dysentery, cryptosporidiosis, giardiasis, Cutaneous leishmaniasis: Chiclero ulcer, espundia, pianbols, uta, and buba (in the Americas); oriental sore, Aleppo boil (in the Old World); Bagdad boil, Delhi boil, Bauru ulcer, Visceral leishmaniasis: kala-azar, Microsporidiosis, Anisakiasis, Trichinosis, Angiostrongylosis, eosinophilic meningitis or meningoencephalitis (*A. cantonensis*), abdominal angiostrongylosis (*A. costaricensis*), Uncinariasis, Necatoriasis, Hookworm Disease, Capillariasis, Brugiasis, Toxocariasis, Oesophagostomiasis, Strongyloidiasis, Trichostrongylosis, Ascaridiasis, Diphyllobothriasis, Sparganosis, Hydatidosis, Hydatid Disease, *Echinococcus granulosis*, Cystic hydatid disease, Tapeworm Infection, Schistosoma and the like.

Treatment of malignant diseases caused by infectious pathogens are contemplated as well. Examples of such diseases include, but are not limited to, osteosarcoma, leukemia, lymphoma, Burkitt lymphoma caused by EBV, Rous sarcoma caused by Rous retrovirus, Kaposi' sarcoma caused by herpes virus type 8, adult T-cell leukemia caused by HTLV-I retrovirus, or hairy cell leukemia caused by HTLV-II, and many other tumors and leukemias caused by infectious agents and viruses.

In one embodiment, the one or more proteins used to treat one or more of the above diseases includes, but is not limited to, erythropoetin, ghrelin, osteoprotegerin, RANKL, RANKL decoy, TNF-α antagonist, an IL-1 antagonist, G-CSF, GM-CSF, IFN-α, IFN-γ, angiostatin, endostatin, TNF-α, PP1DCY-LSRLOC, β-glucuronidase, and IL-12. In another embodiment, the one or more proteins of the invention includes, but is not limited to, IL-1, IL-2, IL-12, IL-3, IL-4, IL-5, IL-7, IL-8, IL-9, IL-10R DN or a subunit thereof, IL-15, IL-18, IL-21, IL-23, IL-24, IL-27, GM-CSF, IFN-alpha, IFN-gamma, IFN-alpha 1, IFN alpha 2, IL-15-R-alpha, CCL3 (MIP-1a), CCL5 (RANTES), CCL7 (MCP3), XCL1 (lymphotactin), CXCL1 (MGSA-alpha), CCR7, CCL19 (MIP-3b), CXCL9 (MIG), CXCL10 (IP-10), CXCL12 (SDF-1), CCL21 (6Ckine), OX40L, 4-1BBL, CD40, CD70, GITRL, LIGHT, b-Defensin, HMGB1, Flt3L, IFN-beta, TNF-alpha, dnFADD, BCG, TGF-alpha, PD-L1 RNAi, a PD-L1 antisense oligonucleotide, TGFbRII DN, ICOS-L, and S100.

In one embodiment, the vector administered to the mammal afflicted with one or more of the disclosed diseases is an adenoviral vector. In one embodiment, the vector comprises a polynucleotide encoding a gene switch. In one aspect, the gene switch is an EcR-based gene switch. In another embodiment, the polynucleotide encoding a gene switch comprises a first transcription factor sequence under the control of a first promoter and a second transcription factor sequence under the control of a second promoter, wherein the proteins encoded by said first transcription factor sequence and said second transcription factor sequence interact to form a protein complex which functions as a ligand-dependent transcription factor. In one aspect, the ligand is a diacylhydrazine. In another aspect, the ligand is selected from RG-115819, RG-115932, and RG-115830. In yet another aspect, the ligand is an amidoketone or an oxadiazoline.

In another embodiment, the present invention can be used to treat one or more lysosomal storage diseases in a mammal. In one aspect, the mammal is a human. In another aspect, the mammal is a non-human animal. Examples of lysosmal storage diseases that can be treated according to the invention include, but are not limited to, Pompe disease/Glycogen storage disease type II, Gaucher Disease (Type I, Type II, Type III), Fabry disease, Mucopolysaccharidosis II (Hunter syndrome), Mucopolysaccharidosis VI (Maroteaux-Lamy syndrome), Mucopolysaccharidosis I, Metachromatic Leukodystrophy, Neuronal Ceroid Lipofuscinoses or CLN6 disease (Atypical Late Infantile, Late Onset variant, Early Juvenile, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis), Batten-Spielmeyer-Vogt/Juvenile NCL/CLN3 disease, Sanfilippo syndrome Type A, Sanfilippo syndrome Type B, Sanfilippo syndrome Type C, Sanfilippo syndrome Type D, MPSI Hurler Syndrome, Niemann-Pick Disease (Type A, Type B, Type C, Type D), Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Farber disease, Fucosidosis, Galactosialidosis (Goldberg Syndrome), GM1 gangliosidosis (Infantile, Late infantile/Juvenile, Adult/Chronic), I-Cell disease/Mucolipidosis II, Infantile Free Sialic Acid Storage Disease/ISSD, Juvenile Hexosaminidase A Deficiency, Krabbe disease (Infantile Onset, Late Onset), Mucopolysaccharidoses disorders (Pseudo-Hurler polydystrophy/Mucolipidosis IIIA, Scheie Syndrome, MPS I Hurler-Scheie Syndrome, Morquio Type A/MPS IVA, Morquio Type B/MPS IVB, MPS IX Hyaluronidase Deficiency, Sly Syndrome (MPS VII), Mucolipidosis I/Sialidosis, Mucolipidosis IIIC, Mucolipidosis type IV), Multiple sulfatase deficiency, Pycnodysostosis, Sandhoff disease/Adult Onset/GM2 gangliosidosis, Sandhoff disease/GM2 gangliosidosis—Infantile, Sandhoff disease/GM2 gangliosidosis—Juvenile, Schindler disease, Salla disease, Infantile Sialic Acid Storage Disease, Tay-Sachs/GM2 gangliosidosis, Wolman disease, Asparylglucosaminuria, and prosaposin.

It will be appreciated that Sanfilippo syndrome Type A is synonymous with Sanfilippo syndrome Type A/MPS IIIA, Sanfilippo syndrome Type B is synonymous with Sanfilippo syndrome Type B/MPS IIIB, Sanfilippo syndrome Type C is synonymous with Sanfilippo syndrome Type C/MPS IIIC, Sanfilippo syndrome Type D is synonymous with Sanfilippo syndrome Type D/MPS IIID.

In one embodiment, the one or more proteins expressed by the vector of the invention used to treat one or more of the above lysosomal storage diseases includes, but is not limited to, a-galactosidase A, Arylsulfatase A, a-glucosidase, b-glucosidase, glucocerebrosidase, CLN6 protein, Juvenile associated with CLN3, N-sulfoglucosamine sulfohyrolase (SGSH), a-N-acetylglucosaminidase, acetyl-CoA-glucosaminide acetyltransferase, N-acetylglucosamine-6-sulfatase, a-L-iduronidase, arylsulfatase B, acid sphingomyelinase, and iuduronate sulfatase.

In one embodiment, the vector administered to the mammal afflicted with one or more of the disclosed lysosomal storage diseases is an adenoviral vector. In one embodiment, the vector comprises a polynucleotide encoding a gene switch. In one aspect, the gene switch is an EcR-based gene switch. In another embodiment, the polynucleotide encoding a gene switch comprises a first transcription factor sequence under the control of a first promoter and a second transcription factor sequence under the control of a second promoter, wherein the proteins encoded by said first transcription factor sequence and said second transcription factor sequence interact to form a protein complex which functions as a ligand-dependent transcription factor. In one aspect, the ligand is a diacylhydrazine. In another aspect, the ligand is selected from RG-115819, RG-115932, and RG-115830. In yet another aspect, the ligand is an amidoketone or an oxadiazoline.

In another embodiment, the present invention can be used to treat one or more liver disease in a mammal. In one aspect, the mammal is a human. In another aspect, the mammal is a non-human animal. In one aspect, the liver disease is Hepatitis B. In another aspect, the liver disease is Hepatitis C. In one embodiment, the protein expressed by a vector of the invention is IFN-$\alpha$. In another embodiment, the protein expressed by a vector of the invention is one or more of the liver diseases comprises ceruloplasmin.

A non-limiting example of a human liver chimeric mouse model for hepatitis B and C virus infection and treatment is disclosed in Bissig, K. D. et al., *J. Clin. Investigation* 120: 924 (2010). Another non-limiting example of a human hepatocyte model is the humanized mouse system marketed by Yecuris™ (Portland, Oreg.).

A non-limiting example of an encephalitis model useful for evaluating antiviral/antiinfective treatment is disclosed in O'Brien, L. et al., *J. General Virology* 90: 874-882 (2009).

Non-limiting examples influenza models useful for evaluating antiviral/antiinfective treatment is disclosed in Beilharz, M. W. et al., *Biochemical Biophysical Research Communications* 355: 740-744 (2007); and Koerner, I. et al., *J. Virology* 81: 2025-2030 (2007).

In one embodiment, the vector administered to the mammal afflicted with one or more of the disclosed liver diseases is an adenoviral vector. In another embodiment, the vector is not an adenoviral vector. In another embodiment, the vector is a plasmid. In one embodiment, the vector comprises a polynucleotide encoding a gene switch. In one aspect, the gene switch is an EcR-based gene switch. In another embodiment, the polynucleotide encoding a gene switch comprises a first transcription factor sequence under the control of a first promoter and a second transcription factor sequence under the control of a second promoter, wherein the proteins encoded by said first transcription factor sequence and said second transcription factor sequence interact to form a protein complex which functions as a ligand-dependent transcription factor. In one aspect, the ligand is a diacylhydrazine. In another aspect, the ligand is selected from RG-115819, RG-115932, and RG-115830. In yet another aspect, the ligand is an amidoketone or an oxadiazoline.

The invention provides engineering of cells, e.g., immune cells and TSC, to conditionally express a protein having the function of an immunomodulator and, optionally, IL-12 and therapeutic uses and/or applications for the treatment of cancer or tumors or both. In vitro engineered immune cells and TSC that conditionally express a protein having the function of an immunomodulator and optionally IL-12 are a safe improvement over constitutive production of the protein(s). Additionally, the ability to control the timing and level of immunomodulator and optionally IL-12 expression provides improved control of the efficacy of the treatment. Therefore, in vitro engineered immune cells and TSC may be formulated into pharmaceutical compositions as therapeutics for the treatment of a cancer or a tumor in a human or a non-human organism. Alternatively, in vitro engineered populations of immune cells, TSC or subsets thereof may be used as vehicles to conditionally deliver an immunomodulator and optionally IL-12 protein production to a specific area (normal tissue, cancer, or tumor) in the body of a human or non-human organism. The immune cells may be autologous or non-autologous dendritic cells. The dendritic cells may be isolated from bone marrow or from peripheral blood circulation. In human patients, dendritic cell populations may be isolated via a leukophoresis procedure, where a white blood cell fraction is isolated and removed and other blood components are re-infused to the patient.

In another embodiment, the dendritic cells may be prepared by transfecting human hematopoietic stem cells with a vector of the invention expressing a protein having the function of an immunomodulator and optionally a protein having the function of IL-12, and differentiating the transfected stem cell to give a dendritic cell. See U.S. Pat. No. 6,734,014.

In one embodiment, a nucleic acid adenoviral vector is provided containing a gene switch, wherein the coding sequences for VP16-RXR and Gal4-EcR are separated by the EMCV internal ribosome entry site (IRES) sequence are inserted into the adenoviral shuttle vector under the control of the human ubiquitin C promoter. For example, the coding sequences for the p40 and p35 subunits of IL12 separated by an IRES sequence, and placed under the control of a synthetic inducible promoter, are inserted upstream of the ubiquitin C promoter. In another example, the coding sequence of TNF-alpha, which is placed under the control of a synthetic inducible promoter, is inserted upstream of the ubiquitin C promoter.

In another embodiment, the invention provides a shuttle vector carrying transcription units (VP16-RXR and Gal4-EcR) for the two fusion proteins and inducible IL-12 or TNF-alpha subunits recombined with the adenoviral backbone (AdEasyl) in *E. coli* BJ5183 cells. After verifying the recombinant clone, the plasmid carrying the rAd.RheoIL12 genome is grown in and purified from XL10-Gold cells, digested off the plasmid backbone and packaged by transfection into HEK 293 cells or CHO cells.

Purification of the vector to enhance the concentration can be accomplished by any suitable method, such as by density gradient purification (e.g., cesium chloride (CsCl)) or by chromatography techniques (e.g., column or batch chromatography). For example, the vector of the invention can be subjected to two or three CsCl density gradient purification steps. The vector, e.g., a replication-deficient adenoviral vector, is desirably purified from cells infected with the replication-deficient adenoviral vector using a method that comprises lysing cells infected with adenovirus, applying the lysate to a chromatography resin, eluting the adenovirus from the chromatography resin, and collecting a fraction containing adenovirus.

In a particular embodiment, the resulting primary viral stock is amplified by re-infection of HEK 293 cells or CHO cells and is purified by CsCl density-gradient centrifugation.

In one embodiment the immunomodulator, e.g., TNF-alpha, and/or IL-12 gene is a wild-type gene sequence. In another embodiment, the immunomodulator, e.g., TNF-alpha, and/or IL-12 gene is a modified gene sequence, e.g., a chimeric sequence or a sequence that has been modified to use preferred codons.

In one embodiment, the immunomodulator, e.g., TNF-alpha, and/or IL-12 gene is the human wild type sequence. In another embodiment, the sequence is at least 85% identical to wild type human sequence, e.g., at least 90%, 95%, or 99% identical to wild type human sequence. In a further embodiment, the gene sequence encodes the human polypeptide. In another embodiment, the gene encodes a polypeptide that is at least 85% identical to wild type human polypeptide e.g., at least 90%, 95%, or 99% identical to wild type human polypeptide.

In one embodiment, the IL-12 gene is the wild type mouse IL-12 sequence. In another embodiment, the sequence is at least 85% identical to wild type mouse IL-12, e.g., at least 90%, 95%, or 99% identical to wild type mouse IL-12. In a further embodiment, the IL-12 gene sequence encodes the mouse IL-12 polypeptide. In another embodiment, the gene encodes a polypeptide that is at least 85% identical to wild type mouse IL-12, e.g., at least 90%, 95%, or 99% identical to wild type mouse IL-12.

DC may be isolated from bone marrow from humans, mice, or other mammals. The dendritic cells may be isolated from the blood of humans, mice or other mammals. In human patients, dendritic cell populations may be isolated via a leukophoresis procedure as is known in the art, where a white blood cell fraction is isolated and removed and other blood components are re-infused to the patient. In one embodiment, DC are derived from murine bone marrow as previously described (Tatsumi et al., 2003). Briefly, wild-type or EGFP Tg mouse bone marrow (BM) is cultured in conditioned medium (CM) supplemented with 1000 units/ml recombinant murine granulocyte/macrophage colony-stimulating factor and recombinant mIL-4 (Peprotech, Rocky Hill, N.J.) at 37° C. in a humidified, 5% $CO_2$ incubator for 7 days. $CD11c^+$ DC are then isolated, e.g., using specific MACS™ beads, per the manufacturer's instructions (Miltenyi Biotec, Auburn, Calif.). $CD11c^+$ DC produced in this manner are >95% pure based on morphology and co-expression of the CD11b, CD40, CD80, and class I and class II MHC antigens.

One embodiment of the invention provides engineered immune cells and TSC conditionally expressing a protein having the function of an immunomodulator and optionally IL-12 suitable for therapeutic applications for the treatment of cancer, or tumors or both as gene therapy in human or non-human organism. In an embodiment, the invention provides engineered immune cells and TSC containing the gene switch.

In another embodiment, the invention provides engineered immune cells and TSC containing at least a portion of an ecdysone receptor. In another embodiment, the invention provides engineered immune cells and TSC containing an ecdysone receptor-based gene switch. In another embodiment, the invention provides engineered immune cells and TSC containing RheoSwitch. In another embodiment, the invention provides a kit comprising engineered immune cells and TSC containing a gene switch and a ligand that modulates the gene switch. In another embodiment, the kits further comprise a diacylhydrazine ligand. In another embodiment, the kit further comprises RG-115830 or RG-115932.

In one embodiment, the invention provides an engineered population of immune cells and TSC. In one embodiment, day 7 cultured DC are treated with recombinant adenovirus encoding an immunomodulator and/or IL-12 driven off a constitutive or inducible promoter, or are infected with mock, control adenovirus vector (rAdψ5), over a range of multiplicity of infection (MOIs). After 48 h, infected DC are harvested and analyzed for phenotype and for production of an immunomodulator and/or IL-12 using a specific ELISA kit (BD-PharMingen, San Diego, Calif.), with a lower level of detection of 62.5 pg/ml.

In another embodiment, the invention provides in vitro engineered population of immune cells and TSC comprising a vector, e.g., a DNA vector, having a gene switch capable of conditionally expressing a protein having the function of an immunomodulator and/or IL-12, and further comprising activating ligand. In a further embodiment, the invention provides a method of treating cancer, e.g., melanoma or glioma, by administering engineered DC to a patient and then administering an activating ligand, such as RG-115819, RG-115830 or RG-115932, to said patient. In certain embodiments, the invention is directed to a method of treating cancer, e.g., melanoma or prostate cancer, comprising administering an adenovirus comprising a polynucleotide conditionally expressing an immunomodulator, e.g., TNF-alpha, and administering an activating ligand. The patient may be a human or an animal with cancer. The treatment methods and products, engineered cells, kits, and ligands have application in human therapy and in veterinary animal therapy. Therefore, the products and methods are contemplated to be used for human and veterinary animal purposes.

Thus, in one embodiment, the polynucleotide expressing the immunomodulator, e.g., TNF-alpha, and activating ligand are co-administered to a patient having a cancer. The activating ligand is generally administered over a number of days, e.g., before and after administration of the polynucleotide. If systemic toxicity due to the immunomodulator, e.g., TNF-alpha, develops, then administration of the activating ligand can be reduced or eliminated in an effort to attenuated the side effects.

In another embodiment, the polynucleotide expressing the immunomodulator, e.g., TNF-alpha, and activating ligand are co-administered to a patient suffering from one one or more lysosomal storage diseases, or one or more liver diseases. The activating ligand is generally administered over a number of days, e.g., before and after administration of the polynucleotide. If systemic toxicity develops, then administration of the activating ligand can be reduced or eliminated in an effort to attenuated the side effects.

In certain embodiments, the invention provides a method of reducing a tumor size comprising administering an adenoviral vector, which comprises a polynucleotide conditionally expressing an immunomodulator, e.g., TNF-alpha, and administering an activating ligand. Also provided is a method of preventing a tumor formation comprising administering an adenoviral vector, which comprises a polynucleotide conditionally expressing an immunomodulator, e.g., TNF-alpha, and administering an activating ligand. In some embodiments, the invention provides a method of reducing or ameliorating one or more symptom of a neoplastic disorder comprising administering an adenoviral vector, which comprises a polynucleotide conditionally expressing an immunomodulator, e.g., TNF-alpha, and administering an activating ligand. In particular, the composition comprising the vector, e.g., adenoviral vector, conditionally expressing an immunomodulator can reduce, prevent, or ameliorate systemic toxicity in the treated subject compared to a vector that constitutively expresses the immunomodulator.

In certain embodiments, the invention provides a method of treating one or more disease or one or more lysosomal storage disease, or one or more liver disease in mammals comprising administering an adenoviral vector, which comprises a polynucleotide conditionally expressing one or more proteins and administering an activating ligand. In some embodiments, the invention provides a method of reducing or ameliorating one or more symptom of one or more disease or one or more lysosomal storage disease, or one or more liver disease in mammals comprising administering an adenoviral vector, which comprises a polynucleotide conditionally expressing an immunomodulator, e.g., TNF-alpha, and administering an activating ligand.

Protein-based tags reduce or eliminate the need for highly specific post-translational modifications for effective targeting. Useful protein-based tags include, but are not limited to, IGF2R targeting (IGF2 (GILT)/IGF2 engineering), transferrin receptor targeting (transferrin, TfR-targeting peptides), and Tat protein (in which cell surface heparin sulfate proteoglycans (HSPGs) mediate internalization of Tat).

Other proteins that target to the lysosome than can be used as a tag include, but are not limited to, Vitamin D binding protein, folate binding protein, lactotransferrin, sex hormone binding globulin, transthyretin, pro saposin, retinol binding protein, Apo lipoprotein B, Apo lipoprotein E, prolactin, receptor associated protein (in one embodiment, without the HNEL sequence), native transferrin, and mutant transferring (e.g., the K225E/R651A mutant or the K225E/K553A mutant).

In one embodiment, the expression construct also encodes one or more of a reporter sequence, a localization tag sequence, and a detection tag sequence. It will further be appreciated that the composition of the invention or the methods of using the composition can be combined with any chemotherapeutic agent or agents (e.g., to provide a combined therapeutic regimen) that eliminates, reduces, inhibits or controls the growth of neoplastic cells or tumors in vivo. As used herein the terms “chemotherapeutic agent” or “chemotherapeutics” shall be held to mean any therapeutic compound that is administered to treat or prevent the growth of tumors in vivo. In particular, chemotherapeutic agents compatible with the invention comprise both “traditional” chemotherapeutic agents such as small molecules and more recently developed biologics such as antibodies, cytokines, antisense molecules, etc. that are used to reduce or retard the growth of malignant cells.

In one aspect, the invention provides a pharmaceutical composition suitable for administration to a human or a non-human comprising a population of in vitro engineered immune cells or TSC or a vector, e.g., an adenoviral vector, expressing a protein having the function of an immunomodulator, e.g., TNF-alpha, and/or IL-12, wherein the formulation is suitable for administration by intratumoral administration. In another embodiment, a composition, e.g., pharmaceutical composition, comprises a vector conditionally expressing an immunomodulator, e.g., TNF-alpha. In some embodiments, the composition comprises about $1\times10^5$ or more particle units (pu) of the gene transfer vector. A "particle unit" is a single vector particle. In certain embodiments, the composition comprises about $1\times10^6$ particle units of the gene transfer vector (e.g., about $1\times10^7$ or more particle units, about $1\times10^8$ or more particle units, or about $1\times10^9$ or more particle units). In other embodiments, the composition comprises about $1\times10^{10}$ or more pu, $1\times10^{11}$ or more pu, $1\times10^{12}$ or more pu, $1\times10^{13}$ or more pu, $1\times10^{14}$ or more pu, or $1\times10^{15}$ or more pu of the gene transfer vector, especially of a viral vector, such as a replication-deficient adenoviral vector. The number of particle units of the gene transfer vector in the composition can be determined using any suitable method known, such as by comparing the absorbance of the composition with the absorbance of a standard solution of gene transfer vector (i.e., a solution of known gene transfer vector concentration) as described further herein.

The invention further provides a pharmaceutical composition comprising an activating ligand, such as RG-115819, RG-115830 or RG-115932, wherein the composition is suitable for administration by intraperitoneal, oral, or subcutaneous administration.

A composition of the invention, e.g., a composition comprising an engineered DC, a vector (e.g., an adenoviral vector), or an activating ligand, can further comprise a pharmaceutically acceptable carrier. The carrier can be any suitable carrier for the an engineered dendritic cells, gene transfer vector, or activating ligand. Suitable carriers for the composition are described in U.S. Pat. No. 6,225,289. The carrier typically will be liquid, but also can be solid, or a combination of liquid and solid components. The carrier desirably is a pharmaceutically acceptable (e.g., a physiologically or pharmacologically acceptable) carrier (e.g., excipient or diluent). Pharmaceutically acceptable carriers are well known and are readily available. The choice of carrier will be determined, at least in part, by the particular components in the composition and the particular method used to administer the composition. The composition can further comprise any other suitable components, especially for enhancing the stability of the composition and/or its end-use. Accordingly, there is a wide variety of suitable formulations of the composition of the invention.

Formulations suitable for oral administration include (a) liquid solutions, such as an effective amount of the active ingredient dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base (such as gelatin and glycerin, or sucrose and acacia), and emulsions, gels, and the like containing, in addition to the active ingredient, such excipients as are known in the art.

For example, the composition comprising the vector, the population of the immune cells or TSCs, or the in vitro engineered cells can comprise a buffering agent, e.g., TRIS. In one embodiment, the composition can comprise TRIS and/or glycerin. In another embodiment, the composition also comprises acidifiers, anionic or nonionic surfactants, compatibility agents, and/or diluents.

Formulations suitable for administration via inhalation include aerosol formulations. The aerosol formulations can be placed into pressurized acceptable propellants, such as dichlorodifluoromethane, propane, nitrogen, and the like. They also can be formulated as non-pressurized preparations, for delivery from a nebulizer or an atomizer.

Formulations suitable for parenteral administration include aqueous and nonaqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described.

Formulations suitable for anal administration can be prepared as suppositories by mixing the active ingredient with a variety of bases such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

In addition, the composition can comprise additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the gene transfer vector and physiological distress. Immune system suppressors can be administered with the composition method to reduce any immune response to the gene transfer vector itself or associated with a disorder. Alternatively, immune enhancers can be included in the composition to upregulate the body's natural defenses against disease. Moreover, cytokines can be administered with the composition to attract immune effector cells to the tumor site.

In the particular embodiment described herein, the invention provides a method for treating a tumor, comprising the steps in order of:

a. administering intratumorally in a mammal a population of an in vitro engineered immune cells or TSC; and
b. administering to said mammal a therapeutically effective amount of an activating ligand.

In one embodiment, the activating ligand is administered at substantially the same time as the composition comprising the in vitro engineered immune cells or TSC or the vector, e.g., adenoviral vector, e.g., within one hour before or after administration of the cells or the vector compositions. In another embodiment, the activating ligand is administered at or less than about 24 hours after administration of the in vitro engineered immune cells or TSC or the vector. In still another embodiment, the activating ligand is administered at or less than about 48 hours after the in vitro engineered immune cells or TSC or the vector. In another embodiment, the ligand is RG-115932. In another embodiment, the ligand is administered at a dose of about 1 to 50 mg/kg/day. In another embodiment, the ligand is administered at a dose of about 30 mg/kg/day. In another embodiment, the ligand is administered daily for a period of 7 to 28 days. In another embodiment, the ligand is administered daily for a period of 14 days. In another embodiment, about $1\times10^6$ to $1\times10^8$ cells are administered. In another embodiment, about $1\times10^7$ cells are administered.

In one embodiment, dendritic cells are engineered to conditionally express IL-2 and IL-12. IL-2 exerts potent immunoregulatory effects on effector and regulatory T, NK and NK-T cells. It is expected that expressing IL-2 and IL-12 in cells will result in reciprocal upregulation of each others receptor and induce different by complementary biological effects by virtue of separate signaling pathways. It is also expected that the combination of IL-2 and IL-12 will lengthen the duration of immune stimulation and reduce the effective dose of cells that may be more tolerated by the animal. See Dietrich 2002, Wigginton 2002, 2001, 1996 and Koyama, 1997, McDermott and Atkins 2008; Berntsen et al 2008; Tarhini et al 2008; Heemskerk et al 2008; Horton et al 2008. The polynucleotide sequences of IL-2 are available under accession numbers U25676 (human); NM_008366 (mouse); NM_204153 (chicken); and NM_053836 (rat). The polynucleotide sequences of IL-12 are available under accession numbers NM_000882 (human IL12A); NM_002187 (human IL12B); NM_008351 (mouse IL12a); NM_008352 (mouse IL12b); NM_213588 (chicken IL12A); NM_213571 (chicken IL12B); NM_053390 (rat IL12a); and NM_022611 (rat IL12b). SEQ ID NOS: 13, 15, 21 and 23 code for human and mouse IL-12 and subunits thereof.

In another embodiment, dendritic cells are engineered to conditionally express IL18 and IL-12. IL-18 induces IFN-gamma production and promotes T helper cell development and NK activation. In addition, IL-18 can augment GM-CSF production and decrease IL-10 production. It is expected that expressing IL-18 and IL-12 will overcome the limitations observed when either cytokine is administered alone. It is expected that expression of IL-12 and IL-18 in dendritic cells will stimulate more vigorous tumor antigen-specific Th1 responses than when dendritic cells are transduced with either cytokine alone.

The intratumoral injection of DCs engineered to secrete both IL-12 and IL-18 mediated the highest levels of INF-γ production and complete tumor rejection (Tatsumi 2003). See, Vujanovic, 2006. See also Coughlin, 1998, Subleski, 206, Tatsumi, 2003, and Sabel, 2007; Shiratori et al 2007; Lian et al 2007; Iinuma et al 2006. See above for IL-12 polynucleotide sequences. The polynucleotide sequences of IL-18 are available under accession numbers U90434 (human); NM_008360 (mouse); EU747333 (chicken); and AY258448 (rat).

In another embodiment, dendritic cells are engineered to conditionally express IL15 and IL-12. IL-15 shares some biologic activities with IL-2 that also makes it potentially useful for therapies against cancer. IL-15 stimulates the proliferation of NK cells and activated T cells, and supports the expansion of effector T cells. It has been reported that IL-15 presentation synergized with IL-12 for enhanced IFN-gamma production by NK cells. Koka, 2004; Basak 2008; Lasek et al 2004. Intratumoral delivery of IL-15 and IL-12 induced significant tumor regression in a melanoma model (Lasek 1999). See above for the IL-12 polynucleotide sequences. SEQ ID NOS: 11 and 19 code for the human and mouse IL-15. FIGS. 2 and 4 are plasmid maps for expression systems which may be used for the human and mouse IL-12 and IL-15.

Figure 7:
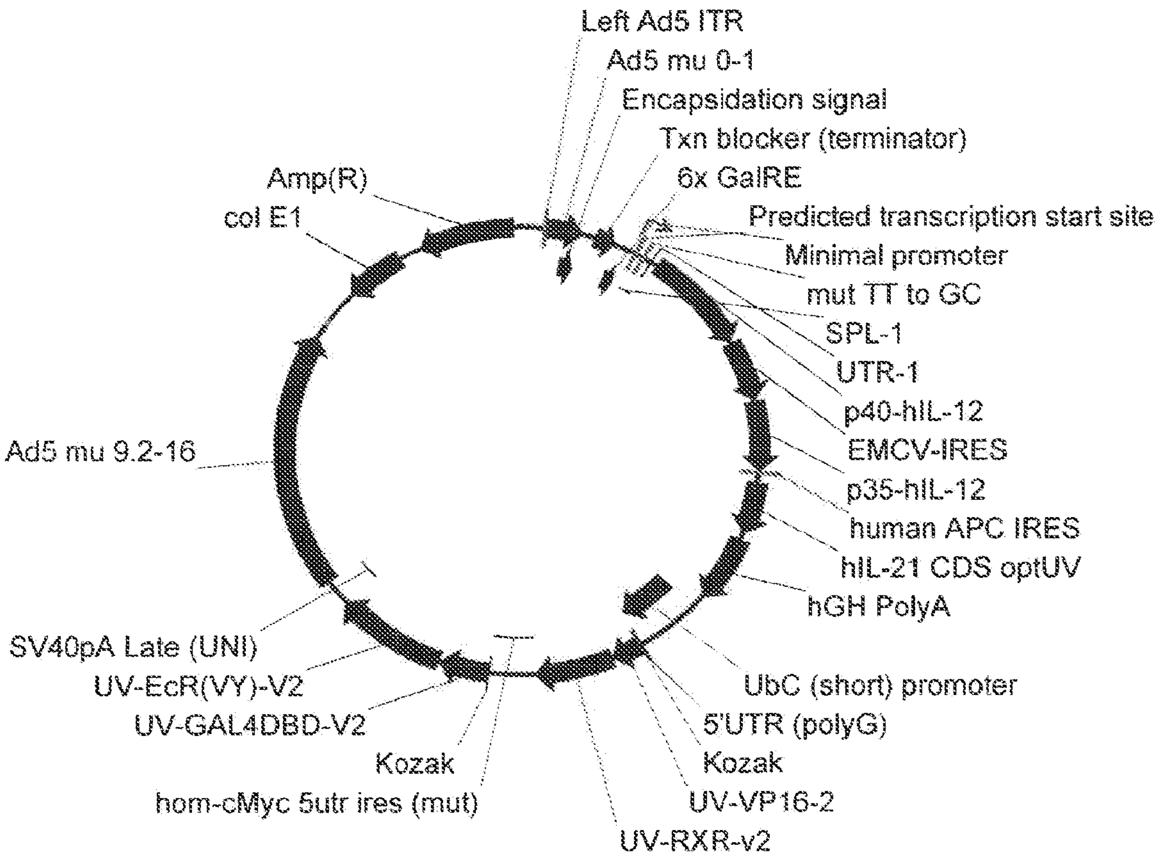
FIG. 7 shows a plasmid map for a regulated promoter expression system for a tricistronic transcript encoding hIL-12 and hIL-21.
Figure 8:
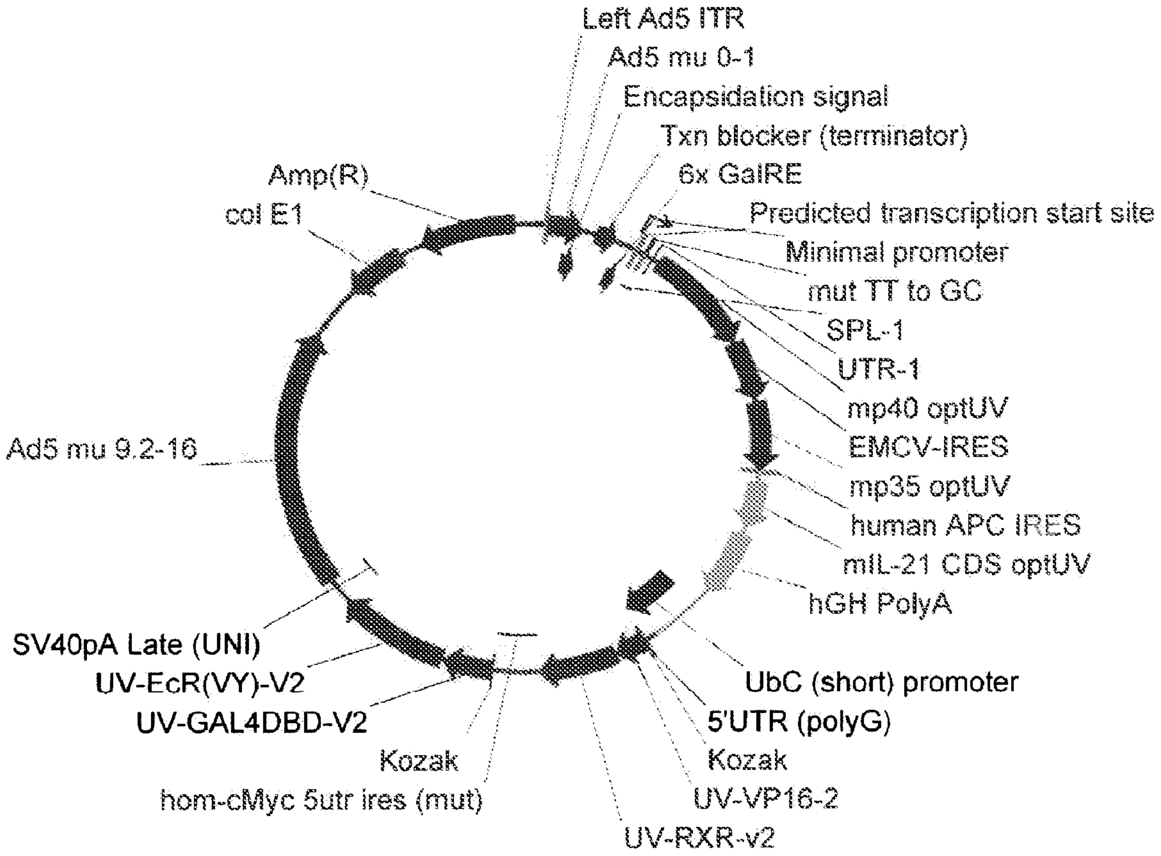
FIG. 8 shows a plasmid map for a regulated promoter expression system for a tricistronic transcript encoding mIL-12 and mIL-21.
Figure 9:
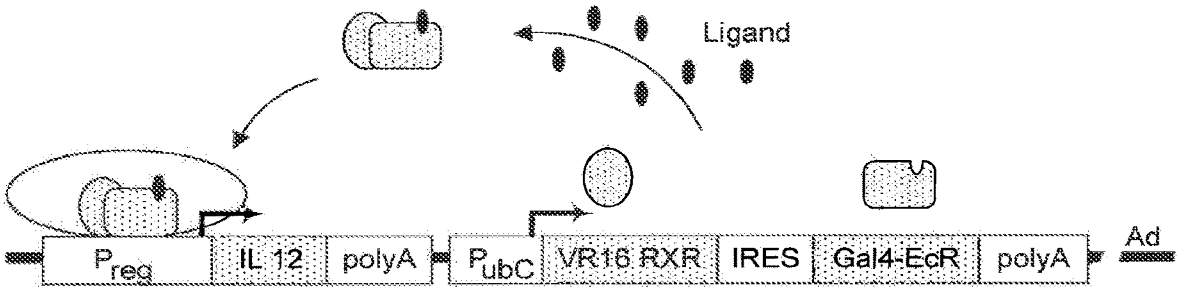
FIG. 9 shows the structure of the vector rAd.RheoIL12 in which the E1 and E3 regions have been deleted and the RheoSwitch® Therapeutic System (RTS)-IL-12 components replace the E1 region. The box labeled "IL12" represents the IL-12p40 and IL-12p35 coding sequences separated by IRES.

In another embodiment, dendritic cells are engineered to conditionally express IL21 and IL-12. IL-21 and its receptor shares sequence homology with IL-2 and IL-15. IL21 promotes the expansion and maturation of NK cells. The biologic effects of IL-21 potentially synergize with IL-12 as treatment of NK cells with IL-21 results in a significant upregulation of IL-12 receptor. In addition, IL-21 can enhance IL-12 signal transduction and cooperated for increased IFN-gamma production. See above for IL-12 polynucleotide sequences. The polynucleotide sequences of IL-21, are available under accession numbers AF254069 (human); NM_021782 (mouse); NM_001024835 (chicken); and NM_001108943 (rat). SEQ ID NOS: 6, 7, 8, 9, and 17 code for human and mouse IL-21. SEQ ID NOS: 1 and 2 are polynucleotide constructs that code for mouse and human IL-12 and IL-21. FIGS. 7 and 8 are plasmid maps for expression systems which may be used to express human and mouse IL-12 and IL-21, respectively.

In another embodiment, dendritic cells are engineered to conditionally express TNF-alpha and IL-12. TNF-alpha is a potent activator of immune cells and mediates antitumor properties. In addition, TNF-alpha can synergize with IL-12 for enhanced expression of IFN-gamma and IL-12 receptor on T cells. In an animal study, application of both IL-12 and TNF-alpha resulted in tumor infiltration by DN8+ T cells, significant IFN-gamma production, and subsequent tumor regression. See Sabel, 2003, 2004, 2007, Taniguchi, 1998, Lasek, 2000; and Xia et al 2008. See above for IL-12 polynucleotide sequences. The polynucleotide sequences coding for TNF-alpha are available from under accession numbers X02910 (human); NM_013693 (mouse); and BC107671 (rat).

In another embodiment, dendritic cells are engineered to conditionally express IL7 and IL-12. IL-7 is a member of the IL-2 family and is important for T cell and B cell lymphophoiesis. IL-7 regulates the homeostasis of survival and proliferation of naïve and memory CD8+ T cells. IL-7 has been proved to enhance CTL generation against tumors. In addition, IL-12 acts directed on CD8+ T cells to enhance IL-7 mediated proliferation. Further, it has been reported that IL-7 and IL-12 synergistically enhance CD8+ T cell cytotoxicity. Mehrotra, 1995; Sharma et al 2003; Tirapu et al 2002. Thus, it is expected that IL-7 and IL-12 coexpression will provide more optimal antitumor responses. See above for polynucleotide sequences coding for IL-12. The polynucleotide sequences coding for IL-7 are available under accession numbers J04156 (human); NM_008371 (mouse); NM_001037833 (chicken); and NM_013110 (rat).

In another embodiment, dendritic cells are engineered to conditionally express GM-CSF and IL-12. GM-CSF regulates hematopoietic progenitor cell differentiation and proliferation, and plays a particularly important role in the maturation of professional antigen presenting cells (APC) such as dendritic cells. GM-CSF also enhances the capacity of dendritic cells to process and present antigens. GM-CSF functions differently than IL-12 and both elicit significant antitumor responses in animal studies. The combination of IL-12 (T cell activation) and GM-CSF (dendritic cell activation) is expected to result in more potent antitumor immunity. In animal studies, GM-CSF in combination with IL-12 treatment significantly suppressed tumor growth in multiple cancer models. Wang, 2001; Chang, 2007; Jean, 2004; Nair, 2006; Hill 2002; Small et al 2007. In human trials, GM-CSF+IL-12 were used successfully for treating myeloma patients, where the combined actions of both cytokines led to a reduction in circulating B cells. Rasmussen, 2003; Hansson, 2007; Abdalla, 2007. It is expected that coexpression of GM-CSF and IL-12 in a single cell will avoid unwanted systemic effects such as reductions in circulating B cells. See above for polynucleotide sequences coding for IL12. The polynucleotide sequences of GM-CSF are available under accession numbers M11734 (human); NM_009969 (mouse); EU520303 (chicken); NM_001037660 (rat Csf2ra); and NM_133555 (rat Csf2rb).

In another embodiment, dendritic cells are engineered to conditionally express a chemokine (e.g., CCL3 (MIP-1a), CCL5 (RANTES), CCL7 (MCP3), XCL1 (lymphotactin), CCL19 (MIP-3b), CXCL9 (MIG), CXCL10 (IP-10), CXCL12 (SDF-1), or CCL21 (6Ckine)) and IL-12. Chemokines are chemoattractant cytokines that regulate the trafficking and activation of leukocytes and other cell types under a variety of inflammatory and noninflammatory conditions. Inflammatory cytokines control the recruitment of leukocytes in inflammation and tissue injury. Homeostatic chemokines fulfill housekeeping functions such as navigating leukocytes (e.g., dendritic cells) to and within secondary lymphoid organs as well as in bone marrow and the thymus during hematopoiesis. In animal studies, intratumoral co-injection of two separate adenoviruses expressing IL-12 and CXCL10 led to 100% regression of tumor nodules derived from the CT26 murine colorectal adenocarcinoma cell line. Narvaiza et al., 2000. Emtage et al., 1999, describe two double recombinant adenovirus vectors expressing either IL2 and XCL1 (lymphotactin) or IL-12 and XCL1. Intratumoral injection of the vectors breast adenocarcinoma tumors in mice elicited potent antitumor responses and gave rise to protective immunity. In other animal studies, co transduction of adenoviral vectors expressing IL-12 and CCL27 resulted in tumor regression and long term specific immunity. Gao et al., 2007. Thus, it is expected that the coexpression of a chemokine and IL-12 according to the invention will result in synergistic antitumor activity.

In another embodiment, dendritic cells are engineered to conditionally express an antiangiogenic cytokine (e.g., IP-10 and Mig) and IL-12. IP-10 and Mig are chemoattractants for T cells and NK cells and their ability to inhibit angiogenesis is dependent on NK cells. Animal studies have shown that combination therapy with two adenoviruses, one expressing IP10 and another expressing IL-12, resulted in marked antitumoral synergy. Narvaiza et al., 2000. In other studies, adenovirus vectors expressing IP10 or MIG and/or IL-12 were administered intratumorally in a murine model of mammary adenocarcinoma and fibrosarcoma. It was found that administration of IP-10 or MIG in combination with IL-12 resulted in considerable tumor regression and increased survival time of tumor-bearing animals as compared to IP 10, MIG, IL-12 alone or control treated animals, with the IP-10, IL12 combination being most effective. Palmer, 2001. See also Mazzolini, 2003; and Huang 2004. Thus, it is expected that the coexpression of an antiangiogenic cytokine and IL-12 will result in synergistic antitumor activity.

To demonstrate an effective IL-12-mediated gene therapy, a conditional cDNA expression system is used that allows one to turn on an immunomodulator and/or IL-12 production by immune cells or TSC at various time points post-intratumoral injection. Based on the results in the aggressive B16 melanoma model in C57BL/6 mice, the following conclusions are made: 1) elevated levels of IL-12 are secreted from DC.RheoIL12 in the presence of the activating ligand RG-115830 but not in the absence of the ligand; 2) intratumoral DC.RheoIL 12-based therapy is as effective as intratumoral DC.cIL12-based therapy as long as RG-115830 is administered to treated animals within 24 h of DC injection (and at later time points of ligand provision, RG-115830 therapy fails); 3) IL-12 expression in DC appears to prolong the survival of these cells in the tumor microenvironment and is associated with higher numbers of intratumorally-injected DC that migrate to tumor-draining lymph nodes; and 4) the strongest immune correlate to therapy outcome is the level of tumor-specific $CD8^+$ T cells cross-primed by the therapy and not the number of injected DC sustained in the tumor microenvironment. Overall, these data suggest that DC.IL12-based therapies likely succeed based on their positive influence on the afferent (cross-priming) of Type-1 $CD8^+$ T cell effectors and not on later efferent events, such as injected DC-mediated recruitment of anti-tumor T cells into the tumor microenvironment, etc.

Prior to intratumoral injection, the cells (immune cells or TSC) may be treated with a factor to stimulate the activity of the cells. For example, the cells may be treated with a co-stimulatory molecule such as positive co-stimulatory molecule including OX40L, 4-1BBL, CD40, CD40L, GITRL, CD70, LIGHT or ICOS-L or a negative costimulatory molecule such as anti-CTLA4, anti-PD-L1 or anti-PD-L2 antibodies. For example, the cells (e.g., immune cells or TSC) may be incubated with a cell expressing one or more co-stimulatory molecule, e.g., J588 lymphoma cells expressing CD40 ligand molecule. In another embodiment, the cells (immune cells or TSC) may be treated with a counter immune suppressant molecule (tolerance inhibitor) such as anti-TGF-beta antibodies (for inhibiting TGF signaling within the microenvironment), anti-IL10 antibodies, TGF-bRII DN (to inhibit TGF signaling within gene modified cells), IL-10R DN, dnFADD (to inhibit cell death pathways within the cells), anti-SOCS1 antibodies, siRNA or decoy (to inhibit suppressive cytokine signaling within the cells), or anti-TGFa antibodies.

The recombinant adenoviruses carrying the polynucleotide sequences shown in FIGS. 1-8 are produced. For example, hIL-21 is produced by cotransfection of the hIL-21 expression vector, linearized by restriction digestion at a site upstream of the left ITR, and the appropriate (example E3 deleted) adenoviral backbone in a permissive cell line such as HEK293 cells. The adenoviral vector carrying the murine immunomodulatory genes is used for transduction of murine dendritic cells or TSC for use in murine therapeutic models. For human therapeutic application, a polynucleotide encoding the human homologue of the immunomodulatory gene is inserted in the appropriate vector. The adenoviral vector for human therapeutic application is produced under GMP conditions. Example of a treatment outline (clinical trial) for stage III/IV melanoma patients is as follows: The treatment in this case involves an intratumoral injection of the adenoviral transduced dendritic cells and 14 daily oral administration of the activator drug (ligand). Subjects are screened 30 days to one week prior to the clinical trial. Each subject is asked to sign an informed consent before any procedures are initiated. The investigator will inform all subjects of the nature, aims, duration, potential hazards, and procedures to be performed during the trial and the possibility that their medical records may be reviewed by FDA. Subjects (a total of 16 to 20) are randomly grouped into 4 cohorts. All cohorts will receive an intratumoral injection of up to $5\times10^7$ transduced dendritic cells approximately 3 hours after the first dose of oral administration of the ligand. The 4 cohorts differ in the daily oral dose of ligand received: example cohort 1=0.01 mg/kg: cohort 2=0.3 mg/kg; cohort 3=1 mg/kg; cohort 4=3 mg/kg. During the course of the treatment, blood is drawn at specified time intervals for evaluation of single dose and steady state pharmacokinetics of the Activator Drug and its major metabolites. Also, blood is drawn at specified time points for the evaluation of humoral and cellular immune responses against the viral vector, RTS components and the tumor. Urine is collected and blood drawn at specific time points for serum chemistry, urinalysis, and hematology (safety profile). Tumor and/or draining lymph node biopsies are taken at specified time points to assess the transgene expression and the immune response to the tumor as a result of the therapy. Criteria for early termination are established for patients in case of adverse events, and the adverse events are recorded. The patients are followed up at 1, 2, 3 and 4 months for adverse events and therapeutic outcome.

In another embodiment, a subject in need of treatment of a tumor is (a) administered dendritic cells engineered to express an immunomodulator, for example, an immunomodulator disclosed herein, either constitutively or conditionally, and/or (b) a vector expressing an immunomodulator, for example, an immunomodulator disclosed herein, either constitutively or conditionally, is injected intratumorally to the subject. In one embodiment, the dentritic cells are engineered to express an Ad-immunomodulator vector, and particularly the Ad-RTS-immunomodulator vector. In another embodiment, the vector that is injected intratumorally to the subject is an Ad-immunomodulator vector, and particularly the Ad-RTS-immunomodulator vector.

In another embodiment, a subject in need of treatment of a tumor is (a) administered dendritic cells engineered to express IL-12, either constitutively or conditionally, and (b) a vector expressing IL-12, either constitutively or conditionally, is injected intratumorally to the subject. In one embodiment, the dentritic cells are engineered to express an Ad-IL-12 vector, and particularly the Ad-RTS-IL-12 vector. In another embodiment, the vector that is injected intratumorally to the subject is an Ad-IL12 vector, and particularly the Ad-RTS-IL-12 vector.

In another embodiment, a subject in need of treatment of a tumor is (a) administered dendritic cells engineered to express IL-12, either constitutively or conditionally, and (b) the subject is administered one or more anticancer chemotherapeutic agents. In one embodiment, the engineered dentritic cells are engineered to express an Ad-IL-12 vector, and particularly the Ad-RTS-IL-12 vector. The one or more anticancer chemotherapeutic agents can be administered prior to the engineered dendritic cells are administered, after the engineered dendritic cells are administered, or concurrently with the administration of the engineered dendritic cells. In another embodiment, the anticancer chemotherapeutic is paclitaxel, a paclitaxel derivative or analog, temozolomide, a temozolomide derivative or analog, sunitinib, a sunitinib derivative or analog, gemcitabine, or a gemcitabine derivative or analog.

In another embodiment, a subject in need of treatment of a tumor is (a) administered dendritic cells engineered to express IL-12, either constitutively or conditionally, (b) a vector expressing IL-12, either constitutively or conditionally, is injected intratumorally to the subject, and (c) the subject is administered one or more anticancer chemotherapeutic agents. In one embodiment, the dentritic cells are engineered to express an Ad-L-12 vector, and particularly the Ad-RTS-IL-12 vector. In another embodiment, the vector that is injected intratumorally to the subject is an Ad-IL-12 vector, and particularly the Ad-RTS-IL-12 vector. The one or more anticancer chemotherapeutic agents can be administered prior to the engineered dendritic cells and the vector expressing IL-12 are administered, after the engineered dendritic cells and vector expressing IL-12 are administered, or concurrently with the administration of the engineered dendritic cells and the vector expressing IL-12. In one embodiment, the anticancer chemotherapeutic is paclitaxel, a paclitaxel derivative or analog, temozolomide, a temozolomide derivative or analog, sunitinib, a sunitinib derivative or analog, gemcitabine, or a gemcitabine derivative or analog.

In another embodiment, a subject in need of treatment of a tumor is (a) administered dendritic cells engineered to express an immunomodulator, for example, an immunomodulator disclosed herein, either constitutively or conditionally, and (b) the subject is administered one or more anticancer chemotherapeutic agents. In one embodiment, the engineered dentritic cells are engineered to express an Ad-immunomodulator vector, and particularly the Ad-RTS-immunomodulator vector. The one or more anticancer chemotherapeutic agents can be administered prior to the engineered dendritic cells are administered, after the engineered dendritic cells are administered, or concurrently with the administration of the engineered dendritic cells. In one embodiment, the anticancer chemotherapeutic is paclitaxel, a paclitaxel derivative or analog, temozolomide, a temozolomide derivative or analog, sunitinib, a sunitinib derivative or analog, gemcitabine, or a gemcitabine derivative or analog.

In another embodiment, a subject in need of treatment of a tumor is (a) administered dendritic cells engineered to express an immunomodulator, for example, an immunomodulator disclosed herein, either constitutively or conditionally, (b) a vector expressing an immunomodulator, for example, an immunomodulator disclosed herein, either constitutively or conditionally, is injected intratumorally to the subject, and (c) the subject is administered one or more anticancer chemotherapeutic agents. In one embodiment, the dentritic cells are engineered to express an Ad-immunomodulator vector, and particularly the Ad-RTS-immunomodulator vector. In another embodiment, the vector that is injected intratumorally to the subject is an Ad-immunomodulator vector, and particularly the Ad-RTS-immunomodulator vector. The one or more anticancer chemotherapeutic agents can be administered prior to the engineered dendritic cells and the vector expressing the immunomodulator are administered, after the engineered dendritic cells and vector expressing the immunomodulator are administered, or concurrently with the administration of the engineered dendritic cells and the vector expressing the immunomodulator. In one embodiment, the anticancer chemotherapeutic is paclitaxel, a paclitaxel derivative or analog, temozolomide, a temozolomide derivative or analog, sunitinib, a sunitinib derivative or analog, gemcitabine, or a gemcitabine derivative or analog.

In any of the methods of the present invention, the disease or disorder may be a disease or disorder disclosed in the present application. In one embodiment, the disease or disorder is a disease or disorder listed in Table 1 herein. In another embodiment, the disease or disorder is a disease or disorder listed in Table 3 herein.

In any of the methods of the present invention, the cancer or tumor may be a disease or disorder disclosed in the present application. In one embodiment, the cancer or tumor is a cancer or tumor listed in Table 1 herein. In another embodiment, the cancer or tumor is a cancer or tumor listed in Table 3 herein.

It is possible to measure the effect of an immunomodulator and/or IL-12 expression on a population of cells by measuring the level of expression or activity of the Th1/Tc1 type cytokine, IFN-gamma in a biological sample from a patient.

For the purposes of the invention, the invention provides a method for determining the efficacy of an in vitro engineered immune- or TSC-based therapeutic regimen in a cancer patient, comprising:

a. measuring the level of expression or the level of activity or both of interferon-gamma (IFN-gamma) in a first biological sample obtained from a human patient before administration of in vitro engineered cells, e.g., immune cells or TSC, thereby generating a control level;

b. administering intratumorally to said patient the in vitro engineered cells;

c. administering to said patient an effective amount of activating ligand;

d. measuring the level of expression or the level of activity or both of IFN-gamma in a second biological sample obtained from said patient at a time following administration of said activating ligand, thereby generating data for a test level; and e. comparing the control level to the test level of IFN-gamma, wherein data showing an increase in the level of expression, activity, or both of IFN-gamma in the test level relative to the control level indicates that the therapeutic treatment regimen is effective in said patient. The invention may also optionally comprise the additional steps of f. taking biopsy and counting tumor infiltrating lymphocytes (TIL) and/or g. observing tumor regression in response to the treatment.

The term "subject" means an intact insect, plant or animal. It is also anticipated that the ligands will work equally well when the subject is a fungus or yeast. Animals for use with the invention include, but are not limited to, vertebrates, e.g., mammals such as humans, rodents, monkeys, and other animals, with humans or mice being more preferred. Other animals include veterinary animals such as dogs, cats, horses, cattle, sheep, goats, pigs and the like.

The invention further provides a method of increasing expression of the immunomodulator, e.g., TNF-alpha, by introducing into the vector, e.g., a replication-deficient adenoviral vector, one or more regulatory sequence and optionally a nucleic acid encoding a signal peptide, wherein the vector conditionally express the immunomodulator. As used herein, the term "protein expression" includes without limitation transcription, post-transcription, translation, and/or post-translation. Also included in the invention is a method of increasing mRNA or protein expression of an immunomodulator, e.g., TNF-alpha, comprising generating a vector conditionally expressing TNF-alpha, wherein said vector further comprises one or more regulatory sequences connected to the polynucleotide sequence encoding said TNF-alpha, and adding an activating ligand, thereby inducing expression of the immunomodulator, wherein said one or more regulatory sequences and/or signal peptides improves expression of said TNF-alpha. Various regulatory regions for the invention including, but not limited to, 5' untranslated region (5'UTR), 3' UTR, or both have been described. In one embodiment, the 5' UTR is 5U2. 5U2 is a fusion canine SERCA2 intron 2 with a mutated putative consensus poly-A site, with exon 2 splice donor flanking on the 5' end and exon 3 splice acceptor flanking on the 3' end followed by a portion of the portion of bovine casein 5'UTR. In another embodiment, the 3' regulatory region is a polyadenylation signal of SV40 or hGH.

In certain embodiments, the method of the invention is also directed to improving TNF-alpha secretion by generating a vector conditionally expressing TNF-alpha, wherein said vector further comprises a signal peptide, thereby increasing secretion of TNF-alpha compared to a vector comprising the TNF-alpha native signal peptide gene, e.g., TNF-alpha wild-type signal peptide. In particular, the signal peptide used in the invention is codon-optimized. In a specific embodiment, the signal peptide is encoded by IL-2 wildtype signal peptide gene. In a further specific embodiment, the signal peptide is encoded by codon-optimized IL-2 signal peptide gene.

Without wishing to be bound by theory, it is expected that the invention will support the use of intratumorally administered in vitro engineered immune- and TSC based gene therapy in the clinical setting, focusing on the objective clinical response as a primary study endpoint, and cross-primed anti-tumor $CD8^+$ T cells (producing IFN-gamma) as a secondary study endpoint. The ability to turn the immunomodulator and/or IL-12 expression on and off in vivo adds an element of safety and therapeutic control to the treatment in that both the timing and level of protein expression may be controlled by the administration of ligand, and further that the timing of immunomodulator and/or IL-12 expression is expected to be critical to the therapeutic effectiveness of the method.

The invention further supports the therapeutic applications of in vitro engineered cells with conditionally expressed genes of interest as innovative approaches for the effective and efficient treatment of human diseases.

The present invention also provides methods for treating a tumor, reducing a tumor size, or preventing a tumor formation in a mammal in need thereof, in which a vector for conditionally expressing protein(s) having the function(s) of one or more immunomodulators that is not contained within a cell, is administered intratumorally to tumor microenvironments. In this embodiment, the vector is administered to the tumor without being packaged in a cell, such as immune cell or a TSC. The present invention also provides methods for treating a disease in a mammal in need thereof, in which a vector for conditionally expressing protein(s) having the function(s) of one or more immunomodulators that is not contained within a cell, is administered to said mammal. In this embodiment, the vector is administered to the tumor without being packaged in a cell, such as immune cell or a TSC.

In one embodiment, immune cells, TSC, dendritic cells, or bone marrow dendritic cells are not administered intratumorally with the vector.

In another embodiment, a vector of the invention that is not contained within a cells is administered intratumorally simulataneously with, before, or after immune cells, TSC, dendritic cells, or bone marrow dendritic cells are administered intratumorally.

In one embodiment, the vector of the invention that is not contained within a cell is administered intratumorally to the same lesion as the immune cells or TSC are administered. In another embodiment, the vector of the invention that is not contained within a cell is administered intratumorally to a different lesion than the immune cells or TSC are administered.

In one embodiment, the vector is administered to the same lesion(s) in each cycle of administration. In another embodiment, the vector that is administered is not administered to the same lesion(s) in each cycle of administration.

In one embodiment, the tumor is a tumor of any of the cancers listed herein, e.g., in Tables 1 and 3. In another embodiment, the tumor is a melanoma tumor, a colorectal tumor, a pancreatic tumor, a breast tumor, a lung tumor or a renal tumor. In another embodiment, the tumor is a malignant melanoma. In a another embodiment, the tumor is a Stage III C or a Stage IV malignant melanoma.

In one embodiment, the intratumoral dosage is at least about $1.0\times10^{9}$ viral particles per cycle of vector administration. In another embodiment, the intratumoral dosage is at least about $1.0\times10^{10}$ viral particles per cycle of vector administration. In another embodiment, the intratumoral dosage is about $1.0\times10^{9}$ to about $1.0\times10^{13}$ viral particles per cycle of vector administration. In another embodiment, the intratumoral dosage is about $1.0\times10^{10}$ to about $1.0\times10^{13}$ viral particles per cycle of vector administration. In another embodiment, the intratumoral dosage is about $1.0\times10^{10}$, about $1.0\times10^{11}$, about $1.0\times10^{12}$ or about $1.0\times10^{13}$ viral particles per cycle of vector administration. In one embodiment, the vector is AD-RTS-IL-12.

In another embodiment, the present invention further provides methods for treating a liver disease in a mammal in need thereof, in which a vector for conditionally expressing protein(s) that is not contained within a cell, is administered to said mammal.

In another embodiment, the present invention further provides methods for treating a lysosomoal storage disease in a mammal in need thereof, in which a vector for conditionally expressing protein(s) that is not contained within a cell, is administered to said mammal.

In another embodiment, the present invention further provides methods for treating a disease in a non-human mammal in need thereof, in which a vector for conditionally expressing protein(s) that is not contained within a cell, is administered to said mammal.

The activating ligand dosage is about 5-100 mg/day, e.g., about 5, 10, 15, 20, 25, 30, 35, 40, 45, 50, 55, 60, 65, 70, 75, 80, 85, 90, 95 or 100 mg/day. In one embodiment, the activating ligand is administered at least once a day. In another embodiment, the activating ligand is administered once a day for about 14 days.

In one embodiment, at least two dosages of the vector (e.g., about $1\times10^{11}$ and $1\times10^{12}$) are used in combination with at least three different dosage levels of the activating ligand (e.g., about 5 mg/day to about 100 mg/day).

One of ordinary skill in the art will be able to optimize dosages in order to provide range of effective plasma levels of the vector, for various degrees of activating ligand activation.

In one embodiment, the dosage of activating ligand administered to the subject is changed over the period of administration of the activating ligand within the cycle of intratumoral vector administration. In another embodiment, the dosage of activating ligand administered to the subject is decreased over the period of administration of the activating ligand within the cycle of intratumoral vector administration. In another embodiment, the dosage of activating ligand administered to the subject is increased (escalated) over the period of administration of the activating ligand within the cycle of intratumoral vector administration.

In one embodiment, the subject is treated with 2, 3, 4, 5, 6, 7, 8, 9 or 10 cycles of intratumoral vector administration. In another embodiment, the subject is treated with 3-7 cycles of intratumoral vector administration. In another embodiment, the subject is treated with 4-6 cycles of intratumoral vector administration. In another embodiment, the subject is treated with 5 or 6 cycles of intratumoral vector administration. In another embodiment, the subject is treated with 6 cycles of intratumoral vector administration.

In one embodiment, each cycle of intratumoral vector administration is performed 1, 2, 3, 4, 5, 6, 7, 8, 9 or 10 weeks apart. In another embodiment, each cycle of intratumoral vector administration is performed 4 weeks apart.

In one embodiment, the dosage of the vector is changed in each subsequent cycle of intratumoral vector administration. In another embodiment, the dosage of the vector is decreased in each subsequent cycle of intratumoral vector administration. In another embodiment, the dosage of the vector is increased in each subsequent cycle of intratumoral vector administration.

In one embodiment, the dosages of vector and activating ligand, the number and length of the cycles of intratumoral vector administration, the frequency of vector administration and the frequency of activating ligand administration is set forth in Table 8 in Example 11 herein.

In one embodiment, the invention also provides a pharmaceutical composition comprising pharmaceutically acceptable carrier and a vector of the invention that is not contained within a cell. Suitable carriers include, but are not limited to, saline, distilled water, sodium chloride solutions, the mixtures of sodium chloride and inorganic salts or their similar mixtures, the solutions of materials such as mannitol, lactose, dextran, and glucose, amino acid solutions such as glycine and arginine, the mixtures of organic acid solutions or salt solutions and glucose solutions, aqueous and non-aqueous, isotonic sterile injection solutions, which can contain antioxidants, chelating agents, buffers, bacteriostats, and solutes that render the formulation isotonic, and aqueous and nonaqueous sterile suspensions that can include suspending agents, solubilizers, thickening agents, stabilizers, and preservatives. The formulations can be presented in unit dose or multidose sealed containers, such as ampules and vials, and can be stored in a freeze-dried (lyophilized) condition requiring only the addition of the sterile liquid carrier, for example, water, for injections, immediately prior to use.

In the event of conflict between any teaching or suggestion of any reference cited herein and the specification, the latter shall prevail, for purposes of the invention.

All patents, patent applications and publications cited herein are fully incorporated by reference in their entireties.

It is to be understood that the foregoing described embodiments and exemplifications are not intended to be limiting in any respect to the scope of the invention, and that the claims presented herein are intended to encompass all embodiments and exemplifications whether or not explicitly presented herein.

U.S. application Ser. No. 12/247,738, entitled "Engineered Dendritic Cells And Uses For Treatment Of Cancer," filed Oct. 8, 2008, is hereby incorporated by reference in its entirety. U.S. application Ser. No. 12/241,018, entitled "Therapeutic Gene-Switch Constructs And Bioreactors For The Expression Of Biotherapeutic Molecules, And Uses Thereof," filed Sep. 29, 2008, is also hereby incorporated by reference in its entirety.

Example 1

A study is undertaken to determine the dose of dendritic cells and the most effective cytokine that is able to induce tumor-specific immune responses and antitumor activity in a Renca renal cell cancer tumor model Two tumor cell lines are used in this study: Renca and Renca-HA. The latter cell line is made by transfection of Renca cells with influenza virus hemagglutinin (HA). The advantage of Renca-HA model is the ability to trace antigen-specific T cells, since both CD8 and CD4 specific HA-derived epitopes are known and have been used.

Specific Aim—determine the induction of HA-specific immune responses after intratumoral administration of dendritic cells.

The Renca-HA tumor is established subcutaneously in BALB/c mice. When the tumor becomes palpable, dendritic cells are injected intratumorally. Dendritic cell administration is be repeated twice at 7-day intervals, for a total of 3 administrations.

The following groups of mice are used (each group includes 3 mice):

1. Untreated mice;
2. Mice treated with $5\times10^5$ dendritic cells transduced with control plasmid;
3. Mice treated with $10^6$ dendritic cells transduced with control plasmid;
4. Mice treated with $5\times10^6$ dendritic cells transduced with control plasmid;
5. The same as groups 2-4 using dendritic cells transduced with IL-12;
6. The same as groups 2-4 using dendritic cells transduced with IL-15; and
7. The same as groups 2-4 using dendritic cells transduced with IL-21.

To test the effect of combination of different cytokines, mice are treated simultaneously with:

8. $5\times10^5$ dendritic cells transduced with IL-12, and $5\times10^5$ dendritic cells transduced with IL-15,
9. $5\times10^5$ dendritic cells transduced with IL-12 and $5\times10^5$ dendritic cells transduced with IL-21, and
10. $5\times10^5$ dendritic cells transduced with IL-15 and $5\times10^5$ dendritic cells transduced with IL-21.

Four days after the last administration, lymph nodes of tumor-bearing mice are collected, and cells are stimulated with either MHC class I matched peptide (to detect $CD8^+$ T cell responses) or MHC class II matched peptide (to detect $CD4^+$ T cell responses).

The following assays are used:

1. ELISPOT IFN-γ and IL-2;
2. T-cell proliferation;
3. Detection of TNFα, IL-10, IL-4, and GM-CSF release by lymph node cells.

In addition, NK activity of lymph node cells is evaluated using YAC cells as targets.

In parallel, cells are stimulated with anti-CD3/CD28 antibodies to evaluate nonspecific response of T cells, The most effective dose of dendritic cells capable of inducing antigen-specific immune responses are determined.

Specific Aim 2—evaluate antitumor activity of dendritic cells transduced with cytokine genes.

Only those cytokine transduced dendritic cells that demonstrated statistically significant induction of immune responses are used in further experiments.

Treatment of Renca-HA tumor-bearing mice is performed as described in specific aim 1. One dose of DCs transduced with cytokines that shows specific activity in previous experiments is used. As a control, dendritic cells transduced with control adenovirus are used. To achieve statistical significance, each group includes 10 mice.

Tumor growth is evaluated. Renca-HA tumor contains an immunogeneic epitope that is useful for immunological monitoring and initial testing of antitumor effect. However, to verify potential antitumor activity of the treatment non-transfected tumor cells needs to be used. Therefore, the experiments described above are repeated using the Renca tumor model.

Example 2

The safety, tolerance, transgene function, and immunological effects of intratumoral injection(s) of adenoviral transduced autologous dendritic cells engineered to express hIL-12 and one or more other immunodulators under control of the RTS, in subjects with stage III and IV melanoma will be evaluated through procedures such as those described below.

A study involving study subjects with stage III and IV melanoma will be conducted in 4 cohorts (groups) of subjects each subject receiving a single intratumoral injection (into a melanoma tumor) of adenoviral transduced autologous (reinserted into the same subject that they came from) dendritic cells (DCs) engineered to express human interleukin-12 (hIL-12), and one or more other immunodulators, at a dose of $5\times10^7$ in combination with daily oral doses of activator drug (activating ligand). The study will use injections of dendritic cells transduced ex vivo (after the cells are removed from the subjects) with adenoviral vector for inducible expression of human IL-12 and one or more other immunodulators. The production off IL-12 and the one or more or other immunomodulators is "turned on" (induced) from the injected DCs through the activation of the RTS by the oral administration of the activator drug (RG-115932). Safety and tolerance will be assessed through physical examinations (including ECOG performance status), vital signs measurements, serum chemistry, urinalysis, hematology, adverse events "side-effects", and antibodies and cellular immune response to the adenovirus, components of RTS, and the Activator Drug. To evaluate progress, single dose and steady-state pharmacokinetics/ADME of oral Activator Drug and its major metabolites, analysis of hIL-12 levels, other immunomodulator levels, and cellular immune response (T cells) in biopsies of the target tumors, draining lymph nodes, and peripheral circulation, as well as a serum cytokine profile will be measured.

For instance, 16 subjects with stage III and IV melanoma are divided into four cohorts with cohorts 1 and 2 containing three subjects and cohorts 3 and 4 containing 5 subjects. All subjects will receive a single intratumoral injection of $5\times10^7$ autologous DC transduced with adenoviral vector encoding human IL-12 and one or more other immunodulators under the RTS control. For example, the subjects are administered an intratumoral injection of autologous DC transduced with adenoviral vector encoding human IL-12 under the RTS control and an immunomodulator such as IL-15 or IL-21.

The subjects will receive a single daily oral dose of activator drug (cohort 1: 0.01 mg/kg, cohort 2: 0.1 mg/kg, cohort 3: 1.0 mg/kg or cohort 4: 3 mg/kg) the first dose starting approximately 3 hours prior to the DC injection on day 1 and continuing for 13 more consecutive days. Additional injection(s) of adenovirally transduced autologous dendritic cells in combination with 14 single (once) daily oral doses of activator drug may be administered to eligible subjects who meet the criteria for retreatment. Safety, tolerance, and dendritic cell function are assessed for all subjects in each group of cohort 1 for up to one month after injection of the in vitro engineered dendritic cells before enrolling subjects to receive the next highest dose of the activator drug. The safety assessment will continue in all subjects for 3 months after the initial injection of the engineered dendritic cells with the possibility of extending the follow-up period to a total of six months to monitor subject safety if toxicity is observed or the subject receives additional injection(s) of the dendritic cells.

Such a study demonstrates the safety and tolerance of a single or multiple intratumoral injection(s) of adenoviral transduced autologous dendritic cells in combination with an oral activator drug in subjects with melanoma. The study provides steady-state pharmacokinetics/ADME of the oral activator drug. The study demonstrates functionality of the RTS in subjects by measuring hIL-12 expression and the expression of the one or more other immunomodulators of adenovirus transduced autologous dendritic cells in target tumor and/or draining lymph nodes in response to the activation of the RTS by the oral administration of the activator drug. Furthermore, the study demonstrates the immunological effects of the adenoviral transduced autologous dendritic cells in terms of the cellular immune response in the target tumor, draining lymph nodes, and peripheral circulation following oral administration of the activator drug.

Melanoma is selected as an exemplary cancer, particularly with respect to melanoma. Melanoma in particular among solid tumors has been shown to respond to immunotherapy approaches, and melanoma tumors are readily accessible for intratumoral injection and biopsy. The subjects included in the study have unresectable stage III or IV melanoma, which has at least 0.5 cm in diameter, any tumor thickness, any number of lymph node involvement, in-transit metastases, or distant metastases.

Preparation of Adenovirus Harboring the RheoSwitch Therapeutic System, hIL-12 and One or More Other Immunomodulatiors The recombinant DNA is transferred to dendritic cells (DC) by ex vivo adenoviral vector transduction. The recombinant DNA is used to express human IL-12(p70) and one or more other immunodulators from intratumorally injected immature dendritic cells which confers survival and stimulates maturation of DC in the tumor environment resulting in their subsequent migration to the draining lymph nodes. This leads to a bias toward the differentiation of T helper cells to Th1 type and also activation of tumor-specific cytotoxic T cells by cross priming with the tumor antigens.

The recombinant DNA used as the recombinant adenoviral vector allows the expression of human IL-12 and one or more other immunodulators under the control of the RheoSwitch® Therapeutic System (RTS). The RTS comprises a bicistronic message expressed from the human Ubiquitin C promoter and codes for two fusion proteins: Gal4-EcR and VP16-RXR. Gal4-EcR is a fusion between the DNA binding domain (amino acids 1-147) of yeast Gal4 and the DEF domains of the ecdysone receptor from the insect *Choristoneura fumiferana*. In another embodiment, the RTS consists of a bicistronic message expressed from the human Ubiquitin C promoter and codes for two fusion proteins: Gal4-EcR and VP16-RXR. Gal4-EcR is a fusion between the DNA binding domain (amino acids 1-147) of yeast Gal4 and the DEF domains of the ecdysone receptor from the insect *Choristoneura fumiferana*. VP16-RXR is a fusion between the transcription activation domain of HSV-VP16 and the EF domains of a chimeric RXR derived from human and locust sequences. These Gal4-EcR and VP16-RXR sequences are separated by an internal ribosome entry site (IRES) from EMCV. These two fusion proteins dimerize when Gal4-EcR binds to a small molecule drug (RG-115932) and activate transcription of hIL-12 and one or more other immunodulators from a Gal4-responsive promoter that contains six Gal4-binding sites and a synthetic minimal promoter. The RTS transcription unit described above is placed downstream of the hIL-12 and one or more other immunodulators transcription units. This whole RTS-hIL12-immunomodulator cassette is incorporated into the adenovirus 5 genome at the site where the E1 region has been deleted. The adenoviral backbone also lacks the E3 gene. A map for the adenoviral vector Ad-RTS-hIL-12 is shown in FIG. 8 of US 2009/0123441 A1.

The recombinant adenoviral vector used in this study contains the following exemplary regulatory elements in addition to the viral vector sequences: Human Ubiquitin C promoter, Internal ribosome entry site derived from EMCV, an inducible promoter containing 6 copies of Gal4-binding site, 3 copies of SP-1 binding sites, and a synthetic minimal promoter sequence, SV40 polyadenylation sites, and a transcription termination sequence derived from human alpha-globin gene. It should be understood that other regulatory elements could be utilized as alternatives.

An exemplary recombinant adenoviral vector Ad-RTS-hIL-12-immunomodulator(s) is produced in the following manner. The coding sequences for the receptor fusion proteins, VP16-RXR and Gal4-EcR separated by the EMCV-IRES (internal ribosome entry site), are inserted into the adenoviral shuttle vector under the control of the human ubiquitin C promoter (constitutive promoter). Subsequently, the coding sequences for the p40 and p35 subunits of hIL-12 separated by IRES, and one or more other immunomodulators, is placed under the control of a synthetic inducible promoter containing 6 copies of Gal4-binding site are inserted upstream of the ubiquitin C promoter and the receptor sequences. The shuttle vector contains the adenovirus serotype 5 sequences from the left end to map unit 16 (mu16), from which the E1 sequences are deleted and replaced by the RTS, IL-12 and one or more other immunomodulator sequences (RTS-hIL-12). The shuttle vector carrying the RTS-hIL12-immunodulator(s) is tested by transient transfection in HT-1080 cells for Activator Drug-dependent IL-12 and other immunomodulator(s) expression. The shuttle vector is then recombined with the adenoviral backbone by cotransfection into HEK 293 cells to obtain recombinant adenovirus Ad-RTS-hIL-12-immunomodulator(s). The adenoviral backbone contains sequence deletions of mu 0 to 9.2 at the left end of the genome and the E3 gene. The shuttle vector and the adenoviral backbone contain the overlapping sequence from mu 9.2 to mu 16 that allows the recombination between them and production of the recombinant adenoviral vector. Since the recombinant adenoviral vector is deficient in the E1 and E3 regions, the virus is replication-deficient in normal mammalian cells. However, the virus can replicate in HEK 293 cells that harbor the adenovirus-5 E1 region and hence provide the E1 function in trans.

An exemplary recombinant adenoviral vector is produced in the following manner: The linearized shuttle vector carrying the DNA elements for inducible expression of human IL12 and one or more other immunomodulators, and the adenoviral backbone are co-transfected into HEK293 cells. Recombination between the overlapping sequences on the shuttle vector and the viral backbone results in the production of recombinant adenovirus and is packaged into viral particles in the HEK293 cells. The HEK293 cells are grown in DMEM containing fetal bovine serum.

The virus used for the proposed study was purified by CsCl density gradient centrifugation. The recombinant adenovirus undergoes two rounds of plaque purification and the resulting seed stock is used to produce a master viral bank (MVB) by amplification in HEK293 cells from a fully characterized master cell bank. The MVB undergoes extensive cGMP/GLP release tests including replication competent adenovirus (RCA), sterility, *mycoplasma*, adventitious viruses, retrovirus, human viruses HIV1/2, HTLV1/2, HAV, HBV, HCV, EBV, B19, CMV, HHV-6, 7 and 8, bovine and porcine virus, complete vector sequencing and functional testing by AD-induced expression of IL-12 and one or more other immunomodulators in human cell lines.

The virus from MVB may be used for production of the purified virus in a cGMP facility and may again undergo release tests including identity, RCA, sterility, *mycoplasma*, adventitious viruses, viral particle-to-infectious units ratio, contamination of host cell DNA, endotoxin and proteins and functional testing by AD-induced expression of IL-12 and one or more other immunomodulators in human cell lines.

A suitable method for producing recombinant adenovirus is also set forth in Anderson, R. D., *Gene Therapy* 7: 1034-1038 (2000).

A suitable method for recombinant adenovirus into host cells is set forth in Komita, H. et al., *Cancer Gene Therapy* 16: 883-891 (2009)

Transduction of Autologous Dendritic Cells by Adenovirus Containing hIL-12 Transgene and One or More Other Immunodulators and RheoSwitch® Therapeutic System (RTS)

Dendritic cells derived from the human subjects are transduced ex vivo and injected into the tumor. The DC will be characterized before viral transduction for viability, purity (typically >80% cells showing DC phenotype), sterility, *mycoplasma* and endotoxin. After viral transduction, the cells are washed repeatedly to remove any unabsorbed virus. Supernatant from the last wash will be tested for the content of residual virus by PCR. Since the DCs are transduced ex vivo by adenoviral vector (non-integrating virus) and the life span of DCs after intratumoral injection and the subsequent migration to draining lymph nodes is short, it is not expected that the viral DNA will be incorporated into any non-target cells. The protocol used for adenoviral transduction of DCs is expected to yield 80-90% transduction and is considered very efficient.

Harvesting of PBMC by Leukapheresis:

Subjects undergo a standard 90 to 120 minutes leukapheresis at the Apheresis Unit of the UPCI Outpatient. The leukapheresis procedure involves the removal of blood from a vein in one arm; the passage of blood through a centrifuge (cell separator), where its components are separated and one or more components are removed; and the return of the remaining components to the subject's vein in the same or other arm. No more than 15% of the subject's total blood volume is withdrawn at any one time as blood is processed through the cell separator device. In the cell separator, blood is separated into plasma, platelets, white cells and red blood cells. White blood cells (WBC) are removed and all the other components are returned into the subject's circulation. Every attempt is made to use two peripheral IV lines for this procedure. If that is not possible, a central line may be necessary. The subject has to be cleared by physician to undergo leukapheresis, and is routinely screened for vital signs (including blood pressure) prior to the procedure.

Processing:

After collection, the leukapack is delivered by hand to the CPL, and is immediately processed by centrifugal elutriation in ELUTRA™, This is a closed system validated for clinical use. The monocyte fraction is recovered, and after the recovery and viability of cells are established, they are transferred to an Aastrom cartridge for 6-day culture in the presence of IL-4 and GM-CSF. All processing and washing procedures are performed under sterile conditions.

Initial Plating:

Monocytes recovered from a single leukapack are counted in the presence of a trypan blue dye to determine the number of viable cells. Monocytes are evaluated for purity by flow cytometry. Monocytes are resuspended at 5 to $10\times10^6$ cells/mL in serum-free and antibiotic-free CellGenix medium, containing 1,000 IU/mL of IL-4 and 1,000 IU/mL of GM-CSF per SOP-CPL-0166, and placed in an Aastrom cartridge. A minimum loading volume of 50 ml and a minimum cell number are required for cassette inoculation.

Culture:

The Aastrom cartridge is placed in the incubator in the Replicell System, a fully closed, cGMP-compatible automated culture device for immature DC generation.

Immature DC Harvest:

On day 6, the Aastrom cartridge is removed from the incubator and immature DCs are harvested. The cells are recovered by centrifugation at 1,500 rpm, washed in CellGenix medium, counted in the presence of a trypan blue dye and checked for morphologic and phenotypic characteristics.

Viability:

This is determined by performing hemocytometer cell counts in the presence of trypan blue. Generally, >95% of harvested cells are viable, i.e., exclude a trypan blue dye. If viability is less than 70% the immature DCs will be discarded.

Phenotyping:

The cells generated in culture are counted by microscopic observation on a hemocytometer, and a preliminary differential count (DC vs. lymphocytes) is obtained using a trypan blue dye. Confirmation of the differential count is made by flow cytometry, gating on DC vs. lymphocytes and using high forward and side scatter properties of immature DC as the criterion for their identification. Immature DCs routinely contain >80% of cells with dendritic cell morphology and have DC phenotype.

IL-12p70 Potency Assay:

It has been established that mature DCs (mDCs) have the ability to produce IL-12p70 spontaneously or upon activation with CD40L with or without addition of innate immunity signals (e.g., LPS). A standardized IL-12p70 production assay was recently established and is applicable to small samples or large lots of DC vaccines generated under a variety of conditions. The current potency assay consists of two distinct steps, the first involving co-incubation of responder DCs with J588 lymphoma cells stably transfected with the human CD40 ligand gene as stimulators. The second step involves testing of supernatants from these co-cultures for levels of IL12p70 secreted by DCs stimulated with J558/CD40L+/−LPS in the Luminex system. This potency assay has an inter-assay CV of 18.5% (n=30) and a broad dynamic range, which facilitates evaluation of various DC products characterized by vastly different levels of IL-12p70 production. The normal range for the assay established using DC products generated from monocytes of 13 normal donors was 8-999 pg/mL, with a mean of 270 pg/mL Production and Release Criteria for Dendritic Cells Each lot of the in vitro generated dendritic cells is tested for the presence of microbial contaminants (aerobic and anaerobic bacteria, fungi and *mycoplasma*), as well as endotoxin and are phenotypically and functionally characterized. All dendritic cells to be injected into subjects will be fresh and will not undergo croypreservation.

Quality Assurance Testing of DC:

DC generated as described above are evaluated for sterility, viability, purity, potency and stability. Criteria for release of the cellular product are established and rigorously followed.

Viability:

The cells generated in culture are counted by microscopic observation on a hemacytometer, and a differential count (DC vs. lymphocytes) is obtained using a trypan blue dye. This count provides the percentage of viable cells in the tested culture. More than 70% cell viability by trypan blue exclusion and minimum 70% cells expressing HLA-DR and CD86 as the monocyte-derived DC markers are required for passing the release criteria. Additional markers may be included for exploratory analysis such as CD83 and CCR7 for assessing the DC maturation status, and CD3 and CD19 to assess the lymphocytes contamination.

Purity:

Two-color flow cytometry analysis of cells stained with FITC- and PE-conjugated mAbs is used to determine that the DC population identified morphologicallly expresses the surface antigens defined for DC and lack the monocyte and T and B cell lineage antigens. For vaccine preparation, the DC generated must express HLA-DR and CD86 and must not express CD3, CD19, or CD14. To be considered as mDC, the cells must express CD83+ and CCR7+.

Potency:

To define a measure of potency for the DC, we determine their ability to produce IL-12p70 as described above.

Sterility:

DC are tested by bacterial (Aerobic and anaerobic) and fungal cultures using the BD Bactec system (Becton Dickinson Co., Sparks, Md.) at the University of Pittsburgh Medical Center Microbiology Laboratory. Final results of the microbial cultures are available in 14 days. Prior to release of the DC for vaccine use, a gram stain is performed and must be negative for the presence of microorganisms.

The IMCPL tests for *mycoplasma* by the use of the Gen-Probe *Mycoplasma* Tissue Culture Rapid Detection System (Gen-Probe, Inc. San Diego, Calif.), which is based on nucleic acid hybridization technology. Endotoxin testing is performed using the Limulus Amoebocyte Lysate Pyrogen Plus assay (Bio Whittaker, Inc., Walkerville, Md.). Endotoxin testing is performed on the cell culture at the time of harvest and prior to release of the final product. The acceptable endotoxin level is <5 EU/kg body weight. Untransduced and transduced dendritic cells will be cryopreserved for future analysis.

It is expected that all the transduced cells will express the transgene. More than 80% of the DCs are expected to be transduced. The product will be biologically active since the native coding sequence is maintained in the transgene. The viral-transduced DCs injected into the tumor are of immature DC phenotype and do not express IL-12 and one or more other immunomodulators until they undergo maturation, and hence at this stage, the expression of IL-12 and one or more other immunomodulators is mostly from the transgene. Since the expression of the IL-12 and one or more other immunomodulators transgene is induced by the small molecule activator drug RG-115932 in a dose dependent way, one can control the level of transgene expression in the transduced DCs to the desired levels. A small portion of the transduced DCs prepared for administration to the human subjects may be tested in vitro for the activator drug-dependent induction of expression of IL12 and one or more other immunomodulators. Expression of IL-12 and one or more other immunomodulators may be assayed by ELISA with a sensitivity of 4 ng/ml.

It is expected that in vitro induction of IL-12 and one or more other immunomodulators from cells transduced by the vector used in the proposed study yields about 500 ng IL-12 and one or more other immunomodulators per 10 cells in 24 hours, determined by ELISA. In preclinical studies using mouse model of melanoma, intratumoral injection of $10^6$ or more transduced DCs show efficacy. However, it is expected that the required intratumoral injection may show efficacy at levels below this amount and therefore injections of $5\times10^7$ transduced DCs may be utilized as a starting point to determine if less or greater amounts are required.

For instance, in vitro, human and mouse cell lines and primary dendritic cells transduced with recombinant adenoviral vector carrying the genes for IL12 and one or more other immunomodulators show induction of IL12 expression in response to the activator drug in a dose dependent way.

6.3. Formulation of Activator Drug

The activator drug used herein is formulated in any one of the following formulations:

(1) 100% Labrasol;

(2) Listerine flavored Labrasol (Latitude Pharmaceuticals Inc., USA) comprising (a) menthol, (b) thymol, (c) eucalyptol, (d) aspartame, (e) sodium saccharine, (f) citric acid, (g) peppermint flavor, (h) cream flavor, (i) labrasol;

(3) Miglyol 812 and phospholipon 90G (Latitude Pharmaceuticals Inc., USA); or (4) Miglyol 812, phospholipon 90G and Vitamin E tocopheryl polyethylene glycol succinate (Latitude Pharmaceuticals Inc., USA).

Delivery

While a variety of concentrations and specific protocols may be imagined, one example for treating patients would include patients receiving intratumoral injection(s) of transduced autologous dendritic cells (AdDCs) at a concentration of $5\times10^7$ suspended in sterile saline engineered to express hIL-12 (human interleukin 12) and one or more other immunodulators under control of the RTS, in combination with the oral activator drug (RG-115932).

Initial Treatment

Day 1 Inpatient Visit: On day 1, a baseline physical examination (including vital signs, weight, and ECOG status) is performed. Urine is collected and blood drawn for baseline serum chemistry, urinanalysis, and hematology (safety profile). Approximately 3 hours before the intratumoral injection of the in vitro engineered dendritic cells, each subject is dosed with an activator drug (cohort 1-0.01 mg/kg, 0.3 mg/kg, 1.0 mg/kg, and 3 mg/kg) immediately after a meal. Blood is drawn at specified time intervals (predose, 0.5, 1, 1.5, 2, 4, 6, 8, 12, 16, and 24 hours after the AD dose) on day 1 for evaluation of single dose pharmacokinetics of the activator drug and its major metabolites. Each subject receives a single intratumoral injection of adenoviral transduced autologous dendritic cells at a concentration of $5\times10^7$ cells, engineered to express hIL-12 and one or more other immunomodulators under the control of the RTS. The subjects are carefully monitored for local injection site reactions and/or hypersensitivity reactions. Day 2 through 14 Inpatient Visit: On days 2 through 14, each subject is dosed with the activator drug immediately after a meal. Vital signs and adverse events are collected daily on days 2 through 14. On day 4-24 hours, biopsies of the tumor and/or draining lymph nodes are removed from approximately 50% of the subjects for measurement of hIL-12 and cellular immune response. On day 8, weight is measured. On day 8+24 hours, biopsies of the tumor and/or draining lymph nodes are removed from subjects who did not have a biopsy performed on day 4 for measurement of hIL-12 and one or more other immunomodulators and cellular immune response. Blood is drawn on day 4±24 hours and day 8±24 hours for assay of potential antibodies and cellular immune response against the adenovirus and/or the RTS components. A serum cytokine profile is also obtained to determine if the expression of other cytokines is affected by treatment with the hIL-12 and one or more other immunomodulators transgene. On day 8, urine is collected and blood is drawn for baseline serum chemistry, urine analysis, and hematology (safety profile). On Day 8, blood is drawn at specified time intervals (predose, 0.5, 1, 2, 4, 6, 8, 12, 16, and 24 hours after the AD dose) for evaluation of steady-state pharmacokinetics/ADME of the activator drug and its major metabolites.

Day 14 Inpatient Visit: On day 14, each subject is dosed with the Activator Drug immediately after a meal. Each subject receives a physical examination (including vital signs, height, weight and ECOG status). Urine is collected and blood is drawn for serum chemistry, urinalysis, and hematology (safety profile). Blood is drawn on day 14±24 hours for assay of potential antibodies and cellular immune response against the adenovirus and/or the RTS components. A serum cytokine profile is also obtained to determine if the expression of other cytokines is affected.

Blood is collected from the subjects at specified inpatient and outpatient visits to measure potential antibodies and cellular immune response to the adenovirus and components of the RTS. Blood is obtained for a baseline serum cytokine profile. The AdVeGFP infectivity blocking type assay is used to detect an antibody response to the adenoviral vector (Gambotto, Robins et al. 2004). Antibody response to the RTS components will be assessed by western blot and/or ELISA using serum from the patient and the RTS proteins produced from an expression vector. In addition, multiplex cytokine testing will be done in the serum by Luminex for IL-12, IFN-gamma, IP-10, and other Th1/Th2 cytokines such as IL-2, TNF-alpha, IL-4, IL-5, and IL-10. These antibody and cytokine assays will need about 10 ml of blood.

Potential Antibody and Cellular Immune Response to Adenovirus and/or Components of the RTS: Blood will be collected from the subjects at specified inpatient and outpatient visits to evaluate the potential antibody and cellular immune response to the adenovirus and components of the RTS and tumor antigens. The AdVeGFP infectivity blocking type assay will be used to detect an antibody response to the adenoviral vector (Nwanegbo, et al. 2004). Antibody response to the RTS components will be assessed by western blot and/or ELISA using serum from the subjects and the RTS proteins produced from an expression vector. In addition, multiplex cytokine testing will be done in the serum by Luminex for IL-12, IFN-gamma, IP-10, and other Th1/Th2 cytokines such as IL-2, TNFα, IL-4, IL-5 and IL-10. These antibody and cytokine assays will need about 10 ml of blood.

The cellular immune response assays use about 50-60 ml blood and CD4 and CD8 T cell subsets will be separated from it. The separated T cells will be mixed with autologous DCs transduced with empty AdV vector, AdV-RTS, or AdV-RTS-hIL12-immunomodulator(s) vectors in an ELISPOT assay for IFN-gamma production by the T cells activated by the AdV- and RTS-derived antigens, if any. Similar assays will be performed using the tumor cells as such and/or DCs expressing shared melanoma antigens to assess the early immune response to the tumor. Additional assays may also be performed as necessary.

Pregnancy Testing:

Females of childbearing potential is administered a urine pregnancy test at the screening visit and before the first inpatient visit of the retreatment phase. The testing is performed at least 72, 48, 24, or 12 hours prior to the administration of Activator Drug during both the initial treatment and all retreatment periods. If the urine pregnancy test is positive, then confirmation will be obtained with a serum pregnancy test. If pregnancy is confirmed, the subject will not be allowed to enter the trial or continue into the retreatment phase. The pregnancy testing may be reperformed as many times as necessary.

Concomitant Medication Inquiry:

At screening, and before the first inpatient visit of the retreatment phase, each subject will be asked to provide a list of concurrent medications to determine any possible relationship to adverse events that occur during the trial and follow-up phase.

Retreatment Criteria:

If a subject has tolerated prior AdDC inoculation without adverse reactions that are limiting, and has shown no progression of disease or symptomatic decline at the time of potential retreatment, they will be considered for retreatment. If, in the opinion of the principal investigator, and treating physician there is a potential clinical benefit for additional intratumoral injection(s) of AdDCs in combination with Activator Drug (maximum tolerated dose from cohort 1) for 14 consecutive days, retreatment will be offered to the subject, provided the following criteria are met:

1. There have been no limiting toxicities,
2. The subject's disease is stable or showing clinical or subjective signs of improvement, and
3. There is no evidence of antibody or cellular immune response to adenovirus components of RheoSwitch® Therapeutic System.

Assessment of Transgene Function and Immunological Effects:

Punch or excisional biopsies of the tumor and associated draining lymph nodes will be collected during screening (day −12 to day −7), day 4, day 8 and day 14 of the trial and at month 1 of the follow-up for in vivo assessment of transgene expression of hIL-12 and one or more other immunomodulators, and cellular immune response. Fine needle aspiration biopsies of the tumor and associated draining lymph nodes will be collected on day −12 to −7 and day 14 of the retreatment period for in vivo assessment of transgene expression of hIL-12 and one or more other immunomodulators, and cellular immune response. Biopsies will be evaluated by standard light microscopy and immunohistochemistry to assess cellular infiltration of T cells into the tumor and draining lymph nodes. Biopsy sections will be read by a pathologist unaware of study subject background. To distinguish between endogenous and induced IL-12 expression by DCs in the tumor and draining lymph nodes, RT-PCR on RNA will be used with appropriately designed primers. Blood will be drawn for a serum cytokine profile at screening, day 4, day 8 and day 14 of the trial, at month 1 of the follow-up and on day −12 to −7, day 8 and day 14 of the retreatment period. A serum cytokine profile will be obtained to determine if the expression of other cytokines is affected by treatment with the hIL-12 transgene. Multiplex cytokine testing will be done in the serum by Luminex for IL-12, IFN-gamma, IP-10, and other Th1/Th2 cytokines such as IL-2, TNFa, IL-4, IL-5 and IL-10. These antibody and cytokine assays will need about 10 ml of blood.

Single Dose and Steady-State Pharmacokinetics of Activator Drug:

Blood will be drawn at specified time intervals (predose, 0.5, 1, 1.5, 2, 4, 6, 8, 12, 16, and 24 hours after the morning dose) on day 1 of the trial for evaluation of single dose pharmacokinetics and on day 8 of the trial for measurement of steady state pharmacokinetics/ADME of the Activator Drug and its major metabolites. Plasma will be evaluated by HPLC to obtain the following steady-state pharmacokinetic endpoints of the Activator Drug and major metabolites: Cmax (maximum observed plasma concentration), Tmax (time to maximum observed plasma concentration), Ctrough (minimum observed plasma concentration computed as the average of the concentrations at 0 and 24 hours), C24h (plasma concentration at 24 hours), AUC24h (area under plasma concentration-time curve from time 0 to 24 hours), Ke (apparent elimination rate), and T 112 (apparent half-life).

IL is to be understood that the foregoing described embodiments and exemplifications are not intended to be limiting in any respect to the scope of the invention, and that the claims presented herein are intended to encompass all embodiments and exemplifications whether or not explicitly presented herein.

Example 3

Figure 11:
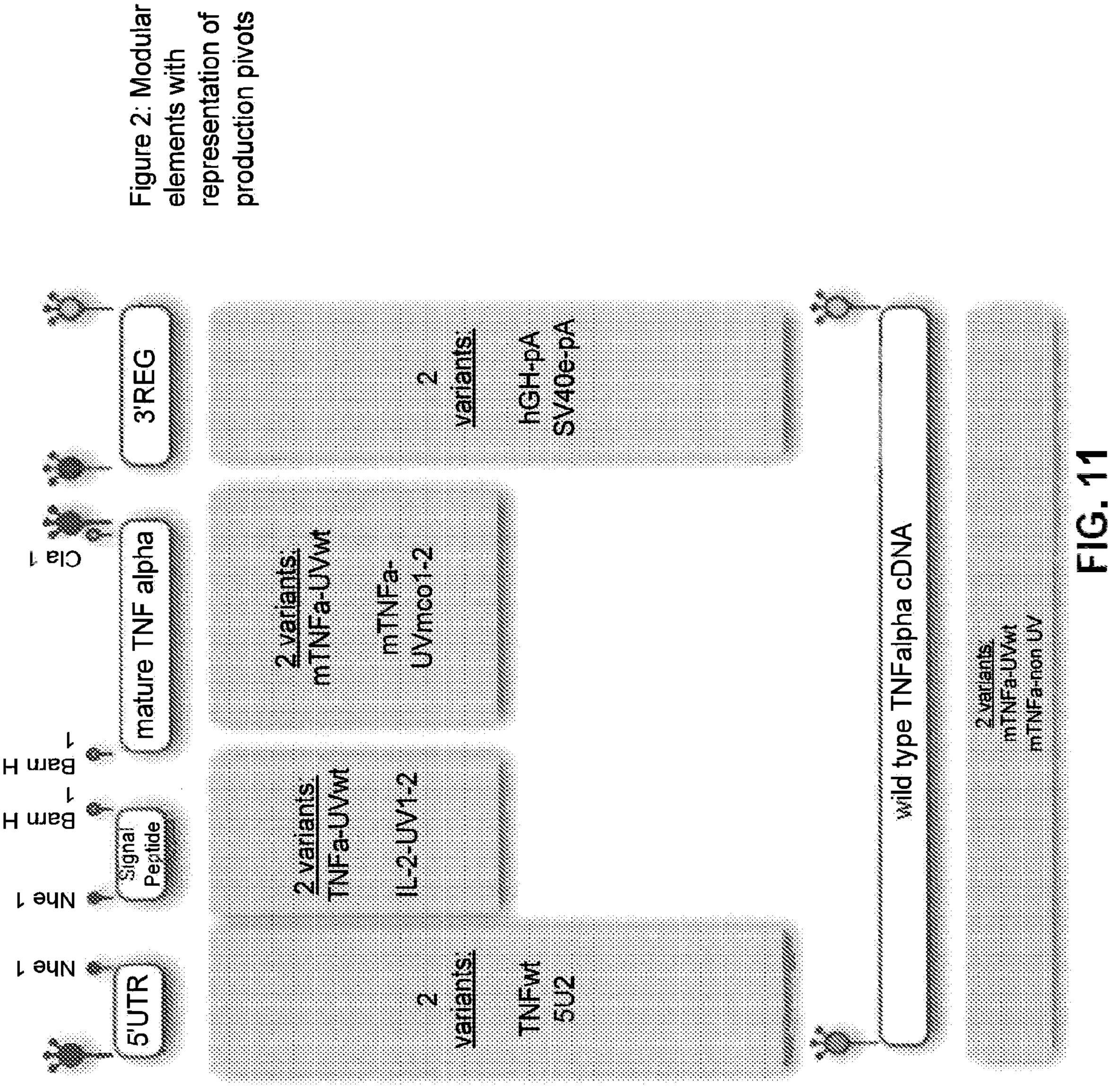
FIG. 11 shows modular elements with representation of production pivots.

A matrix of rationally-selected, modular gene components can be rapidly assembled into DNA expression constructs through application of a combinatorial transgene technology such as ULTRAVECTOR®. To demonstrate that assembled gene components, which individually affect transcription, post-transcription, translation, and post-translational process, can together impact gene expression level, RheoSwitch technology was used, optionally, in combination with artificial 5'UTRs, various 3' Reg+poly(A) signals (SV40 and hGH), signal peptides (TNF-alpha and IL-2), and codon optization (+/−) schemes to modulate transcription increases the capacity of a cell to produce and secrete TNF-alpha. FIG. 11 illustrates the modular elements used, and graphically represents each modular element flanked by unique restriction sites to provide a method for the precise assembly of modular combinations.

Figure 12:
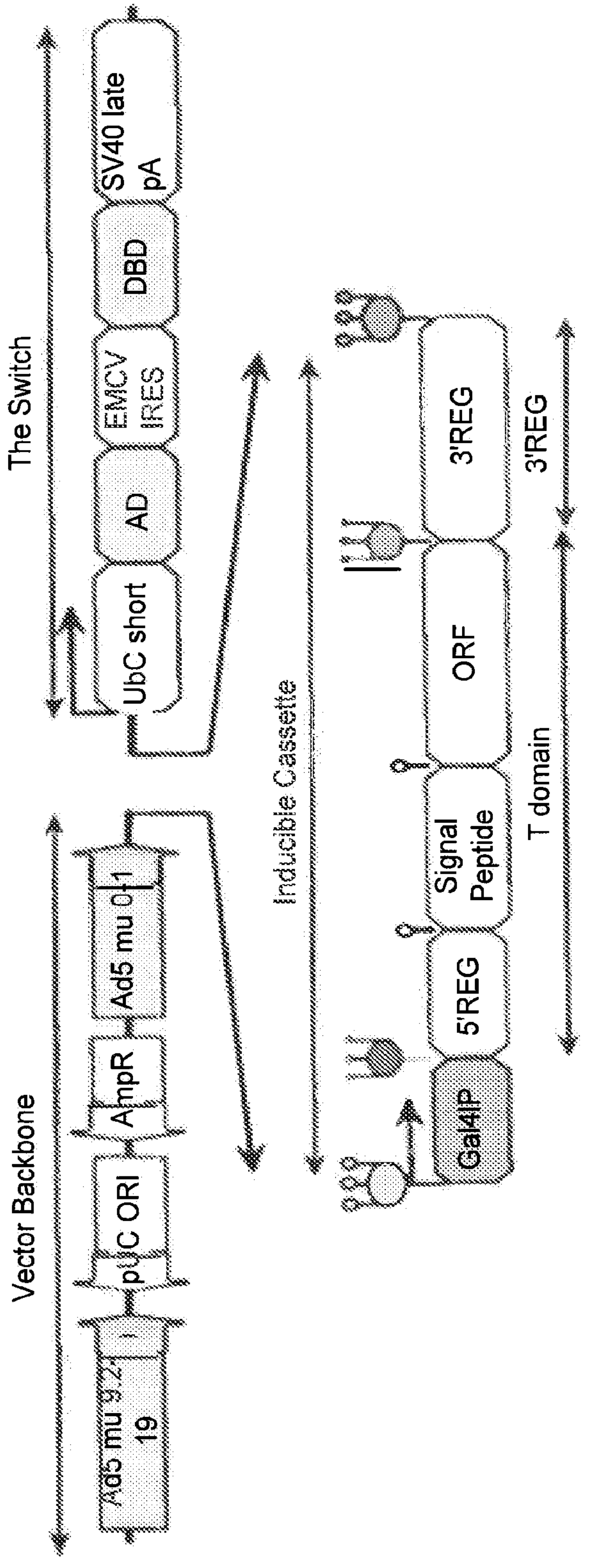
FIG. 12 shows a schematic diagram of adenovirus-compatible ULTRAVECTOR® backbone with switch and inducible modular synthetic gene.

Modular assembly was carried out in the context of a DNA backbone designed to accept synthetic genes. One example of an ULTRAVECTOR® backbone engineered for adenoviral packaging is depicted in FIG. 12 Combinatorial modular design combines well with adenoviral delivery of a therapeutic as it allows for the use of compact regulatory sequences which can be shorter than those found in nature.

In Vitro Assessment of Modular Combinations

TABLE 7

A matrix yielding 11 test vectors and DNA assembled

Figure 13:
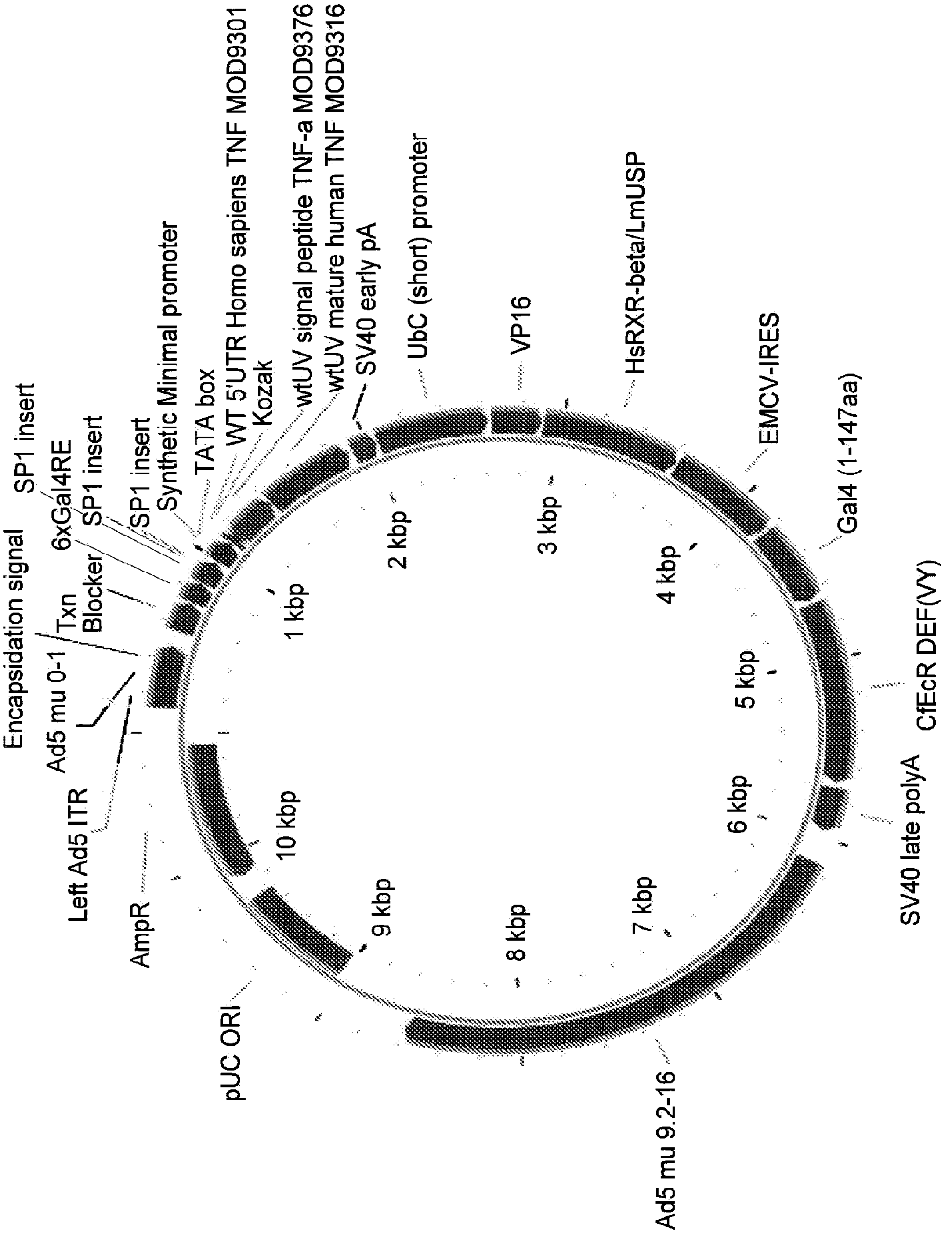
FIG. 13 shows an adenoviral vector map (Vector 43318) for a regulated promoter expression system comprising TNFwt 5'UTR, TNFwtUV signal peptide, TNFwt UV open reading frame (ORF), and 3' regulatory region of SV40e+pA.
Figure 14:
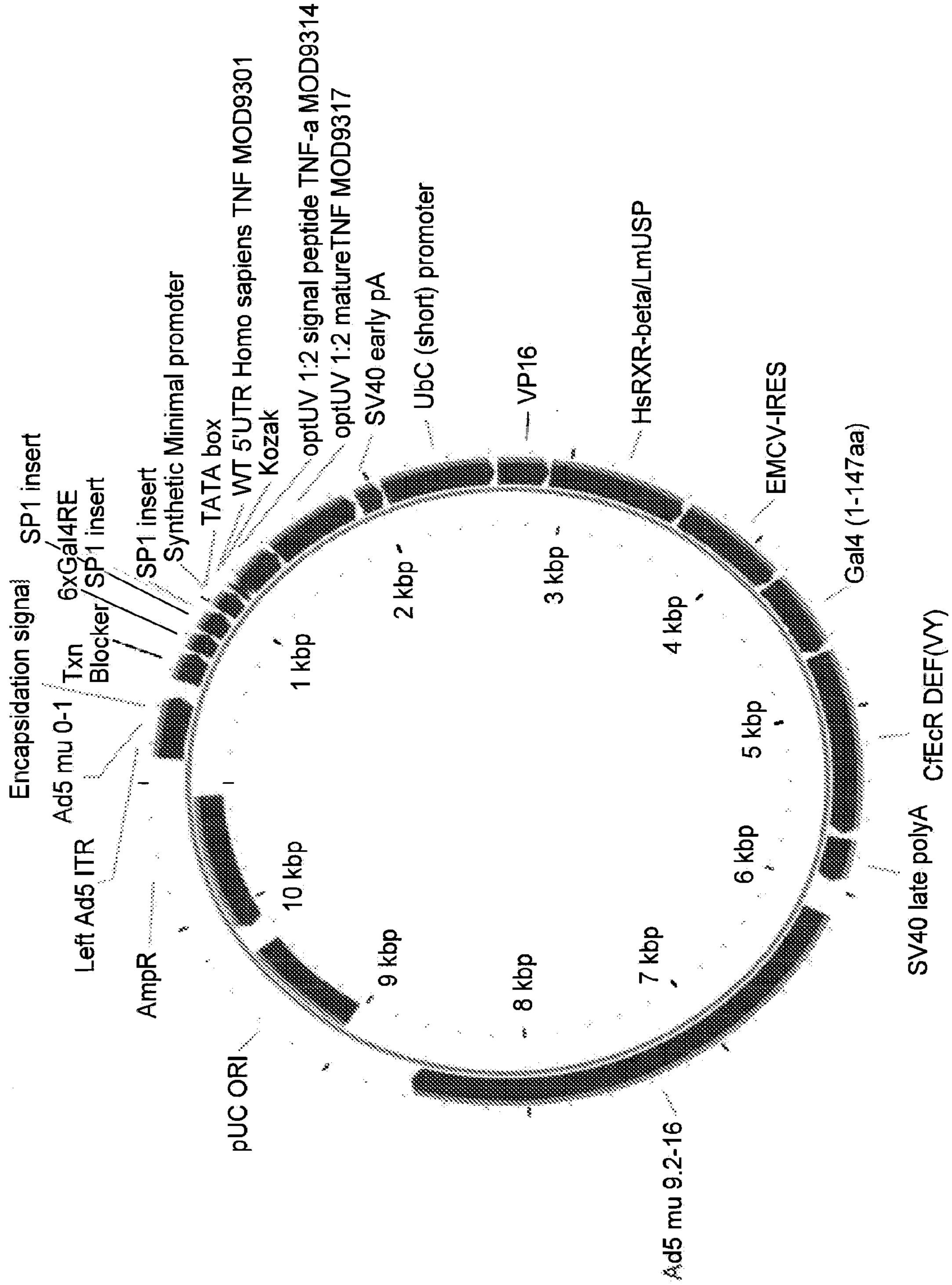
FIG. 14 shows an adenoviral vector map (Vector 43319) for a regulated promoter expression system comprising TNFwt 5'UTR, TNFoptUV signal peptide, TNFopt UV ORF, and 3' regulatory region of SV40e+pA.
Figure 15:
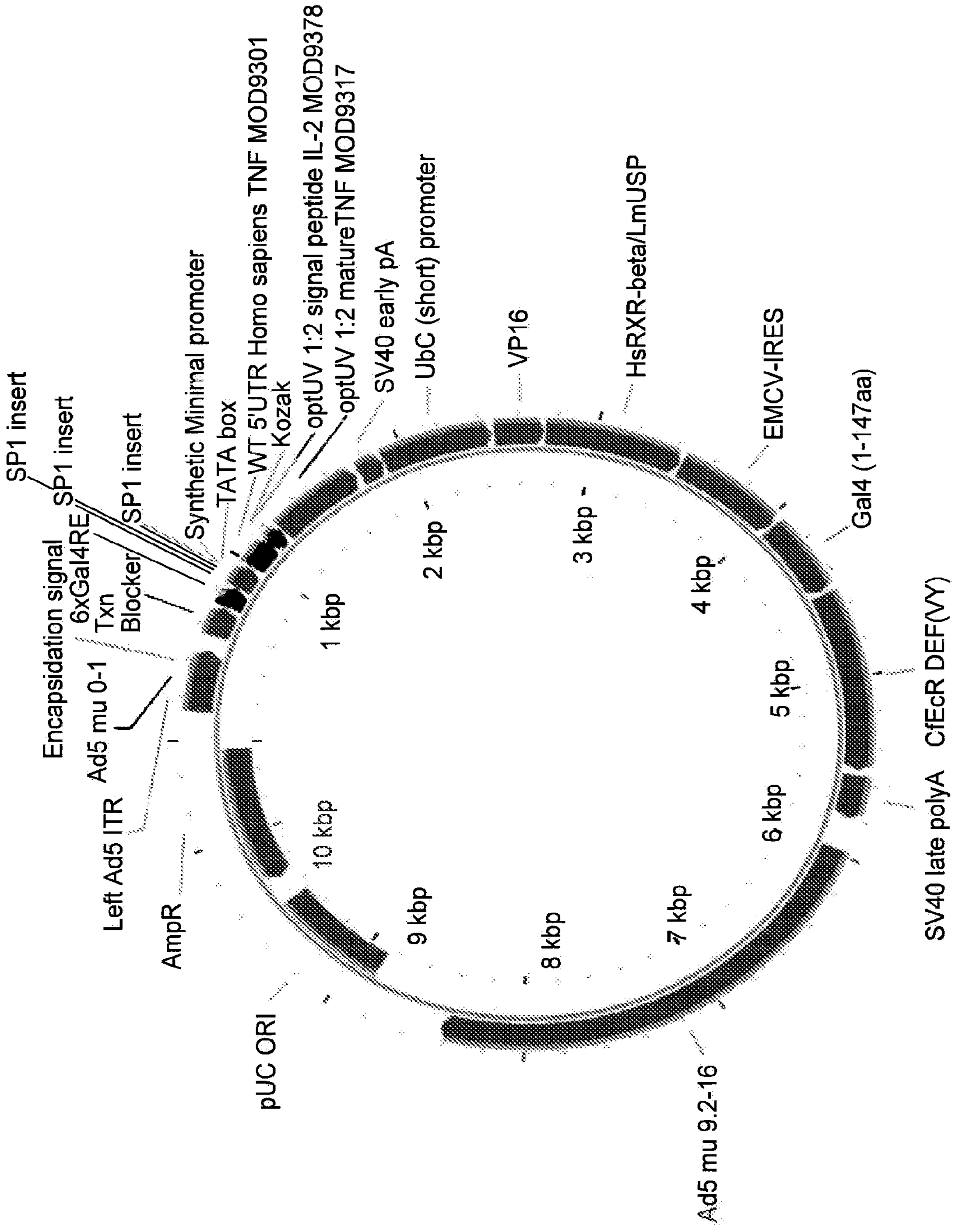
FIG. 15 shows an adenoviral vector map (Vector 43320) for a regulated promoter expression system comprising TNFwt 5'UTR, IL-2optUV signal peptide, TNFoptUV ORF, and 3' regulatory region of SV40e+pA.
Figure 16:
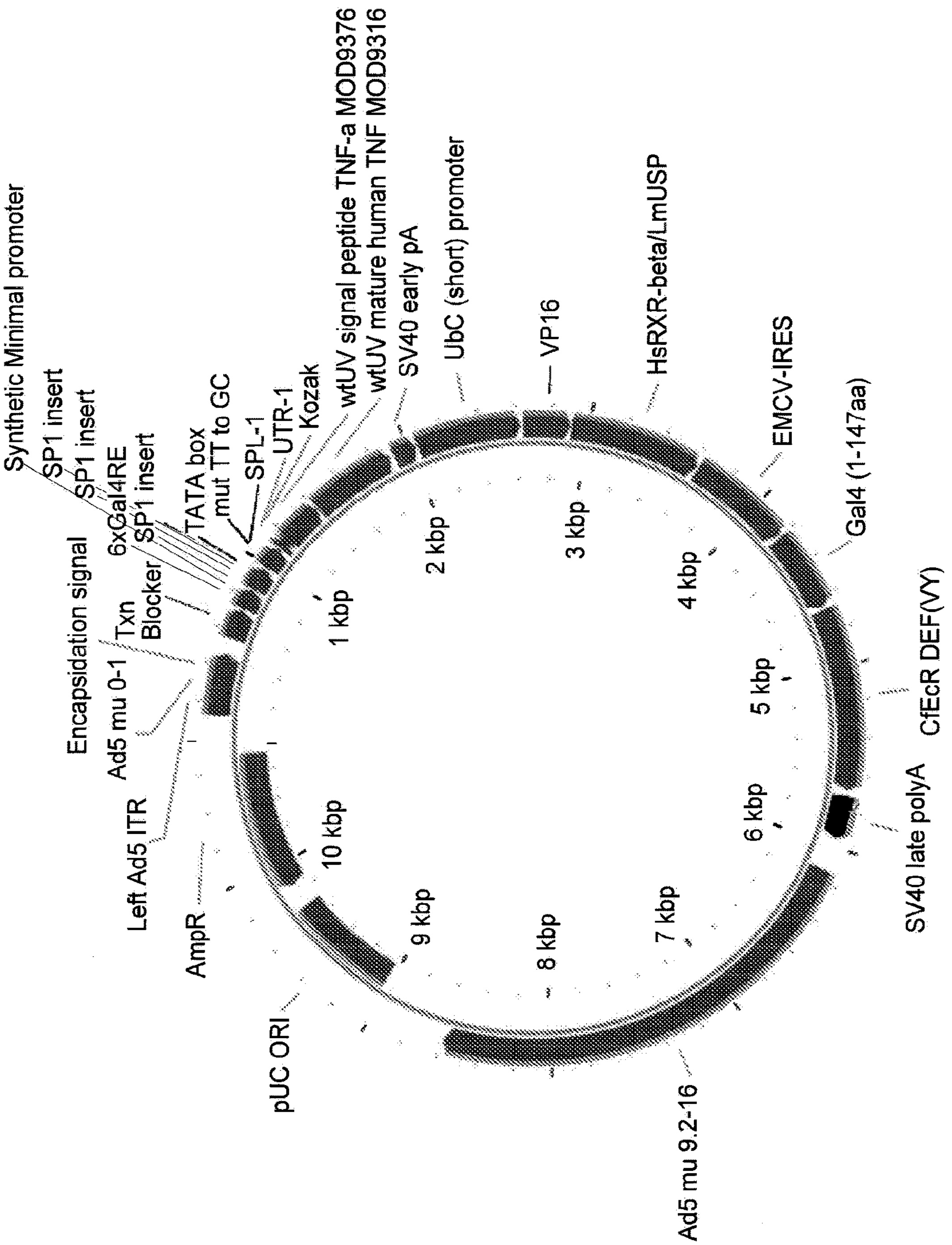
FIG. 16 shows an adenoviral vector map (Vector 43321) for a regulated promoter expression system comprising 5U2 5'UTR, TNFwtUV signal peptide, TNFwtUV ORF, and 3' regulatory region of SV40e+pA.
Figure 17:
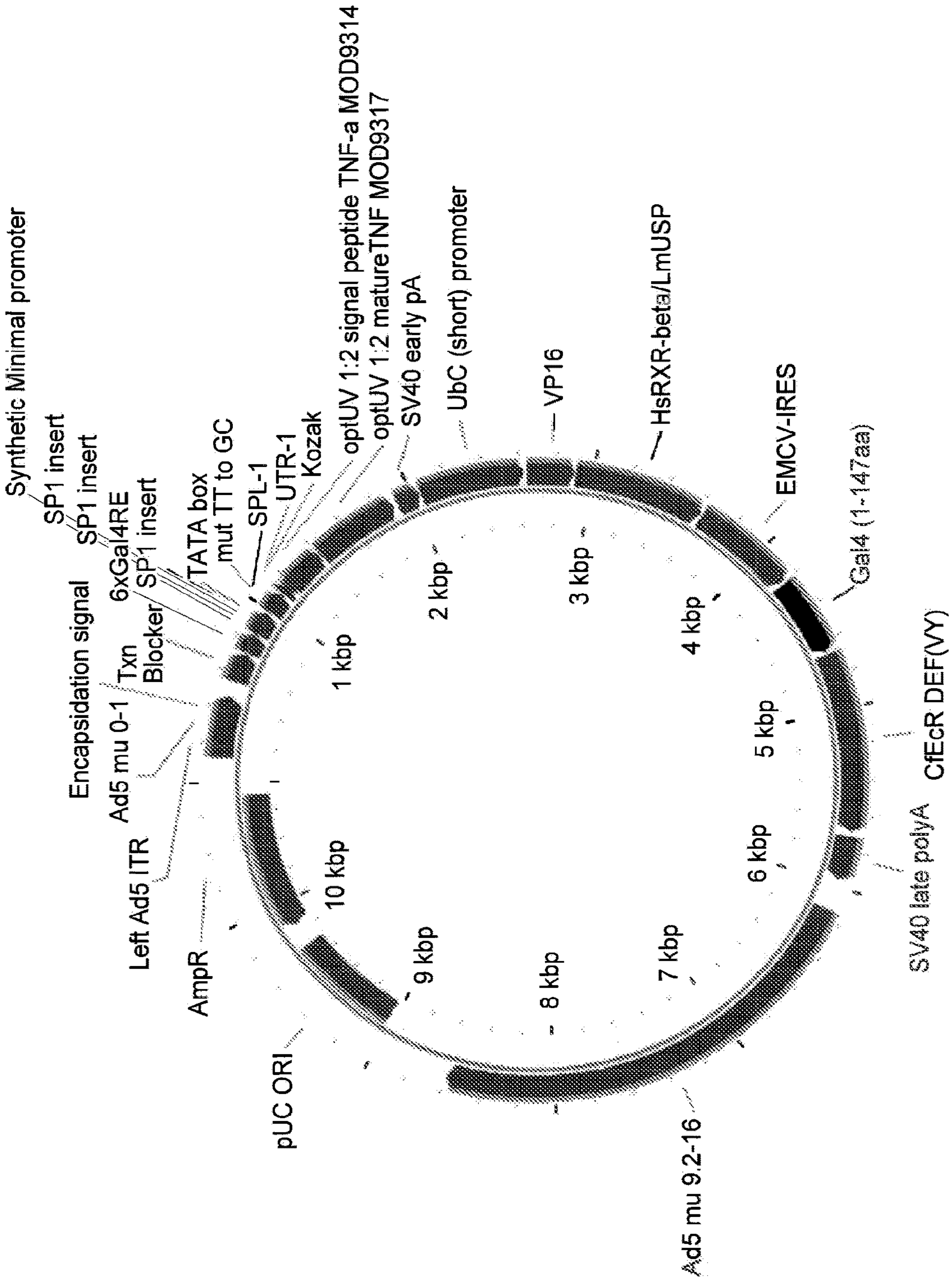
FIG. 17 shows an adenoviral vector map (Vector 43322) for a regulated promoter expression system comprising 5U2 5'UTR, TNFoptUV signal peptide, TNFoptUV ORF, and 3' regulatory region of SV40e+pA.
Figure 18:
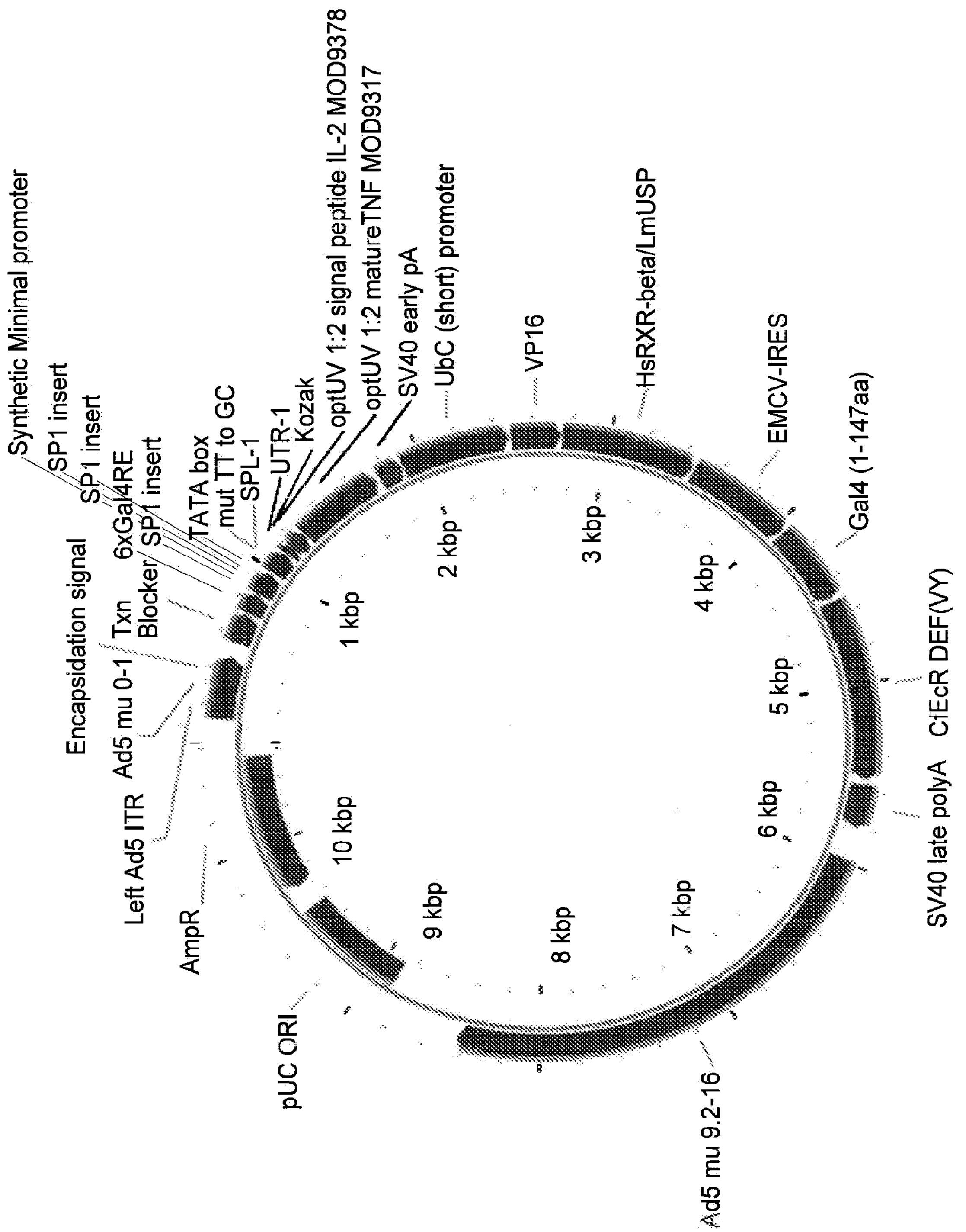
FIG. 18 shows an adenoviral vector map (Vector 43323) for a regulated promoter expression system comprising 5U2 5'UTR, IL-2optUV signal peptide, TNFoptUV ORF, and 3' regulatory region of SV40e+pA.
Figure 19:
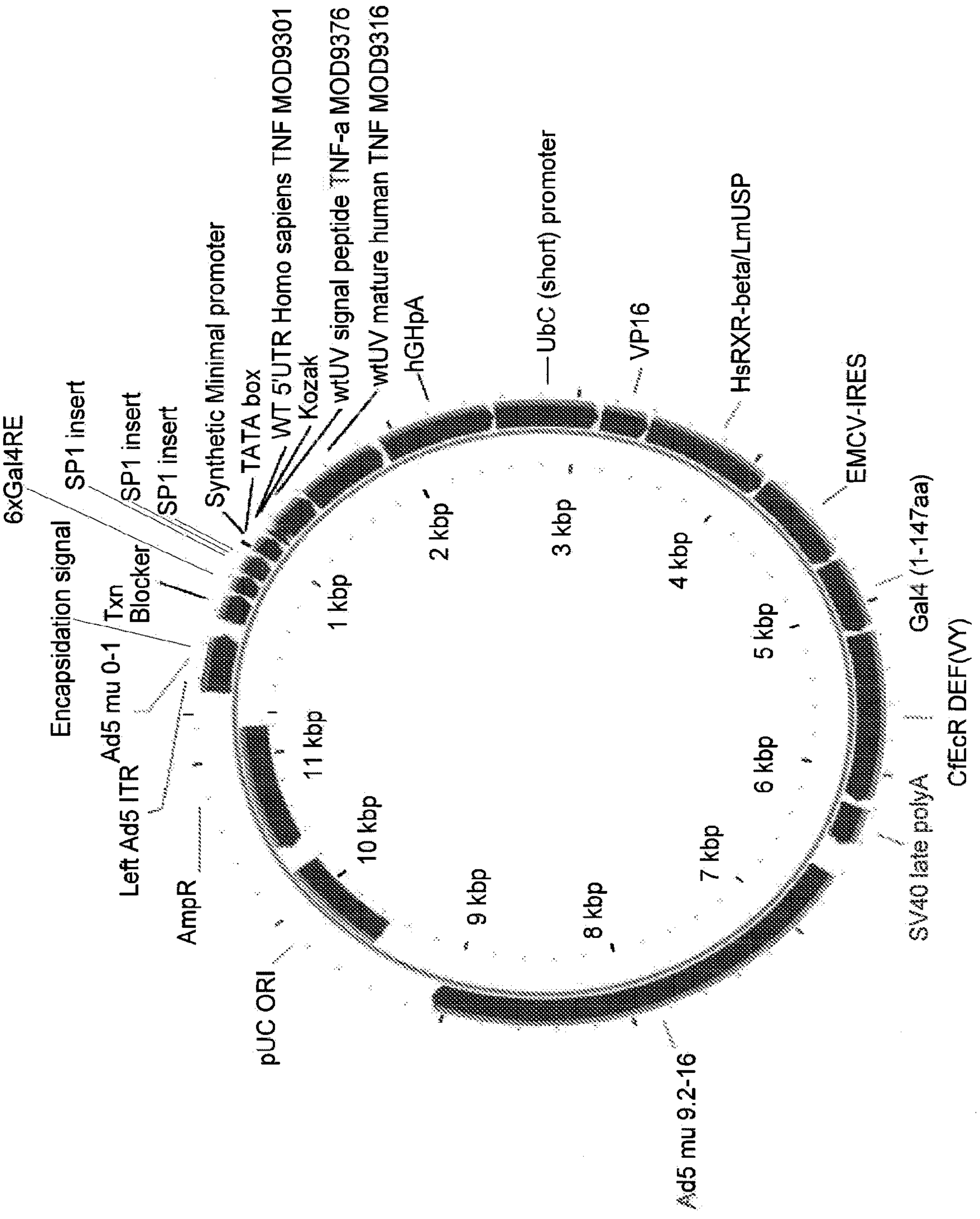
FIG. 19 shows an adenoviral vector map (Vector 43324) for a regulated promoter expression system comprising TNFwt 5'UTR, TNFwtUV signal peptide, TNFwtUV ORF, and 3' regulatory region of hGH+pA.
Figure 20:
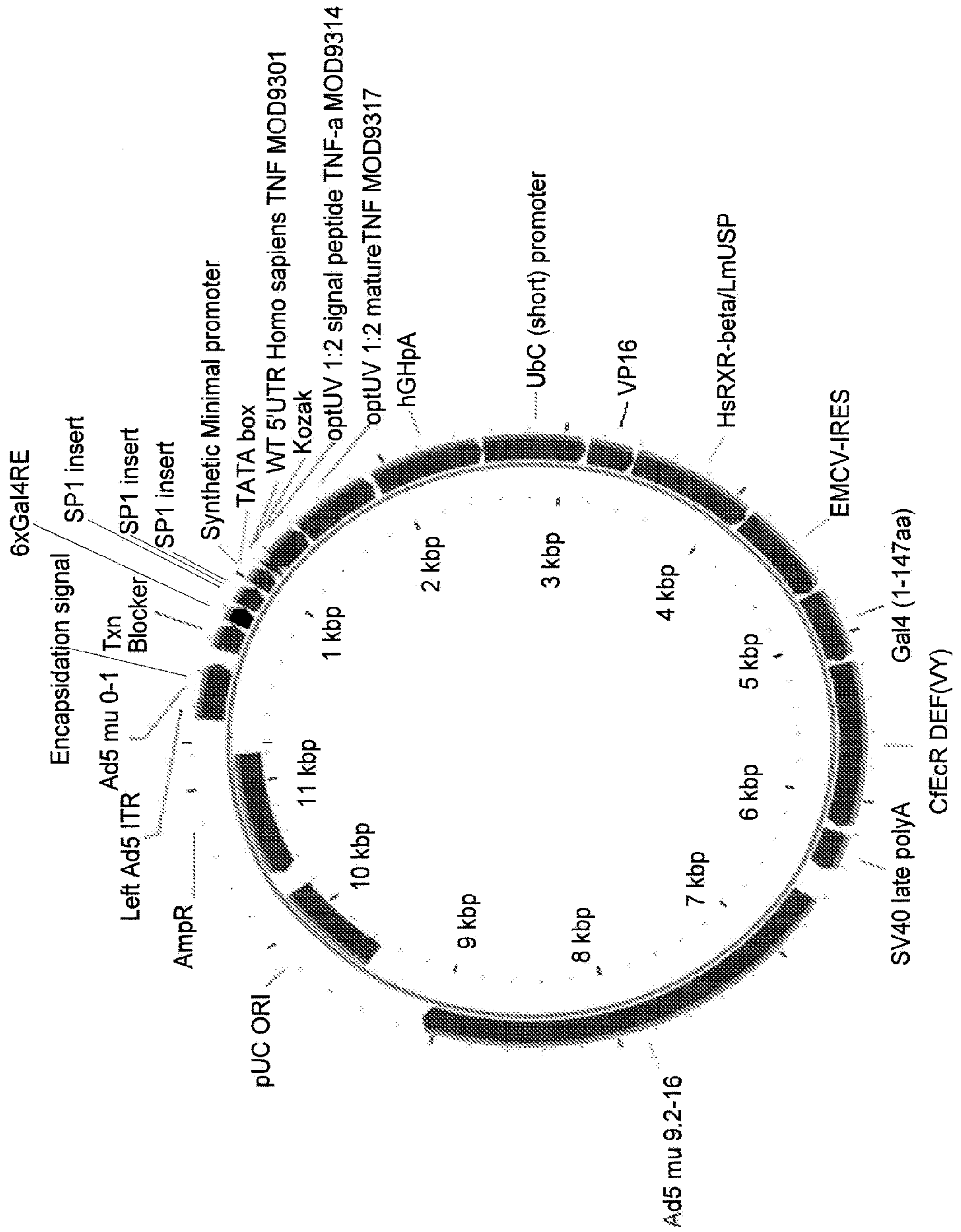
FIG. 20 shows an adenoviral vector map (Vector 43325) for a regulated promoter expression system comprising TNFwt 5'UTR, TNFoptUV signal peptide, TNFoptUV ORF, and 3' regulatory region of hGH+pA.
Figure 21:
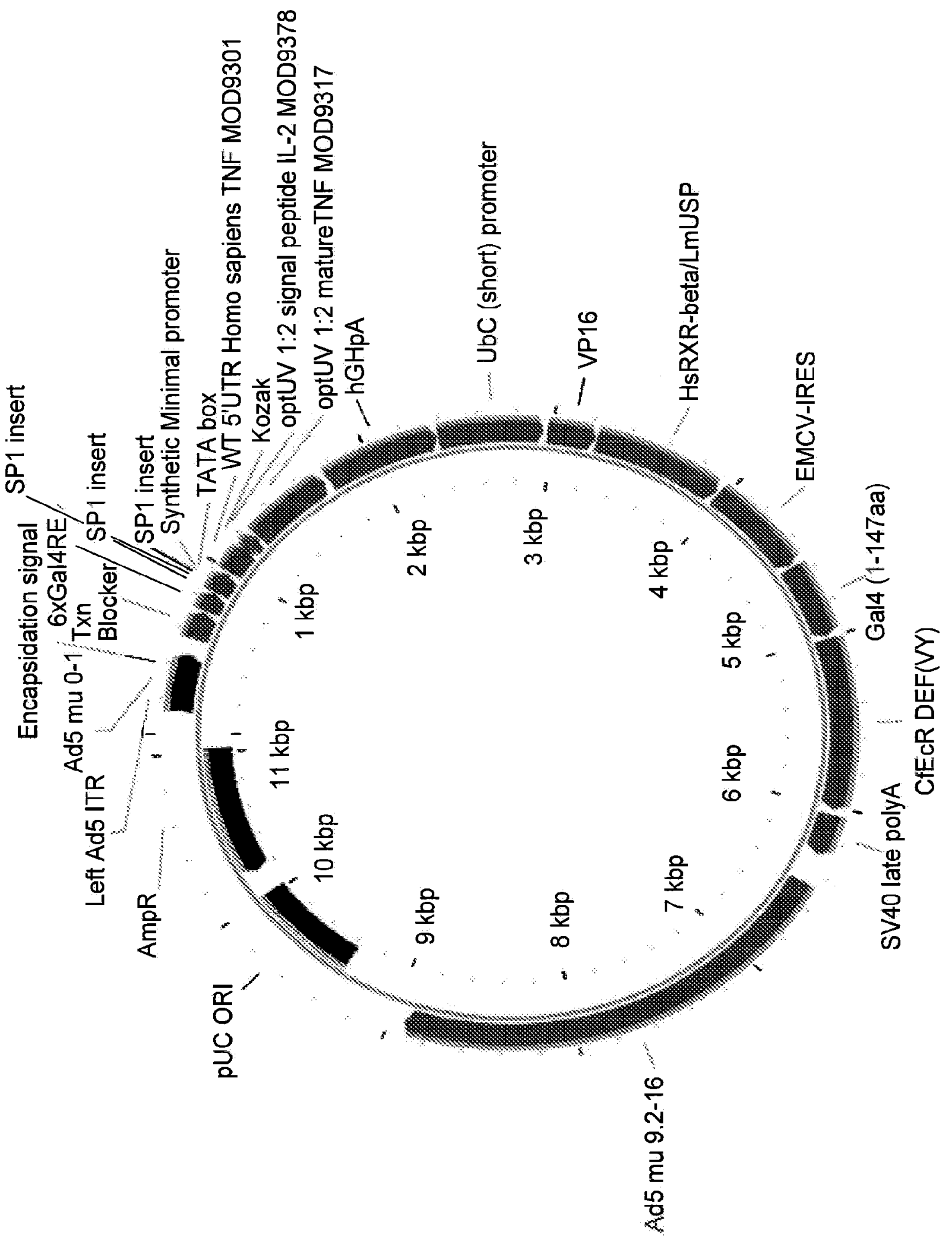
FIG. 21 shows an adenoviral vector map (Vector 43326) for a regulated promoter expression system comprising TNFwt 5'UTR, IL-2optUV signal peptide, TNFoptUV ORF, and 3' regulatory region of hGH+pA.
Figure 22:
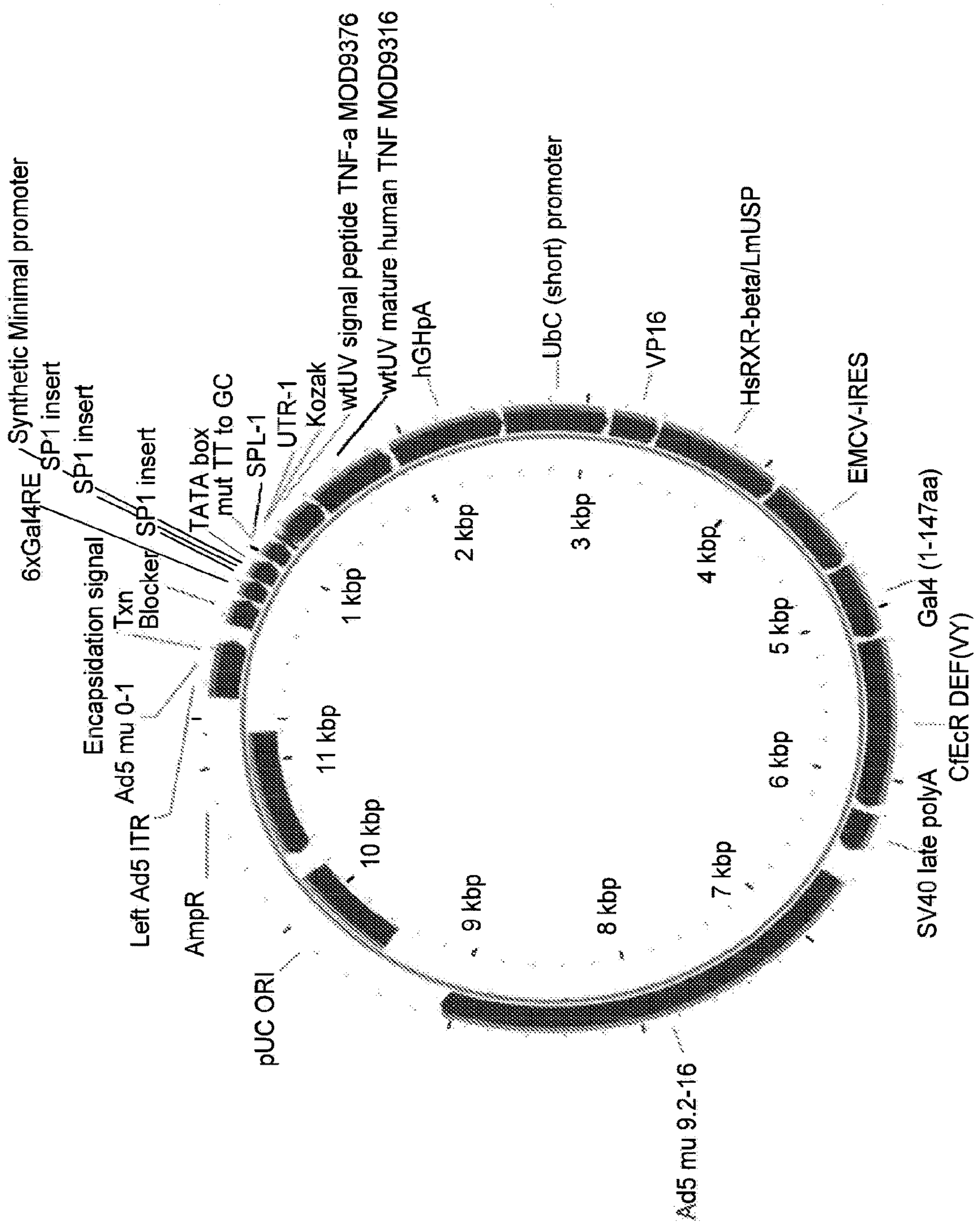
FIG. 22 shows an adenoviral vector map (Vector 43327) for a regulated promoter expression system comprising 5U2 5'UTR, TNFwtUV signal peptide, TNFwtUV ORF, and 3' regulatory region of hGH+pA.
Figure 24:
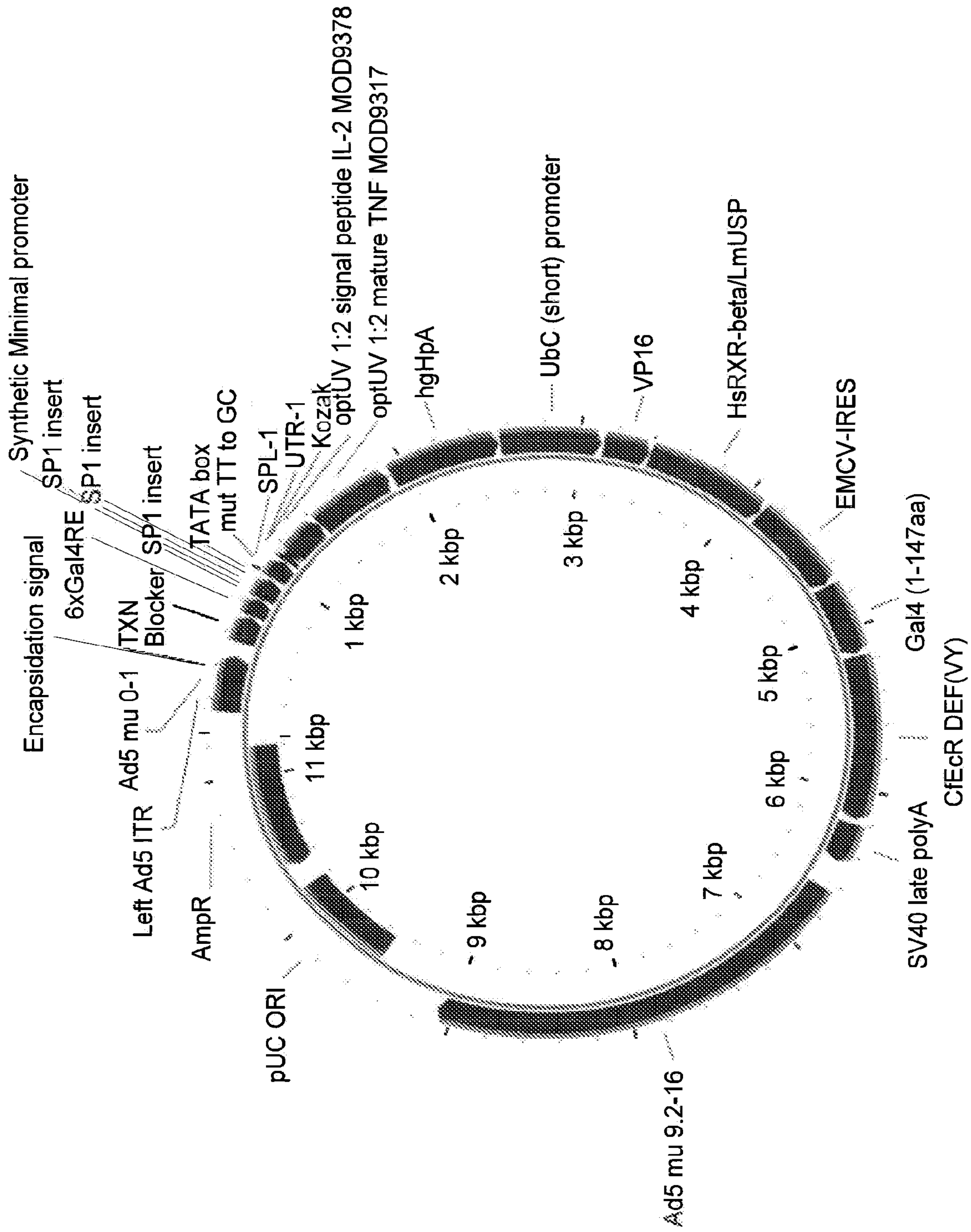
FIG. 24 shows an adenoviral vector map (Vector 43329) for a regulated promoter expression system comprising 5U2 5'UTR, TNFwtUV signal peptide, TNFwtUV ORF, and 3' regulatory region of hGH+pA.

| Vector | 5'UTR | Signal Peptide | ORF (CDS) | 3'Reg | FIG. |
|---|---|---|---|---|---|
| 43318 (17) | TNFwt (1) | TNFwtUV (4) | TNFwtUV (6) | SV40e + pA (8) | FIG. 13 |
| 43319 (18) | TNFwt (1) | TNFOptUV (1, 2)(5) | TNFoptUV (7) | SV40e + pA (8) | FIG. 14 |
| 43320 (19) | TNFwt (1) | IL-2optUV (3) | TNFoptUV (7) | SV40e + pA (8) | FIG. 15 |
| 43321 (20) | 5U2 (2) | TNFwtUV (4) | TNFwtUV (6) | SV40e + pA (8) | FIG. 16 |
| 43322 (21) | 5U2 (2) | TNFOptUV (1, 2)(5) | TNFoptUV (7) | SV40e + pA (8) | FIG. 17 |
| 43323 (22) | 5U2 (2) | IL-2optUV (3) | TNFoptUV (7) | SV40e + pA (8) | FIG. 18 |
| 43324 (23) | TNFwt (1) | TNFwtUV (4) | TNFwtUV (6) | hGH + pA (9) | FIG. 19 |
| 43325 (24) | TNFwt (1) | TNFOptUV (1, 2)(5) | TNFoptUV (7) | hGH + pA (9) | FIG. 20 |
| 43326 (25) | TNFwt (1) | IL-2optUV (3) | TNFoptUV (7) | hGH + pA (9) | FIG. 21 |
| 43327 (26) | 5U2 (2) | TNFwtUV (4) | TNFwtUV (6) | hGH + pA (9) | FIG. 22 |
| 43329 (28) | 5U2 (2) | IL-2optUV (3) | TNFoptUV (7) | hGH + pA (9) | FIG. 24 |

Vectors were transiently transfected into the HEK293T cell line to assess which modular combinations result in increased TNF-alpha output. To induce the expression of TNF-alpha, ligand or vehicle control was administered to cells. Supernatant was collected and TNF-alpha levels were measured via ELISA, To set a baseline approximating wild type, vector 43318 contains the UV conformed wild type TNF-alpha 5'UTR, signal peptide, coding sequence, and SV40pA 3' Reg. Individually, module changes of Opt(1,2) codon optimization of the TNF-alpha signal peptide or mature protein coding sequence result in incremental increases in protein secretion (vectors 43319, 43320). Additional modular substitution of the 5U2 5'UTR for the TNF-wt 5'UTR further elevates secretion levels (vectors 43322, 43323). Highest secretion of TNF-alpha is achieved when the wild type 5'UTR, signal peptide, and coding sequence modules are substituted with 5U2, IL2, and TNFOptUV respective mods (vector 43329).

Figure 25:
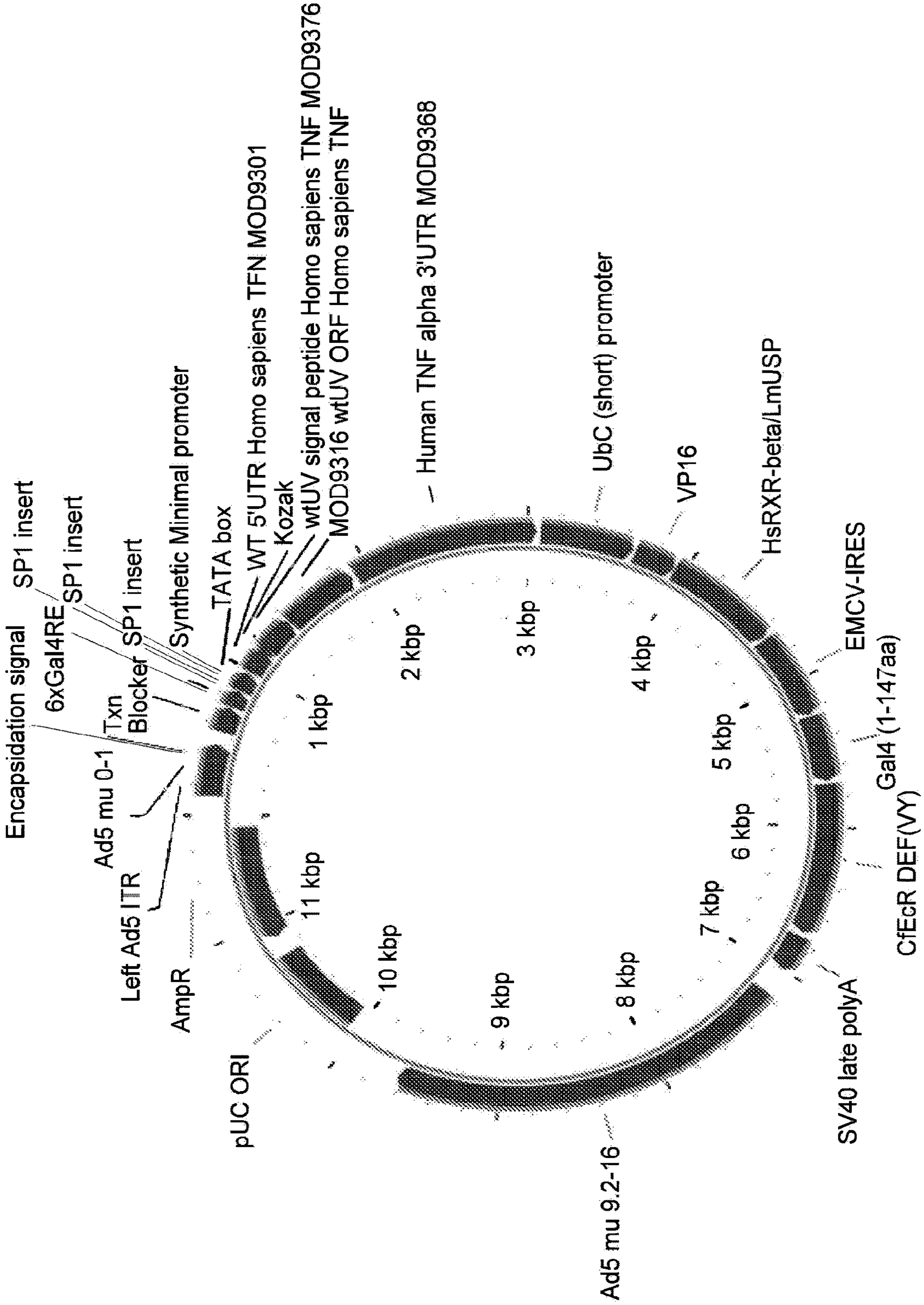
FIG. 25 shows an adenoviral vector map (Vector 43533) for a regulated promoter expression system comprising TNFwt5'UTR, TNFwtUV signal peptide, TNFwtUV ORF, and TNFwt 3'UTR.
Figure 26:
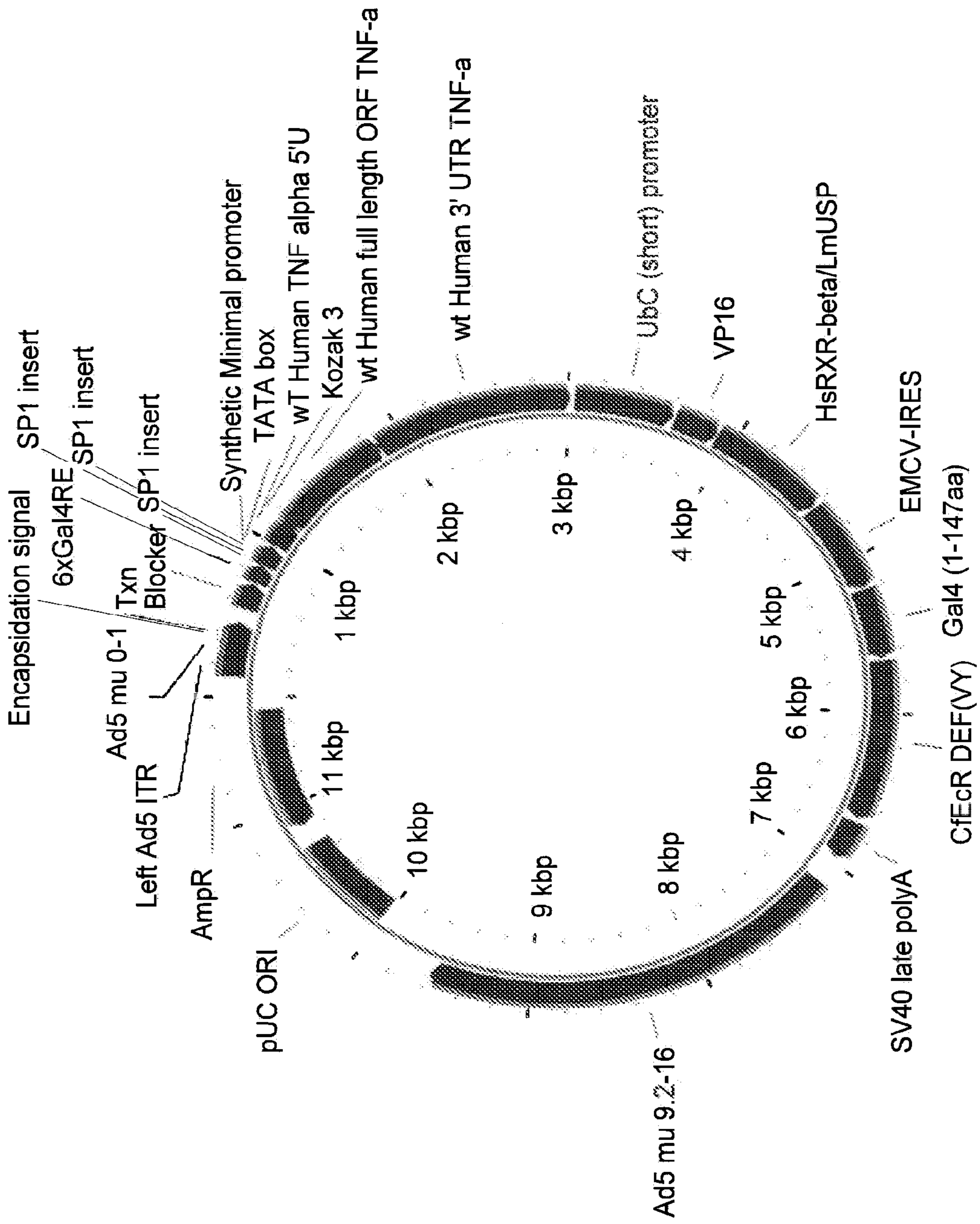
FIG. 26 shows an adenoviral vector map (Vector 43534) for a regulated promoter expression system comprising TNFwt 5'UTR, TNF full-length ORF, and TNFwt 3'UTR.
Figure 27:
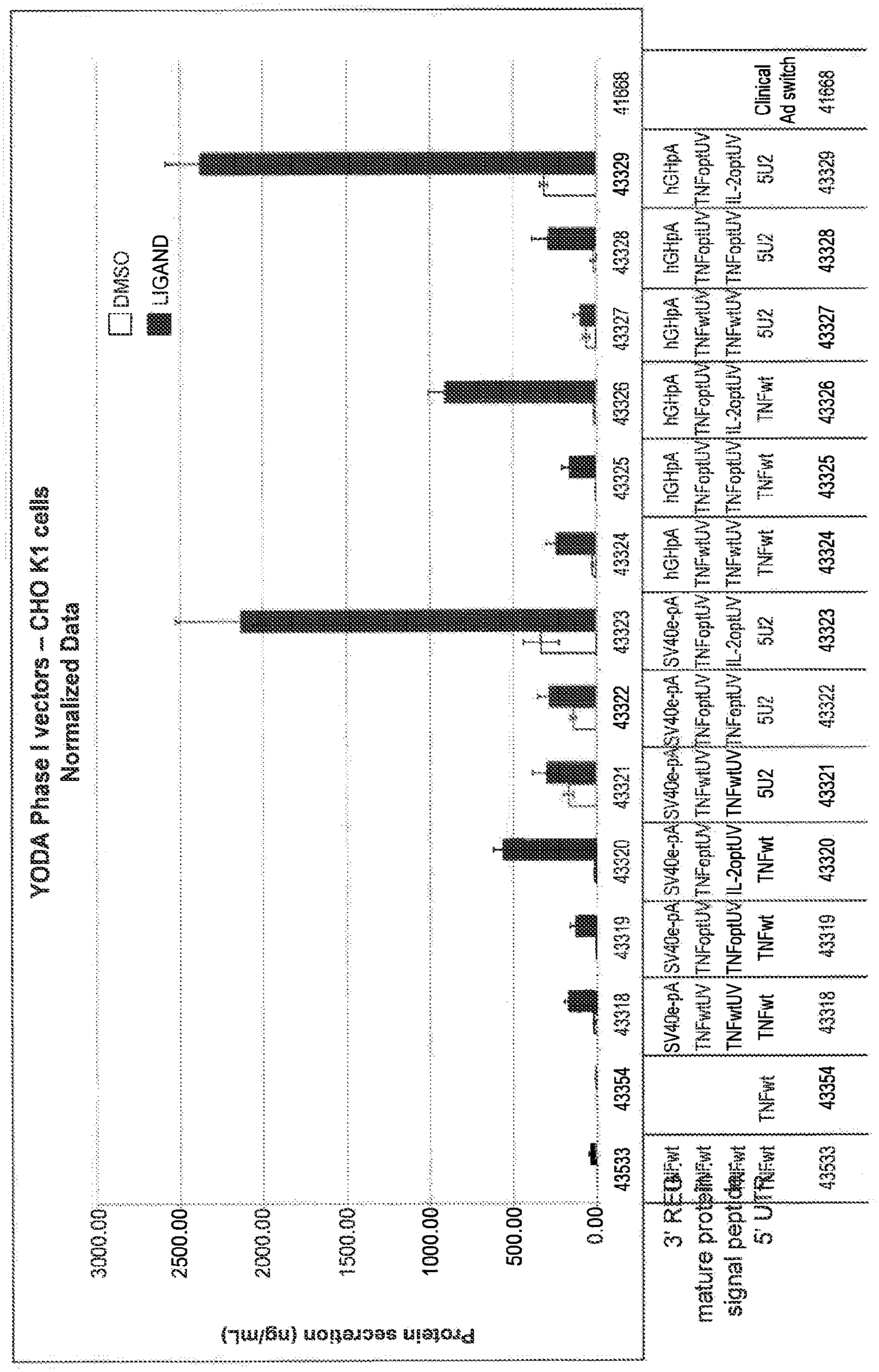
FIG. 27 shows a graph showing normalized secreted protein levels of TNF-alpha following transfection of HEK293 cells with vectors with varied PT3 components (−/+) induction via RHEOSWITCH® ligand.
Figure 28:
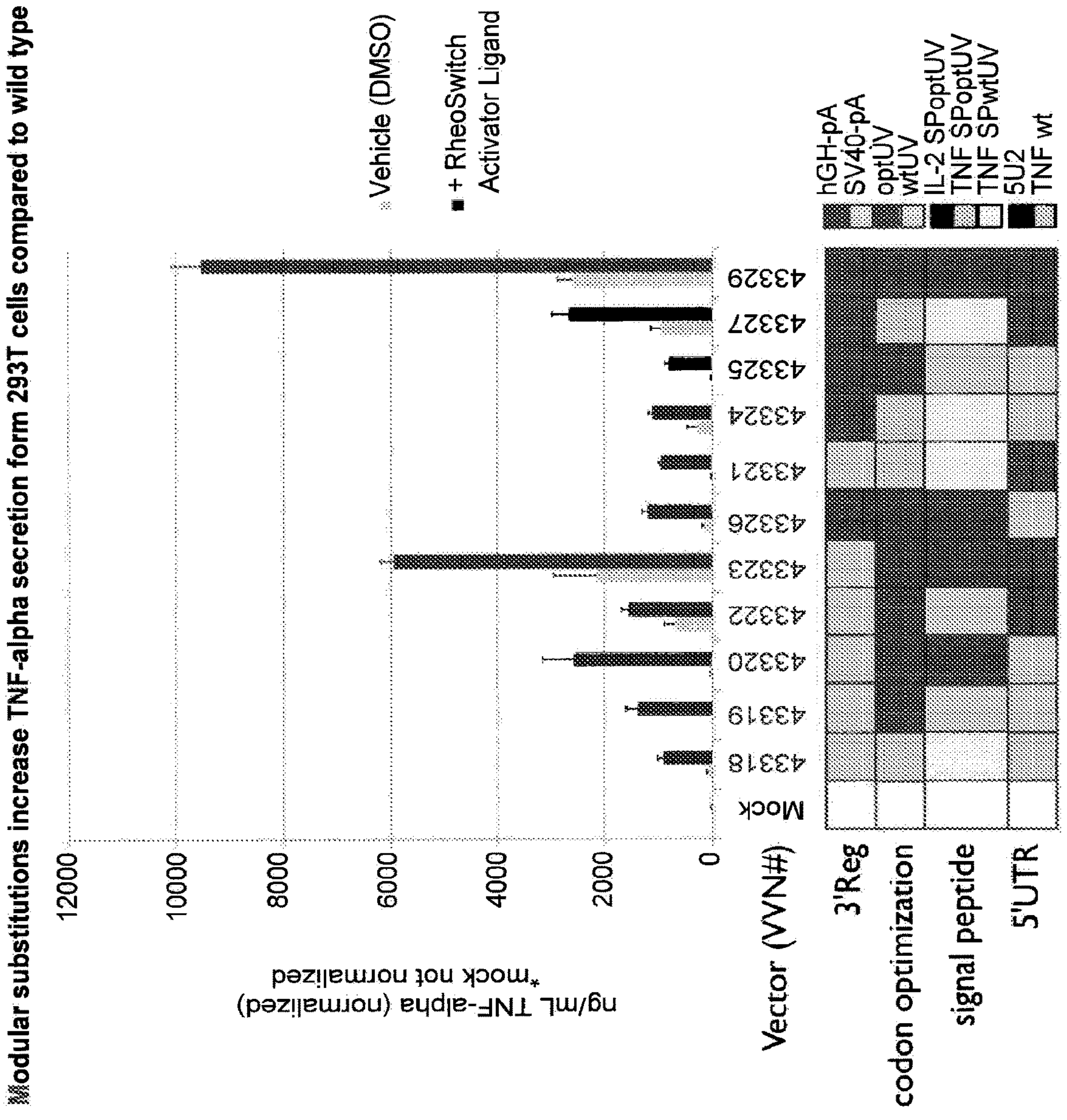
FIG. 28 shows a graph depicting normalized secreted protein levels of TNF-alpha following transfection of CHO—K1 cells with vectors with varied PT3 components (−/+) induction via RHEOSWITCH® ligand.
Figure 29:
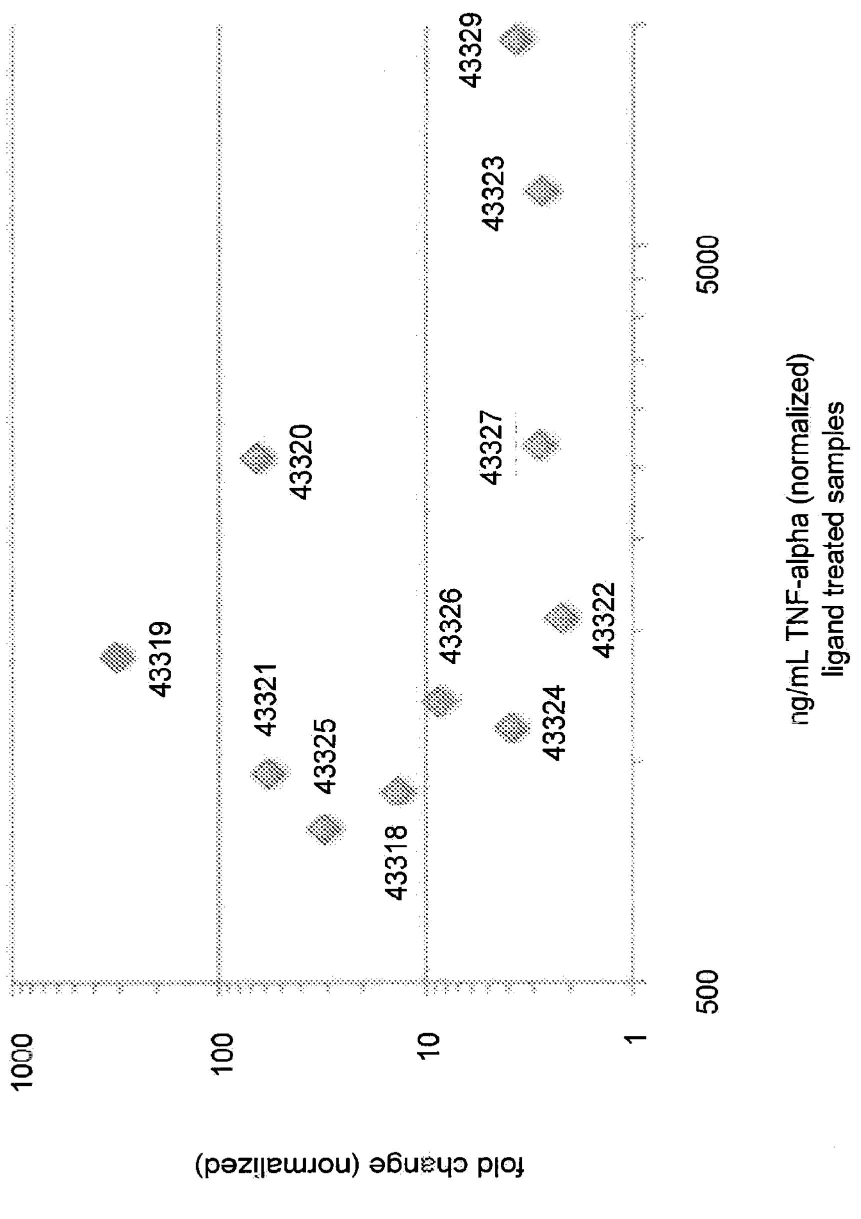
FIG. 29 shows fold differences in TNF-alpha secretion following transfection of HEK293 cells.
Figure 30:
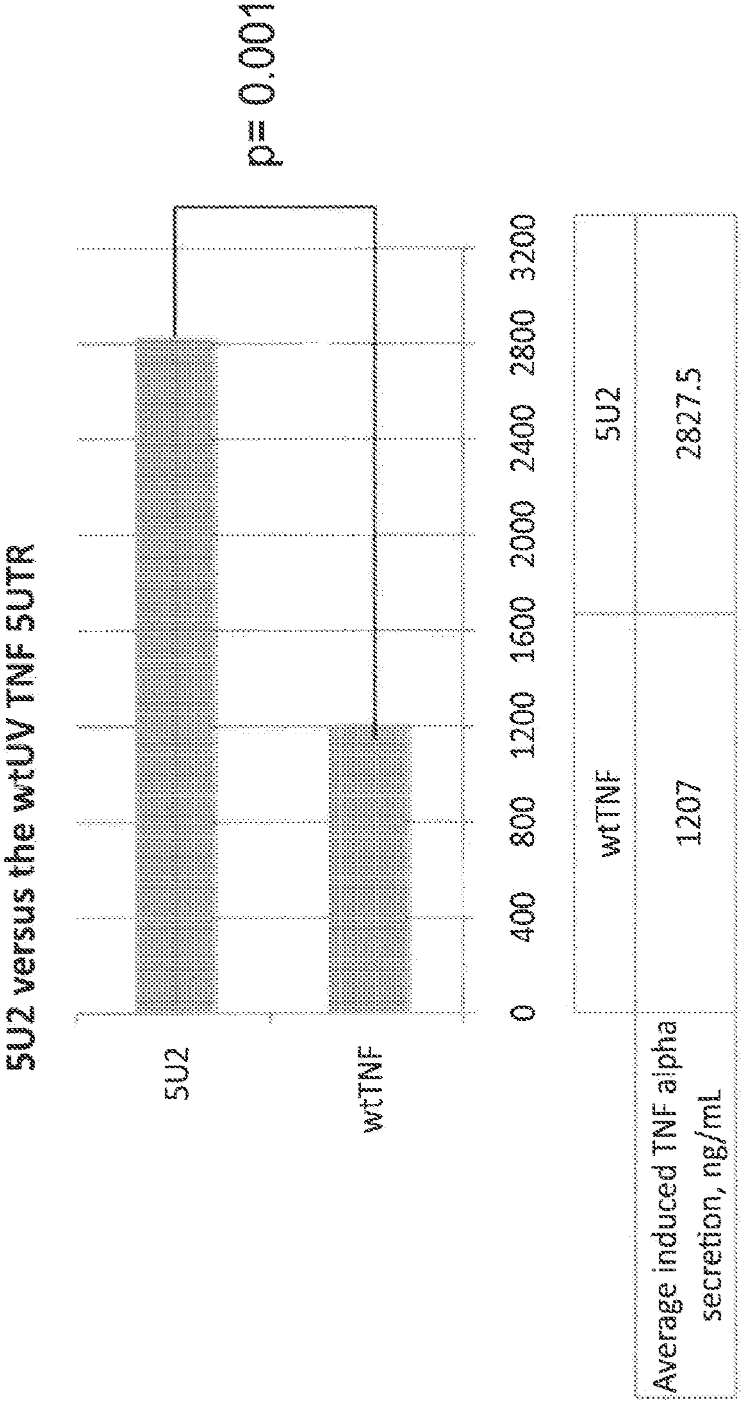
FIG. 30 shows protein secretion differences between 5U2 5'UTR and wtUV TNF-alpha 5'UTR.

To demonstrate that the increased secretion of TNF-alpha is not cell type dependent, the 11 experimental vectors were transfected into CHO—K1 cells and 2 control vectors were added (see FIG. 27). Vector 43534 (FIG. 26) and vector 43533 (FIG. 25)) contain wild type TNF-alpha modules to serve as controls. Vector 43534 is composed of the wild type TNF-alpha sequence without the ULTRAVECTOR® assembly pivots present. Notably, the presence of ULTRAVECTOR® assembly pivots does not adversely effect the production and secretion of THF-alpha. In this data set we also demonstrate that substitution of the TNF-alpha wild type 3' Reg with either the SV40e or hGH containing polyA modules results in an increase in TNF-alpha secretion. Maximal TNF-alpha output was achieved with the 5U2, IL2 signal peptide, TNFOptUV, and hGHpA combination. The data from CHO—K1 cells exhibits the same trend of incremental increase with each module substitution of 5U2 in the 5'UTR, IL-2 signal peptide, and TNFOptUV coding sequence. Interestingly, the magnitude of increase is slightly different in the two cell types. This illustrates that while the modules perform similarly in each cell type, physiologic differences in specific cell or tissue type may influence the magnitude of modular substitution effect. Increasing the combinatorial matrix to include more modules in each category may allow for identification of superior combination depending cell type or tissue tested. Examples of additional modules that could be included in a larger matrix are included as SEQ ID NOs: 41-46.

Example 4. Assessment of Therapeutic Candidate in an Animal Model

To demonstrate the effectiveness of inducible optimized TNF-alpha constructs to treat cancer, for instance, prostrate cancer or head and neck cancer, a head and neck cancer mouse model of the disease can be employed. A single gene knockout of Smad4 has been demonstrated to yield a spontaneous model of malignant human head and neck squamous cell carcinoma (HNSCC). (PMID: 19841536)

In the absence of such a mouse strain, human derived HNSCC tumor cells can be implanted into nude mice. Post tumor establishment the optimized TNF-alpha constructs can be introduced into the tumor with adenovirus. Varying doses of ligand can be administered to the mouse to regulate the level of optimized TNF-alpha produced. Tumor burden will be measured and tumor necrosis assessed to identify potential therapeutic candidates from the optimized TNF-alpha constructs.

Example 5. Therapeutic Embodiment Example

An engineered TNF-a□lpha transgene is administered to a patient by intratumoral injection of a non-replicative adenovirus DNA vector. This gene program encodes the mammalian-codon optimized mature cytokine, fused with a codon-optimized signal peptide for IL-2. In turn, the transgene cds (IL-2 SP+ TNF-alpha) is flanked by a wildtype TNF-alpha 5'UTR and the SV40 3' Reg+poly(A) signal, and its expression is controlled by RheoSwitch technology via administration of a cautiously “dialed-in” dose of activator ligand (i.e., the DNA embodied in vector VVN-43320, see FIG. 15). Preliminary data show that this combination of DNA elements yields the highest possible induction of secreted TNF-alpha while still affording “tight” and “non-leaky” control of its expression. That is, the uninduced, basal level of expression remains low in this transgene configuration, and would be less likely to exert uncontrolled, off-target effects on the patient.

In an alternative embodiment of the invention, the engineered TNF-alpha □transgene is administered by adenovirus to a patient in a modular DNA configuration similar to vector VVN-43329 (see FIG. 24), which exhibits both high basal expression and highest transgene expression. This DNA employs the artificially engineered 5'U2 and the hGH poly(A) signal, as well as full mammalian codon optimization and the IL-2 signal peptide. Control of systemic toxicity in the patient is achieved by use of a low adenovirus MOI in the intratumoral injection. To a lesser extent, expression level and temporal control is also modulated through the RheoSwitch activator ligand. Additional control of this gene product’s distribution could be achieved through incorporation of tissue-specific miRNA response elements that could prohibit off-target expression in the vital organs, or through artificially engineering the adenoviral capsid for enhanced tropism.

Figure 23:
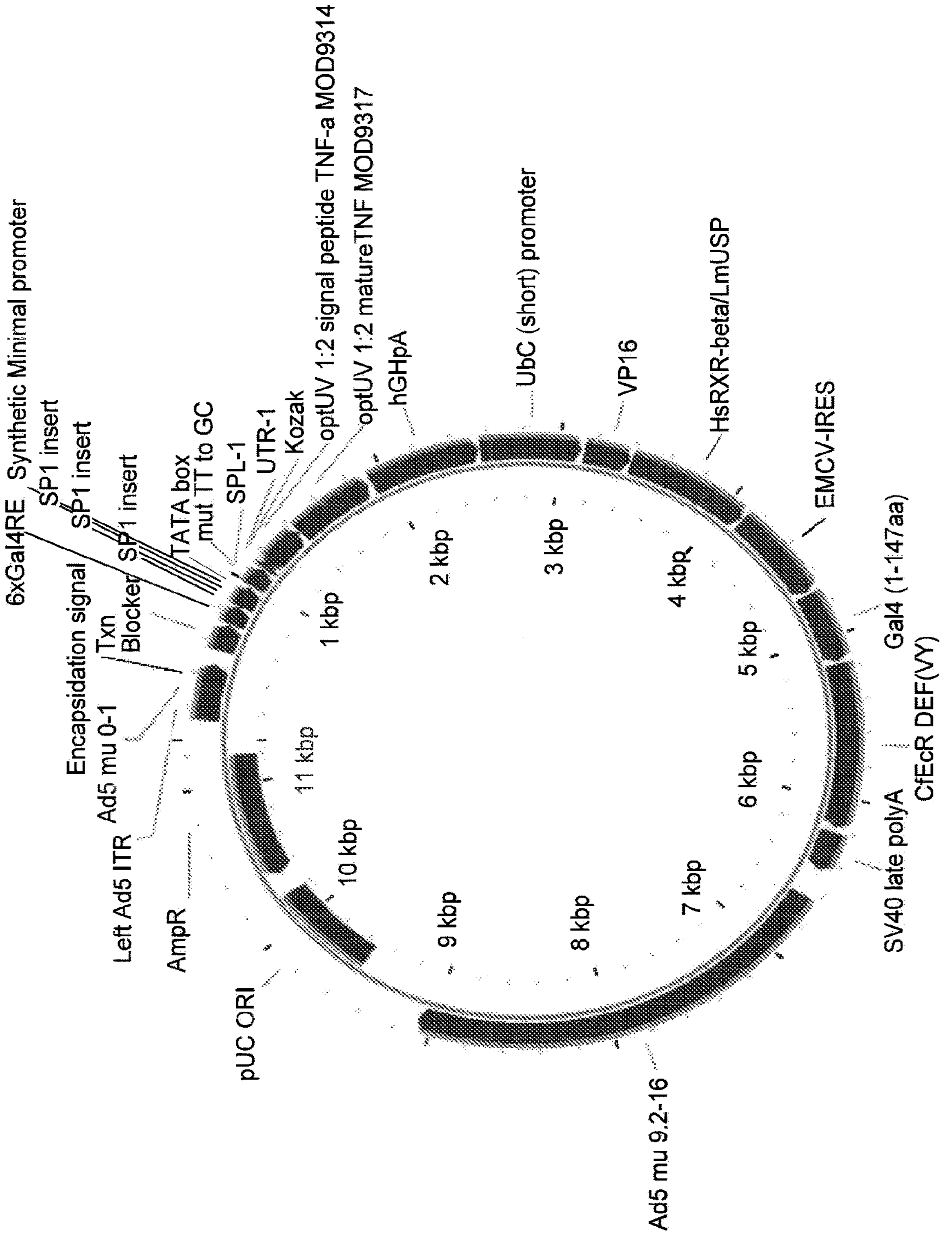
FIG. 23 shows an adenoviral vector map (Vector 43328) for a regulated promoter expression system comprising 5U2 5'UTR, TNFwtUV signal peptide, TNFwtUV ORF, and 3' regulatory region of hGH+pA.

In an additional embodiment of the invention, the engineered TNF-alpha □transgene is similar to the DNA in VVN-43328 (FIG. 23), which is hypothesized to confer high stability to the artificial mRNA through the 5'U2 element. However, this construct does not make use of an IL-2 signal peptide for enhanced secretion, and it retains wild-type sequence from DNA that encodes the N'-terminus of TNF-alpha. For unknown reasons, high level secretion of artificial TNF-alpha□ could well prove to be detrimental to patient outcomes regardless of context, whereas the natural mechanism of “cytokine shedding” via metalloproteinases might limit patient toxicity by confining the factor to its tumor milieu. If natural shedding of exogenous TNF-alpha D still demonstrates off-target effects, its ectodomain stalk could be truncated by mutation to prohibit solubilization by native proteases, and the factor would potentiate activity through cell-cell contacts as a de facto Type II transmembrane protein. Alternatively, a transgene similar to the construct described by vector VVN-43328 could encode a constitutively expressed TNF-a□lpha with a mutated stalk ectodomain containing a cleavage site for an exogenous protease. This exogenous protease, would, in turn be under a RheoSwitch technology-controlled promoter element, only to be expressed in the presence of the activator ligand. Thus, cleavage and in vivo solubility (but not surface expression) of the TNF-a□lpha will be controlled through modular transgene elements.

Example 6. Anti-Tumor Efficacy of Ad-RTS-IL-12

The anti-tumor effect of Ad-RTS-IL-12 has been evaluated in a series of murine tumor models of melanoma, colorectal, pancreatic, breast, lung and renal cancers. An exemplary dose response experiment is shown below. Immuno-competent female C57bl/6 mice (6-8 week old) were inoculated subcutaneously with B16F0 murine melanoma cancer cells. Eleven days after tumor cell inoculation, when macroscopic tumor nodules were evident (tumor volumes averaged approx. 40 $mm^3$), the mice were separated into groups of 5 animals each. There were 9 groups including: control saline treated; activator ligand treated; Ad-RTS-mIL12 (1ee10 vp) alone and 6 groups were treated with different doses of vector Ad-RTS-mIL-12 (1e7, 1e8, 1e9, 5e9, 1e10, 5e10 viral particles) plus activator ligand. Mice in the +ligand groups were provided 100 mg/kg activator ligand in 2018 Teklad Global 18% Protein Rodent Diet (Harlan Laboratories) chow (1000 mg ligand/kg chow) one day before the vector administration. The mice in control groups received 2018 Teklad Global 18% Protein Rodent Diet chow. A single administration of Ad-RTS-mIL12 in 100 ul PBS was injected into tumor on day 12. Tumor volume and body weights were measured every 2-3 days using calipers and a weight scale, and the animals were followed until control tumors reached 2000 $mm^3$. Data were uploaded into Study Log animal study software.

As shown in FIG. 31, substantial anti-tumor effect was observed at Ad-RTS-IL-12 doses above 1ee8 vp (range 73-99%). The lowest dose of Ad-RTS-IL-12 tested, 1ee7 vp, did not demonstrate anti-tumor effect. In the absence of activator ligand, high dose Ad-RTS-IL-12 at 1ee10 vp showed no effect, illustrating the requirement for combination of both Ad-RTS-IL-12 and activator ligand. Treatment of ligand by itself showed no effect. Therefore, this study illustrates the potent anti-tumor effects mediated by AdRTS-IL-12 in combination with activator ligand.

Body weight analyses are presented in FIG. 32. Animals treated at the highest dose level (5ee10 vp) of Ad-RTS-IL-12 showed transient weight loss on day 19, but recovered by day 26. Animals in the treatment other groups did not show any clear dose response relationship and only minor changes in weight gain were observed.

Example 7. Efficacy of Ad-RTS-IL-12 in the Lewis Lung Cancer Model

Female, 6- to 8-week-old C57b/6 immunocompetent mice were inoculated subcutaneously (s.c.) with murine Lewis lung carcinoma cells (LLC). Five days post cell inoculation, the mice were randomized and assigned to treatment and control groups (n=5) for a total of four groups—no treatment (control), activator (RG-115932) alone, AdRTS-mIL12 alone and Ad-RTS-mIL12 plus activator. The cohorts receiving activator (L) were fed (2018 Teklad Global 18% Protein Rodent Diet (Harlan Laboratories) chow blended with activator (1000 mg/kg chow) ad libitum. Cohorts receiving treatment with Ad-RTS-mIL12 alone or no treatment continued to receive a regular diet. Treatment was initiated when the tumor reached 28±6 $mm^3$. The Ad-RTS-mIL12 (1e10 vp/100 ul in PBS) was given to mice through intratumoral (i.t.) injection on Day 6, 9 and 13 post tumor cell inoculation. Activator chow (L) was started to given to mice 24 hr prior to vector administration. Tumor size and body weight of each mouse were monitored three times a week using calipers and a weight scale until the end of experiment. The experiment was terminated when the mice tumor size exceeded >1200 $mm^3$. Data were uploaded into Study Log animal study software.

The post treatment tumor volume is shown in FIG. 33A. The Lewis lung tumor bearing mice in control and activator (L) alone groups displayed approximately similar tumor growth kinetics. Three doses of Ad-RTS-mIL12 alone led to intermediate tumor growth. Importantly, Ad-RTS-mIL12 with activator (L) produced marked tumor growth inhibition (78%) relative to control group. This data suggests Ad-RTS-mIL12 in the presence of activator inhibits Lewis lung tumor growth. Body weight was monitored as an indicator of toxicity. No major body weight loss was found during the course of the experiment.

Example 8. Anti-Tumor Efficacy of Ad-RTS-IL-12 in a Melanoma Model

Female, 6- to 8-week-old C57b/6 immunocompetent mice were inoculated subcutaneously (s.c.) with murine melanoma cancer cells (B16F0). Ten days post cell inoculation, the mice were randomly assigned to treatment and control groups (n=5) for a total of nine groups: no treatment (control), activator (L) (RG-115932) alone, and AdRTS-mIL12 alone, and Ad-RTS-mIL12 with different activator dose (50, 100, 250, 500 and 1000 mg/kg) of ligand. The cohorts receiving activator (L) were fed rodent 2018 Teklad Global 18% Protein Rodent Diet chow blended with activator (1000 mg/kg chow) ad libitum. Cohorts receiving treatment with Ad-RTS-mIL12 alone or no treatment continued to receive a regular 2018 Teklad Global 18% Protein Rodent Diet chow diet. Treatment was initiated when the tumor reached 56-18 $mm^3$. A single dose of Ad-RTSmIL12 (1e10 vp/100 ul in PBS) was given to mice through intratumoral (i.t.) injection on Day 13 post tumor cell inoculation. The activator (L) chow was given to mice 24 hr prior to vector injection. Tumor size and body weight of each mouse were monitored three times a week using calipers and a weight scale until the end of experiment. The experiment was terminated when the tumor size exceeded >2000 $mm^3$. Data were uploaded into Study Log animal study software.

The post treatment tumor volume and body weight changes are shown in FIGS. 34A and 34B. The melanoma tumor bearing mice in control and activator (L) alone groups showed similar aggressive tumor growth. The tumor growth kinetics indicated that the activator chow did not have anti-tumor activity. A slight tumor growth inhibition (12%) was observed on day 26 when animals received a single dose Ad-RTS-mIL12 (1e10 vp) without ligand. Treatment with Ad-RTS-mIL12 plus activator (L) resulted in tumor growth inhibition (73-98%) compared to control mice. A single dose Ad-RTS-mIL12 with 50 mg/kg activator (L) produced significant tumor reduction relative to control tumors. Notably, significant anti-tumor activity (90-98%) was evident as dose activator chow increased from 100-1000 mg/kg, compared to 50 mg/kg activator chow. This data clearly show that Ad-RTS-mIL12 is active in the melanoma model and exhibits a broad therapeutic activator ligand dose window. Body weight was monitored as an indicator of toxicity. On Day 13 and 17, slight transient body weight changes (<5%) was found in 1000 mg/kg activator dose. No major body weight loss was found during the rest of the experiment. No activator dose response related body weight changes were found. The treatment with AdRTS-mIL12 under different doses was well tolerated without any sign of any toxicity.

Example 9. Anti-Tumor Efficacy of Ad-RTS-IL-12 in a Colon Cancer Model

Female, 6- to 8-week-old Balb/C immunocompetent mice were inoculated subcutaneously (s.c.) with luciferase expressing stable murine colon cancer cells (CT26Luc). Ten days post cell inoculation, the mice were randomly assigned to treatment and control groups (n=5) for a total of three groups—no treatment (control), activator (L) (RG-115932) alone, and Ad-RTS-mIL12 plus activator. The cohorts receiving activator (L) were fed 2018 Teklad Global 18% Protein Rodent Diet chow (Harlan Laboratories) blended with activator (1000 mg/kg chow) ad libitum. Cohorts receiving no treatment continued to receive 2018 Teklad Global 18% Protein Rodent Diet chow. Treatment was initiated when the tumor reached 40+17 $mm^3$. The Ad-RTS-mIL12 (1e10 vp/100 ul in PBS) was given to mice through intratumoral (i.t.) injection on Day 11 and 18 post tumor cell inoculation. The activator (L) chow was given to mice 24 hr prior to vector injection. Tumor size and body weight of each mouse were monitored three times a week using calipers and a weight scale until the end of experiment. The experiment was terminated when the mouse tumor size exceeds >2000 $mm^3$. Data were uploaded into Study Log animal study software.

The post treatment tumor volume and body weight changes are shown in FIGS. 35A and 35B. The colon carcinoma bearing mice in control and activator (L) alone groups showed similar aggressive tumor growth. The tumor growth kinetics indicated that the activator chow did not inhibit tumor growth. Two doses of Ad-RTS-mIL12 plus activator (L) alone resulted in complete regression and tumor growth inhibition (100%) compared to control mice. Notably, five out of five animals were completely tumor free as a result of Ad-RTS-mIL12 treatment. Mice rendered tumor-free following Ad-RTSmIL12 treatment were re-challenged with parental CT26Luc cells. Five naïve Balb/c animals were also inoculated subcutaneously with CT26Luc as control group. The control animals developed tumor nodules as expected. Importantly, tumors did not develop in all the rechallenged animals at four weeks post rechallenge. This study indicates that the AdRTS-mIL12 therapy developed strong anti-tumor immunity against the aggressive colon cancer model. Body weight was monitored as an indicator of toxicity. No major body weight loss was found during the course of the experiment.

Example 10. Anti-Tumor Efficacy of Ad-RTS-IL-12 in a Pancreatic Cancer Model

Female, 6- to 8-week-old C57b/6 immuno competent mice were inoculated subcutaneously (s.c.) with syngenic PAN02 pancreatic cancer cells (ATCC). Six days post cell inoculation, the mice were randomized into groups of five animals each in four groups—no treatment, activator (RG-115932) alone, Ad-RTS-mIL12 alone and Ad-RTS-mIL12 plus activator. The cohorts receiving activator ligand were fed 2018 Teklad Global 18% Protein Rodent Diet chow (Harlan Laboratories) blended with activator (1000 mg/kg chow) ad libitum. Cohorts receiving treatment with Ad-RTS-mIL12 alone or no treatment continued to receive 2018 Teklad Global 18% Protein Rodent Diet chow. Mice received treatment with a single intratumoral (i.t.) injection of Ad-RTS-mIL12 at dose level of 1e10 vp/100 ul in PBS, on Day 7 and Day 14 post tumor cell implantation. The tumor size averaged STGT $mm^3$ at the time of vector treatment initiation.

Tumor size and body weight of each mouse were monitored three times a week until the end of experiment. The experiment was terminated when the mice tumor size exceeded 600 $mm^3$. Since pancreatic tumors grow very slowly, we defined as the termination of the experiment. The tumor growth in mice receiving no treatment was normal.

In this tumor model, minor tumor growth delay was noticed in mice receiving treatment with either activator alone or Ad-RTS-mIL12 alone. In contrast, tumor growth in all Ad-RTS-mIL12 treated mice was dramatically inhibited (97%) in comparison with that in the control mice that received no treatment. Body weight was measured throughout the experiment using calipers and a weigh scale as a measure of toxicity. The body weight of animals injected with Ad-RTS-mIL12 showed no significant body weight decrease following administration except a transient body weight decrease (<5%) on Day 12-13. In addition, no pathological behavior (lethargy, ruffle fur, limping, dehydration, hunched posture etc) was observed in any animals. Tumor regression was maintained until day 37, when control animals were sacrificed. Data were uploaded into Study Log animal study software.

The results are shown in FIGS. 36A and 36B.

Example 11. Anti-Tumor Efficacy of Ad-RTS-IL-12 in a Breast Cancer Model

The aim of this study was to evaluate the intratumoral treatment with Ad-RTS-mIL12 for its efficacy and toxicity in murine breast cancer model.

Six- to eight-week-old female BalbC mice were purchased from Charles River Laboratories or Harlan (USA). Animal care and experimental procedure were performed according to the Intrexon's Institutional Animal Care and Use Committee guideline.

Murine breast carcinoma (4T1) cell lines were purchased from ATCC (Manassas, Va.). The 4T1 cells were grown in Roswell Park Memorial Institute medium (RPMI) 1640 (ATCC, Manassas, Va. The medium was supplemented with heat-inactivated fetal calf serum (FCS) 10% v/v, 2-mM L-glutamine (Atlanta Biologicals, Inc, Lawrenceville, Ga.), 100 IU/ml penicillin G, and 100 µg/ml streptomycin. The cells were grown at 37° C. in 5% C02. All cell lines were routinely tested and found to be free of *mycoplasma.*

Female, 6- to 8-week-old BALB/c immune-competent mice were inoculated subcutaneously (s.c.) with syngenic breast cancer (4T1) cells, 1e5 cells/50 ul. Eight days post cell inoculation, the mice were randomized into groups of five animals each in four groups—no treatment, activator alone, Ad-RTS-mIL12 alone and Ad-RTS-mIL12 plus activator. The cohorts receiving activator ligand were fed rodent chow blended with activator (1000 mg/kg) ad libitum. Cohorts receiving treatment with Ad-RTS-mIL12 alone or no treatment continued to receive standard diet (Harlan Laboratories, USA). Activator ligand is administered through a custom diet created from Harlan Teklad (a custom diet division of Harlan) formulated at 1000 mg of activator ligand to 1 Kg of the same chow which is administered to the control animals. Mice received treatment with a single intratumoral (i.t.) injection of Ad-RTS-mIL12 at dose level of 1e10 vp/100 ul in PBS, on Day 9, 12 and 14 post tumor cell implantation. The mean tumor size volume was 36 $mm^3$ at the time of vector treatment initiation. Tumor size and body weight of each mouse were monitored three times a week until the end of experiment. The experiment was terminated when the mice tumor size exceeded >1000 $mm^3$.

Eight days post inoculation with breast cancer 4T1 cells, mice were randomized and assigned to treatment and control groups (n=5/group) for a total of four groups—no treatment (control), activator alone (L), Ad-RTS-mIL12 alone and Ad-RTS-mIL12 plus activator, as shown in the Table below.

Treatment Design for Breast (4T1) Tumor Model

| Group | N | Activator Ligand (L) Chow | Regular Rodent Chow | Intratumoral Administration | Treatment initiated after cell inoculation | Tumor Size, Body Weight |
|---|---|---|---|---|---|---|
| 1 | 5 | No | Yes | | | Mon, Wed and Fri |
| 2 | 5 | Yes | No | | | Mon, Wed and Fri |
| 3 | 5 | No | Yes | Ad-RTS-mIL12 | Day 9, 12, 14 | Mon, Wed and Fri |
| 4 | 5 | Yes | No | Ad-RTS-mIL12 | Day 9, 12, 14 | Mon, Wed and Fri |

Treatment was initiated when the tumor reached mean volume of 36 $mm^3$. The post treatment tumor volume is shown in FIG. 39A. The 4T1 tumor bearing mice in control, Ad-RTS-IL-12 treated and activator ligand (L) alone groups displayed tumor growth inhibition ~20% and 35% respectively on Day 26 (FIG. 39A). Importantly, three doses of Ad-RTS-mIL12 with activator ligand led to marked tumor growth inhibition (82%), relative to control group (p<0.005). This data suggests Ad-RTS-mIL12 in the presence of activator exhibits potent anti-tumor activity in breast cancer (4T1) model. Body weight was monitored as an indicator of toxicity. No major body weight loss or deaths were found during the course of the experiment (FIG. 39B).

The results demonstrate that direct intratumoral injection of Ad-RTS-mIL12 plus activator ligand is highly effective for inducing tumor regression and is safe in breast cancer model. The anti-tumor activity was significant (p<0.005) in this model,

Example 12. Clinical Protocol for Administration of Immune Cell Free Ad-RTS-IL-12 Vector Following is a clinical protocol that can be used to practice the invention in the form of the administration of Ad-RTS-IL-12 vector for the treatment of unresectable stage III C or IV malignant melanoma.

The objectives of this phase 1b clinical trial are to assess safety and objective response, tumor response rate, and immunological and other biological activities of six treatment cycles of intratumoral injections of Ad-RTS-IL-12 in combination with 14 daily oral doses of activating ligand. Ad-RTS-IL-12 dose will initially (first cycle) be administered at $1\times10^{11}$ viral particles (vp) together with a 5 mg/day dose of activating ligand. The doses of both virus particles and activating ligand will then be escalated for each repeat treatment cycle for each patient, according to a fixed schedule (Table 8), provided that the preceding treatment cycle was tolerated by the patient.

The objectives of this phase 1b study are as follows:

1. Evaluate safety and tolerance of repeated treatment cycles of intratumoral injections of AD-RTS-IL-12 in an intra-patient escalating dose in combination with escalating doses of activating ligand in patients with unresectable Stage III C or IV malignant melanoma.

2. Obtain indications of efficacy by using diagnostic CT scans (Response Evaluation Criteria In Solid Tumors (RECIST 1.1) criteria), PET scans and photographs (as applicable).

3. Evaluate functionality of the RheoSwitch Therapeutic System™ (RTS™) in patients by evaluating the immunological effects of AD-RTS-IL-12 in combination with activating ligand, in terms of cellular immune response (particularly gene expression of IL-12 and other cytokines, frequency of cytotoxic T lymphocytes and Tregs) and other biological activities (e.g. apoptosis and immune cell infiltration) in the injected target tumor(s), tumor involved draining lymph nodes (if accessible) and in the peripheral circulation, and to correlate changes in the immunological and other biological parameters with prior activating ligand dose and with tumor response.

4. Evaluate the extent of the uptake of AD-RTS-IL-12 into tumor cells and into dendritic cells and macrophages in the tumor, to determine which cells uptake the virus whether the extent of uptake is dependent on the AD-RTS-IL-12 dose. Determine the inflammatory response and immune responses (cellular, such as cytotoxic lymphocytes and Tregs, and induction of cytokines) in the tumor, tumor-involved draining lymph nodes (if accessible) and in the peripheral circulation. The changes in the immunological and other biological parameters will be correlated with AD-RTS-IL-12 and activating ligand dose and with tumor response.

5. Evaluate the pharmacokinetic profile during steady state in each cycle on Days 8-9 in a subset of patients.

6. Evaluate QT/QTc intervals in ECGs obtained by Holter monitoring, in the patients who will undergo PK evaluation.

Indication:

Unresectable Stage III C (in transit), Stage IV (M1a, M1b or M1c (LDH≤2×ULN) malignant melanoma with at least 4 accessible lesions.

Study Design:

Phase 1b, open label, single arm, multicenter evaluation of safety, tolerance, tumor response (RECIST 1.1), and immunological and other biological effects, of six treatment cycles, each lasting for 28 days, each with an intra-tumoral injection of AdRTS-IL-12 in combination with 14 once daily, oral doses of activating ligand. The dose of both AD-RTS-IL-12 and activating ligand will be escalated according to FIG. 1 and Table 1 for all patients who tolerated the preceding treatment cycle.

Study Population:

Males and females of all races, ≥18 years of age, with unresectable Stage III C or IV malignant melanoma with ECOG performance status of 0-1, who have a minimum of 4 accessible lesions (longest diameter≤3 cm; shortest diameter≥1 cm) or palpable tumor-involved lymph nodes (longest diameter≤5 cm; shortest≥1.5 cm) for intra-tumoral injections or biopsies.

Sample Size:

A minimum of 12 and a maximum of 28 patients, with Stage III C or IV melanoma will be entered into this study. All patients in this protocol will be entered into a single arm, with intra-patient dose escalation of AD-RTS-IL-12 and activating ligand with each repeated treatment cycle according to FIG. 1 and Table 1, providing that the preceding treatment cycle was well tolerated.

Test Product:

During each cycle, the patients will be treated with a combination of the oral activating ligand and an intra-tumoral injection of a gene therapy (Ad-RTS-IL-12) engineered to express inducible hIL-12 in a dose-dependent response to activating ligand. AD-RTS-IL-12 will be prepared at a central manufacturing site and then frozen and sent to the appropriate clinical site. All patients will receive intra-tumoral injections (one per cycle for up to six cycles, 4 weeks apart) of AD-RTS-IL-12 (approximately $1.0\times10^{11}$ and $1.0\times10^{12}$ total viral particles per injection). The patients will also receive a single daily oral dose of activating ligand for 14 consecutive days during each cycle. The AD-RTS-IL-12 and/or the activating ligand dose will be escalated intra-patient at the start of cycles 2 to 6 (see Table 8), in all patients who tolerated the preceding treatment cycle. AD-RTS-IL-12 will be injected into a different lesion at each cycle, and if the number of lesions is limited, the injections will be done in sequential rotation. One of the minimum of four accessible lesions will not be injected as that lesion will be used to evaluate the systemic effect of AD-RTS-IL-12. Patient dosing will be staggered at least 24 hours apart. Each intra-tumoral injection will occur once during a cycle, approximately 3 hours (±30 minutes) after the first dose of activating ligand.

Dosage:

Activating Ligand: lowest dose/day: 5 mg; intermediate dose/day: 20 mg; highest dose/day: 100 mg. Activating Ligand will be administered during the first 14 days of each cycle.

Ad-RTS-IL-12: dose: approximately $1.0\times10^{11}$ or $1.0\times10^{12}$ viral particles/tumor per injection suspended in a total volume of 0.5 ml sterile solution, with the injection volume distributed throughout the lesion, especially in the area of the tumor margin.

TABLE 8

Dosing Schedule

| Cycle | AD-RTS-IL-12 dose (intratumorally) Viral Particles (VP) | No. Inj/cycle | Activating Ligand mg/daily dose (oral) | Number of Activating Ligand doses/cycle |
|---|---|---|---|---|
| 1 | $1.0\times10^{11}$ | 1 (Day 1) | 5 | 14 (Days 1-14) |
| 2 | $1.0\times10^{11}$ | 1 (Day 1) | 20 | 14 (Days 1-14) |
| 3 | $1.0\times10^{11}$ | 1 (Day 1) | 100 | 14 (Days 1-14) |
| 4 | $1.0\times10^{12}$ | 1 (Day 1) | 5 | 14 (Days 1-14) |
| 5 | $1.0\times10^{12}$ | 1 (Day 1) | 20 | 14 (Days 1-14) |
| 6 | $1.0\times10^{12}$ | 1 (Day 1) | 100 | 14 (Days 1-14) |

Treatment with the next higher dose level will not begin until the safety and tolerability of the preceding treatments have been confirmed. If MTD is defined, no further escalation will occur.

Route of Administration:

Activating Ligand: solution in a soft gelatin capsule taken orally within 30 minutes of a meal;

AD-RTS-IL-12:

To be injected on the first day of each cycle into one accessible tumor lesions or tumor-involved (palpable) draining lymph nodes when necessary.

Method of Patient Assignment:

All patients will receive treatment according to Table 8 and be entered into one arm. Safety and tolerance will be rigorously assessed for all patients, during and after each treatment cycle. Dose escalation can only take place if the preceding cycle treatment was tolerated.

Trial Duration:

This study will last for each patient for approximately 28 weeks after screening.

After a period of up to 23 days for screening evaluation (Days −30 to −7), the patients will be approved for participation into the study. On Days −6 to −2, baseline biopsies will be performed and on Day 0, the baseline evaluation of cardiac function using Holter monitoring will be done in the patients who are evaluated for PK. On Day 1 of each cycle, the approved patient will start receiving the experimental treatments (one intra-tumoral injection of AD-RTS-IL-12 and one oral dose of activating ligand). Activating ligand treatment in each cycle will continue for a total of 14 days, followed by 14 days of washout and observation for safety. The study treatment consists of 6 cycles, each lasting a total of 28 days including 14 days of follow-up. A post-treatment follow-up evaluation will be performed at 6 weeks after the last injection (4 weeks after the last dose of activating ligand). Viral DNA in blood will be determined. If viral DNA is present at 6 weeks after the last injection, further viral DNA assessments will be continued. However, if two consecutive negative results by Q-PCR for each source is demonstrated, no more tests will be necessary.

Primary Endpoints:

Safety and tolerance will be assessed by physical examinations (including ECOG performance status), QT/QTc interval in ECGs (in PK patients), vital signs, serum chemistry, urinalysis, hematology, and by reports of patients of any adverse events. Objective response and response rate, as assessed by CT scans.

Secondary Endpoints:

Steady-state pharmacokinetics of activating ligand, in a subset of eight patients (four per AD-RTS-IL-12 dose level).

b. Extent of inflammatory and immune response (cellular, such as cytotoxic lymphocytes and Tregs, and induction of cytokines) in the tumor, in tumor-involved draining lymph nodes (if accessible) and in the peripheral circulation, as a result of the treatment.

c. Correlate changes in the immunological and other biological parameters with AD-RTS-IL-12 and activating ligand dose and with tumor response.

d. Efficacy also assessed by PET scans and photographs.

e. Long-term follow-up will occur for up to 5 years. Patients will be contacted annually by the investigator.

Inclusion Criteria:

a. Males or females of all races≥18 years of age;

b. Unresectable Stage III C (in transit) or Stage IV melanoma (M1a, M1b, M1c with LDH≤2×ULN), arising from primary cutaneous, mucosal, or subungal melanoma of any tumor thickness or from an unknown primary site;

c. A minimum of 4 accessible nonvisceral lesions (longest diameter≤3 cm; shortest≥1 cm) or palpable tumor-involved lymph nodes (longest diameter≤5 cm; shortest≥1.5 cm) for intra-tumoral injections or biopsies. At least one lesion will not be injected.

d. ECOG performance status of 0 or 1;

e. Patients without visible brain metastases as assessed by contrast-enhanced MRI scan at the time of screening or within 30 days prior to study entry;

f. Adequate baseline hematological and organ function, assessed by laboratory values within 30 days prior to treatment with study treatments and prior to repeat treatment cycles and activating ligand dose escalation as follows: hemoglobin≥10 g/L, granulocytes>2500/$mm^3$, lymphocytes>1000/$mm^3$, platelets>100,000/$mm^3$, serum creatinine<1.5×ULN, AST, ALT, alkaline phosphatase<2.5×ULN, LDH≤2×ULN, serum bilirubin<1.5×ULN, absolute neutrophils>500/$mm^3$;

g. An expected survival of at least approximately 6 months in the opinion of the investigator (as assessed mainly on performance status);

h. Females must be post-menopausal or surgically sterile or practice effective contraception; Men who are not surgically sterile and whose partners are not postmenopausal or surgically sterile must practice effective contraception;

i. Normal coagulation parameters as measured by PT/PTT;

j. Signed, IRB-approved voluntary informed consent.

Exclusion Criteria:

a. Active, acute viral, bacterial, or fungal infections requiring specific therapy;

b. HIV-infection due to concerns about ability to mount an effective immune response;

c. Active autoimmune disease requiring steroids (>10 mg prednisolone or comparable) or other immunosuppressive therapy;

d. Patients with detectable brain metastases at the time of screening (or within 30 days prior to study entry), as assessed by contrast-enhanced MRI scans;

e. Patients with lesions>3 cm (LD) or palpable, tumor-involved lymph nodes>5 cm (LD);

f. Patients with a hemoglobin of <10 g/L;

g. Presence of Stage IV visceral metastases or other distant metastases if LDH>2×ULN;

h. Patients who have previously been treated with AD-RTS-IL-12 or activating ligand;

i. Patients who have previously been treated with intra-tumoral gene therapy.

J. Recipients of organ allografts;

k. Other concurrent clinically active malignant disease, with the exception of other cancers of the skin;

l. Less than 30 days (before the first dose of study medication) have elapsed since the completion of prior chemotherapy, hormonal therapy, radiotherapy, immunotherapy, or any first line therapy;

m. Clinically significant cerebrovascular disease;

n. History of or concurrent severe cardiac insufficiency (New York Heart Association Class III or IV) or coronary artery disease;

o. Acute medical conditions such as ischemic heart or lung disease that may be considered an unacceptable anesthetic or operative risk;

p. History of or current bleeding or clotting disorders;

q. Concurrent immunosuppressive therapy such as corticosteroids (>10 mg prednisolone or comparable) and cyclosporin A;

r. Concurrent investigational treatments, or treatment with any investigational treatment within the past 30 days (prior to the first dose of study medication);

s. Concurrent medications that are metabolized by the CYP450 3A4 pathway;

t. Females who are lactating or pregnant;

u. Patients who have a history of hypersensitivity that may relate to any component of the product, e.g. to benzoic acid that might be related to activating ligand, which contains two benzene rings;

v. Any medical or psychiatric condition which, in the opinion of the investigator, would unacceptably reduce the safety or delivery of the proposed treatment, or would preclude obtaining voluntary informed consent.

Statistical Methods:

Objective response (CR+PR) will be based on changes in size of injected and uninjected tumor lesion(s) as well as palpable tumor-involved lymph nodes by CT scans [utilizing Response Evaluation Criteria In Solid Tumors (RECIST 1.1)]. PET scans and/or photographs will be used to evaluate changes in metabolic activity or size (cutaneous lesions), respectively.

The primary analysis of OS and ORR will include confidence interval, and will be performed when sample size reaches 12, 16, 20, 24 patients, and at 6 weeks after treatment of the last patient.

Demographic, immunologic and biologic activity measures, as well as safety parameters including adverse event rates and laboratory values, will be analyzed descriptively at end of follow-up. The results will be summarized in tables, graphs and patient-by-patient listings.

Descriptive statistics, including mean, median, standard deviation and histogram, will be used to summarize continuous measures. Frequency counts will be used for categorical variables, including objective tumor response. Immunological and biological activities will be correlated with the antitumor effect. These statistics will be provided by stratum (size of tumor lesions: <1 cm longest diameter [LD], >1 cm LD; size of involved DLN: ≤3 cm LD, >3 cm LD; location of lesions: visceral, non-visceral; Injection status of lesions: injected, non-injected.) The statistics will be performed by end of each treatment cycle and overall. For overall analysis, observations will be combined across strata but not across cycles.

Compliance:

The trials are performed in compliance with current Good Clinical Practice (cGCP).

LITERATURE

Abdalla, 2007.

Abdi K, Singh N, Matzinger P (2006). T-cell control of IL-12p75 production. *Scand J Immunol* 64: 83-92.

Adorini L (1999). Interleukin-12, a key cytokine in Th1-mediated autoimmune diseases. *Cell Mol Life Sci* 55: 1610-25.

Adorini L (2001). Interleukin 12 and autoimmune diabetes. *Nat Genet* 27: 131-2.

Adorini L, Gregori S, Harrison L C (2002). Understanding autoimmune diabetes: insights from mouse models. *Trends Mol Med* 8: 31-8.

Adorini L, Gregori S, Magram J, Trembleau S (1996). The role of IL-12 in the pathogenesis of Th1 cell-mediated autoimmune diseases. *Ann N Y Acad Sci* 795: 208-15.

Akhtar N, Padilla M L, Dickerson E B, Steinberg H, Breen M, Auerbach R et al (2004). Interleukin-12 inhibits tumor growth in a novel angiogenesis canine hemangiosarcoma xenograft model. *Neoplasia* 6: 106-16.

Akiyama Y, Watanabe M, Maruyama K, Ruscetti F W, Wiltrout R H, Yamaguchi K (2000). Enhancement of antitumor immunity against B16 melanoma tumor using genetically modified dendritic cells to produce cytokines. *Gene Ther* 7: 2113-21.

Al-Mohanna F, Saleh S, Parhar R S, Collison K (2002). IL-12-dependent nuclear factor-kappaB activation leads to de novo synthesis and release of IL-8 and TNF-alpha in human neutrophils. *J Leukoc Biol* 72: 995-1002.

Aliberti J C, Cardoso M A, Martins G A, Gazzinelli R T, Vieira L Q, Silva J S (1996). Interleukin-12 mediates resistance to *Trypanosoma cruzi* in mice and is produced by murine macrophages in response to live trypomastigotes. *Infect Immun* 64: 1961-7.

Allavena P, Paganin C, Zhou D, Bianchi G, Sozzani S, Mantovani A (1994). Interleukin-12 is chemotactic for natural killer cells and stimulates their interaction with vascular endothelium. *Blood* 84: 2261-8.

Alli R S, Khar A (2004). Interleukin-12 secreted by mature dendritic cells mediates activation of NK cell function. *FEBS Lett* 559: 71-6.

Alzona M, Jack H M, Simms P E, Ellis T M (1996). Interleukin-12 activates interferongamma production by targeted activation of CD30+ T cells. *Ann N Y Acad Sci* 795: 127-36.

Amemiya K, Meyers J L, Trevino S R, Chanh T C, Norris S L, Waag D M (2006). Interleukin-12 induces a Th1-like response to *Burkholderia mallei* and limited protection in BALB/c mice. *Vaccine* 24: 1413-20.

Araujo M I, Bliss S K, Suzuki Y, Alcaraz A, Denkers E Y, Pearce E J (2001). Interleukin-12 promotes pathologic liver changes and death in mice coinfected with *Schistosoma mansoni* and *Toxoplasma gondii*. *Infect Immun* 69: 1454-62.

Arulanandam B P, Van Cleave V H, Metzger D W (1999). IL-12 is a potent neonatal vaccine adjuvant. *Eur J Immunol* 29: 256-64.

Athie M V, Flotow H, Hilyard K L, Cantrell D A (2000). IL-12 selectively regulates STAT4 via phosphatidylinositol 3-kinase and Ras-independent signal transduction pathways. *Eur J Immunol* 30: 1425-34.

Athie-Morales V, Smits H H, Cantrell D A, Hilkens C M (2004). Sustained IL-12 signaling is required for Th1 development. *J Immunol* 172: 61-9.

Atkins M B, Robertson M J, Gordon M, Lotze M T, DeCoste M, DuBois J S et al (1997). Phase I evaluation of intravenous recombinant human interleukin 12 in patients with advanced malignancies. *Clin Cancer Res* 3: 409-17.

Berard F, Blanco P, Davoust J, Neidhart-Berard E M, Nouri-Shirazi M, Taquet N et al (2000). Cross-priming of naive CD8 T cells against melanoma antigens using dendritic cells loaded with killed allogeneic melanoma cells. *J Exp Med* 192: 1535-44.

Bertagnolli M M, Lin BY, Young D, Herrmann S H (1992). IL-12 augments antigen-dependent proliferation of activated T lymphocytes. *J Immunol* 149: 3778-83.

Bhardwaj N, Seder R A, Reddy A, Feldman M V (1996). IL-12 in conjunction with dendritic cells enhances antiviral CD8+ CTL responses in vitro. *J Clin Invest* 98: 715-22.

Biedermann T, Lametschwandtner G, Tangemann K, Kund J, Hinteregger S, Carballido-Perrig N et al (2006). IL-12 instructs skin homing of human Th2 cells. *J Immunol* 177: 3763-70.

Brunda M J, Gately M K (1994). Antitumor activity of interleukin-12. *Clin Immunol Immunopathol* 71: 253-5.

Buchanan J M, Vogel L A, Van Cleave V H, Metzger D W (1995). Interleukin 12 alters the isotype-restricted antibody response of mice to hen eggwhite lysozyme. *Int Immunol* 7: 1519-28.
Chang, 2007.
Coughlin, 1998.
Dietrich 2002.
Emtage et al., "Adenoviral Vectors Expressing Lymphotactin and Interleukin 2 or Lymphotactin and Interleukin 12 Synergize to Facilitate Tumor Regression in Murine Breast Cancer Models," *Hum. Gene Ther.* 10:697 (1999).
Faure F, Even J, Kourilsky P (1998). Tumor-specific immune response: current in vitro analyses may not reflect the in vivo immune status. *Crit Rev Immunol* 18: 77-86.
Gao et al., "Cotransduction of CCL27 gene can improve the efficacy and safety of IL-12 gene therapy for cancer," *Gene Ther.* 14:491-502 (2007)
Hansson, 2007.
Heinzerling L, Burg G, Dummer R, Maier T, Oberholzer P A, Schultz J et al (2005). Intratumoral injection of DNA encoding human interleukin 12 into patients with metastatic melanoma: clinical efficacy. *Hum Gene Ther* 16: 35-48.
Hill 2002.
Itoh T, Storkus W J, Gorelik E, Lotze M T (1994). Partial purification of murine tumor-associated peptide epitopes common to histologically distinct tumors, melanoma and sarcoma, that are presented by H-2Kb molecules and recognized by CD8+ tumor-infiltrating lymphocytes. *J Immunol* 153: 1202-15.
Jean, 2004.
Kang W K, Park C, Yoon H L, Kim W S, Yoon S S, Lee M H et al (2001). Interleukin 12 gene therapy of cancer by peritumoral injection of transduced autologous fibroblasts: outcome of a phase I study. *Hum Gene Ther* 12: 671-84.
Koka, 2004.
Koyama, 1997
Lasek, 2000.
Mehrotra, 1995.
Narvaiza et al., "Intratumoral coinjection of two adenoviruses, one encoding the chemokine IFN-gamma-inducible protein-10 and another encoding IL-12, results in marked antitumoral synergy," *J. Immunol.* 164:3112 (2000).
Nair, 2006.
Narvaiza et al., Intratumoral Coinjection of Two Adenoviruses, One Encoding the Chemokine IFN-γ-Inducible Protein-10 and Another Encoding IL-12, Results in Marked Antitumoral Synergy," *J. Immunol.* 164:3112-3122 (2000).
Palmer et al., "Combined CXC chemokine and interleukin-12 gene transfer enhances antitumor activity," *Gene Ther.* 8:282-290 (2001).
Rasmussen, 2003.
Romani L, Puccetti P, Bistoni F (1997). Interleukin-12 in infectious diseases. *Clin Microbiol Rev* 10: 611-36.
Rothe H, Burkart V, Faust A, Kolb H (1996). Interleukin-12 gene expression mediates the accelerating effect of cyclophosphamide in autoimmune disease. *Ann N Y Acad Sci* 795: 397-9.
Sabel, 2003, 2004, 2007.
Sangro B, Mazzolini G, Ruiz J, Herraiz M, Quiroga J, Herrero I et al (2004). Phase I trial of intratumoral injection of an adenovirus encoding interleukin-12 for advanced digestive tumors. *J Clin Oncol* 22: 1389-97.
Sangro B, Melero I, Qian C, Prieto J (2005). Gene therapy of cancer based on interleukin 12. *Curr Gene Ther* 5: 573-81.
Satoh Y, Esche C, Gambotto A, Shurin G V, Yurkovetsky Z R, Robbins P D et al (2002). Local administration of IL-12-transfected dendritic cells induces antitumor immune responses to colon adenocarcinoma in the liver in mice. *J Exp Ther Oncol* 2: 337-49.
Satoskar A R, Rodig S, Telford S R, 3rd, Satoskar A A, Ghosh S K, von Lichtenberg F et al (2000). IL-12 gene-deficient C57B L/6 mice are susceptible to *Leishmania donovani* but have diminished hepatic immunopathology. *Eur J Immunol* 30: 834-9.
Schopf L R, Bliss J L, Lavigne L M, Chung C L, Wolf S F, Sypek J P (1999). Interleukin-12 is capable of generating an antigen-specific Th1-type response in the presence of an ongoing infection-driven Th2-type response. *Infect Immun* 67: 2166-71.
Subleski, 2006.
Svane I M, Boesen M, Engel A M (1999). The role of cytotoxic T-lymphocytes in the prevention and immune surveillance of tumors—lessons from normal and immunodeficient mice. *Med Oncol* 16: 223-38.
Taniguchi, 1998.
Tatsumi T, Huang J, Gooding W E, Gambotto A, Robbins P D, Vujanovic N L et al (2003). Intratumoral delivery of dendritic cells engineered to secrete both interleukin (IL)-12 and IL-18 effectively treats local and distant disease in association with broadly reactive Tc1-type immunity. *Cancer Res* 63: 6378-86.
Thomas G R, Chen Z, Enamorado I, Bancroft C, Van Waes C (2000). IL-12- and IL-2-induced tumor regression in a new murine model of oral squamous-cell carcinoma is promoted by expression of the CD80 co-stimulatory molecule and interferon-gamma. *Int J Cancer* 86: 368-74.
Trinchieri G (2003). Interleukin-12 and the regulation of innate resistance and adaptive immunity. *Nat Rev Immunol* 3: 133-46.
Triozzi P L, Allen K O, Carlisle R R, Craig M, LoBuglio A F, Conry R M (2005). Phase I study of the intratumoral administration of recombinant canarypox viruses expressing B7.1 and interleukin 12 in patients with metastatic melanoma. *Clin Cancer Res* 11: 4168-75.
Tsung K, Meko J B, Peplinski G R, Tsung Y L, Norton J A (1997). IL-12 induces T helper 1-directed antitumor response. *J Immunol* 158: 3359-65.
Vujanovic, 2006.
Wang, 2001.
Wigginton 2002, 2001, 1996
Wolf S F, Sieburth D, Sypek J (1994). Interleukin 12: a key modulator of immune function. *Stem Cells* 12: 154-68.
Yamanaka R, Zullo S A, Ramsey J, Yajima N, Tsuchiya N, Tanaka R et al (2002). Marked enhancement of antitumor immune responses in mouse brain tumor models by genetically modified dendritic cells producing Semliki Forest virus-mediated interleukin-12. *J Neurosurg* 97: 611-8.
Yuminamochi E, Koike T, Takeda K, Horiuchi I, Okumura K (2007). Interleukin-12- and interferon-gamma-mediated natural killer cell activation by *Agaricus blazei* Murill. *Immunology.*
McDermott, D. F. and Atkins, M. B. (2008) Immunotherapy of metastatic renal cell carcinoma.
Cancer J. 14, 320-324.
Berntsen, A., Trepiakas, R., Wenandy, L., Geertsen, P. F., thor Straten, P., Andersen, M. H., Pedersen, A. E., Claesson, M. H., Lorentzen, T., Johansen, J. S. and Svane, I. M.

(2008) Therapeutic dendritic cell vaccination of patients with metastatic renal cell carcinoma: a clinical phase 1/2 trial. J. Immunother. 31, 771-780.

Tarhini, A. A., Kirkwood, J. M., Gooding, W. E., Moschos, S. and Agarwala, S. S. (2008) A phase 2 trial of sequential temozolomide chemotherapy followed by high-dose interleukin 2 immunotherapy for metastatic melanoma. Cancer. 113, 1632-1640.

Heemskerk, B., Liu, K., Dudley, M. E., Johnson, L. A., Kaiser, A., Downey, S., Zheng, Z., Shelton, T. E., Matsuda, K., Robbins, P. F., Morgan, R. A., Rosenberg, S. A. (2008) Adoptive cell therapy for patients with melanoma, using tumor-infiltrating lymphocytes genetically engineered to secrete interleukin-2. Hum Gene Ther. 19, 496-510.

Horton, H. M., Lalor, P. A. and Rolland, A. P. (2008) IL-2 plasmid electroporation: from preclinical studies to phase I clinical trial. Methods Mol Biol. 423, 361-372.

Shiratori, I., Suzuki, Y., Oshiumi, H., Begum, N. A., Ebihara, T., Matsumoto, M., Hazeki, K., Kodama, K., Kashiwazaki, Y. and Seya, T. (2007) Recombinant interleukin-12 and interleukin-18 antitumor therapy in a guinea-pig hepatoma cell implant model.

Cancer Sci. 98, 1936-1942.

Lian H, Jin N, Li X, Mi Z, Zhang J, Sun L, Li X, Zheng H, Li P. (2007) Induction of an effective anti-tumor immune response and tumor regression by combined administration of IL-18 and Apoptin. Cancer Immunol Immunother. 56, 181-192.

Iinuma, H., Okinaga, K., Fukushima, R., Inaba, T., Iwasaki, K., Okinaga, A., Takahashi, I. and Kaneko, M. (2006) Superior protective and therapeutic effects of IL-12 and IL-18 gene-transduced dendritic neuroblastoma fusion cells on liver metastasis of murine neuroblastoma. J. Immunol. 176, 3461-3469.

Basak, G. W., Zapala, L., Wysocki, P. J., Mackiewicz, A., Jakóbisiak, M. and Lasek, W. (2008) Interleukin 15 augments antitumor activity of cytokine gene-modified melanoma cell vaccines in a murine model. Oncol Rep. 19, 1173-1179.

Lasek, W., Basak, G., Switaj, T., Jakubowska, A. B., Wysocki, P. J., Mackiewicz, A., Drela, N., Jalili, A., Kamiiski, R., Kozar, K. and Jakóbisiak, M. (2004) Complete tumour regressions induced by vaccination with IL-12 gene-transduced tumour cells in combination with IL-15 in a melanoma model in mice. Cancer Immunol Immunother. 53, 363-372.

Xia, Y., Dai, J., Lu, P., Huang, Y., Zhu, Y. and Zhang, X. (2008) Distinct effect of CD40 and TNF-signaling on the chemokine/chemokine receptor expression and function of the human monocyte-derived dendritic cells. Cell Mol Immunol. 5, 121-131.

Sharma, S., Batra, R. K., Yang, S. C., Hillinger, S., Zhu, L., Atianzar, K., Strieter, R. M., Riedl, K., Huang, M. and Dubinett, S. M. (2003) Interleukin-7 gene-modified dendritic cells reduce pulmonary tumor burden in spontaneous murine bronchoalveolar cell carcinoma. Hum Gene Ther. 14, 1511-1524.

Tirapu, I., Rodriguez-Calvillo, M., Qian, C., Duarte, M., Smerdou, C., Palencia, B., Mazzolini, G., Prieto, J. and Melero, I. (2002) Cytokine gene transfer into dendritic cells for cancer treatment. Curr. Gene Ther. 2, 79-89.

Small, E. J., Sacks, N., Nemunaitis, J., Urba, W. J., Dula, E., Centeno, A. S., Nelson, W. G., Ando, D., Howard, C., Borellini, F., Nguyen, M., Hege, K. and Simons, J. W. (2007) Granulocyte macrophage colony-stimulating factor-secreting allogeneic cellular immunotherapy for hormone-refractory prostate cancer. Clin Cancer Res. 13, 3883-3891.

Huang, H. and Xiang, J. (2004) Synergistic effect of lymphotactin and interferon gamma-inducible protein-10 transgene expression in T-cell localization and adoptive T-cell therapy of tumors. Int. J. Cancer. 109, 817-825.

What is claimed is:

1. A method for treating a glioblastoma in a mammal, the method comprising:

A) intratumorally administering to the glioblastoma in the mammal at least $1.0\times10^{11}$ viral particles of a viral vector comprising a polynucleotide encoding an ecdysone receptor-based gene switch, wherein said polynucleotide comprises:

(1) a polynucleotide sequence comprising a first transcription factor coding sequence and a second transcription factor coding sequence under the control of a promoter, wherein the proteins encoded by the first transcription factor coding sequence and the second transcription factor coding sequence interact to form a ligand-dependent transcription factor complex, wherein the first transcription factor coding sequence comprises a nucleic acid sequence encoding a VP-16 transactivation domain and a retinoic acid-X-receptor (RXR) polypeptide, wherein the second transcription factor coding sequence comprises a nucleic acid sequence encoding a GAL-4 DNA binding domain and a *Choristoneura fumiferna* ecdysone receptor ligand binding domain, and (2) a polynucleotide encoding a polypeptide having a function of IL-12 that is at least 90% identical to IL-12 operably linked to a promoter which is activated by said ligand-dependent transcription factor complex, wherein the function of IL-12 is production of IFN-gamma; and B) administering to the mammal about 10 mg to about 20 mg of a diacylhydrazine ligand that activates the ligand-dependent transcription factor complex, wherein the ligand is first administered to the mammal in a time period from 24 hours before administration of the vector to 24 hours following administration of the vector, and wherein the ligand is administered daily for a period of 7 to 28 days following the first administration.

2. The method of claim 1, wherein the ligand is administered daily for a period of 14 days.

3. The method of claim 1, wherein the vector is an adenoviral vector.

4. The method of claim 1, wherein the ligand is administered orally.

5. The method of claim 1, wherein the RXR polypeptide is a genetically engineered chimera comprising vertebrate RXR and invertebrate RXR ligand binding domains, and wherein said vertebrate RXR ligand binding domain is a human RXR ligand binding domain.

6. The method of claim 1, wherein said *Choristoneura fumiferna* ecdysone receptor ligand binding domain comprises a genetically engineered substitution mutation compared to the naturally occurring *Choristoneura fumiferna* ecdysone receptor ligand binding domain.

7. The method of claim 1, wherein the diacylhydrazine ligand is selected from the group consisting of RG-115819, RG-115830 and RG-115932.

8. The method of claim 1, wherein the polypeptide having a function of IL-12 is at least 95% identical to IL-12.

9. The method of claim 1, wherein the polypeptide having a function of IL-12 is at least 99% identical to IL-12.

10. The method of claim 1, wherein the mammal is administered from about $1.0\times10^{11}$ to about $1.0\times10^{12}$ viral particles of the viral vector.

11. A method for treating a glioblastoma in a mammal, the method comprising:

A) intratumorally administering to the glioblastoma in the mammal at least $1.0\times10^{11}$ viral particles of a viral vector comprising a polynucleotide encoding an ecdysone receptor-based gene switch, wherein said polynucleotide comprises:

(1) a polynucleotide sequence comprising a first transcription factor coding sequence and a second transcription factor coding sequence under the control of a promoter, wherein the proteins encoded by the first transcription factor coding sequence and the second transcription factor coding sequence interact to form a ligand-dependent transcription factor complex, wherein the first transcription factor coding sequence comprises a nucleic acid sequence encoding a VP-16 transactivation domain and a retinoic acid-X-receptor (RXR) polypeptide, wherein the second transcription factor coding sequence comprises a nucleic acid sequence encoding a GAL-4 DNA binding domain and a *Choristoneura* fumiferna ecdysone receptor ligand binding domain, and (2) a polynucleotide encoding a polypeptide having a function of IL-12 that is at least 90% identical to IL-12 operably linked to a promoter which is activated by said ligand-dependent transcription factor complex, wherein the function of IL-12 is production of IFN-gamma; and B) administering to the mammal about 10 mg of a diacylhydrazine ligand that activates the ligand-dependent transcription factor complex, wherein the ligand is first administered to the mammal in a time period from 24 hours before administration of the vector to 24 hours following administration of the vector, and wherein the ligand is administered daily for a period of 7 to 28 days following the first administration.

12. The method of claim 11, wherein the ligand is administered daily for a period of 14 days.

13. The method of claim 11, wherein the vector is an adenoviral vector.

14. The method of claim 11, wherein the ligand is administered orally.

15. The method of claim 11, wherein the RXR polypeptide is a genetically engineered chimera comprising vertebrate RXR and invertebrate RXR ligand binding domains, and wherein said vertebrate RXR ligand binding domain is a human RXR ligand binding domain.

16. The method of claim 11, wherein said *Choristoneura fumiferna* ecdysone receptor ligand binding domain comprises a genetically engineered substitution mutation compared to the naturally occurring *Choristoneura fumiferna* ecdysone receptor ligand binding domain.

17. The method of claim 11, wherein the diacylhydrazine ligand is selected from the group consisting of RG-115819, RG-115830 and RG-115932.

18. The method of claim 11, wherein the polypeptide having a function of IL-12 is at least 95% identical to IL-12.

19. The method of claim 11, wherein the polypeptide having a function of IL-12 is at least 99% identical to IL-12.

20. The method of claim 11, wherein the mammal is administered from about $1.0\times10^{11}$ to about $1.0\times10^{12}$ viral particles of the viral vector.

21. A method for treating a glioblastoma in a mammal, the method comprising:

A) intratumorally administering to the glioblastoma in the mammal at least $1.0\times10^{11}$ viral particles of a viral vector comprising a polynucleotide encoding an ecdysone receptor-based gene switch, wherein said polynucleotide comprises:

(1) a polynucleotide sequence comprising a first transcription factor coding sequence and a second transcription factor coding sequence under the control of a promoter, wherein the proteins encoded by the first transcription factor coding sequence and the second transcription factor coding sequence interact to form a ligand-dependent transcription factor complex, wherein the first transcription factor coding sequence comprises a nucleic acid sequence encoding a VP-16 transactivation domain and a retinoic acid-X-receptor (RXR) polypeptide, wherein the second transcription factor coding sequence comprises a nucleic acid sequence encoding a GAL-4 DNA binding domain and a *Choristoneura* fumiferna ecdysone receptor ligand binding domain, and (2) a polynucleotide encoding a polypeptide having a function of IL-12 that is at least 90% identical to IL-12 operably linked to a promoter which is activated by said ligand-dependent transcription factor complex, wherein the function of IL-12 is production of IFN-gamma; and B) administering to the mammal about 20 mg of a diacylhydrazine ligand that activates the ligand-dependent transcription factor complex, wherein the ligand is first administered to the mammal in a time period from 24 hours before administration of the vector to 24 hours following administration of the vector, and wherein the ligand is administered daily for a period of 7 to 28 days following the first administration.

22. The method of claim 21, wherein the ligand is administered daily for a period of 14 days.

23. The method of claim 21, wherein the vector is an adenoviral vector.

24. The method of claim 21, wherein the ligand is administered orally.

25. The method of claim 21, wherein the RXR polypeptide is a genetically engineered chimera comprising vertebrate RXR and invertebrate RXR ligand binding domains, and wherein said vertebrate RXR ligand binding domain is a human RXR ligand binding domain.

26. The method of claim 21, wherein said *Choristoneura fumiferna* ecdysone receptor ligand binding domain comprises a genetically engineered substitution mutation compared to the naturally occurring *Choristoneura fumiferna* ecdysone receptor ligand binding domain.

27. The method of claim 21, wherein the diacylhydrazine ligand is selected from the group consisting of RG-115819, RG-115830 and RG-115932.

28. The method of claim 21, wherein the polypeptide having a function of IL-12 is at least 95% identical to IL-12.

29. The method of claim 21, wherein the polypeptide having a function of IL-12 is at least 99% identical to IL-12.

30. The method of claim 21, wherein the mammal is administered from about $1.0\times10^{11}$ to about $1.0\times10^{12}$ viral particles of the viral vector.

* * * * *